(12) United States Patent
Lazar et al.

(10) Patent No.: US 7,930,107 B2
(45) Date of Patent: *Apr. 19, 2011

(54) METHODS OF GENERATING VARIANT PROTEINS WITH INCREASED HOST STRING CONTENT

(75) Inventors: Gregory Alan Lazar, Alhambra, CA (US); John R. Desjarlais, Pasadena, CA (US); Philip W. Hammond, Sierra Madre, CA (US)

(73) Assignee: Xencor, Inc., Monrovia, CA (US)

( * ) Notice: Subject to any disclaimer, the term of this patent is extended or adjusted under 35 U.S.C. 154(b) by 141 days.

This patent is subject to a terminal disclaimer.

(21) Appl. No.: 11/981,794

(22) Filed: Oct. 31, 2007

(65) Prior Publication Data

US 2008/0167449 A1   Jul. 10, 2008

Related U.S. Application Data

(63) Continuation of application No. 11/004,590, filed on Dec. 3, 2004, now Pat. No. 7,657,380.

(60) Provisional application No. 60/527,167, filed on Dec. 4, 2003, provisional application No. 60/581,613, filed on Jun. 21, 2004, provisional application No. 60/601,665, filed on Aug. 13, 2004, provisional application No. 60/619,483, filed on Oct. 14, 2004.

(51) Int. Cl.
*G01N 33/48* (2006.01)
*C12Q 1/68* (2006.01)
*C12P 21/08* (2006.01)

(52) U.S. Cl. ............ 702/19; 435/6; 530/387.1; 702/20

(58) Field of Classification Search .................. None
See application file for complete search history.

(56) References Cited

U.S. PATENT DOCUMENTS

| | | |
|---|---|---|
| 4,943,533 A | 7/1990 | Mendolsohn |
| 5,530,101 A | 6/1996 | Queen |
| 5,585,089 A | 12/1996 | Queen |
| 5,693,761 A | 12/1997 | Queen |
| 5,693,762 A | 12/1997 | Queen |
| 5,712,120 A | 1/1998 | Rodriquez |
| 5,723,323 A | 3/1998 | Kauffman |
| 5,763,192 A | 6/1998 | Kauffman |
| 5,814,476 A | 9/1998 | Kauffman |
| 5,817,483 A | 10/1998 | Kauffman |
| 5,821,337 A | 10/1998 | Carter |
| 5,824,514 A | 10/1998 | Kauffman |
| 5,859,205 A | 1/1999 | Adair |
| 6,054,297 A | 4/2000 | Carter |
| 6,180,370 B1 | 1/2001 | Carter |
| 6,188,965 B1 | 2/2001 | Mayo et al. |
| 6,269,312 B1 | 7/2001 | Mayo |
| 6,352,842 B1 | 3/2002 | Short |
| 6,358,709 B1 | 3/2002 | Short |
| 6,361,974 B1 | 3/2002 | Short |
| 6,365,377 B1 | 4/2002 | Patton |
| 6,403,312 B1 | 6/2002 | Dahiyat |
| 6,407,213 B1 | 6/2002 | Carter |
| 6,708,120 B1 | 3/2004 | Mayo |
| 6,737,056 B1 | 5/2004 | Presta |
| 6,792,356 B2 | 9/2004 | Mayo |
| 6,804,611 B2 | 10/2004 | Mayo |
| 6,950,754 B2 | 9/2005 | Mayo |
| 7,231,328 B2 | 6/2007 | Desjarlais |
| 2002/0048772 A1 | 4/2002 | Dahiyat |
| 2002/0090648 A1 | 7/2002 | Dahiyat |
| 2002/0119492 A1 | 8/2002 | Chirino |
| 2003/0022285 A1 | 1/2003 | Chirino |
| 2003/0049654 A1 | 3/2003 | Dahiyat |
| 2003/0130827 A1 | 7/2003 | Bentzien et al. |
| 2003/0153043 A1 | 8/2003 | Carr et al. |
| 2004/0002587 A1 | 1/2004 | Watkins |
| 2004/0043429 A1 | 3/2004 | Dahiyat |
| 2004/0043430 A1 | 3/2004 | Dahiyat |
| 2004/0132101 A1 | 7/2004 | Lazar |
| 2005/0038610 A1 | 2/2005 | Mayo |
| 2005/0054832 A1 | 3/2005 | Lazar |
| 2005/0064555 A1 | 3/2005 | Marshall |
| 2005/0143929 A1 | 6/2005 | Desjarlais |
| 2005/0244403 A1 | 11/2005 | Lazar |
| 2006/0003412 A1 | 1/2006 | Chamberlain et al. |
| 2006/0121032 A1 | 6/2006 | Dahiyat |
| 2006/0134105 A1 | 6/2006 | Lazar |
| 2007/0166309 A1 | 7/2007 | Lazar et al. |

FOREIGN PATENT DOCUMENTS

| | | |
|---|---|---|
| EP | 1 951 757 A2 | 8/2008 |
| JP | 08/280387 | 10/1996 |
| WO | WO 96/40210 | 12/1996 |
| WO | WO 98/47089 | 10/1998 |
| WO | WO 98/52976 | 11/1998 |
| WO | WO 98/59244 | 12/1998 |
| WO | WO 00/23564 | 4/2000 |
| WO | WO 00/42561 | 7/2000 |
| WO | WO/0042072 | 7/2000 |
| WO | WO 01/21823 | 3/2001 |
| WO | WO 01/59066 A2 | 8/2001 |
| WO | WO 01/70947 A3 | 9/2001 |
| WO | WO 02/00165 | 1/2002 |
| WO | WO 02/22826 A2 | 3/2002 |
| WO | WO 02/068453 A2 | 9/2002 |
| WO | WO 02/068698 | 9/2002 |
| WO | WO 02/069232 | 9/2002 |
| WO | WO 02/77187 | 10/2002 |
| WO | WO 02/079232 | 10/2002 |
| WO | WO 03/000405 A2 | 1/2003 |
| WO | WO 03/002607 | 1/2003 |
| WO | WO 03/014325 A2 | 2/2003 |

(Continued)

OTHER PUBLICATIONS

U.S. Appl. No. 11/488,984, filed Jul. 18, 2006, Desjarlais.

(Continued)

*Primary Examiner* — Shubo (Joe) Zhou
(74) *Attorney, Agent, or Firm* — Morgan Lewis & Bockius LLP; Robin M. Silva, Esq.

(57) ABSTRACT

The present invention relates to novel methods for generating variant proteins with increased host string content, and proteins that are engineered using these methods.

14 Claims, 154 Drawing Sheets

FOREIGN PATENT DOCUMENTS

| | | |
|---|---|---|
| WO | WO 03/025154 A2 | 3/2003 |
| WO | WO 03/043583 A2 | 5/2003 |
| WO | WO 03/048321 A2 | 6/2003 |
| WO | WO 03/059282 A | 7/2003 |
| WO | WO 2004/029207 | 4/2004 |
| WO | WO 2004/029207 A | 4/2004 |
| WO | WO 2004/063351 | 7/2004 |
| WO | WO 2004/074455 A2 | 9/2004 |
| WO | WO 2005/056606 A | 6/2005 |
| WO | WO 2005/056759 A | 6/2005 |
| WO | WO2007/044616 A2 | 4/2007 |

OTHER PUBLICATIONS

U.S. Appl. No. 10/339,788, filed Jan. 8, 2003, Chirino.
U.S. Appl. No. 60/222,697, filed Aug. 2, 2000, Li.
Adenot et at., "Peptides quantitative stucture-function relationships: An automated mutation strategy to design peptides and pseudopeptides from substitutio matrices" 1999, *J. Mol. Graph. Model.* 17: 292-309.
Al-Lazikani et al., "Standard Conformations for the Canonical Structures of Immunoglobulins" 1997, *J. Mol. Biol.* 273: 927-948.
Amstutz et al., 2001, "In vitro display technologies: novel developments and applications" *Curr Opin Biotechnol* 12:400-405.
Arnold et al:, "The Majority of Immunogenic Epitopes Generate CD4+ T Cells That Are Dependent on MHC Class II-Bound Peptide-Flanking Residues" 2002, *J Immunology* 169(2): 739-49.
Barbie & Lefranc, "The Human Immunoglobulin Kappa Variable (IGKV) Genes and Joining (IGKJ) Segments" 1998, *Exp Clin Immunogenet* 15(3):171-83.
Benhar et al., "Highly Efficient Selection of Phage Antibodies Mediated by Display of Angigen as Lp-OmpA Fusions on Live Bacteria" 2000, *J Mol Biol* 301:893-904.
Boder & Wittrup, "Yeast Surface display for screening combinatorial polypeptide libraries"1997, *Nat Biotechnol* 15:553-557.
Boder & Wittrup, "Yeast Surface Display for Directed Evolution of Protein Expression, Affinity, and Stabiliy" 2000, *Methods Enzymol* 328:430-44.
Bowen et al. "Functional Effects of CD30 on a Large Granular Lymphoma Cell Line YT"Journal of Immunology, 1993, 151: 5896.
Bowie & Sauer, "Identifying determinants of folding and activity for a protein of unknown structure" 1989, *Proc. Nat. Acad. Sci. USA* 86: 2152-2156.
Bowie et al., "Deciphering the Message in Protein Sequences: Tolerance to Amino Acid Substitutions"1990, *Science* 247: 1306-1310.
Bruggemann et al., 1997, "Production of human antibody repertoires in transgenic mice"*Curr Opin Biotechnol* 8:455-458.
Canfield & Morrison, "The-Binding Affinity of Human IgG for its High Affinity Fc Receptor is Determined by Mulitpile Amino Acids in the Cg2 Domain and is Modulated by the Hinge Region" 1991, J. Exp. Med. 173: 1483-1491.
Chappel et al., "Identification of a Secondary FcγRI Binding-Site within a Genetically Engineered Human IgG Antobidy" 1993, Journal of Biological Chemistry 268:25124-25131.
Chappel et al., "Identification of the Fcγ receptor class I binding site in human IgG through the use of recombinant IgG1/IgG2 hybrid and point-mutated antibodies"1991, Proc. Natl. Acad. Sci. USA 88(20): 9036-9040.
Chen et al., 2001, "Isolation of high-affinity ligand-binding proteins by perplasmic expression with cytometric screening(PECS)" *Nat Biotechnol* 19:537-542.
Chothia & Lesk, "Canonical Structures for the Hypervariable Regions of Immunoglobulins" 1987, *J. Mol. Biol.* 196:901-917.
Chothia, C. et al., "Conformations of immunoglobulin hypervariable regions" *Nature* 342, 877-883 (1989).
Clark, "Antibody humanization: a case of the Emperor's new clothes?" 2000, *Immunol Today* 21:397-402.
Coco et al., "DNA shuffling method for generating highly recombined genes and evolved enzymes" 2001, *Nat Biotechnol* 19:354-359.
Cox et al. Eur J Immunol. "A directory of human germn-line $V_x$ segments reveals a strong bias in their usage" Apr. 1994:24(4):827-36.

Crameri et al., "DNA Shuffling of a family of genes from diverse species accelerates directed evolution" 1998, *Nature* 391:288-291.
Davies et al., "Expression of GnTIII ina Recombinant Anti-CD20 CHO Production Cell Line: Expression of Antibodies with Altered Glycoforms Leads to an Increase In ADCC Through Higher Affinity for FcγRIII" 2001, *Biotechnol Bioeng* 74:288-294.
Desjarlais & Berg, "Use of a zinc-finger consensus sequence framework and specificity rules to design specific DNA binding proteins" 1993, *Proc Natl Acad Sci USA* 90(6):2256-60.
Fields & Song, "A Novel Genetic System to Detect Protein-protein Interactions" 1989, *Nature* 340:245-246.
Forsthuber et al., "T Cell Epitopes of Human Myelin Oligodendrocyte Glycoprotein Identified in HLA-DR4(DRB1*0401) Transgenic Mice are Encephalitogenic and are Presented by Human B Cells" 2001, *J. Immunol.* 167:119-125.
Georgiou et al., "Practical applications of engineering Gram-negative bacterial cell surfaces" 1993, *Trends Biotechnol* 11:6-10.
Georgiou et al., "Display of hterologous proteins on the surface of microorganisms: from the screening of libraries to live recombinant vaccines" 1997, *Nat Biotechnol* 15:29-34.
Griffiths et al., "Strategies for selection of antibodies by phage display" 1998, *Curr Opin Biotechnol* 9:102-108.
Hammer et al., "Precise Prediction of Major Histocompatability Complex Class II-Peptide Interaction Based on Peptide Side Chain Scanning"1994, *J. Exp Med.* 180: 2353-2358.
Hanes et al., "In vitro selection and evolution of functional proteins by using ribosome display"1997, *Proc Natl Acad Sci USA*94:4937-4942.
Hayhurst & Georgiou, "High Throughput antibody isolation"2001, *Curr Opin Chem Biol* 5:683-689.
Henikoff & Henikoff, "Position-based Seqeunce Weights" 1994, *J Mol Biol* 243(4):574-8.
Henikoff & Henikoff, "Amino acid substitution matrices from protein blocks" 1992; *Proc. Nat. Acad. Sci. USA* 89: 10915-10919.
Henikoff & Henikoff, "Using substitution probabilities to improve position-specific scoring matrices"1996, *Comput. Appl. Biosci.* 12: 135-143.
Henikoff & Henikoff, "Amino Acid Substitution Matrices" 2000, *Adv Protein Chem* 54:73-97.
Henikoff,"Scores for sequence searches and alignments"1996, *Curr. Opin. Struct. Biol.* 6: 353-360.
Hinton et al., "Engineered Human IgG Antibodies with Longer Serum Half-lives in Primates"2004, J. Biol. Chem..279(8): 6213-6216.
Idusogie et al., "Engineered Antibodies with Increased Activity to Recruit Complement" 2001, J. Immunology 166:2571-2572.
Johnson & Wu, "Kabat Database and its applications: 30 years after the first variability plot" 2000, *Nucleic Acids Res* 28:214-218.
Johnson & Wu, "Kabat Database and its applications: future directions"2001, *Nucleic Acids Res* 29:205-206.
Johnsson & Varshavsky, "Split ubiquitin as a sensor of protein interactions in vivo " 1994, *Proc Natl Acad Sci USA* 91:10340-10344.
Jung et al., "Surface display of *Zymomonas mobilis* levansucrase by using the ice-nucleation protein of *Pseudomonas syringae*" 1998, *Nat Biotechnol* 16:576-80.
Kikuchi et al., "An effective family shuffling method using single-stranded DNA" 2000, Gene 243:133-137.
Kikuchi et al., "Novel family shuffling methods for the in vitro evolution of enzymes" (1999) *Gene* 236:159-167.
Kolkman & Stemmer, "Directed evolution of proteins by exon shuffling" 2001, *Nat Biotechnol* 19:423-428.
Krebber et al.,"Selectively-infective Phage (SIP): A Mechanistic Dissection of a Novel in vivo Selection for Protein-ligand interactions" 1997, *J Mol Biol* 268:619-630.
Lee et al., "Surface-displayed viral antigens on *Salmonella* carrier vaccine" 2000, *Nat Biotechnol* 18:645-648.
Lefranc et al., "IMGT, the international ImMunoGeneTics database" 1999, *Nucleic Acids Res* 27:209-212.
Lefranc et al., "IMGT, the international ImMunoGeneTics database" 2001, *Nucleic Acids Res* 29:207-209.
Lefranc et al.; "IMGT, the international ImMunoGeneTics database" 2003, *Nucleic Acids Res* 31:307-310.

Lehmann & Wyss, "Engineering proteins for thermostability: the use of sequence alignments versus rational design and directed evolution" 2001, *Curr Opin Biotechnol* 12(4): 371-5.

Lehmann et al., "The consensus concept for thermostability engineering of proteins" 2000, *Biochim Biophys Acta* 1543(2):408-415.

Lehmann et al., "From DNA sequence to improved functionality: using protein sequence comparisons to rapidly design a thermostable consensus phytase" 2000, *Protein Eng* 13(1):49-57.

Lim et al., "Structural and Energetic Consequences of Disruptive Mutations in a Protein Core" 1992, *Biochem.* 31: 4324-4333.

Lowman et al., "Selecting High-Affinity Binding Proteins by Monovalent Phage Display" 1991, *Biochemistry* 30:10832-10838.

Lutz et al., "Creating multiple-crossover DNA libraries independent of sequence identity" 2001, *Proc Natl Acad Sci USA* 98:11248-11253.

MacCallum et al., "Antibody-antigen Interactions: Contact Analysis and Binding Site Topography" 1996; *J. Mol. Biol.* 262: 732-745.

Mallios, "Class II MHC quantitative binding motifs derived from a large molecular database with a versatile iterative stepwise discriminant analysis meta-algorithm" 1999, *Bioinformatics* 15: 432-439.

Mallios, "Predicting class I MHC/peptide, multi-level binding with an iterative stepwise discriminant analysis meta-algorithm" 2001, *Bioinformatics* 17: 942-948.

Malmborg et al., "Selective Phage Infection Mediated by Epitope Expression on F Pilus" 1997, J Mol Biol 273:544-551.

Marshall et al., "Prediction of Peptide Affinity to HLA DRB1*0401" 1995, *J. Immunol.* 154: 5927-5933.

Matsuda et al., "The Complete Nucleotide Sequence of the Human Immunoglobulin Heavy Chain Variable Region Locus" 1998, *J.Exp Med* 188: 2151-2162.

Mattheakis et al., "An in vitro polysome display system for identifying ligands from very large peptide libraries" 1994, *Proc Natl Acad Sci USA* 91:9022-9026.

Maynard & Georgiou, "Antibody Engineering" 2000, *Annu Rev Biomed Eng* 2:339-76.

Meidenbauer et al., "Generation of PSA-Reactive Effector Cells After Vaccination With a PSA-Based Vaccine in Patients with Prostate Cancer" 2000, *Prostate* 43; 88-100.

Modjtahedi et al, "Phase 1 trial and tumour localisation of the anti-EGFR monoclonal antibody ICR62 in head and neck or lung cancer" 1996; *Br J Cancer*, 73(2):228-235.

Modjtahedi et al, "Targeting of Cells Expressing Wild-type EGFR and Type III Mutant EGFR (EGFRVIII) by Anti-EGFR MAB ICR62: a Two Pronged Attack for Tumour Therapy " 2003, *Int J Cancer*, 105(2):273-280.

Modjtahedi et al., "The human EGF receptor as a target for cancer therapy: six new rat mAbs against the receptor on the breast carcinoma MDA-MB 468" 1993, *Br J Cancer* 1993; 67(2):247-253.

Modjtahedi et al., "Antitumor Activity of Combinations of Antibodies Directed Against Different Epitopes on the Extracellular Domain of the Human EGF Receptor" 1993, *J. Cell Biophys.* 1993, 22(1-3)129-146.

Nemoto et al., "In vitro virus: bonding of mRNA bearing puroycin at the 3'-terminal end to the C-terminal end of its encoded protein on the ribosome in vitro" 1997, *FEBS Lett.* 414:405-408.

Pallares et al., "The Human Immunoglobulin Heavy Variable Genes" 1999, *Exp Clin Immunogenet* 16(1): 36-60.

Pelletier et al., "Oligomerization domain-directed reassembly of active dihydrofolate reductase from rationally designed fragments" 1998, *Proc Natl Acad Sci USA* 95:12141-12146.

Raha et al., "Prediction of amino acid sequence from structure" 2000, *Protein Sci.* 9: 1106-1119.

Rath & Davidson, "The design of a hyperstable mutant of the Abp1p SH3 domain by sequence alignment analysis" 2000, *Protein Sci,* 9(12):2457-2469.

Redpath et al., "The Influence of the Hinge Region Length in Binding of Human IgG to Human Fcγ Receptors" 1998, Human Immunology, 59, 720-727.

Reidhaar-Olson & Sauer, "Funcionality Acceptable Substitutios in Two α-Helical Regions of λ Repressor" 1990, *Proteins* 7: 306-316.

Ritter et al., "Serological Analysis of Human Anti-Human Antibody Responses in Colon Cancer Patients Treated with Repeated Doses of Humanized Monoclonal Antibody A33" 2001, *Cancer Research* 61: 6851-6859.

Roberts & Szostak, "RNA-peptide fusions for the in vitro selection of peptides and proteins" 1997, *Proc Natl Acad Sci USA* 94:12297-12302.

Ruiz et al., "IMGT, the international ImMunoGeneTicsdatabase" 2000 *Nucleic Acids Re.* 28:219-221.

Schmittel et al., "Application of the IFN-γ ELISPOT assay to quantify T cell responses against proteins" 2001, *J. Immunol Meth.*, 24: 17-24.

Schultes & Whiteside; "Monitoring of Immune responses to CA125 with an IFN-γ ELISPOT assay" 2003, *J. Immunol Methods* 279, 1-15.

Shao et al., "Random-priming in vitro recombination: an effective tool for directed evolution" 1998, *Nucleic Acids Res* 26:681-683.

Shields et al.,"Lack of Fucose on Human IgG1 N-Linked Oligosaccharide Improves Binding to Human FcγRIII and Antibody-dependent Cellular Toxicity" 2002, *J Biol Chem* 277:26733-26740.

Shinkawa et al., "The Absence of Fucose but not the presence of Galactose or Bisecting N-Aceytlglucosamine of Human IgG1 Complex type Oligosaccharides Shows the Critical role of Enahncing Antibody-dependnet Cellular Cytotoxicity" 2003, *J Biol Chem* 278:3466-3473.

Skerra, "A general vector, pASK84, for cloning, bacterial production , and single-step purification of antibody $F_{ab}$ fragments" 1994, Gene 141: 79-84.

Smith, "Filamentous Fusion Phage: Novel Expression Vectors That Display Cloned Antigens on the virion surface" 1985, *Science* 228:1315-1317.

Sonderstrup et al. "HLA class II transgenic mice: models of the human CD4+ T-cell immune response", 1999, *Immunol. Rev.* 172:335-343.

Stickler et al., "CD4+ T-Cell Epitope Determination Using Unexposed Human Donor Peripheral Blood Mononuclear Cells" 2000, *J. Immunotherapy*, 23, 654-660.

Sturniolo et al., "Generation of tissue-specific and promiscuous HLA ligand databases using DNA microarrays and virtual HLA class II matrices" 1999 *Nature Biotech.* 17: 555-561.

Tao et al., "Structural Features of Human Immunoglobulin G that Determine Isotype-specific Differences in Complement Activation" 1993, J. Exp. Med. 178: 661-667.

Tao et al., 1991, "The Differential Ability of Human IgG1 and IgG4 to Activate Complement is Determined by the COOH-termnal Seqeunce of the $C_H2$ Domain" J . Exp. Med. 173: 1025-1028.

Topham et al., "Prediction of the stability of protein mutants based on structural environment-dependent amino acid substitution and propensity tables" 1997, *Prot. Eng.* 10: 7-21.

Tsurushita & Vasquez, 2004, Humanization of Monoclonal Antibodies, Molecular Biology of B Cells, 533-545, Elsevier Science (USA).

Umaña et al., "Engineered glycoforms of an antineuro blastoma IgG1 with optimized antibody-dependent cellular cytotoxic activity" 1999, *Nat Biotechnol* 17:176-180.

Visintin et al., "Selection of antibodies for intracellular function using a two-hybrid in vivo system" 1999, *Proc Natl Acad Sci USA* 96:11723-11728.

Whitehorn et al., "A Generic Method for Expression and use of "Tagged" soluble versions of cell surface receptors" 1995, *Bio/technology* 13:1215-1219.

Witrrup, "Protein Engineering by cell-surface display" 2001, *Curr Opin Biotechnol*, 12:395-399.

Zachau, "The immunoglobulin K Gene Families of Human and Mouse: a cottage industry approach" 2000, Biol Chem 381:951-954.

Zhao et al., "Molecular evoluton by staggered extension process (StEP) in vitro recombination" 1998, *Nat Biotechnol* 16:258-261.

Zhou et al., "A Novel Strategy by the Action of Ricin that Connects Phenotype and Genotype Without Loss of the Diversity of Libraries" 2002, *J Am Chem Soc* 124, 538-543.

Shields, R. L., et al., "High Resolution Mapping of the Binding Site on Human IgG1 for FcγRI, FcγRII, FcγRIII, and FcRn and Design of IgG1 Varients with Improved Binding to the FcγR" *J. Biol. Chem.*. 276(9):6591-6604 (2001).

Yamane-Ohnuki N. et al., "Establishment of FUT8 knockout chinese hamster ovary cells: an ideal host cell line for producing completely defucosylated antibodies with enhanced antibody-dependent cellular cytoxicity", *Biotechnology and Bioengineering Interscience Publishers*, London, GB, vol. 87, No. 5, Sep. 5, 2004.

Lazar et al. "A molecular immunology approach to antibody humanization and functional optimization" *Molecular Immunology, Pergamon*, 44(8):1986-1998, (2006).

Human Germline VH Sequences

```
                  Chain            FR1                        CDR1                   FR2
                  Kabat   1         2         3            3              4
                          1234567890123456789012345ab6789012345ab6789
                                                                        1234567890123456789
SEQ ID NO.:1      VH_1-2   QVQLVQSGAEVKKPGASVKVSCKASGYTFTGYYMH          WVRQAPGQGLEWMG
SEQ ID NO.:2      VH_1-3   QVQLVQSGAEVKKPGASVKVSCKASGYTFTSYAMH          WVRQAPGQRLEWMG
SEQ ID NO.:3      VH_1-8   QVQLVQSGAEVKKPGASVKVSCKASGYTFTSYDIN          WVRQATGQGLEWMG
SEQ ID NO.:4      VH_1-18  QVQLVQSGAEVKKPGASVKVSCKASGYTFTSYGIS          WVRQAPGQGLEWMG
SEQ ID NO.:5      VH_1-24  QVQLVQSGAEVKKPGASVKVSCKVSGYTLTELSMH          WVRQAPGKGLEWMG
SEQ ID NO.:6      VH_1-45  QMQLVQSGAEVKKTGSSVKVSCKASGYTFTYRYLH          WVRQAPGQALEWMG
SEQ ID NO.:7      VH_1-46  QVQLVQSGAEVKKPGASVKVSCKASGYTFTSYYMH          WVRQAPGQGLEWMG
SEQ ID NO.:8      VH_1-58  QMQLVQSGPEVKKPGTSVKVSCKASGFTFTSSAVQ          WVRQARGQRLEWIG
SEQ ID NO.:9      VH_1-69  QVQLVQSGAEVKKPGSSVKVSCKASGGTFSSYAIS          WVRQAPGQGLEWMG
SEQ ID NO.:10     VH_1-f   EVQLVQSGAEVKKPGATVKISCKVSGYTFTDYYMH          WVQQAPGKGLEWMG SEQ ID NO.:11     VH_2-5   QITLKESGPTLVKPTQTLTLTCTFSGFSLSTSGVGVGWIRQPPGKALEWLA
SEQ ID NO.:12     VH_2-26  QVTLKESGPVLVKPTETLTLTCTVSGFSLSNARMGVSWIRQPPGKALEWLA
SEQ ID NO.:13     VH_2-70  QVTLRESGPALVKPTQTLTLTCTFSGFSLSTSGMCVSWIRQPPGKALEWLA SEQ ID NO.:14     VH_3-7   EVQLVESGGGLVQPGGSLRLSCAASGFTFSSYWMS          WVRQAPGKGLEWVA
SEQ ID NO.:15     VH_3-9   EVQLVESGGGLVQPGRSLRLSCAASGFTFDDYAMH          WVRQAPGKGLEWVS
SEQ ID NO.:16     VH_3-11  QVQLVESGGGLVKPGGSLRLSCAASGFTFSDYYMS          WIRQAPGKGLEWVS
SEQ ID NO.:17     VH_3-13  EVQLVESGGGLVQPGGSLRLSCAASGFTFSDYYMS          WVRQATGKGLEWVS
SEQ ID NO.:18     VH_3-15  EVQLVESGGGLVKPGGSLRLSCAASGFTFSNAWMS          WVRQAPGKGLEWVG
SEQ ID NO.:19     VH_3-16  EVQLVESGGGLVQPGGSLRLSCAASGFTFSNSDMN          WARKAPGKGLEWVS
SEQ ID NO.:20     VH_3-19  TVQLVESGGGLVEPGGSLRLSCAASGFTFSNSDMN          WVRQAPGKGLEWVS
SEQ ID NO.:21     VH_3-20  EVQLVESGGGVVRPGGSLVKPGGSLRLSCAASGFTFDDYGMS  WVRQAPGKGLEWVS
SEQ ID NO.:22     VH_3-21  EVQLVESGGGLVKPGGSLRLSCAASGFTFSSYSMN          WVRQAPGKGLEWVS
SEQ ID NO.:23     VH_3-23  EVQLLESGGGLVQPGGSLRLSCAASGFTFSSYAMS          WVRQAPGKGLEWVS
```

```
        CDR2                         FR3                                              CDR3
   5         6         7         8         9            10
012abc3456789012345678901234567890123456789012abc34567890123456789012abc3456789012abcdefghijk12

RINP   NSGGTNYAQKFQGRVTSTRDTSISTAYMELSRLRSDDTVVYYCAR
WINA   GNGNTKYSQKFQGRVTITRDTSASTAYMELSSLRSEDTAVYYCAR
WMNP   NSGNTGYAQKFQGRVTMTRNTSISTAYMELSSLRSEDTAVYYCAR
WISA   YNGNTNYAQKLQGRVTMTDTSTSTAYMELRSLRSDDTAVYYCAR
GFDP   EDGETIYAQKFQGRVTMTEDTSTDTAYMELSSLRSEDTAVYYCAT
WITP   FNGNTNYAQKFQDRVTITRDKSMSTAYMELSSLRSEDTAMYYCAR
IINP   SGGSTSYAQKFQGRVTMTRDTSTSTVYMELSSLRSEDTAVYYCAR
WIVV   GSGNTNYAQKFQERVTITRDMSTSTAYMELSSLRSEDTAVYYCAA
GIIP   IFGTANYAQKFQGRVTITADESTSTAYMELSSLRSEDTAVYYCAR
LVDP   EDGETIYAEKFQGRVTITADTSTDTAYMELSSLRSEDTAVYYCAT

LIY    WNDDKRYSPSLKSRLTITKDTSKNQVVLTMTNMDPVDTATYYCAHR
HIF    SNDEKSYSTSLKSRLTISKDTSKSQVVLTMTNMDPVDTATYYCARI
LID    WDDDKYYSTSLKTRLTISKDTSKNQVVLTMTNMDPVDTATYYCARI

NIKQ   DGSEKYYVDSVKGRFTISRDNAKNSLYLQMNSLRAEDTAVYYCAR
GISW   NSGSIGYADSVKGRFTISRDNAKNSLYLQMNSLRAEDTALYYCAKD
YISS   SGSTTYYADSVKGRFTISRDNAKNSLYLQMNSLRAEDTAVYYCAR
AIGT   AGDT YYPGSVKGRFTISRENAKNSLYLQMNSLRAEDTAVYYCAR
RIKSKTDGGTTDYAAPVKGRFTISRDDSKNTLYLQMNSLKTEDTAVYYCTT
GVSW   NGSRTHYVDSVKRRFIISRDNSRNSLYLQKNRRAEDMAVYYCVR
GVSW   NGSRTHYADSVKGRFTISRDNSRNFLYQQMNSLRPEDMAVYYCVR
GINW   NGGSTGYADSVKGRFTISRDNAKNSLYLQMNSLRAEDTAVYYCAR
SISS   SSSYIYYADSVKGRFTISRDNAKNSLYLQMNSLRAEDTALYHCAR
AISG   SGGSTYYADSVKGRFTISRDNSKNTLYLQMNSLRAEDTAVYYCAK
```

FIG. 1a-2

| SEQ ID NO.:24 | VH_3-30 | QVQLVESGGGVVQPGRSLRLSCAASGFTFSSYAMH WVRQAPGKGLEWVA |
| SEQ ID NO.:25 | VH_3-30-3 | QVQLVESGGGVVQPGRSLRLSCAASGFTFSSYAMH WVRQAPGKGLEWVA |
| SEQ ID NO.:26 | VH_3-33 | QVQLVESGGGVVQPGRSLRLSCAASGFTFSSYGMH WVRQAPGKGLEWVA |
| SEQ ID NO.:27 | VH_3-35 | EVQLVESGGGLVQPGGSLRLSCAASGFTFSNSDMN WVHQAPGKGLEWVS |
| SEQ ID NO.:28 | VH_3-38 | EVQLVESGGGLVQPRGSLRLSCAASGFTVSSNEMS WIRQAPGKGLEWVS |
| SEQ ID NO.:29 | VH_3-43 | EVQLVESGGGVVQPGGSLRLSCAASGFTFDDYTMH WVRQAPGKGLEWVS |
| SEQ ID NO.:30 | VH_3-48 | EVQLVESGGGLVQPGGSLRLSCAASGFTFSSYSMN WVRQAPGKGLEWVS |
| SEQ ID NO.:31 | VH_3-49 | EVQLVESGGGLVQPGRSLRLSCTASGFTFGDYAMS WFRQAPGKGLEWVG |
| SEQ ID NO.:32 | VH_3-53 | EVQLVESGGGLIQPGGSLRLSCAASGFTVSSNYMS WVRQAPGKGLEWVS |
| SEQ ID NO.:33 | VH_3-64 | EVQLVESGGGLVQPGGSLRLSCAASGFTFSSYAMH WVRQAPGKGLEYVS |
| SEQ ID NO.:34 | VH_3-66 | EVQLVESGGGLVQPGGSLRLSCAASGFTVSSNYMS WVRQAPGKGLEWVS |
| SEQ ID NO.:35 | VH_3-72 | EVQLVESGGGLVQPGGSLRLSCAASGFTFSDHYMD WVRQAPGKGLEWVG |
| SEQ ID NO.:36 | VH_3-73 | EVQLVESGGGLVQPGGSLKLSCAASGFTFSGSAMH WVRQASGKGLEWVG |
| SEQ ID NO.:37 | VH_3-74 | EVQLVESGGGLVQPGGSLRLSCAASGFTFSSYWMH WVRQAPGKGLVWVS |
| SEQ ID NO.:38 | VH_3-d | EVQLVESRGVLVQPGGSLRLSCAASGFTVSSNEMS WVRQAPGKGLEWVS |
| SEQ ID NO.:39 | VH_4-4 | QVQLQESGPGLVKPPGTLSLTCAVSGGSISSSNNWS WVRQPPGKGLEWIG |
| SEQ ID NO.:40 | VH_4-28 | QLQLQESGPGLVKPSDTLSLTCAVSGYSISISSNNWG WIRQPPGKGLEWIG |
| SEQ ID NO.:41 | VH_4-30-2 | QVQLQESGSGLVKPSQTLSLTCAVSGGSISGGYSWS WIRQPPGKGLEWIG |
| SEQ ID NO.:42 | VH_4-30-4 | QVQLQESGPGLVKPSQTLSLTCTVSGGSISSGDYYWS WIRQPPGKGLEWIG |
| SEQ ID NO.:43 | VH_4-31 | QVQLQESGPGLVKPSQTLSLTCTVSGGSISGGYYWS WIRQPPGKGLEWIG |
| SEQ ID NO.:44 | VH_4-34 | QVQLQQWGAGLLKPSETLSLTCAVYGGSFSGYYWS WIRQPPGKGLEWIG |
| SEQ ID NO.:45 | VH_4-39 | QLQLQESGPGLVKPSETLSLTCTVSGGSISSSSYYWG WIRQPPGKGLEWIG |
| SEQ ID NO.:46 | VH_4-59 | QVQLQESGPGLVKPSETLSLTCTVSGGSISSYYWS WIRQPPGKGLEWIG |
| SEQ ID NO.:47 | VH_4-61 | QVQLQESGPGLVKPSETLSLTCTVSGGSVSSGSYYWS WIRQPPGKGLEWIG |
| SEQ ID NO.:48 | VH_4-b | QVQLQESGPGLVKPSETLSLTCAVSGYSISSGYYWG WIRQPPGKGLEWIG |
| SEQ ID NO.:49 | VH_5-51 | EVQLVQSGAEVKKPGESLKISCKGSGYTFTSYWIG WVRQMPGKGLEWMG |
| SEQ ID NO.:50 | VH_5-a | EVQLVQSGAEVKKPGESLRISCKGSGYSFTSYWIS WVRQMPGKGLEWMG |
| SEQ ID NO.:51 | VH_6-1 | QVQLQQSGPGLVKPSQTLSLTCAISGDSVSSNSAAWNWIRQSPSRGLEWLG |
| SEQ ID NO.:52 | VH_7-4-1 | QVQLVQSGSELKKPGASVKVSCKASGYTFTSYAMN WVRQAPGQGLEWMG |
| SEQ ID NO.:53 | VH_7-81 | QVQLVQSGHEVKQPGASVKVSCKASGYSFTTYGMN WVPQAPGQGLEWMG |

FIG. 1a-3

```
VISY  DGSNKYYADSVKGRFTISRDNSKNTLYLQMNSLRAEDTAVYYCAR
VISY  DGSNKYYADSVKGRFTISRDNSKNTLYLQMNSLRAEDTAVYYCAR
VIWY  DGSNKYYADSVKGRFTISRDNSKNTLYLQMNSLRAEDTAVYYCAR
GVSW  NGSRTHYADSVKGRFIISRDNSRNTLYLQTNSLRAEDTAVYYCVR
SIS   GGSTYYADSRKGRFTISRDNSKNTLYLQMNNLRAEGTAAYYCARY
LISW  DGGSTYYADSVKGRFTISRDNSKNSLYLQMNSLRTEDTALYYCAKD
YISS  SSSTIYVADSVKGRFTISRDNAKNSLYLQMNSLRAEDTAVYYCAR
FIRSKAYGGTTEYTASVKGRFTISRDGSKSIAYLQMNSLKTEDTAVYYCTR
VIY   SGGSTYYADSVKGRFTISRDNSKNTLYLQMNSLRAEDTAVYYCAR
AISS  NGGSTYYANSVKGRFTISRDNSKNTLYLQMGSLRAEDMAVYYCAR
VIY   SGGSTYYADSVKGRFTISRDNSKNTLYLQMNSLKTEDTAVYYCAR
RTRNKANSYTTEYAASVKGRFTISRDDSKNSLYLQMNSLKTEDTAVYYCAR
RIRSKANSYATAYAASVKGRFTISRDDSKNTAYLQMNSLKTEDTAVYYCTR
RINS  DGSSTSYADSVKGRFTISRDNAKNTLYLQMNSLRAEDTAVYYCAR
SIS   GGSTYYADSRKGRFTISRDNSKNTLHLQMNSLRAEDTAVYYCKK
EIY   HSGSTNYNPSLKSRVTISVDKSKNQFSLKLSSVTAADTAVYYCAR
YIY   YSGSTYYNPSLKSRVTMSVDTSKNQFSLKLSSVTAVDTAVYYCAR
YIY   HSGSTYYNPSLKSRVTISVDRSKNQFSLKLSSVTAADTAVYYCAR
YIY   YSGSTYYNPSLKSRVTISVDTSKNQFSLKLSSVTAADTAVYYCAR
YIY   YSGSTYYNPSLKSLVTISVDTSKNQFSLKLSSVTAADTAVYYCAR
EIN   HSGSTNYNPSLKSRVTISVDTSKNQFSLKLSSVTAADTAVYYCAR
SIY   YSGSTNYNPSLKSRVTISVDTSKNQFSLKLSSVTAADTAVYYCAR
YIY   YSGSTYYNPSLKSRVTISVDTSKNQFSLKLSSVTAADTAVYYCAR
YIY   YSGSTNYNPSLKSRVTISVDTSKNQFSLKLSSVTAADTAVYYCAR
SIY   HSGSTYYNPSLKSRVTISVDTSKNQFSLKLSSVTAADTAVYYCAR

IIYP  GDSDTRYSPSFQGQVTISADKSISTAYLQWSSLKASDTAMYYCAR
RIDP  SDSYTNYSPSFQGHVTISADKSISTAYLQWSSLKASDTAMYYCAR

RTYYR SKWYNDYAVSVKSRITINPDTSKNQFSLQLNSVTPEDTAVYYCAR

WINT  NTGNPTYAQGFTGRFVFSLDTSVSTAYLQICSLKAEDTAVYYCAR
WFNT  YTGNPTYAQGFTGRFVFSMDTSASTAYLQISSLKAEDMAMYYCAR
```

Human Germline VLk Sequences

```
                         FR1                      CDR1                    FR2
                          1          2          3                          4
            1234567890123456789012345678901234567abcdef8901234567890123456789
Kabat
```

| SEQ ID NO. | Chain | Sequence |
|---|---|---|
| SEQ ID NO.:54 | VLk_1-5 | DIQMTQSPSTLSASVGDRVTITCRASQ SISSWLAWYQQKPGKAPKLLIY |
| SEQ ID NO.:55 | VLk_1-6 | AIQMTQSPSSLSASVGDRVTITCRASQ GIRNDLGWYQQKPGKAPKLLIY |
| SEQ ID NO.:56 | VLk_1-8 | AIRMTQSPSSFSASTGDRVTITCRASQ GISSYLAWYQQKPGKAPKLLIY |
| SEQ ID NO.:57 | VLk_1D-8 | VIWMTQSPSLLSASTGDRVTISCRMSQ GISSYLAWYQQKPGKAPELLIY |
| SEQ ID NO.:58 | VLk_1-9 | DIQLTQSPSFLSASVGDRVTITCRASQ GISSYLAWYQQKPGKAPKLLIY |
| SEQ ID NO.:59 | VLk_1-12 | DIQMTQSPSSVSASVGDRVTITCRASQ GISSWLAWYQQKPGKAPKLLIY |
| SEQ ID NO.:60 | VLk_1D-12 | DIQMTQSPSSVSASVGDRVTITCRASQ GISSWLAWYQQKPGKAPKLLIY |
| SEQ ID NO.:61 | VLk_1-13 | AIQLTQSPSSLSASVGDRVTITCRASQ GISSALAWYQQKPGKAPKLLIY |
| SEQ ID NO.:62 | VLk_1D-13_02 | AIQLTQSPSSLSASVGDRVTITCRASQ GISSALAWYQQKPGKAPKLLIY |
| SEQ ID NO.:63 | VLk_1-16 | DIQMTQSPSSLSASVGDRVTITCRASQ GISNYLAWYQQKPGKAPKSLIY |
| SEQ ID NO.:64 | VLk_1D-16 | DIQMTQSPSSLSASVGDRVTITCRASQ GISWLAWYQQKPEKAPKLLIY |
| SEQ ID NO.:65 | VLk_1-17 | DIQMTQSPSSLSASVGDRVTITCRASQ GIRNDLGWYQQKPGKAPKRLIY |
| SEQ ID NO.:66 | VLk_1D-17 | NIQMTQSPSAMSASVGDRVTITCRARQ GISNVLAWFQQKPGKVPKHLIY |
| SEQ ID NO.:67 | VLk_1-27 | DIQMTQSPSSLSASVGDRVTITCQASQ GISNYLAWYQQKPGKVPKLLIY |
| SEQ ID NO.:68 | VLk_1-33 | DIQMTQSPSSLSASVGDRVTITCQASQ DISNYLNWYQQKPGKAPKLLIY |
| SEQ ID NO.:69 | VLk_1D-33 | DIQMTQSPSSLSASVGDRVTITCQASQ DISNYLNWYQQKPGKAPKLLIY |
| SEQ ID NO.:70 | VLk_1-37 | DIQLTQSPSSLSASVGDRVTITCRVSQ GISSYLNWRQKPGKVPKLLIY |
| SEQ ID NO.:71 | VLk_1D-37 | DIQLTQSPSSLSASVGDRVTITCRVSQ GISSYLNWYQQKPGKVPKLLIY |
| SEQ ID NO.:72 | VLk_1-39 | DIQMTQSPSSLSASVGDRVTITCRASQ GISSYLNWYQQKPGKAPKLLIY |
| SEQ ID NO.:73 | VLk_1D-39 | DIQMTQSPSSLSASVGDRVTITCRASQ SISSYLNWYQQKPGKAPKLLIY |
| SEQ ID NO.:74 | VLk_1D-42 | DIQMIQSPSFLSASVGDRVSIICWASE GISSNLAWYLQKPGKSPKLFLY |
| SEQ ID NO.:75 | VLk_1D-43 | AIRMTQSPFFSLSASVGDRVTITCWASQ GISSYLAWYQQKPAKAPKLFIY |

FIG. 1b

| FIG. 1b-1 | FIG. 1b-2 |
|---|---|
| FIG. 1b-3 | FIG. 1b-4 |

FIG. 1b-2

```
         CDR2                         FR3                             CDR3
    5             6         7         8         9
   0123456789012345678901234567890123456789012345abcdef67
   DASSLESGVPSRFSGSGSGTEFTLTISSLQPDDFATYYCQQYNSYS
   AASSLQSGVPSRFSGSGSGTDFTLTISSLQPEDFATYYCLQDYNYP
   AASTLQSGVPSRFSGSGSGTDFTLTISCLQSEDFATYYCQQYYSYP
   AASTLQSGVPSRFSGSGSGTDFTLTISCLQSEDFATYYCQQYYSFP
   AASTLQSGVPSRFSGSGSGTEFTLTISSLQPEDFATYYCQQYLNSYP
   AASSLQSGVPSRFSGSGSGTDFTLTISSLQPEDFATYYCQQANSFP
   AASSLQSGVPSRFSGSGSGTDFTLTISSLQPEDFATYYCQQANSFP
   DASSLESGVPSRFSGSGSGTDFTLTISSLQPEDFATYYCQQFNNYP
   DASSLESGVPSRFSGSGSGTDFTLTISSLQPEDFATYYCQQYNSYP
   AASSLQSGVPSRFSGSGSGTDFTLTISSLQPEDFATYYCQQYNSYP
   AASSLQSGVPSRFSGSGSGTEFTLTISSLQPEDFATYYCLQHNSYP
   AASSLQSGVPSRFSGSGSGTDFTLTISSLQPEDFATYYCLQHNSYP
   AASSLQSGVPSRFSGSGSGTDFTLTISSLQPEDVATYYCQKYNSAP
   DASNLETGVPSRFSGSGSGTDFTLTFTISSLQPEDIATYYCQQYDNLP
   DASNLETGVPSRFSGSGSGTDFTLTFTISSLQPEDIATYYCQQYDNLP
   SASNLQSGVPSRFSGSGSGTDFTLTISSLQPEDVATYYGQRTYNAP
   SASNLQSGVPSRFSGSGSGTDFTLTISSLQPEDVATYYGQRTYNAP
   AASSLQSGVPSRFSGSGSGTDFTLTISSLQPEDFATYYCQQYSTP
   AASSLQSGVPSRFSGSGSGTDFTLTISSLKPEDFATYYCQQYSTP
   DAKDLHPGVSSRFSGRGSGTDFTLTIISLKPEDFAAYYCKQDFSYP
   YASSLQSGVPSRFSGSGSGTDYTLTISSLQPEDFATYYCQQYSTP
```

| | | |
|---|---|---|
| SEQ ID NO.:76 | VLk_2-24 | DIVMTQTPLSSPVTLGQPASISCRSSQSLVHS DGNTYLSWLQQRFGQPPRLLIY |
| SEQ ID NO.:77 | VLk_2D-24 | DIVMTQTPLSSPVTLGQPASISFRSSQSLVHS DGNTYLSWLQQRPGQPPRLLIY |
| SEQ ID NO.:78 | VLk_2-28 | DIVMTQSPLSLPVTLGQPASISCRSSQSLLHS NGYNYLDWYLQKPGQSPQLLIY |
| SEQ ID NO.:79 | VLk_2D-28 | DIVMTQSPLSLPVTPGEPASISCRSSQSLLHS NGYNYLDWYLQKPGQSPQLLIY |
| SEQ ID NO.:80 | VLk_2D-29 | DIVMTQTPLSLSVTPGQPASISCKSSQSLLHS DGKTYLYWYLQKPGQPPQLLIY |
| SEQ ID NO.:81 | VLk_2-29_2 | DIVMTQTPLSLSVTPGQPASISCKSSQSLLHS DGKTYLYWYLQKPGQSPQLLIY |
| SEQ ID NO.:82 | VLk_2-30 | DVVMTQSPLSLPVTLGQPASISCRSSQSLVYS DGNTYLNWFQQRPGQSPRRLIY |
| SEQ ID NO.:83 | VLk_2D-30 | DVVMTQSPLSLPVTLGQPASISCRSSQSLVYS DGNTYLNWFQQRPGQSPRRLIY |
| SEQ ID NO.:84 | VLk_2-40 | DIVMTQTPLSLPVTPGEPASISCRSSQSLLDSDDGNTYLDWYLQKPGQSPQLLIY |
| SEQ ID NO.:85 | VLk_2D-40 | DIVMTQTPLSLPVTPGEPASISCRSSQSLLDSDDGNTYLDWYLQKPGQSPQLLIY |
| SEQ ID NO.:86 | VLk_3-7 | EIVMTQSPPTLSLSPGERVTLSCRASQ VSSSYLTWYQQKPGQAPRLLIY |
| SEQ ID NO.:87 | VLk_3D-7 | EIVMTQSPATLSLSPGERATLSCRASQ VSSSYLSWYQQKPGQAPRLLIY |
| SEQ ID NO.:88 | VLk_3-11 | EIVLTQSPATLSLSPGERATLSCRASQ SVSSYLAWYQQKPGQAPRLLIY |
| SEQ ID NO.:89 | VLk_3D-11 | EIVMTQSPATLSLSPGERATLSCRASQ GVSSYLAWYQQKPGQAPRLLIY |
| SEQ ID NO.:90 | VLk_3-15 | EIVMTQSPATLSVSPGERATLSCRASQ SVSSNLAWYQQKPGQAPRLLIY |
| SEQ ID NO.:91 | VLk_3D-15 | EIVMTQSPATLSVSPGERATLSCRASQ SVSSNLAWYQQKPGQAPRLLIY |
| SEQ ID NO.:92 | VLk_3-20 | EIVLTQSPGTLSLSPGERATLSCRASQ VSSSYLAWYQQKPGQAPRLLIY |
| SEQ ID NO.:93 | VLk_3D-20 | EIVLTQSPATLSLSPGERATLSCGASQ VSSSYLAWYQQKPGLAPRLLIY |
| SEQ ID NO.:94 | VLk_4-1 | DIVMTQSPDSLAVSLGERATINCKSSQSVLYSSNNKNYLAWYQQKPGQPPKLLIY |
| SEQ ID NO.:95 | VLk_5-2 | ETTLTQSPAFMSATPGDKVNISCKASQ DIDDDMNWYQQKPGEAAIFIIQ |
| SEQ ID NO.:96 | VLk_6-21 | EIVLTQSPDFQSVTPKEKVTITCRASQ SIGSSLHWYQQKPDQSPKLLIK |
| SEQ ID NO.:97 | VLk_6D-21 | EIVLTQSPDFQSVTPKEKVTITCRASQ SIGSSLHWYQQKPFQSPKLLIK |
| SEQ ID NO.:98 | VLk_6D-41 | DVVMTQSPAFLSVTPGEKVTITCQASE GIGNYLYWYQQKPDQAPKLLIK |

*FIG. 1b-3*

```
KISNRFSGVPDRFSGSGAGTDFTLKISRVEAEDVGVYYCMQATQFP
KVSNRFSGVPDRFSGSGAGTDFTLKISRVEAEDVGVYYCTQATQFP
LGSNRASGVPDRFSGSGSTDFTLKISRVEAEDVGVYYCMQALQTP
LGSNRASGVPDRFSGSGSTDFTLKISRVEAEDVGVYYCMQALQTP
EVSNRFSGVPDRFSGSGSTDFTLKISRVEAEDVGVYYCMQSIQLP
EVSSRFSGVPDRFSGSGSTDFTLKISRVEAEDVGVYYCMQGIHLP
KVSNRDSGVPDRFSGSGSTDFTLKISRVEAEDVGVYYCMQGTHWP
KVSNWDSGVPDRFSGSGSTDFTLKISRVEAEDVGVYYCMQGTHWP
TLSYRASGVPDRFSGSGSTDFTLKISRVEAEDVGVYYCMQRIEFP
TLSYRASGVPDRFSGSGSTDFTLKISRVEAEDVGVYYCMQRIEFP
GASTRATSIPARFSGSGSGTDFTLTISSLQPEDFAVYYCQQDHNLP
GASTRATGIPARFSGSGSGTDFTLTISSLQPEDFAVYYCQQDYNLP
DASNRATGIPARFSGSGSGTDFTLTISSLEPEDFAVYYCQQRSNWP
DASNRATGIPARFSGSGPGTDFTLTISSLEPEDFAVYYCQQRSNWH
GASTRATGIPARFSGSGSGTEFTLTISSLQSEDFAVYYCQQYNNWP
GASTRATGIPARFSGSGSGTEFTLTISSLQSEDFAVYYCQQYNNWP
GASSRATGIPDRFSGSGSGTDFTLTISRLEPEDFAVYYCQQYGSSP
DASSRATGIPDRFSGSGSGTDFTLTISRLEPEDFAVYYCQQYGSSP

WASTRESGVPDRFSGSGSGTDFTLTISSLQAEDVAVYYCQQYYSTP

EATTLVPGIPPRFSGSYGTDFTLTINNIESEDAAYYFCLQHDNFP

YASQSFSGVPSRFSGSGSGTDFTLTINSLEAEDAATYYCHQSSSLP
YASQSFSGVPSRFSGSGSGTDFTLTINSLEAEDAATYYCHQSSSLP
YASQSISGVPSRFSGSGSGTDFTFTISSLEAEDAATYYCQQGNKHP
```

*FIG. 1b-4*

```
                              9   10
                  Kabat       678901234567

SEQ ID NO.:99   IGKJ1         WTFGQGTKVEIK
SEQ ID NO.:100  IGKJ2         YTFGQGTKLEIK
SEQ ID NO.:101  IGKJ3         FTFGPGTKVDIK
SEQ ID NO.:102  IGKJ4         LTFGGGTKVEIK
SEQ ID NO.:103  IGKJ5         ITFGQGTRLEIK 10            11
                  Kabat       1234567890123

SEQ ID NO.:104  IGHJ1         AEYFQHWGQGTLVTVSS
SEQ ID NO.:105  IGHJ2         YWYFDLWGRGTLVTVSS
SEQ ID NO.:106  IGHJ3             AFDVWGQGTMVTVSS
SEQ ID NO.:107  IGHJ4             YFDYWGQGTLVTVSS
SEQ ID NO.:108  IGHJ5            NWFDSWGQGTLVTVSS
SEQ ID NO.:109  IGHJ6         YYYYYGMDVWGQGTTVTVSS
```

```
SEQ ID NO.:110  QVQLQQSGPELVKPGASLKLSCTASGFNIK
SEQ ID NO.:111  QVQLVQSGAEVKKPGASVKVSCKASGYTFT
```
}  FIG. 2a

IDstring(i=15) = 6

```
SEQ ID NO.:110  VH_m4D5   QVQLQQSGPELVKPGASLKLSCTASGFNIK    IDepitope(i=15) = 6
SEQ ID NO.:111  VH_1-2    QVQLVQSGAEVKKPGASVKVSCKASGYTFT    IDepitope(i=15) = 4
SEQ ID NO.:112  VH_2-5    QITLKESGPTLVKPTQTLTLTCTFSGFSLS    IDepitope(i=15) = 6
SEQ ID NO.:113  VH_3-7    EVQLVESGGGLVQPGGSLRLSCAASGFTFS    IDepitope(i=15) = 3
SEQ ID NO.:114  VH_4-4    QVQLQESGPGLVKPPGTLSLTCAVSGGSIS    IDepitope(i=15) = 6
SEQ ID NO.:115  VH_5-51   EVQLVQSGAEVKKPGESLKISCKGSGYSFT    IDepitope(i=15) = 6
SEQ ID NO.:116  VH_6-1    QVQLQQSGPGLVKPSQTLSLTCAISGDSVS    IDepitope(i=15) = 3
SEQ ID NO.:117  VH_7-4-1  QVQLVQSGSELKKPGASVKVSCKASGYTFT    IDepitope(i=15) = 6
```
} FIG. 2b IDmax(i=15) = 6

```
SEQ ID NO.:110  VH_m4D5   QVQLQQSGPELVKPGASLKLSCTASGFNIK
SEQ ID NO.:111  VH_1-2    QVQLVQSGAEVKKPGASVKVSCKASGYTFT
SEQ ID NO.:112  VH_2-5    QITLKESGPTLVKPTQTLTLTCTFSGFSLS
SEQ ID NO.:113  VH_3-7    EVQLVESGGGLVQPGGSLRLSCAASGFTFS
SEQ ID NO.:114  VH_4-4    QVQLQESGPGLVKPPGTLSLTCAVSGGSIS
SEQ ID NO.:115  VH_5-51   EVQLVQSGAEVKKPGESLKISCKGSGYSFT
SEQ ID NO.:116  VH_6-1    QVQLQQSGPGLVKPSQTLSLTCAISGDSVS
SEQ ID NO.:117  VH_7-4-1  QVQLVQSGSELKKPGASVKVSCKASGYTFT
```

ID(i=1)max = 9    ID(i=12)max = 6
ID(i=2)max = 8    ID(i=13)max = 7
ID(i=3)max = 8    ID(i=14)max = 7
ID(i=4)max = 8    ID(i=15)max = 6
ID(i=5)max = 8    ID(i=16)max = 6
ID(i=6)max = 8    ID(i=17)max = 7
ID(i=7)max = 7    ID(i=18)max = 7
ID(i=8)max = 7    ID(i=19)max = 7
ID(i=9)max = 7    ID(i=20)max = 7
ID(i=10)max = 7   ID(i=21)max = 6
ID(i=11)max = 7   ID(i=22)max = 5

HSC(s) = 78.3

} FIG. 2c

SEQ ID NO.: 118
DIVLTQSPASLAVSLGQRATISCKASQSVDFDGDSYMNWYQQKPGQPPKVLIYAAS
NLESGIPARFSGSGSGTDFTLNIHPVEEEDAATYYCQQSNEDPWTFGGGTKLEIK
*FIG. 3a*
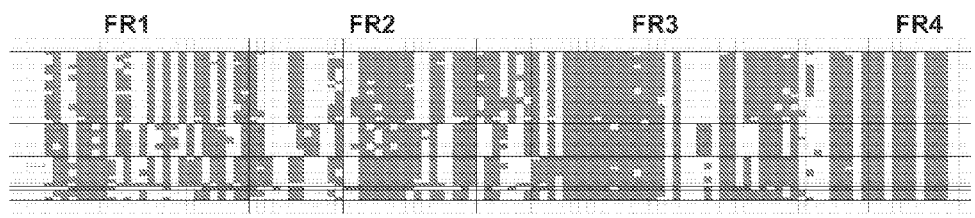
*FIG. 3b*
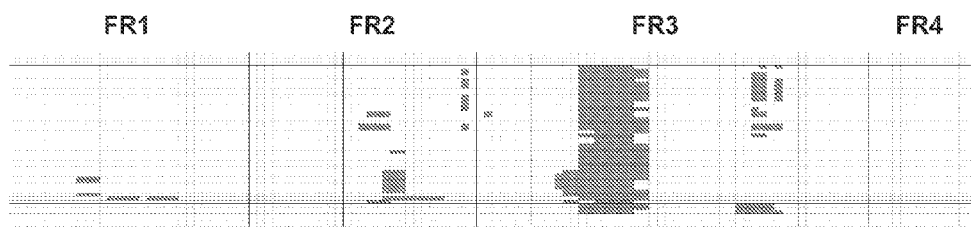
*FIG. 3c*
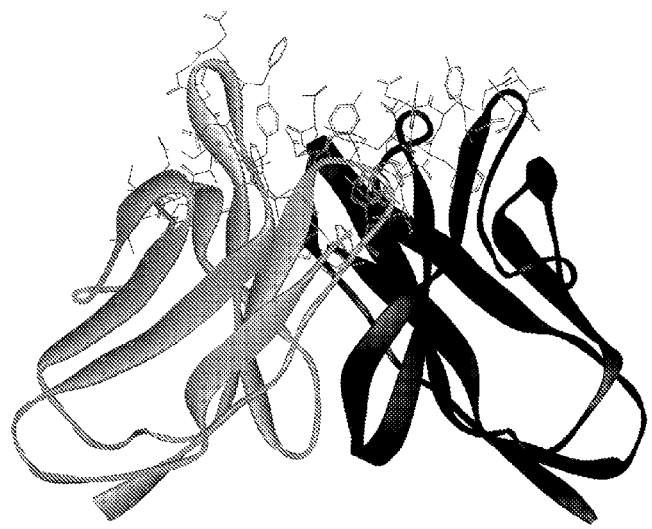
*FIG. 3d*

SEQ ID NO.: 119
QIQLQQSGPEVVKPGASVKISCKASGYTFTDYYITWVKQKPGQGLEWIGWIYPGSG
NTKYNEKFKGKATLTVDTSSSTAFMQLSSLTSEDTAVYFCANYGNYWFAYWGQGT
QVTVSA
FIG. 4a
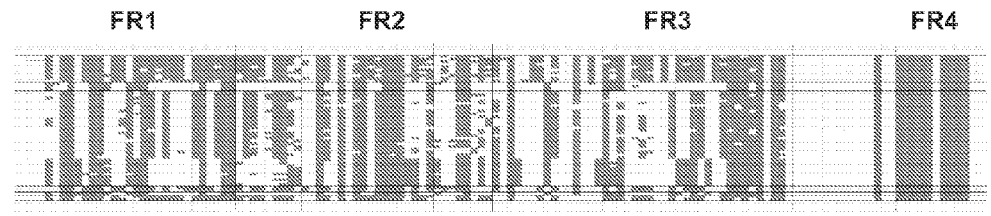
FIG. 4b
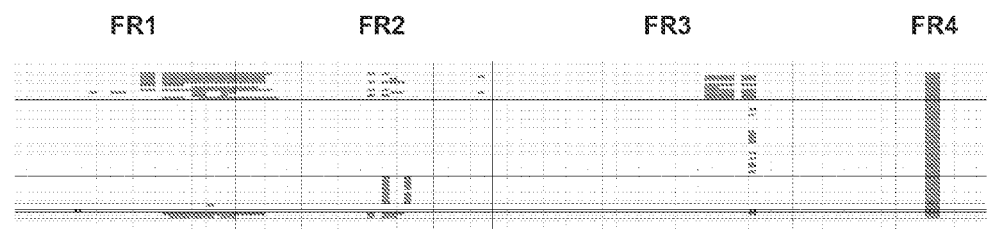
FIG. 4c
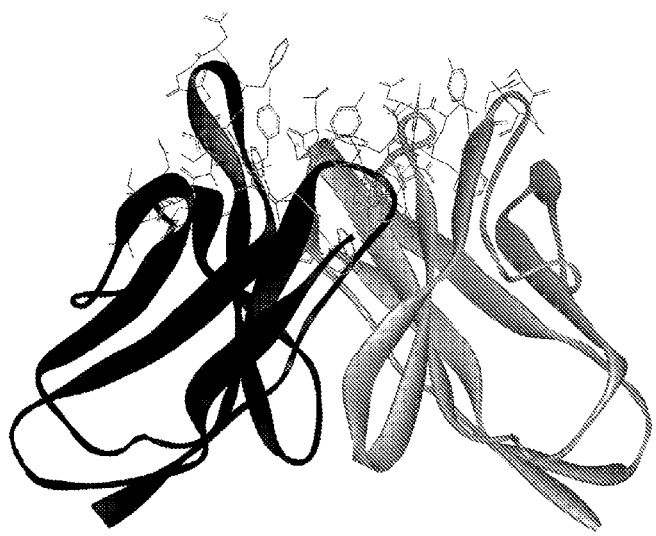
FIG. 4d

SEQ ID NO.: 120
DIVMTQSPDSLAVSLGERATINCKSSQSVDFDGDSYLAWYQQKPGQPPKLLIYAAS
NLESGVPDRFSGSGSGTDFTLTISSLQAEDVAVYYCQQSNEDPWTFGGGTKLEIK
*FIG. 5a*
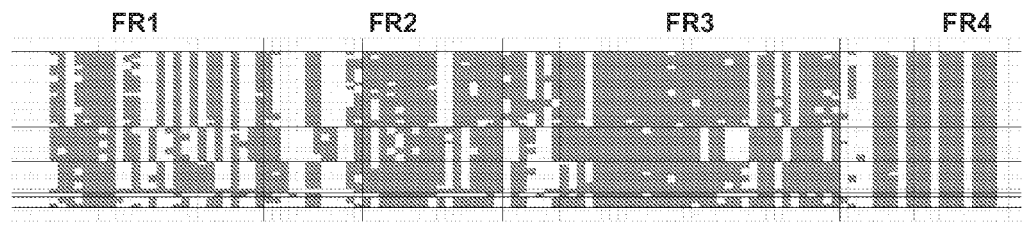
*FIG. 5b*
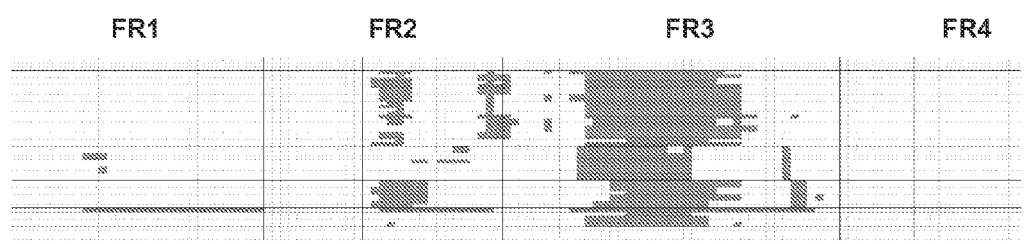
*FIG. 5c*
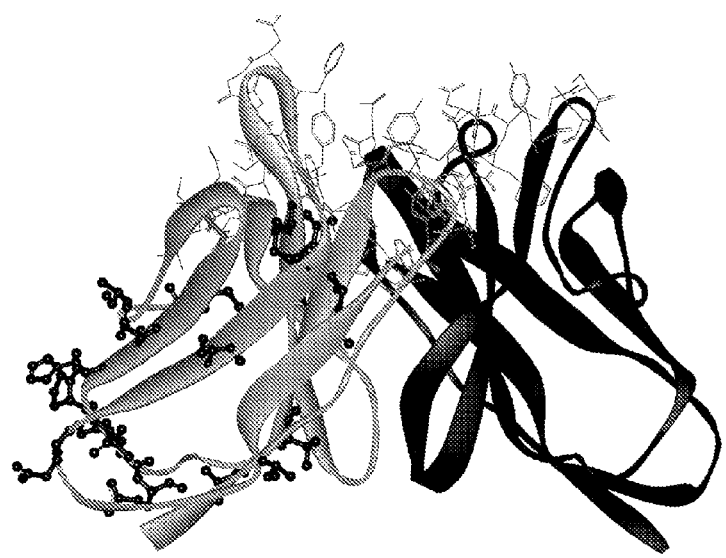
*FIG. 5d*

SEQ ID NO.: 121
QVQLVQSGAEVKKPGASVKVSCKASGYTFTDYYMHWVRQAPGQRLEWMGWIYP
GSGNTKYSQKFQGRVTITRDTSASTAYMELSSLRSEDTAVYYCARYGNYWFAYWG
QGTLVTVSS
*FIG. 6a*
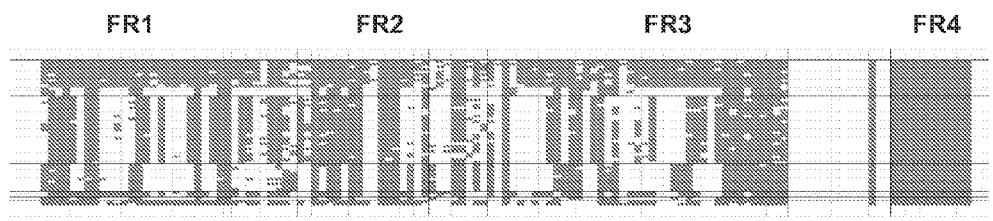
*FIG. 6b*
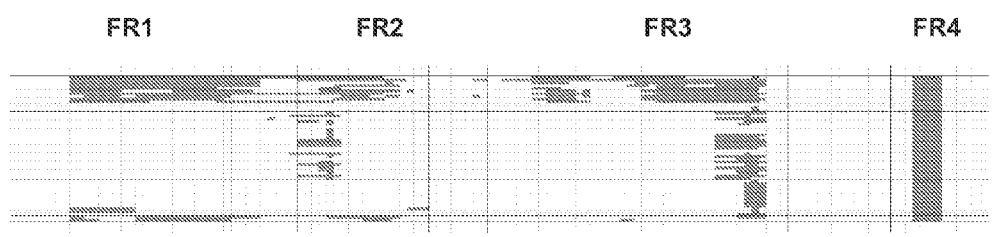
*FIG. 6c*
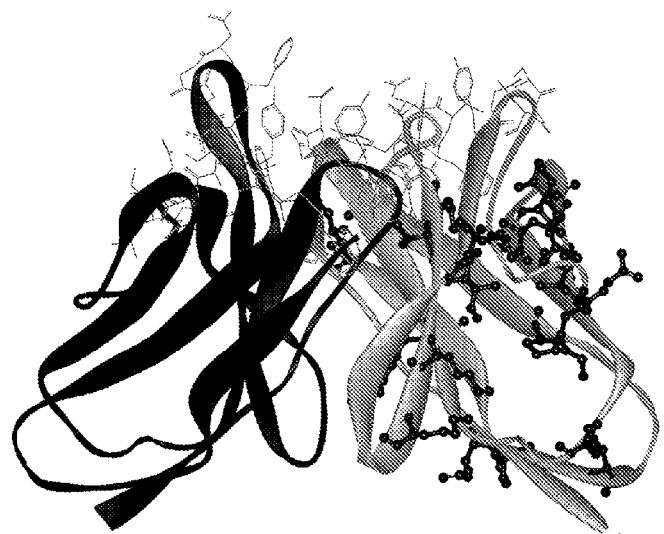
*FIG. 6d*

| FIG. 7a-1 | FIG. 7a-2 | FIG. 7a-3 | FIG. 7a-4 | FIG. 7a-5 | FIG. 7a-6 | FIG. 7a-7 |
|---|---|---|---|---|---|---|

*FIG. 7a*

| FIG. 7b-1 | FIG. 7b-2 | FIG. 7b-3 | FIG. 7b-4 | FIG. 7b-5 | FIG. 7b-6 | FIG. 7b-7 | FIG. 7b-8 |
|---|---|---|---|---|---|---|---|
| FIG. 7b-9 | FIG. 7b-10 | FIG. 7b-11 | FIG. 7b-12 | FIG. 7b-13 | FIG. 7b-14 | FIG. 7b-15 | FIG. 7b-16 |

*FIG. 7b*

AC10 VL HEC Calculation 1

| (WT) SEQ ID NO.:118 | Iter | Structural Consensus | Structural Precedence | HSC | HSS | N₉max | FRH | Muts | Kabat WT Cluster |
|---|---|---|---|---|---|---|---|---|---|
| SEQ ID NO.:122 | 1 | 0.55 | 0.60 | 0.86 | 0.42 | 44 | 0.45 | 10 | 6.79 |
| SEQ ID NO.:123 | 3 | 0.55 | 0.61 | 0.86 | 0.42 | 44 | 0.45 | 10 | 6.55 |
| SEQ ID NO.:124 | 4 | 0.56 | 0.57 | 0.86 | 0.43 | 45 | 0.38 | 13 | 6.21 |
| SEQ ID NO.:125 | 5 | 0.57 | 0.61 | 0.86 | 0.43 | 45 | 0.58 | 12 | 5.55 |
| SEQ ID NO.:126 | 6 | 0.55 | 0.56 | 0.86 | 0.43 | 45 | 0.33 | 13 | 6.45 |
| SEQ ID NO.:127 | 16 | 0.56 | 0.60 | 0.86 | 0.43 | 45 | 0.51 | 12 | 5.79 |
| SEQ ID NO.:128 | 17 | 0.55 | 0.59 | 0.86 | 0.43 | 45 | 0.49 | 13 | 6.59 |
| SEQ ID NO.:129 | 33 | 0.56 | 0.60 | 0.86 | 0.43 | 45 | 0.49 | 13 | 6.34 |
| SEQ ID NO.:130 | 9 | 0.55 | 0.58 | 0.86 | 0.43 | 45 | 0.49 | 12 | 6.48 |
| SEQ ID NO.:131 | 13 | 0.54 | 0.57 | 0.86 | 0.43 | 45 | 0.49 | 12 | 6.72 |
| SEQ ID NO.:132 | 14 | 0.55 | 0.61 | 0.86 | 0.42 | 44 | 0.73 | 12 | 6.31 |
| SEQ ID NO.:133 | 35 | 0.55 | 0.58 | 0.86 | 0.42 | 44 | 0.64 | 12 | 7.14 |
| SEQ ID NO.:134 | 11 | 0.57 | 0.62 | 0.87 | 0.48 | 51 | 0.43 | 15 | 6.24 |
| SEQ ID NO.:135 | 25 | 0.57 | 0.63 | 0.87 | 0.48 | 51 | 0.55 | 16 | 6.55 |
| SEQ ID NO.:136 | 31 | 0.56 | 0.62 | 0.87 | 0.48 | 51 | 0.31 | 15 | 6.48 |
| SEQ ID NO.:137 | 19 | 0.57 | 0.64 | 0.87 | 0.48 | 51 | 0.51 | 16 | 6.31 |
| SEQ ID NO.:138 | 36 | 0.58 | 0.66 | 0.87 | 0.48 | 51 | 0.61 | 15 | 6.14 |
| SEQ ID NO.:139 | 12 | 0.56 | 0.63 | 0.87 | 0.48 | 51 | 0.45 | 14 | 6.52 |
| SEQ ID NO.:140 | 27 | 0.56 | 0.63 | 0.87 | 0.48 | 51 | 0.63 | 15 | 6.83 |
| SEQ ID NO.:141 | 39 | 0.57 | 0.63 | 0.87 | 0.48 | 51 | 0.53 | 18 | 7.66 |
| SEQ ID NO.:142 | 15 | 0.56 | 0.64 | 0.86 | 0.47 | 50 | 0.62 | 13 | 6.90 |
| SEQ ID NO.:143 | 24 | 0.56 | 0.61 | 0.86 | 0.47 | 50 | 0.44 | 15 | 7.86 |
| SEQ ID NO.:144 | 28 | 0.56 | 0.62 | 0.86 | 0.47 | 50 | 0.54 | 14 | 7.07 |
| SEQ ID NO.:145 | 29 | 0.56 | 0.64 | 0.86 | 0.47 | 50 | 0.44 | 12 | 6.59 |
| SEQ ID NO.:146 | 32 | 0.55 | 0.63 | 0.86 | 0.47 | 50 | 0.40 | 12 | 6.83 |
| SEQ ID NO.:147 | 38 | 0.56 | 0.63 | 0.86 | 0.47 | 50 | 0.44 | 14 | 7.69 |
| SEQ ID NO.:148 | 7 | 0.54 | 0.54 | 0.85 | 0.40 | 42 | 0.48 | 12 | 10.14 |
| SEQ ID NO.:149 | 8 | 0.55 | 0.55 | 0.85 | 0.40 | 42 | 0.48 | 12 | 9.90 |
| SEQ ID NO.:150 | 23 | 0.54 | 0.55 | 0.86 | 0.45 | 48 | 0.52 | 16 | 10.41 |
| SEQ ID NO.:151 | 2 | 0.55 | 0.52 | 0.86 | 0.42 | 43 | 0.51 | 14 | 4.75 |
| SEQ ID NO.:152 | 10 | 0.56 | 0.57 | 0.86 | 0.41 | 42 | 0.62 | 16 | 4.75 |
| SEQ ID NO.:153 | 18 | 0.56 | 0.51 | 0.86 | 0.42 | 43 | 0.37 | 15 | 4.00 |
| SEQ ID NO.:154 | 22 | 0.56 | 0.54 | 0.86 | 0.42 | 43 | 0.40 | 15 | 4.25 |
| SEQ ID NO.:155 | 20 | 0.56 | 0.57 | 0.86 | 0.42 | 43 | 0.53 | 16 | 3.75 |
| SEQ ID NO.:156 | 21 | 0.56 | 0.53 | 0.86 | 0.42 | 43 | 0.35 | 17 | 4.25 |
| SEQ ID NO.:157 | 30 | 0.55 | 0.56 | 0.86 | 0.41 | 42 | 0.48 | 14 | 5.38 |
| SEQ ID NO.:158 | 34 | 0.55 | 0.56 | 0.86 | 0.41 | 42 | 0.48 | 14 | 5.38 |
| SEQ ID NO.:159 | 26 | 0.62 | 0.67 | 0.86 | 0.46 | 48 | 0.69 | 17 | 0.50 |
| SEQ ID NO.:160 | 37 | 0.63 | 0.68 | 0.86 | 0.46 | 48 | 0.81 | 16 | 0.50 |

FIG. 7a-1

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|
| D | I | V | L | T | Q | S | P | A | S | L | A | V | S | L | G | Q | R | A | T |
| D | I | V | L | T | Q | S | P | D | S | L | A | V | S | L | G | E | R | A | T |
| D | I | V | L | T | Q | S | P | D | S | L | A | V | S | L | G | E | R | A | T |
| D | I | V | L | T | Q | S | P | D | S | L | A | V | S | L | G | E | R | A | T |
| D | I | V | L | T | Q | S | P | D | S | L | A | V | S | L | G | E | R | A | T |
| D | I | V | L | T | Q | S | P | D | S | L | A | V | S | L | G | E | R | A | T |
| D | I | V | L | T | Q | S | P | D | S | L | A | V | S | L | G | E | R | A | T |
| D | I | V | L | T | Q | S | P | D | S | L | A | V | S | L | G | E | R | A | T |
| D | I | V | L | T | Q | S | P | D | S | L | A | V | S | L | G | E | R | A | T |
| D | I | V | L | T | Q | S | P | D | S | L | A | V | S | L | G | E | R | A | T |
| D | I | V | L | T | Q | S | P | D | S | L | A | V | S | L | G | E | R | A | T |
| D | I | V | L | T | Q | S | P | A | T | L | S | V | S | P | G | E | R | A | T |
| D | I | V | L | T | Q | S | P | A | T | L | S | L | S | P | G | E | R | A | T |
| D | I | V | L | T | Q | S | P | A | T | L | S | V | S | P | G | E | R | A | T |
| D | I | V | L | T | Q | S | P | G | T | L | S | L | S | P | G | E | R | A | T |
| D | I | V | L | T | Q | S | P | A | T | L | S | L | S | P | G | E | R | A | T |
| D | I | V | L | T | Q | S | P | A | T | L | S | V | S | P | G | E | R | A | T |
| D | I | V | L | T | Q | S | P | A | T | L | S | L | S | P | G | E | R | A | T |
| D | I | V | L | T | Q | S | P | G | T | L | S | L | S | P | G | E | R | V | T |
| D | I | V | L | T | Q | S | P | A | T | L | S | L | S | P | G | E | R | A | T |
| D | I | V | L | T | Q | S | P | G | T | L | S | L | S | P | G | E | R | V | T |
| D | I | V | L | T | Q | S | P | G | T | L | S | L | S | P | G | E | R | A | T |
| D | I | V | L | T | Q | S | P | A | T | L | S | V | S | P | G | E | R | A | T |
| D | I | V | L | T | Q | S | P | A | T | L | S | V | S | P | G | E | R | A | T |
| D | I | V | L | T | Q | S | P | A | T | L | S | L | S | P | G | E | R | V | T |
| D | I | V | L | T | Q | S | P | D | S | L | A | V | S | L | G | E | R | A | T |
| D | I | V | L | T | Q | S | P | D | S | L | A | V | S | L | G | E | R | A | T |
| D | I | V | L | T | Q | S | P | G | T | L | S | L | S | P | G | E | R | A | T |
| D | I | V | L | T | Q | S | P | L | S | L | P | V | T | L | G | Q | P | A | S |
| D | I | V | L | T | Q | T | P | L | S | L | S | V | T | P | G | Q | P | A | S |
| D | I | V | L | T | Q | S | P | L | S | L | P | V | T | L | G | Q | P | A | S |
| D | I | V | L | T | Q | S | P | L | S | L | P | V | T | L | G | Q | P | A | S |
| D | I | V | L | T | Q | S | P | L | S | L | P | V | T | P | G | E | P | A | S |
| D | I | V | L | T | Q | T | P | L | S | L | S | V | T | P | G | Q | P | A | S |
| D | I | V | L | T | Q | S | P | L | S | L | P | V | T | P | G | E | P | A | S |
| D | I | V | L | T | Q | T | P | L | S | L | S | V | T | P | G | Q | P | A | S |
| D | I | V | L | T | Q | S | P | S | F | L | S | A | S | V | G | D | R | V | T |
| D | I | V | L | T | Q | S | P | S | S | L | S | A | S | V | G | D | R | V | T |

*FIG. 7a-2*

| 21 | 22 | 23 | 24 | 25 | 26 | 27 | 27a | 27b | 27c | 27d | 28 | 29 | 30 | 31 | 32 | 33 | 34 |
|----|----|----|----|----|----|----|-----|-----|-----|-----|----|----|----|----|----|----|----|
| I | S | C | K | A | S | Q | S | V | D | F | – | – | D | G | D | S | Y | M | N |
| L | S | C | G | A | S | Q | S | V | D | F | – | – | D | G | D | S | Y | M | N |
| L | S | C | R | A | S | Q | S | V | D | F | – | – | D | G | D | S | Y | M | N |
| L | S | C | R | A | S | Q | S | V | D | F | – | – | D | G | D | S | Y | M | N |
| L | S | C | R | A | S | Q | S | V | D | F | – | – | D | G | D | S | Y | M | N |
| L | S | C | G | A | S | Q | S | V | D | F | – | – | D | G | D | S | Y | M | N |
| L | S | C | G | A | S | Q | S | V | D | F | – | – | D | G | D | S | Y | M | N |
| L | S | C | G | A | S | Q | S | V | D | F | – | – | D | G | D | S | Y | M | N |
| L | S | C | R | A | S | Q | S | V | D | F | – | – | D | G | D | S | Y | M | N |
| L | S | C | R | A | S | Q | S | V | D | F | – | – | D | G | D | S | Y | M | N |
| L | S | C | G | A | S | Q | S | V | D | F | – | – | D | G | D | S | Y | M | N |
| L | S | C | R | A | S | Q | S | V | D | F | – | – | D | G | D | S | Y | M | N |
| L | S | C | G | A | S | Q | S | V | D | F | – | – | D | G | D | S | Y | M | N |
| L | S | C | R | A | S | Q | S | V | D | F | – | – | D | G | D | S | Y | M | N |
| L | S | C | R | A | S | Q | S | V | D | F | – | – | D | G | D | S | Y | M | N |
| L | S | C | G | A | S | Q | S | V | D | F | – | – | D | G | D | S | Y | M | N |
| L | S | C | G | A | S | Q | S | V | D | F | – | – | D | G | D | S | Y | M | N |
| L | S | C | R | A | S | Q | S | V | D | F | – | – | D | G | D | S | Y | M | N |
| L | S | C | R | A | S | Q | S | V | D | F | – | – | D | G | D | S | Y | M | N |
| L | S | C | R | A | S | Q | S | V | D | F | – | – | D | G | D | S | Y | M | N |
| L | S | C | R | A | S | Q | S | V | D | F | – | – | D | G | D | S | Y | M | N |
| L | S | C | R | A | S | Q | S | V | D | F | – | – | D | G | D | S | Y | M | N |
| L | S | C | R | A | S | Q | S | V | D | F | – | – | D | G | D | S | Y | M | N |
| L | S | C | G | A | S | Q | S | V | D | F | – | – | D | G | D | S | Y | M | N |
| L | S | C | R | A | S | Q | S | V | D | F | – | – | D | G | D | S | Y | M | N |
| L | S | C | G | A | S | Q | S | V | D | F | – | – | D | G | D | S | Y | M | N |
| L | S | C | R | A | S | Q | S | V | D | F | – | – | D | G | D | S | Y | M | N |
| I | S | C | R | A | S | Q | S | V | D | F | – | – | D | G | D | S | Y | M | N |
| I | S | C | R | A | S | Q | S | V | D | F | – | – | D | G | D | S | Y | M | N |
| I | S | C | R | A | S | Q | S | V | D | F | – | – | D | G | D | S | Y | M | N |
| I | S | C | R | A | S | Q | S | V | D | F | – | – | D | G | D | S | Y | M | N |
| I | S | C | R | A | S | Q | S | V | D | F | – | – | D | G | D | S | Y | M | N |
| I | S | C | R | A | S | Q | S | V | D | F | – | – | D | G | D | S | Y | M | N |
| I | S | C | R | A | S | Q | S | V | D | F | – | – | D | G | D | S | Y | M | N |
| I | T | C | R | A | S | Q | S | V | D | F | – | – | D | G | D | S | Y | M | N |
| I | T | C | R | A | S | Q | S | V | D | F | – | – | D | G | D | S | Y | M | N |

*FIG. 7a-3*

| 35 | 36 | 37 | 38 | 39 | 40 | 41 | 42 | 43 | 44 | 45 | 46 | 47 | 48 | 49 | 50 | 51 | 52 | 53 | 54 |
|---|---|---|---|---|---|---|---|---|---|---|---|---|---|---|---|---|---|---|---|
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |
| W | Y | Q | Q | K | P | G | Q | P | P | K | V | L | I | Y | A | A | S | N | L |

*FIG. 7a-4*

| | 55 | 56 | 57 | 58 | 59 | 60 | 61 | 62 | 63 | 64 | 65 | 66 | 67 | 68 | 69 | 70 | 71 | 72 | 73 | 74 |
|---|---|---|---|---|---|---|---|---|---|---|---|---|---|---|---|---|---|---|---|---|
| | E | S | G | I | P | A | R | F | S | G | S | G | S | G | T | D | F | T | L | N |
| | E | S | G | I | P | A | R | F | S | G | S | G | S | G | T | D | F | T | L | T |
| | E | S | G | I | P | A | R | F | S | G | S | G | S | G | T | D | F | T | L | T |
| | E | S | G | I | P | A | R | F | S | G | S | G | S | G | T | D | F | T | F | T |
| | E | S | G | I | P | A | R | F | S | G | S | G | S | G | T | D | F | T | L | T |
| | E | S | G | I | P | A | R | F | S | G | S | G | S | G | T | D | F | T | F | T |
| | E | S | G | I | P | A | R | F | S | G | S | G | S | G | T | D | F | T | L | T |
| | E | S | G | I | P | A | R | F | S | G | S | G | S | G | T | D | F | T | L | T |
| | E | S | G | I | P | A | R | F | S | G | S | G | S | G | T | D | F | T | L | T |
| | E | S | G | I | P | A | R | F | S | G | S | G | S | G | T | D | F | T | L | T |
| | E | S | G | I | P | A | R | F | S | G | S | G | S | G | T | D | F | T | L | T |
| | E | S | G | I | P | A | R | F | S | G | S | G | S | G | T | D | F | T | L | T |
| | E | S | G | I | P | A | R | F | S | G | S | G | S | G | T | D | F | T | L | T |
| | E | S | G | I | P | A | R | F | S | G | S | G | S | G | T | D | F | T | F | T |
| | E | S | G | I | P | A | R | F | S | G | S | G | S | G | T | D | F | T | F | T |
| | E | S | G | I | P | A | R | F | S | G | S | G | S | G | T | D | F | T | F | T |
| | E | S | G | I | P | A | R | F | S | G | S | G | S | G | T | D | F | T | L | T |
| | E | S | G | I | P | A | R | F | S | G | S | G | S | G | T | D | F | T | L | T |
| | E | S | G | I | P | A | R | F | S | G | S | G | S | G | T | D | F | T | L | T |
| | E | S | G | I | P | A | R | F | S | G | S | G | S | G | T | D | F | T | L | T |
| | E | S | G | I | P | A | R | F | S | G | S | G | S | G | T | D | F | T | L | T |
| | E | S | G | I | P | A | R | F | S | G | S | G | S | G | T | D | F | T | L | T |
| | E | S | G | I | P | A | R | F | S | G | S | G | S | G | T | D | F | T | L | T |
| | E | S | G | I | P | A | R | F | S | G | S | G | S | G | T | D | F | T | L | T |
| | E | S | G | I | P | A | R | F | S | G | S | G | S | G | T | D | F | T | L | T |
| | E | S | G | I | P | A | R | F | S | G | S | G | S | G | T | D | F | T | L | K |
| | E | S | G | I | P | A | R | F | S | G | S | G | S | G | T | D | F | T | L | K |
| | E | S | G | I | P | A | R | F | S | G | S | G | S | G | T | D | F | T | L | K |
| | E | S | G | I | P | A | R | F | S | G | S | G | S | G | T | D | F | T | L | T |
| | E | S | G | I | P | A | R | F | S | G | S | G | S | G | T | D | F | T | L | T |
| | E | S | G | I | P | A | R | F | S | G | S | G | S | G | T | D | F | T | F | T |
| | E | S | G | I | P | A | R | F | S | G | S | G | S | G | T | D | F | T | L | T |
| | E | S | G | I | P | A | R | F | S | G | S | G | S | G | T | D | F | T | L | T |
| | E | S | G | I | P | A | R | F | S | G | S | G | S | G | T | D | F | T | F | T |
| | E | S | G | I | P | A | R | F | S | G | S | G | S | G | T | D | F | T | L | T |
| | E | S | G | I | P | A | R | F | S | G | S | G | S | G | T | D | F | T | L | T |
| | E | S | G | I | P | A | R | F | S | G | S | G | S | G | T | D | F | T | L | T |
| | E | S | G | I | P | A | R | F | S | G | S | G | S | G | T | D | F | T | L | T |

FIG. 7a-5

| 75 | 76 | 77 | 78 | 79 | 80 | 81 | 82 | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|
| I | H | P | V | E | E | D | | A | A | T | Y | Y | C | Q | Q | S | N | E | D |
| I | N | S | L | E | A | E | D | A | A | T | Y | Y | C | Q | Q | S | N | E | D |
| I | N | S | L | E | A | E | D | A | A | T | Y | Y | C | Q | Q | S | N | E | D |
| I | S | S | L | Q | P | E | D | F | A | T | Y | Y | C | Q | Q | S | N | E | D |
| I | S | S | L | Q | P | E | D | F | A | T | Y | Y | C | Q | Q | S | N | E | D |
| I | S | S | L | Q | P | E | D | F | A | T | Y | Y | C | Q | Q | S | N | E | D |
| I | S | S | L | Q | P | E | D | F | A | T | Y | Y | C | Q | Q | S | N | E | D |
| I | S | S | L | Q | P | D | D | F | A | T | Y | Y | C | Q | Q | S | N | E | D |
| I | S | S | L | Q | P | D | D | F | A | T | Y | Y | C | Q | Q | S | N | E | D |
| I | S | C | L | Q | S | E | D | F | A | T | Y | Y | C | Q | Q | S | N | E | D |
| I | S | C | L | Q | S | E | D | F | A | T | Y | Y | C | Q | Q | S | N | E | D |
| I | S | S | L | E | P | E | D | F | A | V | Y | Y | C | Q | Q | S | N | E | D |
| I | S | R | L | E | P | E | D | F | A | V | Y | Y | C | Q | Q | S | N | E | D |
| I | S | S | L | Q | P | E | D | F | A | T | Y | Y | C | Q | Q | S | N | E | D |
| I | S | S | L | Q | P | E | D | F | A | T | Y | Y | C | Q | Q | S | N | E | D |
| I | S | S | L | Q | P | E | D | F | A | T | Y | Y | C | Q | Q | S | N | E | D |
| I | S | S | L | Q | P | E | D | F | A | T | Y | Y | C | Q | Q | S | N | E | D |
| I | S | C | L | Q | S | E | D | F | A | T | Y | Y | C | Q | Q | S | N | E | D |
| I | S | C | L | Q | S | E | D | F | A | T | Y | Y | C | Q | Q | S | N | E | D |
| I | S | S | L | Q | P | D | D | F | A | T | Y | Y | C | Q | Q | S | N | E | D |
| I | N | S | L | E | A | E | D | A | A | T | Y | Y | C | Q | Q | S | N | E | D |
| I | N | S | L | E | A | E | D | A | A | T | Y | Y | C | Q | Q | S | N | E | D |
| I | N | S | L | E | A | E | D | A | A | T | Y | Y | C | Q | Q | S | N | E | D |
| I | N | S | L | E | A | E | D | A | A | T | Y | Y | C | Q | Q | S | N | E | D |
| I | N | S | L | E | A | E | D | A | A | T | Y | Y | C | Q | Q | S | N | E | D |
| I | S | R | V | E | A | E | D | V | G | V | Y | Y | C | Q | Q | S | N | E | D |
| I | S | R | V | E | A | E | D | V | G | V | Y | Y | C | Q | Q | S | N | E | D |
| I | S | R | V | E | A | E | D | V | G | V | Y | Y | C | Q | Q | S | N | E | D |
| I | S | C | L | Q | S | E | D | F | A | T | Y | Y | C | Q | Q | S | N | E | D |
| I | S | S | L | E | P | E | D | F | A | V | Y | Y | C | Q | Q | S | N | E | D |
| I | S | S | L | Q | P | E | D | F | A | T | Y | Y | C | Q | Q | S | N | E | D |
| I | S | S | L | Q | P | D | D | F | A | T | Y | Y | C | Q | Q | S | N | E | D |
| I | S | S | L | Q | P | E | D | F | A | T | Y | Y | C | Q | Q | S | N | E | D |
| I | S | S | L | Q | P | E | D | F | A | T | Y | Y | C | Q | Q | S | N | E | D |
| I | N | S | L | E | A | E | D | A | A | T | Y | Y | C | Q | Q | S | N | E | D |
| I | N | S | L | E | A | E | D | A | A | T | Y | Y | C | Q | Q | S | N | E | D |
| I | S | S | L | Q | P | E | D | F | A | T | Y | Y | C | Q | Q | S | N | E | D |
| I | S | S | L | Q | P | E | D | F | A | T | Y | Y | C | Q | Q | S | N | E | D |

*FIG. 7a-6*

| | | | 95 | 96 | 97 | 98 | 99 | 100 | 101 | 102 | 103 | 104 | 105 | 106 | 107 |
|---|---|---|---|---|---|---|---|---|---|---|---|---|---|---|---|
| – | – | P | W | T | F | G | G | T | K | | L | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |
| – | – | P | W | T | F | G | G | G | T | K | X | E | I | K |

*FIG. 7a-7*

*FIG. 7b-1*  AC10 VH HEC Calculation 1

| | | | | | | | | Kabat |
|---|---|---|---|---|---|---|---|---|
| (WT) SEQ ID NO.:119 | Iter | Structural Consensus | Structural Precedence | HSC | HSS | $N_g$max | FRH | WT Muts Cluster |
| SEQ ID NO.:161 | 1 | 0.47 | 0.62 | 0.81 | 0.42 | 49 | 0.88 | 18 | 5.41 |
| SEQ ID NO.:162 | 17 | 0.48 | 0.62 | 0.81 | 0.42 | 49 | 0.76 | 17 | 5.23 |
| SEQ ID NO.:163 | 42 | 0.47 | 0.62 | 0.81 | 0.42 | 49 | 0.71 | 18 | 5.74 |
| SEQ ID NO.:164 | 2 | 0.46 | 0.60 | 0.81 | 0.42 | 49 | 0.65 | 19 | 6.38 |
| SEQ ID NO.:165 | 6 | 0.47 | 0.62 | 0.81 | 0.42 | 50 | 0.58 | 18 | 5.33 |
| SEQ ID NO.:166 | 14 | 0.47 | 0.62 | 0.81 | 0.42 | 50 | 0.58 | 17 | 5.15 |
| SEQ ID NO.:167 | 7 | 0.47 | 0.64 | 0.81 | 0.43 | 50 | 0.80 | 18 | 4.92 |
| SEQ ID NO.:168 | 15 | 0.48 | 0.64 | 0.81 | 0.43 | 50 | 0.76 | 17 | 4.74 |
| SEQ ID NO.:169 | 33 | 0.48 | 0.64 | 0.81 | 0.43 | 50 | 0.72 | 18 | 5.26 |
| SEQ ID NO.:170 | 10 | 0.48 | 0.64 | 0.81 | 0.42 | 49 | 0.76 | 17 | 5.33 |
| SEQ ID NO.:171 | 12 | 0.47 | 0.61 | 0.81 | 0.42 | 49 | 0.63 | 19 | 6.77 |
| SEQ ID NO.:172 | 36 | 0.47 | 0.61 | 0.81 | 0.42 | 49 | 0.63 | 18 | 5.92 |
| SEQ ID NO.:173 | 16 | 0.47 | 0.62 | 0.81 | 0.43 | 50 | 0.54 | 18 | 5.72 |
| SEQ ID NO.:174 | 20 | 0.45 | 0.61 | 0.81 | 0.42 | 49 | 0.51 | 20 | 7.41 |
| SEQ ID NO.:175 | 23 | 0.46 | 0.59 | 0.81 | 0.42 | 49 | 0.55 | 19 | 6.67 |
| SEQ ID NO.:176 | 37 | 0.46 | 0.60 | 0.81 | 0.42 | 49 | 0.59 | 18 | 5.82 |
| SEQ ID NO.:177 | 26 | 0.46 | 0.62 | 0.81 | 0.42 | 49 | 0.61 | 19 | 6.49 |
| SEQ ID NO.:178 | 28 | 0.46 | 0.61 | 0.81 | 0.42 | 49 | 0.59 | 18 | 6.46 |
| SEQ ID NO.:179 | 41 | 0.46 | 0.61 | 0.81 | 0.42 | 49 | 0.55 | 19 | 7.31 |
| SEQ ID NO.:180 | 30 | 0.46 | 0.62 | 0.81 | 0.42 | 49 | 0.63 | 18 | 5.92 |
| SEQ ID NO.:181 | 40 | 0.47 | 0.62 | 0.81 | 0.42 | 49 | 0.63 | 17 | 5.74 |
| SEQ ID NO.:182 | 32 | 0.46 | 0.62 | 0.81 | 0.42 | 49 | 0.80 | 20 | 7.00 |
| SEQ ID NO.:183 | 50 | 0.47 | 0.63 | 0.81 | 0.43 | 50 | 0.62 | 19 | 5.62 |
| SEQ ID NO.:184 | 51 | 0.48 | 0.63 | 0.81 | 0.43 | 50 | 0.62 | 18 | 5.44 |
| SEQ ID NO.:185 | 35 | 0.46 | 0.63 | 0.81 | 0.43 | 50 | 0.62 | 21 | 7.67 |
| SEQ ID NO.:186 | 39 | 0.46 | 0.61 | 0.81 | 0.42 | 49 | 0.69 | 20 | 7.79 |
| SEQ ID NO.:187 | 44 | 0.45 | 0.62 | 0.81 | 0.43 | 50 | 0.56 | 21 | 7.95 |
| SEQ ID NO.:188 | 49 | 0.46 | 0.62 | 0.81 | 0.42 | 49 | 0.73 | 20 | 6.92 |
| SEQ ID NO.:189 | 53 | 0.45 | 0.62 | 0.81 | 0.42 | 50 | 0.50 | 20 | 7.38 |
| SEQ ID NO.:190 | 4 | 0.48 | 0.61 | 0.81 | 0.46 | 53 | 0.66 | 21 | 7.95 |
| SEQ ID NO.:191 | 13 | 0.47 | 0.59 | 0.81 | 0.46 | 53 | 0.66 | 21 | 8.69 |
| SEQ ID NO.:192 | 22 | 0.47 | 0.59 | 0.81 | 0.46 | 53 | 0.75 | 21 | 8.36 |
| SEQ ID NO.:193 | 25 | 0.48 | 0.61 | 0.81 | 0.46 | 53 | 0.70 | 20 | 7.44 |
| SEQ ID NO.:194 | 38 | 0.48 | 0.61 | 0.81 | 0.46 | 53 | 0.75 | 21 | 7.62 |
| SEQ ID NO.:195 | 45 | 0.47 | 0.58 | 0.81 | 0.45 | 53 | 0.55 | 20 | 8.59 |
| SEQ ID NO.:196 | 48 | 0.47 | 0.59 | 0.81 | 0.46 | 53 | 0.58 | 22 | 9.05 |
| SEQ ID NO.:197 | 52 | 0.48 | 0.61 | 0.81 | 0.46 | 53 | 0.58 | 21 | 8.13 |
| SEQ ID NO.:198 | 43 | 0.46 | 0.59 | 0.81 | 0.46 | 53 | 0.74 | 23 | 10.41 |
| SEQ ID NO.:199 | 11 | 0.48 | 0.58 | 0.81 | 0.38 | 44 | 0.75 | 20 | 9.13 |

FIG. 7b-2

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|----|----|----|----|----|----|----|----|----|----|----|
| Q | I | Q | L | Q | S | G | P | E | V  | V  | K  | P  | G  | A  | S  | V  | K  | I  |    |
| Q | I | Q | L | V | Q | S | G | A | E  | V  | K  | K  | P  | G  | A  | S  | V  | K  | V  |
| Q | I | Q | L | V | Q | S | G | A | E  | V  | K  | K  | P  | G  | A  | S  | V  | K  | V  |
| Q | I | Q | L | V | Q | S | G | A | E  | V  | K  | K  | P  | G  | S  | S  | V  | K  | V  |
| Q | I | Q | L | V | Q | S | G | H | E  | V  | K  | Q  | P  | G  | A  | S  | V  | K  | V  |
| Q | I | Q | L | V | Q | S | G | P | E  | V  | K  | K  | P  | G  | T  | S  | V  | K  |    |
| Q | I | Q | L | V | Q | S | G | P | E  | V  | K  | K  | P  | G  | T  | S  | V  | K  |    |
| Q | I | Q | L | V | Q | S | G | A | E  | V  | K  | K  | P  | G  | A  | S  | V  | K  |    |
| Q | I | Q | L | V | Q | S | G | A | E  | V  | K  | K  | P  | G  | A  | S  | V  | K  | V  |
| Q | I | Q | L | V | Q | S | G | A | E  | V  | K  | K  | P  | G  | S  | S  | V  | K  |    |
| Q | I | Q | L | V | Q | S | G | A | E  | V  | K  | K  | P  | G  | A  | S  | V  | K  |    |
| Q | I | Q | L | V | Q | S | G | S | E  | L  | K  | K  | P  | G  | A  | S  | V  | K  |    |
| Q | I | Q | L | V | Q | S | G | S | E  | L  | K  | K  | P  | G  | A  | S  | V  | K  |    |
| Q | I | Q | L | V | Q | S | G | H | E  | V  | K  | Q  | P  | G  | A  | S  | V  | K  | V  |
| Q | I | Q | L | V | Q | S | G | P | E  | V  | K  | K  | P  | G  | T  | S  | V  | K  | V  |
| Q | I | Q | L | V | Q | S | G | P | E  | V  | K  | K  | P  | G  | T  | S  | V  | K  |    |
| Q | I | Q | L | V | Q | S | G | P | E  | V  | K  | K  | P  | G  | T  | S  | V  | K  |    |
| Q | I | Q | L | V | Q | S | G | H | E  | V  | K  | Q  | P  | G  | A  | S  | V  | K  |    |
| Q | I | Q | L | V | Q | S | G | P | E  | V  | K  | K  | P  | G  | T  | S  | V  | K  | V  |
| Q | I | Q | L | V | Q | S | G | P | E  | V  | K  | K  | P  | G  | T  | S  | V  | K  |    |
| Q | I | Q | L | V | Q | S | G | P | E  | V  | K  | K  | P  | G  | T  | S  | V  | K  |    |
| Q | I | Q | L | V | Q | S | G | P | E  | V  | K  | K  | P  | G  | T  | S  | V  | K  | V  |
| Q | I | Q | L | V | Q | S | G | A | E  | V  | K  | K  | P  | G  | A  | S  | V  | K  |    |
| Q | I | Q | L | V | Q | S | G | S | E  | L  | K  | K  | P  | G  | A  | S  | V  | K  |    |
| Q | I | Q | L | V | Q | S | G | S | E  | L  | K  | K  | P  | G  | A  | S  | V  | K  |    |
| Q | I | Q | L | V | Q | S | G | S | E  | L  | K  | K  | P  | G  | A  | S  | V  | K  | V  |
| Q | I | Q | L | V | Q | S | G | H | E  | V  | K  | Q  | P  | G  | A  | S  | V  | K  | V  |
| Q | I | Q | L | V | Q | S | G | H | E  | V  | K  | Q  | P  | G  | A  | S  | V  | K  | V  |
| Q | I | Q | L | V | Q | S | G | S | E  | L  | K  | K  | P  | G  | A  | S  | V  | K  |    |
| Q | I | Q | L | V | Q | S | G | P | E  | V  | K  | K  | P  | G  | T  | S  | V  | K  | V  |
| Q | I | Q | L | V | Q | S | G | A | E  | V  | K  | K  | P  | G  | S  | S  | V  | K  |    |
| Q | I | Q | L | V | Q | S | G | A | E  | V  | K  | K  | P  | G  | S  | S  | V  | K  |    |
| Q | I | Q | L | V | Q | S | G | A | E  | V  | K  | K  | P  | G  | A  | S  | V  | K  | V  |
| Q | I | Q | L | V | Q | S | G | A | E  | V  | K  | K  | P  | G  | A  | S  | V  | K  | V  |
| Q | I | Q | L | V | Q | S | G | A | E  | V  | K  | K  | P  | G  | A  | S  | V  | K  | V  |
| Q | I | Q | L | V | Q | S | G | P | E  | V  | K  | K  | P  | G  | T  | S  | V  | K  | V  |
| Q | I | Q | L | V | Q | S | G | S | E  | L  | K  | K  | P  | G  | A  | S  | V  | K  |    |
| Q | I | Q | L | V | Q | S | G | S | E  | L  | K  | K  | P  | G  | A  | S  | V  | K  | V  |
| Q | I | Q | L | V | Q | S | G | A | E  | V  | K  | K  | P  | G  | A  | S  | V  | K  | V  |
| Q | I | Q | L | V | E | S | G | G | L  | V  | K  | P  | G  | A  | S  | V  | K  | V  |    |

FIG. 7b-3

| 21 | 22 | 23 | 24 | 25 | 26 | 27 | 28 | 29 | 30 | 31 | 32 | 33 | 34 | 35 | 36 | 37 | 38 |
|----|----|----|----|----|----|----|----|----|----|----|----|----|----|----|----|----|----|
| S | C | K | A | S | G | Y | T | F | T | D | — — | Y | Y | I | T | W | V | K |
| | | | | | | | | | | | | | | | | | |
| S | C | K | A | S | G | Y | T | F | T | D | — — | Y | Y | I | T | W | V | R |
| S | C | K | A | S | G | Y | T | F | T | D | — — | Y | Y | I | T | W | V | R |
| S | C | K | A | S | G | Y | T | F | T | D | — — | Y | Y | I | T | W | V | R |
| S | C | K | A | S | G | Y | T | F | T | D | — — | Y | Y | I | T | W | V | R |
| S | C | K | A | S | G | Y | T | F | T | D | — — | Y | Y | I | T | W | V | |
| S | C | K | A | S | G | Y | T | F | T | D | — — | Y | Y | I | T | W | V | R |
| S | C | K | A | S | G | Y | T | F | T | D | — — | Y | Y | I | T | W | V | R |
| S | C | K | A | S | G | Y | T | F | T | D | — — | Y | Y | I | T | W | V | R |
| S | C | K | A | S | G | Y | T | F | T | D | — — | Y | Y | I | T | W | V | R |
| S | C | K | A | S | G | Y | T | F | T | D | — — | Y | Y | I | T | W | V | R |
| S | C | K | A | S | G | Y | T | F | T | D | — — | Y | Y | I | T | W | V | R |
| S | C | K | A | S | G | Y | T | F | T | D | — — | Y | Y | I | T | W | V | R |
| S | C | K | A | S | G | Y | T | F | T | D | — — | Y | Y | I | T | W | V | R |
| S | C | K | A | S | G | Y | T | F | T | D | — — | Y | Y | I | T | W | V | R |
| S | C | K | A | S | G | Y | T | F | T | D | — — | Y | Y | I | T | W | V | R |
| S | C | K | A | S | G | Y | T | F | T | D | — — | Y | Y | I | T | W | V | R |
| S | C | K | A | S | G | Y | T | F | T | D | — — | Y | Y | I | T | W | V | R |
| S | C | K | A | S | G | Y | T | F | T | D | — — | Y | Y | I | T | W | V | R |
| S | C | K | A | S | G | Y | T | F | T | D | — — | Y | Y | I | T | W | V | R |
| S | C | K | A | S | G | Y | T | F | T | D | — — | Y | Y | I | T | W | V | R |
| S | C | K | A | S | G | Y | T | F | T | D | — — | Y | Y | I | T | W | V | R |
| S | C | K | A | S | G | Y | T | F | T | D | — — | Y | Y | I | T | W | V | R |
| S | C | K | A | S | G | Y | T | F | T | D | — — | Y | Y | I | T | W | V | R |
| S | C | K | A | S | G | Y | T | F | T | D | — — | Y | Y | I | T | W | V | R |
| S | C | K | A | S | G | Y | T | F | T | D | — — | Y | Y | I | T | W | V | R |
| S | C | K | A | S | G | Y | T | F | T | D | — — | Y | Y | I | T | W | V | R |
| S | C | K | A | S | G | Y | T | F | T | D | — — | Y | Y | I | T | W | V | R |
| S | C | K | A | S | G | Y | T | F | T | D | — — | Y | Y | I | T | W | V | R |
| S | C | K | A | S | G | Y | T | F | T | D | — — | Y | Y | I | T | W | V | R |
| S | C | K | A | S | G | Y | T | F | T | D | — — | Y | Y | I | T | W | V | R |

FIG. 7b-4

| 39 | 40 | 41 | 42 | 43 | 44 | 45 | 46 | 47 | 48 | 49 | 50 | 51 | 52 | 52a | 53 | 54 | 55 |
|---|---|---|---|---|---|---|---|---|---|---|---|---|---|---|---|---|---|
| Q | K | P | G | Q | G | L | E | W | I | G | W | I | Y | P | G | S | G |
| Q | A | T | G | Q | G | L | E | W | M | G | W | I | Y | P | G | — | — | S | G |
| Q | A | P | G | Q | G | L | E | W | M | G | W | I | Y | P | G | — | — | S | G |
| Q | A | P | G | Q | G | L | E | W | M | G | W | I | Y | P | G | — | — | S | G |
| Q | A | T | G | Q | G | L | E | W | M | G | W | I | Y | P | G | — | — | S | G |
| Q | A | T | G | Q | G | L | E | W | M | G | W | I | Y | P | G | — | — | S | G |
| Q | A | P | G | Q | G | L | E | W | M | G | W | I | Y | P | G | — | — | S | G |
| Q | A | T | G | Q | G | L | E | W | M | G | W | I | Y | P | G | — | — | S | G |
| Q | A | P | G | Q | G | L | E | W | M | G | W | I | Y | P | G | — | — | S | G |
| Q | A | P | G | Q | G | L | E | W | M | G | W | I | Y | P | G | — | — | S | G |
| Q | A | P | G | Q | G | L | E | W | M | G | W | I | Y | P | G | — | — | S | G |
| Q | A | P | G | Q | G | L | E | W | M | G | W | I | Y | P | G | — | — | S | G |
| Q | A | P | G | Q | G | L | E | W | M | G | W | I | Y | P | G | — | — | S | G |
| Q | A | P | G | Q | G | L | E | W | M | G | W | I | Y | P | G | — | — | S | G |
| Q | A | T | G | Q | G | L | E | W | M | G | W | I | Y | P | G | — | — | S | G |
| Q | A | T | G | Q | G | L | E | W | M | G | W | I | Y | P | G | — | — | S | G |
| Q | A | T | G | Q | G | L | E | W | M | G | W | I | Y | P | G | — | — | S | G |
| Q | A | T | G | Q | G | L | E | W | M | G | W | I | Y | P | G | — | — | S | G |
| Q | A | P | G | Q | G | L | E | W | M | G | W | I | Y | P | G | — | — | S | G |
| Q | A | P | G | Q | G | L | E | W | M | G | W | I | Y | P | G | — | — | S | G |
| Q | A | T | G | Q | G | L | E | W | M | G | W | I | Y | P | G | — | — | S | G |
| Q | A | P | G | Q | G | L | E | W | M | G | W | I | Y | P | G | — | — | S | G |
| Q | A | T | G | Q | G | L | E | W | M | G | W | I | Y | P | G | — | — | S | G |
| Q | A | P | G | Q | G | L | E | W | M | G | W | I | Y | P | G | — | — | S | G |
| Q | A | P | G | Q | G | L | E | W | M | G | W | I | Y | P | G | — | — | S | G |
| Q | A | P | G | Q | G | L | E | W | M | G | W | I | Y | P | G | — | — | S | G |
| Q | A | P | G | Q | G | L | E | W | M | G | W | I | Y | P | G | — | — | S | G |
| Q | A | T | G | Q | G | L | E | W | M | G | W | I | Y | P | G | — | — | S | G |
| Q | A | P | G | Q | G | L | E | W | M | G | W | I | Y | P | G | — | — | S | G |
| Q | A | P | G | Q | G | L | E | W | M | G | W | I | Y | P | G | — | — | S | G |
| Q | A | T | G | Q | G | L | E | W | M | G | W | I | Y | P | G | — | — | S | G |
| Q | A | P | G | Q | G | L | E | W | M | G | W | I | Y | P | G | — | — | S | G |
| Q | A | T | G | Q | G | L | E | W | M | G | W | I | Y | P | G | — | — | S | G |
| Q | A | P | G | Q | G | L | E | W | M | G | W | I | Y | P | G | — | — | S | G |
| Q | A | T | G | Q | G | L | E | W | M | G | W | I | Y | P | G | — | — | S | G |
| Q | A | P | G | Q | G | L | E | W | M | G | W | I | Y | P | G | — | — | S | G |
| Q | A | P | G | Q | G | L | E | W | M | G | W | I | Y | P | G | — | — | S | G |
| Q | A | T | G | Q | G | L | E | W | M | G | W | I | Y | P | G | — | — | S | G |

FIG. 7b-5

| 56 | 57 | 58 | 59 | 60 | 61 | 62 | 63 | 64 | 65 | 66 | 67 | 68 | 69 | 70 | 71 | 72 | 73 | 74 | 75 |
|----|----|----|----|----|----|----|----|----|----|----|----|----|----|----|----|----|----|----|----|
| N | T | K | Y | N | E | K | F | K | G | K | A | T | L | T | V | D | T | S | S |
| N | T | K | Y | N | E | K | F | Q | G | R | V | T | S | T | V | D | T | S | I |
| N | T | K | Y | N | E | K | F | Q | G | R | V | T | S | T | V | D | T | S | I |
| N | T | K | Y | N | E | K | F | Q | G | R | V | T | S | T | V | D | T | S | I |
| N | T | K | Y | N | E | K | F | Q | G | R | V | T | S | T | V | D | T | S | I |
| N | T | K | Y | N | E | K | F | Q | G | R | V | T | I | T | V | D | T | S | A |
| N | T | K | Y | N | E | K | F | Q | G | R | V | T | I | T | V | D | T | S | A |
| N | T | K | Y | N | E | K | F | Q | G | R | V | T | I | T | V | D | T | S | A |
| N | T | K | Y | N | E | K | F | Q | G | R | V | T | I | T | V | D | T | S | A |
| N | T | K | Y | N | E | K | F | Q | G | R | V | T | I | T | V | D | T | S | A |
| N | T | K | Y | N | E | K | F | Q | G | R | V | T | M | T | V | D | T | S | T |
| N | T | K | Y | N | E | K | F | Q | G | R | V | T | S | T | V | D | T | S | I |
| N | T | K | Y | N | E | K | F | Q | G | R | V | T | S | T | V | D | T | S | I |
| N | T | K | Y | N | E | K | F | Q | G | R | V | T | I | T | V | D | T | S | A |
| N | T | K | Y | N | E | K | F | Q | G | R | V | T | M | T | V | D | T | S | T |
| N | T | K | Y | N | E | K | F | Q | G | R | V | T | S | T | V | D | T | S | I |
| N | T | K | Y | N | E | K | F | Q | G | R | V | T | S | T | V | D | T | S | I |
| N | T | K | Y | N | E | K | F | Q | G | R | V | T | M | T | V | D | T | S | T |
| N | T | K | Y | N | E | K | F | Q | G | R | V | T | M | T | V | N | T | S | I |
| N | T | K | Y | N | E | K | F | Q | G | R | V | T | M | T | V | N | T | S | I |
| N | T | K | Y | N | E | K | F | Q | G | R | V | T | M | T | V | D | T | S | T |
| N | T | K | Y | N | E | K | F | Q | G | R | V | T | M | T | V | D | T | S | T |
| N | T | K | Y | N | E | K | F | Q | G | R | V | T | M | T | V | D | T | S | T |
| N | T | K | Y | N | E | K | F | Q | G | R | V | T | I | T | V | D | T | S | A |
| N | T | K | Y | N | E | K | F | Q | G | R | V | T | I | T | V | D | T | S | A |
| N | T | K | Y | N | E | K | F | Q | G | R | V | T | I | T | V | D | T | S | A |
| N | T | K | Y | N | E | K | F | Q | G | R | V | T | M | T | V | D | T | S | T |
| N | T | K | Y | N | E | K | F | Q | G | R | V | T | I | T | V | D | T | S | A |
| N | T | K | Y | N | E | K | F | Q | G | R | V | T | M | T | V | N | T | S | A |
| N | T | K | Y | N | E | K | F | Q | G | R | V | T | I | T | V | D | T | S | A |
| N | T | K | Y | N | E | S | L | K | S | R | V | T | I | S | V | D | T | S | A |
| N | T | K | Y | N | E | S | L | K | S | L | V | T | I | S | V | D | T | S | A |
| N | T | K | Y | N | E | S | L | K | S | L | V | T | I | S | V | D | T | S | A |
| N | T | K | Y | N | E | S | L | K | S | R | V | T | I | S | V | D | T | S | A |
| N | T | K | Y | N | E | S | L | K | S | L | V | T | I | S | V | D | T | S | A |
| N | T | K | Y | N | E | S | L | K | S | L | V | T | I | S | V | D | T | S | A |
| N | T | K | Y | N | E | S | L | K | S | R | V | T | I | S | V | D | T | S | A |
| N | T | K | Y | N | E | S | L | K | S | L | V | T | I | S | V | D | T | S | A |
| N | T | K | Y | N | E | K | F | Q | G | R | V | T | S | T | V | D | T | S | I |

FIG. 7b-6

| 76 | 77 | 78 | 79 | 80 | 81 | 82 | 82a | 82b | 82c | 83 | 84 | 85 | 86 | 87 | 88 | 89 | 90 | 91 | 92 |
|---|---|---|---|---|---|---|---|---|---|---|---|---|---|---|---|---|---|---|---|
| S | T | A | F | M | Q | L | S | S | L | T | S | E | D | T | A | V | Y | F | C |
| S | T | A | Y | M | E | L | S | S | L | R | S | E | D | T | A | V | Y | F | C |
| S | T | A | Y | M | E | L | S | S | L | R | S | E | D | T | A | V | Y | F | C |
| S | T | A | Y | M | E | L | S | S | L | R | S | E | D | T | A | V | Y | F | C |
| S | T | A | Y | M | E | L | S | S | L | R | S | E | D | T | A | V | Y | F | C |
| S | T | A | Y | M | E | L | S | S | L | R | S | E | D | T | A | V | Y | F | C |
| S | T | A | Y | M | E | L | S | S | L | R | S | E | D | T | A | V | Y | F | C |
| S | T | A | Y | M | E | L | S | S | L | R | S | E | D | T | A | V | Y | F | C |
| S | T | A | Y | M | E | L | S | S | L | R | S | E | D | T | A | V | Y | F | C |
| S | T | A | Y | M | E | L | S | S | L | R | S | E | D | T | A | V | Y | F | C |
| S | T | A | Y | M | E | L | S | S | L | R | S | E | D | T | A | V | Y | F | C |
| S | T | A | Y | M | E | L | S | S | L | R | S | E | D | T | A | M | Y | F | C |
| S | T | A | Y | M | E | L | S | S | L | R | S | E | D | T | A | V | Y | F | C |
| S | T | A | Y | M | E | L | S | S | L | R | S | E | D | T | A | V | Y | F | C |
| S | T | A | Y | M | E | L | R | S | L | R | S | D | D | T | A | V | Y | F | C |
| S | T | A | Y | M | E | L | S | S | L | R | S | E | D | T | A | M | Y | F | C |
| S | T | A | Y | M | E | L | S | S | L | R | S | E | D | T | A | V | Y | F | C |
| S | T | A | Y | M | E | L | S | S | L | R | S | E | D | T | A | V | Y | F | C |
| S | T | A | Y | M | E | L | S | S | L | R | S | E | D | T | A | V | Y | F | C |
| S | T | A | Y | M | E | L | S | S | L | R | S | E | D | T | A | M | Y | F | C |
| S | T | A | Y | M | E | L | S | S | L | R | S | E | D | T | A | V | Y | F | C |
| S | T | A | Y | M | E | L | S | S | L | R | S | E | D | T | A | V | Y | F | C |
| S | T | A | Y | M | E | L | R | S | L | R | S | D | D | T | A | V | Y | F | C |
| S | T | A | Y | M | E | L | S | S | L | R | S | E | D | T | A | V | Y | F | C |
| S | T | A | Y | M | E | L | S | S | L | R | S | E | D | T | A | V | Y | F | C |
| S | T | A | Y | M | E | L | S | R | L | R | S | D | D | T | V | V | Y | F | C |
| S | T | A | Y | M | E | L | R | S | L | R | S | D | D | T | V | V | Y | F | C |
| S | T | A | Y | M | E | L | S | R | L | R | S | D | D | T | A | V | Y | F | C |
| S | T | A | Y | M | E | L | S | S | L | R | S | E | D | T | V | V | Y | F | C |
| S | T | A | Y | M | E | L | S | R | L | R | S | D | D | T | V | V | Y | F | C |
| S | T | A | Y | M | E | L | S | S | L | R | S | E | D | T | A | V | Y | F | C |
| S | T | A | Y | M | E | L | S | S | L | R | S | E | D | T | A | V | Y | F | C |
| S | T | A | Y | M | E | L | S | S | L | R | S | E | D | T | A | V | Y | F | C |
| S | T | A | Y | M | E | L | S | S | L | R | S | E | D | T | A | V | Y | F | C |
| S | T | A | Y | M | E | L | S | S | L | R | S | E | D | T | A | V | Y | F | C |
| S | T | A | Y | M | E | L | S | S | L | R | S | E | D | T | A | V | Y | F | C |
| S | T | A | Y | M | E | L | S | S | L | R | S | E | D | T | A | V | Y | F | C |
| S | T | A | Y | M | E | L | S | S | L | R | S | E | D | T | A | V | Y | F | C |
| S | T | A | Y | M | E | L | S | R | L | R | S | D | D | T | V | V | Y | F | C |
| S | T | A | Y | M | E | L | S | S | L | R | S | E | D | T | A | V | Y | F | C |

FIG. 7b-7

| 93 | 94 | 95 | 96 | 97 | | | | | | 98 | 99 | 100 | 101 | 102 | 103 | 104 | 105 | 106 |
|---|---|---|---|---|---|---|---|---|---|---|---|---|---|---|---|---|---|---|
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |
| A | N | Y | G | N | — | — | — | — | — | Y | W | F | A | Y | W | G | Q | G |

FIG. 7b-8

| 107 | 108 | 109 | 110 | 111 | 112 | 113 |
|-----|-----|-----|-----|-----|-----|-----|
| T | Q | V | T | V | S | A |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |

| | | | | | | | | |
|---|---|---|---|---|---|---|---|---|
| SEQ ID NO.:200 | 3 | 0.46 | 0.57 | 0.81 | 0.40 | 45 | 0.53 | 22 | 5.18 |
| SEQ ID NO.:201 | 5 | 0.46 | 0.58 | 0.81 | 0.40 | 45 | 0.67 | 21 | 4.09 |
| SEQ ID NO.:202 | 56 | 0.46 | 0.56 | 0.81 | 0.39 | 45 | 0.47 | 21 | 3.91 |
| SEQ ID NO.:203 | 8 | 0.47 | 0.59 | 0.81 | 0.42 | 49 | 0.71 | 22 | 4.73 |
| SEQ ID NO.:204 | 18 | 0.48 | 0.60 | 0.81 | 0.42 | 49 | 0.65 | 20 | 3.73 |
| SEQ ID NO.:205 | 29 | 0.47 | 0.59 | 0.81 | 0.42 | 49 | 0.55 | 21 | 3.91 |
| SEQ ID NO.:206 | 19 | 0.47 | 0.58 | 0.81 | 0.42 | 49 | 0.55 | 20 | 3.55 |
| SEQ ID NO.:207 | 31 | 0.47 | 0.58 | 0.81 | 0.38 | 45 | 0.60 | 20 | 4.36 |
| SEQ ID NO.:208 | 34 | 0.45 | 0.56 | 0.81 | 0.41 | 48 | 0.40 | 22 | 6.36 |
| SEQ ID NO.:209 | 54 | 0.46 | 0.57 | 0.81 | 0.42 | 50 | 0.42 | 22 | 5.55 |
| SEQ ID NO.:210 | 46 | 0.45 | 0.58 | 0.81 | 0.40 | 45 | 0.60 | 23 | 6.09 |
| SEQ ID NO.:211 | 9 | 0.48 | 0.58 | 0.81 | 0.46 | 53 | 0.68 | 23 | 2.83 |
| SEQ ID NO.:212 | 24 | 0.47 | 0.57 | 0.81 | 0.46 | 53 | 0.68 | 23 | 3.50 |
| SEQ ID NO.:213 | 21 | 0.47 | 0.58 | 0.81 | 0.46 | 53 | 0.57 | 24 | 3.83 |
| SEQ ID NO.:214 | 27 | 0.47 | 0.57 | 0.81 | 0.46 | 53 | 0.47 | 25 | 3.83 |
| SEQ ID NO.:215 | 47 | 0.49 | 0.55 | 0.81 | 0.45 | 52 | 0.60 | 24 | 4.50 |
| SEQ ID NO.:216 | 57 | 0.48 | 0.55 | 0.81 | 0.45 | 52 | 0.46 | 25 | 5.83 |
| SEQ ID NO.:217 | 55 | 0.50 | 0.56 | 0.80 | 0.36 | 41 | 0.51 | 26 | |

FIG. 7b-9

| Q | I | Q | L | V | Q | S | G | H | E | V | K | Q | P | G | A | S | V | K | V |
|---|---|---|---|---|---|---|---|---|---|---|---|---|---|---|---|---|---|---|---|
| Q | I | Q | L | V | Q | S | G | A | E | V | K | K | P | G | A | S | V | K | V |
| Q | I | Q | L | V | Q | S | G | P | E | V | K | K | P | G | T | S | V | K | V |
| Q | I | Q | L | V | Q | S | G | S | E | L | K | K | P | G | A | S | V | K | V |
| Q | I | Q | L | V | Q | S | G | A | E | V | K | K | P | G | A | S | V | K | V |
| Q | I | Q | L | V | Q | S | G | A | E | V | K | K | P | G | S | S | V | K | V |
| Q | I | Q | L | V | Q | S | G | P | E | V | K | K | P | G | T | S | V | K | V |
| Q | I | Q | L | V | Q | S | G | P | E | V | K | K | P | G | T | S | V | K | V |
| Q | I | Q | L | V | Q | S | G | P | E | V | K | K | P | G | T | S | V | K | V |
| Q | I | Q | L | V | Q | S | G | P | E | V | K | K | P | G | T | S | V | K | V |
| Q | I | Q | L | V | Q | S | G | A | E | V | K | K | T | G | S | S | V | K | V |
| Q | I | Q | L | V | Q | S | G | A | E | V | K | K | P | G | A | S | V | K | V |
| Q | I | Q | L | V | Q | S | G | A | E | V | K | K | P | G | A | S | V | K | V |
| Q | I | Q | L | V | Q | S | G | A | E | V | K | K | P | G | A | S | V | K | V |
| Q | I | Q | L | V | Q | S | G | A | E | V | K | K | P | G | S | S | V | K | V |
| Q | I | Q | L | V | Q | S | G | A | E | V | K | K | P | G | A | S | V | K | V |
| Q | I | Q | L | V | Q | S | G | H | E | V | K | Q | P | G | A | S | V | K | V |
| Q | I | Q | L | V | E | S | G | G | G | L | V | K | P | G | G | S | L | R | L |

FIG. 7b-10

| S | C | K | A | S | G | Y | T | F | T | D |   |   | Y | Y | I | T | W | V | R |
|---|---|---|---|---|---|---|---|---|---|---|---|---|---|---|---|---|---|---|---|
| S | C | K | A | S | G | Y | T | F | T | D | — | — | Y | Y | I | T | W | V | R |
| S | C | K | A | S | G | Y | T | F | T | D | — | — | Y | Y | I | T | W | V | R |
| S | C | K | A | S | G | Y | T | F | T | D | — | — | Y | Y | I | T | W | V | R |
| S | C | K | A | S | G | Y | T | F | T | D | — | — | Y | Y | I | T | W | V | R |
| S | C | K | A | S | G | Y | T | F | T | D |   |   | Y | Y | I | T | W | V | R |
| S | C | K | A | S | G | Y | T | F | T | D |   |   | Y | Y | I | T | W | V | R |
| S | C | K | A | S | G | Y | T | F | T | D | — | — | Y | Y | I | T | W | V | R |
| S | C | K | A | S | G | Y | T | F | T | D | — | — | Y | Y | I | T | W | V | R |
| S | C | K | A | S | G | Y | T | F | T | D | — | — | Y | Y | I | T | W | V | R |
| S | C | K | A | S | G | Y | T | F | T | D |   |   | Y | Y | I | T | W | V | R |
| S | C | K | A | S | G | Y | T | F | T | D | — | — | Y | Y | I | T | W | V | R |
| S | C | K | A | S | G | Y | T | F | T | D | — | — | Y | Y | I | T | W | V | R |
| S | C | K | A | S | G | Y | T | F | T | D | — | — | Y | Y | I | T | W | V | R |
| S | C | K | A | S | G | Y | T | F | T | D | — | — | Y | Y | I | T | W | V | R |
| S | C | K | A | S | G | Y | T | F | T | D |   | — | Y | Y | I | T | W | V | R |
| S | C | A | A | S | G | Y | T | F | T | D | — | — | Y | Y | I | T | W | V | R |

FIG. 7b-11

| Q | A | T | G | Q | G | L | E | W | M | G | W | I | Y | P | G | — | — | S | G |
|---|---|---|---|---|---|---|---|---|---|---|---|---|---|---|---|---|---|---|---|
| Q | A | T | G | Q | G | L | E | W | M | G | W | I | Y | P | G | — | — | S | G |
| Q | A | T | G | Q | G | L | E | W | M | G | W | I | Y | P | G | — | — | S | G |
| Q | A | T | G | Q | G | L | E | W | M | G | W | I | Y | P | G | — | — | S | G |
| Q | A | P | G | Q | G | L | E | W | M | G | W | I | Y | P | G | — | — | S | G |
| Q | A | P | G | Q | G | L | E | W | M | G | W | I | Y | P | G | — | — | S | G |
| Q | A | P | G | Q | G | L | E | W | M | G | W | I | Y | P | G | — | — | S | G |
| Q | A | P | G | Q | G | L | E | W | M | G | W | I | Y | P | G | — | — | S | G |
| Q | A | T | G | Q | G | L | E | W | M | G | W | I | Y | P | G | — | — | S | G |
| Q | A | T | G | Q | G | L | E | W | M | G | W | I | Y | P | G | — | — | S | G |
| Q | A | P | G | Q | G | L | E | W | M | G | W | I | Y | P | G | — | — | S | G |
| Q | A | P | G | Q | G | L | E | W | M | G | W | I | Y | P | G | — | — | S | G |
| Q | A | P | G | Q | G | L | E | W | M | G | W | I | Y | P | G | — | — | S | G |
| Q | A | T | G | Q | G | L | E | W | M | G | W | I | Y | P | G | — | — | S | G |
| Q | A | T | G | Q | G | L | E | W | M | G | W | I | Y | P | G | — | — | S | G |
| Q | A | P | G | Q | G | L | E | W | M | G | W | I | Y | P | G | — | — | S | G |
| Q | A | P | G | Q | G | L | E | W | M | G | W | I | Y | P | G | — | — | S | G |
| Q | A | P | G | Q | G | L | E | W | M | G | W | I | Y | P | G | — | — | S | G |

FIG. 7b-12

| N | T | K | Y | N | E | K | F | Q | G | R | V | T | S | T | V | D | T | S | I |
|---|---|---|---|---|---|---|---|---|---|---|---|---|---|---|---|---|---|---|---|
| N | T | K | Y | N | E | K | F | Q | G | R | V | T | S | T | V | D | T | S | I |
| N | T | K | Y | N | E | K | F | Q | G | R | V | T | S | T | V | D | T | S | I |
| N | T | K | Y | N | E | K | F | Q | G | R | V | T | I | T | V | D | T | S | A |
| N | T | K | Y | N | E | K | F | Q | G | R | V | T | I | T | V | D | T | S | A |
| N | T | K | Y | N | E | K | F | Q | G | R | V | T | I | T | V | D | T | S | A |
| N | T | K | Y | N | E | K | F | Q | G | R | V | T | I | T | V | D | T | S | A |
| N | T | K | Y | N | E | K | F | Q | G | R | V | T | M | T | V | D | T | S | T |
| N | T | K | Y | N | E | K | F | Q | G | R | V | T | I | T | V | D | T | S | A |
| N | T | K | Y | N | E | K | F | Q | G | R | V | T | M | T | V | N | T | S | I |
| N | T | K | Y | N | E | S | L | K | S | R | V | T | I | S | V | D | T | S | V |
| N | T | K | Y | N | E | S | L | K | S | L | V | T | I | S | V | D | T | S | V |
| N | T | K | Y | N | E | S | L | K | S | R | V | T | M | S | V | D | T | S | V |
| N | T | K | Y | N | E | S | L | K | S | R | V | T | I | S | V | D | T | S | V |
| N | T | K | Y | N | E | S | L | K | S | R | V | T | I | S | V | D | T | S | K |
| N | T | K | Y | N | E | S | L | K | S | R | V | T | I | S | V | D | T | S | K |
| N | T | K | Y | N | E | K | F | Q | G | R | V | T | M | T | V | D | T | S | T |

FIG. 7b-13

| S | T | A | Y | L | Q | I | C | S | L | K | A | E | D | T | A | V | Y | F | C |
|---|---|---|---|---|---|---|---|---|---|---|---|---|---|---|---|---|---|---|---|
| S | T | A | Y | L | Q | I | C | S | L | K | A | E | D | T | A | V | Y | F | C |
| S | T | A | Y | L | Q | I | C | S | L | K | A | E | D | T | A | V | Y | F | C |
| S | T | A | Y | L | Q | I | C | S | L | K | A | E | D | T | A | V | Y | F | C |
| S | T | A | Y | L | Q | I | C | S | L | K | A | E | D | T | A | V | Y | F | C |
| S | T | A | Y | L | Q | I | C | S | L | K | A | E | D | T | A | V | Y | F | C |
| S | T | A | Y | L | Q | I | C | S | L | K | A | E | D | T | A | V | Y | F | C |
| S | T | A | Y | L | Q | W | S | S | L | K | A | S | D | T | A | M | Y | F | C |
| S | T | A | Y | L | Q | I | S | S | L | K | A | E | D | M | A | M | Y | F | C |
| S | T | A | Y | L | Q | I | C | S | L | K | A | E | D | T | A | V | Y | F | C |
| S | T | A | Y | L | Q | I | C | S | L | K | A | E | D | T | A | V | Y | F | C |
| S | T | A | Y | L | Q | I | C | S | L | K | A | E | D | T | A | V | Y | F | C |
| S | T | A | Y | L | Q | I | C | S | L | K | A | E | D | T | A | V | Y | F | C |
| S | T | A | Y | L | Q | I | C | S | L | K | A | E | D | T | A | V | Y | F | C |
| S | I | A | Y | L | Q | M | N | S | L | K | T | E | D | T | A | V | Y | F | C |
| S | I | A | Y | L | Q | M | N | S | L | K | T | E | D | T | A | V | Y | F | C |
| S | T | A | Y | L | Q | I | C | S | L | K | A | E | D | T | A | V | Y | F | C |

*FIG. 7b-14*

| A | N | Y | G | N | _ | _ | _ | _ | _ | _ | Y | W | F | A | Y | W | G | Q | G |
|---|---|---|---|---|---|---|---|---|---|---|---|---|---|---|---|---|---|---|---|
| A | N | Y | G | N | _ | _ | _ | _ | _ | _ | Y | W | F | A | Y | W | G | Q | G |
| A | N | Y | G | N | _ | _ | _ | _ | _ | _ | Y | W | F | A | Y | W | G | Q | G |
| A | N | Y | G | N | _ | _ | _ | _ | _ | _ | Y | W | F | A | Y | W | G | Q | G |
| A | N | Y | G | N | _ | _ | _ | _ | _ | _ | Y | W | F | A | Y | W | G | Q | G |
| A | N | Y | G | N | _ | _ | _ | _ | _ | _ | Y | W | F | A | Y | W | G | Q | G |
| A | N | Y | G | N | _ | _ | _ | _ | _ | _ | Y | W | F | A | Y | W | G | Q | G |
| A | N | Y | G | N | _ | _ | _ | _ | _ | _ | Y | W | F | A | Y | W | G | Q | G |
| A | N | Y | G | N | _ | _ | _ | _ | _ | _ | Y | W | F | A | Y | W | G | Q | G |
| A | N | Y | G | N | _ | _ | _ | _ | _ | _ | Y | W | F | A | Y | W | G | Q | G |
| A | N | Y | G | N | _ | _ | _ | _ | _ | _ | Y | W | F | A | Y | W | G | Q | G |
| A | N | Y | G | N | _ | _ | _ | _ | _ | _ | Y | W | F | A | Y | W | G | Q | G |
| A | N | Y | G | N | _ | _ | _ | _ | _ | _ | Y | W | F | A | Y | W | G | Q | G |
| A | N | Y | G | N | _ | _ | _ | _ | _ | _ | Y | W | F | A | Y | W | G | Q | G |
| A | N | Y | G | N | _ | _ | _ | _ | _ | _ | Y | W | F | A | Y | W | G | Q | G |
| A | N | Y | G | N | _ | _ | _ | _ | _ | _ | Y | W | F | A | Y | W | G | Q | G |

SEQ ID NO.: 218
DIVLTQSPATLSLSPGERATLSCRASQSVDFDGDSYMNWYQQKPGQPPKVLIYAAS
NLESGIPARFSGSGSGTDFTLTISSLQPEDFATYYCQQSNEDPWTFGGGTKVEIK
FIG. 8a
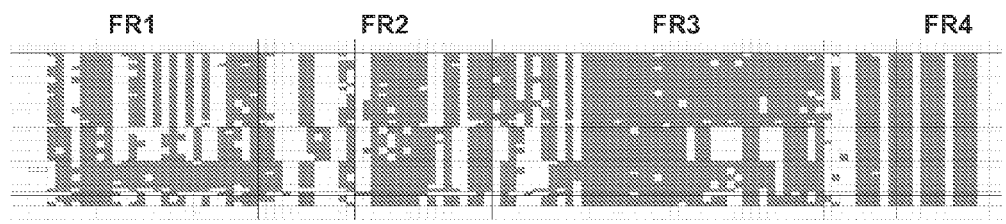
FIG. 8b
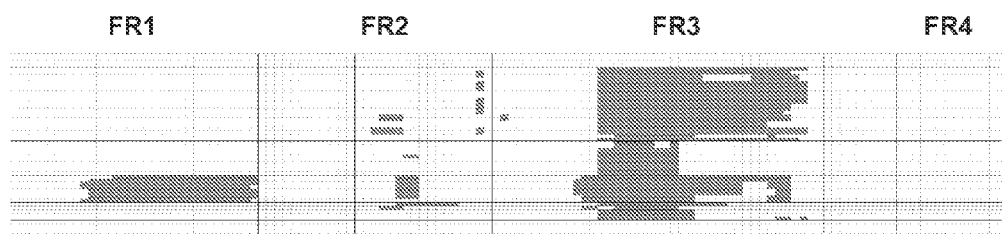
FIG. 8c
FIG. 8d SEQ ID NO.: 219
DIVLTQSPSSLSASVGDRVTITCRASQSVDFDGDSYMNWYQQKPGQPPKVLIYAAS
NLESGIPARFSGSGSGTDFTLTISSLQPEDFATYYCQQSNEDPWTFGGGTKVEIK
*FIG. 9a*
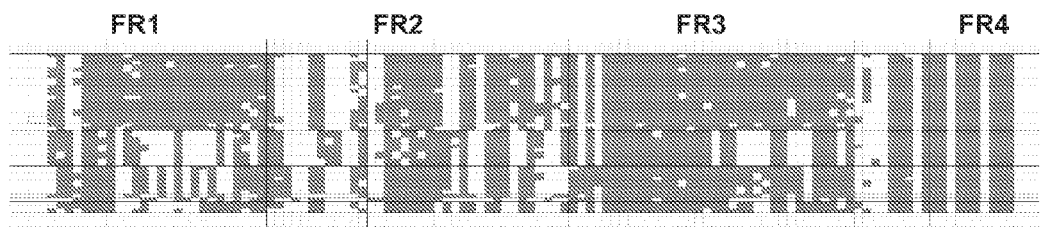
*FIG. 9b*
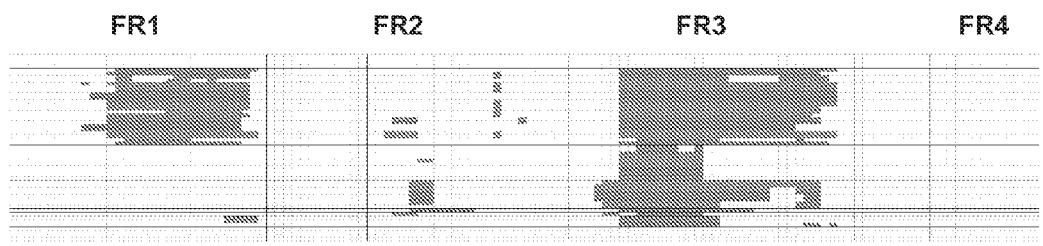
*FIG. 9c*
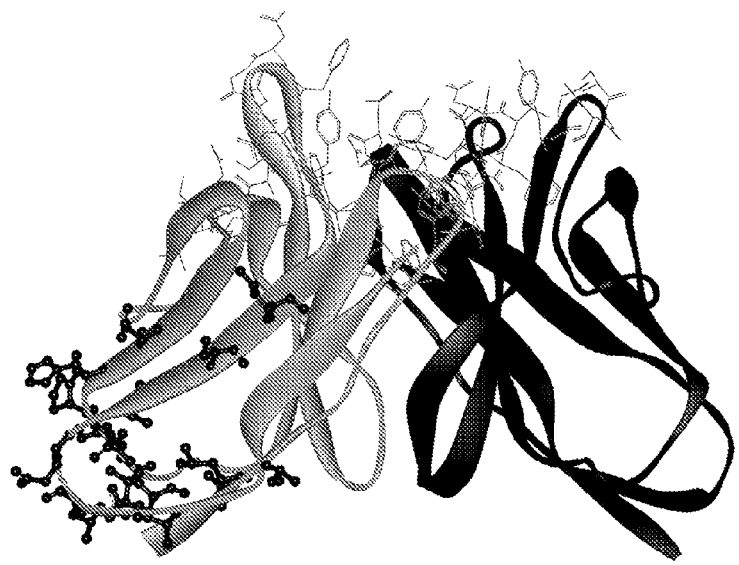
*FIG. 9d*

SEQ ID NO.: 220
DIVLTQSPDSLAVSLGERATINCKASQSVDFDGDSYMNWYQQKPGQPPKVLIYAAS
NLESGIPARFSGSGSGTDFTLTINSLEAEDAATYYCQQSNEDPWTFGGGTKVEIK
*FIG. 10a*
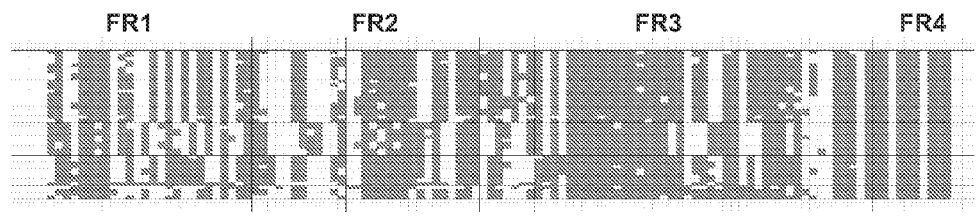
*FIG. 10b*
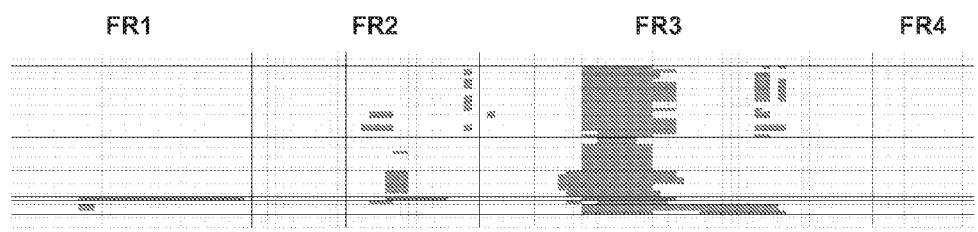
*FIG. 10c*
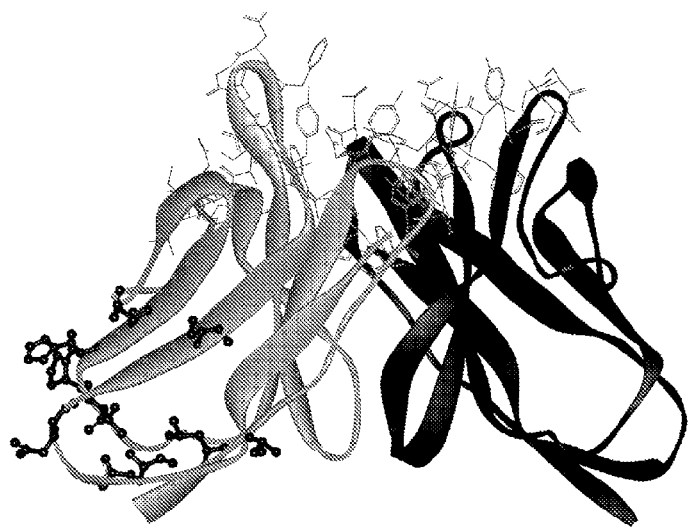
*FIG. 10d*

SEQ ID NO.: 221
QIQLVQSGPEVKKPGASVKVSCKASGYTFTDYYITWVRQAPGQGLEWMGWIYPG
SGNTKYNEKFQGRVTITVDTSASTAYMELSSLRSEDTAVYFCANYGNYWFAYWGQ
GTLVTVSS
FIG. 11a
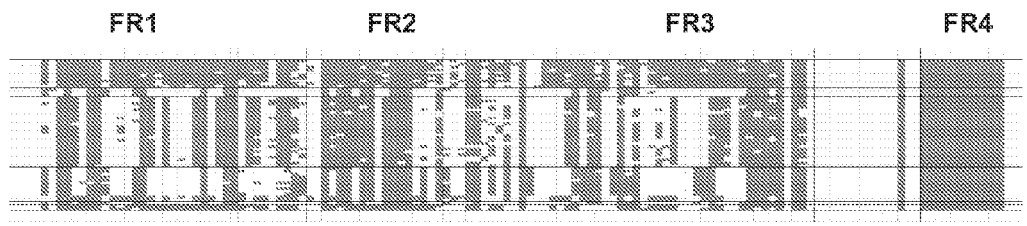
FIG. 11b
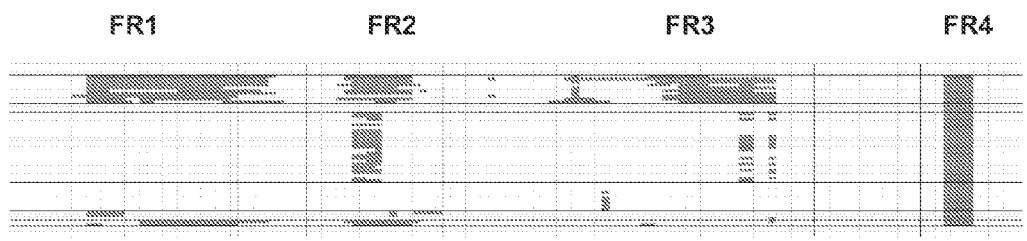
FIG. 11c
FIG. 11d

SEQ ID NO.: 222
QIQLVESGGGLVKPGGSLRLSCAASGYTFTDYYITWVRQAPGQGLEWMGWIYPG
SGNTKYNEKFQGRVTMTVDTSTSTAYMELSSLRSEDTAVYFCANYGNYWFAYWG
QGTLVTVSS
*FIG. 12a*
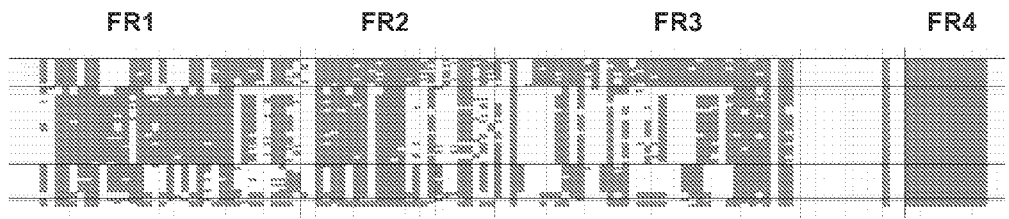
*FIG. 12b*
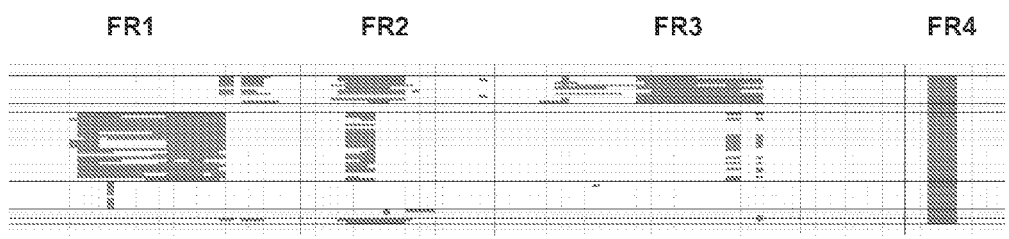
*FIG. 12c*
*FIG. 12d*

SEQ ID NO.: 223
QIQLVQSGPEVKKPGASVKVSCKASGYTFTDYYITWVRQAPGQGLEWMGWIYPG
SGNTKYNEKFQGRFVFSVDTSASTAYLQISSLKAEDTAVYFCANYGNYWFAYWGQ
GTLVTVSS
FIG. 13a
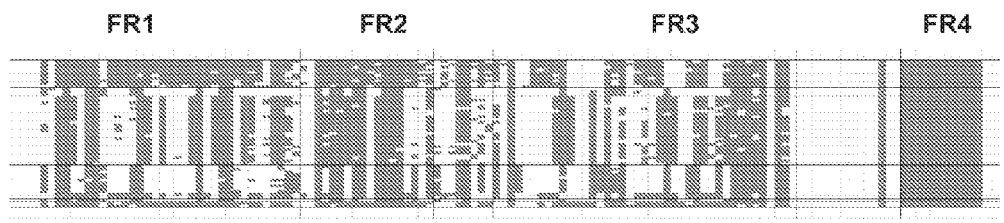
FIG. 13b
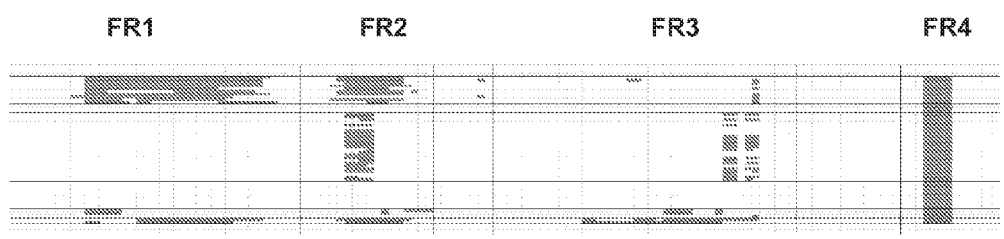
FIG. 13c
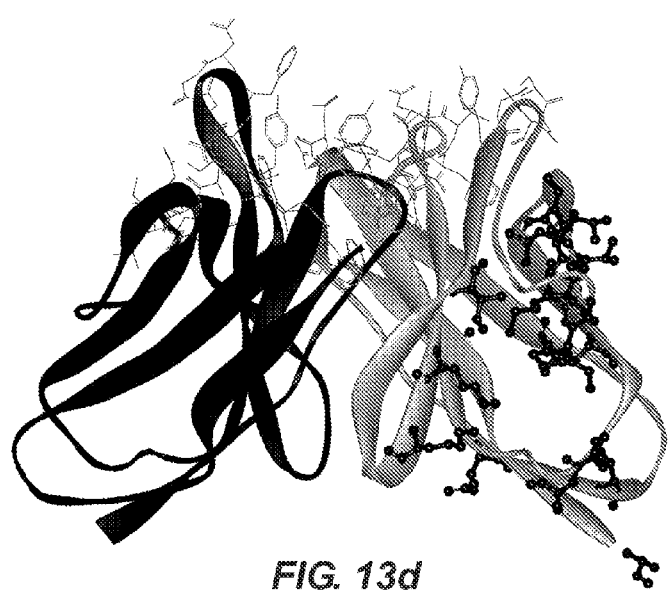
FIG. 13d SEQ ID NO.: 224
EIVLTQSPDSLAVSLGERATINCKASQSVDFDGDSYLNWYQQKPGQPPKVLIYAAST
LQSGVPSRFSGSGSGTDFTLTINSLEAEDAATYYCQQSNEDPWTFGGGTKVEIK
*FIG. 20a*
*FIG. 20b*
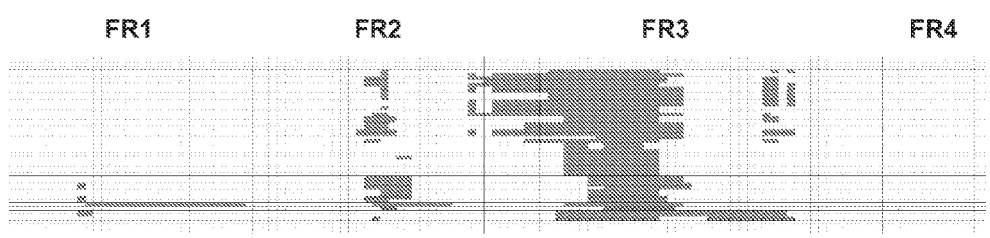
*FIG. 20c*
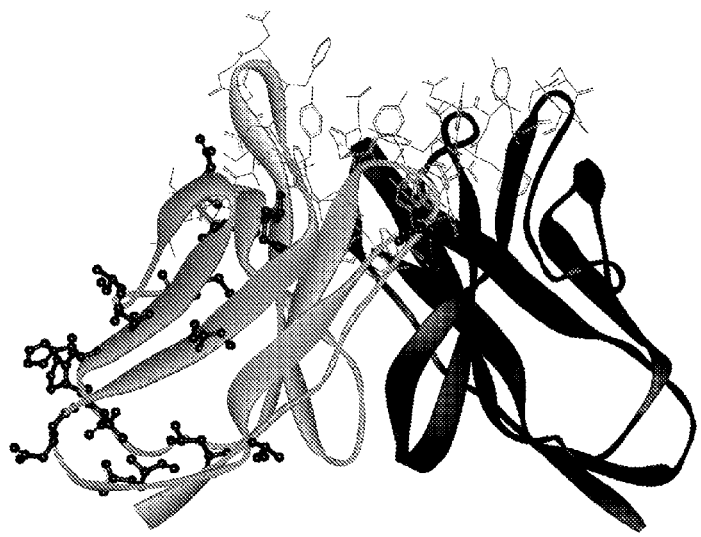
*FIG. 20d*

SEQ ID NO.: 225
AIVLTQSPDSLAVSLGERATINCKASQSVDFDGDSYLNWYQQKPGQPPKVLIYAAST
LETGVPSRFSGSGSGTDFTLTINSLEAEDAATYYCQQSNEDPWTFGGGTKVEIK
*FIG. 21a*
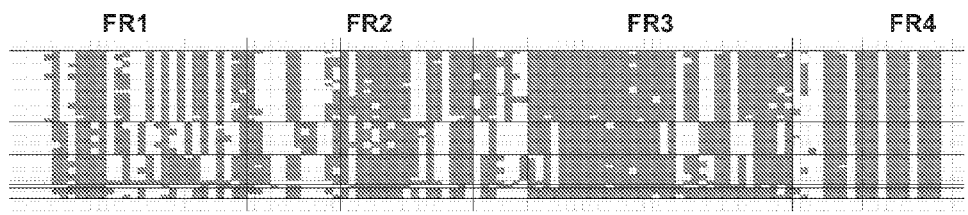
*FIG. 21b*
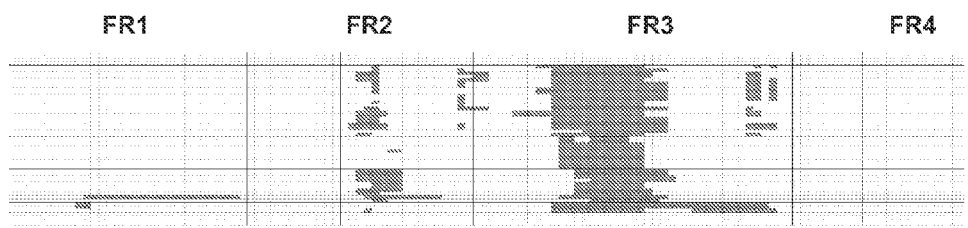
*FIG. 21c*
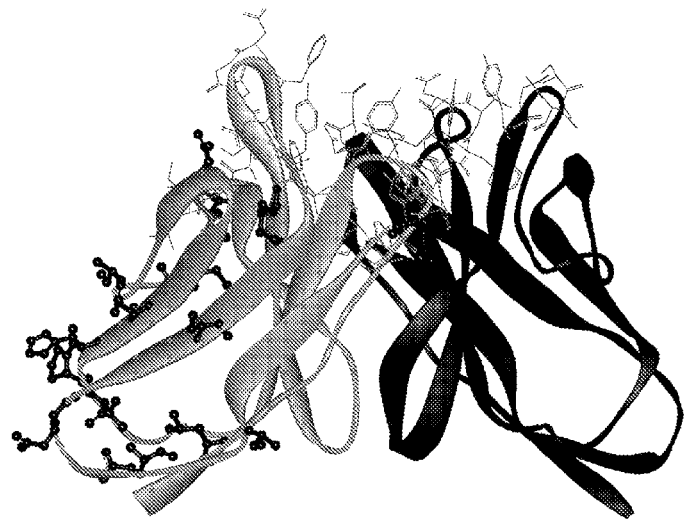
*FIG. 21d*

SEQ ID NO.: 226
QLQLVQSGPEVKKPGASVKVSCKVSGYTFTDYYITWVRQAPGQALEWMGWIYPG
SGNTKYNEKFQGRFVFSVDTSASTAYLQISSLKAEDTAVYFCANYGNYWFAYWGQ
GTLVTVSS
*FIG. 22a*
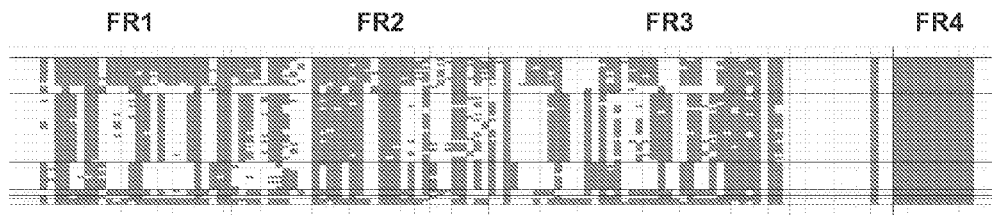
*FIG. 22b*
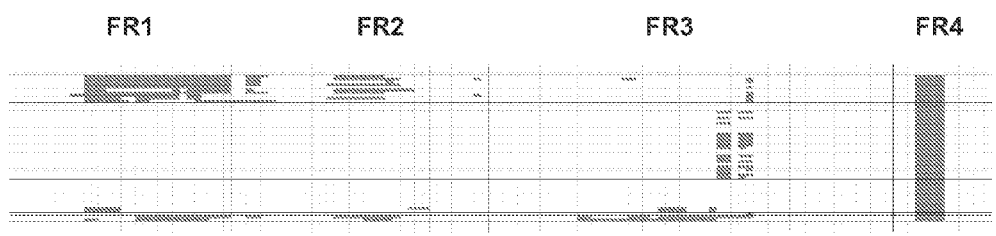
*FIG. 22c*
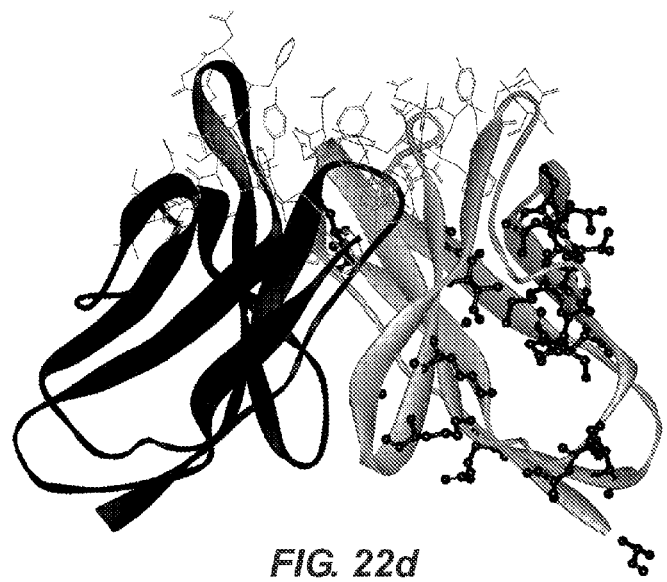
*FIG. 22d*

SEQ ID NO.: 227
QLQLVQSGAEVKKPGASVKVSCKVSGYTFTDYYITWVRQAPGQALEWMGWIYPG
SGNTKYSQKFQGRFVFSVDTSASTAYLQISSLKAEDTAVYYCANYGNYWFAYWGQ
GTLVTVSS
*FIG. 23a*
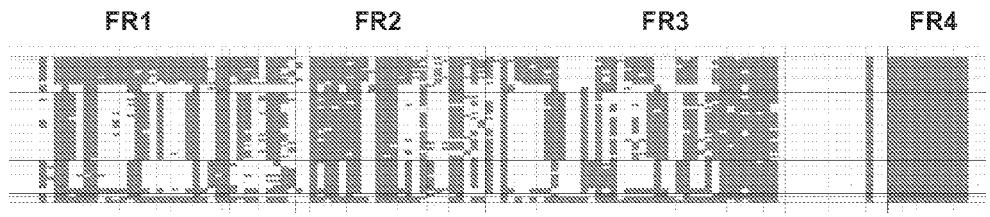
*FIG. 23b*
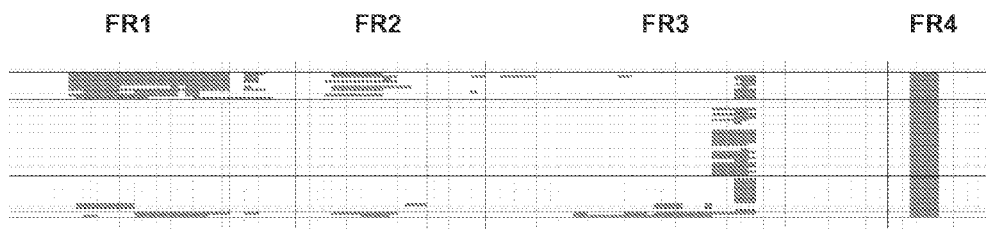
*FIG. 23c*
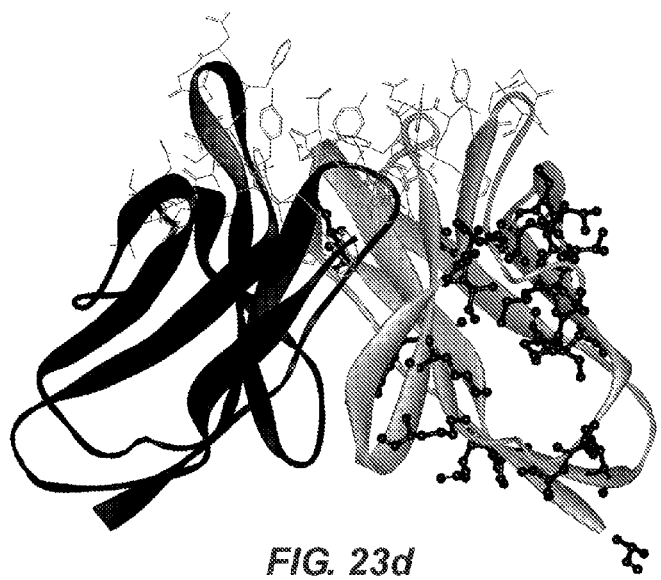
*FIG. 23d*

SEQ ID NO.: 228
QLQLVQSGAEVKKPGASVKVSCKVSGYTFTSYYISWVRQAPGQALEWMGWIYAG
SGNTKYSQKFQGRFVFSVDTSASTAYLQISSLKAEDTAVYYCANYGNYWFAYWGQ
GTLVTVSS
*FIG. 24a*
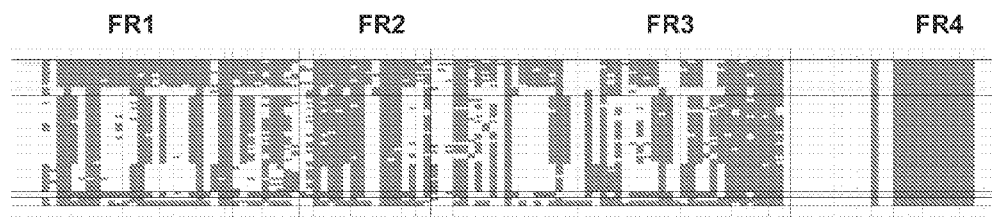
*FIG. 24b*
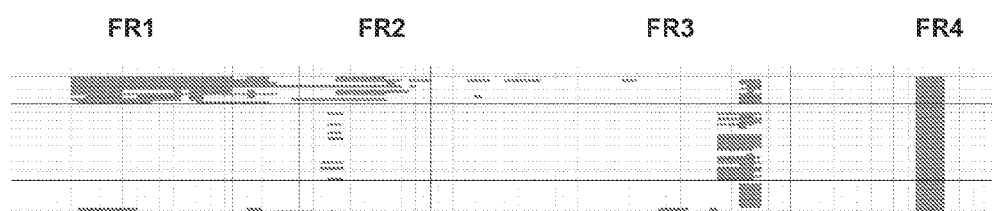
*FIG. 24c*
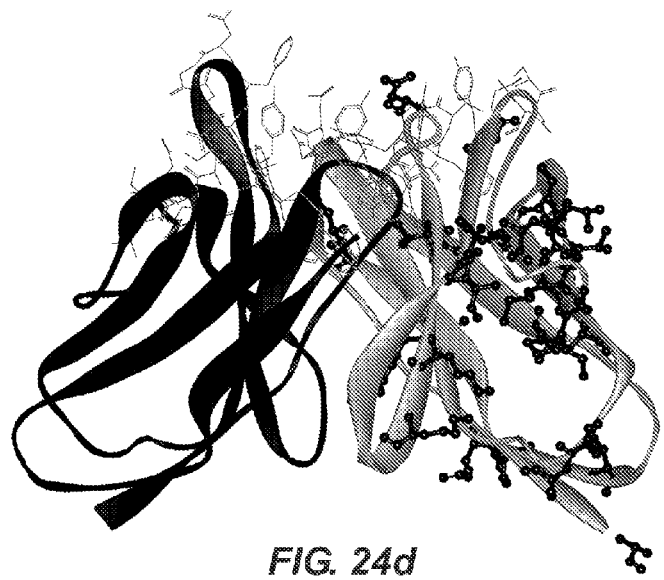
*FIG. 24d*

Anti-CD30 Light Chain

SEQ ID NO.:229
EIVLTQSPDSLAVSLGERATINCKASQSVDFDGDSYLNWYQQKPGQPPKVLIYA
ASTLQSGVPSRFSGSGSGTDFTLTINSLEAEDAATYYCQQSNEDPWTFGGGTK
VEIKRTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTKSFN
RGEC

FIG. 25a

Anti-CD30 IgG1 Heavy Chain Comprising Possible Fc Variants

SEQ ID NO.:230
QLQLVQSGAEVKKPGASVKVSCKVSGYTFTSYYISWVRQAPGQALEWMGWIY
AGSGNTKYSQKFQGRFVFSVDTSASTAYLQISSLKAEDTAVYYCANYGNYWFA
YWGQGTLVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKVD
KKAEPKSCDKTHTCPPCPAPELLGGP$X_1$VFLFPPKPKDTLMISRTPEVTCVV$X_2$
DVSHEDPEVKFNWYVDGVEVHNAKTKPREEQYNSTYRVVSVLTVLHQDWLNG
KEYKCKVSNKALP$X_3$P$X_4$EKTISKAKGQPREPQVYTLPPSRDELTKNQVSLTCL
VKGFYPSDIAVEWESNGQPENNYKTTPPVLDSDGSFFLYSKLTVDKSRWQQG
NVFSCSVMHEALHNHYTQKSLSLSPGK

| Position | EU Index Position | WT | Possible Substitutions |
|---|---|---|---|
| $X_1$ | 239 | S | D,E,N,Q,T |
| $X_2$ | 264 | V | I,T,Y |
| $X_3$ | 330 | A | Y,L,I |
| $X_4$ | 332 | I | D,E,N,Q |

FIG. 25b

Anti-CD30 Fc Variant IgG1 Heavy Chain

SEQ ID NO.:231
QLQLVQSGAEVKKPGASVKVSCKVSGYTFTSYYISWVRQAPGQALEWMGWIY
AGSGNTKYSQKFQGRFVFSVDTSASTAYLQISSLKAEDTAVYYCANYGNYWFA
YWGQGTLVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKVD
KKAEPKSCDKTHTCPPCPAPELLGGPDVFLFPPKPKDTLMISRTPEVTCVVVDV
SHEDPEVKFNWYVDGVEVHNAKTKPREEQYNSTYRVVSVLTVLHQDWLNGKE
YKCKVSNKALPLPEEKTISKAKGQPREPQVYTLPPSRDELTKNQVSLTCLVKGF
YPSDIAVEWESNGQPENNYKTTPPVLDSDGSFFLYSKLTVDKSRWQQGNVFS
CSVMHEALHNHYTQKSLSLSPGK

FIG. 25c

Anti-CD30 IgG2 Heavy Chain Comprising Possible Fc Variants

SEQ ID NO.:232
QLQLVQSGAEVKKPGASVKVSCKVSGYTFTSYYISWVRQAPGQALEWMGWIY
AGSGNTKYSQKFQGRFVFSVDTSASTAYLQISSLKAEDTAVYYCANYGNYWFA
YWGQGTLVTVSSASTKGPSVFPLAPCSRSTSESTAALGCLVKDYFPEPVTVSW
NSGALTSGVHTFPAVLQSSGLYSLSSVVTVPSSNFGTQTYTCNVDHKPSNTKVD
KTVERKCCVECPPCPAP$Z_1Z_2Z_3Z_4$GP$X_1$VFLFPPKPKDTLMISRTPEVTCVV$X_2$
DVSHEDPEVQFNWYVDGVEVHNAKTKPREEQFNSTFRVVSVLTVVHQDWLNG
KEYKCKVSNK$Z_5$LP$X_3$P$X_4$EKTISKTKGQPREPQVYTLPPSREEMTKNQVSLTCL
VKGFYPSDIAVEWESNGQPENNYKTTPPMLDSDGSFFLYSKLTVDKSRWQQG
NVFSCSVMHEALHNHYTQKSLSLSPGK

| Position | EU Index Position | WT | Possible Substitutions |
|---|---|---|---|
| $X_1$ | 239 | S | D,E,N,Q,T |
| $X_2$ | 264 | V | I,T,Y |
| $X_3$ | 330 | A | Y,L,I |
| $X_4$ | 332 | I | D,E,N,Q |
| $Z_1$ | 233 | P | E |
| $Z_2$ | 234 | V | L |
| $Z_3$ | 235 | A | L |
| $Z_4$ | 236 | - | G |
| $Z_5$ | 327 | G | A |

*FIG. 25d*

Anti-CD30 Fc Variant IgG2 Heavy Chain

SEQ ID NO.:233
QLQLVQSGAEVKKPGASVKVSCKVSGYTFTSYYISWVRQAPGQALEWMGWIY
AGSGNTKYSQKFQGRFVFSVDTSASTAYLQISSLKAEDTAVYYCANYGNYWFA
YWGQGTLVTVSSASTKGPSVFPLAPCSRSTSESTAALGCLVKDYFPEPVTVSW
NSGALTSGVHTFPAVLQSSGLYSLSSVVTVPSSNFGTQTYTCNVDHKPSNTKV
DKTVERKCCVECPPCPAPELLGGPDVFLFPPKPKDTLMISRTPEVTCVVVDVS
HEDPEVQFNWYVDGVEVHNAKTKPREEQFNSTFRVVSVLTVVHQDWLNGKEY
KCKVSNKGLPLPEEKTISKTKGQPREPQVYTLPPSREEMTKNQVSLTCLVKGFY
PSDIAVEWESNGQPENNYKTTPPMLDSDGSFFLYSKLTVDKSRWQQGNVFSC
SVMHEALHNHYTQKSLSLSPGK

*FIG. 25e*

SEQ ID NO.: 234
DILLTQSPVILSVSPGERVSFSCRASQSIGTNIHWYQQRTNGSPRLLIKYASESISGIP
SRFSGSGSGTDFTLSINSVESEDIADYYCQQNNNWPTTFGAGTKLELK
*FIG. 26a*
*FIG. 26b*
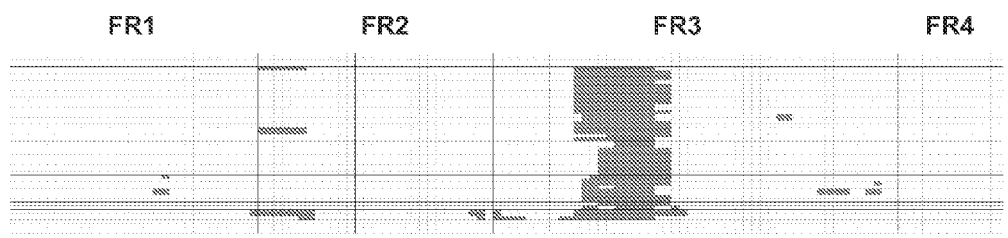
*FIG. 26c*
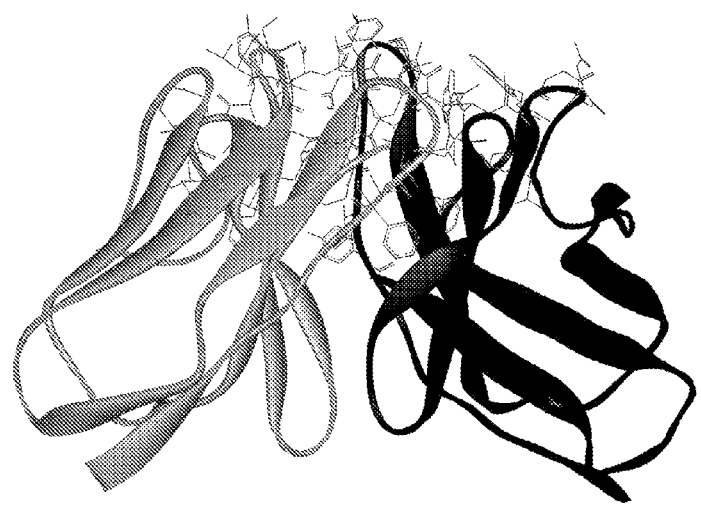
*FIG. 26d*

SEQ ID NO.: 235
QVQLKQSGPGLVQPSQSLSITCTVSGFSLTNYGVHWVRQSPGKGLEWLGVIWSG
GNTDYNTPFTSRLSINKDNSKSQVFFKMNSLQSNDTAIYYCARALTYYDYEFAYWG
QGTLVTVSA
*FIG. 27a*
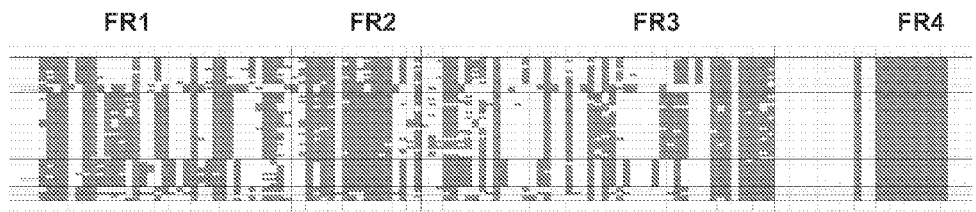
*FIG. 27b*
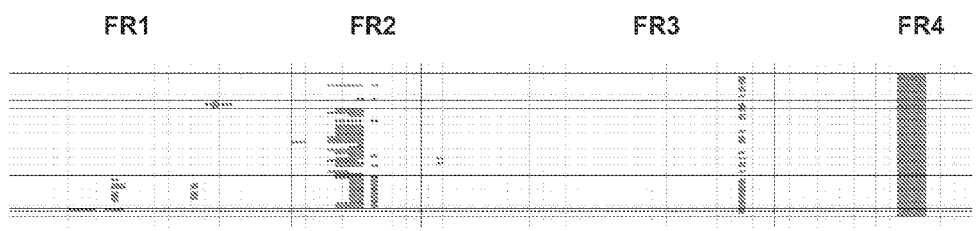
*FIG. 27c*
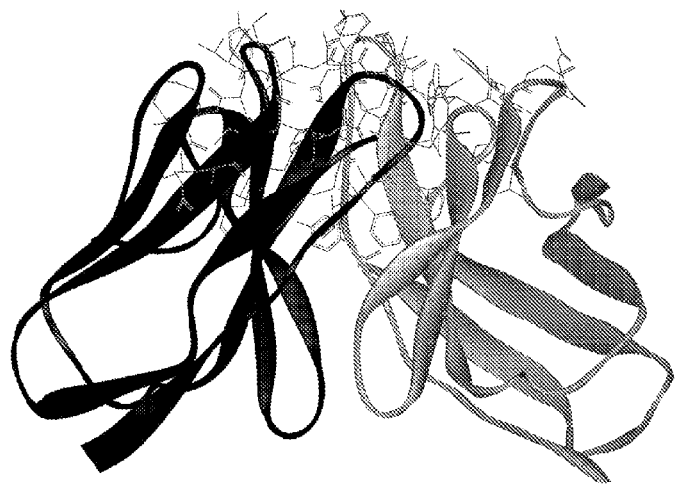
*FIG. 27d*

SEQ ID NO.: 236
EIVLTQSPDFQSVTPKEKVTITCRASQSIGTNLHWYQQKPDQSPKLLIKYASESISG
VPSRFSGSGSGTDFTLTINSLEAEDAATYYCHQNNNWPTTFGAGTKLEIK
*FIG. 28a*
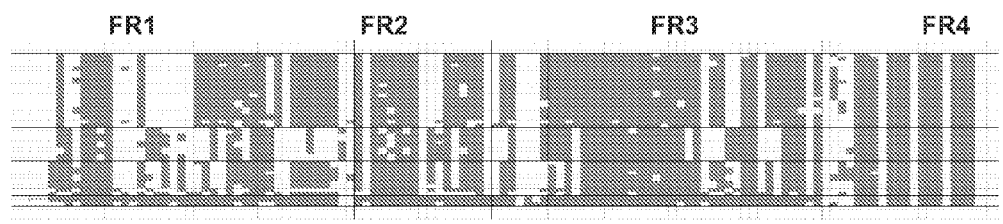
*FIG. 28b*
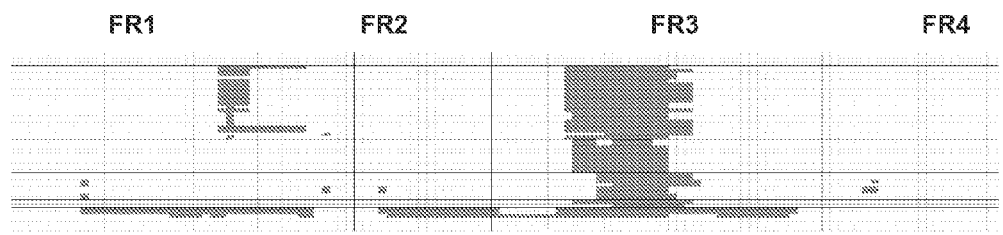
*FIG. 28c*
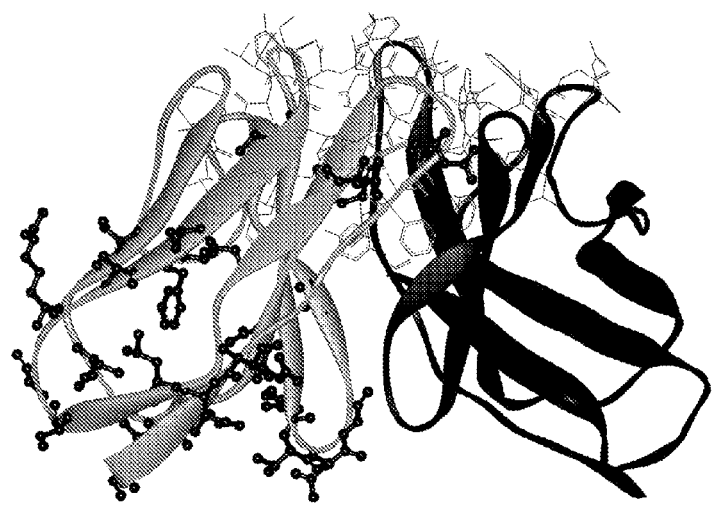
*FIG. 28d*

SEQ ID NO.: 237
QVQLQESGPGLVKPSQTLSLTCTVSGFSLTNYGWSWIRQPPGKGLEWIGYIWSGG
NTYYNPSLKSRVTISVDTSKNQFSLKLSSVTAADTAVYYCARALTYYDYEFAYWGQ
GTLVTVSS
*FIG. 29a*
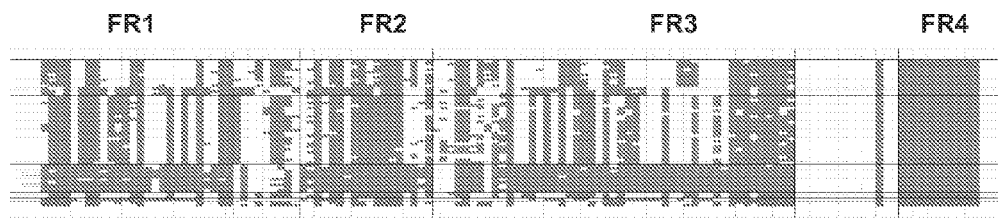
*FIG. 29b*
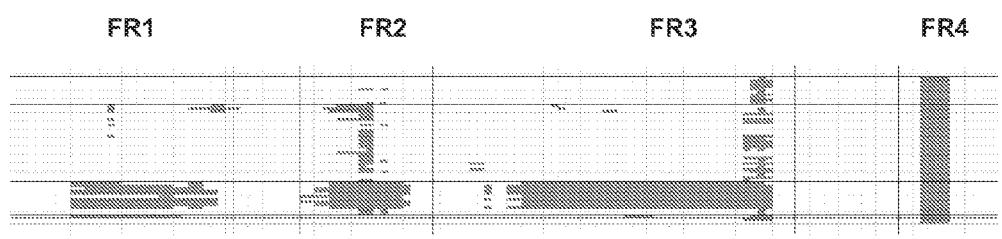
*FIG. 29c*
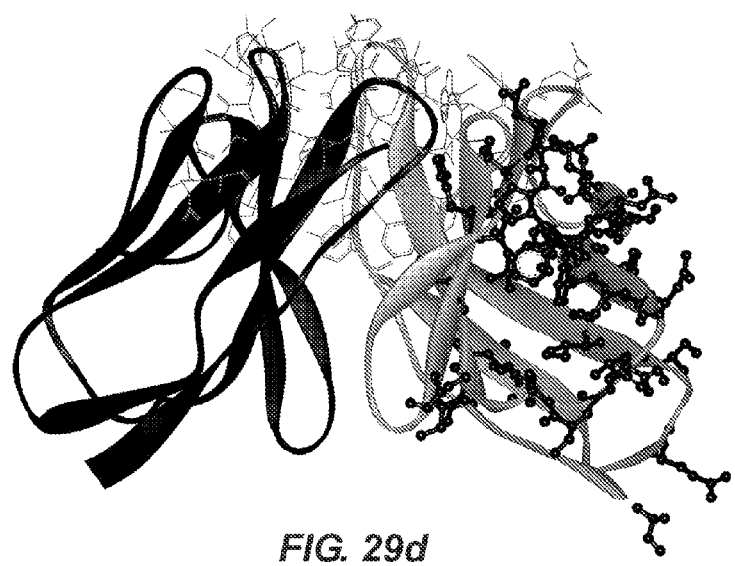
*FIG. 29d*

C225 VL HEC Calculation 1

| | | | | | | | Kabat | |
|---|---|---|---|---|---|---|---|---|
| (WT) SEQ ID NO.:234 | | | | | | | WT | |
| | Iter | Structural Consensus | Structural Precedence | HSC | HSS | $N_9$max | FRH | Muts |
| SEQ ID NO.:238 | 68 | 0.55 | 0.62 | 0.92 | 0.57 | 58 | 0.45 | 17 |
| SEQ ID NO.:239 | 94 | 0.56 | 0.60 | 0.92 | 0.57 | 58 | 0.47 | 18 |
| SEQ ID NO.:240 | 21 | 0.55 | 0.61 | 0.92 | 0.57 | 58 | 0.52 | 17 |
| SEQ ID NO.:241 | 16 | 0.54 | 0.61 | 0.92 | 0.57 | 58 | 0.52 | 17 |
| SEQ ID NO.:242 | 59 | 0.58 | 0.60 | 0.92 | 0.58 | 60 | 0.50 | 20 |
| SEQ ID NO.:243 | 86 | 0.54 | 0.58 | 0.92 | 0.57 | 58 | 0.67 | 17 |
| SEQ ID NO.:244 | 31 | 0.57 | 0.58 | 0.92 | 0.58 | 60 | 0.72 | 19 |
| SEQ ID NO.:245 | 25 | 0.54 | 0.58 | 0.92 | 0.57 | 58 | 0.67 | 16 |
| SEQ ID NO.:246 | 3 | 0.53 | 0.58 | 0.92 | 0.57 | 58 | 0.67 | 16 |
| SEQ ID NO.:247 | 41 | 0.55 | 0.58 | 0.92 | 0.57 | 58 | 0.45 | 17 |
| SEQ ID NO.:248 | 2 | 0.54 | 0.58 | 0.92 | 0.57 | 58 | 0.67 | 16 |
| SEQ ID NO.:249 | 54 | 0.53 | 0.57 | 0.91 | 0.51 | 52 | 0.75 | 17 |
| SEQ ID NO.:250 | 28 | 0.53 | 0.58 | 0.92 | 0.52 | 53 | 0.62 | 16 |
| SEQ ID NO.:251 | 78 | 0.53 | 0.58 | 0.92 | 0.52 | 53 | 0.62 | 16 |
| SEQ ID NO.:252 | 5 | 0.55 | 0.56 | 0.92 | 0.55 | 56 | 0.55 | 19 |
| SEQ ID NO.:253 | 8 | 0.54 | 0.56 | 0.92 | 0.55 | 56 | 0.55 | 19 |
| SEQ ID NO.:254 | 45 | 0.52 | 0.55 | 0.91 | 0.52 | 53 | 0.51 | 16 |
| SEQ ID NO.:255 | 4 | 0.52 | 0.55 | 0.91 | 0.52 | 53 | 0.51 | 16 |
| SEQ ID NO.:256 | 34 | 0.52 | 0.54 | 0.92 | 0.53 | 54 | 0.50 | 17 |
| SEQ ID NO.:257 | 6 | 0.52 | 0.55 | 0.92 | 0.53 | 54 | 0.50 | 16 |
| SEQ ID NO.:258 | 19 | 0.52 | 0.55 | 0.92 | 0.53 | 54 | 0.50 | 16 |
| SEQ ID NO.:259 | 17 | 0.52 | 0.55 | 0.92 | 0.53 | 54 | 0.50 | 16 |
| SEQ ID NO.:260 | 1 | 0.52 | 0.55 | 0.91 | 0.52 | 53 | 0.51 | 16 |
| SEQ ID NO.:261 | 76 | 0.53 | 0.54 | 0.91 | 0.52 | 53 | 0.57 | 17 |
| SEQ ID NO.:262 | 55 | 0.54 | 0.54 | 0.91 | 0.52 | 53 | 0.57 | 17 |
| SEQ ID NO.:263 | 48 | 0.53 | 0.53 | 0.91 | 0.52 | 53 | 0.53 | 17 |

*FIG. 30a-1*

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|
| D | I | L | L | T | Q | S | P | V | I | L | S | V | S | P | G | E | R | V | S |
| D | I | L | L | T | Q | S | P | G | T | L | S | L | S | P | G | E | R | V | T |
| D | I | L | L | T | Q | S | P | A | T | L | S | L | S | P | G | E | R | V | T |
| D | I | L | L | T | Q | S | P | A | T | L | S | L | S | P | G | E | R | V | T |
| D | I | L | L | T | Q | S | P | A | T | L | S | V | S | P | G | E | R | A | T |
| D | I | L | L | T | Q | S | P | S | S | L | S | A | S | V | G | D | R | V | T |
| D | I | L | L | T | Q | S | P | G | T | L | S | L | S | P | G | E | R | A | T |
| D | I | L | L | T | Q | S | P | S | F | L | S | A | S | V | G | D | R | V | T |
| D | I | L | L | T | Q | S | P | G | T | L | S | L | S | P | G | E | R | V | T |
| D | I | L | L | T | Q | S | P | A | T | L | S | V | S | P | G | E | R | A | T |
| D | I | L | L | T | Q | S | P | A | T | L | S | V | S | P | G | E | R | A | T |
| D | I | L | L | T | Q | S | P | A | T | L | S | L | S | P | G | E | R | V | T |
| D | I | L | L | T | Q | S | P | A | F | L | S | V | T | P | G | E | R | A | T |
| D | I | L | L | T | Q | S | P | A | T | L | S | V | S | P | G | E | R | A | T |
| D | I | L | L | T | Q | S | P | A | T | L | S | L | S | P | G | E | R | V | T |
| D | I | L | L | T | Q | S | P | S | S | L | S | A | S | V | G | D | R | V | T |
| D | I | L | L | T | Q | S | P | S | F | L | S | A | S | V | G | D | R | V | T |
| D | I | L | L | T | Q | S | P | G | T | L | S | L | S | P | G | E | R | V | T |
| D | I | L | L | T | Q | S | P | A | T | L | S | V | S | P | G | E | R | A | T |
| D | I | L | L | T | Q | S | P | G | T | L | S | L | S | P | G | E | R | A | T |
| D | I | L | L | T | Q | S | P | A | T | L | S | V | S | P | G | E | R | A | T |
| D | I | L | L | T | Q | S | P | G | T | L | S | L | S | P | G | E | R | V | T |
| D | I | L | L | T | Q | S | P | A | T | L | S | L | S | P | G | E | R | V | T |
| D | I | L | L | T | Q | S | P | A | T | L | S | L | S | P | G | E | R | V | T |
| D | I | L | L | T | Q | S | P | A | T | L | S | V | S | P | G | E | R | A | T |
| D | I | L | L | T | Q | S | P | A | T | L | S | L | S | P | G | E | R | V | T |
| D | I | L | L | T | Q | S | P | A | T | L | S | V | S | P | G | E | R | A | T |

*FIG. 30a-2*

| 21 | 22 | 23 | 24 | 25 | 26 | 27 | 28 | 29 | 30 | | | | | | 31 | 32 | 33 | 34 |
|----|----|----|----|----|----|----|----|----|----|---|---|---|---|---|----|----|----|----|
| F | S | C | R | A | S | Q | S | I | G | — | — | — | — | — | T | N | I | H |
| | | | | | | | | | | | | | | | | | | |
| | L | S | C | R | A | S | Q | S | I | G | — | — | — | — | — | T | N | I | H |
| | L | S | C | R | A | S | Q | S | I | G | — | — | — | — | — | T | N | I | H |
| | L | S | C | R | A | S | Q | S | I | G | — | — | — | — | — | T | N | I | H |
| | L | S | C | R | A | S | Q | S | I | G | — | — | — | — | — | T | N | I | H |
| | I | T | C | R | A | S | Q | S | I | G | — | — | — | — | — | T | N | I | H |
| | L | S | C | R | A | S | Q | S | I | G | — | — | — | — | — | T | N | I | H |
| | I | T | C | R | A | S | Q | S | I | G | — | — | — | — | — | T | N | I | H |
| | L | S | C | R | A | S | Q | S | I | G | — | — | — | — | — | T | N | I | H |
| | L | S | C | R | A | S | Q | S | I | G | — | — | — | — | — | T | N | I | H |
| | L | S | C | R | A | S | Q | S | I | G | — | — | — | — | — | T | N | I | H |
| | L | S | C | R | A | S | Q | S | I | G | — | — | — | — | — | T | N | I | H |
| | L | S | C | R | A | S | Q | S | I | G | — | — | — | — | — | T | N | I | H |
| | L | S | C | R | A | S | Q | S | I | G | — | — | — | — | — | T | N | I | H |
| | L | S | C | R | A | S | Q | S | I | G | — | — | — | — | — | T | N | I | H |
| | I | T | C | R | A | S | Q | S | I | G | — | — | — | — | — | T | N | I | H |
| | I | T | C | R | A | S | Q | S | I | G | — | — | — | — | — | T | N | I | H |
| | L | S | C | R | A | S | Q | S | I | G | — | — | — | — | — | T | N | I | H |
| | L | S | C | R | A | S | Q | S | I | G | — | — | — | — | — | T | N | I | H |
| | L | S | C | R | A | S | Q | S | I | G | — | — | — | — | — | T | N | I | H |
| | L | S | C | R | A | S | Q | S | I | G | — | — | — | — | — | T | N | I | H |
| | L | S | C | R | A | S | Q | S | I | G | — | — | — | — | — | T | N | I | H |
| | L | S | C | R | A | S | Q | S | I | G | — | — | — | — | — | T | N | I | H |
| | L | S | C | R | A | S | Q | S | I | G | — | — | — | — | — | T | N | I | H |
| | L | S | C | R | A | S | Q | S | I | G | — | — | — | — | — | T | N | I | H |
| | L | S | C | R | A | S | Q | S | I | G | — | — | — | — | — | T | N | I | H |

*FIG. 30a-3*

| 35 | 36 | 37 | 38 | 39 | 40 | 41 | 42 | 43 | 44 | 45 | 46 | 47 | 48 | 49 | 50 | 51 | 52 | 53 | 54 |
|----|----|----|----|----|----|----|----|----|----|----|----|----|----|----|----|----|----|----|----|
| W | Y | Q | Q | R | T | N | G | S | P | R | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | L | Q | K | P | G | K | S | P | K | L | L | I | K | Y | A | S | E | S |
| W | Y | L | Q | K | P | G | K | S | P | K | L | L | I | K | Y | A | S | E | S |
| W | Y | L | Q | K | P | G | Q | S | P | Q | L | L | I | K | Y | A | S | E | S |

*FIG. 30a-4*

| 55 | 56 | 57 | 58 | 59 | 60 | 61 | 62 | 63 | 64 | 65 | 66 | 67 | 68 | 69 | 70 | 71 | 72 | 73 | 74 |
|----|----|----|----|----|----|----|----|----|----|----|----|----|----|----|----|----|----|----|----|
|    |    |    |    |    |    |    |    |    |    |    |    |    |    |    |    |    |    |    |    |
| I  | S  | G  | I  | P  | S  | R  | F  | S  | G  | S  | G  | S  | G  | T  | D  | F  | T  | L  | S  |
|    |    |    |    |    |    |    |    |    |    |    |    |    |    |    |    |    |    |    |    |
| I  | S  | G  | I  | P  | S  | R  | F  | S  | G  | S  | G  | S  | G  | T  | D  | F  | T  | L  | T  |
| I  | S  | G  | I  | P  | S  | R  | F  | S  | G  | S  | G  | S  | G  | T  | D  | F  | T  | L  | T  |
| I  | S  | G  | I  | P  | S  | R  | F  | S  | G  | S  | G  | S  | G  | T  | D  | F  | T  | L  | T  |
| I  | S  | G  | I  | P  | S  | R  | F  | S  | G  | S  | G  | S  | G  | T  | D  | F  | T  | L  | T  |
| I  | S  | G  | I  | P  | S  | R  | F  | S  | G  | S  | G  | S  | G  | T  | D  | F  | T  | L  | T  |
| I  | S  | G  | I  | P  | S  | R  | F  | S  | G  | S  | G  | S  | G  | T  | D  | F  | T  | L  | T  |
| I  | S  | G  | I  | P  | S  | R  | F  | S  | G  | S  | G  | S  | G  | T  | D  | F  | T  | L  | T  |
| I  | S  | G  | I  | P  | S  | R  | F  | S  | G  | S  | G  | S  | G  | T  | D  | F  | T  | L  | T  |
| I  | S  | G  | I  | P  | S  | R  | F  | S  | G  | S  | G  | S  | G  | T  | D  | F  | T  | L  | T  |
| I  | S  | G  | I  | P  | S  | R  | F  | S  | G  | S  | G  | S  | G  | T  | D  | F  | T  | L  | T  |
| I  | S  | G  | I  | P  | S  | R  | F  | S  | G  | S  | G  | S  | G  | T  | D  | F  | T  | L  | T  |
| I  | S  | G  | I  | P  | S  | R  | F  | S  | G  | S  | G  | S  | G  | T  | D  | F  | T  | L  | T  |
| I  | S  | G  | I  | P  | S  | R  | F  | S  | G  | S  | G  | S  | G  | T  | D  | F  | T  | L  | T  |
| I  | S  | G  | I  | P  | S  | R  | F  | S  | G  | S  | G  | S  | G  | T  | D  | F  | T  | L  | T  |
| I  | S  | G  | I  | P  | S  | R  | F  | S  | G  | S  | G  | S  | G  | T  | D  | F  | T  | L  | T  |
| I  | S  | G  | I  | P  | S  | R  | F  | S  | G  | S  | G  | S  | G  | T  | D  | F  | T  | L  | T  |
| I  | S  | G  | I  | P  | S  | R  | F  | S  | G  | S  | G  | S  | G  | T  | D  | F  | T  | L  | T  |
| I  | S  | G  | I  | P  | S  | R  | F  | S  | G  | S  | G  | S  | G  | T  | D  | F  | T  | L  | T  |
| I  | S  | G  | I  | P  | S  | R  | F  | S  | G  | S  | G  | S  | G  | T  | D  | F  | T  | L  | T  |
| I  | S  | G  | I  | P  | S  | R  | F  | S  | G  | S  | G  | S  | G  | T  | D  | F  | T  | L  | T  |
| I  | S  | G  | I  | P  | S  | R  | F  | S  | G  | S  | G  | S  | G  | T  | D  | F  | T  | L  | T  |
| I  | S  | G  | I  | P  | S  | R  | F  | S  | G  | S  | G  | S  | G  | T  | D  | F  | T  | L  | T  |
| I  | S  | G  | I  | P  | S  | R  | F  | S  | G  | S  | G  | S  | G  | T  | D  | F  | T  | L  | T  |
| I  | S  | G  | I  | P  | S  | R  | F  | S  | G  | S  | G  | S  | G  | T  | D  | F  | T  | L  | T  |
| I  | S  | G  | I  | P  | S  | R  | F  | S  | G  | S  | G  | S  | G  | T  | D  | F  | T  | L  | T  |

*FIG. 30a-5*

| 75 | 76 | 77 | 78 | 79 | 80 | 81 | 82 | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|
| I | N | S | V | E | S | E | D | I | A | D | Y | Y | C | Q | Q | N | N | N | W |
| I | S | S | L | E | P | E | D | F | A | V | Y | Y | C | Q | Q | N | N | N | W |
| I | S | S | L | Q | P | E | D | F | A | T | Y | Y | C | Q | Q | N | N | N | W |
| I | S | S | L | E | P | E | D | F | A | V | Y | Y | C | Q | Q | N | N | N | W |
| I | S | S | L | E | P | E | D | F | A | V | Y | Y | C | Q | Q | N | N | N | W |
| I | S | S | L | Q | S | E | D | F | A | V | Y | Y | C | Q | Q | N | N | N | W |
| I | N | S | L | E | A | E | D | A | A | T | Y | Y | C | Q | Q | N | N | N | W |
| I | N | S | L | E | A | E | D | A | A | T | Y | Y | C | Q | Q | N | N | N | W |
| I | N | S | L | E | A | E | D | A | A | T | Y | Y | C | Q | Q | N | N | N | W |
| I | S | S | L | Q | P | E | D | I | A | T | Y | Y | C | Q | Q | N | N | N | W |
| I | N | S | L | E | A | E | D | A | A | T | Y | Y | C | Q | Q | N | N | N | W |
| I | N | S | L | E | A | E | D | A | A | T | Y | Y | C | Q | Q | N | N | N | W |
| I | N | S | L | E | A | E | D | V | A | V | Y | Y | C | Q | Q | N | N | N | W |
| I | N | S | L | E | A | E | D | V | A | V | Y | Y | C | Q | Q | N | N | N | W |
| I | N | N | I | E | S | E | D | A | A | T | Y | Y | C | Q | Q | N | N | N | W |
| I | N | N | I | E | S | E | D | A | A | T | Y | Y | C | Q | Q | N | N | N | W |
| I | N | N | I | E | S | E | D | F | A | V | Y | Y | C | Q | Q | N | N | N | W |
| I | N | N | I | E | S | E | D | F | A | V | Y | Y | C | Q | Q | N | N | N | W |
| I | N | N | I | E | S | E | D | A | A | T | Y | Y | C | Q | Q | N | N | N | W |
| I | N | N | I | E | S | E | D | A | A | T | Y | Y | C | Q | Q | N | N | N | W |
| I | N | N | I | E | S | E | D | A | A | T | Y | Y | C | Q | Q | N | N | N | W |
| I | N | N | I | E | S | E | D | A | A | T | Y | Y | C | Q | Q | N | N | N | W |
| I | N | N | I | E | S | E | D | F | A | V | Y | Y | C | Q | Q | N | N | N | W |
| I | S | S | L | E | A | E | D | A | A | T | Y | Y | C | Q | Q | N | N | N | W |
| I | N | S | L | E | A | E | D | A | A | T | Y | Y | C | Q | Q | N | N | N | W |
| I | N | S | L | E | A | E | D | A | A | T | Y | Y | C | Q | Q | N | N | N | W |

*FIG. 30a-6*

| | | 95 | 96 | 97 | 98 | 99 | 100 | 101 | 102 | 103 | 104 | 105 | 106 | 107 |
|---|---|---|---|---|---|---|---|---|---|---|---|---|---|---|
| – | – | P | T | T | F | G | Q | G | T | K | V | E | I | K |
| – | – | P | T | T | F | G | Q | G | T | K | X | E | I | K |
| – | – | P | T | T | F | G | Q | G | T | K | X | E | I | K |
| – | – | P | T | T | F | G | Q | G | T | K | X | E | I | K |
| – | – | P | T | T | F | G | Q | G | T | K | X | E | I | K |
| – | – | P | T | T | F | G | Q | G | T | K | X | E | I | K |
| – | – | P | T | T | F | G | Q | G | T | K | X | E | I | K |
| – | – | P | T | T | F | G | Q | G | T | K | X | E | I | K |
| – | – | P | T | T | F | G | Q | G | T | K | X | E | I | K |
| – | – | P | T | T | F | G | Q | G | T | K | X | E | I | K |
| – | – | P | T | T | F | G | Q | G | T | K | X | E | I | K |
| – | – | P | T | T | F | G | Q | G | T | K | X | E | I | K |
| – | – | P | T | T | F | G | Q | G | T | K | X | E | I | K |
| – | – | P | T | T | F | G | Q | G | T | K | X | E | I | K |
| – | – | P | T | T | F | G | Q | G | T | K | X | E | I | K |
| – | – | P | T | T | F | G | Q | G | T | K | X | E | I | K |
| – | – | P | T | T | F | G | Q | G | T | K | X | E | I | K |
| – | – | P | T | T | F | G | Q | G | T | K | X | E | I | K |
| – | – | P | T | T | F | G | Q | G | T | K | X | E | I | K |
| – | – | P | T | T | F | G | Q | G | T | K | X | E | I | K |
| – | – | P | T | T | F | G | Q | G | T | K | X | E | I | K |
| – | – | P | T | T | F | G | Q | G | T | K | X | E | I | K |
| – | – | P | T | T | F | G | Q | G | T | K | X | E | I | K |
| – | – | P | T | T | F | G | Q | G | T | K | X | E | I | K |
| – | – | P | T | T | F | G | Q | G | T | K | X | E | I | K |

*FIG. 30a-7*

| FIG. 30a-1 | FIG. 30a-2 | FIG. 30a-3 | FIG. 30a-4 | FIG. 30a-5 | FIG. 30a-6 | FIG. 30a-7 |
|---|---|---|---|---|---|---|

*FIG. 30a*

C225 VH HEC Calculation 2

| | Iter | Structural Consensus | Structural Precedence | HSC | HSS | N$_g$max | FRH | Kabat WT Muts |
|---|---|---|---|---|---|---|---|---|
| (WT) SEQ ID NO.:235 | | | | | | | | |
| SEQ ID NO.:264 | 23 | 0.48 | 0.51 | 0.79 | 0.42 | 47 | 0.40 | 20 |
| SEQ ID NO.:265 | 5 | 0.49 | 0.51 | 0.79 | 0.42 | 47 | 0.49 | 20 |
| SEQ ID NO.:266 | 7 | 0.47 | 0.50 | 0.79 | 0.42 | 46 | 0.41 | 20 |
| SEQ ID NO.:267 | 3 | 0.48 | 0.50 | 0.79 | 0.42 | 46 | 0.46 | 20 |
| SEQ ID NO.:268 | 4 | 0.48 | 0.50 | 0.79 | 0.42 | 47 | 0.38 | 20 |
| SEQ ID NO.:269 | 27 | 0.47 | 0.50 | 0.79 | 0.42 | 46 | 0.39 | 20 |
| SEQ ID NO.:270 | 9 | 0.47 | 0.49 | 0.79 | 0.43 | 48 | 0.40 | 21 |
| SEQ ID NO.:271 | 2 | 0.48 | 0.49 | 0.79 | 0.43 | 48 | 0.50 | 21 |
| SEQ ID NO.:272 | 49 | 0.47 | 0.49 | 0.78 | 0.41 | 45 | 0.40 | 20 |
| SEQ ID NO.:273 | 100 | 0.47 | 0.49 | 0.79 | 0.43 | 48 | 0.38 | 21 |
| SEQ ID NO.:274 | 1 | 0.46 | 0.43 | 0.79 | 0.43 | 48 | 0.35 | 23 |

*FIG. 30b-1*

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|----|----|----|----|----|----|----|----|----|----|----|
| Q | V | Q | L | K | Q | S | G | P | G | L | V | Q | P | S | Q | S | L | S | I |
| Q | V | Q | L | Q | Q | S | G | P | G | L | V | K | P | S | Q | T | L | S | L |
| Q | V | Q | L | Q | Q | S | G | P | G | L | V | K | P | S | Q | T | L | S | L |
| Q | V | Q | L | Q | Q | S | G | P | G | L | V | K | P | S | Q | T | L | S | L |
| Q | V | Q | L | Q | Q | S | G | P | G | L | V | K | P | S | Q | T | L | S | L |
| Q | V | Q | L | Q | Q | S | G | P | G | L | V | K | P | S | Q | T | L | S | L |
| Q | V | Q | L | Q | Q | S | G | P | G | L | V | K | P | S | Q | T | L | S | L |
| Q | V | Q | L | Q | Q | S | G | P | G | L | V | K | P | S | Q | T | L | S | L |
| Q | V | Q | L | Q | Q | S | G | P | G | L | V | K | P | S | Q | T | L | S | L |
| Q | V | Q | L | Q | Q | S | G | P | G | L | V | K | P | S | Q | T | L | S | L |
| Q | V | Q | L | Q | Q | S | G | P | G | L | V | K | P | S | Q | T | L | S | L |
| Q | V | Q | L | Q | Q | S | G | P | G | L | V | K | P | S | Q | T | L | S | L |

*FIG. 30b-2*

| 21 | 22 | 23 | 24 | 25 | 26 | 27 | 28 | 29 | 30 | 31 | | 32 | 33 | 34 | 35 | 36 | 37 | 38 |
|---|---|---|---|---|---|---|---|---|---|---|---|---|---|---|---|---|---|---|
| T | C | T | V | S | G | F | S | L | T | N | _ | _ | Y | G | V | H | W | V | R |
| T | C | T | V | S | G | F | S | L | T | N | _ | _ | Y | G | V | H | W | V | R |
| T | C | T | V | S | G | F | S | L | T | N | _ | _ | Y | G | V | H | W | V | R |
| T | C | T | V | S | G | F | S | L | T | N | _ | _ | Y | G | V | H | W | V | R |
| T | C | T | V | S | G | F | S | L | T | N | _ | _ | Y | G | V | H | W | V | R |
| T | C | T | V | S | G | F | S | L | T | N | _ | _ | Y | G | V | H | W | V | R |
| T | C | T | V | S | G | F | S | L | T | N | _ | _ | Y | G | V | H | W | V | R |
| T | C | T | V | S | G | F | S | L | T | N | _ | _ | Y | G | V | H | W | V | R |
| T | C | T | V | S | G | F | S | L | T | N | _ | _ | Y | G | V | H | W | V | R |
| T | C | T | V | S | G | F | S | L | T | N | _ | _ | Y | G | V | H | W | V | R |
| T | C | T | V | S | G | F | S | L | T | N | _ | _ | Y | G | V | H | W | V | R |

*FIG. 30b-3*

| 39 | 40 | 41 | 42 | 43 | 44 | 45 | 46 | 47 | 48 | 49 | 50 | 51 | 52 | 53 | 54 | | | | 55 |
|---|---|---|---|---|---|---|---|---|---|---|---|---|---|---|---|---|---|---|---|
| Q | S | P | G | K | G | L | E | W | L | G | V | I | W | S | G | — | — | — | G |
| Q | A | P | G | K | G | L | E | W | V | A | V | I | W | S | G | — | — | — | G |
| Q | A | P | G | K | G | L | E | W | V | A | V | I | W | S | G | — | — | — | G |
| Q | A | P | G | K | G | L | E | W | V | A | V | I | W | S | G | — | — | — | G |
| Q | A | P | G | K | G | L | E | W | V | A | V | I | W | S | G | — | — | — | G |
| Q | A | P | G | K | G | L | E | W | V | A | V | I | W | S | G | | | | G |
| Q | A | P | G | K | G | L | E | W | V | A | V | I | W | S | G | — | — | — | G |
| Q | A | P | G | K | G | L | E | W | V | A | V | I | W | S | G | — | — | — | G |
| Q | A | P | G | K | G | L | E | W | V | A | V | I | W | S | G | — | — | — | G |
| Q | A | P | G | K | G | L | E | W | V | A | V | I | W | S | G | — | — | — | G |
| Q | A | P | G | K | G | L | E | W | V | A | V | I | W | S | G | | | | G |
| Q | A | P | G | K | G | L | E | W | V | A | V | I | W | S | G | — | — | — | G |

FIG. 30b-4

| 56 | 57 | 58 | 59 | 60 | 61 | 62 | 63 | 64 | 65 | 66 | 67 | 68 | 69 | 70 | 71 | 72 | 73 | 74 | 75 |
|----|----|----|----|----|----|----|----|----|----|----|----|----|----|----|----|----|----|----|----|
| N | T | D | Y | N | T | P | F | T | S | R | L | S | I | N | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |

FIG. 30b-5

| 76 | 77 | 78 | 79 | 80 | 81 | 82 | 82a | 82b | 82c | 83 | 84 | 85 | 86 | 87 | 88 | 89 | 90 | 91 | 92 |
|----|----|----|----|----|----|----|-----|-----|-----|----|----|----|----|----|----|----|----|----|----|
| S | Q | V | F | F | K | M | N | S | L | Q | S | N | D | T | A | I | Y | Y | C |
| S | Q | V | V | L | Q | M | N | S | L | K | T | E | D | T | A | V | Y | Y | C |
| S | Q | V | V | L | Q | M | N | S | L | R | A | E | D | T | A | V | Y | Y | C |
| S | Q | V | V | L | T | M | N | S | L | K | T | E | D | T | A | V | Y | Y | C |
| S | Q | V | V | L | T | M | N | S | L | R | A | E | D | T | A | V | Y | Y | C |
| S | Q | V | V | L | Q | M | N | S | L | R | A | G | D | T | A | V | Y | Y | C |
| S | Q | V | V | L | T | M | N | S | L | R | A | G | D | T | A | V | Y | Y | C |
| S | I | V | Y | L | Q | M | N | S | L | K | T | E | D | T | A | V | Y | Y | C |
| S | I | V | Y | L | Q | M | N | S | L | R | A | E | D | T | A | V | Y | Y | C |
| S | Q | V | V | L | T | M | R | S | L | R | S | D | D | T | A | V | Y | Y | C |
| S | I | V | Y | L | Q | M | N | S | L | R | A | G | D | T | A | V | Y | Y | C |
| S | T | V | Y | L | Q | W | S | S | L | K | A | S | D | T | A | M | Y | Y | C |

*FIG. 30b-6*

| 93 | 94 | 95 | 96 | 97 | | | | 98 | 99 | 100 | 100a | 100b | 100c | 101 | 102 | 103 | 104 | 105 | 106 |
|---|---|---|---|---|---|---|---|---|---|---|---|---|---|---|---|---|---|---|---|
| A | R | A | L | T | – | – | – | Y | Y | D | Y | E | F | A | Y | W | G | Q | G |
| A | R | A | L | T | – | – | – | Y | Y | D | Y | E | F | A | Y | W | G | Q | G |
| A | R | A | L | T | – | – | – | Y | Y | D | Y | E | F | A | Y | W | G | Q | G |
| A | R | A | L | T | – | – | – | Y | Y | D | Y | E | F | A | Y | W | G | Q | G |
| A | R | A | L | T | – | – | – | Y | Y | D | Y | E | F | A | Y | W | G | Q | G |
| A | R | A | L | T | – | – | – | Y | Y | D | Y | E | F | A | Y | W | G | Q | G |
| A | R | A | L | T | – | – | – | Y | Y | D | Y | E | F | A | Y | W | G | Q | G |
| A | R | A | L | T | – | – | – | Y | Y | D | Y | E | F | A | Y | W | G | Q | G |
| A | R | A | L | T | – | – | – | Y | Y | D | Y | E | F | A | Y | W | G | Q | G |
| A | R | A | L | T | – | – | – | Y | Y | D | Y | E | F | A | Y | W | G | Q | G |
| A | R | A | L | T | – | – | – | Y | Y | D | Y | E | F | A | Y | W | G | Q | G |
| A | R | A | L | T | – | – | – | Y | Y | D | Y | E | F | A | Y | W | G | Q | G |

FIG. 30b-7

| 107 | 108 | 109 | 110 | 111 | 112 | 113 |
|---|---|---|---|---|---|---|
| T | L | V | T | V | S | A |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |

*FIG. 30b-8*

| FIG. 30b-1 | FIG. 30b-2 | FIG. 30b-3 | FIG. 30b-4 | FIG. 30b-5 | FIG. 30b-6 | FIG. 30b-7 | FIG. 30b-8 |

*FIG. 30b*

FIG. 31a-1    C225 VL HEC Calculation 2

(WT) SEQ ID NO.:234

| | Iter | Structural Consensus | Structural Precedence | HSC | HSS | N₉max | FRH | Muts | Kabat WT Cluster |
|---|---|---|---|---|---|---|---|---|---|
| SEQ ID NO.:275 | 1 | 0.54 | 0.58 | 0.92 | 0.57 | 58 | 0.55 | 21 | 3.13 |
| SEQ ID NO.:276 | 12 | 0.54 | 0.57 | 0.92 | 0.57 | 58 | 0.55 | 22 | 3.63 |
| SEQ ID NO.:277 | 51 | 0.54 | 0.57 | 0.92 | 0.57 | 58 | 0.50 | 22 | 3.63 |
| SEQ ID NO.:278 | 48 | 0.53 | 0.55 | 0.92 | 0.57 | 58 | 0.55 | 21 | 4.13 |
| SEQ ID NO.:279 | 28 | 0.52 | 0.55 | 0.92 | 0.58 | 60 | 0.75 | 22 | 4.13 |
| SEQ ID NO.:280 | 35 | 0.52 | 0.52 | 0.92 | 0.58 | 60 | 0.75 | 23 | 4.75 |
| SEQ ID NO.:281 | 49 | 0.53 | 0.55 | 0.92 | 0.58 | 60 | 0.75 | 23 | 3.63 |
| SEQ ID NO.:282 | 38 | 0.53 | 0.60 | 0.92 | 0.57 | 58 | 0.78 | 19 | 5.25 |
| SEQ ID NO.:283 | 2 | 0.56 | 0.59 | 0.92 | 0.58 | 60 | 0.50 | 22 | 3.50 |
| SEQ ID NO.:284 | 17 | 0.57 | 0.60 | 0.92 | 0.58 | 60 | 0.50 | 22 | 3.25 |
| SEQ ID NO.:285 | 47 | 0.58 | 0.61 | 0.92 | 0.58 | 60 | 0.50 | 22 | 4.25 |
| SEQ ID NO.:286 | 15 | 0.57 | 0.57 | 0.92 | 0.58 | 60 | 0.72 | 20 | 3.75 |
| SEQ ID NO.:287 | 32 | 0.56 | 0.57 | 0.92 | 0.58 | 60 | 0.72 | 20 | 4.00 |
| SEQ ID NO.:288 | 40 | 0.57 | 0.58 | 0.92 | 0.58 | 60 | 0.52 | 22 | 3.75 |
| SEQ ID NO.:289 | 55 | 0.59 | 0.61 | 0.92 | 0.58 | 60 | 0.58 | 22 | 4.50 |
| SEQ ID NO.:290 | 21 | 0.54 | 0.50 | 0.92 | 0.56 | 58 | 0.48 | 22 | 6.25 |
| SEQ ID NO.:291 | 3 | 0.54 | 0.57 | 0.92 | 0.57 | 58 | 0.45 | 19 | 4.78 |
| SEQ ID NO.:292 | 4 | 0.53 | 0.59 | 0.92 | 0.57 | 58 | 0.45 | 19 | 4.65 |
| SEQ ID NO.:293 | 5 | 0.54 | 0.58 | 0.92 | 0.57 | 58 | 0.45 | 18 | 4.10 |
| SEQ ID NO.:294 | 7 | 0.55 | 0.60 | 0.92 | 0.57 | 58 | 0.47 | 20 | 3.75 |
| SEQ ID NO.:295 | 14 | 0.55 | 0.61 | 0.92 | 0.57 | 58 | 0.45 | 19 | 3.68 |
| SEQ ID NO.:296 | 20 | 0.54 | 0.58 | 0.92 | 0.57 | 58 | 0.50 | 18 | 4.30 |
| SEQ ID NO.:297 | 22 | 0.54 | 0.58 | 0.92 | 0.57 | 58 | 0.45 | 18 | 4.38 |
| SEQ ID NO.:298 | 23 | 0.54 | 0.57 | 0.92 | 0.57 | 58 | 0.40 | 20 | 4.38 |
| SEQ ID NO.:299 | 25 | 0.54 | 0.57 | 0.92 | 0.57 | 58 | 0.40 | 21 | 4.45 |
| SEQ ID NO.:300 | 27 | 0.55 | 0.61 | 0.92 | 0.57 | 58 | 0.50 | 19 | 3.88 |
| SEQ ID NO.:301 | 30 | 0.54 | 0.61 | 0.92 | 0.57 | 58 | 0.47 | 19 | 4.38 |
| SEQ ID NO.:302 | 33 | 0.54 | 0.55 | 0.92 | 0.57 | 58 | 0.41 | 19 | 4.80 |
| SEQ ID NO.:303 | 34 | 0.54 | 0.61 | 0.92 | 0.57 | 58 | 0.45 | 18 | 4.20 |
| SEQ ID NO.:304 | 36 | 0.55 | 0.59 | 0.92 | 0.57 | 58 | 0.57 | 19 | 4.15 |
| SEQ ID NO.:305 | 37 | 0.55 | 0.59 | 0.92 | 0.57 | 58 | 0.47 | 19 | 3.95 |
| SEQ ID NO.:306 | 39 | 0.55 | 0.59 | 0.92 | 0.57 | 58 | 0.52 | 19 | 3.80 |
| SEQ ID NO.:307 | 41 | 0.55 | 0.59 | 0.92 | 0.57 | 58 | 0.41 | 20 | 4.43 |
| SEQ ID NO.:308 | 43 | 0.54 | 0.58 | 0.92 | 0.57 | 58 | 0.34 | 19 | 4.85 |
| SEQ ID NO.:309 | 45 | 0.54 | 0.59 | 0.92 | 0.57 | 58 | 0.45 | 20 | 4.58 |
| SEQ ID NO.:310 | 46 | 0.54 | 0.59 | 0.92 | 0.57 | 58 | 0.45 | 21 | 4.65 |
| SEQ ID NO.:311 | 53 | 0.56 | 0.60 | 0.92 | 0.57 | 58 | 0.47 | 19 | 3.58 |
| SEQ ID NO.:312 | 54 | 0.55 | 0.59 | 0.92 | 0.57 | 58 | 0.45 | 18 | 4.00 |
| SEQ ID NO.:313 | 56 | 0.54 | 0.60 | 0.92 | 0.57 | 58 | 0.45 | 18 | 4.58 |

FIG. 31a-2

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|----|----|----|----|----|----|----|----|----|----|----|
|   |   | D | I | L | L | T | Q | S | P  | V  | I  | L  | S  | V  | S  | P  | G  | E  | R  | V | S |
|   |   | D | I | L | L | T | Q | S | P  | A  | F  | L  | S  | V  | T  | P  | G  | E  | K | V | T |
|   |   | D | I | L | L | T | Q | S | P  | A  | F  | L  | S  | V  | T  | P  | G  | E  | K | V | T |
|   |   | D | I | L | L | T | Q | S | P  | A  | F  | L  | S  | V  | T  | P  | G  | E  | K | V | T |
|   |   | D | I | L | L | T | Q | S | P  | A  | F  | L  | S  | V  | T  | P  | G  | E  | K | V | T |
|   |   | D | I | L | L | T | Q | S | P  | D  | F  | Q  | S  | V  | T  | P  | K  | E  | K | V | T |
|   |   | D | I | L | L | T | Q | S | P  | D  | F  | Q  | S  | V  | T  | P  | K  | E  | K | V | T |
|   |   | D | I | L | L | T | Q | S | P  | D  | F  | Q  | S  | V  | T  | P  | K  | E  | K | V | T |
|   |   | D | I | L | L | T | Q | S | P  | A  | F  | L  | S  | V  | T  | P  | G  | E  | K | V |   |
|   |   | D | I | L | L | T | Q | S | P  | S  | F  | L  | S  | A  | S  | V  | G  | D  | R | V | T |
|   |   | D | I | L | L | T | Q | S | P  | S  | S  | L  | S  | A  | S  | V  | G  | D  | R | V | T |
|   |   | D | I | L | L | T | Q | S | P  | S  | F  | L  | S  | A  | S  | V  | G  | D  | R | V | T |
|   |   | D | I | L | L | T | Q | S | P  | S  | S  | L  | S  | A  | S  | V  | G  | D  | R | V | T |
|   |   | D | I | L | L | T | Q | S | P  | S  | F  | L  | S  | A  | S  | V  | G  | D  | R | V | T |
|   |   | D | I | L | L | T | Q | S | P  | S  | S  | L  | S  | A  | S  | V  | G  | D  | R | V | T |
|   |   | D | I | L | L | T | Q | S | P  | S  | S  | L  | S  | A  | S  | V  | G  | D  | R | V | T |
|   |   | D | I | L | L | T | Q | S | P  | S  | S  | L  | S  | A  | S  | V  | G  | D  | R | V | T |
|   |   | D | I | L | L | T | Q | S | P  | A  | T  | L  | S  | L  | S  | P  | G  | E  | R | V | T |
|   |   | D | I | L | L | T | Q | S | P  | A  | T  | L  | S  | V  | S  | P  | G  | E  | R | A | T |
|   |   | D | I | L | L | T | Q | S | P  | A  | T  | L  | S  | V  | S  | P  | G  | E  | R | A | T |
|   |   | D | I | L | L | T | Q | S | P  | G  | T  | L  | S  | L  | S  | P  | G  | E  | R | A | T |
|   |   | D | I | L | L | T | Q | S | P  | A  | T  | L  | S  | V  | S  | P  | G  | E  | R | A | T |
|   |   | D | I | L | L | T | Q | S | P  | A  | T  | L  | S  | V  | S  | P  | G  | E  | R | A | T |
|   |   | D | I | L | L | T | Q | S | P  | G  | T  | L  | S  | L  | S  | P  | G  | E  | R | V | T |
|   |   | D | I | L | L | T | Q | S | P  | A  | T  | L  | S  | V  | S  | P  | G  | E  | R | A | T |
|   |   | D | I | L | L | T | Q | S | P  | G  | T  | L  | S  | L  | S  | P  | G  | E  | R | A | T |
|   |   | D | I | L | L | T | Q | S | P  | A  | T  | L  | S  | V  | S  | P  | G  | E  | R | A | T |
|   |   | D | I | L | L | T | Q | S | P  | G  | T  | L  | S  | L  | S  | P  | G  | E  | R | A | T |
|   |   | D | I | L | L | T | Q | S | P  | A  | T  | L  | S  | V  | S  | P  | G  | E  | R | A | T |
|   |   | D | I | L | L | T | Q | S | P  | A  | T  | L  | S  | L  | S  | P  | G  | E  | R | V | T |
|   |   | D | I | L | L | T | Q | S | P  | G  | T  | L  | S  | L  | S  | P  | G  | E  | R | V | T |
|   |   | D | I | L | L | T | Q | S | P  | G  | T  | L  | S  | L  | S  | P  | G  | E  | R | V | T |
|   |   | D | I | L | L | T | Q | S | P  | A  | T  | L  | S  | L  | S  | P  | G  | E  | R | A | T |
|   |   | D | I | L | L | T | Q | S | P  | A  | T  | L  | S  | L  | S  | P  | G  | E  | R | V | T |
|   |   | D | I | L | L | T | Q | S | P  | A  | T  | L  | S  | L  | S  | P  | G  | E  | R | V | T |
|   |   | D | I | L | L | T | Q | S | P  | A  | T  | L  | S  | V  | S  | P  | G  | E  | R | A | T |
|   |   | D | I | L | L | T | Q | S | P  | G  | T  | L  | S  | L  | S  | P  | G  | E  | R | A | T |
|   |   | D | I | L | L | T | Q | S | P  | A  | T  | L  | S  | L  | S  | P  | G  | E  | R | V | T |
|   |   | D | I | L | L | T | Q | S | P  | A  | T  | L  | S  | L  | S  | P  | G  | E  | R | V | T |
|   |   | D | I | L | L | T | Q | S | P  | G  | T  | L  | S  | L  | S  | P  | G  | E  | R | V | T |

FIG. 31a-3

| 21 | 22 | 23 | 24 | 25 | 26 | 27 | 28 | 29 | 30 | | | | | 31 | 32 | 32 | 34 |
|---|---|---|---|---|---|---|---|---|---|---|---|---|---|---|---|---|---|
| F | S | C | R | A | S | Q | S | I | G | — | — | — | — | T | N | I | H |
| I | T | C | R | A | S | Q | S | I | G | — | — | — | — | T | N | I | H |
| I | T | C | R | A | S | Q | S | I | G | — | — | — | — | T | N | I | H |
| I | T | C | R | A | S | Q | S | I | G | — | — | — | — | T | N | I | H |
| I | T | C | R | A | S | Q | S | I | G | — | — | — | — | T | N | I | H |
| I | T | C | R | A | S | Q | S | I | G | — | — | — | — | T | N | I | H |
| I | T | C | R | A | S | Q | S | I | G | — | — | — | — | T | N | I | H |
| I | T | C | R | A | S | Q | S | I | G | — | — | — | — | T | N | I | H |
| I | T | C | R | A | S | Q | S | I | G | — | — | — | — | T | N | I | H |
| I | T | C | R | A | S | Q | S | I | G | — | — | — | — | T | N | I | H |
| I | T | C | R | A | S | Q | S | I | G | — | — | — | — | T | N | I | H |
| I | T | C | R | A | S | Q | S | I | G | — | — | — | — | T | N | I | H |
| I | T | C | R | A | S | Q | S | I | G | — | — | — | — | T | N | I | H |
| I | T | C | R | A | S | Q | S | I | G | — | — | — | — | T | N | I | H |
| I | T | C | R | A | S | Q | S | I | G | — | — | — | — | T | N | I | H |
| L | S | C | R | A | S | Q | S | I | G | — | — | — | — | T | N | I | H |
| L | S | C | R | A | S | Q | S | I | G | — | — | — | — | T | N | I | H |
| L | S | C | R | A | S | Q | S | I | G | — | — | — | — | T | N | I | H |
| L | S | C | R | A | S | Q | S | I | G | — | — | — | — | T | N | I | H |
| L | S | C | R | A | S | Q | S | I | G | — | — | — | — | T | N | I | H |
| L | S | C | R | A | S | Q | S | I | G | — | — | — | — | T | N | I | H |
| L | S | C | R | A | S | Q | S | I | G | — | — | — | — | T | N | I | H |
| L | S | C | R | A | S | Q | S | I | G | — | — | — | — | T | N | I | H |
| L | S | C | R | A | S | Q | S | I | G | — | — | — | — | T | N | I | H |
| L | S | C | R | A | S | Q | S | I | G | — | — | — | — | T | N | I | H |
| L | S | C | R | A | S | Q | S | I | G | — | — | — | — | T | N | I | H |
| L | S | C | R | A | S | Q | S | I | G | — | — | — | — | T | N | I | H |
| L | S | C | R | A | S | Q | S | I | G | — | — | — | — | T | N | I | H |
| L | S | C | R | A | S | Q | S | I | G | — | — | — | — | T | N | I | H |
| L | S | C | R | A | S | Q | S | I | G | — | — | — | — | T | N | I | H |
| L | S | C | R | A | S | Q | S | I | G | — | — | — | — | T | N | I | H |
| L | S | C | R | A | S | Q | S | I | G | — | — | — | — | T | N | I | H |
| L | S | C | R | A | S | Q | S | I | G | — | — | — | — | T | N | I | H |

FIG. 31a-4

| 35 | 36 | 37 | 38 | 39 | 40 | 41 | 42 | 43 | 44 | 45 | 46 | 47 | 48 | 49 | 50 | 51 | 52 | 53 | 54 |
|---|---|---|---|---|---|---|---|---|---|---|---|---|---|---|---|---|---|---|---|
| W | Y | Q | Q | R | T | N | G | S | P | R | L | L | I | K | Y | A | S | E | S |
| | | | | | | | | | | | | | | | | | | | |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |

FIG. 31a-5

| | 55 | 56 | 57 | 58 | 59 | 60 | 61 | 62 | 63 | 64 | 65 | 66 | 67 | 68 | 69 | 70 | 71 | 72 | 73 | 74 |
|---|---|---|---|---|---|---|---|---|---|---|---|---|---|---|---|---|---|---|---|---|
| | | | I | S | G | I | P | S | R | F | S | G | S | G | S | G | T | D | F | T | L | S |
| | | | I | S | G | I | P | S | R | F | S | G | S | G | S | G | T | D | F | T | L | T |
| | | | I | S | G | I | P | S | R | F | S | G | S | G | S | G | T | D | F | T | L | T |
| | | | I | S | G | I | P | S | R | F | S | G | S | G | S | G | T | D | F | T | F | T |
| | | | I | S | G | I | P | S | R | F | S | G | S | G | S | G | T | D | F | T | L | T |
| | | | I | S | G | I | P | S | R | F | S | G | S | G | S | G | T | D | F | T | L | T |
| | | | I | S | G | I | P | S | R | F | S | G | S | G | S | G | T | D | F | T | L | T |
| | | | I | S | G | I | P | S | R | F | S | G | S | G | S | G | T | D | F | T | L | T |
| | | | I | S | G | I | P | S | R | F | S | G | S | G | S | G | T | D | F | T | L | T |
| | | | I | S | G | I | P | S | R | F | S | G | S | G | S | G | T | D | F | T | L | T |
| | | | I | S | G | I | P | S | R | F | S | G | S | G | S | G | T | D | F | T | L | T |
| | | | I | S | G | I | P | S | R | F | S | G | S | G | S | G | T | D | F | T | L | T |
| | | | I | S | G | I | P | S | R | F | S | G | S | G | S | G | T | D | F | T | L | T |
| | | | I | S | G | I | P | S | R | F | S | G | S | G | S | G | T | D | F | T | F | T |
| | | | I | S | G | I | P | S | R | F | S | G | S | G | S | G | T | D | F | T | F | T |
| | | | I | S | G | I | P | S | R | F | S | G | S | G | S | G | T | D | F | T | L | K |
| | | | I | S | G | I | P | S | R | F | S | G | S | G | S | G | T | D | F | T | L | T |
| | | | I | S | G | I | P | S | R | F | S | G | S | G | S | G | T | D | F | T | L | T |
| | | | I | S | G | I | P | S | R | F | S | G | S | G | S | G | T | D | F | T | L | T |
| | | | I | S | G | I | P | S | R | F | S | G | S | G | S | G | T | D | F | T | L | T |
| | | | I | S | G | I | P | S | R | F | S | G | S | G | S | G | T | D | F | T | L | T |
| | | | I | S | G | I | P | S | R | F | S | G | S | G | S | G | T | D | F | T | L | T |
| | | | I | S | G | I | P | S | R | F | S | G | S | G | S | G | T | D | F | T | L | T |
| | | | I | S | G | I | P | S | R | F | S | G | S | G | S | G | T | D | F | T | L | T |
| | | | I | S | G | I | P | S | R | F | S | G | S | G | S | G | T | D | F | T | F | T |
| | | | I | S | G | I | P | S | R | F | S | G | S | G | S | G | T | D | F | T | F | T |
| | | | I | S | G | I | P | S | R | F | S | G | S | G | S | G | T | D | F | T | L | T |
| | | | I | S | G | I | P | S | R | F | S | G | S | G | S | G | T | D | F | T | F | T |
| | | | I | S | G | I | P | S | R | F | S | G | S | G | S | G | T | D | F | T | L | T |
| | | | I | S | G | I | P | S | R | F | S | G | S | G | S | G | T | D | F | T | L | T |
| | | | I | S | G | I | P | S | R | F | S | G | S | G | S | G | T | D | F | T | L | T |
| | | | I | S | G | I | P | S | R | F | S | G | S | G | S | G | T | D | F | T | L | T |
| | | | I | S | G | I | P | S | R | F | S | G | S | G | S | G | T | E | F | T | L | T |
| | | | I | S | G | I | P | S | R | F | S | G | S | G | S | G | T | E | F | T | L | T |
| | | | I | S | G | I | P | S | R | F | S | G | S | G | S | G | T | D | F | T | L | T |
| | | | I | S | G | I | P | S | R | F | S | G | S | G | S | G | T | D | F | T | L | T |
| | | | I | S | G | I | P | S | R | F | S | G | S | G | S | G | T | D | F | T | L | T |
| | | | I | S | G | I | P | S | R | F | S | G | S | G | S | G | T | D | F | T | L | T |
| | | | I | S | G | I | P | S | R | F | S | G | S | G | S | G | T | D | F | T | L | T |

FIG. 31a-6

| 75 | 76 | 77 | 78 | 79 | 80 | 81 | 82 | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|
| I | N | S | V | E | S | E | D | I | A | D | Y | Y | C | Q | Q | N | N | N | W |
| I | S | S | L | Q | P | E | D | F | A | V | Y | Y | C | Q | Q | N | N | N | W |
| I | S | S | L | Q | P | D | D | F | A | T | Y | Y | C | Q | Q | N | N | N | W |
| I | S | S | L | Q | P | E | D | F | A | T | Y | Y | C | Q | Q | N | N | N | W |
| I | S | C | L | Q | S | E | D | F | A | T | Y | Y | C | Q | Q | N | N | N | W |
| I | S | S | L | E | P | E | D | F | A | V | Y | Y | C | Q | Q | N | N | N | W |
| I | S | R | L | E | P | E | D | F | A | V | Y | Y | C | Q | Q | N | N | N | W |
| I | S | S | L | Q | P | E | D | F | A | T | Y | Y | C | Q | Q | N | N | N | W |
| I | N | S | L | E | A | E | D | A | A | T | Y | Y | C | Q | Q | N | N | N | W |
| I | S | S | L | Q | A | E | D | V | A | V | Y | Y | C | Q | Q | N | N | N | W |
| I | S | S | L | Q | A | E | D | V | A | V | Y | Y | C | Q | Q | N | N | N | W |
| I | S | S | L | Q | P | E | D | F | A | V | Y | Y | C | Q | Q | N | N | N | W |
| I | N | S | L | E | A | E | D | A | A | T | Y | Y | C | Q | Q | N | N | N | W |
| I | N | S | L | E | A | E | D | A | A | T | Y | Y | C | Q | Q | N | N | N | W |
| I | S | S | L | E | A | E | D | A | A | T | Y | Y | C | Q | Q | N | N | N | W |
| I | S | S | L | Q | P | E | D | I | A | T | Y | Y | C | Q | Q | N | N | N | W |
| I | S | R | V | E | A | E | D | V | G | V | Y | Y | C | Q | Q | N | N | N | W |
| I | S | C | L | Q | S | E | D | F | A | T | Y | Y | C | Q | Q | N | N | N | W |
| I | S | S | L | Q | A | E | D | V | A | T | Y | Y | C | Q | Q | N | N | N | W |
| I | S | S | L | Q | P | E | D | T | A | T | Y | Y | C | Q | Q | N | N | N | W |
| I | S | S | L | Q | P | E | D | F | A | T | Y | Y | C | Q | Q | N | N | N | W |
| I | S | S | L | Q | P | E | D | F | A | V | Y | Y | C | Q | Q | N | N | N | W |
| I | S | S | L | Q | S | E | D | F | A | V | Y | Y | C | Q | Q | N | N | N | W |
| I | S | S | L | Q | P | E | D | I | A | T | Y | Y | C | Q | Q | N | N | N | W |
| I | S | S | L | Q | P | E | D | F | A | T | Y | Y | C | Q | Q | N | N | N | W |
| I | S | S | L | Q | P | E | D | F | A | T | Y | Y | C | Q | Q | N | N | N | W |
| I | S | S | L | Q | P | E | D | F | A | V | Y | Y | C | Q | Q | N | N | N | W |
| I | S | S | L | Q | S | E | D | F | A | V | Y | Y | C | Q | Q | N | N | N | W |
| I | S | S | L | Q | P | E | D | I | A | T | Y | Y | C | Q | Q | N | N | N | W |
| I | S | S | L | Q | S | E | D | F | A | V | Y | Y | C | Q | Q | N | N | N | W |
| I | S | S | L | Q | P | E | D | F | A | V | Y | Y | C | Q | Q | N | N | N | W |
| I | S | S | L | Q | P | E | D | F | A | T | Y | Y | C | Q | Q | N | N | N | W |
| I | S | S | L | Q | P | E | D | I | A | T | Y | Y | C | Q | Q | N | N | N | W |
| I | S | S | L | Q | P | E | D | F | A | T | Y | Y | C | Q | Q | N | N | N | W |
| I | S | S | L | Q | P | E | D | I | A | T | Y | Y | C | Q | Q | N | N | N | W |
| I | S | S | L | Q | P | D | D | F | A | T | Y | Y | C | Q | Q | N | N | N | W |
| I | S | S | L | Q | P | D | D | F | A | T | Y | Y | C | Q | Q | N | N | N | W |
| I | S | S | L | Q | P | E | D | F | A | T | Y | Y | C | Q | Q | N | N | N | W |
| I | S | S | L | Q | P | E | D | I | A | T | Y | Y | C | Q | Q | N | N | N | W |
| I | S | S | L | Q | S | E | D | F | A | V | Y | Y | C | Q | Q | N | N | N | W |

FIG. 31a-7

| | | | 95 | 96 | 97 | 98 | 99 | 100 | 101 | 102 | 103 | 104 | 105 | 106 | 107 |
|---|---|---|---|---|---|---|---|---|---|---|---|---|---|---|---|
| | | | | | | | | | | | | | | | |
| – | – | P | T | T | F | G | A | G | T | K | L | E | L | K |
| | | | | | | | | | | | | | | | |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |

| | | | | | | | | |
|---|---|---|---|---|---|---|---|---|
| SEQ ID NO.:314 | 6 | 0.53 | 0.57 | 0.92 | 0.57 | 58 | 0.45 | 19 | 4.93 |
| SEQ ID NO.:315 | 31 | 0.54 | 0.58 | 0.92 | 0.57 | 58 | 0.45 | 19 | 4.55 |
| SEQ ID NO.:316 | 9 | 0.55 | 0.61 | 0.92 | 0.57 | 58 | 0.59 | 20 | 4.58 |
| SEQ ID NO.:317 | 10 | 0.54 | 0.61 | 0.92 | 0.57 | 58 | 0.50 | 19 | 4.88 |
| SEQ ID NO.:318 | 11 | 0.55 | 0.61 | 0.92 | 0.57 | 58 | 0.50 | 19 | 4.78 |
| SEQ ID NO.:319 | 26 | 0.55 | 0.62 | 0.92 | 0.57 | 58 | 0.52 | 18 | 4.08 |
| SEQ ID NO.:320 | 42 | 0.55 | 0.60 | 0.92 | 0.57 | 58 | 0.67 | 20 | 4.95 |
| SEQ ID NO.:321 | 16 | 0.53 | 0.58 | 0.92 | 0.57 | 58 | 0.45 | 19 | 4.88 |
| SEQ ID NO.:322 | 18 | 0.53 | 0.60 | 0.92 | 0.57 | 58 | 0.48 | 19 | 5.03 |
| SEQ ID NO.:323 | 8 | 0.53 | 0.58 | 0.92 | 0.57 | 58 | 0.67 | 17 | 5.48 |
| SEQ ID NO.:324 | 13 | 0.54 | 0.58 | 0.92 | 0.57 | 58 | 0.67 | 17 | 5.38 |
| SEQ ID NO.:325 | 19 | 0.54 | 0.58 | 0.92 | 0.57 | 58 | 0.67 | 18 | 5.18 |
| SEQ ID NO.:326 | 50 | 0.53 | 0.57 | 0.92 | 0.57 | 58 | 0.67 | 18 | 5.55 |
| SEQ ID NO.:327 | 24 | 0.54 | 0.57 | 0.92 | 0.57 | 58 | 0.47 | 19 | 5.28 |
| SEQ ID NO.:328 | 29 | 0.53 | 0.56 | 0.92 | 0.57 | 58 | 0.47 | 19 | 5.38 |
| SEQ ID NO.:329 | 52 | 0.53 | 0.54 | 0.91 | 0.53 | 54 | 0.50 | 21 | 8.88 |
| SEQ ID NO.:330 | 44 | 0.51 | 0.51 | 0.92 | 0.55 | 56 | 0.43 | 20 | 8.58 |

*FIG. 31a-8*

| D | I | L | L | T | Q | S | P | G | T | L | S | L | S | P | G | E | R | V | T |
|---|---|---|---|---|---|---|---|---|---|---|---|---|---|---|---|---|---|---|---|
| D | I | L | L | T | Q | S | P | A | T | L | S | L | S | P | G | E | R | V | T |
| D | I | L | L | T | Q | S | P | A | T | L | S | L | S | P | G | E | R | A | T |
| D | I | L | L | T | Q | S | P | A | T | L | S | V | S | P | G | E | R | A | T |
| D | I | L | L | T | Q | S | P | A | T | L | S | L | S | P | G | E | R | V | T |
| D | I | L | L | T | Q | S | P | A | T | L | S | L | S | P | G | E | R | V | T |
| D | I | L | L | T | Q | S | P | G | T | L | S | L | S | P | G | E | R | A | T |
| D | I | L | L | T | Q | S | P | A | T | L | S | V | S | P | G | E | R | A | T |
| D | I | L | L | T | Q | S | P | A | T | L | S | V | S | P | G | E | R | A | T |
| D | I | L | L | T | Q | S | P | A | T | L | S | V | S | P | G | E | R | A | T |
| D | I | L | L | T | Q | S | P | A | T | L | S | L | S | P | G | E | R | V | T |
| D | I | L | L | T | Q | S | P | A | T | L | S | L | S | P | G | E | R | A | T |
| D | I | L | L | T | Q | S | P | G | T | L | S | L | S | P | G | E | R | A | T |
| D | I | L | L | T | Q | S | P | A | T | L | S | L | S | P | G | E | R | V | T |
| D | I | L | L | T | Q | S | P | A | T | L | S | V | S | P | G | E | R | A | T |
| D | I | L | L | T | Q | S | P | D | S | L | A | V | S | L | G | E | R | A | T |
| D | I | L | L | T | Q | S | P | G | T | L | S | L | S | P | G | E | R | A | T |

*FIG. 31a-9*

| L | S | C | R | A | S | Q | S | I | G | | | | | | T | N | I | H |
|---|---|---|---|---|---|---|---|---|---|---|---|---|---|---|---|---|---|---|
| L | S | C | R | A | S | Q | S | I | G | — | — | — | — | — | T | N | I | H |
| L | S | C | R | A | S | Q | S | I | G | — | — | — | — | — | T | N | I | H |
| L | S | C | R | A | S | Q | S | I | G | — | — | — | — | — | T | N | I | H |
| L | S | C | R | A | S | Q | S | I | G | — | — | — | — | — | T | N | I | H |
| L | S | C | R | A | S | Q | S | I | G | — | — | — | — | — | T | N | I | H |
| L | S | C | R | A | S | Q | S | I | G | — | — | — | — | — | T | N | I | H |
| L | S | C | R | A | S | Q | S | I | G | — | — | — | — | — | T | N | I | H |
| L | S | C | R | A | S | Q | S | I | G | — | — | — | — | — | T | N | I | H |
| L | S | C | R | A | S | Q | S | I | G | — | — | — | — | — | T | N | I | H |
| L | S | C | R | A | S | Q | S | I | G | | | | | | T | N | I | H |
| L | S | C | R | A | S | Q | S | I | G | — | — | — | — | — | T | N | I | H |
| L | S | C | R | A | S | Q | S | I | G | — | — | — | — | — | T | N | I | H |
| L | S | C | R | A | S | Q | S | I | G | — | — | — | — | — | T | N | I | H |
| L | S | C | R | A | S | Q | S | I | G | — | — | — | — | — | T | N | I | H |
| L | S | C | R | A | S | Q | S | I | G | | | | | | T | N | I | H |

FIG. 31a-10

| W | Y | Q | Q | K | P | D | Q | S | P | K | L | L | I | K | Y | A | S | E | S |
|---|---|---|---|---|---|---|---|---|---|---|---|---|---|---|---|---|---|---|---|
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |
| W | Y | Q | Q | K | P | D | Q | S | P | K | L | L | I | K | Y | A | S | E | S |

*FIG. 31a-11*

| | S | G | I | P | S | R | F | S | G | S | G | S | G | T | D | F | T | L | T |
|---|---|---|---|---|---|---|---|---|---|---|---|---|---|---|---|---|---|---|---|
| | S | G | I | P | S | R | F | S | G | S | G | S | G | T | D | F | T | L | T |
| | S | G | I | P | S | R | F | S | G | S | G | S | G | T | D | F | T | L | T |
| | S | G | I | P | S | R | F | S | G | S | G | S | G | T | D | F | T | L | T |
| | S | G | I | P | S | R | F | S | G | S | G | S | G | T | D | F | T | L | T |
| | S | G | I | P | S | R | F | S | G | S | G | S | G | T | D | F | T | L | T |
| | S | G | I | P | S | R | F | S | G | S | G | S | G | T | D | F | T | L | T |
| | S | G | I | P | S | R | F | S | G | S | G | S | G | T | D | F | T | L | T |
| | S | G | I | P | S | R | F | S | G | S | G | S | G | T | E | F | T | L | T |
| | S | G | I | P | S | R | F | S | G | S | G | S | G | T | D | F | T | L | T |
| | S | G | I | P | S | R | F | S | G | S | G | S | G | T | D | F | T | L | T |
| | S | G | I | P | S | R | F | S | G | S | G | S | G | T | D | F | T | L | T |
| | S | G | I | P | S | R | F | S | G | S | G | S | G | T | D | F | T | L | T |
| | S | G | I | P | S | R | F | S | G | S | G | S | G | T | D | F | T | F | T |
| | S | G | I | P | S | R | F | S | G | S | G | S | G | T | D | F | T | F | T |
| | S | G | I | P | S | R | F | S | G | S | G | S | G | T | D | F | T | F | T |
| | S | G | I | P | S | R | F | S | G | S | G | S | G | T | D | F | T | L | K |

FIG. 31a-12

| | S | S | L | Q | A | E | D | V | A | V | Y | Y | C | Q | Q | N | N | N | W |
|---|---|---|---|---|---|---|---|---|---|---|---|---|---|---|---|---|---|---|---|
| | S | S | L | Q | A | E | D | V | A | V | Y | Y | C | Q | Q | N | N | N | W |
| | S | R | L | E | P | E | D | F | A | V | Y | Y | C | Q | Q | N | N | N | W |
| | S | R | L | E | P | E | D | F | A | V | Y | Y | C | Q | Q | N | N | N | W |
| | S | R | L | E | P | E | D | F | A | V | Y | Y | C | Q | Q | N | N | N | W |
| | S | S | L | E | P | E | D | F | A | V | Y | Y | C | Q | Q | N | N | N | W |
| | S | R | L | E | P | E | D | F | A | V | Y | Y | C | Q | Q | N | N | N | W |
| | S | C | L | Q | S | E | D | F | A | T | Y | Y | C | Q | Q | N | N | N | W |
| | S | S | L | E | P | E | D | F | A | V | Y | Y | C | Q | Q | N | N | N | W |
| | N | S | L | E | A | E | D | A | A | T | Y | Y | C | Q | Q | N | N | N | W |
| | N | S | L | E | A | E | D | A | A | T | Y | Y | C | Q | Q | N | N | N | W |
| | N | S | L | E | A | E | D | A | A | T | Y | Y | C | Q | Q | N | N | N | W |
| | N | S | L | E | A | E | D | A | A | T | Y | Y | C | Q | Q | N | N | N | W |
| | S | S | L | E | A | E | D | A | A | T | Y | Y | C | Q | Q | N | N | N | W |
| | S | S | L | E | A | E | D | A | A | T | Y | Y | C | Q | Q | N | N | N | W |
| | S | S | L | E | A | E | D | A | A | T | Y | Y | C | Q | Q | N | N | N | W |
| | S | R | V | E | A | E | D | V | G | V | Y | Y | C | Q | Q | N | N | N | W |

*FIG. 31a-13*

| | | P | T | T | F | G | A | G | T | K | X | E | I | K |
|---|---|---|---|---|---|---|---|---|---|---|---|---|---|---|
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |
| – | – | P | T | T | F | G | A | G | T | K | X | E | I | K |

*FIG. 31a-14*

| FIG. 31a-1 | FIG. 31a-2 | FIG. 31a-3 | FIG. 31a-4 | FIG. 31a-5 | FIG. 31a-6 | FIG. 31a-7 |
|---|---|---|---|---|---|---|
| FIG. 31a-8 | FIG. 31a-9 | FIG. 31a-10 | FIG. 31a-11 | FIG. 31a-12 | FIG. 31a-13 | FIG. 31a-14 |

C225 VH HEC Calculation 2

| (WT) SEQ ID NO.:235 | Iter | Structural Consensus | Structural Precedence | HSC | HSS | $N_g$max | Kabat FRH | Muts | WT Cluster |
|---|---|---|---|---|---|---|---|---|---|
| SEQ ID NO.:331 | 1 | 0.45 | 0.52 | 0.82 | 0.44 | 52 | 0.48 | 24 | 1.80 |
| SEQ ID NO.:332 | 2 | 0.45 | 0.51 | 0.82 | 0.44 | 52 | 0.48 | 23 | 2.00 |
| SEQ ID NO.:333 | 15 | 0.45 | 0.51 | 0.82 | 0.44 | 52 | 0.48 | 24 | 2.20 |
| SEQ ID NO.:334 | 22 | 0.45 | 0.52 | 0.82 | 0.44 | 52 | 0.48 | 25 | 2.00 |
| SEQ ID NO.:335 | 40 | 0.43 | 0.52 | 0.82 | 0.44 | 52 | 0.60 | 28 | 4.80 |
| SEQ ID NO.:336 | 3 | 0.45 | 0.51 | 0.81 | 0.41 | 48 | 0.58 | 27 | |
| SEQ ID NO.:337 | 4 | 0.49 | 0.51 | 0.81 | 0.40 | 47 | 0.47 | 23 | 5.19 |
| SEQ ID NO.:338 | 6 | 0.49 | 0.51 | 0.81 | 0.40 | 47 | 0.47 | 21 | 4.81 |
| SEQ ID NO.:339 | 17 | 0.48 | 0.50 | 0.81 | 0.40 | 47 | 0.34 | 22 | 5.42 |
| SEQ ID NO.:340 | 21 | 0.49 | 0.51 | 0.81 | 0.40 | 47 | 0.47 | 22 | 5.74 |
| SEQ ID NO.:341 | 30 | 0.49 | 0.51 | 0.81 | 0.40 | 47 | 0.47 | 22 | 4.84 |
| SEQ ID NO.:342 | 43 | 0.49 | 0.51 | 0.81 | 0.40 | 47 | 0.47 | 22 | 5.16 |
| SEQ ID NO.:343 | 5 | 0.50 | 0.53 | 0.81 | 0.39 | 46 | 0.46 | 20 | 4.45 |
| SEQ ID NO.:344 | 7 | 0.50 | 0.53 | 0.81 | 0.39 | 46 | 0.48 | 22 | 4.84 |
| SEQ ID NO.:345 | 8 | 0.49 | 0.52 | 0.81 | 0.39 | 46 | 0.46 | 21 | 4.48 |
| SEQ ID NO.:346 | 25 | 0.48 | 0.52 | 0.81 | 0.39 | 46 | 0.35 | 21 | 5.06 |
| SEQ ID NO.:347 | 45 | 0.49 | 0.53 | 0.81 | 0.39 | 46 | 0.39 | 20 | 5.03 |
| SEQ ID NO.:348 | 20 | 0.49 | 0.53 | 0.81 | 0.39 | 46 | 0.48 | 21 | 5.68 |
| SEQ ID NO.:349 | 24 | 0.49 | 0.53 | 0.81 | 0.39 | 46 | 0.41 | 20 | 5.32 |
| SEQ ID NO.:350 | 37 | 0.49 | 0.52 | 0.81 | 0.39 | 46 | 0.39 | 21 | 5.35 |
| SEQ ID NO.:351 | 33 | 0.49 | 0.51 | 0.81 | 0.40 | 47 | 0.40 | 21 | 5.68 |
| SEQ ID NO.:352 | 32 | 0.49 | 0.51 | 0.81 | 0.39 | 46 | 0.46 | 23 | 6.26 |
| SEQ ID NO.:353 | 11 | 0.47 | 0.45 | 0.81 | 0.40 | 47 | 0.36 | 23 | 7.32 |
| SEQ ID NO.:354 | 16 | 0.46 | 0.45 | 0.81 | 0.40 | 47 | 0.32 | 24 | 7.35 |
| SEQ ID NO.:355 | 29 | 0.46 | 0.47 | 0.81 | 0.40 | 47 | 0.32 | 25 | 7.45 |
| SEQ ID NO.:356 | 39 | 0.47 | 0.47 | 0.81 | 0.40 | 47 | 0.45 | 26 | 7.81 |
| SEQ ID NO.:357 | 34 | 0.48 | 0.47 | 0.81 | 0.40 | 47 | 0.40 | 23 | 6.16 |
| SEQ ID NO.:358 | 46 | 0.47 | 0.47 | 0.81 | 0.40 | 47 | 0.34 | 24 | 6.19 |
| SEQ ID NO.:359 | 12 | 0.47 | 0.49 | 0.81 | 0.38 | 45 | 0.47 | 23 | 7.55 |
| SEQ ID NO.:360 | 26 | 0.47 | 0.49 | 0.81 | 0.38 | 45 | 0.47 | 24 | 7.58 |
| SEQ ID NO.:361 | 28 | 0.47 | 0.49 | 0.81 | 0.38 | 45 | 0.38 | 22 | 7.19 |
| SEQ ID NO.:362 | 47 | 0.47 | 0.49 | 0.81 | 0.38 | 45 | 0.33 | 23 | 7.23 |
| SEQ ID NO.:363 | 9 | 0.49 | 0.54 | 0.81 | 0.40 | 47 | 0.60 | 22 | 6.97 |
| SEQ ID NO.:364 | 27 | 0.49 | 0.53 | 0.81 | 0.40 | 47 | 0.47 | 24 | 7.35 |
| SEQ ID NO.:365 | 18 | 0.48 | 0.54 | 0.81 | 0.40 | 47 | 0.38 | 22 | 8.00 |
| SEQ ID NO.:366 | 23 | 0.48 | 0.54 | 0.81 | 0.40 | 47 | 0.36 | 23 | 8.03 |
| SEQ ID NO.:367 | 41 | 0.48 | 0.54 | 0.81 | 0.40 | 47 | 0.55 | 22 | 8.03 |
| SEQ ID NO.:368 | 10 | 0.47 | 0.47 | 0.82 | 0.44 | 52 | 0.37 | 24 | 1.50 |
| SEQ ID NO.:369 | 35 | 0.47 | 0.48 | 0.82 | 0.44 | 52 | 0.42 | 24 | 1.83 |

FIG. 31b-2

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|----|----|----|----|----|----|----|----|----|----|----|
| Q | V | Q | L | K | Q | S | G | P | G | L | V | Q | P | S | Q | S | L | S | I |
| Q | V | Q | L | Q | E | S | G | P | G | L | V | K | P | S | Q | T | L | S | L |
| Q | V | Q | L | Q | Q | S | G | P | G | L | V | K | P | S | Q | T | L | S | L |
| Q | V | Q | L | Q | Q | S | G | P | G | L | V | K | P | S | E | T | L | S | L |
| Q | V | Q | L | Q | E | S | G | P | G | L | V | K | P | S | E | T | L | S | L |
| Q | V | T | L | R | E | S | G | P | A | L | V | K | P | T | Q | T | L | T | L |
| Q | V | T | L | K | E | S | G | P | V | L | V | K | P | T | E | T | L | T | L |
| Q | V | Q | L | Q | E | S | G | P | G | L | V | K | P | S | E | T | L | S | L |
| Q | V | Q | L | Q | Q | S | G | P | G | L | V | K | P | S | Q | T | L | S | L |
| Q | V | Q | L | Q | Q | S | G | P | G | L | V | K | P | S | E | T | L | S | L |
| Q | V | Q | L | Q | E | S | G | P | G | L | V | K | P | S | Q | T | L | S | L |
| Q | V | Q | L | Q | Q | S | G | P | G | L | V | K | P | S | E | T | L | S | L |
| Q | V | Q | L | Q | E | S | G | P | G | L | V | K | P | S | Q | T | L | S | L |
| Q | V | Q | L | Q | Q | S | G | P | G | L | V | K | P | S | Q | T | L | S | L |
| Q | V | Q | L | Q | E | S | G | P | G | L | V | K | P | S | E | T | L | S | L |
| Q | V | Q | L | Q | Q | S | G | P | G | L | V | K | P | S | E | T | L | S | L |
| Q | V | Q | L | Q | Q | S | G | P | G | L | V | K | P | S | E | T | L | S | L |
| Q | V | Q | L | Q | Q | S | G | P | G | L | V | K | P | S | Q | T | L | S | L |
| Q | V | Q | L | Q | E | S | G | P | G | L | V | K | P | S | Q | T | L | S | L |
| Q | V | Q | L | Q | Q | S | G | P | G | L | V | K | P | S | Q | T | L | S | L |
| Q | V | Q | L | Q | E | S | G | P | G | L | V | K | P | S | Q | T | L | S | L |
| Q | V | Q | L | Q | Q | S | G | P | G | L | V | K | P | S | E | T | L | S | L |
| Q | V | Q | L | Q | Q | S | G | P | G | L | V | K | P | S | Q | T | L | S | L |
| Q | V | Q | L | Q | Q | S | G | P | G | L | V | K | P | S | E | T | L | S | L |
| Q | V | Q | L | Q | E | S | G | P | G | L | V | K | P | S | E | T | L | S | L |
| Q | V | Q | L | Q | Q | S | G | P | G | L | V | K | P | S | E | T | L | S | L |
| Q | V | Q | L | Q | E | S | G | P | G | L | V | K | P | S | Q | T | L | S | L |
| Q | V | Q | L | Q | Q | S | G | P | G | L | V | K | P | S | E | T | L | S | L |
| Q | V | Q | L | Q | Q | S | G | P | G | L | V | K | P | S | Q | T | L | S | L |
| Q | V | Q | L | Q | Q | S | G | P | G | L | V | K | P | S | Q | T | L | S | L |
| Q | V | Q | L | Q | E | S | G | P | G | L | V | K | P | S | E | T | L | S | L |
| Q | V | Q | L | Q | Q | S | G | P | G | L | V | K | P | S | Q | T | L | S | L |
| Q | V | Q | L | Q | Q | S | G | P | G | L | V | K | P | S | Q | T | L | S | L |
| Q | V | Q | L | Q | Q | S | G | P | G | L | V | K | P | S | E | T | L | S | L |
| Q | V | Q | L | Q | E | S | G | P | G | L | V | K | P | S | Q | T | L | S | L |

FIG. 31b-3

| 21 | 22 | 23 | 24 | 25 | 26 | 27 | 28 | 29 | 30 | 31 | 32 | 33 | 34 | 35 | 36 | 37 | 38 |
|---|---|---|---|---|---|---|---|---|---|---|---|---|---|---|---|---|---|
| T | C | T | V | S | G | F | S | L | T | N | — | — | Y | G | V | H | W | V | R |
| T | C | T | V | S | G | F | S | L | T | N | — | — | Y | G | V | H | W | V | R |
| T | C | T | V | S | G | F | S | L | T | N | — | — | Y | G | V | H | W | V | R |
| T | C | T | V | S | G | F | S | L | T | N | — | — | Y | G | V | H | W | V | R |
| T | C | T | V | S | G | F | S | L | T | N |   |   | Y | G | V | H | W | V | R |
| T | C | T | V | S | G | F | S | L | T | N |   |   | Y | G | V | H | W | V | R |
| T | C | T | V | S | G | F | S | L | T | N | — | — | Y | G | V | H | W | V | R |
| T | C | T | V | S | G | F | S | L | T | N | — | — | Y | G | V | H | W | V | R |
| T | C | T | V | S | G | F | S | L | T | N | — | — | Y | G | V | H | W | V | R |
| T | C | T | V | S | G | F | S | L | T | N |   |   | Y | G | V | H | W | V | R |
| T | C | T | V | S | G | F | S | L | T | N |   |   | Y | G | V | H | W | V | R |
| T | C | T | V | S | G | F | S | L | T | N | — | — | Y | G | V | H | W | V | R |
| T | C | T | V | S | G | F | S | L | T | N | — | — | Y | G | V | H | W | V | R |
| T | C | T | V | S | G | F | S | L | T | N | — | — | Y | G | V | H | W | V | R |
| T | C | T | V | S | G | F | S | L | T | N | — | — | Y | G | V | H | W | V | R |
| T | C | T | V | S | G | F | S | L | T | N | — | — | Y | G | V | H | W | V | R |
| T | C | T | V | S | G | F | S | L | T | N | — | — | Y | G | V | H | W | V | R |
| T | C | T | V | S | G | F | S | L | T | N | — | — | Y | G | V | H | W | V | R |
| T | C | T | V | S | G | F | S | L | T | N | — | — | Y | G | V | H | W | V | R |
| T | C | T | V | S | G | F | S | L | T | N | — | — | Y | G | V | H | W | V | R |
| T | C | T | V | S | G | F | S | L | T | N | — | — | Y | G | V | H | W | V | R |
| T | C | T | V | S | G | F | S | L | T | N | — | — | Y | G | V | H | W | V | R |
| T | C | T | V | S | G | F | S | L | T | N | — | — | Y | G | V | H | W | V | R |
| T | C | T | V | S | G | F | S | L | T | N | — | — | Y | G | V | H | W | V | R |
| T | C | T | V | S | G | F | S | L | T | N | — | — | Y | G | V | H | W | V | R |
| T | C | T | V | S | G | F | S | L | T | N |   |   | Y | G | V | H | W | V | R |
| T | C | T | V | S | G | F | S | L | T | N | — | — | Y | G | V | H | W | V | R |
| T | C | T | V | S | G | F | S | L | T | N | — | — | Y | G | V | H | W | V | R |

FIG. 31b-4

| 39 | 40 | 41 | 42 | 43 | 44 | 45 | 46 | 47 | 48 | 49 | 50 | 51 | 52 | 53 | 54 | | | | 55 |
|---|---|---|---|---|---|---|---|---|---|---|---|---|---|---|---|---|---|---|---|
| Q | S | P | G | K | G | L | E | W | L | G | V | I | W | S | G | — | — | — | G |
| Q | A | P | G | K | G | L | E | W | V | S | V | I | W | S | G | — | — | — | G |
| Q | A | P | G | K | G | L | E | W | V | S | V | I | W | S | G | — | — | — | G |
| Q | A | P | G | K | G | L | E | W | V | S | V | I | W | S | G | — | — | — | G |
| Q | A | P | G | K | G | L | E | W | V | S | V | I | W | S | G | — | — | — | G |
| Q | A | P | G | K | G | L | E | W | V | S | V | I | W | S | G | | | | G |
| Q | A | P | G | K | G | L | E | W | V | S | V | I | W | S | G | | | | G |
| Q | A | P | G | K | G | L | E | W | V | S | V | I | W | S | G | — | — | — | G |
| Q | A | P | G | K | G | L | E | W | V | S | V | I | W | S | G | — | — | — | G |
| Q | A | P | G | K | G | L | E | W | V | S | V | I | W | S | G | | | | G |
| Q | A | P | G | K | G | L | E | W | V | S | V | I | W | S | G | — | — | — | G |
| Q | A | P | G | K | G | L | E | W | V | S | V | I | W | S | G | — | — | — | G |
| Q | A | P | G | K | G | L | E | W | V | S | V | I | W | S | G | — | — | — | G |
| Q | A | P | G | K | G | L | E | W | V | S | V | I | W | S | G | — | — | — | G |
| Q | A | P | G | K | G | L | E | W | V | S | V | I | W | S | G | — | — | — | G |
| Q | A | P | G | K | G | L | E | W | V | S | V | I | W | S | G | — | — | — | G |
| Q | A | P | G | K | G | L | E | W | V | S | V | I | W | S | G | — | — | — | G |
| Q | A | P | G | K | G | L | E | W | V | S | V | I | W | S | G | — | — | — | G |
| Q | A | P | G | K | G | L | E | W | V | S | V | I | W | S | G | | | | G |
| Q | A | P | G | K | G | L | E | W | V | S | V | I | W | S | G | — | — | — | G |
| Q | A | P | G | K | G | L | E | W | V | S | V | I | W | S | G | — | — | — | G |
| Q | A | P | G | K | G | L | E | W | V | S | V | I | W | S | G | — | — | — | G |
| Q | A | P | G | K | G | L | E | W | V | S | V | I | W | S | G | — | — | — | G |
| Q | A | P | G | K | G | L | E | W | V | S | V | I | W | S | G | — | — | — | G |
| Q | A | P | G | K | G | L | E | W | V | S | V | I | W | S | G | — | — | — | G |
| Q | A | P | G | K | G | L | E | W | V | S | V | I | W | S | G | — | — | — | G |
| Q | A | P | G | K | G | L | E | W | V | S | V | I | W | S | G | — | — | — | G |
| Q | A | P | G | K | G | L | E | W | V | S | V | I | W | S | G | — | — | — | G |
| Q | A | P | G | K | G | L | E | W | V | S | V | I | W | S | G | — | — | — | G |
| Q | A | P | G | K | G | L | E | W | V | S | V | I | W | S | G | — | — | — | G |
| Q | A | P | G | K | G | L | E | W | V | S | V | I | W | S | G | — | — | — | G |
| Q | A | P | G | K | G | L | E | W | V | S | V | I | W | S | G | | | | G |
| Q | A | P | G | K | G | L | E | W | V | S | V | I | W | S | G | | | | G |

FIG. 31b-5

| 56 | 57 | 58 | 59 | 60 | 61 | 62 | 63 | 64 | 65 | 66 | 67 | 68 | 69 | 70 | 71 | 72 | 73 | 74 | 75 |
|---|---|---|---|---|---|---|---|---|---|---|---|---|---|---|---|---|---|---|---|
| N | T | D | Y | N | T | P | F | T | S | R | L | S | I | N | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | S | K | D | N | S | K |
| N | T | D | Y | N | T | S | L | K | S | R | L | T | I | T | K | D | N | S | T |
| N | T | D | Y | N | T | S | L | K | S | R | L | T | I | T | K | D | N | S | T |

FIG. 31b-6

| 76 | 77 | 78 | 79 | 80 | 81 | 82 | 82a | 82b | 82c | 83 | 84 | 85 | 86 | 87 | 88 | 89 | 90 | 91 | 92 |
|----|----|----|----|----|----|----|-----|-----|-----|----|----|----|----|----|----|----|----|----|----|
| S | Q | V | F | F | K | M | N | S | L | Q | S | N | D | T | A | I | Y | Y | C |
| S | Q | V | V | L | T | M | T | N | M | D | P | V | D | T | A | T | Y | Y | C |
| S | Q | V | V | L | T | M | T | N | M | D | P | V | D | T | A | T | Y | Y | C |
| S | Q | V | V | L | T | M | T | N | M | D | P | V | D | T | A | T | Y | Y | C |
| S | Q | V | V | L | T | M | T | N | M | D | P | V | D | T | A | T | Y | Y | C |
| S | Q | V | S | L | K | L | S | S | V | T | A | A | D | T | A | V | Y | Y | C |
| S | I | V | Y | L | Q | M | N | S | L | R | A | E | D | T | A | V | Y | Y | C |
| S | I | V | Y | L | Q | M | N | S | L | R | A | E | D | T | A | V | Y | Y | C |
| S | I | V | Y | L | Q | M | N | S | L | R | A | G | D | T | A | V | Y | Y | C |
| S | I | V | Y | L | Q | M | N | S | L | R | A | G | D | T | A | V | Y | Y | C |
| S | I | V | Y | L | Q | M | N | S | L | R | A | E | D | T | A | V | Y | Y | C |
| S | I | V | Y | L | Q | M | N | S | L | R | A | E | D | T | A | V | Y | Y | C |
| S | Q | V | V | L | Q | M | N | S | L | R | A | E | D | T | A | V | Y | Y | C |
| S | Q | V | V | L | Q | M | N | S | L | R | A | E | D | T | A | V | Y | Y | C |
| S | Q | V | V | L | Q | M | N | S | L | R | A | E | D | T | A | V | Y | Y | C |
| S | Q | V | V | L | Q | M | N | S | L | R | A | G | D | T | A | V | Y | Y | C |
| S | Q | V | V | L | Q | M | N | S | L | R | A | G | D | T | A | V | Y | Y | C |
| S | Q | V | V | L | Q | M | N | S | L | K | T | E | D | T | A | V | Y | Y | C |
| S | Q | V | V | L | Q | M | N | S | L | K | T | E | D | T | A | V | Y | Y | C |
| S | Q | V | V | L | Q | M | N | S | L | K | T | E | D | T | A | V | Y | Y | C |
| S | I | V | Y | L | Q | M | N | S | L | K | T | E | D | T | A | V | Y | Y | C |
| S | Q | V | V | L | Q | M | G | S | L | R | A | E | D | M | A | V | Y | Y | C |
| S | T | V | Y | L | Q | W | S | S | L | K | A | S | D | T | A | M | Y | Y | C |
| S | T | V | Y | L | Q | W | S | S | L | K | A | S | D | T | A | M | Y | Y | C |
| S | T | V | Y | L | Q | W | S | S | L | K | A | E | D | M | A | M | Y | Y | C |
| S | T | V | Y | L | Q | I | S | S | L | K | A | E | D | M | A | M | Y | Y | C |
| S | T | V | Y | L | Q | I | S | C | S | L | K | A | E | D | T | A | M | Y | Y | C |
| S | T | V | Y | L | Q | I | C | S | L | K | A | E | D | M | A | Y | Y | C |
| S | Q | V | V | L | T | M | N | N | L | R | A | E | G | T | A | A | Y | Y | C |
| S | Q | V | V | L | T | M | N | N | L | R | A | E | G | T | A | A | Y | Y | C |
| S | Q | V | V | L | T | M | N | N | L | R | A | E | G | T | A | A | Y | Y | C |
| S | Q | V | V | L | T | M | N | N | L | R | A | E | G | T | A | A | Y | Y | C |
| S | Q | V | S | L | Q | L | N | S | V | T | P | E | D | T | A | V | Y | Y | C |
| S | Q | V | S | L | Q | L | N | S | V | T | P | E | D | T | A | V | Y | Y | C |
| S | Q | V | S | L | K | L | S | S | V | T | A | V | D | T | A | V | Y | Y | C |
| S | Q | V | S | L | K | L | S | S | V | T | A | A | D | T | A | V | Y | Y | C |
| S | Q | V | S | L | K | L | S | S | V | T | A | A | D | T | A | V | Y | Y | C |
| S | T | V | Y | M | E | L | S | S | L | R | S | E | D | T | A | V | Y | Y | C |
| S | T | V | Y | M | E | L | S | S | L | R | S | E | D | T | A | V | Y | Y | C |

FIG. 31b-7

| 93 | 94 | 95 | 96 | 97 | | | | 98 | 99 | 100 | 100a | 100b | 100c | 101 | 102 | 103 | 104 | 105 | 106 |
|---|---|---|---|---|---|---|---|---|---|---|---|---|---|---|---|---|---|---|---|
| A | R | A | L | T | — | — | — | Y | Y | D | Y | E | F | A | Y | W | G | Q | G |
| A | R | A | L | T | — | — | — | Y | Y | D | Y | E | F | A | Y | W | G | Q | G |
| A | R | A | L | T | — | — | — | Y | Y | D | Y | E | F | A | Y | W | G | Q | G |
| A | R | A | L | T | — | — | — | Y | Y | D | Y | E | F | A | Y | W | G | Q | G |
| A | R | A | L | T | — | — | — | Y | Y | D | Y | E | F | A | Y | W | G | Q | G |
| A | R | A | L | T | — | — | — | Y | Y | D | Y | E | F | A | Y | W | G | Q | G |
| A | R | A | L | T | — | — | — | Y | Y | D | Y | E | F | A | Y | W | G | Q | G |
| A | R | A | L | T | — | — | — | Y | Y | D | Y | E | F | A | Y | W | G | Q | G |
| A | R | A | L | T | — | — | — | Y | Y | D | Y | E | F | A | Y | W | G | Q | G |
| A | R | A | L | T | — | — | — | Y | Y | D | Y | E | F | A | Y | W | G | Q | G |
| A | R | A | L | T | — | — | — | Y | Y | D | Y | E | F | A | Y | W | G | Q | G |
| A | R | A | L | T | — | — | — | Y | Y | D | Y | E | F | A | Y | W | G | Q | G |
| A | R | A | L | T | — | — | — | Y | Y | D | Y | E | F | A | Y | W | G | Q | G |
| A | R | A | L | T | — | — | — | Y | Y | D | Y | E | F | A | Y | W | G | Q | G |
| A | R | A | L | T | — | — | — | Y | Y | D | Y | E | F | A | Y | W | G | Q | G |
| A | R | A | L | T | — | — | — | Y | Y | D | Y | E | F | A | Y | W | G | Q | G |
| A | R | A | L | T | — | — | — | Y | Y | D | Y | E | F | A | Y | W | G | Q | G |
| A | R | A | L | T | — | — | — | Y | Y | D | Y | E | F | A | Y | W | G | Q | G |
| A | R | A | L | T | — | — | — | Y | Y | D | Y | E | F | A | Y | W | G | Q | G |
| A | R | A | L | T | — | — | — | Y | Y | D | Y | E | F | A | Y | W | G | Q | G |
| A | R | A | L | T | — | — | — | Y | Y | D | Y | E | F | A | Y | W | G | Q | G |
| A | R | A | L | T | — | — | — | Y | Y | D | Y | E | F | A | Y | W | G | Q | G |
| A | R | A | L | T | — | — | — | Y | Y | D | Y | E | F | A | Y | W | G | Q | G |
| A | R | A | L | T | — | — | — | Y | Y | D | Y | E | F | A | Y | W | G | Q | G |
| A | R | A | L | T | — | — | — | Y | Y | D | Y | E | F | A | Y | W | G | Q | G |
| A | R | A | L | T | — | — | — | Y | Y | D | Y | E | F | A | Y | W | G | Q | G |
| A | R | A | L | T | — | — | — | Y | Y | D | Y | E | F | A | Y | W | G | Q | G |
| A | R | A | L | T | — | — | — | Y | Y | D | Y | E | F | A | Y | W | G | Q | G |
| A | R | A | L | T | — | — | — | Y | Y | D | Y | E | F | A | Y | W | G | Q | G |
| A | R | A | L | T | — | — | — | Y | Y | D | Y | E | F | A | Y | W | G | Q | G |

FIG. 31b-8

| 107 | 108 | 109 | 110 | 111 | 112 | 113 |
|-----|-----|-----|-----|-----|-----|-----|
| T | L | V | T | V | S | A |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |

| | | | | | | | | |
|---|---|---|---|---|---|---|---|---|
| SEQ ID NO.:370 | 36 | 0.47 | 0.48 | 0.82 | 0.44 | 52 | 0.37 | 23 | 1.50 |
| SEQ ID NO.:371 | 38 | 0.47 | 0.47 | 0.82 | 0.44 | 52 | 0.33 | 23 | 2.17 |
| SEQ ID NO.:372 | 48 | 0.47 | 0.48 | 0.82 | 0.44 | 52 | 0.42 | 25 | 1.83 |
| SEQ ID NO.:373 | 31 | 0.44 | 0.45 | 0.81 | 0.42 | 49 | 0.31 | 26 | 3.50 |
| SEQ ID NO.:374 | 13 | 0.46 | 0.48 | 0.82 | 0.40 | 47 | 0.49 | 27 | |
| SEQ ID NO.:375 | 14 | 0.47 | 0.51 | 0.81 | 0.39 | 46 | 0.46 | 25 | |
| SEQ ID NO.:376 | 19 | 0.49 | 0.49 | 0.81 | 0.40 | 47 | 0.49 | 27 | |
| SEQ ID NO.:377 | 42 | 0.48 | 0.49 | 0.80 | 0.36 | 42 | 0.55 | 26 | |
| SEQ ID NO.:378 | 44 | 0.51 | 0.53 | 0.80 | 0.35 | 41 | 0.71 | 25 | |

*FIG. 31b-9*

| Q | V | Q | L | Q | Q | S | G | P | G | L | V | K | P | S | Q | T | L | S | L |
| Q | V | Q | L | Q | Q | S | G | P | G | L | V | K | P | S | Q | T | L | S | L |
| Q | V | Q | L | Q | E | S | G | P | G | L | V | K | P | S | E | T | L | S | L |
| Q | V | Q | L | Q | Q | S | G | P | G | L | V | K | P | S | E | T | L | S | L |
| Q | V | Q | L | V | E | S | G | G | G | L | V | Q | P | G | R | S | L | R | L |
| Q | V | T | L | R | E | S | G | P | A | L | V | K | P | T | Q | T | L | T | L |
| Q | V | Q | L | V | E | S | G | G | G | L | V | Q | P | G | R | S | L | R | L |
| Q | V | Q | L | V | E | S | G | G | G | L | V | Q | P | G | R | S | L | R | L |
| E | V | Q | L | V | E | S | G | G | G | L | V | Q | P | G | R | S | L | R | L |

*FIG. 31b-10*

| T | C | T | V | S | G | F | S | L | T | N |   |   | Y | G | V | H | W | V | R |
|---|---|---|---|---|---|---|---|---|---|---|---|---|---|---|---|---|---|---|---|
| T | C | T | V | S | G | F | S | L | T | N |   |   | Y | G | V | H | W | V | R |
| T | C | T | V | S | G | F | S | L | T | N |   |   | Y | G | V | H | W | V | R |
| T | C | T | V | S | G | F | S | L | T | N |   |   | Y | G | V | H | W | V | R |
| S | C | T | V | S | G | F | S | L | T | N |   |   | Y | G | V | H | W | V | R |
| T | C | T | V | S | G | F | S | L | T | N |   |   | Y | G | V | H | W | V | R |
| S | C | T | V | S | G | F | S | L | T | N |   |   | Y | G | V | H | W | V | R |
| S | C | T | V | S | G | F | S | L | T | N |   |   | Y | G | V | H | W | V | R |
| S | C | T | V | S | G | F | S | L | T | N |   |   | Y | G | V | H | W | V | R |

*FIG. 31b-11*

| Q | A | P | G | K | G | L | E | W | V | S | V | I | W | S | G |   |   |   | G |
|---|---|---|---|---|---|---|---|---|---|---|---|---|---|---|---|---|---|---|---|
| Q | A | P | G | K | G | L | E | W | V | S | V | I | W | S | G | — | — | — | G |
| Q | A | P | G | K | G | L | E | W | V | S | V | I | W | S | G | — | — | — | G |
| Q | A | P | G | K | G | L | E | W | V | S | V | I | W | S | G |   |   |   | G |
| Q | A | P | G | K | G | L | E | W | V | S | V | I | W | S | G |   |   |   | G |
| Q | A | P | G | K | G | L | E | W | V | S | V | I | W | S | G |   |   |   | G |
| Q | A | P | G | K | G | L | E | W | V | S | V | I | W | S | G |   |   |   | G |
| Q | A | P | G | K | G | L | E | W | V | S | V | I | W | S | G |   |   |   | G |
| Q | A | P | G | K | G | L | E | W | V | S | V | I | W | S | G | — | — | — | G |

*FIG. 31b-12*

| N | T | D | Y | N | T | S | L | K | S | R | L | T | I | T | K | D | N | S | T |
| N | T | D | Y | N | T | S | L | K | S | R | L | T | I | T | K | D | N | S | T |
| N | T | D | Y | N | T | S | L | K | S | R | L | T | I | T | K | D | N | S | T |
| N | T | D | Y | N | T | S | L | K | S | R | L | T | I | T | K | D | N | S | T |
| N | T | D | Y | N | T | S | L | K | S | R | L | T | I | S | K | D | N | S | K |
| N | T | D | Y | N | T | S | L | K | S | R | L | T | I | T | K | D | N | S | K |
| N | T | D | Y | N | T | S | L | K | S | R | L | T | I | T | K | D | N | S | T |
| N | T | D | Y | N | T | S | L | K | S | R | L | T | I | S | K | D | N | S | K |
| N | T | D | Y | N | T | S | L | K | S | R | L | T | I | S | K | D | N | S | K |

FIG. 31b-13

| S | T | V | Y | M | E | L | S | S | L | R | S | E | D | T | A | V | Y | Y | C |
| S | T | V | Y | M | E | L | S | S | L | R | S | E | D | T | A | M | Y | Y | C |
| S | T | V | Y | M | E | L | S | S | L | R | S | E | D | T | A | V | Y | Y | C |
| S | T | V | Y | M | E | L | S | R | L | R | S | D | D | T | V | V | Y | Y | C |
| S | Q | V | V | L | T | M | T | N | M | D | P | V | D | T | A | T | Y | Y | C |
| S | Q | V | V | L | Q | M | N | S | L | R | A | E | D | T | A | V | Y | Y | C |
| S | T | V | Y | M | E | L | S | S | L | R | S | E | D | T | A | V | Y | Y | C |
| S | Q | V | S | L | K | L | S | S | V | T | A | V | D | T | A | V | Y | Y | C |
| S | Q | V | V | L | Q | M | N | S | L | K | T | E | D | T | A | V | Y | Y | C |

*FIG. 31b-14*

| A | R | A | L | T |   |   |   | Y | Y | D | Y | E | F | A | Y | W | G | Q | G |
|---|---|---|---|---|---|---|---|---|---|---|---|---|---|---|---|---|---|---|---|
| A | R | A | L | T | – | – | – | Y | Y | D | Y | E | F | A | Y | W | G | Q | G |
| A | R | A | L | T | – | – | – | Y | Y | D | Y | E | F | A | Y | W | G | Q | G |
| A | R | A | L | T |   |   |   | Y | Y | D | Y | E | F | A | Y | W | G | Q | G |
| A | R | A | L | T |   |   |   | Y | Y | D | Y | E | F | A | Y | W | G | Q | G |
| A | R | A | L | T |   |   |   | Y | Y | D | Y | E | F | A | Y | W | G | Q | G |
| A | R | A | L | T |   |   |   | Y | Y | D | Y | E | F | A | Y | W | G | Q | G |
| A | R | A | L | T |   |   |   | Y | Y | D | Y | E | F | A | Y | W | G | Q | G |
| A | R | A | L | T | – | – | – | Y | Y | D | Y | E | F | A | Y | W | G | Q | G |

FIG. 31b-15

| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |

FIG. 31b-16

| FIG. 31b-1 | FIG. 31b-2 | FIG. 31b-3 | FIG. 31b-4 | FIG. 31b-5 | FIG. 31b-6 | FIG. 31b-7 | FIG. 31b-8 |
| FIG. 31b-9 | FIG. 31b-10 | FIG. 31b-11 | FIG. 31b-12 | FIG. 31b-13 | FIG. 31b-14 | FIG. 31b-15 | FIG. 31b-16 |

FIG. 31b

SEQ ID NO.: 379
DILLTQSPATLSLSPGERVTLSCRASQSIGTNIHWYQQKPDQSPKLLIKYASESISGI
PSRFSGSGSGTDFTLTISSLQPEDFADYYCQQNNNWPTTFGAGTKLEIK
*FIG. 32a*
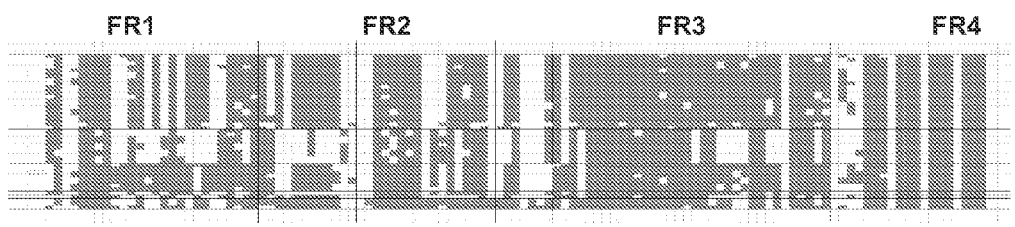
*FIG. 32b*
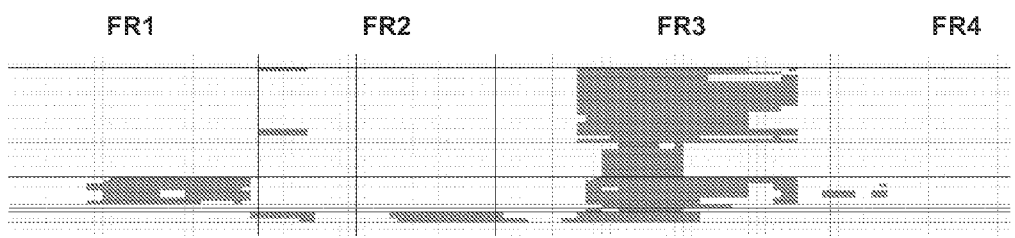
*FIG. 32c*
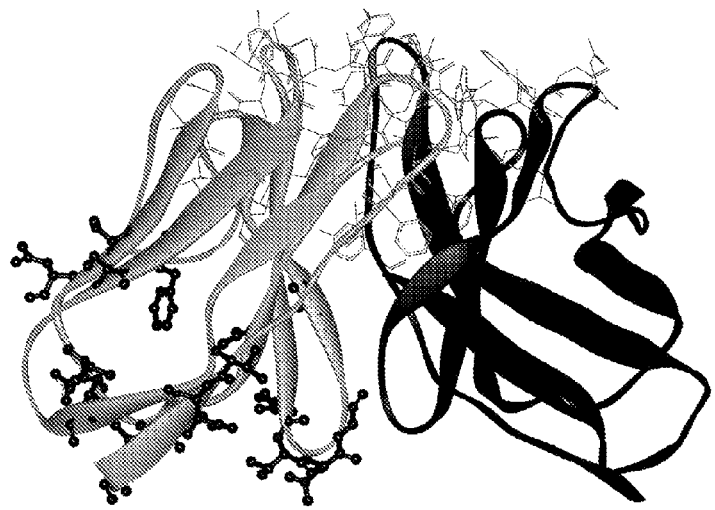
*FIG. 32d*

SEQ ID NO.: 380
DILLTQSPSSLSASVGDRVTITCRASQSIGTNIHWYQQKPDQSPKLLIKYASESISGIP
SRFSGSGSGTDFTLTISSLQAEDVAVYYCQQNNNWPTTFGAGTKLEIK
FIG. 33a
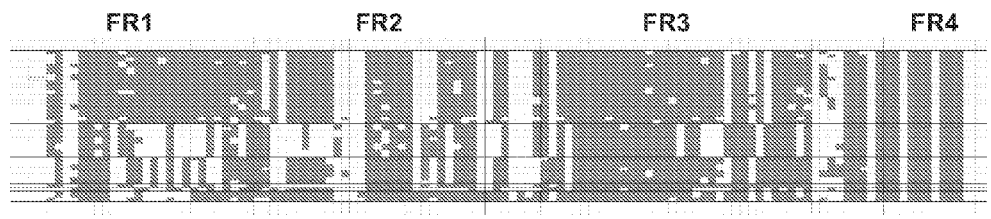
FIG. 33b
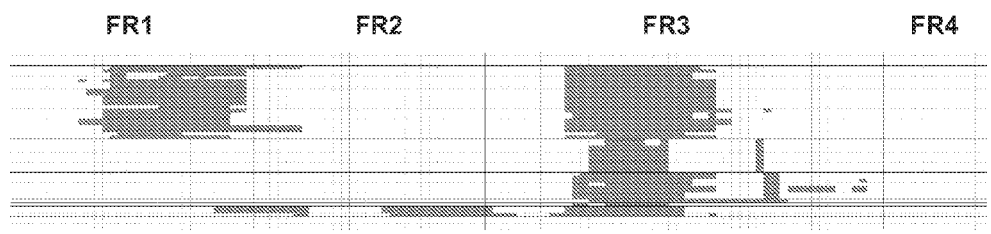
FIG. 33c
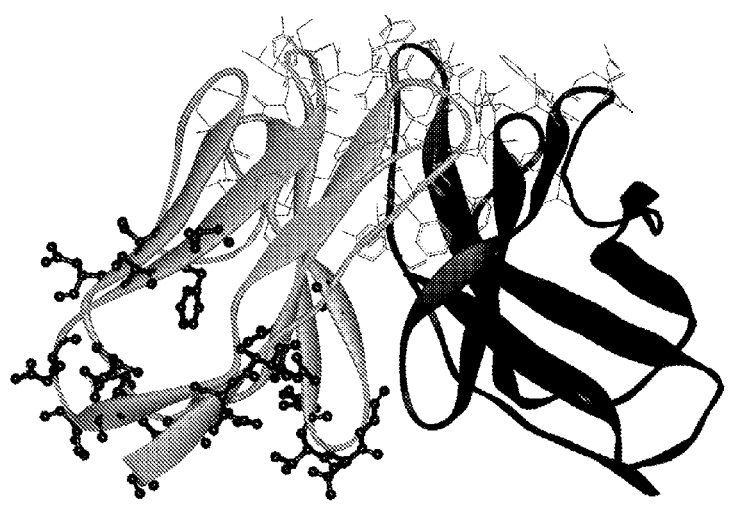
FIG. 33d SEQ ID NO.: 381
DILLTQSPAFLSVTPGEKVTITCRASQSIGTNIHWYQQKPDQSPKLLIKYASESISGIP
SRFSGSGSGTDFTLTINSLEAEDAATYYCQQNNNWPTTFGAGTKLEIK
*FIG. 34a*
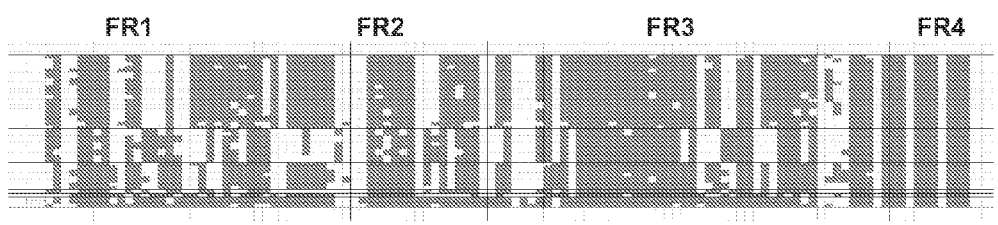
*FIG. 34b*
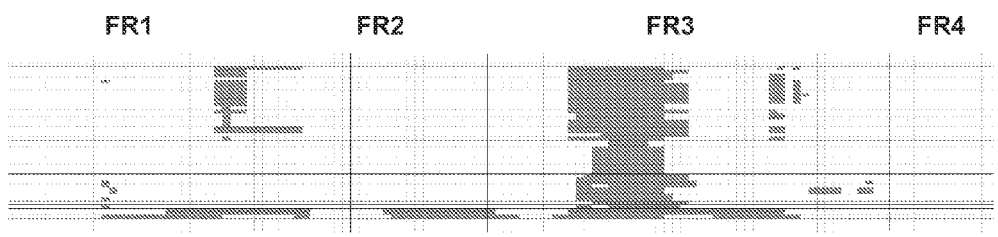
*FIG. 34c*
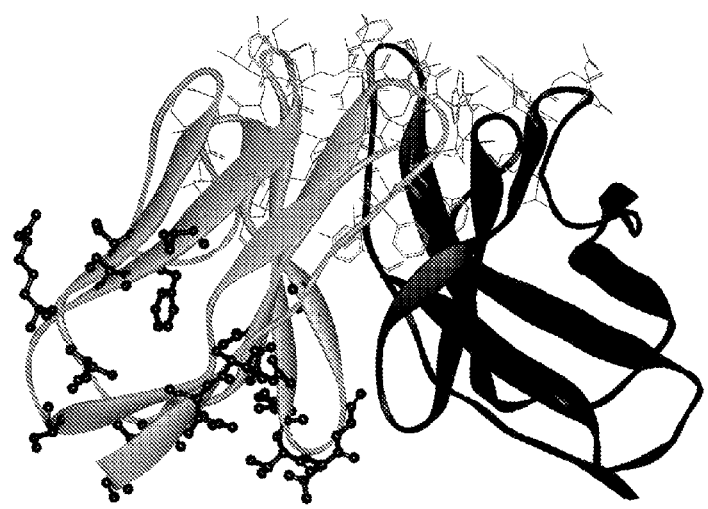
*FIG. 34d*

SEQ ID NO.: 382
QVQLQQSGPGLVKPSQTLSLTCTVSGFSLTNYGVHWVRQAPGKGLEWLGVIWSG
GNTDYNTSLKSRLTISKDNSKSQVVLQMNSLRAEDTAVYYCARALTYYDYEFAYW
GQGTLVTVSS
*FIG. 35a*
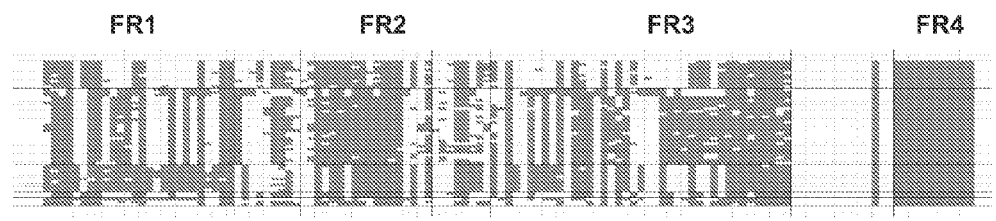
*FIG. 35b*
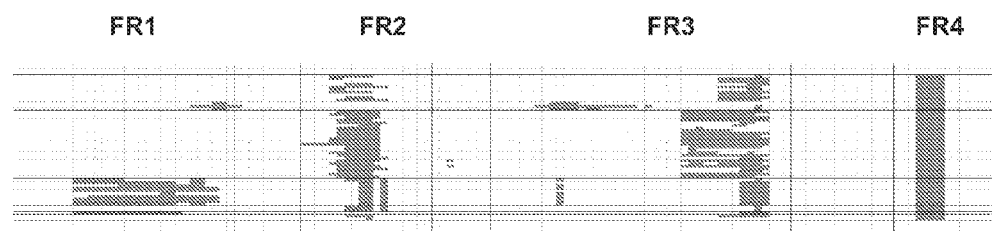
*FIG. 35c*
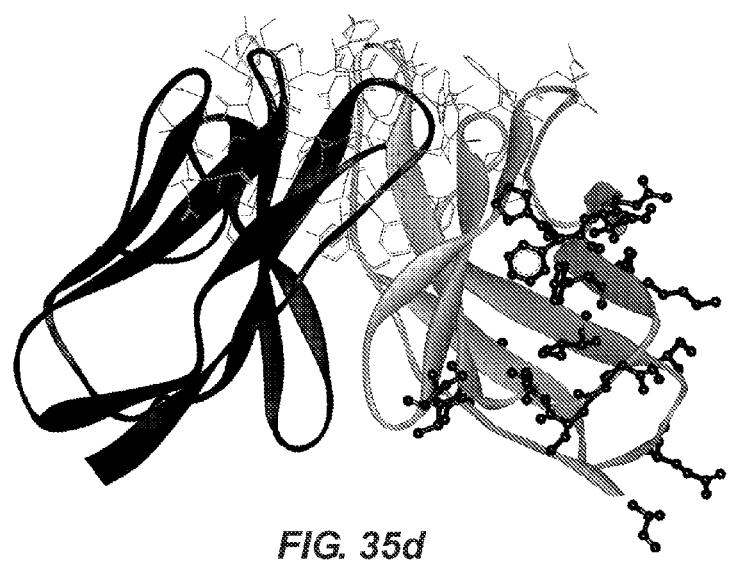
*FIG. 35d*

SEQ ID NO.: 383
QVQLQQSGPGLVKPSQTLSLTCTVSGFSLTNYGVHWVRQAPGKGLEWLGVIWSG
GNTDYNTSLKSRLTISKDNSKSQVVLTMTNMDPVDTATYYCARALTYYDYEFAYWG
QGTLVTVSS
*FIG. 36a*
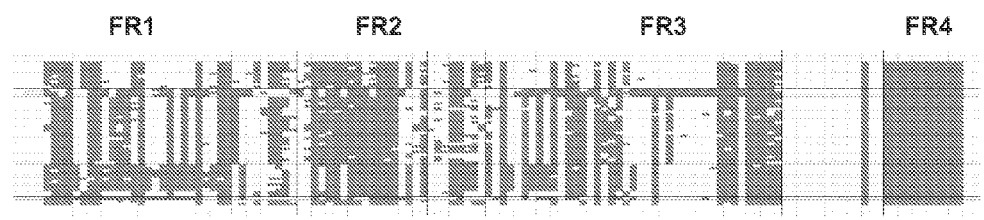
*FIG. 36b*
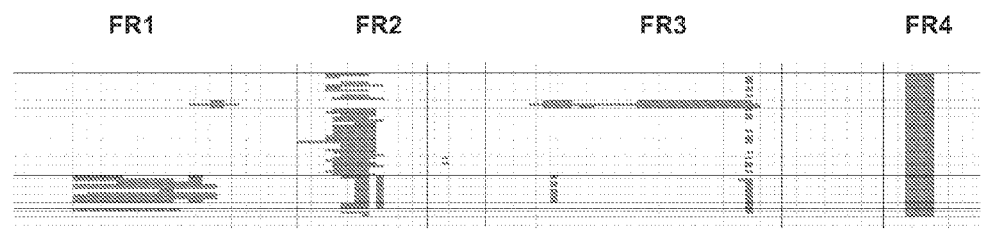
*FIG. 36c*
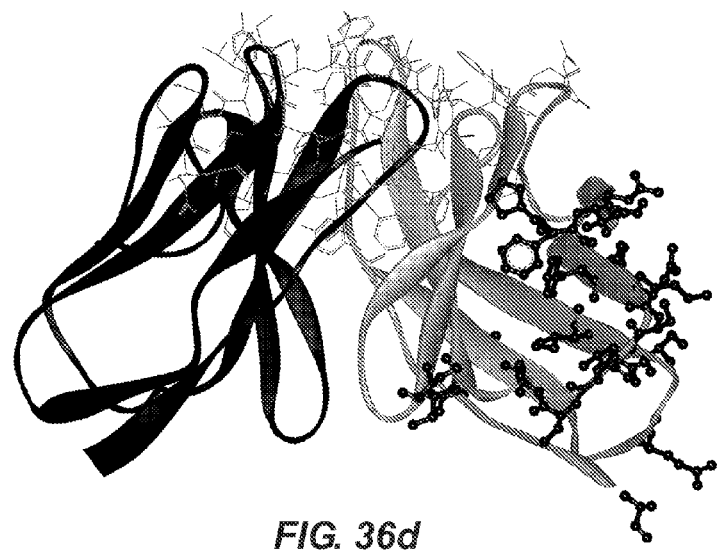
*FIG. 36d*

SEQ ID NO.: 384
QVQLQQSGPGLVKPSQTLSLTCTVSGFSLTNYGVHWVRQAPGKGLEWLGVIWSG
GNTDYNTPLTSRLTINKDNSKSQVVLQMNSLRAEDTAVYYCARALTYYDYEFAYW
GQGTLVTVSS
*FIG. 37a*
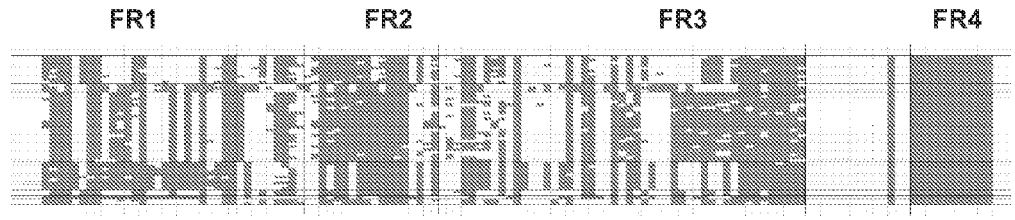
*FIG. 37b*
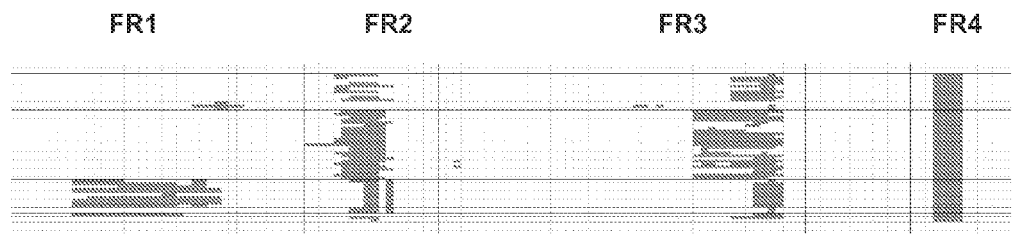
*FIG. 37c*
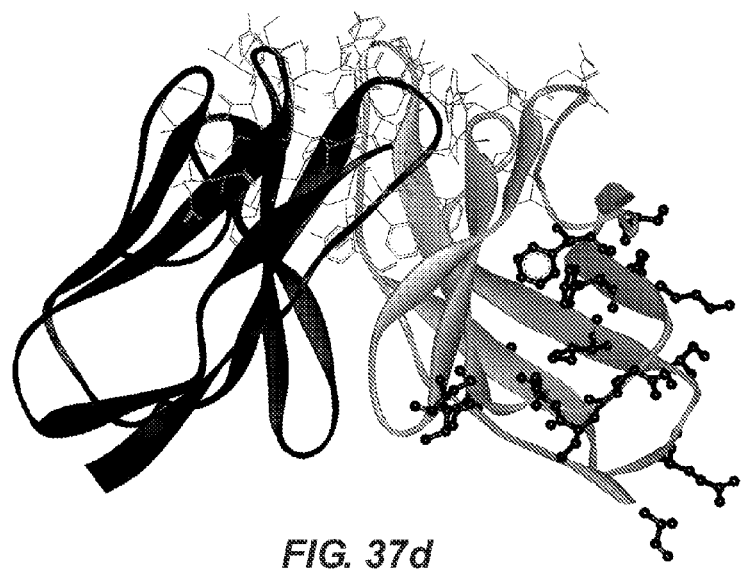
*FIG. 37d*

SEQ ID NO.: 385
QVQLQQSGPGLVKPSQTLSLTCTVSGFSLTNYGVHWVRQAPGKGLEWVGVIWSG
GNTDYNTSVKGRFTISKDNSKSQVYLQMNSLRAEDTAVYYCARALTYYDYEFAYW
GQGTLVTVSS
*FIG. 38a*
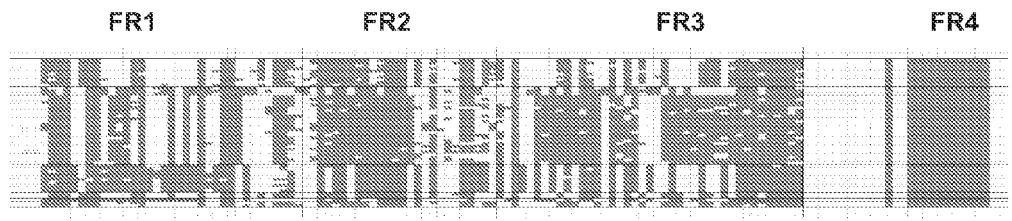
*FIG. 38b*
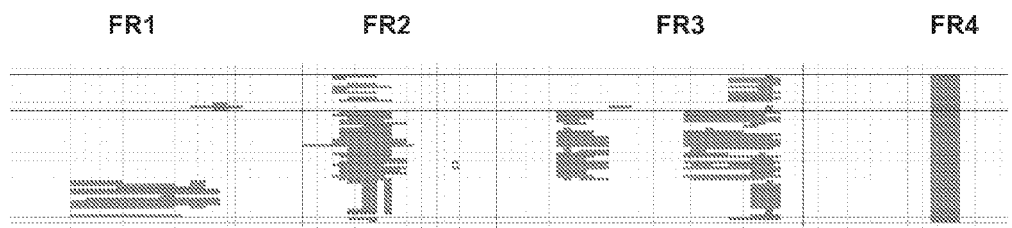
*FIG. 38c*
*FIG. 38d*

SEQ ID NO.: 386
QVQLQQSGPGLVKPSQTLSLTCTVSGFSLTNYGVHWVRQPPGKGLEWIGVIWSG
GNTDYNTSLKSRVTISKDNSKSQVSLKLSSVTAADTAVYYCARALTYYDYEFAYWG
QGTLVTVSS
*FIG. 39a*
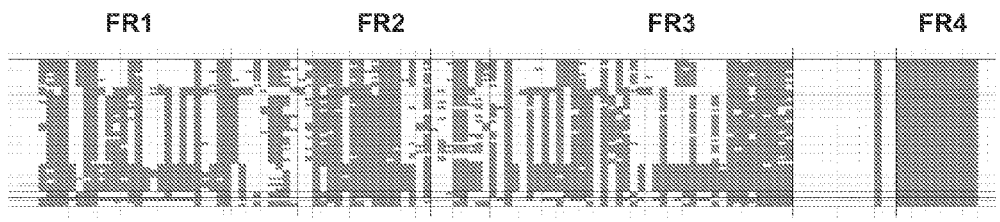
*FIG. 39b*
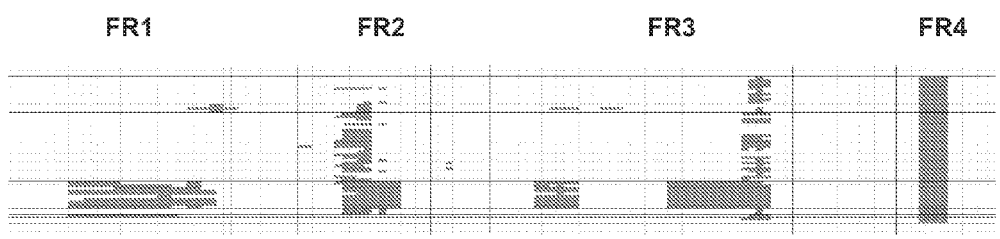
*FIG. 39c*
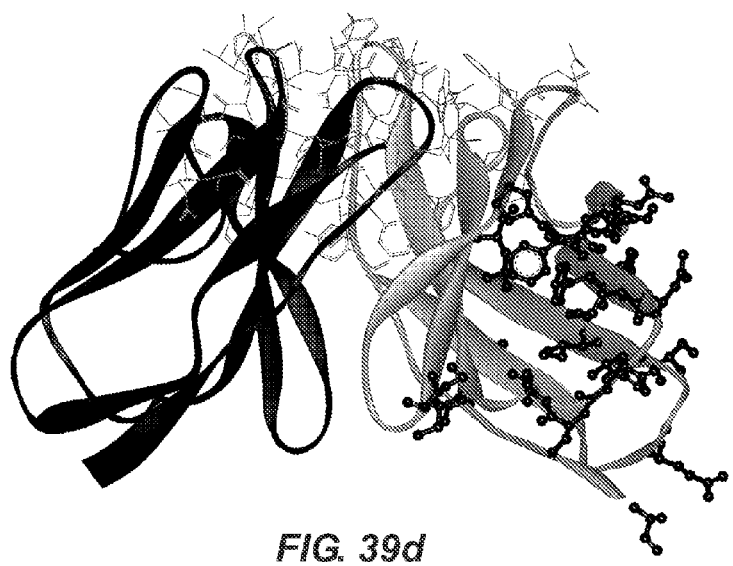
*FIG. 39d*

SEQ ID NO.: 387
QVQLVESGGGLVQPGRSLRLSCAVSGFSLTNYGVHWVRQAPGKGLEWVSVIWSG
GNTDYNTSVKGRFTISKDNSKSTVYLQMNSLRAEDTAVYYCARALTYYDYEFAYW
GQGTLVTVSS
*FIG. 40a*
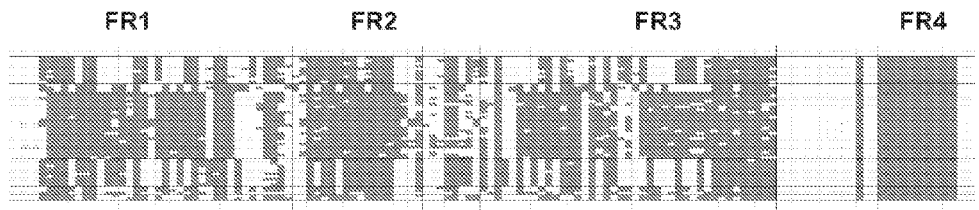
*FIG. 40b*
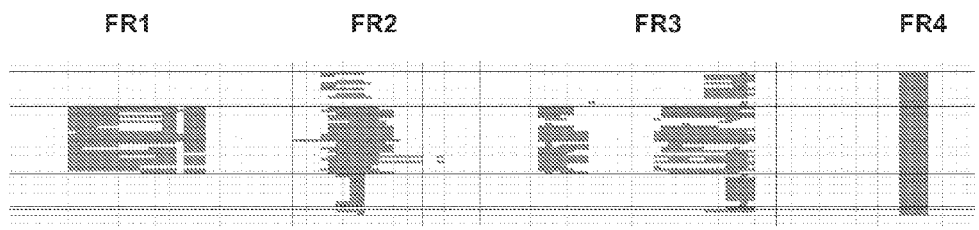
*FIG. 40c*
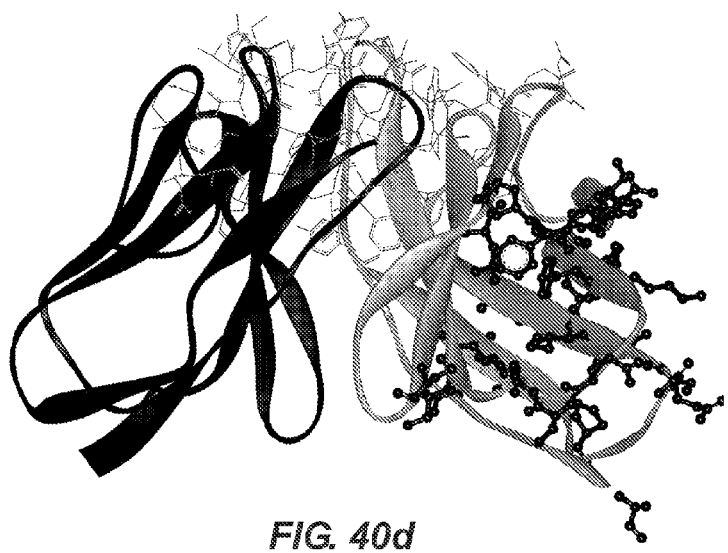
*FIG. 40d*

SEQ ID NO.: 388
DIQMTQSPSFLSASVGDRVTINCKASQNINNYLNWYQQKLGEAPKRLIYNTNNLQT
GIPSRFSGSGSGTDYTLTISSLQPEDFATYFCLQHNSFPTFGAGTKLELK
FIG. 43a
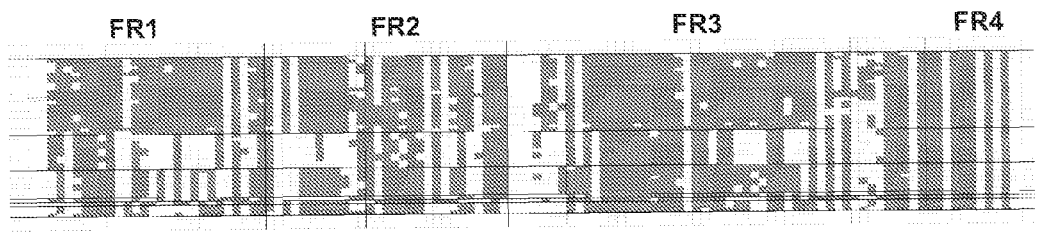
FIG. 43b
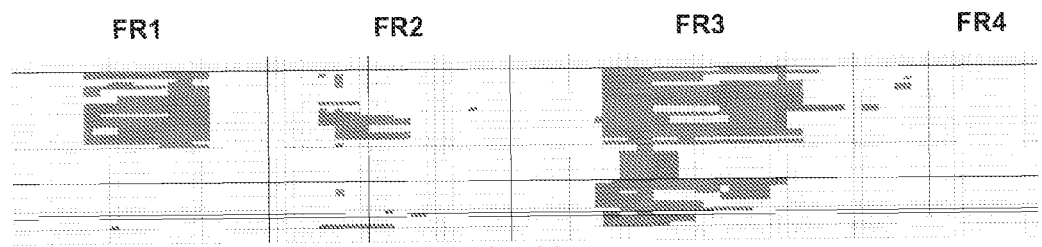
FIG. 43c
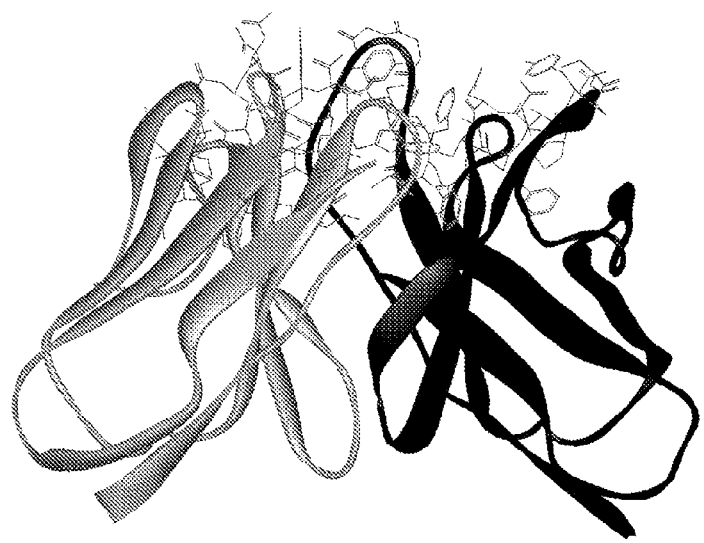
FIG. 43d SEQ ID NO.: 389
QVNLLQSGAALVKPGASVKLSCKGSGFTFTDYKIHWVKQSHGKSLEWIGYFNPNS
GYSTYNEKFKSKATLTADKSTDTAYMELTSLTSEDSATYYCTRLSPGGYYVMDAWG
QGASVTVSS
*FIG. 44a*
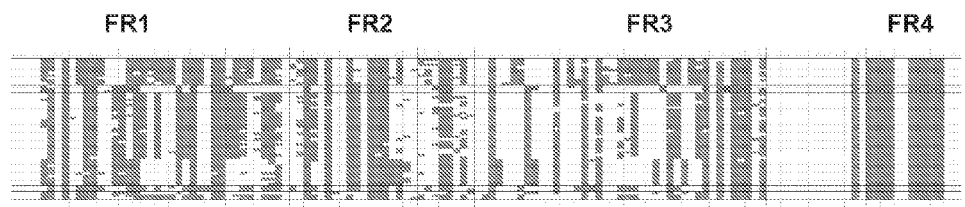
*FIG. 44b*
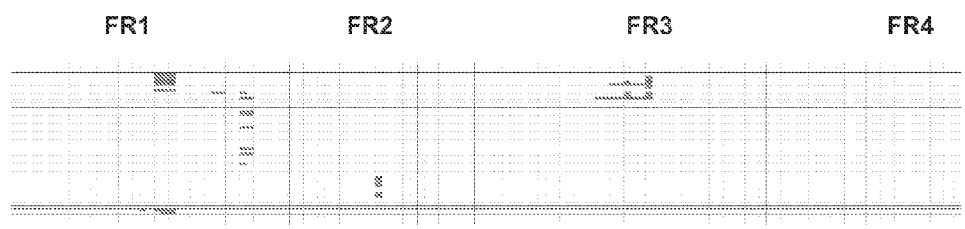
*FIG. 44c*
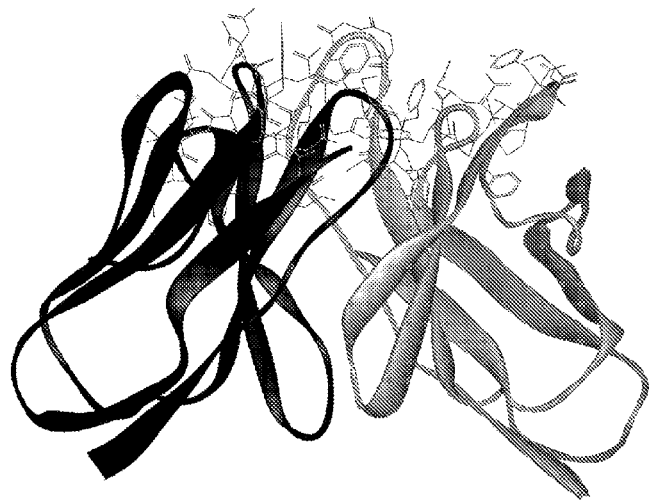
*FIG. 44d*

SEQ ID NO.: 390
DIQMTQSPSSLSASVGDRVTITCRASQNINNYLGWYQQKPGKAPKRLIYNTNNLQT
GVPSRFSGSGSGTEFTLTISSLQPEDFATYYCLQHNSFPTFGAGTKLEIK
*FIG. 45a*
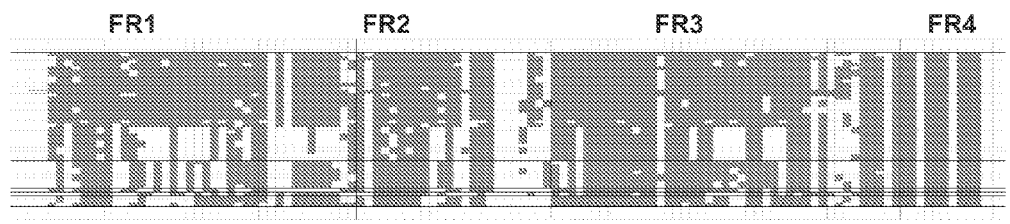
*FIG. 45b*
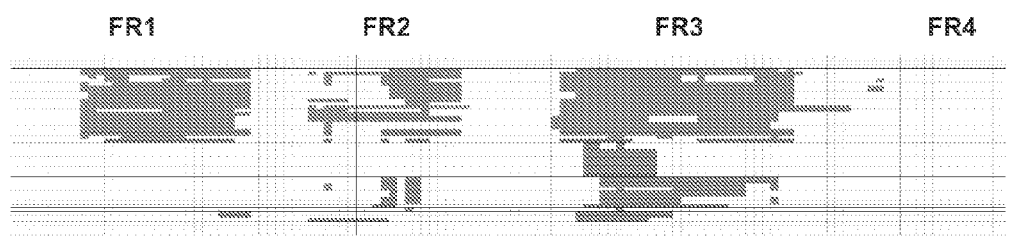
*FIG. 45c*
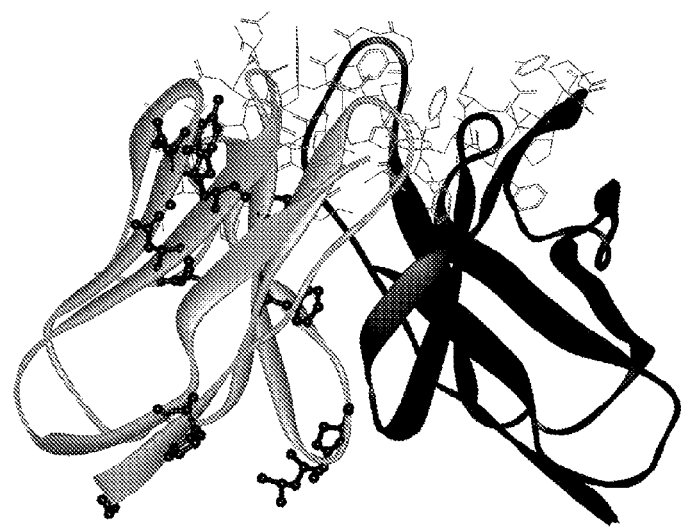
*FIG. 45d*

SEQ ID NO.: 391
EVQLVQSGAEVKKPGATVKISCKVSGFTFTDYKMHWVQQAPGKGLEWMGLVNPN
SGYTIYAEKFQGRVTITADTSTDTAYMELSSLRSEDTAVYYCATLSPGGYYVMDAW
GQGTLVTVSS
*FIG. 46a*
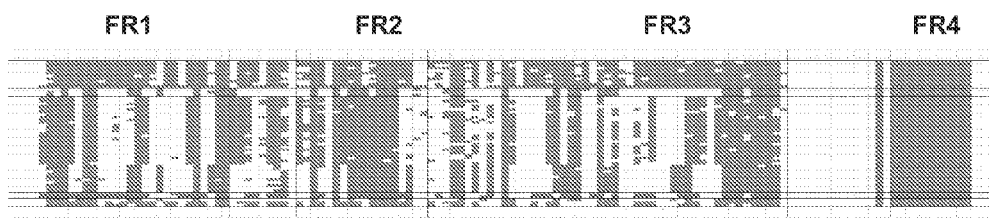
*FIG. 46b*
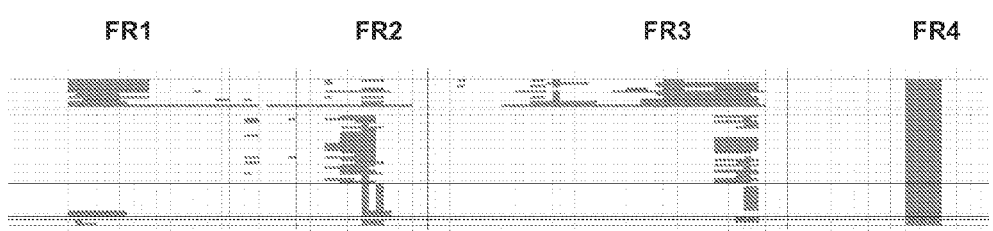
*FIG. 46c*
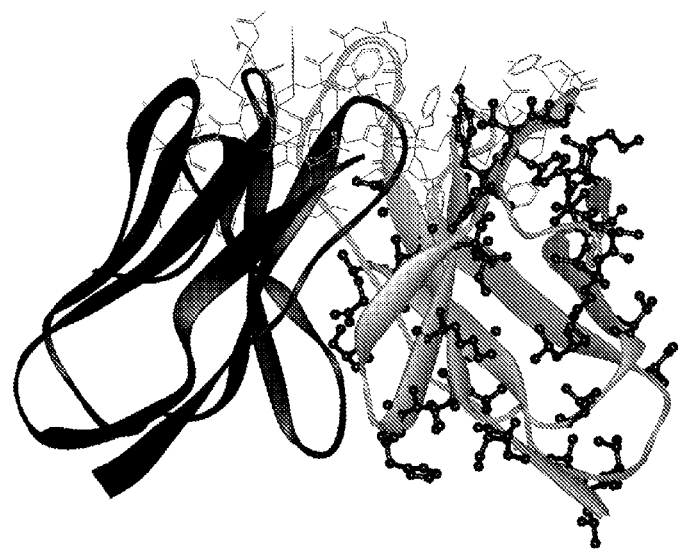
*FIG. 46d*

ICR62 VL HEC Calculation 1

| (WT) SEQ ID NO.:388 | Iter | Structural Consensus | Structural Precedence | HSC | HSS | N$_g$max | Kabat FRH | WT Muts |
|---|---|---|---|---|---|---|---|---|
| SEQ ID NO.:392 | 1 | 0.60 | 0.59 | 0.90 | 0.56 | 56 | 0.48 | 7 |
| SEQ ID NO.:393 | 2 | 0.60 | 0.59 | 0.90 | 0.56 | 56 | 0.48 | 7 |
| SEQ ID NO.:394 | 3 | 0.59 | 0.58 | 0.90 | 0.56 | 56 | 0.50 | 7 |
| SEQ ID NO.:395 | 4 | 0.60 | 0.57 | 0.90 | 0.56 | 56 | 0.59 | 7 |
| SEQ ID NO.:396 | 5 | 0.59 | 0.58 | 0.90 | 0.56 | 56 | 0.50 | 7 |
| SEQ ID NO.:397 | 6 | 0.59 | 0.58 | 0.90 | 0.56 | 56 | 0.50 | 7 |
| SEQ ID NO.:398 | 7 | 0.59 | 0.58 | 0.90 | 0.56 | 56 | 0.50 | 7 |
| SEQ ID NO.:399 | 8 | 0.58 | 0.56 | 0.90 | 0.56 | 56 | 0.48 | 7 |
| SEQ ID NO.:400 | 9 | 0.60 | 0.58 | 0.90 | 0.56 | 56 | 0.66 | 7 |
| SEQ ID NO.:401 | 10 | 0.61 | 0.59 | 0.90 | 0.56 | 56 | 0.64 | 7 |
| SEQ ID NO.:402 | 11 | 0.58 | 0.55 | 0.90 | 0.56 | 56 | 0.52 | 7 |
| SEQ ID NO.:403 | 12 | 0.59 | 0.58 | 0.90 | 0.56 | 56 | 0.50 | 7 |
| SEQ ID NO.:404 | 13 | 0.59 | 0.57 | 0.90 | 0.56 | 56 | 0.48 | 7 |
| SEQ ID NO.:405 | 14 | 0.58 | 0.56 | 0.90 | 0.56 | 56 | 0.48 | 7 |
| SEQ ID NO.:406 | 15 | 0.58 | 0.55 | 0.90 | 0.56 | 56 | 0.52 | 7 |
| SEQ ID NO.:407 | 16 | 0.59 | 0.58 | 0.90 | 0.56 | 56 | 0.50 | 7 |
| SEQ ID NO.:408 | 17 | 0.58 | 0.56 | 0.90 | 0.56 | 56 | 0.48 | 7 |
| SEQ ID NO.:409 | 18 | 0.59 | 0.56 | 0.90 | 0.56 | 56 | 0.52 | 7 |
| SEQ ID NO.:410 | 19 | 0.60 | 0.58 | 0.90 | 0.56 | 56 | 0.66 | 7 |
| SEQ ID NO.:411 | 20 | 0.61 | 0.59 | 0.90 | 0.56 | 56 | 0.64 | 7 |

*FIG. 47a-1*

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|----|----|----|----|----|----|----|----|----|----|----|
| D | I | Q | M | T | Q | S | P | S | F | L | S | A | S | V | G | D | R | V | T |
| D | I | Q | M | T | Q | S | P | S | T | L | S | A | S | V | G | D | R | V | T |
| D | I | Q | M | T | Q | S | P | S | T | L | S | A | S | V | G | D | R | V | T |
| D | I | Q | M | T | Q | S | P | S | T | L | S | A | S | V | G | D | R | V | T |
| D | I | Q | M | T | Q | S | P | S | S | L | S | A | S | V | G | D | R | V | T |
| D | I | Q | M | T | Q | S | P | S | T | L | S | A | S | V | G | D | R | V | T |
| D | I | Q | M | T | Q | S | P | S | T | L | S | A | S | V | G | D | R | V | T |
| D | I | Q | M | T | Q | S | P | S | T | L | S | A | S | V | G | D | R | V | T |
| D | I | Q | M | I | Q | S | P | S | F | L | S | A | S | V | G | D | R | V | T |
| D | I | Q | M | T | Q | S | P | S | S | L | S | A | S | V | G | D | R | V | T |
| D | I | Q | M | T | Q | S | P | S | S | L | S | A | S | V | G | D | R | V | T |
| D | I | Q | M | I | Q | S | P | S | F | L | S | A | S | V | G | D | R | V | T |
| D | I | Q | M | T | Q | S | P | S | T | L | S | A | S | V | G | D | R | V | T |
| D | I | Q | M | T | Q | S | P | S | F | L | S | A | S | V | G | D | R | V | T |
| D | I | Q | M | I | Q | S | P | S | F | L | S | A | S | V | G | D | R | V | T |
| D | I | Q | M | I | Q | S | P | S | F | L | S | A | S | V | G | D | R | V | T |
| D | I | Q | M | T | Q | S | P | S | T | L | S | A | S | V | G | D | R | V | T |
| D | I | Q | M | I | Q | S | P | S | F | L | S | A | S | V | G | D | R | V | T |
| D | I | Q | M | T | Q | S | P | S | T | L | S | A | S | V | G | D | R | V | T |
| D | I | Q | M | T | Q | S | P | S | S | L | S | A | S | V | G | D | R | V | T |
| D | I | Q | M | T | Q | S | P | S | S | L | S | A | S | V | G | D | R | V | T |

FIG. 47a-2

| 21 | 22 | 23 | 24 | 25 | 26 | 27 | 28 | 29 | 30 | | | | | | | 31 | 32 | 33 | 34 |
|---|---|---|---|---|---|---|---|---|---|---|---|---|---|---|---|---|---|---|---|
| I | N | C | K | A | S | Q | N | I | N | — | — | — | — | — | — | N | Y | L | N |
| I | T | C | R | A | S | Q | N | I | N | — | — | — | — | — | — | N | Y | L | N |
| I | T | C | R | A | S | Q | N | I | N | — | — | — | — | — | — | N | Y | L | N |
| I | T | C | Q | A | S | Q | N | I | N | — | — | — | — | — | — | N | Y | L | N |
| I | T | C | W | A | S | Q | N | I | N | — | — | — | — | — | — | N | Y | L | N |
| I | T | C | Q | A | S | Q | N | I | N | — | — | — | — | — | — | N | Y | L | N |
| I | T | C | Q | A | S | Q | N | I | N | — | — | — | — | — | — | N | Y | L | N |
| I | T | C | Q | A | S | Q | N | I | N | — | — | — | — | — | — | N | Y | L | N |
| I | T | C | Q | A | S | Q | N | I | N | — | — | — | — | — | — | N | Y | L | N |
| I | T | C | Q | A | S | Q | N | I | N | — | — | — | — | — | — | N | Y | L | N |
| I | T | C | R | A | S | Q | N | I | N | — | — | — | — | — | — | N | Y | L | N |
| I | T | C | W | A | S | Q | N | I | N | — | — | — | — | — | — | N | Y | L | N |
| I | T | C | Q | A | S | Q | N | I | N | — | — | — | — | — | — | N | Y | L | N |
| I | T | C | R | A | S | Q | N | I | N | — | — | — | — | — | — | N | Y | L | N |
| I | T | C | Q | A | S | Q | N | I | N | — | — | — | — | — | — | N | Y | L | N |
| I | T | C | W | A | S | Q | N | I | N | — | — | — | — | — | — | N | Y | L | N |
| I | T | C | Q | A | S | Q | N | I | N | — | — | — | — | — | — | N | Y | L | N |
| I | T | C | Q | A | S | Q | N | I | N | — | — | — | — | — | — | N | Y | L | N |
| I | T | C | W | A | S | Q | N | I | N | — | — | — | — | — | — | N | Y | L | N |
| I | T | C | Q | A | S | Q | N | I | N | — | — | — | — | — | — | N | Y | L | N |
| I | T | C | R | A | S | Q | N | I | N | — | — | — | — | — | — | N | Y | L | N |

FIG. 47a-3

| 35 | 36 | 37 | 38 | 39 | 40 | 41 | 42 | 43 | 44 | 45 | 46 | 47 | 48 | 49 | 50 | 51 | 52 | 53 | 54 |
|---|---|---|---|---|---|---|---|---|---|---|---|---|---|---|---|---|---|---|---|
| W | Y | Q | Q | K | L | G | E | A | P | K | R | L | I | Y | N | T | N | N | L |
| W | Y | Q | Q | K | P | G | K | A | P | K | R | L | I | Y | N | T | N | N | L |
| W | Y | Q | Q | K | P | G | K | A | P | K | R | L | I | Y | N | T | N | N | L |
| W | Y | Q | Q | K | P | G | K | A | P | K | R | L | I | Y | N | T | N | N | L |
| W | Y | Q | Q | K | P | G | K | A | P | K | R | L | I | Y | N | T | N | N | L |
| W | Y | Q | Q | K | P | G | K | A | P | K | R | L | I | Y | N | T | N | N | L |
| W | Y | Q | Q | K | P | G | K | A | P | K | R | L | I | Y | N | T | N | N | L |
| W | Y | Q | Q | K | P | G | K | A | P | K | R | L | I | Y | N | T | N | N | L |
| W | Y | Q | Q | K | P | G | K | A | P | K | R | L | I | Y | N | T | N | N | L |
| W | Y | Q | Q | K | P | G | K | A | P | K | R | L | I | Y | N | T | N | N | L |
| W | Y | Q | Q | K | P | G | K | A | P | K | R | L | I | Y | N | T | N | N | L |
| W | Y | Q | Q | K | P | G | K | A | P | K | R | L | I | Y | N | T | N | N | L |
| W | Y | Q | Q | K | P | G | K | A | P | K | R | L | I | Y | N | T | N | N | L |
| W | Y | Q | Q | K | P | G | K | A | P | K | R | L | I | Y | N | T | N | N | L |
| W | Y | Q | Q | K | P | G | K | A | P | K | R | L | I | Y | N | T | N | N | L |
| W | Y | Q | Q | K | P | G | K | A | P | K | R | L | I | Y | N | T | N | N | L |
| W | Y | Q | Q | K | P | G | K | A | P | K | R | L | I | Y | N | T | N | N | L |
| W | Y | Q | Q | K | P | G | K | A | P | K | R | L | I | Y | N | T | N | N | L |
| W | Y | Q | Q | K | P | G | K | A | P | K | R | L | I | Y | N | T | N | N | L |
| W | Y | Q | Q | K | P | G | K | A | P | K | R | L | I | Y | N | T | N | N | L |

FIG. 47a-4

| 55 | 56 | 57 | 58 | 59 | 60 | 61 | 62 | 63 | 64 | 65 | 66 | 67 | 68 | 69 | 70 | 71 | 72 | 73 | 74 |
|----|----|----|----|----|----|----|----|----|----|----|----|----|----|----|----|----|----|----|----|
| Q | T | G | I | P | S | R | F | S | G | S | G | S | G | T | D | Y | T | L | T |
| Q | T | G | I | P | S | R | F | S | G | S | G | S | G | T | D | Y | T | L | T |
| Q | T | G | I | P | S | R | F | S | G | S | G | S | G | T | D | Y | T | L | T |
| Q | T | G | I | P | S | R | F | S | G | S | G | S | G | T | D | Y | T | L | T |
| Q | T | G | I | P | S | R | F | S | G | S | G | S | G | T | D | Y | T | L | T |
| Q | T | G | I | P | S | R | F | S | G | S | G | S | G | T | D | Y | T | L | T |
| Q | T | G | I | P | S | R | F | S | G | S | G | S | G | T | D | Y | T | L | T |
| Q | T | G | I | P | S | R | F | S | G | S | G | S | G | T | D | Y | T | L | T |
| Q | T | G | I | P | S | R | F | S | G | S | G | S | G | T | D | Y | T | L | T |
| Q | T | G | I | P | S | R | F | S | G | S | G | S | G | T | D | Y | T | L | T |
| Q | T | G | I | P | S | R | F | S | G | S | G | S | G | T | D | Y | T | L | T |
| Q | T | G | I | P | S | R | F | S | G | S | G | S | G | T | D | Y | T | L | T |
| Q | T | G | I | P | S | R | F | S | G | S | G | S | G | T | D | Y | T | L | T |
| Q | T | G | I | P | S | R | F | S | G | S | G | S | G | T | D | Y | T | L | T |
| Q | T | G | I | P | S | R | F | S | G | S | G | S | G | T | D | Y | T | L | T |
| Q | T | G | I | P | S | R | F | S | G | S | G | S | G | T | D | Y | T | L | T |
| Q | T | G | I | P | S | R | F | S | G | S | G | S | G | T | D | Y | T | L | T |
| Q | T | G | I | P | S | R | F | S | G | S | G | S | G | T | D | Y | T | L | T |
| Q | T | G | I | P | S | R | F | S | G | S | G | S | G | T | D | Y | T | L | T |

*FIG. 47a-5*

| 75 | 76 | 77 | 78 | 79 | 80 | 81 | 82 | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|
| I | S | S | L | Q | P | E | D | F | A | T | Y | F | C | L | Q | H | N | S | F |
| I | S | S | L | Q | P | E | D | F | A | T | Y | F | C | L | Q | H | N | S | F |
| I | S | S | L | Q | P | E | D | F | A | T | Y | F | C | L | Q | H | N | S | F |
| I | S | S | L | Q | P | E | D | F | A | T | Y | F | C | L | Q | H | N | S | F |
| I | S | S | L | Q | P | E | D | F | A | T | Y | F | C | L | Q | H | N | S | F |
| I | S | S | L | Q | P | E | D | F | A | T | Y | F | C | L | Q | H | N | S | F |
| I | S | S | L | Q | P | E | D | F | A | T | Y | F | C | L | Q | H | N | S | F |
| I | S | S | L | Q | P | E | D | F | A | T | Y | F | C | L | Q | H | N | S | F |
| I | S | S | L | Q | P | E | D | F | A | T | Y | F | C | L | Q | H | N | S | F |
| I | S | S | L | Q | P | E | D | F | A | T | Y | F | C | L | Q | H | N | S | F |
| I | S | S | L | Q | P | E | D | F | A | T | Y | F | C | L | Q | H | N | S | F |
| I | S | S | L | Q | P | E | D | F | A | T | Y | F | C | L | Q | H | N | S | F |
| I | S | S | L | Q | P | E | D | F | A | T | Y | F | C | L | Q | H | N | S | F |
| I | S | S | L | Q | P | E | D | F | A | T | Y | F | C | L | Q | H | N | S | F |
| I | S | S | L | Q | P | E | D | F | A | T | Y | F | C | L | Q | H | N | S | F |
| I | S | S | L | Q | P | E | D | F | A | T | Y | F | C | L | Q | H | N | S | F |
| I | S | S | L | Q | P | E | D | F | A | T | Y | F | C | L | Q | H | N | S | F |
| I | S | S | L | Q | P | E | D | F | A | T | Y | F | C | L | Q | H | N | S | F |
| I | S | S | L | Q | P | E | D | F | A | T | Y | F | C | L | Q | H | N | S | F |

*FIG. 47a-6*

| | | | 95 | 96 | 97 | 98 | 99 | 100 | 101 | 102 | 103 | 104 | 105 | 106 | 107 |
|---|---|---|---|---|---|---|---|---|---|---|---|---|---|---|---|
| – | – | P | – | T | F | G | A | G | T | K | L | E | L | K |
| – | – | P | – | T | F | G | A | G | T | K | X | E | I | K |
| – | – | P | – | T | F | G | A | G | T | K | X | E | I | K |
| – | – | P | – | T | F | G | A | G | T | K | X | E | I | K |
| – | – | P | – | T | F | G | A | G | T | K | X | E | I | K |
| – | – | P | – | T | F | G | A | G | T | K | X | E | I | K |
| – | – | P | – | T | F | G | A | G | T | K | X | E | I | K |
| – | – | P | – | T | F | G | A | G | T | K | X | E | I | K |
| – | – | P | – | T | F | G | A | G | T | K | X | E | I | K |
| – | – | P | – | T | F | G | A | G | T | K | X | E | I | K |
| – | – | P | – | T | F | G | A | G | T | K | X | E | I | K |
| – | – | P | – | T | F | G | A | G | T | K | X | E | I | K |
| – | – | P | – | T | F | G | A | G | T | K | X | E | I | K |
| – | – | P | – | T | F | G | A | G | T | K | X | E | I | K |
| – | – | P | – | T | F | G | A | G | T | K | X | E | I | K |
| – | – | P | – | T | F | G | A | G | T | K | X | E | I | K |
| – | – | P | – | T | F | G | A | G | T | K | X | E | I | K |
| – | – | P | – | T | F | G | A | G | T | K | X | E | I | K |

*FIG. 47a-7*

| FIG. 47a-1 | FIG. 47a-2 | FIG. 47a-3 | FIG. 47a-4 | FIG. 47a-5 | FIG. 47a-6 | FIG. 47a-7 |
|---|---|---|---|---|---|---|

*FIG. 47a*

ICR62 VH HEC Calculation 1

| (WT) SEQ ID NO.:389 | Iter | Structural Consensus | Structural Precedence | HSC | HSS | $N_9$max | FRH | Kabat WT Muts |
|---|---|---|---|---|---|---|---|---|
| SEQ ID NO.:412 | 1 | 0.45 | 0.45 | 0.77 | 0.28 | 33 | 0.64 | 20 |
| SEQ ID NO.:413 | 9 | 0.45 | 0.45 | 0.77 | 0.28 | 33 | 0.64 | 20 |
| SEQ ID NO.:414 | 11 | 0.45 | 0.45 | 0.77 | 0.28 | 33 | 0.64 | 20 |
| SEQ ID NO.:415 | 12 | 0.45 | 0.45 | 0.77 | 0.28 | 33 | 0.64 | 20 |
| SEQ ID NO.:416 | 16 | 0.45 | 0.45 | 0.77 | 0.28 | 33 | 0.64 | 20 |
| SEQ ID NO.:417 | 19 | 0.45 | 0.45 | 0.77 | 0.28 | 33 | 0.64 | 20 |
| SEQ ID NO.:418 | 20 | 0.45 | 0.45 | 0.77 | 0.28 | 33 | 0.64 | 20 |
| SEQ ID NO.:419 | 3 | 0.44 | 0.44 | 0.77 | 0.28 | 33 | 0.67 | 20 |
| SEQ ID NO.:420 | 4 | 0.44 | 0.44 | 0.77 | 0.28 | 33 | 0.67 | 20 |
| SEQ ID NO.:421 | 10 | 0.44 | 0.44 | 0.77 | 0.28 | 33 | 0.67 | 20 |
| SEQ ID NO.:422 | 5 | 0.45 | 0.44 | 0.77 | 0.29 | 34 | 0.62 | 21 |
| SEQ ID NO.:423 | 6 | 0.45 | 0.44 | 0.77 | 0.29 | 34 | 0.62 | 21 |
| SEQ ID NO.:424 | 8 | 0.45 | 0.44 | 0.77 | 0.29 | 34 | 0.62 | 21 |
| SEQ ID NO.:425 | 15 | 0.45 | 0.44 | 0.77 | 0.29 | 34 | 0.62 | 21 |
| SEQ ID NO.:426 | 18 | 0.45 | 0.44 | 0.77 | 0.29 | 34 | 0.62 | 21 |
| SEQ ID NO.:427 | 2 | 0.45 | 0.44 | 0.77 | 0.29 | 34 | 0.65 | 21 |
| SEQ ID NO.:428 | 7 | 0.45 | 0.44 | 0.77 | 0.29 | 34 | 0.65 | 21 |
| SEQ ID NO.:429 | 13 | 0.45 | 0.44 | 0.77 | 0.29 | 34 | 0.65 | 21 |
| SEQ ID NO.:430 | 14 | 0.45 | 0.44 | 0.77 | 0.29 | 34 | 0.65 | 21 |
| SEQ ID NO.:431 | 17 | 0.45 | 0.44 | 0.77 | 0.29 | 34 | 0.65 | 21 |

*FIG. 47b-1*

| | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| | Q | V | N | L | L | Q | S | G | A | A | L | V | K | P | G | A | S | V | K | L |
| | Q | V | Q | L | Q | Q | S | G | P | G | L | V | K | P | G | A | S | V | K | V |
| | Q | V | Q | L | Q | Q | S | G | P | G | L | V | K | P | G | A | S | V | K | V |
| | Q | V | Q | L | Q | Q | S | G | P | G | L | V | K | P | G | A | S | V | K | V |
| | Q | V | Q | L | Q | Q | S | G | P | G | L | V | K | P | G | A | S | V | K | V |
| | Q | V | Q | L | Q | Q | S | G | P | G | L | V | K | P | G | A | S | V | K | V |
| | Q | V | Q | L | Q | Q | S | G | P | G | L | V | K | P | G | A | S | V | K | V |
| | Q | V | Q | L | Q | Q | S | G | P | G | L | V | K | P | G | A | S | V | K | V |
| | Q | V | Q | L | Q | Q | S | G | P | G | L | V | K | P | G | A | S | V | K | V |
| | Q | V | Q | L | Q | Q | S | G | P | G | L | V | K | P | G | A | S | V | K | V |
| | Q | V | Q | L | V | E | S | G | G | G | L | V | K | P | G | A | S | V | K | V |
| | Q | V | Q | L | V | E | S | G | G | G | L | V | K | P | G | A | S | V | K | V |
| | Q | V | Q | L | V | E | S | G | G | G | L | V | K | P | G | A | S | V | K | V |
| | Q | V | Q | L | V | E | S | G | G | G | L | V | K | P | G | A | S | V | K | V |
| | Q | V | Q | L | V | E | S | G | G | G | L | V | K | P | G | A | S | V | K | V |
| | Q | V | Q | L | V | E | S | G | G | G | L | V | K | P | G | A | S | V | K | V |
| | Q | V | Q | L | V | E | S | G | G | G | L | V | K | P | G | A | S | V | K | V |
| | Q | V | Q | L | V | E | S | G | G | G | L | V | K | P | G | A | S | V | K | V |
| | Q | V | Q | L | V | E | S | G | G | G | L | V | K | P | G | A | S | V | K | V |

*FIG. 47b-2*

| 21 | 22 | 23 | 24 | 25 | 26 | 27 | 28 | 29 | 30 | 31 | | 32 | 33 | 34 | 35 | 36 | 37 | 38 |
|---|---|---|---|---|---|---|---|---|---|---|---|---|---|---|---|---|---|---|
| S | C | K | G | S | G | F | T | F | T | D | — — | Y | K | I | H | W | V | K |
| | | | | | | | | | | | | | | | | | | |
| S | C | K | G | S | G | F | T | F | T | D | — — | Y | K | I | H | W | V | R |
| S | C | K | G | S | G | F | T | F | T | D | — — | Y | K | I | H | W | V | R |
| S | C | K | G | S | G | F | T | F | T | D | — — | Y | K | I | H | W | V | R |
| S | C | K | G | S | G | F | T | F | T | D | — — | Y | K | I | H | W | V | R |
| S | C | K | G | S | G | F | T | F | T | D | — — | Y | K | I | H | W | V | R |
| S | C | K | G | S | G | F | T | F | T | D | — — | Y | K | I | H | W | V | R |
| S | C | K | G | S | G | F | T | F | T | D | — — | Y | K | I | H | W | V | R |
| S | C | K | G | S | G | F | T | F | T | D | — — | Y | K | I | H | W | V | Q |
| S | C | K | G | S | G | F | T | F | T | D | — — | Y | K | I | H | W | V | Q |
| S | C | K | G | S | G | F | T | F | T | D | — — | Y | K | I | H | W | V | Q |
| S | C | K | G | S | G | F | T | F | T | D | — — | Y | K | I | H | W | V | R |
| S | C | K | G | S | G | F | T | F | T | D | — — | Y | K | I | H | W | V | R |
| S | C | K | G | S | G | F | T | F | T | D | — — | Y | K | I | H | W | V | R |
| S | C | K | G | S | G | F | T | F | T | D | — — | Y | K | I | H | W | V | R |
| S | C | K | G | S | G | F | T | F | T | D | — — | Y | K | I | H | W | V | R |
| S | C | K | G | S | G | F | T | F | T | D | — — | Y | K | I | H | W | V | Q |
| S | C | K | G | S | G | F | T | F | T | D | — — | Y | K | I | H | W | V | Q |
| S | C | K | G | S | G | F | T | F | T | D | — — | Y | K | I | H | W | V | Q |
| S | C | K | G | S | G | F | T | F | T | D | — — | Y | K | I | H | W | V | Q |
| S | C | K | G | S | G | F | T | F | T | D | — — | Y | K | I | H | W | V | Q |

*FIG. 47b-3*

| 39 | 40 | 41 | 42 | 43 | 44 | 45 | 46 | 47 | 48 | 49 | 50 | 51 | 52 | 52a | 53 | 54 | 55 |
|---|---|---|---|---|---|---|---|---|---|---|---|---|---|---|---|---|---|
| Q | S | H | G | K | S | L | E | W | I | G | Y | F | N | P | N | S | G |
| Q | A | P | G | K | S | L | E | W | M | G | Y | F | N | P | N | S | G |
| Q | A | P | G | K | S | L | E | W | M | G | Y | F | N | P | N | S | G |
| Q | A | P | G | K | S | L | E | W | M | G | Y | F | N | P | N | S | G |
| Q | A | P | G | K | S | L | E | W | M | G | Y | F | N | P | N | S | G |
| Q | A | P | G | K | S | L | E | W | M | G | Y | F | N | P | N | S | G |
| Q | A | P | G | K | S | L | E | W | M | G | Y | F | N | P | N | S | G |
| Q | A | P | G | K | S | L | E | W | M | G | Y | F | N | P | N | S | G |
| Q | A | P | G | K | S | L | E | W | M | G | Y | F | N | P | N | S | G |
| Q | A | P | G | K | S | L | E | W | M | G | Y | F | N | P | N | S | G |
| Q | A | P | G | K | S | L | E | W | M | G | Y | F | N | P | N | S | G |
| Q | A | P | G | K | S | L | E | W | M | G | Y | F | N | P | N | S | G |
| Q | A | P | G | K | S | L | E | W | M | G | Y | F | N | P | N | S | G |
| Q | A | P | G | K | S | L | E | W | M | G | Y | F | N | P | N | S | G |
| Q | A | P | G | K | S | L | E | W | M | G | Y | F | N | P | N | S | G |
| Q | A | P | G | K | S | L | E | W | M | G | Y | F | N | P | N | S | G |
| Q | A | P | G | K | S | L | E | W | M | G | Y | F | N | P | N | S | G |
| Q | A | P | G | K | S | L | E | W | M | G | Y | F | N | P | N | S | G |
| Q | A | P | G | K | S | L | E | W | M | G | Y | F | N | P | N | S | G |

*FIG. 47b-4*

| 56 | 57 | 58 | 59 | 60 | 61 | 62 | 63 | 64 | 65 | 66 | 67 | 68 | 69 | 70 | 71 | 72 | 73 | 74 | 75 |
|---|---|---|---|---|---|---|---|---|---|---|---|---|---|---|---|---|---|---|---|
| Y | S | T | Y | N | E | K | F | K | S | K | A | T | L | T | A | D | K | S | T |
| Y | S | T | Y | N | E | K | F | Q | G | R | V | T | I | | T | A | D | K | S | T |
| Y | S | T | Y | N | E | K | F | Q | G | R | V | T | I | | T | A | D | K | S | T |
| Y | S | T | Y | N | E | K | F | Q | G | R | V | T | I | | T | A | D | K | S | T |
| Y | S | T | Y | N | E | K | F | Q | G | R | V | T | I | | T | A | D | K | S | T |
| Y | S | T | Y | N | E | K | F | Q | G | R | V | T | I | | T | A | D | K | S | T |
| Y | S | T | Y | N | E | K | F | Q | G | R | V | T | I | | T | A | D | K | S | T |
| Y | S | T | Y | N | E | K | F | Q | G | R | V | T | I | | T | A | D | K | S | T |
| Y | S | T | Y | N | E | K | F | Q | G | R | V | T | I | | T | A | D | K | S | T |
| Y | S | T | Y | N | E | K | F | Q | G | R | V | T | I | | T | A | D | K | S | T |
| Y | S | T | Y | N | E | K | F | Q | G | R | V | T | I | | T | A | D | K | S | T |
| Y | S | T | Y | N | E | K | F | Q | G | R | V | T | I | | T | A | D | K | S | T |
| Y | S | T | Y | N | E | K | F | Q | G | R | V | T | I | | T | A | D | K | S | T |
| Y | S | T | Y | N | E | K | F | Q | G | R | V | T | I | | T | A | D | K | S | T |
| Y | S | T | Y | N | E | K | F | Q | G | R | V | T | I | | T | A | D | K | S | T |
| Y | S | T | Y | N | E | K | F | Q | G | R | V | T | I | | T | A | D | K | S | T |
| Y | S | T | Y | N | E | K | F | Q | G | R | V | T | I | | T | A | D | K | S | T |
| Y | S | T | Y | N | E | K | F | Q | G | R | V | T | I | | T | A | D | K | S | T |

*FIG. 47b-5*

| 76 | 77 | 78 | 79 | 80 | 81 | 82 | 82a | 82b | 82c | 83 | 84 | 85 | 86 | 87 | 88 | 89 | 90 | 91 | 92 |
|---|---|---|---|---|---|---|---|---|---|---|---|---|---|---|---|---|---|---|---|
| D | T | A | Y | M | E | L | T | S | L | T | S | E | D | S | A | T | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |

FIG. 47b-6

| 93 | 94 | 95 | 96 | 97 | | | | 98 | 99 | 100 | 100a | 100b | 100c | 101 | 102 | 103 | 104 | 105 | 106 |
|---|---|---|---|---|---|---|---|---|---|---|---|---|---|---|---|---|---|---|---|
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |

*FIG. 47b-7*

| 107 | 108 | 109 | 110 | 111 | 112 | 113 |
|-----|-----|-----|-----|-----|-----|-----|
| A | S | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |

FIG. 47b-8

| FIG. 47b-1 | FIG. 47b-2 | FIG. 47b-3 | FIG. 47b-4 | FIG. 47b-5 | FIG. 47b-6 | FIG. 47b-7 | FIG. 47b-8 |

FIG. 47b

ICR62 VH HEC Calculation 2

| | Iter | Structural Consensus | Structural Precedence | HSC | HSS | $N_g$max | Kabat WT FRH | Muts |
|---|---|---|---|---|---|---|---|---|
| (WT) SEQ ID NO.:389 | | | | | | | | |
| SEQ ID NO.:432 | 5 | 0.44 | 0.47 | 0.78 | 0.33 | 39 | 0.85 | 21 |
| SEQ ID NO.:433 | 78 | 0.43 | 0.47 | 0.78 | 0.33 | 39 | 0.82 | 21 |
| SEQ ID NO.:434 | 2 | 0.44 | 0.47 | 0.78 | 0.33 | 39 | 0.56 | 21 |
| SEQ ID NO.:435 | 77 | 0.43 | 0.47 | 0.78 | 0.33 | 39 | 0.54 | 22 |
| SEQ ID NO.:436 | 51 | 0.43 | 0.46 | 0.78 | 0.33 | 39 | 0.56 | 21 |
| SEQ ID NO.:437 | 30 | 0.44 | 0.45 | 0.77 | 0.31 | 36 | 0.92 | 22 |
| SEQ ID NO.:438 | 90 | 0.44 | 0.45 | 0.77 | 0.31 | 36 | 0.89 | 23 |
| SEQ ID NO.:439 | 9 | 0.44 | 0.45 | 0.77 | 0.31 | 36 | 0.61 | 22 |
| SEQ ID NO.:440 | 24 | 0.44 | 0.44 | 0.77 | 0.31 | 36 | 0.89 | 22 |
| SEQ ID NO.:441 | 58 | 0.43 | 0.44 | 0.77 | 0.31 | 36 | 0.58 | 22 |
| SEQ ID NO.:442 | 6 | 0.45 | 0.44 | 0.77 | 0.29 | 34 | 0.62 | 22 |
| SEQ ID NO.:443 | 25 | 0.45 | 0.44 | 0.77 | 0.29 | 34 | 0.62 | 21 |
| SEQ ID NO.:444 | 98 | 0.45 | 0.44 | 0.77 | 0.29 | 34 | 0.65 | 22 |
| SEQ ID NO.:445 | 4 | 0.45 | 0.45 | 0.77 | 0.28 | 33 | 0.64 | 20 |
| SEQ ID NO.:446 | 75 | 0.44 | 0.45 | 0.77 | 0.28 | 33 | 0.64 | 21 |
| SEQ ID NO.:447 | 3 | 0.44 | 0.44 | 0.77 | 0.28 | 33 | 0.67 | 20 |
| SEQ ID NO.:448 | 8 | 0.43 | 0.43 | 0.77 | 0.28 | 33 | 0.64 | 20 |
| SEQ ID NO.:449 | 1 | 0.46 | 0.43 | 0.77 | 0.27 | 31 | 0.68 | 23 |
| SEQ ID NO.:450 | 74 | 0.45 | 0.42 | 0.77 | 0.27 | 31 | 0.68 | 22 |
| SEQ ID NO.:451 | 22 | 0.45 | 0.42 | 0.77 | 0.26 | 31 | 0.65 | 23 |
| SEQ ID NO.:452 | 7 | 0.45 | 0.42 | 0.77 | 0.26 | 31 | 0.65 | 22 |
| SEQ ID NO.:453 | 16 | 0.45 | 0.43 | 0.76 | 0.26 | 30 | 0.70 | 21 |
| SEQ ID NO.:454 | 11 | 0.44 | 0.42 | 0.76 | 0.26 | 30 | 0.67 | 21 |
| SEQ ID NO.:455 | 87 | 0.44 | 0.41 | 0.76 | 0.26 | 30 | 0.70 | 21 |

*FIG. 47c-1*

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|
| Q | V | N | L | L | Q | S | G | A | A | L | V | K | P | G | A | S | V | K | L |
| Q | V | Q | L | V | Q | S | G | A | E | V | K | K | P | G | A | S | V | K | V |
| Q | V | Q | L | V | Q | S | G | A | E | V | K | K | P | G | A | S | V | K | V |
| Q | V | Q | L | V | Q | S | G | S | E | L | K | K | P | G | A | S | V | K | V |
| Q | V | Q | L | V | Q | S | G | S | E | L | K | K | P | G | A | S | V | K | V |
| Q | V | Q | L | V | Q | S | G | S | E | L | K | K | P | G | A | S | V | K | V |
| Q | V | Q | L | V | Q | S | G | A | E | V | K | K | P | G | A | S | V | K | V |
| Q | V | Q | L | V | Q | S | G | A | E | V | K | K | P | G | A | S | V | K | V |
| Q | V | Q | L | V | Q | S | G | S | E | L | K | K | P | G | A | S | V | K | V |
| Q | V | Q | L | V | Q | S | G | A | E | V | K | K | P | G | A | S | V | K | V |
| Q | V | Q | L | V | Q | S | G | S | E | L | K | K | P | G | A | S | V | K | V |
| E | V | Q | L | V | E | S | G | G | G | L | V | K | P | G | A | S | V | K | V |
| Q | V | Q | L | V | E | S | G | G | G | L | V | K | P | G | A | S | V | K | V |
| E | V | Q | L | V | E | S | G | G | G | L | V | K | P | G | A | S | V | K | V |
| Q | V | Q | L | Q | Q | S | G | P | G | L | V | K | P | G | A | S | V | K | V |
| Q | V | Q | L | Q | Q | S | G | P | G | L | V | K | P | G | A | S | V | K | V |
| Q | V | Q | L | Q | Q | S | G | P | G | L | V | K | P | G | A | S | V | K | V |
| Q | V | T | L | R | E | S | G | P | A | L | V | K | P | G | A | S | V | K | V |
| E | V | Q | L | V | E | S | G | G | G | L | V | K | P | G | A | S | V | K | V |
| Q | V | Q | L | V | E | S | G | G | G | L | V | K | P | G | A | S | V | K | V |
| E | V | Q | L | V | E | S | G | G | G | L | V | K | P | G | A | S | V | K | V |
| Q | V | Q | L | V | E | S | G | G | G | L | V | K | P | G | A | S | V | K | V |
| Q | V | Q | L | Q | Q | S | G | P | G | L | V | K | P | G | A | S | V | K | V |
| Q | V | Q | L | Q | Q | S | G | P | G | L | V | K | P | G | A | S | V | K | V |
| Q | V | T | L | R | E | S | G | P | A | L | V | K | P | G | A | S | V | K | V |

*FIG. 47c-2*

| 21 | 22 | 23 | 24 | 25 | 26 | 27 | 28 | 29 | 30 | 31 | | 32 | 33 | 34 | 35 | 36 | 37 | 38 |
|----|----|----|----|----|----|----|----|----|----|----|----|----|----|----|----|----|----|----|
| S | C | K | G | S | G | F | T | F | T | D | _ | _ | Y | K | I | H | W | V | K |
| | | | | | | | | | | | | | | | | | | | |
| S | C | K | G | S | G | F | T | F | T | D | _ | _ | Y | K | I | H | W | V | R |
| S | C | K | G | S | G | F | T | F | T | D | _ | _ | Y | K | I | H | W | V | Q |
| S | C | K | G | S | G | F | T | F | T | D | _ | _ | Y | K | I | H | W | V | R |
| S | C | K | G | S | G | F | T | F | T | D | _ | _ | Y | K | I | H | W | V | R |
| S | C | K | G | S | G | F | T | F | T | D | _ | _ | Y | K | I | H | W | V | Q |
| S | C | K | G | S | G | F | T | F | T | D | _ | _ | Y | K | I | H | W | V | R |
| S | C | K | G | S | G | F | T | F | T | D | _ | _ | Y | K | I | H | W | V | R |
| S | C | K | G | S | G | F | T | F | T | D | _ | _ | Y | K | I | H | W | V | R |
| S | C | K | G | S | G | F | T | F | T | D | _ | _ | Y | K | I | H | W | V | Q |
| S | C | K | G | S | G | F | T | F | T | D | _ | _ | Y | K | I | H | W | V | Q |
| S | C | K | G | S | G | F | T | F | T | D | _ | _ | Y | K | I | H | W | V | R |
| S | C | K | G | S | G | F | T | F | T | D | _ | _ | Y | K | I | H | W | V | R |
| S | C | K | G | S | G | F | T | F | T | D | _ | _ | Y | K | I | H | W | V | Q |
| S | C | K | G | S | G | F | T | F | T | D | _ | _ | Y | K | I | H | W | V | R |
| S | C | K | G | S | G | F | T | F | T | D | _ | _ | Y | K | I | H | W | V | R |
| S | C | K | G | S | G | F | T | F | T | D | _ | _ | Y | K | I | H | W | V | Q |
| S | C | K | G | S | G | F | T | F | T | D | _ | _ | Y | K | I | H | W | V | R |
| S | C | K | G | S | G | F | T | F | T | D | _ | _ | Y | K | I | H | W | V | R |
| S | C | K | G | S | G | F | T | F | T | D | _ | _ | Y | K | I | H | W | V | R |
| S | C | K | G | S | G | F | T | F | T | D | _ | _ | Y | K | I | H | W | V | Q |
| S | C | K | G | S | G | F | T | F | T | D | _ | _ | Y | K | I | H | W | V | Q |
| S | C | K | G | S | G | F | T | F | T | D | _ | _ | Y | K | I | H | W | V | R |
| S | C | K | G | S | G | F | T | F | T | D | _ | _ | Y | K | I | H | W | V | Q |
| S | C | K | G | S | G | F | T | F | T | D | _ | _ | Y | K | I | H | W | V | R |

*FIG. 47c-3*

| 39 | 40 | 41 | 42 | 43 | 44 | 45 | 46 | 47 | 48 | 49 | 50 | 51 | 52 | 52a | 53 | 54 | 55 |
|---|---|---|---|---|---|---|---|---|---|---|---|---|---|---|---|---|---|
| Q | S | H | G | K | S | L | E | W | I | G | Y | F | N | P | N | S | G |
| Q | A | P | G | K | S | L | E | W | M | G | Y | F | N | P | N | — | — | S | G |
| Q | A | P | G | K | S | L | E | W | M | G | Y | F | N | P | N | — | — | S | G |
| Q | A | P | G | K | S | L | E | W | M | G | Y | F | N | P | N | — | — | S | G |
| Q | A | P | G | Q | S | L | E | W | M | G | Y | F | N | P | N | — | — | S | G |
| Q | A | P | G | K | S | L | E | W | M | G | Y | F | N | P | N | — | — | S | G |
| Q | A | P | G | K | S | L | E | W | M | G | Y | F | N | P | N | — | — | S | G |
| Q | A | P | G | Q | S | L | E | W | M | G | Y | F | N | P | N | — | — | S | G |
| Q | A | P | G | K | S | L | E | W | M | G | Y | F | N | P | N | — | — | S | G |
| Q | A | P | G | K | S | L | E | W | M | G | Y | F | N | P | N | — | — | S | G |
| Q | A | P | G | K | S | L | E | W | M | G | Y | F | N | P | N | — | — | S | G |
| Q | A | P | G | K | S | L | E | W | M | G | Y | F | N | P | N | — | — | S | G |
| Q | A | P | G | K | S | L | E | W | M | G | Y | F | N | P | N | — | — | S | G |
| Q | A | P | G | K | S | L | E | W | M | G | Y | F | N | P | N | — | — | S | G |
| Q | A | P | G | Q | S | L | E | W | M | G | Y | F | N | P | N | — | — | S | G |
| Q | A | P | G | K | S | L | E | W | M | G | Y | F | N | P | N | — | — | S | G |
| Q | A | P | G | K | S | L | E | W | M | G | Y | F | N | P | N | — | — | S | G |
| Q | A | P | G | K | S | L | E | W | M | G | Y | F | N | P | N | — | — | S | G |
| Q | A | P | G | K | S | L | E | W | M | G | Y | F | N | P | N | — | — | S | G |
| Q | A | P | G | K | S | L | E | W | M | G | Y | F | N | P | N | — | — | S | G |
| Q | A | P | G | K | S | L | E | W | M | G | Y | F | N | P | N | — | — | S | G |
| Q | A | P | G | K | S | L | E | W | M | G | Y | F | N | P | N | — | — | S | G |
| Q | A | P | G | K | S | L | E | W | M | G | Y | F | N | P | N | — | — | S | G |

*FIG. 47c-4*

| 56 | 57 | 58 | 59 | 60 | 61 | 62 | 63 | 64 | 65 | 66 | 67 | 68 | 69 | 70 | 71 | 72 | 73 | 74 | 75 |
|---|---|---|---|---|---|---|---|---|---|---|---|---|---|---|---|---|---|---|---|
| Y | S | T | Y | N | E | K | F | K | S | K | A | T | L | T | A | D | K | S | T |
| Y | S | T | Y | N | E | K | F | Q | G | R | V | T | I | T | A | D | K | S | T |
| Y | S | T | Y | N | E | K | F | Q | G | R | V | T | I | T | A | D | K | S | T |
| Y | S | T | Y | N | E | K | F | Q | G | R | V | T | I | T | A | D | K | S | T |
| Y | S | T | Y | N | E | K | F | Q | G | R | V | T | I | T | A | D | K | S | T |
| Y | S | T | Y | N | E | K | F | Q | G | R | V | T | I | T | A | D | K | S | T |
| Y | S | T | Y | N | E | S | L | K | S | R | V | T | I | S | A | D | K | S | T |
| Y | S | T | Y | N | E | S | L | K | S | R | V | T | I | S | A | D | K | S | T |
| Y | S | T | Y | N | E | S | L | K | S | R | V | T | I | S | A | D | K | S | T |
| Y | S | T | Y | N | E | S | L | K | S | R | V | T | I | S | A | D | K | S | T |
| Y | S | T | Y | N | E | S | L | K | S | R | V | T | I | S | A | D | K | S | T |
| Y | S | T | Y | N | E | K | F | Q | G | R | V | T | I | T | A | D | K | S | T |
| Y | S | T | Y | N | E | K | F | Q | G | R | V | T | I | T | A | D | K | S | T |
| Y | S | T | Y | N | E | K | F | Q | G | R | V | T | I | T | A | D | K | S | T |
| Y | S | T | Y | N | E | K | F | Q | G | R | V | T | I | T | A | D | K | S | T |
| Y | S | T | Y | N | E | K | F | Q | G | R | V | T | I | T | A | D | K | S | T |
| Y | S | T | Y | N | E | K | F | Q | G | R | V | T | I | T | A | D | K | S | T |
| Y | S | T | Y | N | E | S | L | K | S | R | V | T | I | S | A | D | K | S | T |
| Y | S | T | Y | N | E | S | L | K | S | R | V | T | I | S | A | D | K | S | T |
| Y | S | T | Y | N | E | S | L | K | S | R | V | T | I | S | A | D | K | S | T |
| Y | S | T | Y | N | E | S | L | K | S | R | V | T | I | S | A | D | K | S | T |
| Y | S | T | Y | N | E | S | L | K | S | R | V | T | I | S | A | D | K | S | T |
| Y | S | T | Y | N | E | S | L | K | S | R | V | T | I | S | A | D | K | S | T |
| Y | S | T | Y | N | E | S | L | K | S | R | V | T | I | S | A | D | K | S | T |

FIG. 47c-5

| 76 | 77 | 78 | 79 | 80 | 81 | 82 | 82a | 82b | 82c | 83 | 84 | 85 | 86 | 87 | 88 | 89 | 90 | 91 | 92 |
|---|---|---|---|---|---|---|---|---|---|---|---|---|---|---|---|---|---|---|---|
| D | T | A | Y | M | E | L | T | | | S | L | T | S | E | D | S | A | T | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |
| D | T | A | Y | M | E | L | S | S | L | R | S | E | D | T | A | V | Y | Y | C |

FIG. 47c-6

| 93 | 94 | 95 | 96 | 97 | 98 | 99 | 100 | 100a | 100b | 100c | 101 | 102 | 103 | 104 | 105 | 106 |
|---|---|---|---|---|---|---|---|---|---|---|---|---|---|---|---|---|
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |
| T | R | L | S | P | – | – | – | G | G | Y | Y | V | M | D | A | W | G | Q | G |

*FIG. 47c-7*

| 107 | 108 | 109 | 110 | 111 | 112 | 113 |
|---|---|---|---|---|---|---|
| A | S | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |
| T | L | V | T | V | S | S |

FIG. 47c-8

| FIG. 47c-1 | FIG. 47c-2 | FIG. 47c-3 | FIG. 47c-4 | FIG. 47c-5 | FIG. 47c-6 | FIG. 47c-7 | FIG. 47c-8 |

FIG. 47c

SEQ ID NO.: 456
DIQMTQSPSSLSASVGDRVTITCRASQNINNYLNWYQQKPGKAPKRLIYNTNNLQT
GIPSRFSGSGSGTDYTLTISSLQPEDFATYFCLQHNSFPTFGAGTKLEIK
*FIG. 48a*
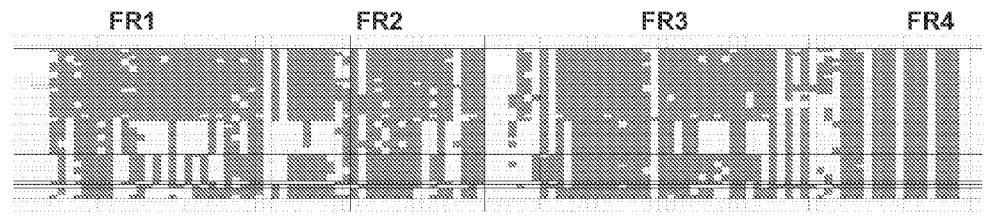
*FIG. 48b*
*FIG. 48c*
*FIG. 48d*

SEQ ID NO.: 457
QVQLQQSGPGLVKPGASVKVSCKGSGFTFTDYKIHWVRQAPGKSLEWMGYFNPN
SGYSTYNEKFQGRVTITADKSTDTAYMELSSLRSEDTAVYYCTRLSPGGYYVMDA
WGQGTLVTVSS
*FIG. 49a*
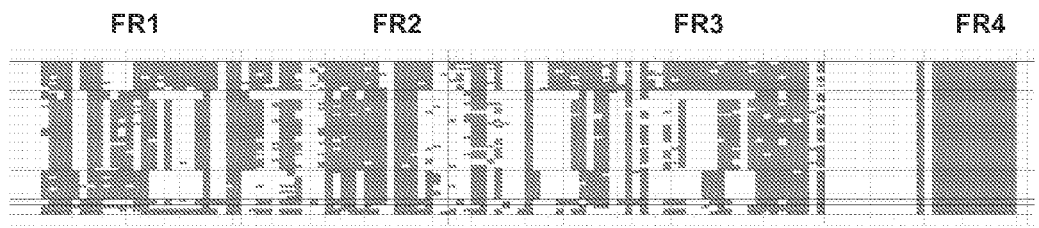
*FIG. 49b*
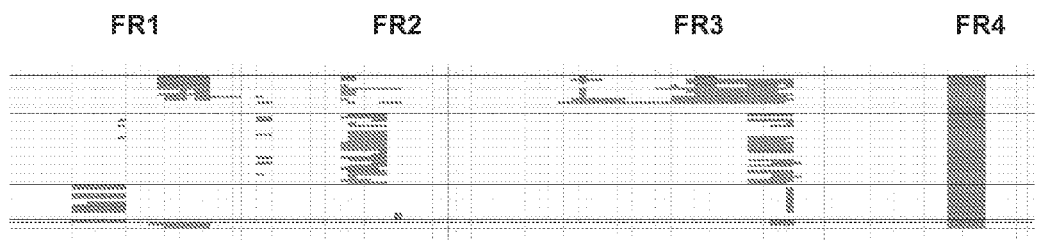
*FIG. 49c*
*FIG. 49d*

SEQ ID NO.: 458
QVQLVQSGAEVKKPGASVKVSCKGSGFTFTDYKIHWVRQAPGKSLEWMGYFNPN
SGYSTYNEKFQGRVTITADKSTDTAYMELSSLRSEDTAVYYCTRLSPGGYYVMDA
WGQGTLVTVSS
*FIG. 50a*
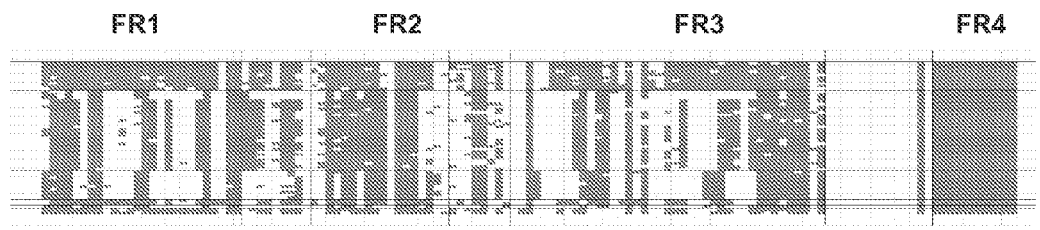
*FIG. 50b*
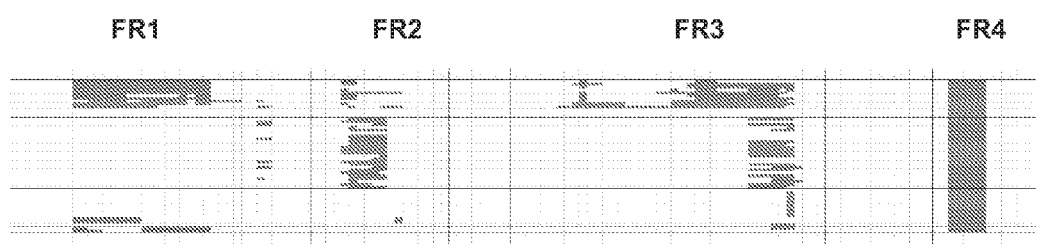
*FIG. 50c*
*FIG. 50d*

METHODS OF GENERATING VARIANT PROTEINS WITH INCREASED HOST STRING CONTENT

This application is a continuation of U.S. application Ser. No. 11/004,590, filed Dec. 3, 2004, now U.S. Pat. No. 7,657,380, issued Feb. 10, 2010 which claims the benefit of under 35 U.S.C. §119(e) to U.S. Ser. Nos. 60/527,167, filed Dec. 4, 2003; 60/581,613, filed Jun. 21, 2004; 60/601,665, filed Aug. 13, 2004; and, 60/619,483, filed Oct. 14, 2004; all of which are expressly incorporated by reference in their entirety.

FIELD OF THE INVENTION

The present invention relates to novel methods for generating variant proteins with increased host string content, and proteins that are engineered using these methods.

BACKGROUND OF THE INVENTION

Many proteins that have the potential to be useful human therapeutics have a xenogeneic origin. The use of xenogeneic proteins for therapeutic purposes may be advantageous for a variety of reasons, including, for example, the established success of hybridoma technology for raising antibodies in rodents, and the possibility of higher efficacy with a xenogeneic protein than with a human counterpart. Although xenogeneic proteins are a rich source of potential therapeutic molecules, they remain a relatively untapped one. One reason for this is that nonhuman proteins are often immunogenic when administered to humans, thereby greatly reducing their therapeutic utility. Additionally, even engineered proteins of human origin may become immunogenic due to changes in the protein sequence.

Immunogenicity is the result of a complex series of responses to a substance that is perceived as foreign, and may include production of neutralizing and non-neutralizing antibodies, formation of immune complexes, complement activation, mast cell activation, inflammation, hypersensitivity responses, and anaphylaxis. Several factors can contribute to protein immunogenicity, including but not limited to protein sequence, route and frequency of administration, and patient population. Immunogenicity may limit the efficacy and safety of a protein therapeutic in multiple ways. Efficacy can be reduced directly by the formation of neutralizing antibodies. Efficacy may also be reduced indirectly, as binding to either neutralizing or non-neutralizing antibodies typically leads to rapid clearance from serum. Severe side effects and even death may occur when an immune reaction is raised. One special class of side effects results when neutralizing antibodies cross-react with an endogenous protein and block its function.

Because of the clinical success of monoclonal antibodies, immunogenicity reduction of these proteins has been an intense area of investigation. Antibodies are a unique system for the development of immunogenicity reduction methods because of the large number of highly conserved antibody sequences and the wealth of high-resolution structural information. A number of strategies for reducing antibody immunogenicity have been developed. The central aim of all of these approaches has been the reduction of nonhuman, and correspondingly immunogenic content, while maintaining affinity for the antigen.

The dominant method in use for antibody immunogenicity reduction, referred to as "humanization", relies principally on the grafting of "donor" (typically mouse or rat) complementarity determining regions (CDRs) onto "acceptor" (human) variable light chain (VL) and variable heavy chain (VH) frameworks (FRs) (Tsurushita & Vasquez, 2004, Humanization of Monoclonal Antibodies, Molecular Biology of B Cells, 533-545, Elsevier Science (USA)). This strategy is referred to as "CDR grafting" (Winter U.S. Pat. No. 5,225,539). "Backmutation" of selected acceptor framework residues to the corresponding donor residues is often required to regain affinity that is lost in the initial grafted construct (U.S. Pat. No. 5,530,101; U.S. Pat. No. 5,585,089; U.S. Pat. No. 5,693,761; U.S. Pat. No. 5,693,762; U.S. Pat. No. 6,180,370; U.S. Pat. No. 5,859,205; U.S. Pat. No. 5,821,337; U.S. Pat. No. 6,054,297; U.S. Pat. No. 6,407,213). Despite the significant clinical application of antibodies engineered using these methods, these methods remain nonrobust with regard to their ability to reduce immunogenicity. A number of humanized antibodies have elicited substantial immune reaction in clinical studies, with incidences of immune response as high as 63% of patients (Ritter et al., 2001, *Cancer Research* 61: 6851-6859).

The incomplete capacity of current humanization methods for immunogenicity reduction are due to significant limitations imposed by the donor-acceptor approach. Historically, the use of a single donor has been part of methods aimed at engineering a single xenogeneic antibody to be suitable as a human biotherapeutic. However, the use of a single acceptor is not required. On the contrary, the use of an acceptor antibody, and the use of global homology to select it, place substantial restrictions on the immunogenicity reduction process. A principal problem is that the use of overall sequence similarity between nonhuman and human sequences as a metric for human immunogenicity is fundamentally flawed. This means of measuring the degree of humanness does not accurately account for the underlying molecular mechanisms of immune response. The immune system does not recognize antigens on the basis of global sequence similarity to human proteins. Rather, immune cells, including antigen presenting cells (APCs), T cells, and B cells, recognize linear or conformational motifs comprising only a handful of residues. A key step in antigen recognition is the formation of peptide-MHC-T cell receptor complexes. APCs express MHC molecules that recognize short (approximately nine residue) linear peptide sequences, referred to as MHC agretopes. T cells express T cell receptors that recognize T cell epitopes in the context of peptide-MHC complexes. T cells that recognize MHC agretopes that are present in human proteins typically undergo apoptosis or become anergic, while T cells that recognize foreign agretopes bound to MHC molecules may participate in an immune response. Thus the relevant quantity for the immunogenicity of a protein is not its global sequence similarity to a human sequence, but rather its sequence content of individual human epitopes.

The donor-acceptor model and the use of global sequence homology that it imposes fails in practice. Because CDRs are treated as inviolable, structural incompatibilities are introduced at the CDR-FR boundaries. Grafting of foreign donor CDRs onto a human acceptor framework creates a substantial number of nonhuman epitopes in each variable chain, including not only the epitopes in the foreign CDRs, but also the large number of epitopes at the FR-CDR boundaries. This FR-CDR incompatibility is evident when one backs away from global homology and looks at more local sequence homologies. CDR grafting generally maximizes the donor-acceptor homology of the frameworks at the expense of the CDRs (Clark, 2000, *Immunology Today* 21: 397-402). Ironically this frequently results in lower global homology to human antibodies. In reality, the "cut and paste" approach to imparting the functional determinants of a nonhuman antibody onto the framework of a human one is unnecessary, as careful analysis of the antigen binding determinants of antibodies shows that, in fact, the majority of CDR residues are not involved in binding antigen (MacCallum et al., 1996, *J. Mol. Biol.* 262: 732-745). FR-CDR incompatibility causes not only immunological problems at the sequence level, but also causes conformational problems at the structural level. As a result, humanization methods based on CDR grafting often result in antigen affinity losses of 10-100-fold, necessitating backmutation to donor residues within the framework. This process of backmutation is a hallmark of essentially all current humanization efforts, and because it introduces yet additional nonhuman epitopes, highlights the inefficiency of these methods.

Methods that take an immune epitope approach to reducing antibody immunogenicity have been explored (U.S. Pat. No. 5,712,120; US 2003/0153043). Central to these methods is the determination of sequences within a xenogeneic antibody that are in fact immunogenic epitopes. Different methods for determination of immunogenicity both theoretical and experimental have been described and include determination of potential for amphipathic helix formation, binding to MHC, reactivity in a T-cell activation assay. A distinguishing feature between these strategies and the present invention is that the present invention makes no presumption as to the immunogenicity of specific epitopes. Rather, the primary goal is to maximize the content of human linear sequence strings in the xenogeneic antibody as determined by comparison to an alignment of human sequences. The relevant sequence dataset comprises strings that are nonimmunogenic for all relevant reasons, including lack of interaction with MHC, lack of interaction with T cell receptor, lack of proper processing necessary for presentation, and tolerance.

It is noted that the methods described in U.S. Pat. No. 5,712,120 and US 2003/0153043 suffer additionally in that they fail to address a significant concern for local level sequence engineering, namely the requirement for maintaining protein structure, stability, solubility, and function. Thus, although the sequence string approach to immunogenicity reduction is more accurate than CDR grafting, it will be optimal when coupled with protein design methodology that takes into account both local sequence content and conformational compatibility at the local and global structural level. In addition to providing scoring functions for assessing host string content, the present invention also describes scoring functions that evaluate other relevant properties of a protein that may be employed for the simultaneous immunogenicity reduction and structural and functional optimization of proteins.

In summary, the donor-acceptor model imposes significant restrictions on the immunogenicity reduction process. With regard to sequence, global sequence homology is an inappropriate metric for immunogenicity. With regard to structure, backmutations are needed to repair conformational incompatibilities, thereby creating or reintroducing nonhuman epitopes. The present invention describes a novel method for antibody immunogenicity reduction that steps outside of the donor-acceptor model, and thus the sequence and structural restrictions it imposes. The central strategy of the described method is that it maximizes the content of human linear sequence strings. In this way immunogenicity is addressed at the local sequence level, typically by utilizing the local sequence information contained in an alignment of human sequences. This strategy not only provides a more accurate measure of the immunogenicity, it enables substitutions to be designed in a forward rather than backward manner to repair problems introduced by the graft. In effect, by addressing immunogenicity at the local sequence string level, the optimal balance between binding determinants and humanness can be designed.

The present invention describes a novel method for reducing the immunogenicity of proteins that leverages the nonimmunogenic information contained in natural human sequences to score protein sequences for immunogenic content at the sequence string level. Furthermore, the described method capitalizes on recent advances in computational sequence and structure-based protein engineering methods to quantitatively and systematically determine the optimal balance between human sequence content and protein functionality. Because of the wealth of human sequence information available for the immunoglobulin protein family, application to human antibodies is emphasized. Applications to other proteins are also possible.

SUMMARY OF THE INVENTION

The invention disclosed herein provides a novel method for reducing the immunogenicity of a protein, wherein the method maximizes the content of sequence strings. In a preferred embodiment, the method of the present invention maximizes the content of human sequence strings.

It is an object of the present invention to provide scoring functions that may be used to evaluate the human sequence string content of a protein. In a preferred embodiment, the scoring function compares the similarity of strings in a protein sequence to the strings that compose a set of natural protein sequences. In another preferred embodiment, the set of sequences is an aligned set of germline sequences. In additional preferred embodiments, the set of sequences contains mature sequences. In the most preferred embodiments, the sequences are human sequences.

It is an object of the present invention to provide scoring functions that may be used to evaluate the structural and/or functional fitness of a protein.

It is an object of the present invention to provide protein variants of a parent protein that are engineered using the methods described herein. In a preferred embodiment, the parent protein is an immunoglobulin.

It is an object of the present invention to provide experimental methods for screening and testing the protein variants of the present invention.

The present invention provides isolated nucleic acids encoding the protein variants described herein. The present invention provides vectors comprising the nucleic acids, optionally, operably linked to control sequences. The present invention provides host cells containing the vectors, and methods for producing and optionally recovering the protein variants.

The present invention provides compositions comprising the protein variants described herein, and a physiologically or pharmaceutically acceptable carrier or diluent.

The present invention provides novel antibodies and Fc fusions that comprise the protein variants disclosed herein. The novel antibodies and Fc fusions may find use in a therapeutic product.

The present invention provides therapeutic treatment and diagnostic uses for the protein variants disclosed herein.

BRIEF DESCRIPTION OF THE DRAWINGS

FIG. 2. The quantities described by equations 1, 2, and 3 are illustrated. In FIG. 2a, IDstring (Equation 1) is illustrated for the string beginning at position i=15, comparing a region of the murine antibody m4D5 VH sequence (VH_m4D5) (SEQ ID NO:110) as parent sequence s with the homologous region from the VH human germline sequence (VH_1-2) (SEQ ID NOS:111) as human sequence h. Only 30 residues from each sequence are shown, and the residues that compose the relevant string are bolded. In FIG. 2b, IDmax (Equation 2) is illustrated for the parent sequence s string that begins at position i=15 (shown in bold) and the homologous regions from an aligned set of 7 VH human germline sequences (SEQ ID NOS:111-117). In FIG. 2c, HSC(s) (Equation 3) is illustrated for all strings (i=1 to i=22) in the parent sequence s and the homologous regions from an aligned set of 7 VH human germline sequences (SEQ I D NOS:111-117).

FIG. 3. Sequence, host string content, and structure of WT AC10 VL. FIG. 3a shows the sequence of the WT AC10 VL (SEQ ID NO:117). FIG. 3b shows the identity of each residue in WT AC10 VL as compared to the corresponding residue in each sequence of the human VLκ germline. The black horizontal lines delineate the 7 different subfamilies as presented in FIG. 1, and the black vertical lines delineate the different framework and CDR regions of the domain (in the order FR1-CDR1-FR2-CDR2-FR3-CDR3-FR4). A grey square indicates that the germline sequence has the same amino acid identity to the residue at the corresponding position in the WT AC10 VL sequence. A white square indicates that the two sequences differ at that position. FIG. 3c shows the continuous 8- and 9-mer strings between WT AC10 VL and each sequence of the human VLκ germline. The black horizontal and vertical lines are as described in FIG. 3b. A grey square indicates that the germline sequence comprises an 9-mer string centered on that position that is an 8 out of 9 or 9 out of 9 identical match to the corresponding string (centered on the corresponding residue) in the WT AC10 VL sequence. FIG. 3d shows the structure of the modeled WT AC10 variable region. The light chain is shown as grey ribbon, the heavy chain is shown as black ribbon, and the CDR residues are indicated as black lines.

FIG. 4. Sequence (SEQ ID NO:119), host string content, and structure of WT AC10 VH. The figure is as described in the figure legend for FIG. 3, except that here the light chain is shown as black ribbon and the heavy chain is shown as grey ribbon.

FIG. 5. Sequence (SEQ ID NO:120), host string content, and structure of CDR grafted AC10 VL. CDR grafted AC10 VL was derived from the CDRs of WT AC10 and the frameworks of the human germline sequence vlk_4-1. Differences between CDR grafted AC10 VL and WT AC10 VL are shown as bolded residues in the sequence in FIG. 5a, and as black ball and sticks in FIG. 5d.

FIG. 6. Sequence (SEQ ID NO:121), host string content, and structure of CDR grafted AC10 VH. CDR grafted AC10 VH was derived from the CDRs of WT AC10 and the frameworks of the human germline sequence vh_1-3 and substitutions Q108L and A113S (Kabat numbering) in FR4

FIG. 7. AC10 VL (SEQ ID NO:118) and VH variants with optimized HSC (SEQ ID NOS:122-160). AC10 VL (SEQ ID NO:119) and VH variants with optimized HSC (SEQ ID NOS:161-217). The nonredundant set of output sequences from the calculations described in Example 1 are shown. For each iteration (Iter) the following are provided: the Structural Consensus; Structural Precedence; Human String Content (HSC); Human String Similarity (HSS); $N_9$max; the Framework Region Homogeneity (FRH); and, the number of mutations from WT (Muts). The output sequences were clustered based on their mutational distance from the other sequences in the set. These clusters are delineated by the horizontal black lines. The "Cluster" column provides this mutational distance quantitatively. Differences between the parent WT AC10 sequence are shown in grey. Positions are numbered according to the Kabat numbering scheme, provided at the top. The light grey regions bracketed by the black horizontal lines indicate residues in or proximal to the Kabat defined CDRs.

FIG. 8. Sequence (SEQ ID NO:218), host string content, and structure of L1 AC10 VL.

FIG. 9. Sequence (SEQ ID NO:219), host string content, and structure of L2 AC10 VL FIG. 10. Sequence (SEQ ID NO:220), host string content, and structure of L3 AC10 VL.

FIG. 11. Sequence (SEQ ID NO:221), host string content, and structure of H1 AC10 VH.

FIG. 12. Sequence (SEQ ID NO:222), host string content, and structure of H2 AC10 VH.

FIG. 13. Sequence (SEQ ID NO:223), host string content, and structure of H3 AC10 VH.

FIG. 11. SPR sensorgrams showing binding of AC10 WT and variant full length antibodies to the CD30 target antigen. The curves consist of an association phase and dissociation phase, the separation being marked by a little spike on each curve.

FIG. 17 shows the dose dependence of ADCC at various antibody concentrations, and the curves represent the fits of the data to a sigmoidal dose-response model using nonlinear regression. Raw data are presented in FIGS. 17*a* and 17*b*, whereas in FIG. 17*c* the data were normalized to a percentage scale of maximal cytotoxicity determined by Triton-X100 lysis of target cells.

FIG. 20. Sequence (SEQ ID NO:224), host string content, and structure of L3.71 AC10 VL.

FIG. 21. Sequence (SEQ ID NO:225), host string content, and structure of L3.72 AC10 VL.

FIG. 22. Sequence (SEQ ID NO:226), host string content, and structure of H3.68 AC10 VH.

FIG. 23. Sequence (SEQ ID NO:227), host string content, and structure of H3.69 AC10 VH.

FIG. 24. Sequence (SEQ ID NO:228), host string content, and structure of H3.70 AC10 VH.

FIG. 25. Amino acid sequences of a AC10 variant antibodies comprising the L3.71 AC10 variant VL with the CLκ constant light chain (FIG. 25*a*) (SEQ ID NO:229) and the H3.70 AC10 variant VH with IgG constant chains (FIGS. 25*b*-25*e*) (SEQ ID NOS:230-233) that may comprise amino acid modifications in the Fc region. FIG. 25*b* (SEQ ID NO:230) provides an IgG1 heavy chain with positions that may be mutated designated in bold as $X_1$, $X_2$, $X_3$, and $X_4$, referring to residues S239, V264, A330, and I332. FIG. 25*c* (SEQ ID NO:231) provides one example of a heavy chain described in FIG. 25*b*, here comprising the H3.70 AC10 variant VH region with the S239D/A330L/I332E IgG1 constant region. FIG. 25*d* (SEQ ID NO:232) provides an IgG2 heavy chain with positions that may be mutated and designated in bold as $X_1$, $X_2$, $X_3$, $X_4$, $Z_1$, $Z_2$, $Z_3$, $Z_4$, and $Z_5$ referring to residues S239, V264, A330, I332, P233, V234, A235, −236, and G237 (here −236 refers to a deletion at EU index position 236). FIG. 25*e* (SEQ ID NO:233) provides one example of a heavy chain described in FIG. 25*d*, here comprising the H3.70 AC10 variant VH region with the S239D/A330L/I332E/P233E/V234L/A235L/−236G IgG2 constant region.

FIG. 26. Sequence (SEQ ID NO:234), host string content, and structure of WT C225 VL.

FIG. 27. Sequence (SEQ ID NO:235), host string content, and structure of WT C225 VH.

FIG. 28. Sequence (SEQ ID NO:236), host string content, and structure of CDR grafted C225 VL, which was derived from the CDRs of WT C225 and the frameworks of the human germline sequence vlk__6D-21 and an L1061 (Kabat numbering) substitution in FR4.

FIG. 29. Sequence (SEQ ID NO:237), host string content, and structure of CDR grafted C225 VH, which was derived from the CDRs of WT C225 and the frameworks of the human germline sequence vh__4-30-4 and an A1135 (Kabat numbering) substitution in FR4.

FIG. 30. C225 VL and VH variants with optimized HSC (SEQ ID NOS:238-274). The nonredundant set of output sequences from the calculations described in Example 2 are shown.

FIG. 31. C225 VL and VH variants with optimized HSC (SEQ ID NOS:275-378). The nonredundant set of output sequences from the calculations described in Example 2 are shown.

FIG. 32. Sequence (SEQ ID NO:379), host string content, and structure of L2 C225 VL.

FIG. 33. Sequence (SEQ ID NO:380), host string content, and structure of L3 C225 VL.

FIG. 34. Sequence (SEQ ID NO:381), host string content, and structure of L4 C225 VL.

FIG. 35. Sequence (SEQ ID NO:382), host string content, and structure of H3 C225 VH.

FIG. 36. Sequence (SEQ ID NO:383), host string content, and structure of H4 C225 VH.

FIG. 37. Sequence (SEQ ID NO:384), host string content, and structure of H5 C225 VH.

FIG. 38. Sequence (SEQ ID NO:385), host string content, and structure of H6 C225 VH.

FIG. 39. Sequence (SEQ ID NO:386), host string content, and structure of H7 C225 VH.

FIG. 40. Sequence (SEQ ID NO:387, host string content, and structure of H8 C225 VH.

FIG. 42 shows the dose dependence of ADCC at various antibody concentrations, normalized to the minimum and maximum levels of lysis for the assay. The curves represent the fits of the data to a sigmoidal dose-response model using nonlinear regression.

FIG. 43. Sequence (SEQ ID NO:388), host string content, and structure of WT ICR62 VL.

FIG. 44. Sequence (SEQ ID NO:389), host string content, and structure of WT ICR62 VH.

FIG. 45. Sequence (SEQ ID NO:390), host string content, and structure of CDR grafted ICR62 VL. CDR grafted ICR62 VL was derived from the CDRs of WT ICR62 and the frameworks of the human germline sequence vlk__1-17 and an L1061 (Kabat numbering) substitution in FR4.

FIG. 46. Sequence (SEQ ID NO:391), host string content, and structure of CDR grafted ICR62 VH. CDR grafted ICR62 VH was derived from the CDRs of WT ICR62 and the frameworks of the human germline sequence vh__14 and substitutions A107T and S108L (Kabat numbering) in FR4.

FIG. 47. ICR62 VL and VH variants with optimized HSC (SEQ ID NOS:392-455).

FIG. 48. Sequence (SEQ ID NO:456), host string content, and structure of L3 ICR62 VL.

FIG. 49. Sequence (SEQ ID NO:457), host string content, and structure of H9 ICR62 VH.

FIG. 50. Sequence (SEQ ID NO:458), host string content, and structure of H10 ICR62 VH.

DETAILED DESCRIPTION OF THE INVENTION

Definitions

Figure 1C:
FIG. 1. Human germ line sequences and diversity. The sequences that are known to encode the human VH chains (FIG. 1*a*) (SEQ ID NOS:1-53), human VL kappa chains (FIG. 1*b*) (SEQ ID NOS:54-98), and VH and VL kappa J chains (FIG. 1c) (SEQ ID NOS:99-109) are shown. The VL lambda germline sequences are not provided. The germline sequences are numbered according to the numbering scheme of Kabat (Kabat et al., 1991, *Sequences of Proteins of Immunological Interest*, 5th Ed., United States Public Health Service, National Institutes of Health, Bethesda). The regions of the variable region are indicated above the numbering in FIGS. 1a and 1b, and these include framework regions 1 through 3 and the CDRs 1 through 3. Positions that make up the Kabat CDRs are underlined. The germline chains are grouped into 7 subfamilies for $V_H$ and 6 subfamilies for $V_L$, as is known in the art, and these subfamilies are grouped together and separated by a blank line. The sequences of the five germlines that make up the IgG light kappa J chains (IGKJ1-IGKJ5), and the six germlines that make up the IgG heavy J chains (IGHJ1-IGHJ5) are shown in FIG. 1c. The kappa and lambda light J chains combine with the VLκ and VLλ germlines respectively to form the light chain variable region, and the heavy J chains combine with the VH germlines and heavy diversity (D) germlines (not shown) to form the heavy chain variable region. The $V_H$ CDR3 is not part of the $V_H$ germ line, and is encoded by the D and J genes.

In order that the invention may be more completely understood, several definitions are set forth below. Such definitions are meant to encompass grammatical equivalents.

By "amino acid" as used herein is meant one of the 20 naturally occurring amino acids or any non-natural analogues that may be present at a specific, defined position.

By "amino acid modification" herein is meant an amino acid substitution, insertion, and/or deletion in a polypeptide sequence. The preferred amino acid modification herein is a substitution.

By "amino acid substitution" or "substitution" herein is meant the replacement of an amino acid at a given position in a protein sequence with another amino acid.

By "antibody" herein is meant a protein consisting of one or more proteins substantially encoded by all or part of the recognized immunoglobulin genes. The recognized immunoglobulin genes, for example in humans, include the kappa (κ), lambda (λ), and heavy chain genetic loci, which together comprise the myriad variable region genes, and the constant region genes mu (μ), delta (δ), gamma (γ), sigma (σ), and alpha (α) which encode the IgM, IgD, IgG, IgE, and IgA isotypes respectively. Antibody herein is meant to include full length antibodies and antibody fragments, and may refer to a natural antibody from any organism, an engineered antibody, or an antibody generated recombinantly for experimental, therapeutic, or other purposes. By "IgG" as used herein is meant a protein belonging to the class of antibodies that are substantially encoded by a recognized immunoglobulin gamma gene. In humans this class comprises IgG1, IgG2, IgG3, and IgG4.

By "corresponding" or "equivalent" residues as meant herein are residues that represent similar or homologous sequence and/or structural environments between a first and second protein, or between a first protein and set of multiple proteins. In order to establish homology, the amino acid sequence of a first protein is directly compared to the sequence of a second protein. After aligning the sequences, using one or more of the homology alignment programs known in the art (for example using conserved residues as between species), allowing for necessary insertions and deletions in order to maintain alignment (i.e., avoiding the elimination of conserved residues through arbitrary deletion and insertion), the residues equivalent to particular amino acids in the primary sequence of the first protein are defined. Alignment of conserved residues preferably should conserve 100% of such residues. However, alignment of greater than 75% or as little as 50% of conserved residues is also adequate to define equivalent residues. Corresponding residues may also be defined by determining structural homology between a first and second protein that is at the level of tertiary structure for proteins whose structures have been determined. In this case, equivalent residues are defined as those for which the atomic coordinates of two or more of the main chain atoms of a particular amino acid residue of the proteins (N on N, CA on CA, C on C and O on O) are within 0.13 nm and preferably 0.1 nm of each other after alignment. Alignment is achieved after the best model has been oriented and positioned to give the maximum overlap of atomic coordinates of non-hydrogen protein atoms of the proteins.

By "CDR" as used herein is meant a Complementarity Determining Region of an antibody variable domain. Systematic identification of residues included in the CDRs have been developed by Kabat (Kabat et al., 1991, Sequences of Proteins of Immunological Interest, 5th Ed., United States Public Health Service, National Institutes of Health, Bethesda) and alternately by Chothia (Chothia & Lesk, 1987, J. Mol. Biol. 196: 901-917; Chothia et al., 1989, Nature 342: 877-883; Al-Lazikani et al., 1997, J. Mol. Biol. 273: 927-948). For the purposes of the present invention, CDRs are defined as a slightly smaller set of residues than the CDRs defined by Chothia. VL CDRs are herein defined to include residues at positions 27-32 (CDR1), 50-56 (CDR2), and 91-97 (CDR3), wherein the numbering is according to Chothia. Because the VL CDRs as defined by Chothia and Kabat are identical, the numbering of these VL CDR positions is also according to Kabat. VH CDRs are herein defined to include residues at positions 27-33 (CDR1), 52-56 (CDR2), and 95-102 (CDR3), wherein the numbering is according to Chothia. These VH CDR positions correspond to Kabat positions 27-35 (CDR1), 52-56 (CDR2), and 95-102 (CDR3).

By "framework" as used herein is meant the region of an antibody variable domain exclusive of those regions defined as CDR's. Each antibody variable domain framework can be further subdivided into the contiguous regions separated by the CDR's (FR1, FR2, FR3 and FR4).

By "qermline" as used herein is meant the set of sequences that compose the natural genetic repertoire of a protein, and its associated alleles.

By "host" as used herein is meant a family, genus, species or subspecies, group of individuals or even a single individual. A host group of individuals can be selected for based upon a variety of criteria, such as MHC allele composition, etc. In a preferred embodiment, a host is canine, murine, primate, or human. In the most preferred embodiment, a host is human.

By "host string" or "host sequence" as used herein is meant a string or sequence that encodes any part of a naturally occurring host protein.

By "humanized" antibody as used herein is meant an antibody comprising a human framework region and one or more CDR's from a non-human (usually mouse or rat) antibody. The non-human antibody providing the CDR's is called the "donor" and the human immunoglobulin providing the framework is called the "acceptor". One says that the donor antibody has been "humanized", by the process of "humanization".

By "identity" as used herein is meant the number of residues in a first sequence that are identical to the residues in a second sequence after alignment of the sequences to achieve the maximum identity.

By "immune epitope" or "epitope" herein is meant a linear sequence of amino acids that is located in a protein of interest. Epitopes may be analyzed for their potential for immunogenicity. Epitopes may be any length, preferably 9-mers.

By "immunogenicity" herein is meant the ability of a protein to elicit an immune response, including but not limited to production of neutralizing and non-neutralizing antibodies, formation of immune complexes, complement activation, mast cell activation, inflammation, and anaphylaxis.

By "immunoglobulin (Ig)" herein is meant a protein consisting of one or more proteins substantially encoded by immunoglobulin genes. Immunoglobulins include but are not limited to antibodies. Immunoglobulins may have a number of structural forms, including but not limited to full length antibodies, antibody fragments, and individual immunoglobulin domains. By "immunoglobulin (Ig) domain" herein is meant a region of an immunoglobulin that exists as a distinct structural entity as ascertained by one skilled in the art of protein structure. Ig domains typically have a characteristic β-sandwich folding topology. The known Ig domains in the IgG class of antibodies are $V_H$, Cγ1, Cγ2, Cγ3, $V_L$, and $C_L$.

By "natural sequence" or "natural protein" as used herein is meant a protein that has been determined to exist absent any experimental modifications. Also included are sequences that can be predicted to exist in nature based on experimentally determined sequences. An example of such a predicted sequence is an antibody that can be predicted to exist based on the established patterns of germline recombination. In this case the large size of the predicted antibody repertoire makes the actual experimental determination of all mature recombined antibodies not practical.

By "parent" or "parent protein" as used herein is meant a protein that is subsequently modified to generate a variant. The parent protein may be a naturally occurring protein, or a variant or engineered version of a naturally occurring protein. Parent protein may refer to the protein itself, compositions that comprise the parent protein, or the amino acid sequence that encodes it. Accordingly, by "parent antibody" as used herein is meant an antibody that is subsequently modified to generate a variant antibody. Accordingly, by "parent sequence" as used herein is meant the sequence that encodes the parent protein or parent antibody.

By "position" as used herein is meant a location in the sequence of a protein. Positions may be numbered sequentially, or according to an established format, for example Kabat, Chothia, and/or the EU index as in Kabat.

By "protein" herein is meant at least two covalently attached amino acids, which includes proteins, polypeptides, oligopeptides and peptides. The protein may be made up of naturally occurring amino acids and peptide bonds, or synthetic peptidomimetic structures.

By "reduced immunogenicity" herein is meant a decreased ability to activate the immune system, when compared to the parent protein. For example, a protein variant can be said to have "reduced immunogenicity" if it elicits neutralizing or non-neutralizing antibodies in lower titer or in fewer patients than the parent protein. A protein variant also can be said to have "reduced immunogenicity" if it shows decreased binding to one or more MHC alleles or if it induces T cell activation in a decreased fraction of patients relative to the parent protein.

By "residue" as used herein is meant a position in a protein and its associated amino acid identity. For example, proline 9 (also referred to as Pro9, also referred to as P9) is a residue in the WT AC10 VH region.

By "scoring function" herein is meant any equation or method for evaluating the fitness of one or more amino acid modifications in a protein. The scoring function may involve a physical or chemical energy term, or may involve knowledge-, statistical-, sequence-based energy terms, and the like.

By "string" as used herein is meant a contiguous sequence that encodes any part of a protein. Strings may comprise any 2 or more linear residues, with the number of contiguous residues being defined by the "window" or "window size". Window sizes of 2-20 are preferred, with 7-13 more preferred, with 9 most preferred.

By "target" as used herein is meant the molecule that is bound specifically by a protein. A target may be a protein, carbohydrate, lipid, or other chemical compound. The target of an antibody is its antigen, also referred to as its target antigen.

By "variable region" as used herein is meant the region of an immunoglobulin that comprises one or more Ig domains substantially encoded by any of the VL (including Vκ and Vλ) and/or $V_H$ genes that make up the light chain (including kappa and lambda) and heavy chain immunoglobulin genetic loci respectively. A light or heavy chain variable region (VL and VH) consists of a "framework" or "FR" region interrupted by three hypervariable regions referred to as "complementarity determining regions" or "CDRs". The extent of the framework region and CDRs have been precisely defined, for example as in Kabat (see "Sequences of Proteins of Immunological Interest," E. Kabat et al., U.S. Department of Health and Human Services, (1983)), and as in Chothia. The framework regions of an antibody, that is the combined framework regions of the constituent light and heavy chains, serves to position and align the CDRs, which are primarily responsible for binding to an antigen.

By "variant protein" or "protein variant", or "variant" as used herein is meant a protein that differs from a parent protein by virtue of at least one amino acid modification. Protein variant may refer to the protein itself, a composition comprising the protein, or the amino sequence that encodes it. Preferably, the protein variant has at least one amino acid modification compared to the parent protein, e.g. from about one to about ten amino acid modifications, and preferably from about one to about five amino acid modifications compared to the parent. The protein variant sequence herein will preferably possess at least about 80% homology with a parent protein sequence, and most preferably at least about 90% homology, more preferably at least about 95% homology. Accordingly, by "immunoglobulin variant" as used herein is meant an immunoglobulin that differs from a parent immunoglobulin by virtue of at least one amino acid modification.

By "wild type or WT" herein is meant an amino acid sequence or a nucleotide sequence that is found in nature and includes allelic variations. A WT protein has an amino acid sequence or a nucleotide sequence that has not been intentionally modified.

The protein variants of the present invention may be derived from parent proteins that are themselves from a wide range of sources. The parent protein may be substantially encoded by one or more genes from any organism, including but not limited to humans, mice, rats, rabbits, camels, llamas, dromedaries, monkeys, preferably mammals and most preferably humans and mice and rats. Although in a preferred embodiment the parent protein is nonhuman, in some embodiments of the present invention the parent protein may be human or similar to human. The parent protein may comprise more than one protein chain, and thus may be a monomer or an oligomer, including a homo- or hetero-oligomer. In a preferred embodiment, the parent protein is an antibody, referred to as the parent antibody. The parent antibody need not be naturally occurring. For example, the parent antibody may be an engineered antibody, including but not limited to nonhuman and chimeric antibodies. The parent antibody may be fully human, obtained for example using transgenic mice (Bruggemann et al., 1997, *Curr Opin Biotechnol* 8:455-458) or human antibody libraries coupled with selection methods (Griffiths et al., 1998, *Curr Opin Biotechnol* 9:102-108). The parent antibody need not be naturally occurring. For example, the parent antibody may be an engineered antibody, including but not limited to chimeric antibodies and humanized antibodies (Clark, 2000, *Immunol Today* 21:397-402). The parent antibody may be an engineered variant of an antibody that is substantially encoded by one or more natural antibody genes. In one embodiment, the parent antibody has been affinity matured, as is known in the art, or engineered in some other way. The parent antibodies of the present invention may be substantially encoded by immunoglobulin genes belonging to any of the antibody classes, and may comprise sequences belonging to the IgG class of antibodies, including IgG1, IgG2, IgG3, or IgG4, or alternatively the IgA (including subclasses IgA1 and IgA2), IgD, IgE, IgG, or IgM classes of antibodies.

Virtually any binding partner or antigen may be targeted by the proteins of the present invention. A number biotherapeutic proteins and antibodies that are approved for use, in clinical trials, or in development may thus benefit from immunogenicity reduction methods of the present invention. In a preferred embodiment, the less immunogenic protein of the present invention is an antibody. The less immunogenic antibody may comprise sequences belonging to the IgG (including IgG1, IgG2, IgG3, or IgG4), IgA (including subclasses IgA1 and IgA2), IgD, IgE, IgG, or IgM classes of antibodies, with the IgG class being preferred. The less immunogenic antibodies of the present invention may be full length antibodies, or antibody fragments. Constant regions need not be present, but if they are, they will likely be substantially identical to human immunoglobulin constant regions.

The constant region of the antibody may be modified in some way to make it more effective therapeutically. For example, the constant region may comprise substitutions that enhance therapeutic properties. Most preferred substitutions and optimized effector function properties are described in U.S. Ser. No. 10/672,280, PCT US03/30249, and U.S. Ser. No. 10/822,231, and U.S. Ser. No. 60/627,774, filed Nov. 12, 2004 and entitled "Optimized Fc Variants". Other known Fc variants that may find use in the present invention include but are not limited to those described in U.S. Pat. No. 6,737,056; PCT US2004/000643; U.S. Ser. No. 10/370,749; PCT/US2004/005112; US 2004/0132101; U.S. Ser. No. 10/672,280; PCT/US03/30249; U.S. Pat. No. 6,737,056, US 2004/0002587; WO 2004/063351; Idusogie et al., 2001, J. Immunology 166:2571-2572; Hinton et al., 2004, J. Biol. Chem. 279(8): 6213-6216. In alternate embodiments, the constant region may comprise one or more engineered glycoforms, as is known in the art (Umaña et al., 1999, *Nat Biotechnol* 17:176-180; Davies et al., 2001, *Biotechnol Bioeng* 74:288-294; Shields et al., 2002, *J Biol Chem* 277: 26733-26740; Shinkawa et al., 2003, *J Biol Chem* 278:3466-3473); (U.S. Pat. No. 6,602,684; U.S. Ser. No. 10/277,370; U.S. Ser. No. 10/113,929; PCT WO 00/61739A1; PCT WO 01/29246A1; PCT WO 02/31140A1; PCT WO 02/30954A1); (Potelligent™ technology [Biowa, Inc., Princeton, N.J.]; GlycoMAb™ glycosylation engineering technology [GLYCART biotechnology AG, Zürich, Switzerland]).

The protein variants of the present invention may find use in a wide range of protein products. In one embodiment the protein is a therapeutic, a diagnostic, or a research reagent, preferably a therapeutic. Alternatively, the protein of the present invention may be used for agricultural or industrial uses. In a preferred embodiment, the protein is a therapeutic that is used to treat a disease. By "disease" herein is meant a disorder that may be ameliorated by the administration of a pharmaceutical composition comprising a protein of the present invention. Diseases include but are not limited to autoimmune diseases, immunological diseases, infectious diseases, inflammatory diseases, neurological diseases, and oncological and neoplastic diseases including cancer. In one embodiment, a protein of the present invention is the only therapeutically active agent administered to a patient. Alternatively, the protein of the present invention is administered in combination with one or more other therapeutic agents, including but not limited to cytotoxic agents, chemotherapeutic agents, cytokines, growth inhibitory agents, anti-hormonal agents, kinase inhibitors, anti-angiogenic agents, cardioprotectants, or other therapeutic agents. The proteins of the present invention may be combined with other therapeutic regimens. For example, in one embodiment, the patient to be treated with the protein may also receive radiation therapy and/or undergo surgery. In an alternate embodiment, the protein of the present invention is conjugated or operably linked to another therapeutic compound. The therapeutic compound may be a cytotoxic agent, a chemotherapeutic agent, a toxin, a radioisotope, a cytokine, or other therapeutically active agent. In yet another embodiment, a protein of the present invention may be conjugated to a protein or molecule for utilization in tumor pretargeting or prodrug therapy. Other modifications of the proteins of the present invention are contemplated herein. For example, the protein may be linked to one of a variety of nonproteinaceous polymers, for example e.g., polyethylene glycol (PEG).

Pharmaceutical compositions are contemplated wherein a protein of the present invention and one or more therapeutically active agents are formulated. Formulations of the proteins of the present invention are prepared for storage by mixing the protein having the desired degree of purity with optional pharmaceutically acceptable carriers, excipients or stabilizers (Remington's Pharmaceutical Sciences 16th edition, Osol, A. Ed., 1980), in the form of lyophilized formulations or aqueous solutions. The formulations to be used for in vivo administration are preferably sterile. The proteins disclosed herein may also be formulated as immunoliposomes, or entrapped in microcapsules. The concentration of the protein of the present invention in the formulation may vary from about 0.1 to 100 weight %. In a preferred embodiment, the concentration of the protein is in the range of 0.003 to 1.0 molar. In order to treat a patient, a therapeutically effective dose of the protein of the present invention may be administered. The exact dose will depend on the purpose of the treatment, and will be ascertainable by one skilled in the art using known techniques. Dosages may range from 0.01 to 100 mg/kg of body weight or greater, for example 0.1, 1, 10, or 50 mg/kg of body weight, with 1 to 10 mg/kg being preferred. Administration of the pharmaceutical composition comprising a protein of the present invention, preferably in the form of a sterile aqueous solution, may be done in a variety of ways, including, but not limited to, orally, subcutaneously, intravenously, intranasally, intraotically, transdermally, topically, intraperitoneally, intramuscularly, intrapulmonary, inhalably, vaginally, parenterally, rectally, or intraocularly. As is known in the art, the pharmaceutical composition may be formulated accordingly depending upon the manner of introduction.

Description of the Methodology

The present invention provides a novel method for reducing the immunogenicity of a protein. A central principle of the described method is that substitutions are designed to maximize the content of human linear sequence strings using an alignment of human sequences. For application to antibodies, this approach to immunogenicity reduction excludes the use of the single donor-acceptor model employed in humanization methods. By stepping outside of the limitations imposed by the need to choose a human acceptor sequence a priori, a more immunologically relevant approach to immunogenicity reduction is enabled. Sequence information and structural information may be used to score potential amino acid substitutions. The scoring results are used to design protein variant libraries, which are subsequently screened experimentally to determine favorable substitutions. Feedback from experimental data may guide subsequent iterations of design and experimental screening, ultimately enabling protein variants to be engineered with the optimal balance between biophysical and immunological constraints.

Sequences

Central to the method described herein is that a set of host sequences provides information as to the degree to which linear sequence strings have the potential to be immunogenic. Thus the set of sequences employed is an important parameter. In the most common embodiment, the sequences are a set of human sequences that are homologous in sequence and/or structure to the parent sequence. As is known in the art, some proteins share a common structural scaffold and are homologous in sequence. This information may be used to gain insight into particular positions in the protein family. Sequence alignments are often carried out to determine which protein residues are conserved and which are not conserved. That is to say, by comparing and contrasting alignments of protein sequences, the degree of variability at a position may be observed, and the types of amino acids that occur naturally at positions may be observed. Thus for the present invention, typically the sequences are aligned such that the conserved or similar residues that exist between the parent sequence and the set of human sequences and among the set of human sequences can be identified. Methods for sequence alignment are well known in the art, and include alignments based on sequence and structural homology.

Protein sequence information can be obtained, compiled, and/or generated from sequence alignments of naturally occurring proteins from any organism, including but not limited to mammals. Because a preferred embodiment of present invention is directed towards immunogenicity reduction for biotherapeutics, the sequences that compose the set are most preferably human. The source of the sequences may vary widely, may be a database that is compiled publicly or privately, and may be may include one or more of the known general protein and nucleic acid sequences databases, including but not limited to SwissProt, GenBank® and Entrez®, and EMBL Nucleotide Sequence Database. Because a preferred embodiment of the present invention is its application to the immunogenicity reduction of immunoglobulins, a number of immunoglobulin databases may be useful for obtaining sequences, including but not limited to the Kabat database (Johnson & Wu, 2001, *Nucleic Acids Res* 29:205-206; Johnson & Wu, 2000, *Nucleic Acids Res* 28:214-218), the IMGT database (IMGT, the international ImMunoGeneTics information system®; Lefranc et al., 1999, *Nucleic Acids Res* 27:209-212; Ruiz et al., 2000 *Nucleic Acids Re.* 28:219-221; Lefranc et al., 2001, *Nucleic Acids Res* 29:207-209; Lefranc et al., 2003, *Nucleic Acids Res* 31:307-310), and VBASE.

As is well known in the art, immunoglobulins possess a high degree of sequence and structural homology, and therefore alignment of sequences provides a wealth of information. Due to the existence of deletions and insertions in these alignments, numbering conventions have been adopted to enable a normalized reference to conserved positions in immunoglobulin families or subfamilies. Those skilled in the art will appreciate that these conventions consist of nonsequential numbering in specific regions of an immunoglobulin sequence, and thus accordingly the positions of any given immunoglobulin as defined by any given numbering scheme will not necessarily correspond to its sequential sequence or to those in an alternate numbering scheme. For all variable regions discussed in the present invention, numbering is according to the numbering scheme of Kabat (Kabat et al., 1991, *Sequences of Proteins of Immunological Interest*, 5th Ed., United States Public Health Service, National Institutes of Health, Bethesda). For all constant region positions discussed in the present invention, number is according to the EU index as in Kabat. Alternate numbering schemes may find use in the present invention, including but not limited that of Chothia (Chothia & Lesk, 1987, *J. Mol. Biol.* 196: 901-917; Chothia et al., 1989, *Nature* 342: 877-883; Al-Lazikani et al., 1997, *J. Mol. Biol.* 273: 927-948).

In a most preferred embodiment, the set of human sequences used is an aligned set of human germline immunoglobulin sequences. For example, FIGS. 1*a*-1*c* (SEQ ID NOS: 1-109) provide the set of sequences that compose the human antibody variable region germline (VH, VL, and J chains), along with the corresponding diversity at each position. The human germline repertoire for immunoglobulin heavy chain variable regions and immunoglobulin light chain kappa variable regions have been reported (Matsuda et al., 1998, *J Exp Med* 188: 2151-2162; Zachau, 2000, Biol Chem 381:951-954; Pallares et al., 1999, *Exp Clin Immunogenet* 16(1): 36-60; Barbie & Lefranc, 1998, *Exp Clin Immunogenet* 15(3): 171-83). The human immunoglobulin kappa variable (IGKV) genes and joining (IGKJ) segments. Barbie V, Lefranc MP). The rationale for use of this type of sequence information as a metric for humanness is that the strings that compose the human germline should be minimally immunogenic. Sequences need not be human genomic or germline sequences. In other preferred embodiments, human antibody variable region sequences are derived not from germline information, but rather from matured antibodies obtained for example from hybridoma technology or cDNA libraries.

For many of the genes in the human immunoglobulin germline, several different alleles have been identified. Although the polymorphisms detected in many of the alleles do not change the amino acid sequence of the gene, in a great number of cases the sequence is changed. In choosing a set of sequences to use in the method described herein, different sets of sequences may be chosen. When choosing a single allele as representative of a specific gene the most cautious approach is to choose that sequence which is closest to the consensus of the entire germline. This subset of sequences would thereby be most likely to be represented within the population as a whole. Alternatively, a much greater sequence diversity could be sampled by choosing representative sequences that are furthest from the consensus. Another approach yielding greater diversity would be to use multiple alleles where they exist for each germline. At this time, there is little or no quantitative data on allele frequency within the population. When allele frequency becomes available, a more informed decision can be made regarding the likelihood of tolerance for a specific non-consensus allele within the target patient population.

When two or more possible substitutions are being evaluated for use at a specific position when both are found in the human germline, the decision may become subjective. In such a case additional information can be incorporated that may reflect different levels of expression of particular genes (Cox et al. Eur J. Immunol. 1994 April; 24(4):827-36). One underlying assumption of such a strategy would be that relative expression level of a particular germline (or corresponding sequence strings) correlates with the relative immunogenicity.

The sequences used for the method disclosed herein are those of homologous proteins with sufficient homology to allow their alignment with the protein whose immunogenicity is being reduced. One might argue that if a particular protein sequence is found anywhere within the expressed human genome that there is innate tolerance to that peptide. Such a proposition greatly increases the number of possible sequences that could be used to reduce the immunogenicity of a protein. In such a case however, alignment of proteins that are not structurally homologous would likely be prohibitive. In addition, the processing of a protein to produce the strings to which tolerance is developed may be structurally determined. Therefore, a specific strings may be nonimmunogenic in its native context but immunogenic in an altered structural context.

Scoring Functions
String Content

In order to evaluate the fitness of protein variants, amino acid modifications in the parent protein may be scored using a variety of scoring functions. Central to preferred embodiment of immunogenicity reduction method described herein is that at least one scoring function is aimed at maximizing the content of host linear sequence strings that are present in a set of host sequences. Typically, but not always, a computer is used to score potential amino acid substitutions.

In one embodiment, substitutions may be scored according to their occupancy in the set of host sequences, i.e., whether or not a given amino acid is part of the diversity at a given position. The use of position-specific alignment information to generate a list of considered amino acids at a variable position is well known in the art; see for example Lehmann & Wyss, 2001, *Curr Opin Biotechnol* 12(4): 371-5; Lehmann et al., 2000, *Biochim Biophys Acta* 1543(2):408-415; Rath & Davidson, 2000, *Protein Sci*, 9(12):2457-69; Lehmann et al., 2000, *Protein Eng* 13(1):49-57; Desjarlais & Berg, 1993, *Proc Natl Acad Sci USA* 90(6):2256-60; Desjarlais & Berg, 1992, *Proteins* 12(2):101-4; Henikoff & Henikoff, 2000, *Adv Protein Chem* 54:73-97; Henikoff & Henikoff, 1994, *J Mol Biol* 243(4):574-8. Thus, for example, for the parent nonhuman VLκ sequence aligned to the human sequences in FIG. 1b (SEQ ID NOS: 54-85), substitutions to be considered at position 1 would be Ala, Asp, Glu, Asn, and Val. In a more preferred embodiment, substitutions are scored based on their frequency in the set of human sequences listed. For example, in the previous example, Asp and Glu occur most frequently at position 1, and thus may be more preferable substitutions that Ala, Asn, or Val. The basis for this scoring function is that the frequency of a given amino acid at a given position in the alignment is proportional to its potential for being in a host string.

Occupancy and frequency provide relatively straightforward approximations for designing substitutions that have the potential for reduced immunogenicity. Their use, however, does not take into account the context of the parent sequence. Although frequency is proportional to the potential for a substitution to increase host content of a string, it is not a direct measure. In order to more accurately incorporate the information present in an aligned set of host sequences into a measure of immunogenicity, an approach can be taken wherein the linearity or contiguity of a given position in the context of the strings that comprise it is considered. In this most preferred embodiment, substitutions in a parent sequence are scored based on the probability of removing a nonhost string and replacing it with a less immunogenic string, namely one present in the set of host sequences. This method of scoring may employ the calculation of identity or percent identity of a parent string to a host string within a window of equivalent positions. In one embodiment, the identity of a string in sequence s to a host string in sequence h, (IDstring), can be presented as the sum of amino acid sequence identities in a given window size, according to equation 1:

$$IDstring(i, w) = \sum_{j=i}^{i+w-1} \delta_{aa^s_j, aa^h_j} \quad \text{Equation 1}$$

where w is the string window size, i is the first position in the string, $aa^s_j$ is the amino acid at position j of sequence s, $aa^h_j$ is the amino acid at position j of the host sequence h, and the Kronecker delta function is used to return a value of 1 for a match (for example if the parent and host amino acids at position j are both serine) and 0 if there is no match (for example if the parent amino acid at position j is a serine but the host amino acid is a leucine). FIG. 2a illustrates equation 1 using a region of the VH of murine anti-Her2 antibody m4D5 (VH_m4D5) (SEQ ID NO: 110) as the parent sequence s and the homologous region from the VH human germline (VH_1-2) as human sequence (SEQ ID NO:111)

In a further embodiment, it is assumed that the most immunologically appropriate measure of host string content at position i is the maximal identity between a string of sequence s and any host sequence in the alignment, as calculated in equation 2:

$$IDmax = \max_{h \in HS} \left( \sum_{j=i}^{i+w-1} \delta_{aa^s_j, aa^h_j} \right) \quad \text{Equation 2}$$

where HS is the set of host sequences. In other words, if IDstring at position i is equal to w for any one of the host sequences, IDmax=was well, and the $i^{th}$ string is assumed to be minimally immunogenic. The concept of the IDmax quantity represented by Equation 2 is illustrated in FIG. 2b.

Finally, these equations can be combined to calculate a single numerical metric for total host string content (HSC) of a sequence s by summing the IDmax values over all pertinent sequence positions, as in equation 3:

$$HSC(s) = 100 \cdot \frac{1}{(L-w+1) \cdot w} \sum_{i=1}^{L-w+1} \max_{h \in HS} \left( \sum_{j=i}^{i+w-1} \delta_{aa_j^s, aa_j^h} \right) \quad \text{Equation 3}$$

where L is the length of the sequence and HS is the set of host sequences in the alignment. A perfectly host sequence would have an HSC of 100. One might alternatively say that such a sequence is 100% host. The concept of the HSC quantity represented by Equation 3 is illustrated in FIG. 2c. In alternative embodiments, Equation 3 can be modified further such that the final score is dependent on the relative usage of each host sequence in the alignment. Strings from sequences that are more frequently expressed by hosts are expected to be more tolerated, and therefore may be given correspondingly higher influence in a scoring system.

In an alternative embodiment, one can measure the exact string content (ESC) as in Equation 3a:

$$ESC(s) = 100 \cdot \frac{1}{(L-w+1)} \sum_{i=1}^{L-w+1} \max_{h \in HS} \delta_{aa_{i \ldots i+w-1}^s, aa_{i \ldots i+w-1}^h}, \quad \text{Equation 3a}$$

where the notation $aa^s_{i \ldots i+w-1}$ refers the contiguous sequence string in protein s from position i to position i+w−1. In this embodiment, only perfect matches of size w are counted in the score.

It is worth noting that, since the scoring systems in Equations 3 and 3a are based on local sequence identity and/or similarity evaluated over windows of defined size, a sequence with high HSC can be constructed of sequence segments that are maximally similar to different members of the set of host sequences at different positions.

The above measure of hostness is likely to be more immunologically relevant than the more commonly used global identity measure of equation 4:

$$globalID = 100 \cdot \max_{h \in HS} \frac{1}{L} \sum_{i=1}^{L} \delta_{aa_i^s, aa_i^h} \quad \text{Equation 4}$$

Equation 4 disregards the extent of contiguous sequence identity, which is particularly relevant for capturing the molecular behavior of the immune system.

Additional scoring functions similar to equations 3 are also possible. For example, as will be appreciated by those skilled in the art, there is some uncertainty regarding the hostness of a string wherein IDmax=w−1, w−2, etc. In one alternative embodiment, sequence similarity is compared instead of identity, using any of a variety of amino acid substitution matrices (e.g. PAM, BLOSUM62, etc.), providing a host string similarity (HSS) score as in equation 5:

$$HSS(s) = \quad \text{Equation 5}$$
$$100 \cdot \frac{1}{L-w+1} \sum_{i=1}^{L-w+1} \max_{h \in HS} \left( e^{\sum_{j=i}^{i+w-1} \left( S_{aa_j^s, aa_j^h} - S_{aa_j^s, aa_j^s} \right)} \right)$$

where S is a substitution score comparing any two amino acids. In yet another alternative, sequence identities are weighted according to the extent of identity, as in equation 6:

$$HSC(s) = 100 \cdot \frac{1}{(L-w+1)} \sum_{i=1}^{L-w+1} f\left( \max_{h \in HS} \left( \sum_{j=i}^{i+w-1} \delta_{aa_j^s, aa_j^h} \right) \right) \quad \text{Equation 6}$$

where f is a continuous or noncontinuous function dependent on IDmax. For example, perfect matches can be weighted greater than near perfect matches (e.g. f(w)=1, f(w−1)=0.5, etc.), and poor matches can be discarded (e.g. f(w−3)=f(w−2)=0).

String Window Size

The fundamental binding units of class I and class II MHC proteins are both 9 amino acids. In a preferred embodiment, the window size w used to create and score parent sequences is 9. However, it is also known that additional peptide flanking residues (PFRs) can influence T-cell recognition (via the TCR) of class II MHC-peptide complexes (see for example Arnold et al., 2002, *J Immunology* 169(2): 739-49), with the residues at positions P−1 (one position before the $1^{st}$ MHC binding position) and P11 being most influential. Because these effects might influence immune tolerance, a desirable goal of the invention, larger window sizes (e.g. 12) can be used. It should be noted however, that sequences optimized with similar window sizes are highly correlated.

Optimization of HSC

Although a definition of string scoring systems is useful, an efficient process for discovering sequences with high HSC is also desirable. It is therefore a further aspect of the invention to provide methods for dynamic optimization of HSC given the described scoring systems.

Desirable features of an optimization method include but are not limited to the following: 1) the output sequences are optimal or near-optimal (subject to design constraints) in their host string content; 2) structural constraints can be used to modulate the nature of the optimized sequences; and 3) multiple near-optimal solutions can be generated. Additionally, in some preferred embodiments, host string content may be maximized using a minimal number of substitutions.

In a preferred embodiment, an iterative algorithm for optimization of HSC works as follows. 1) a parent sequence and set of host sequences are defined; 2) mutational constraints are defined at functionally or structurally important positions, referred to herein as masking—in a preferred embodiment, for antibody applications, positions within or structurally proximal to CDR residue (as defined by herein, or alternatively as defined by Kabat or Chothia) and/or interface are masked, locked, or fixed so that mutations are not possible (in some embodiments this constraint can be relaxed if the potential mutation is a conservative substitution of the parent amino acid). In a preferred embodiment, positions within 5 angstroms of a CDR residue or interface are masked. In other preferred embodiments, positions within 6.5 angstroms of a CDR residue or interface are masked; 3) host sequence segments (up to a defined length: lengths from 1-6 are typical) are collected from the alignment and stored for each position: segments that violate the mutational constraints are not collected; 4) each segment is analyzed for its potential impact on HSC, in the context of the current parent sequence, defined as String Impact (SI) in equation 7:

$$SI(x_m(z)\rightarrow y_m(z)) = HSC(s(y_m)) - HSC(\text{parent}), \quad \text{Equation 7}$$

where $y_m(z)$ is a host segment of length z replacing segment x at position m, and $s(y_m)$ and parent are versions of the parent sequence that include these segments (the parent sequence contains $X_m(z)$). 5) a single string is randomly selected from all stored host strings; the probability of selection is biased and proportional to the impact on HSC and inversely proportional to the number of mutations relative to the current parent sequence, as in Equation 8:

$$P \propto \frac{SI(x_m(z) \to y_m(z))}{\sum_{i=m}^{m+z-1} \delta_{aa_i^{parent}, aa_i^{s(y_m)}}} \qquad \text{Equation 8}$$

This selected string is substituted into the current parent sequence for its corresponding parent amino acids on an amino acid string by amino acid string basis. This kind of selection bias tends to optimize host string content with minimal perturbation of the original sequence. 6) steps 4 and 5 are repeated until no further optimization is possible (no segment substitutions have a favorable impact on host string content).

Such an algorithm is inherently non-deterministic, so independent runs of the algorithm will tend to generate different solutions (this is a favorable feature). In a preferred embodiment, such an algorithm is applied numerous times to generate a diverse array of unique solutions. These solutions can be further clustered such that representative sequences can be prioritized for further analysis. For example, in one embodiment, the solution sequences are clustered into groups of similar sequences according to mutational distance, using a nearest neighbor single linkage hierarchical clustering algorithm to assign sequences to related groups based on similarity scores. Clustering algorithms may be useful for classifying sequences into representative groups. Representative groups may be defined, for example, by similarity. Measures of similarity include, but are not limited to sequence similarity and energetic similarity. Thus the output sequences from computational screening may be clustered around local minima, referred to herein as clustered sets of sequences. Sets of sequences that are close in sequence space may be distinguished from other sets. In one embodiment, diversity across clustered sets of sequences may be sampled by experimentally testing only a subset of sequences within each clustered set. For example, all or most of the clustered sets could be broadly sampled by including the lowest energy sequence from each clustered set of sequences to be experimentally tested. Because the sequence space of solutions with optimized HSC can be large, additional methods can be applied to ensure that a broad set of sequences is created. In a preferred embodiment, individual framework sequences generated by the procedure are clustered separately to generate a list of nonredundant basis framework regions (FRs) with high HSC. These basis FRs are then computationally assembled in all combinations along with the CDRs to generate a secondary list of solution sequences (which will usually have some overlap with the primary set). Alternatively, the basis FRs may be combined into an experimental library, for example a combinatorial library.

Framework Diversity

Application of this algorithm will generate variant protein solutions for which HSC is higher than the original parent sequence. It will also frequently generated solutions in which substituted strings are derived from different members of the alignment. The variant sequences derived using the present invention generally have unique properties relative to sequences generated using other methodologies. For example, in the context of an antibody, the protein variants of the invention frequently derive their host string content from a combination of different host germline sequences. This may be true even within a single FR. Quantification of these properties is useful for defining the nature of sequences derived using the present invention. A clear distinction emerges from a comparison of exact string content (meaning a perfect match over window w) in any single germline sequence versus exact w-mer string content within the set of all germline sequences (content of strings for which IDmax=w). Single germline exact string content (SGESC) of a variant sequence v may thus be defined as:

$$SGESC(v) = 100 \cdot \frac{1}{L-w+1} \cdot \max_{h \in HS} \sum_{i=1}^{L-w+1} \delta_{aa_{i\ldots i+w-1}^y, aa_{i\ldots i+w-1}^h} \qquad \text{Equation 9}$$

This quantity provides the extent to which a string-optimized sequence has string identity with the closest single germline sequence. Using this definition, it is also possible to assess the extent to which the high host string content of a given variant sequence v is derived from a single germline as opposed to multiple germline sequences. Framework region homogeneity (FRH) is defined as follows:

$$FRH(v) = \frac{SGESC(v)}{ESC(v)} \qquad \text{Equation 10}$$

$$= \frac{\max_{h \in HS} \sum_{i=1}^{L-w+1} \delta_{aa_{i\ldots i+w-1}^y, aa_{i\ldots i+w-1}^h}}{\sum_{i=1}^{L-w+1} \max_{h \in HS} \delta_{aa_{i\ldots i+w-1}^s, aa_{i\ldots i+w-1}^h}}$$

In other words, if a variant sequence's exact string content is derived solely from a single germline sequence, the FRH would be close to 1.0. It should be noted that a similar or identical quantity can be defined for non-antibody proteins. Alternatively, as is the case with many of the variant sequences created by the present invention, FRH values can be significantly less than 1, with values ranging from 0.4 to 1.0, indicating, as expected, that sequences with high exact string content can be discovered with contributions from multiple germline subfamilies and sequences. As described more fully in Example 5 below, variant sequences generated using the present invention have high HSC values yet many have low FRH values, indicating their HSC is derived from multiple germline frameworks.

Additional Scoring

The above methods of scoring use the information present in an aligned set of host sequences as a metric of immunogenicity to maximize the content of host linear sequence strings in a parent sequence. In addition to such scoring functions, other scoring functions and methods may be employed. Such additional scoring functions may be aimed at the same goal as the aforementioned linear string scoring function, namely immunogenicity reduction of the parent protein. Alternatively, such additional scoring functions may be used to achieve other goals, for example optimization of protein stability, solubility, expression, pharmacokinetics, and/or aspects of protein function such as affinity of the parent protein for a target ligand, specificity, effector function, and/or enzymatic activity. For example an additional scoring function may be employed to enhance the affinity of an antibody variable domain for its target antigen. Such additional scoring functions may be employed statically or dynamically for the generation of optimized protein variants. A number of embodiments are described below as preferred additional scoring functions that may be used with the aforementioned linear string scoring method of the present invention. However, these are not meant to constrain the invention to these embodiments, and it should be clear that any method of scoring the fitness of an amino acid modification in a parent protein may be coupled with the novel linear string scoring method of the present invention so that optimal protein variants may be designed.

In a preferred embodiment, substitutions are scored based on their structural compatibility with the structure of the parent protein. Such methods of scoring may require the structural coordinates that describe the three-dimensional structure of the protein, for example as obtained by X-ray crystallographic and nuclear magnetic resonance (NMR) techniques. Suitable proteins structures may also be obtained from structural models, which may be generated by methods that are known in the art of structural biology, including but not limited to de novo and homology modeling. Structure-based scoring functions may include any number of potentials that describe or approximate physical or chemical energy terms, including but not limited to a van der Waals potential, a hydrogen bond potential, an atomic solvation potential or other solvation models, a secondary structure propensity potential, an electrostatic potential, a torsional potential, an entropy potential, and/or additional energy terms. In other preferred embodiments, scoring methods may also be derived from sequence information, including but not limited to knowledge-based potentials derived from protein sequence and/or structure statistics, threading potentials, reference energies, pseudo energies, homology-based energies, and sequence biases derived from sequence alignments. In alternately preferred embodiments, both structural and sequence-based potentials are used to generate one or more scoring functions that may be coupled with the linear string scoring method of the present invention.

In a most preferred embodiment, a scoring method is used wherein the structural and functional integrity of substitutions are evaluated using a sequence and structure-based scoring function described in U.S. Ser. No. 60/528,229, filed Dec. 8, 2003, entitled Protein Engineering with Analogous Contact Environments; and U.S. Ser. No. 60/602,566, filed Aug. 17, 2004, entitled Protein Engineering with Analogous Contact Environments. This method combines sequence alignment information and structural information to predict the structural compatibility of one or more substitutions with a protein structure template. Nearest neighbor structure-based scores generated by this method include Structural Consensus and Structural Precedence as provided in the Examples. This method is particularly well suited for application to evaluating the structural fitness of immunoglobulins due to their substantial sequence and structural homology.

In a preferred embodiment, substitutions are scored using a scoring function or computational design program that is substantially similar to Protein Design Automation® (PDA®) technology, as is described in U.S. Pat. No. 6,188,965; U.S. Pat. No. 6,269,312; U.S. Pat. No. 6,403,312; U.S. Pat. No. 6,708,120; U.S. Pat. No. 6,804,611; U.S. Pat. No. 6,792,356; U.S. Ser. No. 09/782,004; U.S. Ser. No. 09/812,034; U.S. Ser. No. 09/927,790; U.S. Ser. No. 10/218,102; U.S. Ser. No. 10/101,499; U.S. Ser. No. 10/218,102; U.S. Ser. No. 10/666,311; U.S. Ser. No. 10/665,307; U.S. Ser. No. 10/888,748; PCT WO 98/07254; PCT WO 99/24229; PCT WO 01/40091; and PCT WO 02/25588. In another preferred embodiment, a computational design method substantially similar to Sequence Prediction Algorithm™ (SPA™) technology is used, as is described in (Raha et al., 2000, *Protein Sci.* 9: 1106-1119), U.S. Ser. No. 09/877,695, and U.S. Ser. No. 10/071,859. In another preferred embodiment, the computational methods described in U.S. Ser. No. 10/339,788, are used.

In another preferred embodiment, optimized sequences are also assessed for surface similarity with host antibodies. Ensuring similarity may be important for reducing the probability of introducing novel 3D epitopes, which are potentially recognized by B-cell receptors. In a preferred embodiment, surface similarity at position i is quantified as follows:

$$surfscore(i) = \max_{k \in HS} e^{f_i^{exp} \cdot \left(\left(\sum_{j=1}^{L} proximity(i,j) * S(aa_j^s, aa_j^k)\right) - \left(\sum_{j=1}^{L} proximity(i,j) * S(aa_j^s, aa_j^t)\right)\right)/T}$$

Equation 11 where $f_i^{exp}$ is the fraction accessibility of position i to solvent, proximity (i,j) is the spatial proximity of positions i and j in the three-dimensional structure of the protein, S is a measure of amino acid similarity, and T is a temperature factor used to tune the stringency of the similarity comparison. It will be appreciated from the equation that if sequences are identical in the region of position i, a surfscore of 1.0 will be approached. Alternatively, a score of 1.0 can also be achieved if a position is completely buried (i.e. $f_i^{exp}=0$), since the position would not be accessible to B-cell receptors. Lower scores represent surface positions for which there are significant differences between the variant sequence and the most similar host sequence. In a preferred embodiment, the proximity between two positions is inversely related to their distance (e.g. a Gaussian or exponential function of the distance), and the proximity of a position to itself is 1.0. In a preferred embodiment, the decay of the proximity function is tuned such that patches of positions correspond to the size of a typical antibody epitope.

Other surface properties may also be desirable. For example, optimized variant sequences may be assessed for the exposure of nonpolar amino acids, which is generally expected to decrease solubility. In such cases, variant sequences with lower nonpolar exposure can be prioritized over alternatives. Surface electrostatic properties may also be assessed for variant sequences. In a preferred embodiment, surface properties are assessed for multiple variants with optimized HSC, in order to limit the set of variants that will be experimentally screened.

In another embodiment, substitution matrices or other knowledge-based scoring methods are used to identify alternate sequences that are likely to retain the structure and function of the protein. Such scoring methods can be used to quantify how conservative a given substitution or set of substitutions is. In most cases, conservative mutations do not significantly disrupt the structure and function of proteins (see for example, Bowie et. al., 1990, *Science* 247: 1306-

1310, Bowie & Sauer, 1989, *Proc. Nat. Acad. Sci. USA* 86: 2152-2156, and Reidhaar-Olson & Sauer, 1990, *Proteins* 7: 306-316). However, non-conservative mutations can destabilize protein structure and reduce activity (see for example, Lim et al., 1992, *Biochem.* 31: 4324-4333). Substitution matrices including but not limited to BLOSUM62 provide a quantitative measure of the compatibility between a sequence and a target structure, which can be used to predict non-disruptive substitution mutations (Topham et al., 1997, *Prot. Eng.* 10: 7-21). The use of substitution matrices to design peptides with improved properties has been disclosed (Adenot et al., 1999, *J. Mol. Graph. Model.* 17: 292-309). Substitution matrices include, but are not limited to, the BLOSUM matrices (Henikoff & Henikoff, 1992, *Proc. Nat. Acad. Sci. USA* 89: 10917, the PAM matrices, the Dayhoff matrix, and the like. For a review of substitution matrices, see for example Henikoff, 1996, *Curr. Opin. Struct. Biol.* 6: 353-360. It is also possible to construct a substitution matrix based on an alignment of a given protein of interest and its homologs; see for example Henikoff & Henikoff, 1996, *Comput. Appl. Biosci.* 12: 135-143.

In a preferred embodiment, other methods for scoring immunogenicity may additionally be used. Most preferably, immunogenicity may be scored using a function that considers peptide binding to one or more MHC molecules. For example, substitutions would be scored such that there are no or a minimal number of immune epitopes that are predicted to bind, with high affinity, to any prevalent MHC alleles. These methods of scoring may be useful, for example, for designing substitutions in VH CDR3, for which scoring using human germline strings may be less straightforward. Several methods of identifying MHC-binding epitopes in protein sequences are known in the art and may be used to score epitopes in an antibody. See for example WO 98/52976; WO 02/079232; WO 00/3317; U.S. Ser. No. 09/903,378; U.S. Ser. No. 10/039,170; U.S. Ser. No. 60/222,697; U.S. Ser. No. 10/339,788; PCT WO 01/21823; and PCT WO 02/00165; Mallios, 1999, *Bioinformatics* 15: 432-439; Mallios, 2001, *Bioinformatics* 17: 942-948; Sturniolo et al., 1999, *Nature Biotech.* 17: 555-561; WO 98/59244; WO 02/069232; WO 02/77187; Marshall et al., 1995, *J. Immunol.* 154: 5927-5933; and Hammer et al., 1994, *J. Exp. Med.* 180: 2353-2358. Sequence-based information can be used to determine a binding score for a given peptide—MHC interaction (see for example Mallios, 1999, *Bioinformatics* 15: 432-439; Mallios, 2001, *Bioinformatics* 17: p 942-948; Sturniolo et. al., 1999, *Nature Biotech.* 17: 555-561). It is possible to use structure-based methods in which a given peptide is computationally placed in the peptide-binding groove of a given MHC molecule and the interaction energy is determined (for example, see WO 98/59244 and WO 02/069232). Such methods may be referred to as "threading" methods. Alternatively, purely experimental methods can be used; for example a set of overlapping peptides derived from the protein of interest can be experimentally tested for the ability to induce T-cell activation and/or other aspects of an immune response. (see for example WO 02/77187). In a preferred embodiment, MHC-binding propensity scores are calculated for each 9-residue frame along the protein sequence using a matrix method (see Sturniolo et. al., supra; Marshall et. al., 1995, *J. Immunol.* 154: 5927-5933, and Hammer et. al., 1994, *J. Exp. Med.* 180: 2353-2358). It is also possible to consider scores for only a subset of these residues, or to consider also the identities of the peptide residues before and after the 9-residue frame of interest. The matrix comprises binding scores for specific amino acids interacting with the peptide binding pockets in different human class II MHC molecule. In the most preferred embodiment, the scores in the matrix are obtained from experimental peptide binding studies. In an alternate preferred embodiment, scores for a given amino acid binding to a given pocket are extrapolated from experimentally characterized alleles to additional alleles with identical or similar residues lining that pocket. Matrices that are produced by extrapolation are referred to as "virtual matrices".

In alternate embodiments, additional scoring functions are employed that predict reactive sites within a protein, such as deamidation sites, glycosylation sites, oxidation sites, proteaytic cleavage sites, and the like.

It will be appreciated by one of skill in the art that the use of combinations of any of the aforementioned scoring functions and/or other scoring functions is contemplated. In one embodiment, this could be accomplished by evaluating the outputs of the results from separate calculations. Alternatively, scoring functions may be combined into one scoring term. This latter strategy enables different scoring terms to be weighted separately, thus providing more control over the relative contributions of the scoring terms, and a greater capacity to tune the scoring function for a desired engineering strategy.

Additional Optimization of Sequences

In a preferred embodiment, after optimized protein variants have been engineered using the aforementioned scoring functions, additional optimization of protein variants may be carried out. In this way, an optimized protein variant can be thought of as primary variant or template for further optimization, and variants of this primary variant can be thought of as secondary variants. Because variant sequences of the invention are preferably derived from a HSC-increasing procedure in which substitution of structurally important positions is disallowed or discouraged (for example masking), it is likely that additional optimization of HSC is possible if those positions are allowed to vary in a secondary analysis. Optimization of other properties is possible, including but are not limited to protein affinity, expression, specificity, solubility, activity, and effector function. Thus the variant sequences derived in the primary analysis can represent variants for further optimization. In a preferred embodiment, the secondary analysis comprises the steps of 1) string analysis of the template sequence to identify secondary amino acid diversity that will have neutral, positive, or minimal impact on HSC; 2) experimental production of secondary variant sequences using the diversity derived in step 1; and 3) experimental screening of secondary variant sequences.

For these purposes, the string impact (SI) of a single substitution at position m from amino acid x to amino acid y can be quantified as in Equation 7 (where segment length z=1). As will be appreciated, the maximum possible string increase (for a single substitution at an internal position) is w and the maximum possible decrease is w.

In a most preferred embodiment, substitutions in a primary variant are chosen as those substitutions that will result in zero or positive string impact, referred to herein as string neutral and string positive substitutions respectively. In other embodiments, substitutions that result in negative string impact, i.e. string negative substitutions, may also be considered for engineering secondary variants. Secondary variants then may be constructed, expressed, and tested experimentally. Secondary substitutions that show favorable properties with respect to antigen affinity, effector function, stability, solubility, expression, and the like, may be combined in subsequent variants to generate a more optimized therapeutic candidate.

Optimization of Non-Xenogeneic Proteins

It can be appreciated that the optimization described above is not restricted to immunogenicity reduction of xenogeneic proteins. Evaluation of potential substitutions for string impact provides an excellent strategy for generating substitution diversity for engineering protein variants with optimized properties. A clear advantage of this approach is that it generates protein variants with minimal immunogenicity risk, the importance of which has been discussed extensively and is a primary goal of the present invention. An additional advantage of this approach is that because the sequences being used to evaluate string impact are typically derived from a set of naturally evolved host sequences, variants designed are effectively enriched for stability, solubility, and other favorable properties. The utility of this capability lies in the fact that there are innumerable amino acid modifications that are detrimental or deleterious to proteins. By screening a quality set of variant diversity, the chances are increased that a protein variant of the desired property will be obtained. The capacity of the string impact approach to generate a quality set of variant diversity derives from the greater tolerance to mutation of positions which sample greater diversity, and the greater propensity of amino acids in a set of naturally evolved sequences to be compatible with a homologous protein's structure, stability, solubility, function, and the like.

This string impact approach to variant design may be applied not only to the generation of secondary variants as described above, but may also be used to engineer amino acid modifications in proteins that are presumably already minimally immunogenic. This may include, for example, natural host proteins. Alternatively, and in a preferred embodiment, the string impact strategy may be applied to engineer modifications in an antibody variable region (VH or VL) that is humanized (Clark, 2000, *Immunol Today* 21:397-402), or "fully human" as obtained for example using transgenic mice (Bruggemann et al., 1997, *Curr Opin Biotechnol* 8:455-458) or human antibody libraries coupled with selection methods (Griffiths et al., 1998, *Curr Opin Biotechnol* 9:102-108). As with optimization of primary variant sequences described above, the string impact analysis described here can be used to identify secondary diversity that will have neutral, positive, or minimal impact on HSC, as well as potentially other favorable properties. Such diversity can then be used to screen for optimized versions of these sequences without increasing the risk of immunogenicity.

Experimental Production, Screening, and Testing

Methods for production and screening of protein variants are well known in the art. General methods for antibody molecular biology, expression, purification, and screening are described in Antibody Engineering, edited by Duebel & Kontermann, Springer-Verlag, Heidelberg, 2001; and Hayhurst & Georgiou, 2001, *Curr Opin Chem Biol* 5:683-689; Maynard & Georgiou, 2000, *Annu Rev Biomed Eng* 2:339-76. Also see the methods described in U.S. Ser. No. 10/339,788, filed on Mar. 3, 2003, U.S. Ser. No. 10/672,280, filed Sep. 29, 2003, and U.S. Ser. No. 10/822,231, filed Mar. 26, 2004.

In one embodiment of the present invention, the library sequences are used to create nucleic acids that encode the member sequences, and that may then be cloned into host cells, expressed and assayed, if desired. These practices are carried out using well-known procedures, and a variety of methods that may find use in the present invention are described in Molecular Cloning—A Laboratory Manual, 3$^{rd}$ Ed. (Maniatis, Cold Spring Harbor Laboratory Press, New York, 2001), and Current Protocols in Molecular Biology (John Wiley & Sons). The nucleic acids that encode the protein variants of the present invention may be incorporated into an expression vector in order to express the protein. Expression vectors typically comprise a protein operably linked, that is placed in a functional relationship, with control or regulatory sequences, selectable markers, any fusion partners, and/or additional elements. The protein variants of the present invention may be produced by culturing a host cell transformed with nucleic acid, preferably an expression vector, containing nucleic acid encoding the protein variants, under the appropriate conditions to induce or cause expression of the protein. A wide variety of appropriate host cells may be used, including but not limited to mammalian cells, bacteria, insect cells, and yeast. For example, a variety of cell lines that may find use in the present invention are described in the ATCC cell line catalog, available from the American Type Culture Collection. The methods of introducing exogenous nucleic acid into host cells are well known in the art, and will vary with the host cell used.

In a preferred embodiment, protein variants are purified or isolated after expression. Proteins may be isolated or purified in a variety of ways known to those skilled in the art. Standard purification methods include chromatographic techniques, electrophoretic, immunological, precipitation, dialysis, filtration, concentration, and chromatofocusing techniques. As is well known in the art, a variety of natural proteins bind antibodies, for example bacterial proteins A, G, and L, and these proteins may find use in the present invention for purification. Purification can often be enabled by a particular fusion partner. For example, proteins may be purified using glutathione resin if a GST fusion is employed, $Ni^{+2}$ affinity chromatography if a His-tag is employed, or immobilized anti-flag antibody if a flag-tag is used. For general guidance in suitable purification techniques, see Protein Purification: Principles and Practice, 3$^{rd}$ Ed., Scopes, Springer-Verlag, NY, 1994.

Protein variants may be screened using a variety of methods, including but not limited to those that use in vitro assays, in vivo and cell-based assays, and selection technologies. Automation and high-throughput screening technologies may be utilized in the screening procedures. Screening may employ the use of a fusion partner or label, for example an immune label, isotopic label, or small molecule label such as a fluorescent or colorimetric dye.

In a preferred embodiment, the functional and/or biophysical properties of protein variants are screened in an in vitro assay. In a preferred embodiment, the protein is screened for functionality, for example its ability to catalyze a reaction or its binding affinity to its target. Binding assays can be carried out using a variety of methods known in the art, including but not limited to FRET (Fluorescence Resonance Energy Transfer) and BRET (Bioluminescence Resonance Energy Transfer)-based assays, AlphaScreen™ (Amplified Luminescent Proximity Homogeneous Assay), Scintillation Proximity Assay, ELISA (Enzyme-Linked Immunosorbent Assay), SPR (Surface Plasmon Resonance, also known as BIACORE®), isothermal titration calorimetry, differential scanning calorimetry, gel electrophoresis, and chromatography including gel filtration. These and other methods may take advantage of some fusion partner or label. Assays may employ a variety of detection methods including but not limited to chromogenic, fluorescent, luminescent, or isotopic labels. The biophysical properties of proteins, for example stability and solubility, may be screened using a variety of methods known in the art. Protein stability may be determined by measuring the thermodynamic equilibrium between folded and unfolded states. For example, protein variants of the present invention may be unfolded using chemical denaturant, heat, or pH, and this transition may be monitored using methods including but not limited to circular dichroism spectroscopy, fluorescence spectroscopy, absorbance spectroscopy, NMR spectroscopy, calorimetry, and proteolysis. As will be appreciated by those skilled in the art, the kinetic parameters of the folding and unfolding transitions may also be monitored using these and other techniques. The solubility and overall structural integrity of a protein variant may be quantitatively or qualitatively determined using a wide range of methods that are known in the art. Methods which may find use in the present invention for characterizing the biophysical properties of protein variants include gel electrophoresis, chromatography such as size exclusion chromatography and reversed-phase high performance liquid chromatography, mass spectrometry, ultraviolet absorbance spectroscopy, fluorescence spectroscopy, circular dichroism spectroscopy, isothermal titration calorimetry, differential scanning calorimetry, analytical ultra-centrifugation, dynamic light scattering, proteolysis, and cross-linking, turbidity measurement, filter retardation assays, immunological assays, fluorescent dye binding assays, protein-staining assays, microscopy, and detection of aggregates via ELISA or other binding assay. Structural analysis employing X-ray crystallographic techniques and NMR spectroscopy may also find use.

In a preferred embodiment, protein variants are screened using one or more cell-based or in vivo assays. For such assays, purified or unpurified proteins are typically added exogenously such that cells are exposed to individual variants or pools of variants belonging to a library. These assays are typically, but not always, based on the function of the protein; that is, the ability of the protein to bind to its target and mediate some biochemical event, for example effector function, ligand/receptor binding inhibition, apoptosis, and the like. Such assays often involve monitoring the response of cells to the protein, for example cell survival, cell death, change in cellular morphology, or transcriptional activation such as cellular expression of a natural gene or reporter gene. For example, such assays may measure the ability of antibody variants to elicit ADCC, ADCP, or CDC. For some assays additional cells or components, that is in addition to the target cells, may need to be added, for example serum complement, or effector cells such as peripheral blood monocytes (PBMCs), NK cells, macrophages, and the like. Such additional cells may be from any organism, preferably humans, mice, rat, rabbit, and monkey. Proteins may cause apoptosis of certain cell lines expressing the target, or they may mediate attack on target cells by immune cells which have been added to the assay. Methods for monitoring cell death or viability are known in the art, and include the use of dyes, immunochemical, cytochemical, and radioactive reagents. For example, caspase staining assays may enable apoptosis to be measured, and uptake or release of radioactive substrates or fluorescent dyes such as alamar blue may enable cell growth or activation to be monitored. In a preferred embodiment, the DELFIA® EuTDA-based cytotoxicity assay (Perkin Elmer, MA) is used. Alternatively, dead or damaged target cells may be monitored by measuring the release of one or more natural intracellular proteins, for example lactate dehydrogenase. Transcriptional activation may also serve as a method for assaying function in cell-based assays. In this case, response may be monitored by assaying for natural genes or proteins which may be upregulated, for example the release of certain interleukins may be measured, or alternatively readout may be via a reporter construct. Cell-based assays may also involve the measure of morphological changes of cells as a response to the presence of a protein. Cell types for such assays may be prokaryotic or eukaryotic, and a variety of cell lines that are known in the art may be employed. Alternatively, cell-based screens are performed using cells that have been transformed or transfected with nucleic acids encoding the variant proteins. That is, protein variants are not added exogenously to the cells. For example, in one embodiment, the cell-based screen utilizes cell surface display. A fusion partner can be employed that enables display of variants on the surface of cells (Witrrup, 2001, *Curr Opin Biotechnol*, 12:395-399).

As is known in the art, a subset of screening methods are those that select for favorable members of a library. The methods are herein referred to as "selection methods", and these methods find use in the present invention for screening protein variants. When protein libraries are screened using a selection method, only those members of a library that are favorable, that is which meet some selection criteria, are propagated, isolated, and/or observed. As will be appreciated, because only the most fit variants are observed, such methods enable the screening of libraries that are larger than those screenable by methods that assay the fitness of library members individually. Selection is enabled by any method, technique, or fusion partner that links, covalently or noncovalently, the phenotype of a protein with its genotype, i.e., the function of a protein with the nucleic acid that encodes it. For example the use of phage display as a selection method is enabled by the fusion of library members to the gene III protein. In this way, selection or isolation of protein variants that meet some criteria, for example binding affinity to the protein's target, also selects for or isolates the nucleic acid that encodes it. Once isolated, the gene or genes encoding variants may then be amplified. This process of isolation and amplification, referred to as panning, may be repeated, allowing favorable protein variants in the library to be enriched. Nucleic acid sequencing of the attached nucleic acid ultimately allows for gene identification.

A variety of selection methods are known in the art that may find use in the present invention for screening protein libraries. These include but are not limited to phage display (Phage display of peptides and proteins: a laboratory manual, Kay et al., 1996, Academic Press, San Diego, Calif., 1996; Lowman et al., 1991, *Biochemistry* 30:10832-10838; Smith, 1985, *Science* 228:1315-1317) and its derivatives such as selective phage infection (Malmborg et al., 1997, *J Mol Biol* 273:544-551), selectively infective phage (Krebber et al., 1997, *J Mol Biol* 268:619-630), and delayed infectivity panning (Benhar et al., 2000, *J Mol Biol* 301:893-904), cell surface display (Witrrup, 2001, *Curr Opin Biotechnol*, 12:395-399) such as display on bacteria (Georgiou et al., 1997, *Nat Biotechnol* 15:29-34; Georgiou et al., 1993, *Trends Biotechnol* 11:6-10; Lee et al., 2000, *Nat Biotechnol* 18:645-648; Jun et al., 1998, *Nat Biotechnol* 16:576-80), yeast (Boder & Wittrup, 2000, *Methods Enzymol* 328:430-44; Boder & Wittrup, 1997, *Nat Biotechnol* 15:553-557), and mammalian cells (Whitehorn et al., 1995, *Bio/technology* 13:1215-1219), as well as in vitro display technologies (Amstutz et al., 2001, *Curr Opin Biotechnol* 12:400-405) such as polysome display (Mattheakis et al., 1994, *Proc Natl Acad Sci USA* 91:9022-9026), ribosome display (Hanes et al., 1997, *Proc Natl Acad Sci USA* 94:4937-4942), mRNA display (Roberts & Szostak, 1997, *Proc Natl Acad Sci USA* 94:12297-12302; Nemoto et al., 1997, *FEBS Lett* 414:405-408), and ribosome-inactivation display system (Zhou et al., 2002, *J Am Chem Soc* 124, 538-543).

Other selection methods that may find use in the present invention include methods that do not rely on display, such as in vivo methods including but not limited to periplasmic expression and cytometric screening (Chen et al., 2001, *Nat*

Biotechnol 19:537-542), the protein fragment complementation assay (Johnsson & Varshavsky, 1994, *Proc Natl Acad Sci USA* 91:10340-10344; Pelletier et al., 1998, *Proc Natl Acad Sci USA* 95:12141-12146), and the yeast two hybrid screen (Fields & Song, 1989, *Nature* 340:245-246) used in selection mode (Visintin et al., 1999, *Proc Natl Acad Sci USA* 96:11723-11728). In an alternate embodiment, selection is enabled by a fusion partner that binds to a specific sequence on the expression vector, thus linking covalently or noncovalently the fusion partner and associated variant library member with the nucleic acid that encodes them. For example, U.S. Ser. No. 09/642,574; U.S. Ser. No. 10/080,376; U.S. Ser. No. 09/792,630; U.S. Ser. No. 10/023,208; U.S. Ser. No. 09/792,626; U.S. Ser. No. 10/082,671; U.S. Ser. No. 09/953,351; U.S. Ser. No. 10/097,100; U.S. Ser. No. 60/366,658; PCT WO 00/22906; PCT WO 01/49058; PCT WO 02/04852; PCT WO 02/04853; PCT WO 02/08023; PCT WO 01/28702; and PCT WO 02/07466 describe such a fusion partner and technique that may find use in the present invention. In an alternative embodiment, in vivo selection can occur if expression of the protein imparts some growth, reproduction, or survival advantage to the cell.

A subset of selection methods referred to as "directed evolution" methods are those that include the mating or breading of favorable sequences during selection, sometimes with the incorporation of new mutations. As will be appreciated by those skilled in the art, directed evolution methods can facilitate identification of the most favorable sequences in a library, and can increase the diversity of sequences that are screened. A variety of directed evolution methods are known in the art that may find use in the present invention for screening protein variants, including but not limited to DNA shuffling (PCT WO 00/42561 A3; PCT WO 01/70947 A3), exon shuffling (U.S. Pat. No. 6,365,377; Kolkman & Stemmer, 2001, *Nat Biotechnol* 19:423-428), family shuffling (Crameri et al., 1998, *Nature* 391:288-291; U.S. Pat. No. 6,376,246), RACHITT™ (Coco et al., 2001, *Nat Biotechnol* 19:354-359; PCT WO 02/06469), STEP and random priming of in vitro recombination (Zhao et al., 1998, *Nat Biotechnol* 16:258-261; Shao et al., 1998, *Nucleic Acids Res* 26:681-683), exonuclease mediated gene assembly (U.S. Pat. No. 6,352,842; U.S. Pat. No. 6,361,974), Gene Site Saturation Mutagenesis™ (U.S. Pat. No. 6,358,709), Gene Reassembly™ (U.S. Pat. No. 6,358,709), SCRATCHY (Lutz et al., 2001, *Proc Natl Acad Sci USA* 98:11248-11253), DNA fragmentation methods (Kikuchi et al., *Gene* 236:159-167), single-stranded DNA shuffling (Kikuchi et al., 2000, *Gene* 243:133-137), and AMEsystem™ directed evolution protein engineering technology (Applied Molecular Evolution) (U.S. Pat. No. 5,824,514; U.S. Pat. No. 5,817,483; U.S. Pat. No. 5,814,476; U.S. Pat. No. 5,763,192; U.S. Pat. No. 5,723,323).

In a preferred embodiment, the immunogenicity of the protein variants is determined experimentally to confirm that the variants do have reduced or eliminated immunogenicity relative to the parent protein. Several methods can be used for experimental confirmation of epitopes. In a preferred embodiment, ex vivo T-cell activation assays are used to experimentally quantitate immunogenicity. In this method, antigen presenting cells and naïve T cells from matched donors are challenged with a peptide or whole protein of interest one or more times. Then, T cell activation can be detected using a number of methods, for example by monitoring production of cytokines or measuring uptake of tritiated thymidine. In the most preferred embodiment, interferon gamma production is monitored using Elispot assays (Schmittel et. al., 2000, *J. Immunol. Meth.*, 24: 17-24). If sera are available from patients who have raised an immune response to protein, it is possible to detect mature T cells that respond to specific epitopes. In a preferred embodiment, interferon gamma or IL-5 production by activated T-cells is monitored using Elispot assays, although it is also possible to use other indicators of T cell activation or proliferation such as tritiated thymidine incorporation or production of other cytokines. Other suitable T cell assays include those disclosed in Meidenbauer et al., 2000, *Prostate* 43, 88-100; Schultes & Whiteside, 2003, *J. Immunol. Methods* 279, 1-15; and Stickler et al., 200, *J. Immunotherapy,* 23, 654-660. In a preferred embodiment, the PBMC donors used for the above-described T cell activation assays will comprise class II MHC alleles that are common in patients requiring treatment for protein responsive disorders. For example, for most diseases and disorders, it is desirable to test donors comprising all of the alleles that are prevalent in the population. However, for diseases or disorders that are linked with specific MHC alleles, it may be more appropriate to focus screening on alleles that confer susceptibility to protein responsive disorders. In a preferred embodiment, the MHC haplotype of PBMC donors or patients that raise an immune response to the wild type or protein variant are compared with the MHC haplotype of patients who do not raise a response. This data may be used to guide preclinical and clinical studies as well as aiding in identification of patients who will be especially likely to respond favorably or unfavorably to the protein therapeutic.

In an alternate preferred embodiment, immunogenicity is measured in transgenic mouse systems. For example, mice expressing fully or partially human class II MHC molecules may be used. In an alternate embodiment, immunogenicity is tested by administering the protein variants to one or more animals, including rodents and primates, and monitoring for antibody formation. Nonhuman primates with defined MHC haplotypes may be especially useful, as the sequences and hence peptide binding specificities of the MHC molecules in nonhuman primates may be very similar to the sequences and peptide binding specificities of humans. Similarly, genetically engineered mouse models expressing human MHC peptide-binding domains may be used (see for example Sonderstrup et al., 1999, *Immunol. Rev.* 172: 335-343; and Forsthuber et al., 2001, *J. Immunol.* 167: 119-125).

The biological properties of the proteins of the present invention may be characterized in cell, tissue, and whole organism experiments. As is known in the art, drugs are often tested in animals, including but not limited to mice, rats, rabbits, dogs, cats, pigs, and monkeys, in order to measure a drug's efficacy for treatment against a disease or disease model, or to measure a drug's pharmacokinetics, toxicity, and other properties. The animals may be referred to as disease models. Therapeutics are often tested in mice, including but not limited to nude mice, SCID mice, xenograft mice, and transgenic mice (including knockins and knockouts). Such experimentation may provide meaningful data for determination of the potential of the protein to be used as a therapeutic. Any organism, preferably mammals, may be used for testing. For example because of their genetic similarity to humans, monkeys can be suitable therapeutic models, and thus may be used to test the efficacy, toxicity, pharmacokinetics, or other property of the proteins of the present invention. Tests of the in humans are ultimately required for approval as drugs, and thus of course these experiments are contemplated. Thus the proteins of the present invention may be tested in humans to determine their therapeutic efficacy, toxicity, immunogenicity, pharmacokinetics, and/or other clinical properties.

In one embodiment of the present invention, a variant antibody for a host as compared to a parent antibody includes two or more amino acid substitutions derived from two or more natural antibodies. In this embodiment, a first resultant variant string in the variant antibody is rendered most homologous to a first natural antibody, a second resultant variant string in the variant antibody is rendered most homologous to the corresponding string in an second natural antibody, the substitutions are not in a CDR, and at least one resultant string is not a consensus of homologous natural sequences. In a preferred embodiment, the variant strings in the variant antibody do not include CDR residues. In a further preferred embodiment, the first and second natural antibodies are from different subfamilies.

In another embodiment of the present invention, a variant antibody for a host as compared to a parent antibody includes two or more amino acid substitutions derived from three or more natural antibodies. In this embodiment, a first resultant variant string in the variant antibody is rendered most homologous to a first natural antibody, a second resultant variant string in the variant antibody is rendered most homologous to the corresponding string in an second natural antibody, a third resultant variant string in the variant antibody is rendered most homologous to the corresponding string in an third natural antibody, the substitutions are not in a CDR, and at least one resultant string is not a consensus of homologous natural sequences. In an additional embodiment, the first, second and third natural antibodies are from different subfamilies. If a further additional embodiment, the variant antibody further comprises a fourth resultant variant string that is rendered most homologous to the corresponding string in a fourth natural antibody. If an additional embodiment, the variant antibody includes at least one substitution that is made at a position that is not surface exposed, the first, second and third natural antibodies are from different antibody groups, one of the substitutions is made at a position that is part of the VH/VL interface, and at least one amino acid substitution is not a back mutation.

In other embodiments, the first, second and third natural antibodies are from different antibody groups.

In other embodiments, the variant antibody includes at least one substitution that is not surface exposed.

In other embodiments, at least one of the substitutions is made at a position that is part of the VH/VL interface.

In other embodiments, the variant antibody includes at least one amino acid substitution is not a back mutation.

In one embodiment of the present invention, a variant antibody for a host as compared to a parent antibody includes a variant VH antibody region with host string content (HSC) greater than about 75%, and a framework region homogeneity (FRH) less than about 60%, wherein the HSC and FRH are calculated with a window size of 9.

In one embodiment of the present invention, a variant antibody for a host as compared to a parent antibody includes a variant VH antibody region with exact string content greater than about 20%; and a framework region homogeneity less than about 60%, wherein the HSC and FRH are calculated with a window size of 9.

In one embodiment of the present invention, a variant antibody for a host as compared to a parent antibody includes a variant VL antibody region with exact string content greater than about 35%, and a framework region homogeneity less than about 60%, wherein HSC and FRH are calculated with a window size of 9.

In one embodiment of the present invention, a variant antibody for a host as compared to a parent antibody includes a first set of one or more amino acid substitutions from a first natural antibody and a second set of one or more amino acid substitutions from a second natural antibody, wherein the identity of said substituted amino acids from said second antibody differ from the corresponding amino acids of said first natural antibody, the substitutions are not in a CDR, and at least one substitution is not a consensus of homologous natural sequences. In an additional embodiment, the variant antibody further includes a third set of one or more amino acids substitutions from a third natural antibody wherein the identity of the substituted amino acids of said third set differ from the identity the corresponding amino acids from said first and second sets of amino acid substitutions. In a further embodiment, the variant antibody includes a fourth set of one or more amino acids from a fourth natural antibody wherein the identity of the substituted amino acids of said fourth set differ from the identity the corresponding amino acids from said first, second and third sets of amino acid substitutions. In other embodiments, the variant antibody includes multiple sets of one or more amino acids from multiple natural antibodies, wherein the identity of the substituted amino acids of any set differ from the identity the corresponding amino acids from the other sets of amino acid substitutions.

EXAMPLES

Examples are provided below to illustrate the present invention. These examples are not meant to constrain the present invention to any particular application or theory of operation.

For reference to immunoglobulin variable regions, positions are numbered according to the Kabat numbering scheme. For reference to immunoglobulin constant regions, positions are numbered according to the EU index as in Kabat (Kabat et al., 1991, *Sequences of Proteins of Immunological Interest*, 5th Ed., United States Public Health Service, National Institutes of Health, Bethesda).

Example 1

Immunogenicity Reduction of AC10

To illustrate application of the method described in the present invention, and to validate its broad applicability to immunogenicity reduction of proteins, a xenogeneic antibody example is provided using as the parent sequence the anti-CD30 antibody AC10 (Bowen et al. Journal of Immunology, 1993, 151: 5896). A structural model of the mouse AC10 variable region was constructed using standard antibody modeling methods known in the art. FIGS. 3 and 4 show the sequences (SEQ ID NOS: 118 and 1190, host string content, and structures of the AC10 VL and VH domains (referred to as L0 AC10 VL and H0 AC10 VH respectively). A CDR graft of this antibody was constructed by placing the AC10 CDRs into the context of the frameworks of the most homologous host germlines, determined to be vlk_4-1 for VL and vh_1-3 for VH using the sequence alignment program BLAST. The sequences (SEQ ID NOS: 120 and 121) and string content of these CDR grafts are shown in FIGS. 5 and 6, along with structures of modeled AC10 highlighting the mutational differences between the CDR grafted AC10 variable chains and WT.

Figure 7B-16:
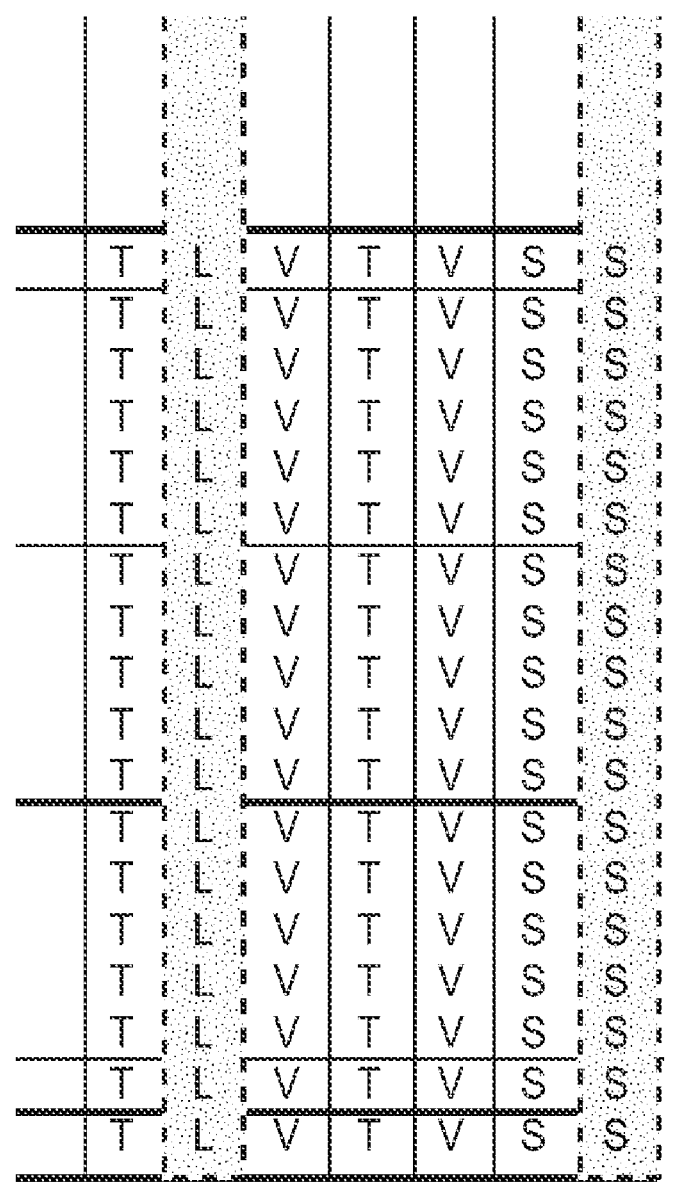

AC10 variants with reduced immunogenicity were generated by applying a string optimization algorithm on the WT AC10 VL and VH sequences. This algorithm heuristically samples multiple amino acid mutations that exist in the diversity of the human VLκ and VH germline sequences, and calculates the host string content (HSC) of each sequence according to Equation 3 described above, using a window size w=9. In this set of calculations, residues in the CDRs and close to a CDR or to the VL/VH interface were masked, that is were not allowed to mutate. CDRs were defined as a slightly smaller set of residues than the CDRs defined by Chothia (Chothia & Lesk, 1987, *J. Mol. Biol.* 196: 901-917; Chothia et al., 1989, *Nature* 342: 877-883; Al-Lazikani et al., 1997, *J. Mol. Biol.* 273: 927-948). For the purposes of the present invention, VL CDRs are herein defined to include residues at positions 27-32 (CDR1), 50-56 (CDR2), and 91-97 (CDR3), wherein the numbering is according to Chothia. Because the VL CDRs as defined by Chothia and Kabat are identical, the numbering of these VL CDR positions is also according to Kabat. For the purposes of the present invention, VH CDRs are herein defined to include residues at positions 27-33 (CDR1), 52-56 (CDR2), and 95-102 (CDR3), wherein the numbering is according to Chothia. These VH CDR positions correspond to Kabat positions 27-35 (CDR1), 52-56 (CDR2), and 95-102 (CDR3). Masked residues in these calculations were set at positions 1-4, 25-34, 36, 38, 43, 44, 46, 48-58, 60, 63-69, 71, 87, and 89-98 for VL, and 2, 4, 24, 26-35, 37, 39, 44, 45, 47, 50-58, 60, 61, 71, 73, 76, 78, 91, and 93-106 for VH, wherein the numbering is according to Kabat. Masking of potentially critical residues is a conservative approach to generating more host antibody variants, however it is but one embodiment of the present invention, and calculations wherein positions are not masked are also contemplated. This calculation was run for AC10 VL and VH in 100 separate interactions, generating a set of diverse AC10 variants with more host string content than WT. FIG. 7 shows the clustered nonredundant set of output sequences from these calculations for the AC10 VL and VH region (SEQ ID NOS:122-217), referred to as AC10 VL HSC Calculation 1 and AC10 VH HSC Calculation 1 respecitvely. For each iteration (Iter), the HSC (Equation 3), HSS (Equation 5), and number (Mut) and identity (shaded residues) of mutations from WT are presented. In addition to the HSC score, each sequence was evaluated for its structural and functional integrity using a nearest neighbor structure-based scoring method (U.S. Ser. No. 60/528,229, filed Dec. 8, 2003, entitled Protein Engineering with Analogous Contact Environments). Two measures of structural fitness, referred to as "Structural Consensus" and "Structural Precedence", are also provided in the FIG. 7. Although the Analogous Contact Environments method is particularly well-suited for antibodies because of the wealth of sequence and structure information, any structure-based and/or sequence-based scoring method may be used to evaluate the structural and functional fitness of the variant sequences. The output sequences were clustered based on their mutational distance from the other sequences in the set, and these clusters are delineated by the horizontal black lines in the Figure. The "Cluster" column provides the quantitative mutational distance between each sequence and the rest of the sequences in its cluster; sequences with a lower cluster value are more representative of that particular sequence cluster.

These calculations were used to generate a set of AC10 VL and VH variants. In some cases, further substitutions were made to output sequences, using string and structural scores, as well as visual inspection of the modeled AC10 structure, to evaluate fitness. FIGS. 8-13 present the sequences (SEQ ID NOS: 218-223), host string content, and mapped mutational differences on the modeled AC10 structure for each of the AC10 VL and VH variants. Iteration 36 from AC10 VL HSC calculation 1 served as the precursor for L1 AC10 VL, iteration 37 served as the precursor for L2 AC10 VL, and iteration 3 served as the precursor for L3 AC10 VL. Iteration 15 from AC10 VH HSC calculation 1 served as the precursor for H1 AC10 HL, iteration 55 served as the precursor for H2 AC10 VH, and iteration 18 served as the precursor for H3 AC10 VH.

Tables 1 and 2 present the number of mutations from the parent sequence, structural fitness scores, and host string scores for the AC10 VL and VH variants as compared to the WT and CDR grafted AC10 sequences. In addition to the aforementioned structural and host string analysis, each sequence was analyzed for its global homology to the host germline. The maximum identity match to the germline for each string in the sequences was also determined, referred to as $N_{ID}$max. This represents the total number of strings in each sequence whose maximum identity to the corresponding strings in the host germline is the indicated value. For w=9, Tables 1 and 2 list $N_9$max, $N_8$max, $N_7$max, and $N_{\leq 6}$max for each sequence. $N_9$max represents the number of strings in the sequence for which 9 of 9 residues match at least one string in the host germline, $N_8$max represents the number of strings for which 8 of 9 residues match at least one string in the host germline, $N_7$max represents the number of strings for which 7 of 9 residues match at least one string in the host germline, and $N_{\leq 8}$max represents the number of strings for which 6 or less residues of 9 residues match at least one string in the host germline. This last category (ID$\leq$6) could, for example, be regarded as the number of poorly scoring strings. In addition to the aforementioned structural and host string analysis, each sequence was analyzed for its global homology to the host germline; Tables 1 and 2 present the most homologous human germline sequence for each sequence (Closest Germline) and corresponding identity to that germline (ID to Closest Germline), determined using the sequence alignment program BLAST. Finally, the Framework region homogeneity (FRH) of each variant was evaluated for w=9, and is presented in Tables 1 and 2, providing the extent to which the host string content of each variant is derived from a single germline as opposed to multiple germline sequences.

TABLE 1

AC10 VL Variants

|  | WT | CDR Graft | L1 | L2 | L3 |
|---|---|---|---|---|---|
| Mutations |  | 18 | 15 | 16 | 9 |
| Structural Consensus | 0.57 | 0.57 | 0.59 | 0.64 | 0.56 |
| Structural Precedence | 0.68 | 0.57 | 0.66 | 0.67 | 0.58 |
| Human String Content | 0.78 | 0.88 | 0.86 | 0.86 | 0.85 |
| Human String Similarity | 0.15 | 0.57 | 0.48 | 0.46 | 0.41 |
| Framework Region Homogeneity | 0.60 | 0.97 | 0.73 | 0.81 | 0.52 |
| $N_9$max | 15 | 61 | 51 | 48 | 42 |
| $N_8$max | 27 | 11 | 13 | 15 | 21 |
| $N_7$max | 31 | 15 | 21 | 22 | 20 |
| $N_{\leq 6}$max | 34 | 20 | 22 | 22 | 24 |
| Closest Germline | 4-1 | 4-1 | 3-11 | 1-39 | 4-1 |
| ID to Closest Germline | 68/101 67% | 86/101 85% | 78/99 79% | 80/99 81% | 75/101 74% |

TABLE 2

AC10 VH Variants

|  | WT | CDR Graft | H1 | H2 | H3 |
|---|---|---|---|---|---|
| Mutations |  | 26 | 16 | 23 | 20 |
| Structural Consensus | 0.49 | 0.48 | 0.48 | 0.50 | 0.47 |
| Structural Precedence | 0.63 | 0.67 | 0.63 | 0.59 | 0.59 |
| Human String Content | 0.69 | 0.87 | 0.81 | 0.81 | 0.80 |
| Human String Similarity | 0.07 | 0.68 | 0.41 | 0.39 | 0.38 |

TABLE 2-continued

| | AC10 VH Variants | | | | |
|---|---|---|---|---|---|
| | WT | CDR Graft | H1 | H2 | H3 |
| Framework Region Homogeneity | 0.60 | 0.86 | 0.65 | 0.47 | 0.55 |
| $N_9$max | 5 | 81 | 48 | 45 | 44 |
| $N_8$max | 31 | 13 | 30 | 32 | 28 |
| $N_7$max | 34 | 8 | 20 | 21 | 24 |
| $N_{\leq 6}$max | 49 | 17 | 21 | 21 | 23 |
| Closest Germline | 1-3 | 1-3 | 1-3 | 1-3 | 7-4-1 |
| ID to Closest Germline | 69/98 70% | 93/98 95% | 83/98 85% | 72/98 73% | 76/98 78% |

An important observation is that, whereas the CDR grafted antibodies are most homologous to a single human germline sequence (the "acceptor" sequence in humanization terminology), the present invention describes variants that are homologous to different host germline sequences in different regions of the sequence. This is evident from the significant differences in Framework region homogeneity (FRH) scores for the AC10 variants of the present invention and CDR grafted AC10 variants. Furthermore, whereas CDR grafted AC10 VL and VH are most homologous to human germline subfamilies 4 (VL) and 1 (VH) respectively across their entire sequences, a number of the AC10 variants are most homologous to different subfamilies in different frameworks. Additionally, whereas the CDR grafted antibodies are most homologous to a single germline sequence that is also the most homologous sequence to the parent sequence, the present invention presents a set of antibodies for a given antibody that are most homologous to different human germline sequences, which need not be the most homologous germline sequence to WT. For example, Table 1 shows that CDR grafted AC10 VL is most homologous to 4-1, which is also the most homologous human germline to the WT AC10 parent. However L1, L2, and L3 are most homologous to three different human germlines –3-11, 1-39, and 4-1 respectively. Thus the variants of the present invention explore a substantially greater amount of diversity than CDR grafted antibodies. One obvious advantage of this is that the method of the present invention provides a greater chance of success with respect to antigen affinity. The choice of an "acceptor" in humanization methods places a single bet; if the donor CDRs are in fact incompatible with the acceptor FRs, a set of back-mutations that regain WT affinity may not exist. In contrast, the method of the present invention enables a greater diversity of sequence and structure space to be sampled in the immunogenicity reduction process, increasing the chances of obtaining a final less immunogenic version with WT affinity or better. An additional advantage of sampling greater sequence diversity is that some sequences may have more optimal properties than others, for example with regard to stability, solubility, and effector function. For example, as disclosed in U.S. Ser. No. 60/614,944, and U.S. Ser. No. 60/619,409, filed Oct. 14, 2004, entitled "Immunoglobulin Variants Outside the Fc Region with Optimized Effector Function", the variable region of an antibody may impact effector functions such as antibody dependent cell-mediated cytotoxicity (ADCC), antibody dependent cell-mediated phagocytosis (ADCP), and complement dependent cytotoxicity (CDC).

The genes for the variable regions of AC10 WT (L0 and H0) and variants (L1, L2, L3, H1, H2, and H3) were constructed using recursive PCR, and subcloned into a the mammalian expression vector pcDNA3.1Zeo (Invitrogen) comprising the full length light kappa (CLκ) and heavy chain IgG1 constant regions. All sequences were sequenced to confirm the fidelity of the sequence. Plasmids containing heavy chain gene (VH-CH1-CH2-CH3) (wild-type or variants) were co-transfected with plasmid containing light chain gene (VL-CLκ) in all combinations (L0/H0, L0/H1, L0/H2, L0/H3, L1/H0, L1/H1, L1/H2, L1/H3, L2/H0, L2/H1, L2/H2, L2/H3, L3/H0, L3/H1, L3/H2, L3/H3) into 293T cells. Here, for example, L2/H3 refers to the L2 AC10 VL paired with H3 AC10 VH. Media were harvested 5 days after transfection, and antibodies were purified from the supernatant using protein A affinity chromatography (Pierce, Catalog #20334).

Figure 14A:
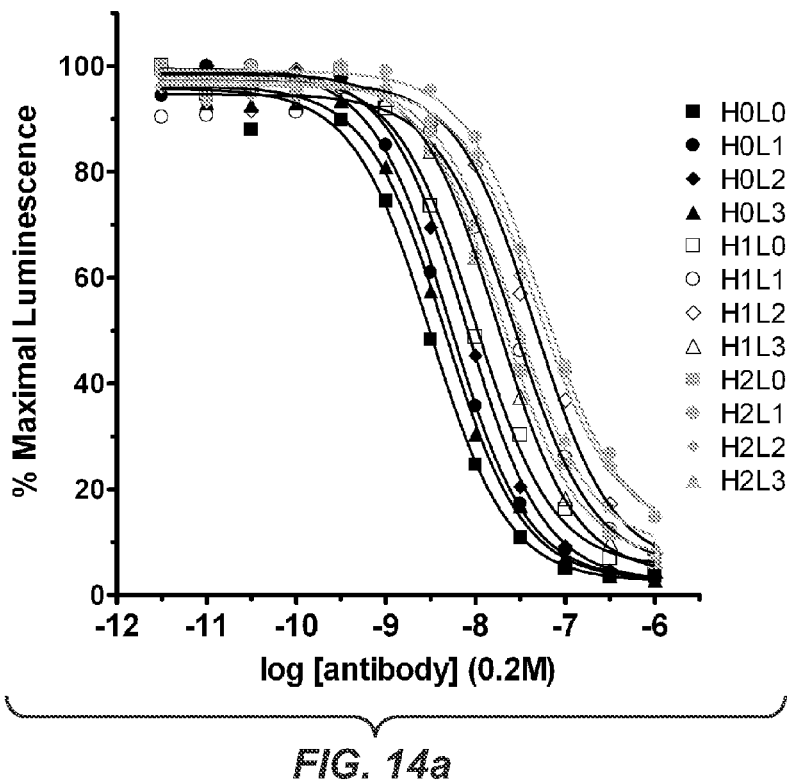
FIG. 14. AlphaScreen™ assay measuring binding between AC10 variants and the target antigen CD30. In the presence of competitor variant antibody, a characteristic inhibition curve is observed as a decrease in luminescence signal. The binding data were normalized to the maximum and minimum luminescence signal for each particular curve, provided by the baselines at low and high antibody concentrations respectively. The curves represent the fits of the data to a one site competition model using nonlinear regression, and the fits provide IC50s for each antibody.
Figure 14B:
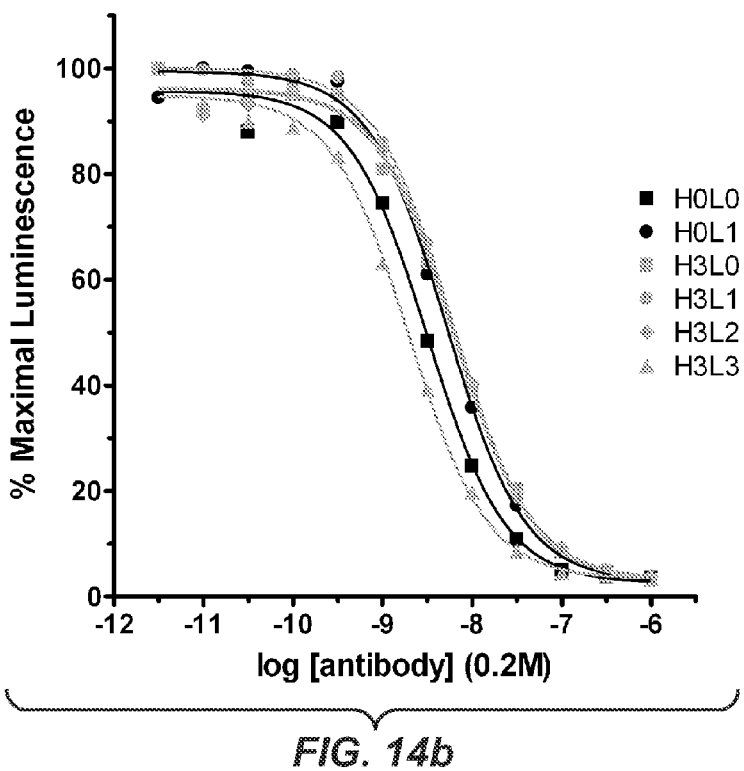

WT and variant antibodies were experimentally tested for their capacity to bind CD30 antigen. Binding affinity to human CD30 by the AC10 WT and variant antibodies was measured using a quantitative and extremely sensitive method, AlphaScreen™ assay. The AlphaScreen™ assay is a bead-based non-radioactive luminescent proximity assay. Laser excitation of a donor bead excites oxygen, which if sufficiently close to the acceptor bead will generate a cascade of chemiluminescent events, ultimately leading to fluorescence emission at 520-620 nm. The AlphaScreen™ assay was applied as a competition assay for screening the antibodies. WT AC10 antibody was biotinylated by standard methods for attachment to streptavidin donor beads (Perkin Elmer). Commercial CD30 was conjugated to digoxigenin (DIG) (Roche Diagnostics) for attachment to anti-DIG acceptor beads (Perkin Elmer). In the absence of competing AC10 variants, WT antibody and CD30 interact and produce a signal at 520-620 nm. Addition of untagged AC10 variant competes with the WT AC10/CD30 interaction, reducing fluorescence quantitatively to enable determination of relative binding affinities. FIGS. 14a and 14b show binding of WT (H0L0) and AC10 variant antibodies to CD30 using the AlphaScreen™ assay. The data were fit to a one site competition model using nonlinear regression, and these fits are represented by the curves in the figure. These fits provide the inhibitory concentration 50% (IC50) (i.e. the concentration required for 50% inhibition) for each antibody, thus enabling the relative binding affinities relative to WT to be determined. Table 3 provides the IC50's and Fold IC50's relative to WT for fits to these binding curves. The AC10 variants display an array of CD30 binding affinities, with a number of variants binding CD30 with affinity comparable to or better affinity than WT AC10.

Figure 15:
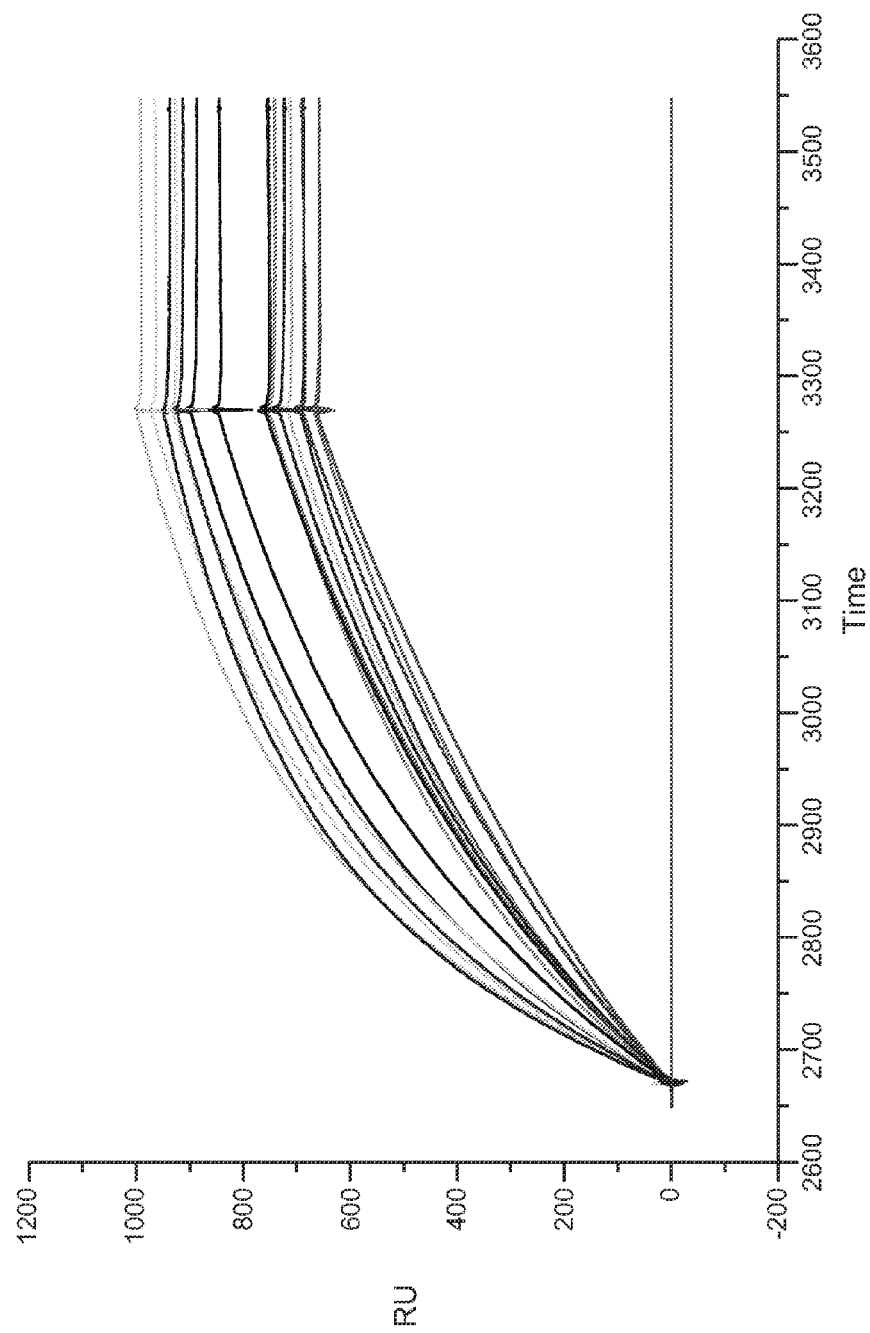
FIG. 15.

Antigen affinity of the AC10 variants was also measured using Surface Plasmon Resonance (SPR) (Biacore, Uppsala, Sweden). SPR allows for the measurement of direct binding rates and affinities of protein-protein interactions, and thus provides an excellent complementary binding assay to the AlphaScreen™ assay. CD30 fused to the Fc region of IgG1 (R&D Systems) was immobilized on a Protein A SPR chip, the surface was blocked with Fc, and WT and variant AC10 antibodies were flowed over the chip at a range of concentrations. The resulting sensorgrams are shown in FIG. 15. Global Langmuir fits were carried out for the concentrations series using the BiaEvaluation curve fitting software, providing the on-rate constant (ka), off-rate constant (kd), and equilibrium binding constant (KD=kd/ka) for the curves. Table 3 provides the KDs and Fold KDs relative to WT for the SPR data. The excellent agreement between the rank ordering of the variants as determined by SPR and AlphaScreen™ assay support the accuracy of the data.

TABLE 3

CD30 Binding of AC10 Variants

| AC10 Variant | SPR KD (nM) | SPR Fold KD | AlphaScreen IC50 (nM) | AlphaScreen Fold IC50 |
|---|---|---|---|---|
| H2L1 | 9.49 | 0.36 | 55.1 | 0.06 |
| H2L2 | 5.95 | 0.57 | 49.2 | 0.06 |
| H1L2 | 7.55 | 0.45 | 45.3 | 0.07 |
| H1L1 | 5.63 | 0.60 | 27.7 | 0.11 |
| H2L3 | 6.75 | 0.50 | 27.2 | 0.12 |
| H2L0 | 8.00 | 0.42 | 19.4 | 0.16 |
| H1L3 | 5.09 | 0.67 | 17.4 | 0.18 |
| H1L0 | 6.39 | 0.53 | 9.77 | 0.32 |
| H0L2 | 3.48 | 0.97 | 7.81 | 0.41 |
| H3L2 | 2.86 | 1.19 | 6.57 | 0.48 |
| H3L0 | 3.08 | 1.10 | 6.18 | 0.51 |
| H3L1 | 2.44 | 1.39 | 6.09 | 0.52 |
| H0L1 | 3.29 | 1.03 | 5.19 | 0.61 |
| H0L3 | 3.00 | 1.13 | 4.61 | 0.69 |
| H0L0 | 3.39 | 1.00 | 3.18 | 1.00 |
| H3L3 | 2.33 | 1.45 | 1.99 | 1.59 |

In addition to assessing the antigen affinity and biophysical properties of the variants of the present invention, they may also be tested for effector functions in the context of a full length antibody. One advantage of generating multiple reduced immunogenicity variants of a parent immunoglobulin is that it enables a greater degree of sequence diversity to be sampled, diversity which may provide optimal properties. Some sequences may have more optimal properties than others, for example with regard to effector function. For example, as disclosed in U.S. Ser. No. 60/614,944, and U.S. Ser. No. 60/619,409, filed Oct. 14, 2004, entitled "Immunoglobulin Variants Outside the Fc Region with Optimized Effector Function", the variable region of an antibody may impact effector functions such as antibody dependent cell-mediated cytotoxicity (ADCC), antibody dependent cell-mediated phagocytosis (ADCP), and complement dependent cytotoxicity (CDC).

Figure 16A:
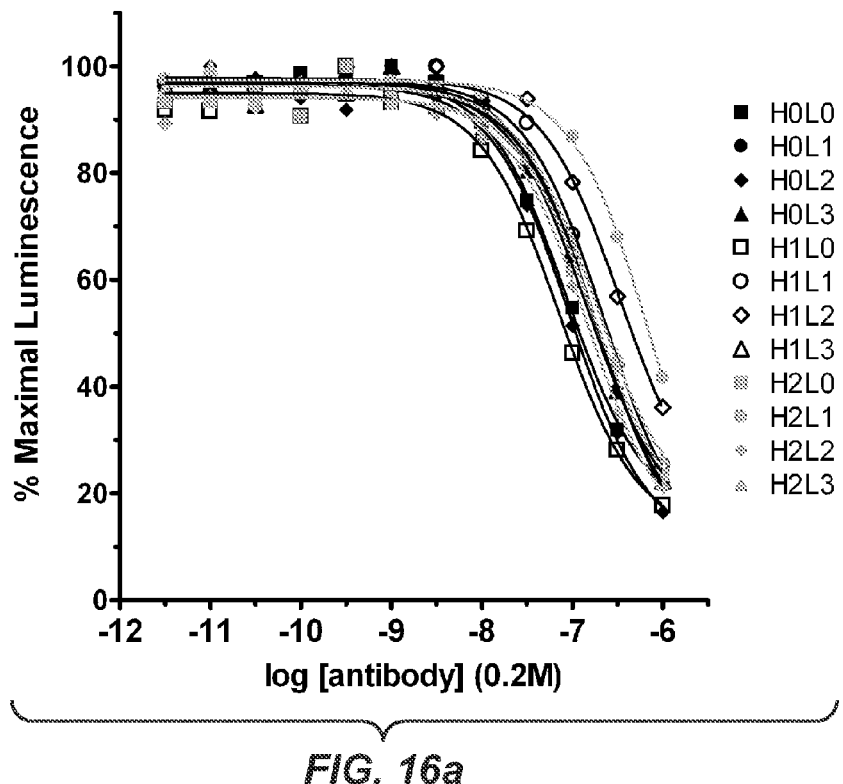
FIG. 16. AlphaScreen™ assay measuring binding between AC10 variants and human V158 FcγRIIIa.
Figure 16B:
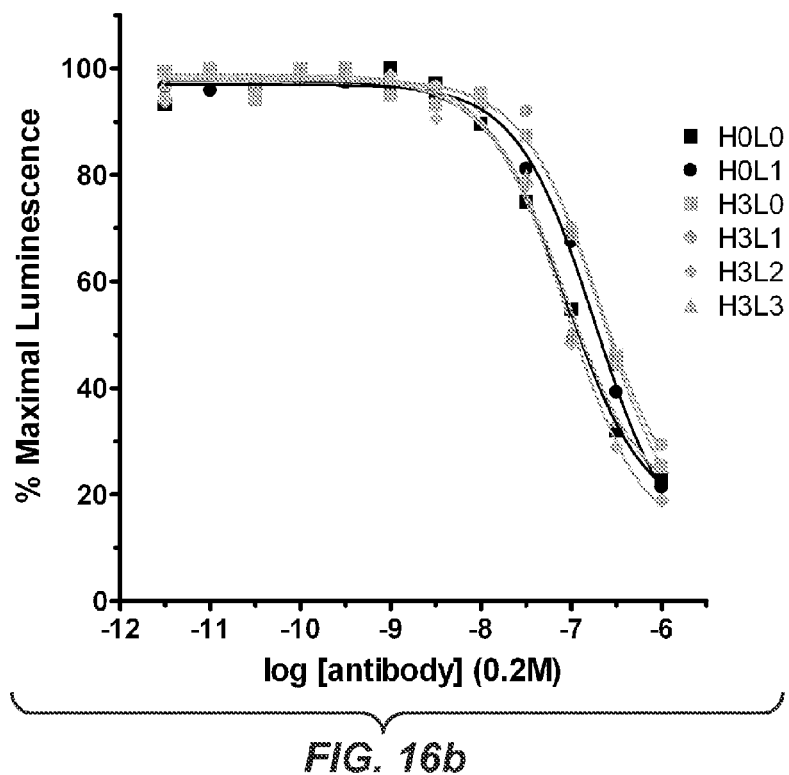

In order to explore any differences in capacity to mediate effector function, the affinities of the AC10 variants for FcγRIIIa were measured using the AlphaScreen™ assay. The extracellular region of human V158 FcγRIIIa was obtained by PCR from a clone obtained from the Mammalian Gene Collection (MGC:22630), and the receptor was fused with glutathione S-Transferase (GST) to enable screening. Tagged FcγRIIIa was transfected in 293T cells, and media containing secreted FcγRIIIa were harvested and purified. The AlphaScreen™ assay was applied as a competition assay for screening AC10 variants for binding to FcγRIIIa. Biotinylated WT AC10 antibody was bound to streptavidin donor beads (Perkin Elmer), and GST-fused human V158 FcγRIIIa was bound to anti-GST acceptor beads (Perkin Elmer). The binding data are shown in FIGS. 16a and 16b, and the resulting IC50's and Fold IC50's relative to WT are provided in Table 4. FcγRIIIa affinity of the AC10 variants was also measured using SPR. GST-fused human FcγRIIIa (V158 isoform) was immobilized on a chip, and WT and variant AC10 antibodies were flowed over the chip at a range of concentrations. Binding constants were obtained from fitting the data using standard curve-fitting methods. The equilibrium dissociation constants (KDs) obtained from the fits to these binding curves, and the calculated fold improvement or reduction relative to WT (Fold KD) are shown in Table 4.

TABLE 4

FcγRIIIa Binding of AC10 Variants

| AC10 Variant | SPR KD (nM) | SPR Fold KD | AlphaScreen IC50 (nM) | AlphaScreen Fold IC50 |
|---|---|---|---|---|
| H2L1 | 14.9 | 1.25 | 751 | 0.12 |
| H2L2 | 4.01 | 4.64 | 146 | 0.60 |
| H1L2 | 1.6.6 | 1.12 | 340 | 0.26 |
| H1L1 | 11.2 | 1.66 | 221 | 0.39 |
| H2L3 | 3.52 | 5.28 | 183 | 0.48 |
| H2L0 | 12.9 | 1.44 | 175 | 0.50 |
| H1L3 | 11.2 | 1.66 | 178 | 0.49 |
| H1L0 | 22.0 | 0.85 | 71.6 | 1.22 |
| H0L2 | 9.09 | 2.05 | 93.8 | 0.93 |
| H3L2 | 3.57 | 5.21 | 88.7 | 0.98 |
| H3L0 | 20.0 | 0.93 | 216 | 0.40 |
| H3L1 | 17.4 | 1.07 | 209 | 0.42 |
| H0L1 | 11.6 | 1.60 | 183 | 0.48 |
| H0L3 | 12.7 | 1.46 | 146 | 0.60 |
| H0L0 | 18.6 | 1.00 | 87.2 | 1.00 |
| H3L3 | 6.13 | 3.03 | 83.5 | 1.04 |

Figure 17A:
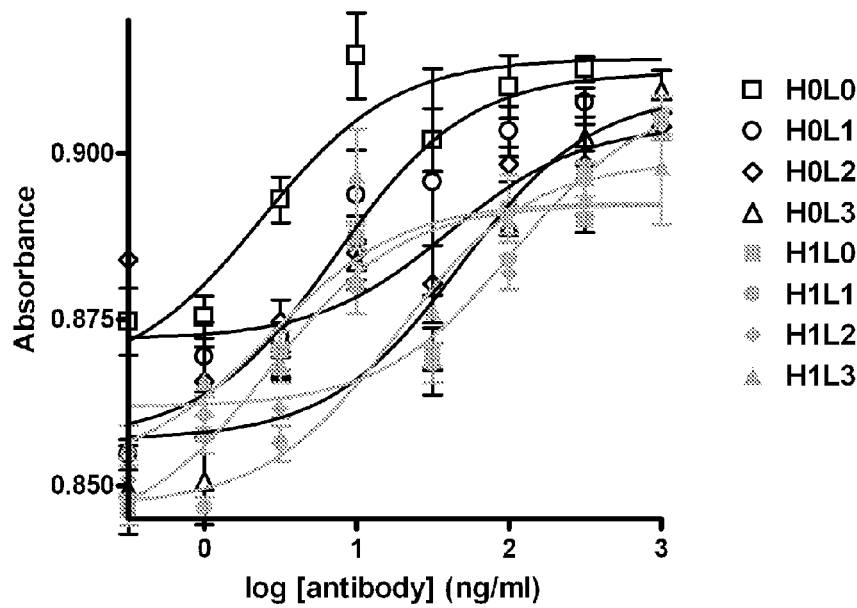
FIG. 17. Cell-based ADCC assay of WT and AC10 variants. Purified human peripheral blood monocytes (PBMCs) were used as effector cells, L540 Hodgkin's lymphoma cells were used as target cells, and lysis was monitored by measuring LDH activity using the Cytotoxicity Detection Kit (LDH, Roche Diagnostic Corporation, Indianapolis, Ind.). Samples were run in triplicate to provide error estimates (n=3, +/−S.D.).
Figure 17B:
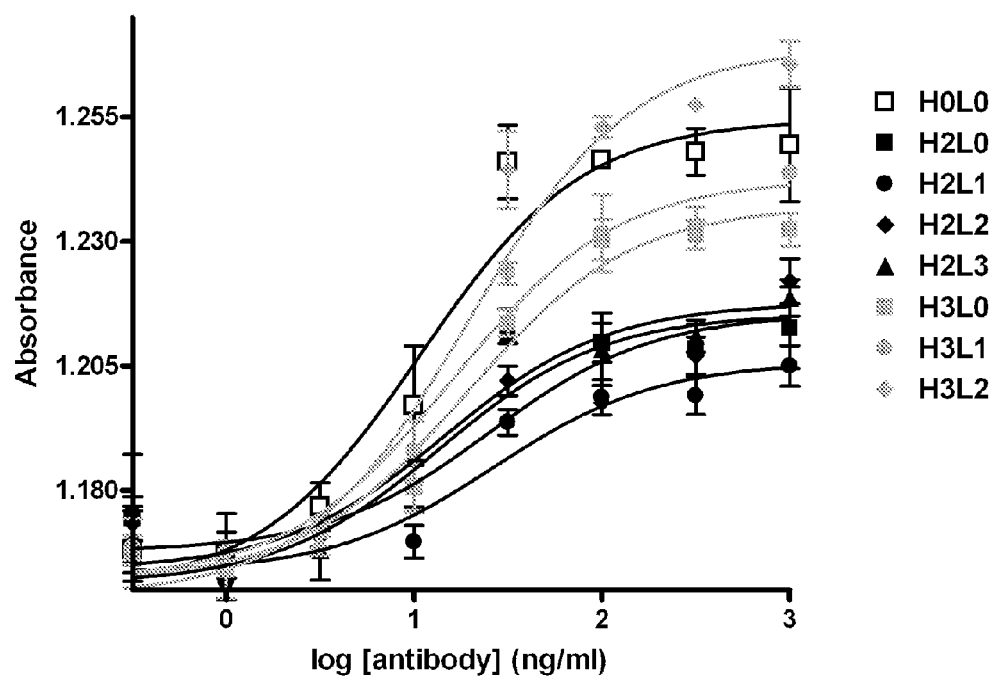
Figure 17C:
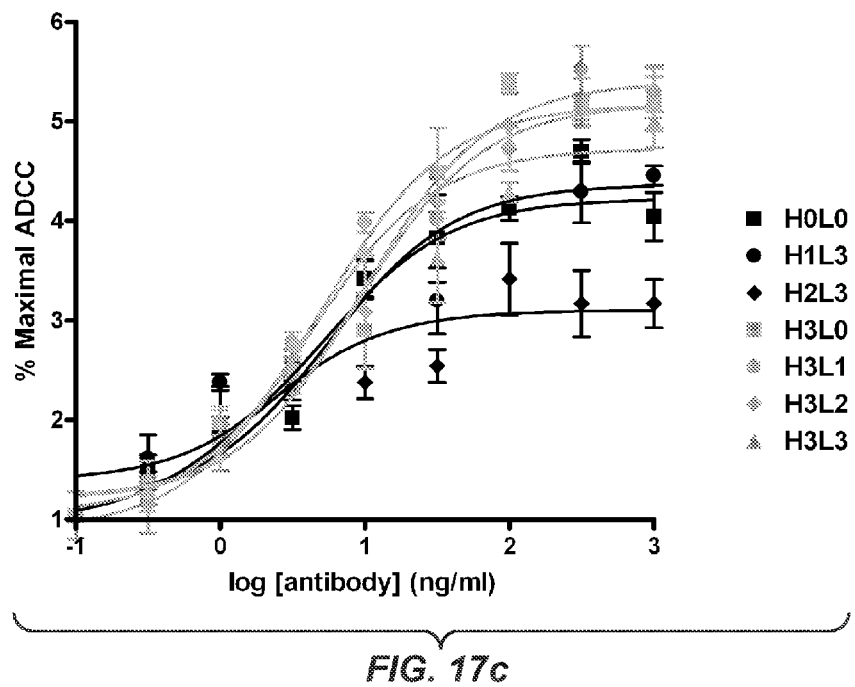

To assess the capacity of the AC10 variants to mediate effector function against CD30 expressing cells, the AC10 variants were tested in a cell-based ADCC assay. Human peripheral blood monocytes (PBMCs) were isolated from buffy-coat and used as effector cells, and CD30 positive L540 Hodgkin's lymphoma cells were used as target cells. L540 target cells were seeded at 20,000 per well in 96-well plates and treated with designated antibodies in triplicates starting at 1 μg/ml and in reduced concentrations in ½ log steps. PBMCs isolated using a Ficoll gradient and allotyped as FcγRIIIa 158 V/F were added at 25-fold excess of L540 cells and co-cultured for 4 hrs before processing for LDH activity using the Cytotoxicity Detection Kit (LDH, Roche Diagnostic Corporation, Indianapolis, Ind.) according to the manufacturer's instructions. The plates were read using a Wallac 1420 Victor$^2$. FIGS. 17a-17c show the results. The graphs show that the antibodies differ not only in their EC50, reflecting their relative potency, but also in the maximal level of ADCC attainable by the antibodies at saturating concentrations, reflecting their relative efficacy. These two terms, potency and efficacy, are sometimes used loosely to refer to desired clinical properties. In the current experimental context, however, they are denoted as specific quantities, and therefore are here explicitly defined. By "potency" as used in the current experimental context is meant the EC50 of an EGFR targeting protein. By "efficacy" as used in the current experimental context is meant the maximal possible effector function of an antibody at saturating levels. Differences in capacity to mediate ADCC may be due to differences in antigen affinity, different capacities of the variant variable regions to effect FcγR binding, or both. Regardless, the contribution of an antibody variable region to FcγR binding and effector function may be an important parameter for selecting a clinical candidate. The choice of an antibody clinical candidate based in whole or in part on the impact on effector function of the variable region represents a novel dimension in antibody therapeutics.

Figure 18A:
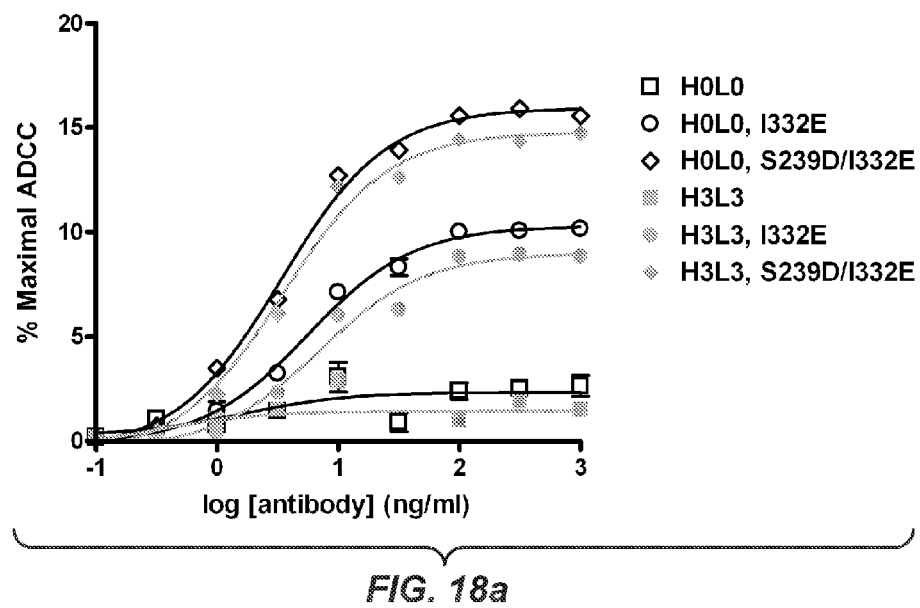
FIG. 18. Cell-based assay measuring ADCC capacity of WT (H0/L0) and H3/L3 AC10 antibodies comprising Fc variants that provide enhanced effector function. Raw data were normalized to a percentage scale of maximal cytotoxicity determined by Triton-X100 lysis of target cells.
Figure 18B:
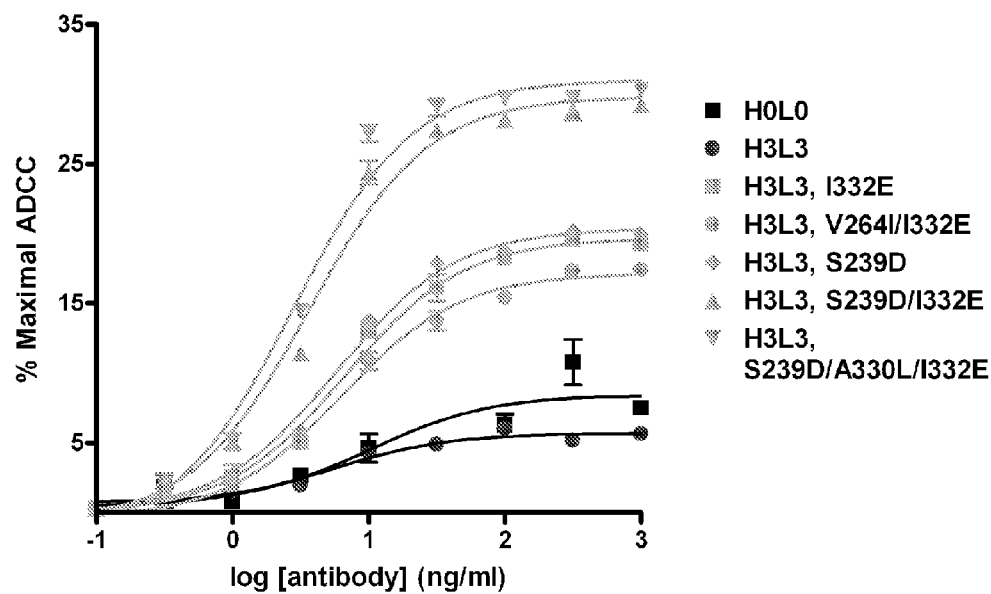
Figure 19:
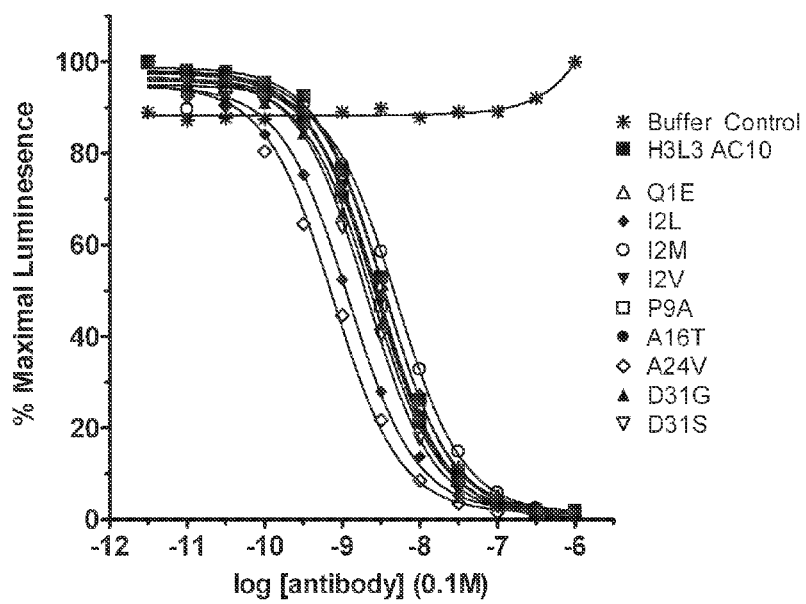
FIG. 19. AlphaScreen™ assay measuring binding between select H3L3 secondary AC10 variants and the target antigen CD30.

Based on the CD30 binding, FcγRIIIa binding, and ADCC results, the H3/L3 AC10 variant was chosen as a potential biotherapeutic candidate. Because this antibody is intended for clinical use as an anti-cancer therapeutic, it may be advantageous to optimize its effector function. As previously described, substitutions can be engineered in the constant region of an antibody to provide favorable clinical properties. In a most preferred embodiment, one or more amino acid modifications that provide optimized binding to FcγRs and/or enhanced effector function described in U.S. Ser. No. 10/672,280, PCT US03/30249, and U.S. Ser. No. 10/822,231, and U.S. Ser. No. 60/627,774, filed Nov. 12, 2004 and entitled "Optimized Fc Variants", are combined with the AC10 variants of the present invention. A number of optimized Fc variants obtained from these studies, including I332E, S239D, V264I/I332E, S239D/I332E, and S239D/A330L/I332E, were constructed in the H0/L0 and H3/L0 AC10 antibodies using quick change mutagenesis (Stratagene). Antibodies were expressed and purified as described above. FIGS. 18a and 18b show the results of the ADCC assay, carried out as described above, comparing WT (H0/L0) and H3/L3 AC10 in combination with the optimized Fc variants. Considerable enhancements in potency and efficacy are observed for the Fc variant antibodies as compared to H0/L0 and H3/L3 AC10.

As described above, because variant sequences of the invention are preferably derived from a HSC-increasing procedure in which substitution of structurally important positions is disallowed (or discouraged), it is likely that additional optimization of HSC is possible if those positions are allowed to vary in a secondary analysis. It is noted that, due to residue masking, mutations in the variants occur distal to the CDRs and VL/VH interface. This is in contrast to CDR grafted antibodies, which have mutations in the parent that are at or near these critical regions and thus have a significantly greater potential for perturbing antigen affinity. This is corroborated by the fact that CDR grafted antibodies typically require backmutations to the donor sequence to regain WT affinity for antigen. Such backmutations are usually made out of structural and immunogenic context with respect to host sequences, and cause dramatic reductions in the host string content of the final variant. In contrast, the variants presented herein are simultaneously optimized for host string and structural fitness within the same context, and no backmutations need be made. Nonetheless, one or more subsequent substitutions may be explored to increase antigen affinity or further improve HSC, for example by mutating residues that were masked in the calculations and/or residues in or close to the CDRs or VL/VH interface. Thus the H3/L3 variant can be thought of as a primary variant or template for further optimization, and variants of H3/L3 can be thought of as secondary variants. In contrast to backmutating as with CDR grafted antibodies, secondary substitutions in the variants of the present invention will comprise forward or neutral mutations with respect to the host germline, and thus are expected to only improve or unaffected HSC. An additional benefit of generating secondary variants is that, by exploring quality structural and string diversity, it is also possible that other properties can be optimized, for example affinity, activity, specificity, solubility, expression level, and effector function.

String analysis was carried out on the H3/L3 sequence to design a set of secondary substitutions that have neutral, positive, or minimal impact on HSC, and/or that have significant potential for optimization of antigen affinity and/or effector function. Table 5 provides this set of 70 VL (Table 5a) and 64 VH (Table 5b) single mutations. The H3 column provides the WT H3 amino acid, and the Sub column provides the designed substitution. Positions are numbered according to the Kabat numbering format, with Kabat CDR positions bolded. The provided string impact, defined according to Equation 7, describes the difference in HSC between the primary variant sequence, here H3/L3, and the secondary variant sequence.

TABLE 5a

L3 AC10 Secondary Variants

| Variant | Pos (Kabat) | L3 | Sub | String Impact | Fold Prot A | Fold CD30 | Fold FcYRIIIa |
|---|---|---|---|---|---|---|---|
| L3.1 | 1 | D | A | 0 | 0.89 | 1.30 | 0.96 |
| L3.2 | 1 | D | E | 1 | 1.09 | 1.24 | 1.46 |
| L3.3 | 1 | D | N | 0 | 1.24 | 1.66 | 1.35 |
| L3.4 | 1 | D | S | 0 | 0.97 | 1.04 | 1.18 |
| L3.5 | 3 | V | Q | 0 | 1.13 | 1.32 | 1.32 |
| L3.6 | 4 | L | M | 4 | 1.65 | 1.64 | 1.21 |
| L3.7 | 25 | A | S | 6 | | | |
| L3.8 | 27a | S | D | 0 | 1.02 | 0.94 | 0.61 |
| L3.9 | 27b | V | I | 1 | 1.04 | 0.58 | 0.81 |
| L3.10 | 27c | D | L | 5 | | | |
| L3.11 | 27c | D | S | 8 | | | |
| L3.12 | 27c | D | V | 3 | 1.24 | 1.15 | 1.19 |
| L3.13 | 27d | F | D | 0 | 1.07 | 0.32 | 0.98 |
| L3.14 | 27d | F | H | 4 | 0.86 | 0.08 | 0.93 |
| L3.15 | 27d | F | Y | 5 | 1.04 | 0.63 | 1.19 |
| L3.16 | 28 | D | N | −1 | 1.10 | 1.61 | 1.18 |
| L3.17 | 30 | D | K | 4 | 1.01 | 1.21 | 1.24 |
| L3.18 | 30 | D | N | 6 | 1.09 | 1.45 | 0.94 |
| L3.19 | 30 | D | S | 4 | 1.07 | 1.13 | 0.82 |
| L3.20 | 30 | D | Y | 0 | 0.82 | 0.78 | 0.73 |
| L3.21 | 31 | S | D | 0 | 1.01 | 0.81 | 0.95 |
| L3.22 | 31 | S | T | 3 | 1.03 | 0.46 | 0.97 |
| L3.23 | 31 | S | N | −1 | 1.03 | 0.71 | 1.00 |
| L3.24 | 32 | Y | D | 0 | 1.31 | 0.46 | 1.33 |
| L3.25 | 33 | M | L | 8 | 1.38 | 1.36 | 1.37 |
| L3.26 | 34 | N | S | 0 | | | |
| L3.27 | 34 | N | A | −1 | 1.39 | 0.38 | 1.36 |
| L3.28 | 34 | N | D | −6 | 1.19 | 0.41 | 1.76 |
| L3.29 | 46 | V | H | 4 | 0.06 | 0.03 | 0.11 |
| L3.30 | 46 | V | L | 9 | 0.86 | 0.39 | 0.75 |
| L3.31 | 46 | V | R | 4 | | | |
| L3.32 | 46 | V | S | 4 | 1.05 | 0.32 | 0.90 |
| L3.33 | 50 | A | D | 6 | 0.98 | 0.26 | 0.66 |
| L3.34 | 50 | A | S | 5 | 1.01 | 0.47 | 1.20 |
| L3.35 | 50 | A | W | 2 | | | |
| L3.36 | 53 | N | S | 8 | | | |
| L3.37 | 53 | N | T | 5 | 0.99 | 1.26 | 1.01 |
| L3.38 | 54 | L | R | 1 | 1.19 | 1.46 | 1.55 |
| L3.39 | 55 | E | A | 2 | 1.01 | 0.85 | 1.32 |
| L3.40 | 55 | E | Q | 6 | 0.99 | 0.87 | 1.07 |
| L3.41 | 56 | S | T | 8 | 1.50 | 1.80 | 1.23 |
| L3.42 | 58 | I | V | 4 | 1.44 | 1.55 | 0.95 |
| L3.43 | 60 | A | D | 1 | 1.11 | 1.16 | 1.08 |
| L3.44 | 60 | A | S | 2 | 0.82 | 1.08 | 0.85 |
| L3.45 | 67 | S | P | 0 | | | |
| L3.46 | 89 | Q | H | 1 | 1.37 | 0.08 | 1.64 |
| L3.47 | 91 | S | A | 8 | | | |
| L3.48 | 91 | S | G | 9 | 0.85 | 0.29 | 0.80 |
| L3.49 | 91 | S | H | 2 | 1.20 | 0.01 | 1.32 |
| L3.50 | 91 | S | L | 8 | 1.10 | 0.02 | 1.59 |
| L3.51 | 91 | S | Y | 8 | 1.00 | 0.02 | 1.50 |
| L3.52 | 92 | N | I | 3 | | | |
| L3.53 | 92 | N | S | 2 | 3.02 | 0.48 | 1.34 |
| L3.54 | 92 | N | Y | 8 | 1.39 | 0.96 | 1.05 |
| L3.55 | 93 | E | K | 8 | 0.62 | 0.27 | 0.49 |
| L3.56 | 93 | E | N | 8 | 1.06 | 0.64 | 0.84 |
| L3.57 | 93 | E | Q | 2 | | | |
| L3.58 | 93 | E | S | 8 | 0.90 | 0.49 | 0.87 |
| L3.59 | 94 | D | A | 3 | 1.16 | 0.09 | 1.14 |
| L3.60 | 94 | D | F | 9 | 1.22 | 0.02 | 1.19 |
| L3.61 | 94 | D | H | 8 | | | |
| L3.62 | 94 | D | L | 3 | 0.87 | 0.46 | 0.79 |
| L3.63 | 94 | D | S | 1 | 1.74 | 0.57 | 1.42 |
| L3.64 | 94 | D | T | 7 | 1.24 | 0.14 | 1.16 |
| L3.65 | 96 | W | F | | 0.33 | 0.34 | 0.29 |
| L3.66 | 96 | W | I | | 0.75 | 0.00 | 0.57 |
| L3.67 | 96 | W | L | | | | |
| L3.68 | 96 | W | Y | | | | |
| L3.69 | 100 | G | P | | | | |
| L3.70 | 100 | G | Q | | | | |

TABLE 5b

| H3 AC10 Secondary Variants | | | | | | |
|---|---|---|---|---|---|---|
| Variant | Position (Kabat) | H3 | Sub | String Impact | Fold Prot A | Fold CD30 |
| H3.1 | 1 | Q | E | −1 | 0.83 | 1.00 |
| H3.2 | 2 | I | L | 0 | 1.60 | 2.76 |
| H3.3 | 2 | I | M | 2 | 0.88 | 0.68 |
| H3.4 | 2 | I | V | 0 | 0.98 | 1.28 |
| H3.5 | 9 | P | A | 2 | 0.95 | 1.29 |
| H3.6 | 16 | A | T | 2 | 0.89 | 1.13 |
| H3.7 | 24 | A | V | 2 | 1.54 | 4.45 |
| H3.8 | 31 | D | G | 2 | 0.80 | 1.40 |
| H3.9 | 31 | D | S | 2 | 0.82 | 1.65 |
| H3.10 | 33 | Y | D | 2 | 0.68 | 0.07 |
| H3.11 | 33 | Y | G | 3 | 0.96 | 0.73 |
| H3.12 | 33 | Y | W | 0 | 0.84 | 0.00 |
| H3.13 | 34 | I | L | 1 | 0.96 | 1.52 |
| H3.14 | 34 | I | M | 8 | 1.05 | 1.62 |
| H3.15 | 35 | T | D | 1 | 1.55 | 0.05 |
| H3.16 | 35 | T | G | 2 | 1.03 | 0.15 |
| H3.17 | 35 | T | H | 8 | 0.86 | 0.04 |
| H3.18 | 35 | T | N | 4 | 1.07 | 0.13 |
| H3.19 | 35 | T | S | 6 | 0.88 | 1.11 |
| H3.20 | 44 | G | A | 0 | 1.20 | 2.04 |
| H3.21 | 44 | G | R | 0 | 1.36 | 2.60 |
| H3.22 | 50 | W | I | 6 | 1.25 | 0.01 |
| H3.23 | 50 | W | R | 0 | 0.99 | 0.16 |
| H3.24 | 52 | Y | N | 2 | 1.03 | 0.03 |
| H3.25 | 52 | Y | T | 1 | 1.11 | 0.06 |
| H3.26 | 52 | Y | V | 1 | 1.33 | 0.06 |
| H3.27 | 52a | P | A | 1 | 1.02 | 2.00 |
| H3.28 | 52a | P | V | 1 | 1.44 | 1.34 |
| H3.29 | 54 | S | D | 1 | 1.45 | 1.81 |
| H3.30 | 54 | S | N | 5 | 1.13 | 1.45 |
| H3.31 | 58 | K | G | 4 | | |
| H3.32 | 58 | K | I | 2 | 1.22 | 1.09 |
| H3.33 | 58 | K | N | 5 | 1.26 | 0.50 |
| H3.34 | 60 | N | A | 7 | 0.87 | 1.30 |
| H3.35 | 60 | N | P | 0 | | |
| H3.36 | 60 | N | S | 7 | 1.02 | 1.24 |
| H3.37 | 60 | N | T | 0 | 1.12 | 1.01 |
| H3.38 | 60 | N | V | 0 | 1.16 | 1.14 |
| H3.39 | 60 | N | D | 0 | 1.09 | 1.00 |
| H3.40 | 61 | E | Q | 7 | 1.51 | 1.83 |
| H3.41 | 64 | Q | T | 0 | 0.98 | 1.38 |
| H3.42 | 71 | V | L | 4 | 1.10 | 0.66 |
| H3.43 | 71 | V | M | 9 | 1.17 | 0.88 |
| H3.44 | 71 | V | R | 1 | 1.25 | 1.76 |
| H3.45 | 87 | T | M | −1 | 0.99 | 1.14 |
| H3.46 | 89 | V | M | −4 | 1.41 | 1.39 |
| H3.47 | 91 | F | H | 2 | | |
| H3.48 | 91 | F | Y | 9 | 1.32 | 1.60 |
| H3.49 | 93 | A | T | 0 | 1.47 | 0.38 |
| H3.50 | 93 | A | V | 0 | 1.01 | 1.40 |
| H3.51 | 94 | N | A | 9 | 1.51 | 0.08 |
| H3.52 | 94 | N | H | 5 | 1.23 | 1.24 |
| H3.53 | 94 | N | K | 9 | 1.67 | 0.02 |
| H3.54 | 94 | N | R | 9 | 1.26 | 0.00 |
| H3.55 | 94 | N | T | 9 | 1.24 | 0.91 |
| H3.56 | 99 | W | Y | | 1.26 | 0.07 |
| H3.57 | 101 | A | D | | 1.31 | 0.53 |
| H3.58 | 101 | A | Q | | 1.17 | 0.16 |
| H3.59 | 102 | Y | H | | 1.69 | 1.05 |
| H3.60 | 102 | Y | S | | 1.04 | 0.82 |
| H3.61 | 102 | Y | V | | 1.33 | 1.21 |
| H3.62 | 102 | Y | L | | 1.34 | 1.22 |
| H3.63 | 102 | Y | F | | 1.18 | 1.24 |
| H3.64 | 105 | Q | R | | 1.15 | 1.28 |

The secondary H3/L3 variants were constructed using quick change mutagenesis, and the full length antibodies were expressed and purified as described above. H3 variants comprised H3 variant VH chains (H3.1-H3.64) in combination with L3 VL, and L3 variants comprised L3 variant VL chains (L3.1-L3.70) in combination with H3 VH. The AlphaScreen™ assay was used to measure binding of the H3/L3 secondary variants to CD30 and FcγRIIIa (as described earlier), as well as to protein A using biotinylated AC10 bound directly to protein A acceptor beads and streptavidin donor beads. FIG. 19 provides AlphaScreen™ binding curves for binding of select AC10 variants to CD30. The Fold IC50's relative to WT H3/L3 for binding to CD30, FcγRIIIa, and protein A are provided in Table 5. A number of H3/L3 secondary variants provide comparable or improved binding to CD30 antigen relative to the H3/L3 parent, enabling the engineering of additional variants that comprise combinations of these substitutions, which may provide further enhancements in HSC and/or antigen affinity.

Secondary substitutions that show favorable properties with respect to antigen affinity, effector function, stability, solubility, expression, and the like, may be combined in subsequent variants to generate a more optimized therapeutic candidate. Two new VL and three new VH variants were designed that comprise combinations of the described secondary substitutions, referred to as L3.71, L3.72, H3.68, H3.69, and H3.70. FIGS. 20-24 present the sequences (SEQ ID NOS: 224-228), host string content, and mapped mutational differences on the modeled AC10 structure for each of these new AC10 VL and VH variants. Table 6 presents the number of mutations from the parent sequence, structural fitness scores, host string scores, and homology scores for these AC10 VL and VH variants.

TABLE 6

| AC10 Variants | | | | | |
|---|---|---|---|---|---|
| | L3.71 | L3.72 | H3.68 | H3.69 | H3.70 |
| Mutations | 15 | 15 | 23 | 27 | 30 |
| Structural Consensus | 0.56 | 0.55 | 0.46 | 0.46 | 0.45 |
| Structural Precedence | 0.54 | 0.52 | 0.55 | 0.57 | 0.56 |
| Human String Content | 0.88 | 0.87 | 0.80 | 0.83 | 0.84 |
| Human String Similarity | 0.52 | 0.45 | 0.39 | 0.47 | 0.47 |
| Framework Region Homogeneity | 0.47 | 0.51 | 0.33 | 0.40 | 0.42 |
| $N_9$max | 55 | 47 | 46 | 55 | 55 |
| $N_8$max | 19 | 24 | 26 | 26 | 34 |
| $N_7$max | 14 | 17 | 24 | 20 | 12 |
| $N_{\leq 6}$max | 19 | 19 | 23 | 18 | 18 |
| Closest Germline | 4-1 | 4-1 | 7-4-1 | 1-3 | 1-3 |
| ID to Closest | 76/101 | 76/101 | 74/98 | 77/98 | 79/98 |
| Germline | 75% | 75% | 76% | 79% | 81% |

Because the provided AC10 variants antibodies are clinical candidates for anti-cancer therapeutics, it may be advantageous to optimize their effector function. As previously described, substitutions can be engineered in the constant region of an antibody to provide favorable clinical properties. Combinations of the variants of the present invention with Fc modifications that alter effector function are anticipated. In a most preferred embodiment, one or more amino acid modifications that provide optimized binding to FcγRs and/or enhanced effector function described in U.S. Ser. No. 10/672,280, PCT US03/30249, and U.S. Ser. No. 10/822,231, and U.S. Ser. No. 60/627,774, filed Nov. 12, 2004 and entitled "Optimized Fc Variants", are combined with the AC10 variants of the present invention. The optimal anti-CD30 clinical candidate may comprise amino acid modifications that reduce immunogenicity and enhance effector function relative to a parent anti-CD30 antibody. FIGS. 25*a*-25*c* (SEQ ID NOS:229-231) provide the light and heavy chain sequences of AC10 variants that comprise L3.71/H3.70 AC10 as described above, combined with a number of possible variant IgG1 constant regions, comprising one or more modifications at S239, V264, A330, and I332, that provide enhanced effector function.

Although human IgG1 is the most commonly used constant region for therapeutic antibodies, other embodiments may utilize constant regions or variants thereof of other IgG immunoglobulin chains. Effector functions such as ADCC, ADCP, CDC, and serum half-life differ significantly between the different classes of antibodies, including for example human IgG1, IgG2, IgG3, IgG4, IgA1, IgA2, IgD, IgE, IgG, and IgM (Michaelsen et al., 1992, Molecular Immunology, 29(3): 319-326). A number of studies have explored IgG1, IgG2, IgG3, and IgG4 variants in order to investigate the determinants of the effector function differences between them. See for example Canfield & Morrison, 1991, J. Exp. Med. 173: 1483-1491; Chappel et al., 1991, Proc. Natl. Acad. Sci. USA 88(20): 9036-9040; Chappel et al., 1993, Journal of Biological Chemistry 268:25124-25131; Tao et al., 1991, J. Exp. Med. 173: 1025-1028; Tao et al., 1993, J. Exp. Med. 178: 661-667; Redpath et al., 1998, Human Immunology, 59, 720-727. Using methods known in the art, it is possible to determine corresponding or equivalent residues in proteins that have significant sequence or structural homology with each other. By the same token, it is possible to use such methods to engineer amino acid modifications in an antibody or Fc fusion that comprise constant regions from other immunoglobulin classes, for example as described in U.S. Ser. No. 60/621,387 and 60/629,068, to provide optimal properties. As an example, the relatively poor effector function of IgG2 may be improved by replacing key FcγR binding residues with the corresponding amino acids in an IgG with better effector function, for example IgG1. For example, key residue differences between IgG2 and IgG1 with respect to FcγR binding may include P233, V234, A235, –236 (referring to a deletion in IgG2 relative to IgG1), and G327. Thus one or more amino acid modifications in the parent IgG2 wherein one or more of these residues is replaced with the corresponding IgG1 amino acids, P233E, V234L, A235L, –236G (referring to an insertion of a glycine at position 236), and G327A, may provide enhanced effector function. Furthermore, one or more additional amino acid modifications, for example the S239D, V264I, A330L, I332E, or combinations thereof as described above, may provide enhanced FcγR binding and effector function relative to the parent IgG2. FIGS. 25a (SEQ ID NO:229), 25d (SEQ ID NO:232), and 25e (SEQ ID NO:233) illustrate this embodiment, providing the light and heavy chain sequences of AC10 variants that comprise L3.71/H3.70 AC10 combined with a number of possible variant IgG2 constant regions.

The Fc modifications defined in FIG. 25 that provide enhanced effector function are not meant to constrain the invention to only these modifications for effector function optimization. For example, as described in U.S. Pat. No. 6,737,056, PCT US20041000643, U.S. Ser. No. 10/370,749, and PCT/US2004/005112, the substitutions S298A, S298D, K326E, K326D, E333A, K334A, and P396L provide optimized FcγR binding and/or enhanced ADCC. Furthermore, as disclosed in Idusogie et al., 2001, J. Immunology 166: 2571-2572, substitutions K326W, K326Y, and E333S provide enhanced binding to the complement protein C1q and enhanced CDC. As described in Hinton et al., 2004, J. Biol. Chem. 279(8): 6213-6216, substitutions T250Q, T250E, M428L, and M428F provide enhanced binding to FcRn and improved pharmacokinetics. Modifications need not be restricted to the Fc region. It is also possible that the mutational differences in the Fab and hinge regions may provide optimized FcγR and/or C1q binding and/or effector function. For example, as disclosed in U.S. Ser. No. 60/614,944, and U.S. Ser. No. 60/619,409, filed Oct. 14, 2004, entitled "Immunoglobulin Variants Outside the Fc Region with Optimized Effector Function", the Fab and hinge regions of an antibody may impact effector functions such as antibody dependent cell-mediated cytotoxicity (ADCC), antibody dependent cell-mediated phagocytosis (ADCP), and complement dependent cytotoxicity (CDC). Thus immunoglobulin variants comprising substitutions in the Fc, Fab, and/or hinge regions are contemplated. For example, the antibodies may be combined with one or more substitutions in the VL, CL, VH, CH1, and/or hinge regions. Furthermore, further modifications may be made in non IgG1 immunoglobulins to corresponding amino acids in other immunoglobulin classes to provide more optimal properties, as described in U.S. Ser. No. 60/621,387, filed Oct. 21, 2004, entitled "IgG Immunoglobulin Variants with Optimized Effector Function". For example, in one embodiment, an IgG2 antibody, similar to the antibody presented in FIG. 25, may comprise one or more modifications to corresponding amino acids in IgG1 or IgG3 CH1, hinge, CH2, and/or CH3. In another embodiment, an IgG2 antibody, similar to the antibody presented in FIG. 25, may comprise all of the IgG1 CH1 and hinge substitutions, i.e. said IgG2 variant comprises the entire CH1 domain and hinge of IgG1.

Example 2

Immunogenicity Reduction of C225

To illustrate further application of the method described in the present invention, and to validate its broad applicability to immunogenicity reduction of proteins, a second xenogeneic antibody example is provided using the variable region of C225 as the parent sequence (cetuximab, Erbitux®, Imclone®) (U.S. Pat. No. 4,943,533; PCT WO 96/40210). C225 is a murine anti-EGFR antibody, a chimeric version of which is currently approved for the treatment of cancer. A structural model of the murine C225 variable region was constructed using standard antibody modeling methods known in the art. FIGS. 26 and 27 show the sequences (SEQ ID NOS:234- and 235), host string content, and structures of the C225 VL and VH domains. A CDR graft of this antibody was constructed by placing the C225 CDRs into the context of the frameworks of the most homologous human germlines, determined to be vlk__6D-21 for VL and vh__4-30-4 for VH using the sequence alignment program BLAST. The sequences (SEQ ID NOS:236 and 237) and string content of these CDR grafts are shown in FIGS. 28 and 29, along with structures of modeled C225 highlighting the mutational differences between the CDR grafted C225 variable chains and WT.

Variants with reduced immunogenicity were generated by applying a string optimization algorithm on the WT C225 VL and VH sequences, similar to as described above for AC10 except that single instead of multiple amino acid substitutions were sampled. HSC of each sequence was optimized using a window size w=9, and the same set of CDR and VL/VH interface proximal residues were masked. The calculation was run for C225 VL and VH in 100 separate iterations, generating a set of diverse C225 variants with more host string content than WT. FIG. 30 shows the nonredundant set of output sequences from these calculations for the C225 VL and VH regions (SEQ ID NOS:238-274), referred to as C225 VL HSC Calculation 1 and C225 VH HSC Calculation 1, respectively. In addition to the HSC score, the structural consensus and structural precedence of each sequence was evaluated (U.S. Ser. No. 60/528,229, filed Dec. 8, 2003, entitled Protein Engineering with Analogous Contact Environments) in order to evaluate its structural integrity.

A second set of similar calculations were run on the C225 VL and VH sequences, except that the algorithm was allowed to sample multiple amino acid substitutions, rather than only single substitutions, in order to optimize HSC. FIG. 31 shows the nonredundant set of output sequences from these calculations for the C225 VL and VH regions (SEQ ID NOS:275-378), referred to as C225 VL HSC Calculation 2 and C225 VH HSC Calculation 2, respectively. Here, two measure of structural fitness, referred to as "Structural Consensus" and "Structural Precedence" (U.S. Ser. No. 60/528,229 and U.S. Ser. No. 60/602,566), are used to evaluate the structural and functional integrity of the sequences, in addition to HSC score. The output sequences were clustered based on their mutational distance from the other sequences in the set, and these clusters are delineated by the horizontal black lines in the Figure.

The calculations described above and presented in FIGS. 30 and 31 were used to generate a set of C225 VL and VH variants (SEQ ID NOS:238-378). In some cases, further substitutions were made to output sequences, using string and structural scores, as well as visual inspection of the modeled C225 structure, to evaluate fitness. FIGS. 32-40 present the sequences (SEQ ID NOS:379-387), structural scores, string scores, and mapped mutational differences on the modeled $C_{2\text{-}25}$ structure for each of the C225 VL and VH variants. Iteration 21 from C225 VL HSC calculation 1 served as the precursor for L2 C225 VL, iteration 17 from C225 VL HSC calculation 2 served as the precursor for L3 C225 VL, and iteration 38 from C225 VL HSC calculation 2 served as the precursor for L4 C225 VL. Iteration 23 from C225 VH HSC calculation 1 served as the precursor for H3, H4, and H5C225 VH, iteration 5 from C225 VH HSC calculation 2 served as the precursor for H6 C225 VH, iteration 41 from C225 VH HSC calculation 2 served as the precursor for H7 C225 VH, and iteration 44 from C225 VH HSC calculation 2 served as the precursor for H8 C225 VH.

framework region homogeneity. In addition to the aforementioned structural and host string analysis, each sequence was analyzed for its global homology to the human germline; tables 7 and 8 present the most homologous human germline sequence for each sequence (Closest Germline) and corresponding identity to that germline (ID to Closest Germline), determined using the sequence alignment program BLAST.

TABLE 7

C225 VL Variants

|  | WT | CDR Graft | L2 | L3 | L4 |
|---|---|---|---|---|---|
| Mutations |  | 25 | 17 | 21 | 18 |
| Structural Consensus | 0.49 | 0.52 | 0.56 | 0.58 | 0.54 |
| Structural Precedence | 0.53 | 0.56 | 0.57 | 0.59 | 0.57 |
| Human String Content | 0.79 | 0.94 | 0.91 | 0.92 | 0.91 |
| Human String Similarity | 0.15 | 0.65 | 0.51 | 0.58 | 0.57 |
| Framework Region Homogeneity |  | 0.97 | 0.52 | 0.50 | 0.78 |
| $N_9$max | 13 | 69 | 52 | 60 | 58 |
| $N_8$max | 27 | 15 | 28 | 24 | 23 |
| $N_7$max | 37 | 22 | 20 | 16 | 19 |
| $N_{\leq 6}$max | 30 | 1 | 7 | 7 | 7 |
| Closest Germline | 6D-21 | 6D-21 | 3-11 | 1D-13 | 6D-21 |
| ID to Closest | 63/95 | 87/95 | 72/95 | 73/94 | 79/95 |
| Germline | 66% | 91% | 75% | 77% | 83% |

TABLE 8

C225 VH Variants

|  | WT | CDR Graft | H3 | H4 | H5 | H6 | H7 | H8 |
|---|---|---|---|---|---|---|---|---|
| Mutations |  | 33 | 18 | 21 | 15 | 21 | 22 | 28 |
| Structural Consensus | 0.44 | 0.48 | 0.51 | 0.46 | 0.49 | 0.52 | 0.49 | 0.53 |
| Structural Precedence | 0.55 | 0.54 | 0.55 | 0.54 | 0.51 | 0.55 | 0.58 | 0.55 |
| Human String Content | 0.67 | 0.84 | 0.79 | 0.81 | 0.77 | 0.79 | 0.79 | 0.79 |
| Human String Similarity | 0.04 | 0.56 | 0.36 | 0.41 | 0.33 | 0.36 | 0.35 | 0.33 |
| Framework Region Homogeneity |  | 0.97 | 0.45 | 0.52 | 0.50 | 0.50 | 0.76 | 0.77 |
| $N_9$max | 3 | 66 | 42 | 48 | 38 | 42 | 41 | 39 |
| $N_8$max | 23 | 17 | 25 | 24 | 17 | 24 | 21 | 27 |
| $N_7$max | 32 | 10 | 19 | 16 | 26 | 23 | 25 | 23 |
| $N_{\leq 6}$max | 61 | 26 | 33 | 31 | 38 | 30 | 32 | 30 |
| Closest Germline | 4-30-4 | 4-30-4 | 4-30-4 | 2-26 | 4-30-4 | 3-33 | 4-30-4 | 3-33 |
| ID to Closest | 56/99 | 88/99 | 67/99 | 74/99 | 64/99 | 69/99 | 67/99 | 80/99 |
| Germline | 56% | 88% | 66% | 74% | 64% | 70% | 67% | 81% |

Tables 7 and 8 present the mutational, structural fitness, and host string content scores for the C225 VL and VH variants as compared to the WT and CDR grafted C225 sequences. In addition, the maximum identity match to the germline for each string in the sequences was also determined, referred to as $N_{ID}$max. This represents the total number of strings in each sequence whose maximum identity to the corresponding strings in the human germline is the indicated value. For w=9, Tables 7 and 8 list $N_9$max, $N_8$max, $N_7$max, and $N_{\leq 6}$max for each sequence. Also provided is the Again, whereas the CDR grafted C225 antibodies are most homologous to a single human germline sequence, the C225 variants of the present invention are homologous to different human germline sequences in different regions of the sequence. Whereas CDR grafted C225 VH is most homologous to human germline subfamily 4 across its entire sequence, H4C225 VH is most homologous to subfamily 4 in FR1, subfamily 3 in FR2, and subfamily 2 in FR3. Additionally, whereas the CDR grafted antibodies are most homologous to a single germline sequence that is also the most homologous sequence to the parent sequence, the present invention presents a set of antibodies for a given antibody that are most homologous to different human germline sequences, which need not be the most homologous germline sequence to WT. For example, Table 7 shows that CDR grafted C225 VL is most homologous to vlk_6D-21, which is also the most homologous human germline to WT C225. However L2, L3, and L4 are most homologous to three different human germlines—vlk_3-11, vlk_1D-13, and vlk_6D-21 respectively. Thus the variants of the present invention explore a substantially greater amount of diversity than CDR grafted antibodies.

The genes for the C225 variable regions were constructed as described above, and subcloned into a modified pASK84 vector (Skerra, 1994, Gene 141: 79-84) comprising mouse constant regions for expression as Fabs. Select C225 variants were experimentally tested for their capacity to bind EGFR antigen. L2/H3 and L2/H4 C225 Fabs were expressed from the pASK84 vector in *E. Coli* with a His-tag, and purified using Nickel-affinity chromatography. Antigen affinity of the C225 variants was tested using SPR similar to as described above. EGFR extracellular domain (purchased commercially from R&D Systems) was covalently coupled to the dextrane matrix of a CM5 chip using NHS-linkage chemistry. C225 Fabs were reacted with the EGFR sensor chip surface at varying concentrations. Global Langmuir fits were been carried out for the concentrations series using the BiaEvaluation curve fitting software. The on-rate constant (ka), off-rate constant (kd), equilibrium binding constant (KD=kd/ka), and predicted saturation binding signal (Rmax) derived from these fits are presented in Table 9, along with the Chi2 which quantifies the average deviation of the fit curve from the actual data curve. The data indicate that both the L2/H3 and L2/H4 C225 variants bind EGFR antigen.

TABLE 9

SPR data on C225 Variants

| C225 | ka (1/Ms) | kd (1/s) | KD (M) | Rmax (RU) | Chi2 |
|---|---|---|---|---|---|
| L2/H3 | $2.79 \times 10^4$ | $5.35 \times 10^{-3}$ | $1.92 \times 10^{-7}$ | 174 | 8.83 |
| L2/H4 | $1.79 \times 10^4$ | $4.73 \times 10^{-3}$ | $2.64 \times 10^{-7}$ | 153 | 2.69 |

Figure 41:
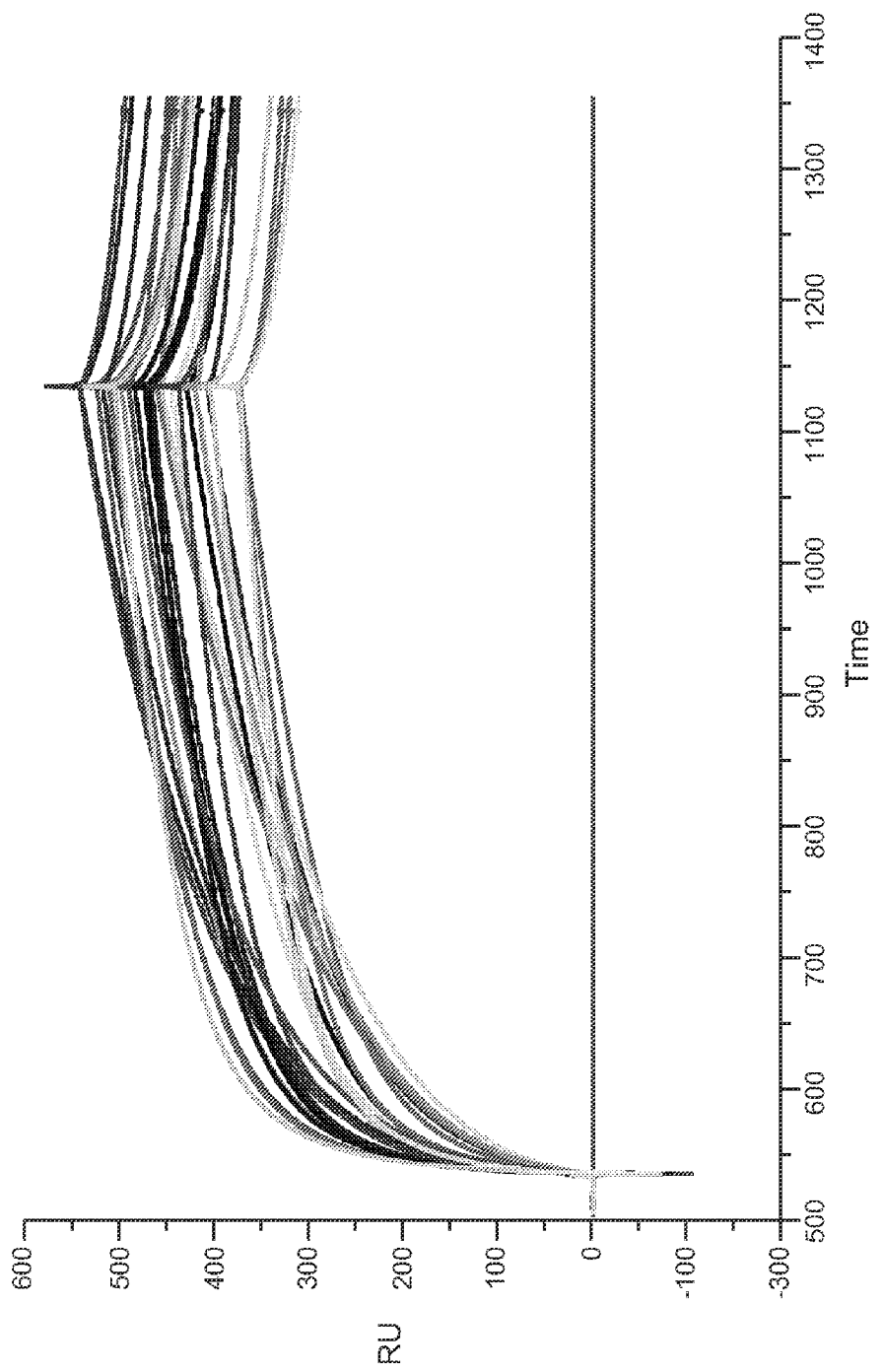
FIG. 41. SPR sensorgrams showing binding of full length antibody C225 variants to the EGFR target antigen. The sensorgrams show binding of C225 WT (L0/H0) and variant (L0/H3, L0/H4, L0/H5, L0/H6, L0/H7, L0/H8, L2/H3, L2/H4, L2/H5, L2/H6, L2/H7, L2/H8, L3/H3, L3/H4, L3/H5, L3/H6, L3/H7, L3/H8, L4/H3, L4/H4, L4/H5, L4/H6, L4/H7, and L4/H8) full length antibodies to the EGFR sensor chip. The curves consist of an association phase and dissociation phase, the separation being marked by a little spike on each curve.
Figure 42A:
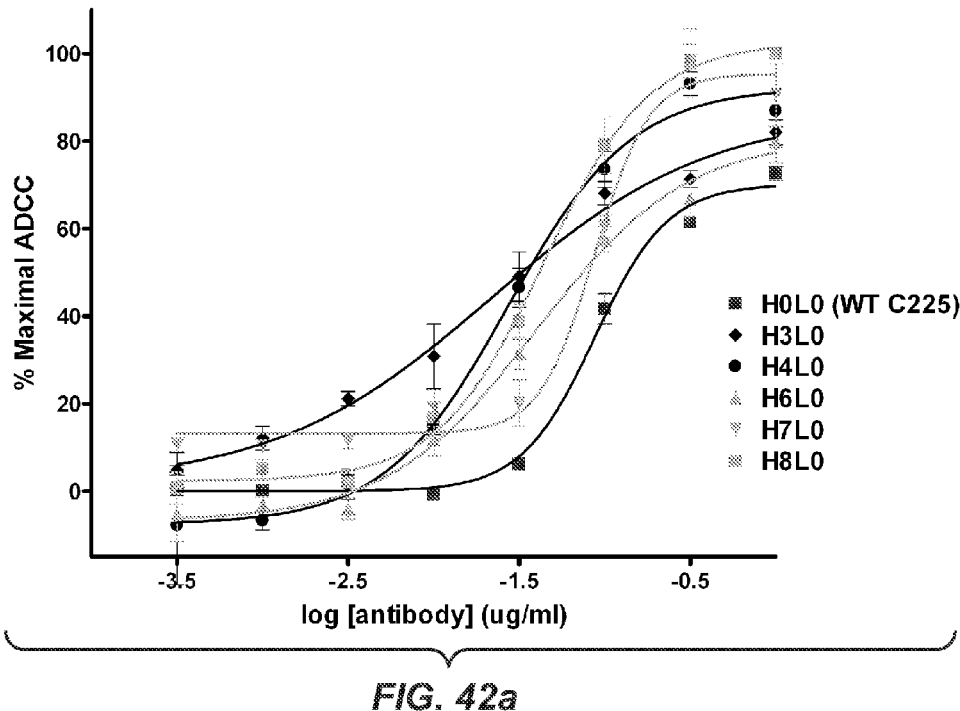
FIG. 42. Cell-based ADCC assay of C225 WT (L0/H0) and variant (L0/H3, L0/H4, L0/H5, L0/H6, L0/H7, L0/H8, L2/H3, L2/H4, L2/H5, L2/H6, L2/H7, L2/H8, L3/H3, L3/H4, L3/H5, L3/H6, L3/H7, L3/H8, L4/H3, L4/H4, L4/H5, L4/H6, L4/H7, and L4/H8) full length antibodies. Purified human peripheral blood monocytes (PBMCs) were used as effector cells, A431 epidermoid carcinoma cells were used as target cells at a 10:1 effector:target cell ratio, and lysis was monitored by measuring LDH activity using the Cytotoxicity Detection Kit (LDH, Roche Diagnostic Corporation, Indianapolis, Ind.). Samples were run in triplicate to provide error estimates (n=3, +/−S.D.).
Figure 42B:
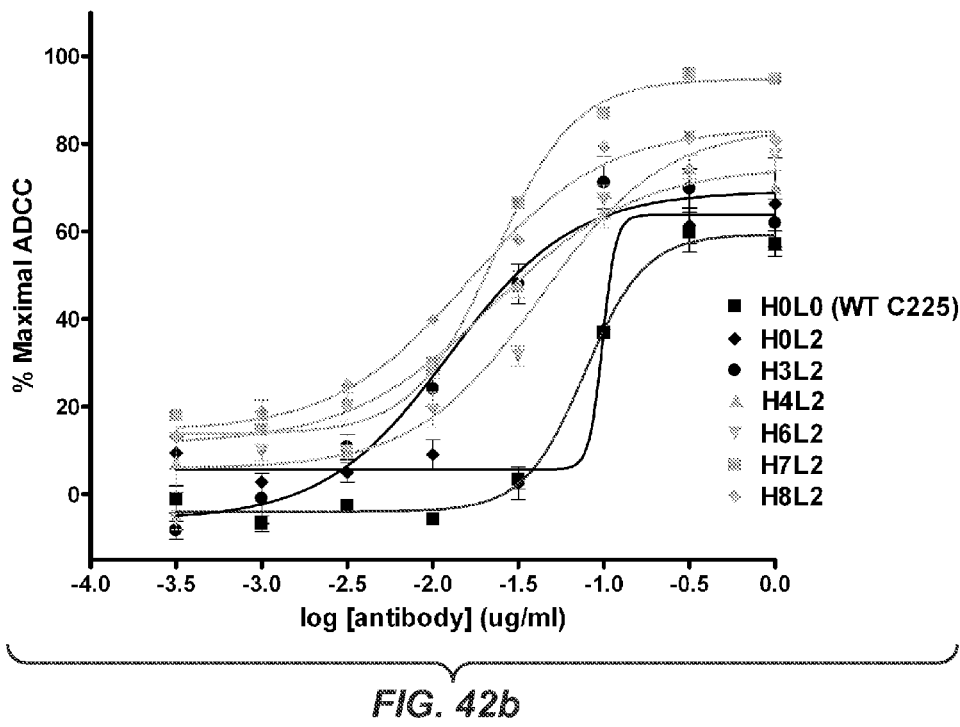
Figure 42C:
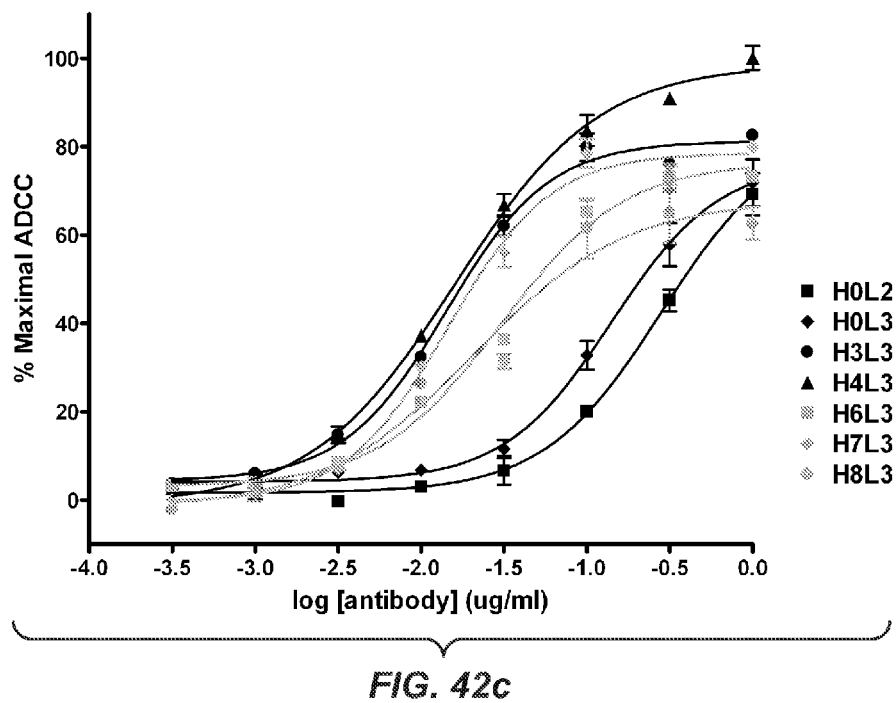
Figure 42D:
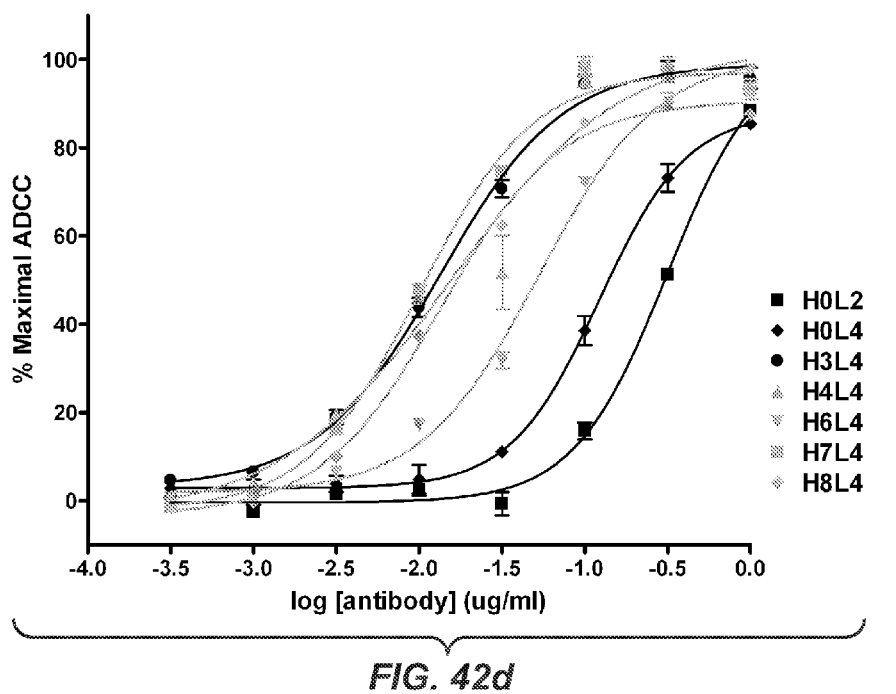

In order to investigate the anti-EGFR variants in the context of a full length antibody, the C225 WT (L0 and H0) and variant (L2, L3, L4, H3, H4, H5, H6, H7, and H8) regions were subcloned into the mammalian expression vector pcDNA3.1Zeo (Invitrogen) as described above. All combinations of the light and heavy chain plasmids were co-transfected into 293T cells, and antibodies were expressed, harvested, and purified as described above. Binding of the C225 WT (L0/H0) and variant (L0/H3, L0/H4, L0/H5, L0/H6, L0/H7, L0/H8, L2/H3, L2/H4, L2/H5, L2/H6, L2/H7, L2/H8, L3/H3, L3/H4, L3/H5, L3/H6, L3/H7, L3/H8, L4/H3, L4/H4, L4/H5, L4/H6, L4/H7, and L4/H8) antibodies was determined using SPR similar to as described above. Full length antibodies were flowed over the EGFR sensor chip described above. FIG. 41 shows the SPR sensorgrams obtained from the experiments. The curves consist of a association phase and dissociation phase, the separation being marked by a little spike on each curve. As a very rough approximation the signal level reached near the end of the association phase can be used as an indicator for relative binding. For all the curves this signal level is within 25% of the average level indicating that none of the antibody variants have significantly lost their ability to bind to EGFR.

To assess the capacity of the anti-EGFR antibodies to mediate effector function against EGFR expressing cells, the C225 variants were tested in a cell-based ADCC assay. Human peripheral blood monocytes (PBMCs) were used as effector cells, A431 epidermoid carcinoma cells were used as target cells, and lysis was monitored by measuring LDH activity using the Cytotoxicity Detection Kit as described above. FIG. 42 shows the dose dependence of ADCC at various antibody concentrations for WT and variant C225 antibodies. The results show that a number of the C225 variants have comparable or better ADCC than WT C225 with respect to potency and efficacy. These data may be weighed together with the antigen affinity data and other data to choose the optimal anti-EGFR clinical candidate. As exemplified above with AC10 variants, combinations of the C225 variants of the present invention with amino acid modifications that alter effector function are contemplated.

Example 3

Immunogenicity Reduction of ICR62

To further illustrate application of the method described in the present invention, and to validate its broad applicability to immunogenicity reduction of proteins, an example is provided using as the parent sequence the anti-EGFR antibody ICR62 (Institute of Cancer Research) (PCT WO 95/20045; Modjtahedi et al., 1993, *J. Cell Biophys.* 1993, 22(1-3):129-46; Modjtahedi et al., 1993, *Br J. Cancer.* 1993, 67(2):247-53; Modjtahedi et al, 1996, *Br J Cancer,* 73(2):228-35; Modjtahedi et al, 2003, *Int J Cancer,* 105(2):273-80). A structural model of the rat ICR62 variable region was constructed using standard antibody modeling methods known in the art. FIGS. 43 and 44 show the sequences (SEQ ID NOS:388 and 389), host string content, and structures of the ICR62 VL and VH domains. A CDR graft of this antibody was constructed by placing the ICR62 CDRs into the context of the frameworks of the most homologous human germlines, determined to be vlk_1-17 for VL and vh_1-f for VH using the sequence alignment program BLAST. The sequences and string content of these CDR grafts are shown in FIGS. 45 and 46 (SEQ ID NOS:390 and 391), along with structures of modeled ICR62 highlighting the mutational differences between the CDR grafted ICR62 variable chains and WT.

Variants with reduced immunogenicity were generated by applying a string optimization algorithm on the WT ICR62 VL and VH sequences, similar to as described above for AC10 except that single instead of multiple amino acid substitutions were sampled. HSC of each sequence was optimized using a window size w=9, and the same set of CDR and VL/VH interface proximal residues were masked. The calculation was run for ICR62 VL and VH in 100 separate interactions, generating a set of diverse ICR62 variants with more host string content than WT. FIG. 47 shows the nonredundant set of output sequences (SEQ ID NOS:392 and 431) from these calculations for the ICR62 VL and VH regions, referred to as ICR62 VL HSC Calculation 1 and ICR62 VH HSC Calculation 1 respectively. In addition to the HSC score, the structural consensus and structural precedence of each sequence was evaluated (U.S. Ser. No. 60/528,229, filed Dec. 8, 2003, entitled Protein Engineering with Analogous Contact Environments) in order to evaluate its structural integrity.

The calculations described above and presented in FIG. 47 were used to generate a set of ICR62 VL and VH variants (SEQ ID NOS:392 and 455). In some cases, further substitutions were made to output sequences, using HSC and Structural Precedence scores, as well as visual inspection of the modeled ICR62 structure, to evaluate fitness. FIGS. 48-50 present the sequences (SEQ ID NOS:456 and 458), host string content, and mapped mutational differences on the modeled ICR62 structure for each of the ICR62 VL and VH variants. Iteration 20 from ICR62 VL HSC calculation 1 served as the precursor for L2 ICR62 VL. Iteration 1 from ICR62 VH HSC calculation 1 served as the precursor for H9, and iteration 5 from ICR62 VH HSC calculation 2 served as the precursor for H10 ICR62 VH.

Tables 10 and 11 present the mutational, structural fitness, and host string content scores for the ICR62 VL and VH variants as compared to the WT and CDR grafted ICR62 sequences. In addition, the maximum identity match to the germline for each string in the sequences, referred to as $N_{ID}$-max, is also provided, as well as the framework region homogeneity. In addition to the aforementioned structural and host string analysis, each sequence was analyzed for its global homology to the host germline; tables 10 and 11 present the most homologous host germline sequence for each sequence (Closest Germline) and corresponding identity to that germline (ID to Closest Germline), determined using the sequence alignment program BLAST.

TABLE 10

ICR62 VL Variants

|  | WT | CDR Graft | L2 |
|---|---|---|---|
| Mutations | 0 | 11 | 6 |
| Structural Consensus | 0.56 | 0.60 | 0.61 |
| Structural Precedence | 0.52 | 0.58 | 0.57 |
| Human String Content | 0.86 | 0.91 | 0.90 |
| Human String Similarity | 0.38 | 0.58 | 0.56 |
| Framework Region Homogeneity | 0.62 | 0.97 | 0.64 |
| $N_9$max | 37 | 59 | 56 |
| $N_8$max | 26 | 21 | 19 |
| $N_7$max | 31 | 18 | 22 |
| $N_{\leq 6}$max | 13 | 9 | 10 |
| Closest Germline | 1-17 | 1-17 | 1-17 |
| ID to Closest Germline | 76/95 | 86/95 | 81/95 |
|  | 80% | 90% | 85% |

TABLE 11

ICR62 VH Variants

|  | WT | CDR Graft | H9 | H10 |
|---|---|---|---|---|
| Mutations | 0 | 34 | 20 | 21 |
| Structural Consensus | 0.43 | 0.44 | 0.46 | 0.45 |
| Structural Precedence | 0.42 | 0.52 | 0.47 | 0.49 |
| Human String Content | 0.64 | 0.85 | 0.79 | 0.79 |
| Human String Similarity | 0.01 | 0.54 | 0.28 | 0.33 |
| Framework Region Homogeneity |  | 1.00 | 0.64 | 0.85 |
| $N_9$max | 1 | 64 | 33 | 39 |
| $N_8$max | 16 | 24 | 33 | 30 |
| $N_7$max | 35 | 14 | 28 | 25 |
| $N_{\leq 6}$max | 67 | 17 | 25 | 25 |
| Closest Germline | 1-f | 1-f | 1-f | 1-f |
| ID to Closest Germline | 60/98 | 92/98 | 72/98 | 77/98 |
|  | 61% | 93% | 73% | 79% |

Again, as observed from the significant differences in FRH and closest germlines, the ICR62 variants are homologous to different host germline sequences in different regions of the sequence. The genes for the ICR62 WT and L2/H9 variable regions were constructed as described above, and subcloned into a modified pASK84 vector (Skerra, 1994, Gene 141: 79-84). The ICR62 Fabs experimentally tested for their capacity to bind EGFR antigen. WT and L2/H9 ICR62 Fabs were expressed from the pASK84 vector in *E. Coli* with a His-tag, and purified using Nickel-affinity chromatography. Antigen affinity of the ICR62 antibodies was tested using SPR similar to as described above, with EGFR covalently coupled to the CM5 chip reacted with ICR62 antibodies at varying concentrations. The fits to the data, as described above, are provided in Table 12. fits were been carried out for the concentrations series using the BiaEvaluation curve fitting software. As can be seen, L2/H9 ICR62 binds with comparable affinity as WT to the EGFR antigen.

TABLE 12

SPR data on ICR62 Variants

| ICR62 | ka (1/Ms) | kd (1/s) | KD (M) | Rmax (RU) | Chi2 |
|---|---|---|---|---|---|
| WT | $9.86 \times 10^4$ | $2.53 \times 10^{-5}$ | $2.57 \times 10^{-10}$ | 402 | 1.86 |
| L2/H9 | $2.35 \times 10^5$ | $1.06 \times 10^{-4}$ | $4.50 \times 10^{-10}$ | 508 | 4.91 |

Example 4

String Diversity Exploration of Immunoglobulins

The generation of mutational diversity based on HSC is much broader than the primary variant-secondary variant strategy described above for H3/L3 AC10. Indeed substitutions can be designed for any parent protein wherein the substitutions result in positive or neutral impact on the host string content of the parent sequence. Again, the advantage of such a strategy is that it generates a diverse set of minimally immunogenic variants that have the potential for optimized properties, including but not limited to antigen affinity, activity, specificity, solubility, expression level, and effector function. Such a set of variants may be designed, for example, to explore diversity for other parent immunoglobulins, including but not limited to nonhuman antibodies, humanized or otherwise engineered antibodies (Clark, 2000, *Immunol Today* 21:397-402), (Tsurushita & Vasquez, 2004, Humanization of Monoclonal Antibodies, Molecular Biology of B Cells, 533-545, Elsevier Science (USA)), and "fully human" antibodies, obtained for example using transgenic mice (Bruggemann et al., 1997, *Curr Opin Biotechnol* 8:455-458) or human antibody libraries coupled with selection methods (Griffiths et al., 1998, *Curr Opin Biotechnol* 9:102-108).

Example 5

Figure 51A:
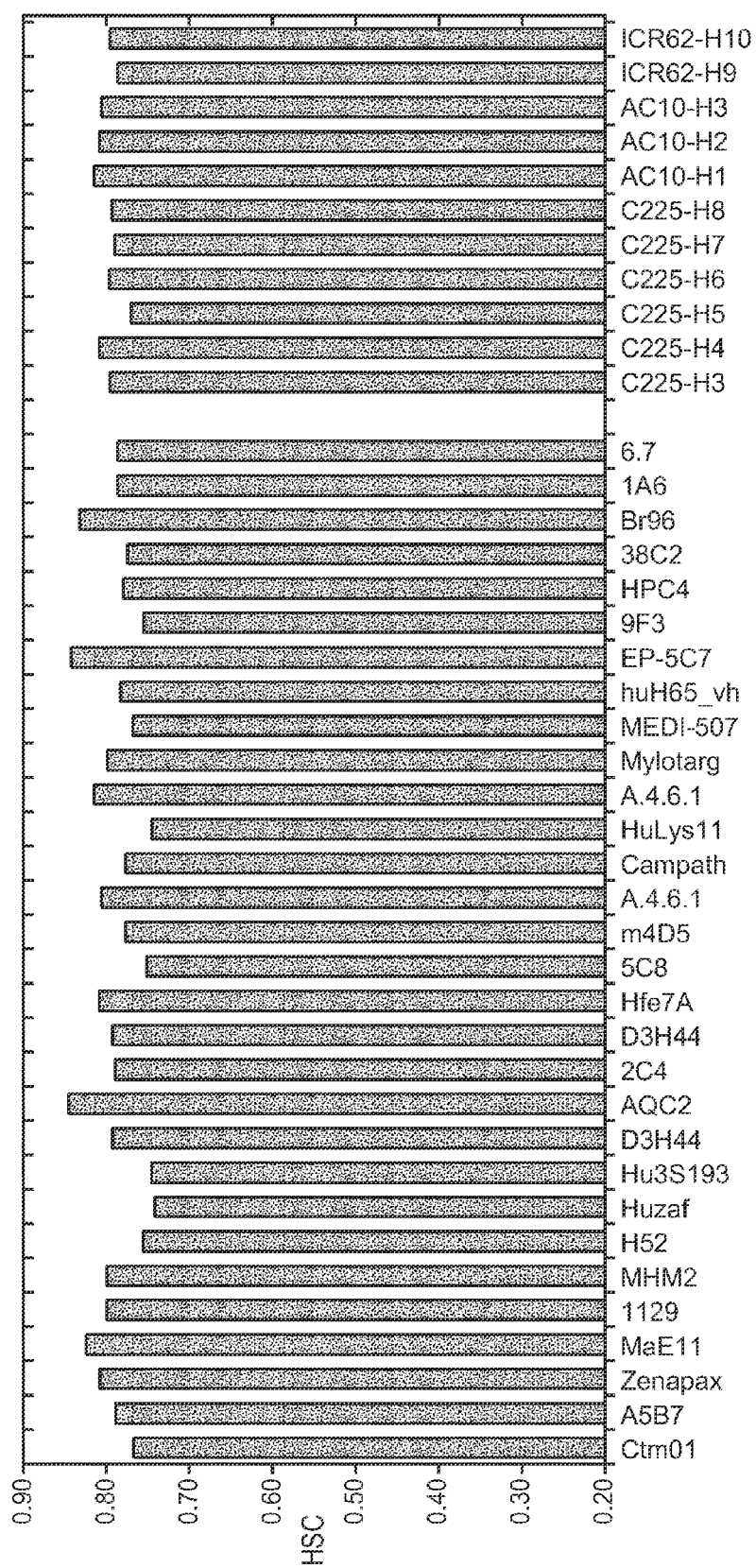
FIG. 51*a* provides the host string content (HSC) as defined by equation 3, FIG. 51*b* provides the exact string content (ESC) as defined by equation 3a, and FIG. 51*c* provides the framework region homogeneity (FRH) as defined by equation 10. Window size w was 9 for all calculations.
Figure 51B:
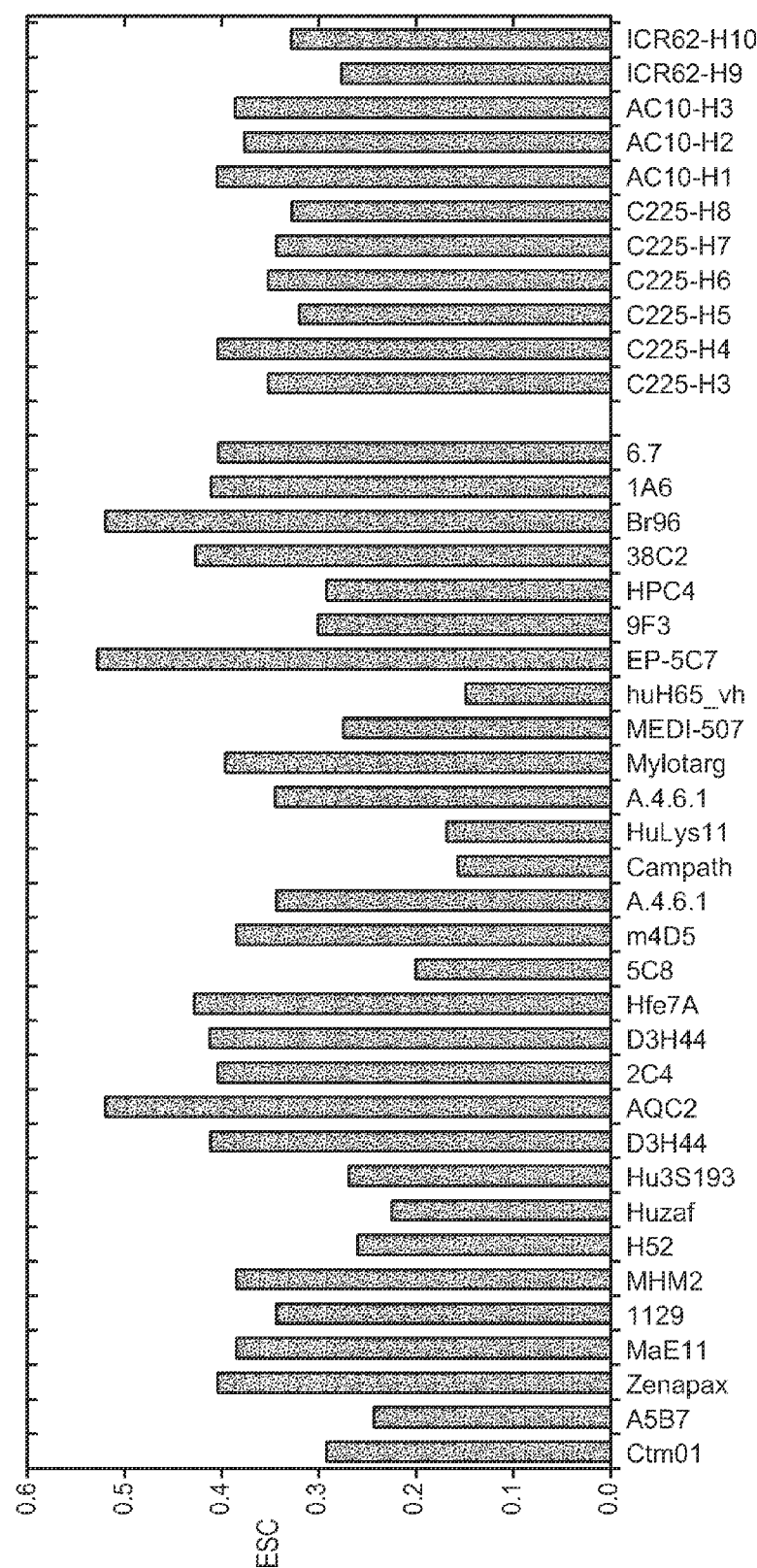
FIG. 51. Comparison of VH sequences humanized by the methods in the prior art versus the present method. Prior art antibodies include Ctm01, A5B7, Zenapax, MaE11, 1129, MHM2, H52, Huzaf, Hu3S193, D3H44, AQC2, 2C4, D3H44, Hfe7A, 5C8, m4D5, A.4.6.1, Campath, HuLys11, A.4.6.1, Mylotarg, MEDI-507, huH65_vh, EP–5C7, 9F3, HPC4, 38C2, Br96, 1A6, and 6.7. Sequences designed using the present invention, including AC10 H1, H2, and H3, C225H3, H4, H5, H6, H7, and H8, and ICR62H9 and H10, are offset to the right.
Figure 51C:
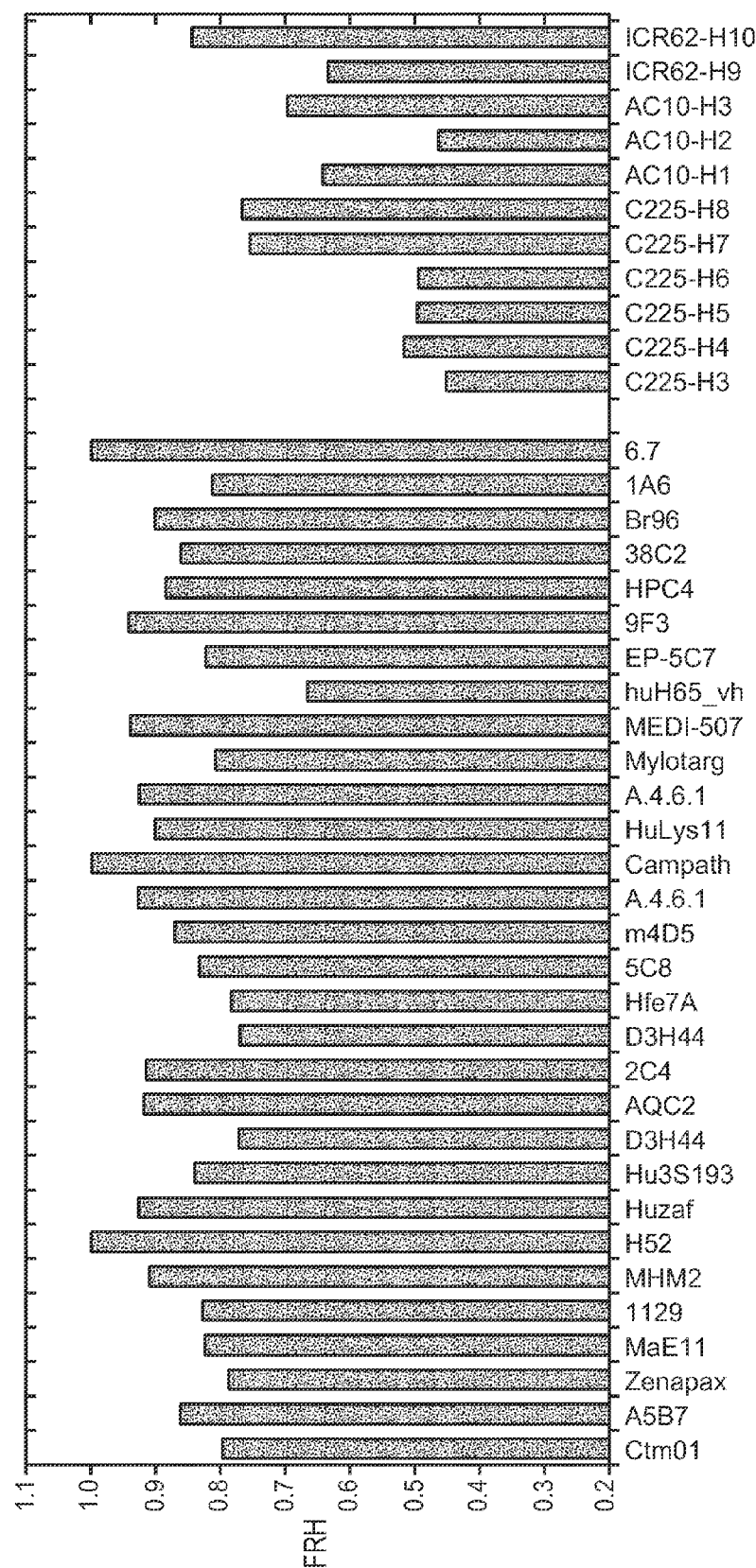
Figure 52A:
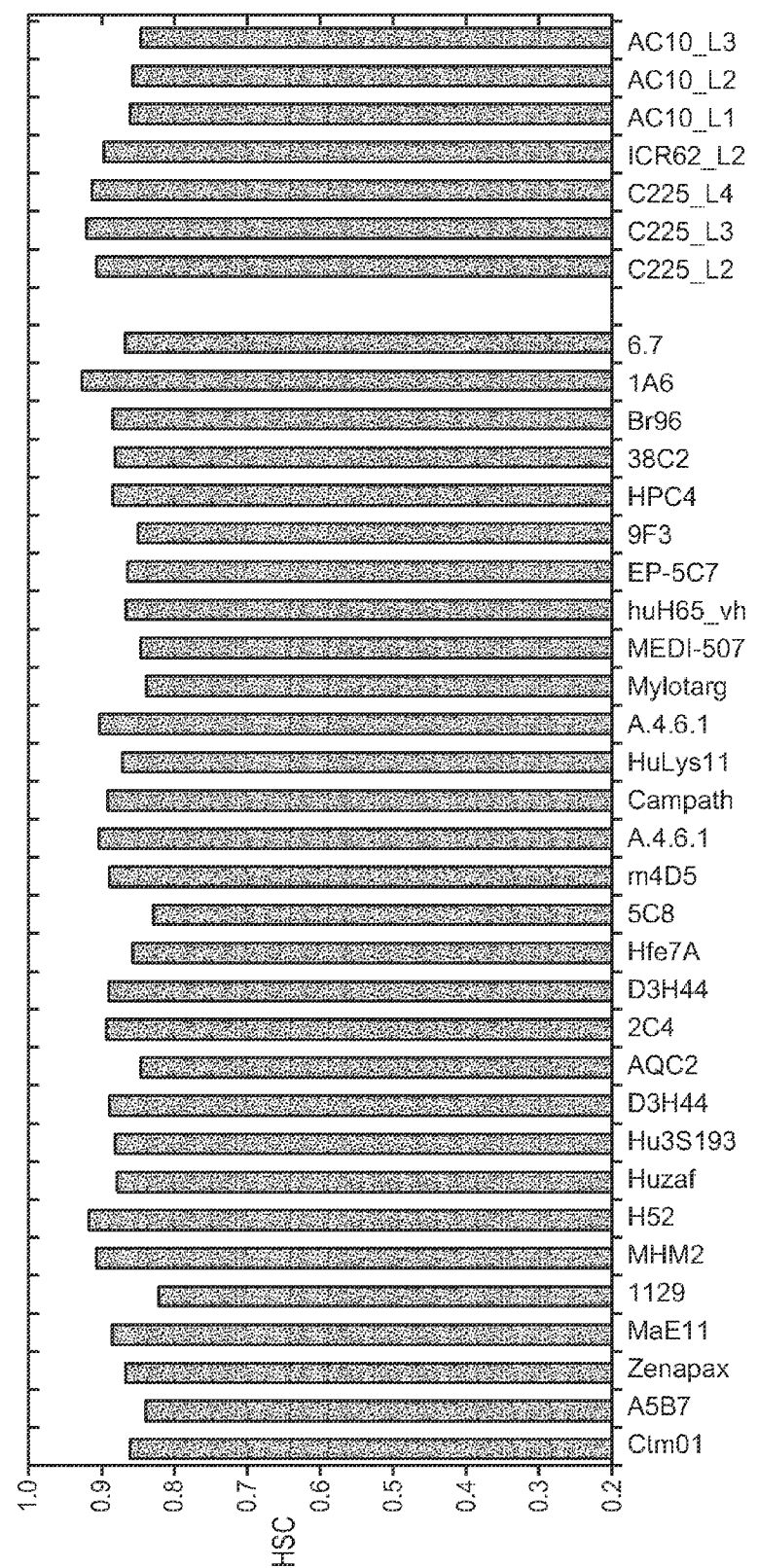
FIG. 52*a* provides the host string content (HSC) as defined by equation 3, FIG. 52*b* provides the exact string content (ESC) as defined by equation 3a, and FIG. 52*c* provides the framework region homogeneity (FRH) as defined by equation 10. Window size w was 9 for all calculations.
Figure 52B:
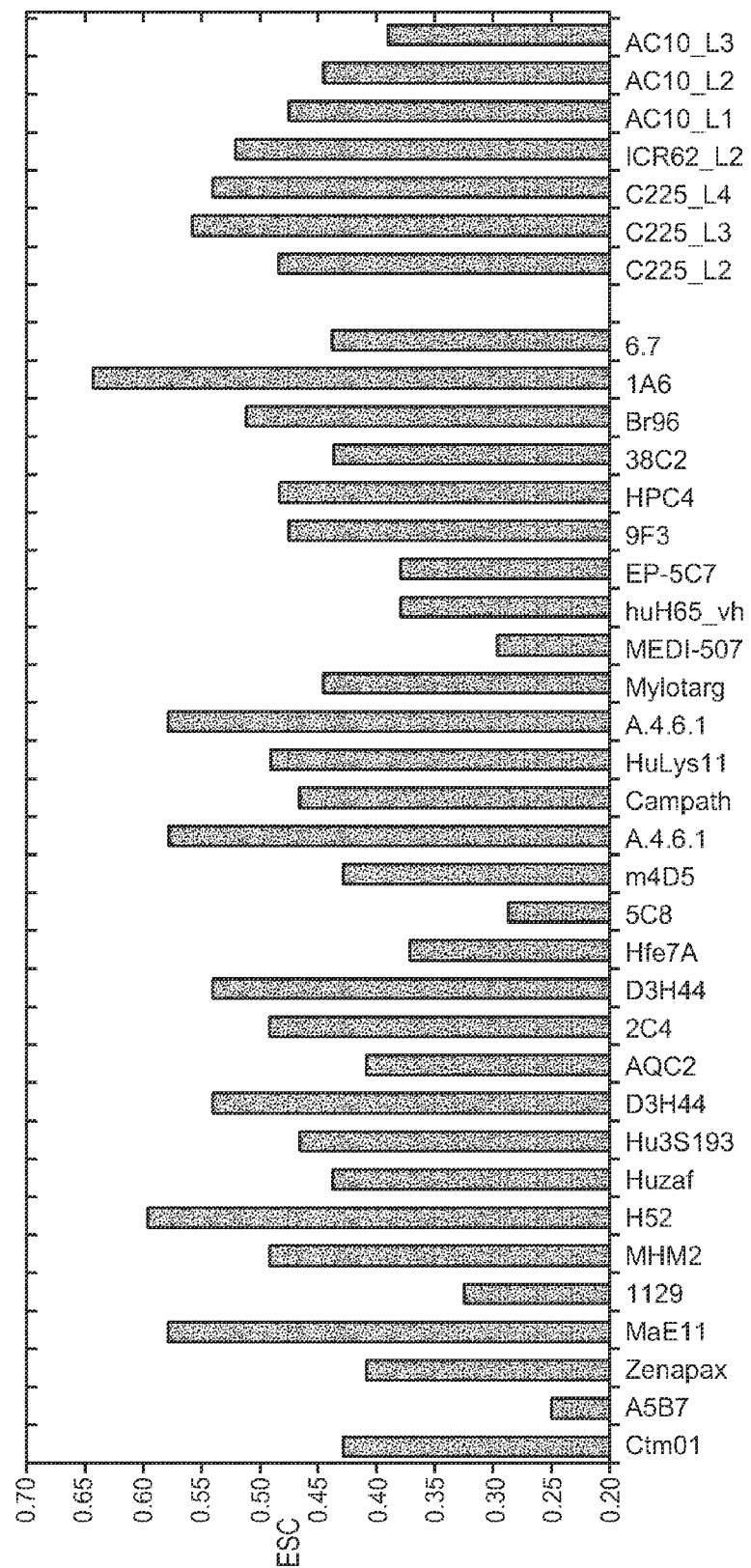
FIG. 52. Comparison of VL sequences humanized by the methods in the prior art versus the present method. Prior art antibodies include Ctm01, A5B7, Zenapax, MaE11, 1129, MHM2, H52, Huzaf, Hu3S193, D3H44, AQC2, 2C4, D3H44, Hfe7A, 5C8, m4D5, A.4.6.1, Campath, HuLys11, A.4.6.1, Mylotarg, MEDI-507, huH65_vh, EP–5C7, 9F3, HPC4, 38C2, Br96, 1A6, and 6.7. Sequences designed using the present invention, including AC10 L1, L2, and L3, C225 L2, L3, L4, and ICR62 L2, are offset to the right.
Figure 52C:
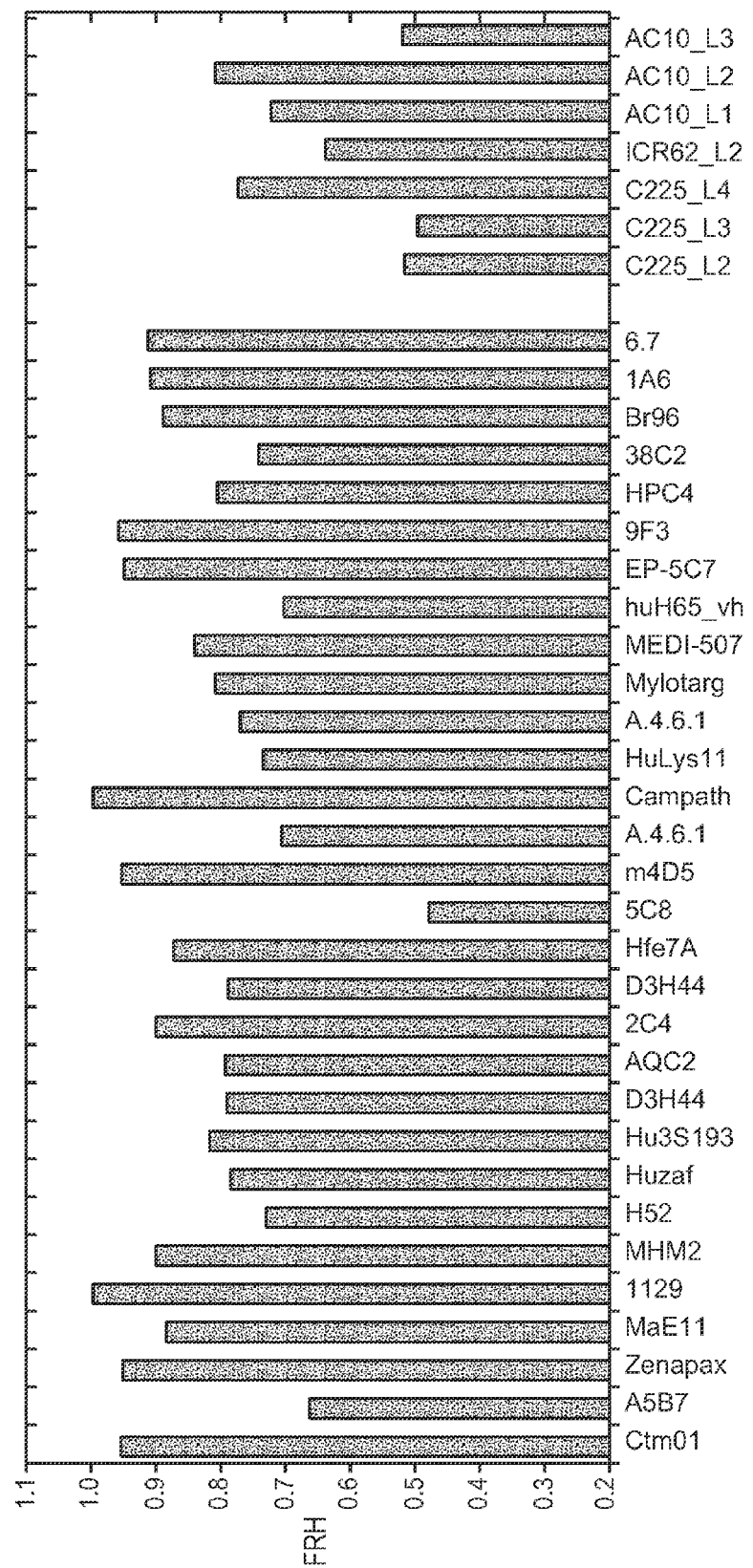

Unique Properties of Variant Proteins Generated by the Methods of the Present Invention The methods described in the present invention generate variant proteins that possess a number of unique properties relative to variant proteins generated by other methods that attempt to achieve the same or similar goal. FIGS. 51 and 52 provide the host string content (HSC, Equation 3), exact string content (ESC, Equation 3a), and framework region homogeneity (FRH, Equation 10) of the AC10, C225, and ICR62 VH (FIG. 51) and VL (FIG. 52) variants of the present invention, compared with a number of antibody variable regions "humanized" by methods in the prior art. If a variant sequence's exact string content is derived solely from a single germline sequence, the FRH would be close to 1.0. Alternatively, as is the case with many of the variant sequences created by the present invention, FRH values can be significantly less than 1, with values ranging from 0.4 to 1.0, indicating, as expected, that sequences with high exact string content can be discovered with contributions from multiple germline subfamilies and sequences. At the same time, the variant sequences engineered using the present invention have high host string content, and thus are predicted to have low potential for immunogenicity in humans. For example, as shown in FIG. 51 variant VH sequences generated using the present invention have HSC values generally higher than 75%, and many of them have FRH values lower than 0.6, indicating their HSC is derived from multiple germline frameworks. As shown in FIG. 52, similar trends apply for variant VL sequences generated using the present invention Whereas particular embodiments of the invention have been described above for purposes of illustration, it will be appreciated by those skilled in the art that numerous variations of the details may be made without departing from the invention as described in the appended claims. All references are herein expressly incorporated by reference.

---

We claim:

1. A method of generating a variant host species antibody variable region as compared to a non-host species antibody variable region, comprising:

A. aligning said non-host species antibody variable region sequence with two or more naturally occurring host species antibody variable region sequences;

B. defining mutational constraints in said non-host species antibody variable region sequence, C. performing until no sequence segment substitution has a favorable string impact on host species string content, i. comparing, for an effect on host species string content, one or more sequence segments of each of said host species antibody variable region sequences to the structurally corresponding sequence segment of said non-host species antibody variable region sequence; and, ii. substituting one sequence segment of said non-host species antibody variable region sequence with a structurally corresponding sequence segment of one of said two or more host species antibody variable region sequences, wherein said substituted sequence segment increases host species string content, wherein said variant host species antibody variable region has increased host species string content as compared to said non-host species antibody variable region, wherein said comparing uses a string window size that is greater than or equal to 9, and, wherein at least one framework region of said variant host species antibody variable region includes a first sequence segment substitution from a first naturally occurring antibody variable region sequence from said two or more naturally occurring host species antibody variable region sequences, and a second sequence segment substitution from a second naturally occurring antibody variable region sequence from said two or more naturally occurring host species antibody variable region sequences, where said host species string content (HSC) is measured by an equation functionally equivalent to:

$$HSC(s) = 100 \cdot \frac{1}{(L-w+1) \cdot w} \sum_{i=1}^{L-w+1} \max_{h \in HS}\left(\sum_{j=i}^{i+w-1} \delta_{aa_j^s, aa_j^h}\right);$$

where L is the length of the sequence, w is the string window size, HS is the set of homologous host species sequences, i is the first position in the string, $aa_j^s$ is the amino acid at position j of sequence s, $aa_j^h$ is the amino acid at position j of the host species sequence h, and the Kronecker delta function is used to return a value of 1 for a match and 0 if there is no match, and, where said string impact (SI) is measured by an equation functionally equivalent to: $SI(x_m(z) \rightarrow y_m(z)) = HSC(s(y_m)) - HSC(parent)$, where $y_m(z)$ is a host species segment of length z replacing segment x at position m, and $s(y_m)$ is a variant of the non-host species sequence that include segment $y_m(z)$, and D. physically synthesizing an antibody comprising said variant host species antibody variable region sequence and screening said antibody.

2. The method according to claim 1, wherein one of said sequence segment substitutions is not the corresponding sequence segment from the most homologous natural sequence.

3. The method according to claim 1, wherein one of the sequence segment substitutions is not the structurally corresponding sequence segment from a consensus of homologous natural sequences.

4. The method according to claim 1, wherein one of the sequence segment substitutions is made at a position that is not surface exposed.

5. The method according to claim 1, wherein more than one variant host species antibody variable region is generated from said method to form a variant host species antibody variable region set.

6. The method according to claim 1, wherein said variant host species antibody variable region set comprises at least two variant host species antibody variable regions that differ by more than about 5 amino acids.

7. The method according to claim 1 wherein said string window size is nine amino acids in length.

8. A method of generating a variant host species antibody variable region as compared to a non-host species antibody variable region, comprising:

A. aligning said non-host species antibody variable region sequence with two or more naturally occurring host species antibody variable region sequences;

B. defining mutational constraints in said non-host species antibody variable region sequence, C. performing until no sequence segment substitution has a favorable string impact on host species string content, i. comparing, for an effect on host species string content, one or more sequence segments of each of said host species antibody variable region sequences to the structurally corresponding sequence segment of said non-host species antibody variable region sequence; and ii. substituting one sequence segment of said non-host species antibody variable region sequence with a structurally corresponding sequence segment of one of said two or more host species antibody variable region sequences, wherein said substituted sequence segment increases host species string content relative to said non-host species antibody variable region, wherein said comparing uses a string window size that is greater than or equal to 9 and less than or equal to 20, and, where said host species string content (HSC) is measured by an equation functionally equivalent to:

$$HSC(s) = 100 \cdot \frac{1}{(L-w+1) \cdot w} \sum_{i=1}^{L-w+1} \max_{h \in HS} \left( \sum_{j=i}^{i+w-1} \delta_{aa_j^s, aa_j^h} \right),$$

where L is the length of the sequence, w is the string window size, HS is the set of homologous host species sequences, i is the first position in the string, $aa_j^s$ is the amino acid at position j of sequence s, $aa_j^h$ is the amino acid at position j of the host species sequence h, and the Kronecker delta function is used to return a value of 1 for a match and 0 if there is no match, and, where said string impact (SI) is measured by an equation functionally equivalent to: $SI(x_m(z) \rightarrow y_m(z)) = HSC(s(y_m)) - HSC(parent)$, where $y_m(z)$ is a host species segment of length z replacing segment x at position m, and $s(y_m)$ is a variant of the non-host species sequence that include segment $y_m(z)$, and D. physically synthesizing an antibody comprising said variant host species antibody variable region sequence and screening said antibody.

9. The method according to claim 8, wherein one of said sequence segment substitutions is not the corresponding sequence segment from the most homologous natural sequence.

10. The method according to claim 8, wherein one of the sequence segment substitutions is not the structurally corresponding sequence segment from a consensus of homologous natural sequences.

11. The method according to claim 8, wherein one of the sequence segment substitutions is made at a position that is not surface exposed.

12. The method according to claim 8, wherein more than one variant host species antibody variable region is generated from said method to form a variant host species antibody variable region set.

13. The method according to claim 12, wherein said variant host species antibody variable region set comprises at least two variant host species antibody variable regions that differ by more than about 5 amino acids.

14. The method according to claim 8, wherein said string window size is nine amino acids in length.

* * * * *

SEQUENCE LISTING

<160> NUMBER OF SEQ ID NOS: 458

<210> SEQ ID NO 1
<211> LENGTH: 98
<212> TYPE: PRT
<213> ORGANISM: Homo sapiens

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Ser Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg

<210> SEQ ID NO 2
<211> LENGTH: 98
<212> TYPE: PRT
<213> ORGANISM: Homo sapiens

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 3
<211> LENGTH: 98
<212> TYPE: PRT
<213> ORGANISM: Homo sapiens

<400> SEQUENCE: 3

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Asp Ile Asn Trp Val Arg Gln Ala Thr Gly Gln Gly Leu Glu Trp Met
        35                  40                  45
Gly Trp Met Asn Pro Asn Ser Gly Asn Thr Gly Tyr Ala Gln Lys Phe
    50                  55                  60
Gln Gly Arg Val Thr Met Thr Arg Asn Thr Ser Ile Ser Thr Ala Tyr
65                  70                  75                  80
Met Glu Leu Ser Ser Leu Arg Ser Glu Asp Thr Ala Val Tyr Tyr Cys
                85                  90                  95
Ala Arg
```

<210> SEQ ID NO 4
<211> LENGTH: 98
<212> TYPE: PRT
<213> ORGANISM: Homo sapiens

<400> SEQUENCE: 4

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Gly Ile Ser Trp Val Arg Gln Ala Pro Gly Gln Gly Leu Glu Trp Met
        35                  40                  45
Gly Trp Ile Ser Ala Tyr Asn Gly Asn Thr Asn Tyr Ala Gln Lys Leu
    50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg
```

<210> SEQ ID NO 5
<211> LENGTH: 98
<212> TYPE: PRT
<213> ORGANISM: Homo sapiens

<400> SEQUENCE: 5

```
Gln Val Gln Leu Val Gln Ser Gly Ala Glu Val Lys Lys Pro Gly Ala
1               5                   10                  15
Ser Val Lys Val Ser Cys Lys Val Ser Gly Tyr Thr Leu Thr Glu Leu
            20                  25                  30
Ser Met His Trp Val Arg Gln Ala Pro Gly Lys Gly Leu Glu Trp Met
        35                  40                  45
Gly Gly Phe Asp Pro Glu Asp Gly Glu Thr Ile Tyr Ala Gln Lys Phe
    50                  55                  60
Gln Gly Arg Val Thr Met Thr Glu Asp Thr Ser Thr Asp Thr Ala Tyr
65                  70                  75                  80
Met Glu Leu Ser Ser Leu Arg Ser Glu Asp Thr Ala Val Tyr Tyr Cys
                85                  90                  95
Ala Thr
```

```
<210> SEQ ID NO 6
<211> LENGTH: 98
<212> TYPE: PRT
<213> ORGANISM: Homo sapiens

<400> SEQUENCE: 6

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Tyr Arg
            20                  25                  30

Tyr Leu His Trp Val Arg Gln Ala Pro Gly Gln Ala Leu Glu Trp Met
        35                  40                  45

Gly Trp Ile Thr Pro Phe Asn Gly Asn Thr Asn Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Ala Arg

<210> SEQ ID NO 7
<211> LENGTH: 98
<212> TYPE: PRT
<213> ORGANISM: Homo sapiens

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 8
<211> LENGTH: 98
<212> TYPE: PRT
<213> ORGANISM: Homo sapiens

<400> SEQUENCE: 8

Gln Met Gln Leu Val Gln Ser Gly Pro Glu Val Lys Lys Pro Gly Thr
1               5                   10                  15

Ser Val Lys Val Ser Cys Lys Ala Ser Gly Phe Thr Phe Thr Ser Ser
            20                  25                  30

Ala Val Gln Trp Val Arg Gln Ala Arg Gly Gln Arg Leu Glu Trp Ile
        35                  40                  45

Gly Trp Ile Val Val Gly Ser Gly Asn Thr Asn Tyr Ala Gln Lys Phe
    50                  55                  60

Gln Glu Arg Val Thr Ile Thr Arg Asp Met Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Ala

<210> SEQ ID NO 9
<211> LENGTH: 98
<212> TYPE: PRT
<213> ORGANISM: Homo sapiens

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 10
<211> LENGTH: 98
<212> TYPE: PRT
<213> ORGANISM: Homo sapiens

<400> SEQUENCE: 10

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr

<210> SEQ ID NO 11
<211> LENGTH: 100
<212> TYPE: PRT
<213> ORGANISM: Homo sapiens

<400> SEQUENCE: 11

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val

```
                 65                  70                  75                  80
Val Leu Thr Met Thr Asn Met Asp Pro Val Asp Thr Ala Thr Tyr Tyr
                 85                  90                  95

Cys Ala His Arg
            100

<210> SEQ ID NO 12
<211> LENGTH: 100
<212> TYPE: PRT
<213> ORGANISM: Homo sapiens

<400> SEQUENCE: 12

Gln Val Thr Leu Lys Glu Ser Gly Pro Val Leu Val Lys Pro Thr Glu
1                5                  10                  15

Thr Leu Thr Leu Thr Cys Thr Val Ser Gly Phe Ser Leu Ser Asn Ala
                 20                  25                  30

Arg Met Gly Val Ser Trp Ile Arg Gln Pro Pro Gly Lys Ala Leu Glu
             35                  40                  45

Trp Leu Ala His Ile Phe Ser Asn Asp Glu Lys Ser Tyr Ser Thr Ser
     50                  55                  60

Leu Lys Ser Arg Leu Thr Ile Ser Lys Asp Thr Ser Lys Ser Gln Val
65                   70                  75                  80

Val Leu Thr Met Thr Asn Met Asp Pro Val Thr Ala Thr Tyr Tyr
                 85                  90                  95

Cys Ala Arg Ile
            100

<210> SEQ ID NO 13
<211> LENGTH: 100
<212> TYPE: PRT
<213> ORGANISM: Homo sapiens

<400> SEQUENCE: 13

Gln Val Thr Leu Arg Glu Ser Gly Pro Ala Leu Val Lys Pro Thr Gln
1                5                  10                  15

Thr Leu Thr Leu Thr Cys Thr Phe Ser Gly Phe Ser Leu Ser Thr Ser
                 20                  25                  30

Gly Met Cys Val Ser Trp Ile Arg Gln Pro Pro Gly Lys Ala Leu Glu
             35                  40                  45

Trp Leu Ala Leu Ile Asp Trp Asp Asp Asp Lys Tyr Tyr Ser Thr Ser
     50                  55                  60

Leu Lys Thr Arg Leu Thr Ile Ser Lys Asp Thr Ser Lys Asn Gln Val
65                   70                  75                  80

Val Leu Thr Met Thr Asn Met Asp Pro Val Asp Thr Ala Thr Tyr Tyr
                 85                  90                  95

Cys Ala Arg Ile
            100

<210> SEQ ID NO 14
<211> LENGTH: 98
<212> TYPE: PRT
<213> ORGANISM: Homo sapiens

<400> SEQUENCE: 14

Glu Val Gln Leu Val Glu Ser Gly Gly Gly Leu Val Gln Pro Gly Gly
1                5                  10                  15

Ser Leu Arg Leu Ser Cys Ala Ala Ser Gly Phe Thr Phe Ser Ser Tyr
                 20                  25                  30
```

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg

<210> SEQ ID NO 15
<211> LENGTH: 99
<212> TYPE: PRT
<213> ORGANISM: Homo sapiens

<400> SEQUENCE: 15

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
 50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
            85                  90                  95

Ala Lys Asp

<210> SEQ ID NO 16
<211> LENGTH: 98
<212> TYPE: PRT
<213> ORGANISM: Homo sapiens

<400> SEQUENCE: 16

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
 50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg

<210> SEQ ID NO 17
<211> LENGTH: 97
<212> TYPE: PRT
<213> ORGANISM: Homo sapiens

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
            35                  40                  45

Ser Ala Ile Gly Thr Ala Gly Asp Thr Tyr Tyr Pro Gly Ser Val Lys
50                      55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg

<210> SEQ ID NO 18
<211> LENGTH: 100
<212> TYPE: PRT
<213> ORGANISM: Homo sapiens

<400> SEQUENCE: 18

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
            35                  40                  45

Gly Arg Ile Lys Ser Lys Thr Asp Gly Gly Thr Thr Asp Tyr Ala Ala
50                      55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr
            100

<210> SEQ ID NO 19
<211> LENGTH: 98
<212> TYPE: PRT
<213> ORGANISM: Homo sapiens

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ser
            20                  25                  30

Asp Met Asn Trp Ala Arg Lys Ala Pro Gly Lys Gly Leu Glu Trp Val
            35                  40                  45

Ser Gly Val Ser Trp Asn Gly Ser Arg Thr His Tyr Val Asp Ser Val
50                      55                  60

Lys Arg Arg Phe Ile Ile Ser Arg Asp Asn Arg Asn Ser Leu Tyr
65                  70                  75                  80

Leu Gln Lys Asn Arg Arg Ala Glu Asp Met Ala Val Tyr Tyr Cys
                85                  90                  95

Val Arg

<210> SEQ ID NO 20
<211> LENGTH: 98
<212> TYPE: PRT
<213> ORGANISM: Homo sapiens

<400> SEQUENCE: 20

Thr Val Gln Leu Val Glu Ser Gly Gly Gly Leu Val Glu Pro Gly Gly
1               5                   10                  15

Ser Leu Arg Leu Ser Cys Ala Ala Ser Gly Phe Thr Phe Ser Asn Ser
            20                  25                  30

Asp Met Asn Trp Val Arg Gln Ala Pro Gly Lys Gly Leu Glu Trp Val
        35                  40                  45

Ser Gly Val Ser Trp Asn Gly Ser Arg Thr His Tyr Ala Asp Ser Val
    50                  55                  60

Lys Gly Arg Phe Ile Ile Ser Arg Asp Asn Ser Arg Asn Phe Leu Tyr
65                  70                  75                  80

Gln Gln Met Asn Ser Leu Arg Pro Glu Asp Met Ala Val Tyr Tyr Cys
                85                  90                  95

Val Arg

<210> SEQ ID NO 21
<211> LENGTH: 98
<212> TYPE: PRT
<213> ORGANISM: Homo sapiens

<400> SEQUENCE: 21

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg

<210> SEQ ID NO 22
<211> LENGTH: 98
<212> TYPE: PRT
<213> ORGANISM: Homo sapiens

<400> SEQUENCE: 22

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

```
<210> SEQ ID NO 23
<211> LENGTH: 98
<212> TYPE: PRT
<213> ORGANISM: Homo sapiens

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 24
<211> LENGTH: 98
<212> TYPE: PRT
<213> ORGANISM: Homo sapiens

<400> SEQUENCE: 24

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 25
<211> LENGTH: 98
<212> TYPE: PRT
<213> ORGANISM: Homo sapiens

<400> SEQUENCE: 25

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg

<210> SEQ ID NO 26
<211> LENGTH: 98
<212> TYPE: PRT
<213> ORGANISM: Homo sapiens

<400> SEQUENCE: 26

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 27
<211> LENGTH: 98
<212> TYPE: PRT
<213> ORGANISM: Homo sapiens

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ser
            20                  25                  30

Asp Met Asn Trp Val His Gln Ala Pro Gly Lys Gly Leu Glu Trp Val
        35                  40                  45

Ser Gly Val Ser Trp Asn Gly Ser Arg Thr His Tyr Ala Asp Ser Val
    50                  55                  60

Lys Gly Arg Phe Ile Ile Ser Arg Asp Asn Ser Arg Asn Thr Leu Tyr
65                  70                  75                  80

Leu Gln Thr Asn Ser Leu Arg Ala Glu Asp Thr Ala Val Tyr Tyr Cys
                85                  90                  95

Val Arg

<210> SEQ ID NO 28
<211> LENGTH: 97
<212> TYPE: PRT
<213> ORGANISM: Homo sapiens

<400> SEQUENCE: 28

Glu Val Gln Leu Val Glu Ser Gly Gly Gly Leu Val Gln Pro Arg Gly
1               5                   10                  15

Ser Leu Arg Leu Ser Cys Ala Ala Ser Gly Phe Thr Val Ser Ser Asn
            20                  25                  30

Glu Met Ser Trp Ile Arg Gln Ala Pro Gly Lys Gly Leu Glu Trp Val
        35                  40                  45

Ser Ser Ile Ser Gly Gly Ser Thr Tyr Tyr Ala Asp Ser Arg Lys Gly
    50                  55                  60

Arg Phe Thr Ile Ser Arg Asp Asn Ser Lys Asn Thr Leu Tyr Leu Gln

-continued

```
                65                  70                  75                  80
Met Asn Asn Leu Arg Ala Glu Gly Thr Ala Tyr Tyr Cys Ala Arg
                    85                  90                  95

Tyr

<210> SEQ ID NO 29
<211> LENGTH: 99
<212> TYPE: PRT
<213> ORGANISM: Homo sapiens

<400> SEQUENCE: 29

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Asp Asp Tyr
            20                  25                  30

Thr Met His Trp Val Arg Gln Ala Pro Gly Lys Gly Leu Glu Trp Val
        35                  40                  45

Ser Leu Ile Ser Trp Asp Gly Ser Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Lys Asp

<210> SEQ ID NO 30
<211> LENGTH: 98
<212> TYPE: PRT
<213> ORGANISM: Homo sapiens

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 31
<211> LENGTH: 100
<212> TYPE: PRT
<213> ORGANISM: Homo sapiens

<400> SEQUENCE: 31

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45
```

```
Gly Phe Ile Arg Ser Lys Ala Tyr Gly Gly Thr Thr Glu Tyr Thr Ala
        50                  55                  60

Ser Val Lys Gly Arg Phe Thr Ile Ser Arg Asp Gly Ser Lys Ser Ile
 65                  70                  75                  80

Ala Tyr Leu Gln Met Asn Ser Leu Lys Thr Glu Asp Thr Ala Val Tyr
                    85                  90                  95

Tyr Cys Thr Arg
            100
```

<210> SEQ ID NO 32
<211> LENGTH: 97
<212> TYPE: PRT
<213> ORGANISM: Homo sapiens

<400> SEQUENCE: 32

```
Glu Val Gln Leu Val Glu Ser Gly Gly Gly Leu Ile Gln Pro Gly Gly
 1               5                   10                  15

Ser Leu Arg Leu Ser Cys Ala Ala Ser Gly Phe Thr Val Ser Ser Asn
                20                  25                  30

Tyr Met Ser Trp Val Arg Gln Ala Pro Gly Lys Gly Leu Glu Trp Val
            35                  40                  45

Ser Val Ile Tyr Ser Gly Gly Ser Thr Tyr Tyr Ala Asp Ser Val Lys
        50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                    85                  90                  95

Arg
```

<210> SEQ ID NO 33
<211> LENGTH: 98
<212> TYPE: PRT
<213> ORGANISM: Homo sapiens

<400> SEQUENCE: 33

```
Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Tyr Val
            35                  40                  45

Ser Ala Ile Ser Ser Asn Gly Gly Ser Thr Tyr Tyr Ala Asn Ser Val
        50                  55                  60

Lys Gly Arg Phe Thr Ile Ser Arg Asp Asn Ser Lys Asn Thr Leu Tyr
 65                  70                  75                  80

Leu Gln Met Gly Ser Leu Arg Ala Glu Asp Met Ala Val Tyr Tyr Cys
                    85                  90                  95

Ala Arg
```

<210> SEQ ID NO 34
<211> LENGTH: 97
<212> TYPE: PRT
<213> ORGANISM: Homo sapiens

<400> SEQUENCE: 34

```
Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Val Ser Ser Asn
```

```
                    20                  25                  30
Tyr Met Ser Trp Val Arg Gln Ala Pro Gly Lys Gly Leu Glu Trp Val
                35                  40                  45
Ser Val Ile Tyr Ser Gly Gly Ser Thr Tyr Tyr Ala Asp Ser Val Lys
            50                  55                  60
Gly Arg Phe Thr Ile Ser Arg Asp Asn Ser Lys Asn Thr Leu Tyr Leu
65                  70                  75                  80
Gln Met Asn Ser Leu Arg Ala Glu Asp Thr Ala Val Tyr Tyr Cys Ala
                85                  90                  95
Arg

<210> SEQ ID NO 35
<211> LENGTH: 100
<212> TYPE: PRT
<213> ORGANISM: Homo sapiens

<400> SEQUENCE: 35

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asp His
                20                  25                  30
Tyr Met Asp Trp Val Arg Gln Ala Pro Gly Lys Gly Leu Glu Trp Val
                35                  40                  45
Gly Arg Thr Arg Asn Lys Ala Asn Ser Tyr Thr Thr Glu Tyr Ala Ala
            50                  55                  60
Ser Val Lys Gly Arg Phe Thr Ile Ser Arg Asp Asp Ser Lys Asn Ser
65                  70                  75                  80
Leu Tyr Leu Gln Met Asn Ser Leu Lys Thr Glu Asp Thr Ala Val Tyr
                85                  90                  95
Tyr Cys Ala Arg
            100

<210> SEQ ID NO 36
<211> LENGTH: 100
<212> TYPE: PRT
<213> ORGANISM: Homo sapiens

<400> SEQUENCE: 36

Glu Val Gln Leu Val Glu Ser Gly Gly Gly Leu Val Gln Pro Gly Gly
1               5                   10                  15
Ser Leu Lys Leu Ser Cys Ala Ala Ser Gly Phe Thr Phe Ser Gly Ser
                20                  25                  30
Ala Met His Trp Val Arg Gln Ala Ser Gly Lys Gly Leu Glu Trp Val
                35                  40                  45
Gly Arg Ile Arg Ser Lys Ala Asn Ser Tyr Ala Thr Ala Tyr Ala Ala
            50                  55                  60
Ser Val Lys Gly Arg Phe Thr Ile Ser Arg Asp Asp Ser Lys Asn Thr
65                  70                  75                  80
Ala Tyr Leu Gln Met Asn Ser Leu Lys Thr Glu Asp Thr Ala Val Tyr
                85                  90                  95
Tyr Cys Thr Arg
            100

<210> SEQ ID NO 37
<211> LENGTH: 98
<212> TYPE: PRT
<213> ORGANISM: Homo sapiens
```

-continued

<400> SEQUENCE: 37

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg
```

<210> SEQ ID NO 38
<211> LENGTH: 96
<212> TYPE: PRT
<213> ORGANISM: Homo sapiens

<400> SEQUENCE: 38

```
Glu Val Gln Leu Val Glu Ser Arg Gly Val Leu Val Gln Pro Gly Gly
1               5                   10                  15

Ser Leu Arg Leu Ser Cys Ala Ala Ser Gly Phe Thr Val Ser Ser Asn
            20                  25                  30

Glu Met Ser Trp Val Arg Gln Ala Pro Gly Lys Gly Leu Glu Trp Val
        35                  40                  45

Ser Ser Ile Ser Gly Gly Ser Thr Tyr Tyr Ala Asp Ser Arg Lys Gly
    50                  55                  60

Arg Phe Thr Ile Ser Arg Asp Asn Ser Lys Asn Thr Leu His Leu Gln
65                  70                  75                  80

Met Asn Ser Leu Arg Ala Glu Asp Thr Ala Val Tyr Tyr Cys Lys Lys
                85                  90                  95
```

<210> SEQ ID NO 39
<211> LENGTH: 98
<212> TYPE: PRT
<213> ORGANISM: Homo sapiens

<400> SEQUENCE: 39

```
Gln Val Gln Leu Gln Glu Ser Gly Pro Gly Leu Val Lys Pro Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Cys Cys
                85                  90                  95

Ala Arg
```

<210> SEQ ID NO 40
<211> LENGTH: 98
<212> TYPE: PRT

<213> ORGANISM: Homo sapiens

<400> SEQUENCE: 40

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Ser Ser Ser
            20                  25                  30

Asn Trp Trp Gly Trp Ile Arg Gln Pro Pro Gly Lys Gly Leu Glu Trp
        35                  40                  45

Ile Gly Tyr Ile Tyr Tyr Ser Gly Ser Thr Tyr Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg

<210> SEQ ID NO 41
<211> LENGTH: 99
<212> TYPE: PRT
<213> ORGANISM: Homo sapiens

<400> SEQUENCE: 41

Gln Leu Gln Leu Gln Glu Ser Gly Ser Gly Leu Val Lys Pro Ser Gln
1               5                   10                  15

Thr Leu Ser Leu Thr Cys Ala Val Ser Gly Gly Ser Ile Ser Ser Gly
            20                  25                  30

Gly Tyr Ser Trp Ser Trp Ile Arg Gln Pro Pro Gly Lys Gly Leu Glu
        35                  40                  45

Trp Ile Gly Tyr Ile Tyr His Ser Gly Ser Thr Tyr Tyr Asn Pro Ser
    50                  55                  60

Leu Lys Ser Arg Val Thr Ile Ser Val Asp Arg Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 42
<211> LENGTH: 99
<212> TYPE: PRT
<213> ORGANISM: Homo sapiens

<400> SEQUENCE: 42

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 43
<211> LENGTH: 99
<212> TYPE: PRT
<213> ORGANISM: Homo sapiens

<400> SEQUENCE: 43

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Leu Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 44
<211> LENGTH: 97
<212> TYPE: PRT
<213> ORGANISM: Homo sapiens

<400> SEQUENCE: 44

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 45
<211> LENGTH: 99
<212> TYPE: PRT
<213> ORGANISM: Homo sapiens

<400> SEQUENCE: 45

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr

Cys Ala Arg

<210> SEQ ID NO 46
<211> LENGTH: 97
<212> TYPE: PRT
<213> ORGANISM: Homo sapiens

<400> SEQUENCE: 46

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 47
<211> LENGTH: 99
<212> TYPE: PRT
<213> ORGANISM: Homo sapiens

<400> SEQUENCE: 47

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 48
<211> LENGTH: 98
<212> TYPE: PRT
<213> ORGANISM: Homo sapiens

<400> SEQUENCE: 48

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

```
Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg

<210> SEQ ID NO 49
<211> LENGTH: 98
<212> TYPE: PRT
<213> ORGANISM: Homo sapiens

<400> SEQUENCE: 49

Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Ser Tyr
                 20                  25                  30

Trp Ile Gly Trp Val Arg Gln Met Pro Gly Lys Gly Leu Glu Trp Met
             35                  40                  45

Gly Ile Ile Tyr Pro Gly Asp Ser Asp Thr Arg Tyr Ser Pro Ser Phe
         50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg

<210> SEQ ID NO 50
<211> LENGTH: 98
<212> TYPE: PRT
<213> ORGANISM: Homo sapiens

<400> SEQUENCE: 50

Glu Val Gln Leu Val Gln Ser Gly Ala Glu Val Lys Lys Pro Gly Glu
  1               5                  10                  15

Ser Leu Arg Ile Ser Cys Lys Gly Ser Gly Tyr Ser Phe Thr Ser Tyr
                 20                  25                  30

Trp Ile Ser Trp Val Arg Gln Met Pro Gly Lys Gly Leu Glu Trp Met
             35                  40                  45

Gly Arg Ile Asp Pro Ser Asp Ser Tyr Thr Asn Tyr Ser Pro Ser Phe
         50                  55                  60

Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg

<210> SEQ ID NO 51
<211> LENGTH: 101
<212> TYPE: PRT
<213> ORGANISM: Homo sapiens

<400> SEQUENCE: 51

Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asn
                 20                  25                  30

Ser Ala Ala Trp Asn Trp Ile Arg Gln Ser Pro Ser Arg Gly Leu Glu
             35                  40                  45
```

```
Trp Leu Gly Arg Thr Tyr Tyr Arg Ser Lys Trp Tyr Asn Asp Tyr Ala
    50                  55                  60
Val Ser Val Lys Ser Arg Ile Thr Ile Asn Pro Asp Thr Ser Lys Asn
65                  70                  75                  80
Gln Phe Ser Leu Gln Leu Asn Ser Val Thr Pro Glu Asp Thr Ala Val
                85                  90                  95
Tyr Tyr Cys Ala Arg
            100

<210> SEQ ID NO 52
<211> LENGTH: 98
<212> TYPE: PRT
<213> ORGANISM: Homo sapiens

<400> SEQUENCE: 52

Gln Val Gln Leu Val Gln Ser Gly Ser Glu Leu Lys Lys Pro Gly Ala
1               5                   10                  15
Ser Val Lys Val Ser Cys Lys Ala Ser Gly Tyr Thr Phe Thr Ser Tyr
                20                  25                  30
Ala Met Asn Trp Val Arg Gln Ala Pro Gly Gln Gly Leu Glu Trp Met
            35                  40                  45
Gly Trp Ile Asn Thr Asn Thr Gly Asn Pro Thr Tyr Ala Gln Gly Phe
    50                  55                  60
Thr Gly Arg Phe Val Phe Ser Leu Asp Thr Ser Val Ser Thr Ala Tyr
65                  70                  75                  80
Leu Gln Ile Cys Ser Leu Lys Ala Glu Asp Thr Ala Val Tyr Tyr Cys
                85                  90                  95
Ala Arg

<210> SEQ ID NO 53
<211> LENGTH: 98
<212> TYPE: PRT
<213> ORGANISM: Homo sapiens

<400> SEQUENCE: 53

Gln Val Gln Leu Val Gln Ser Gly His Glu Val Lys Gln Pro Gly Ala
1               5                   10                  15
Ser Val Lys Val Ser Cys Lys Ala Ser Gly Tyr Ser Phe Thr Thr Tyr
                20                  25                  30
Gly Met Asn Trp Val Pro Gln Ala Pro Gly Gln Gly Leu Glu Trp Met
            35                  40                  45
Gly Trp Phe Asn Thr Tyr Thr Gly Asn Pro Thr Tyr Ala Gln Gly Phe
    50                  55                  60
Thr Gly Arg Phe Val Phe Ser Met Asp Thr Ser Ala Ser Thr Ala Tyr
65                  70                  75                  80
Leu Gln Ile Ser Ser Leu Lys Ala Glu Asp Met Ala Met Tyr Tyr Cys
                85                  90                  95
Ala Arg

<210> SEQ ID NO 54
<211> LENGTH: 95
<212> TYPE: PRT
<213> ORGANISM: Homo sapiens

<400> SEQUENCE: 54

Asp Ile Gln Met Thr Gln Ser Pro Ser Thr Leu Ser Ala Ser Val Gly
1               5                   10                  15
```

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser
                85                  90                  95

<210> SEQ ID NO 55
<211> LENGTH: 95
<212> TYPE: PRT
<213> ORGANISM: Homo sapiens

<400> SEQUENCE: 55

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro
                85                  90                  95

<210> SEQ ID NO 56
<211> LENGTH: 95
<212> TYPE: PRT
<213> ORGANISM: Homo sapiens

<400> SEQUENCE: 56

Ala Ile Arg Met Thr Gln Ser Pro Ser Ser Phe Ser Ala Ser Thr Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Tyr Tyr Ser Tyr Pro
                85                  90                  95

<210> SEQ ID NO 57
<211> LENGTH: 95
<212> TYPE: PRT
<213> ORGANISM: Homo sapiens

<400> SEQUENCE: 57

Val Ile Trp Met Thr Gln Ser Pro Ser Leu Leu Ser Ala Ser Thr Gly
1               5                   10                  15

Asp Arg Val Thr Ile Ser Cys Arg Met Ser Gln Gly Ile Ser Ser Tyr
            20                  25                  30

```
Leu Ala Trp Tyr Gln Gln Lys Pro Gly Lys Ala Pro Glu Leu Leu Ile
            35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Cys Leu Gln Ser
 65                  70                  75                  80

Glu Asp Phe Ala Thr Tyr Tyr Cys Gln Gln Tyr Tyr Ser Phe Pro
                 85                  90                  95

<210> SEQ ID NO 58
<211> LENGTH: 95
<212> TYPE: PRT
<213> ORGANISM: Homo sapiens

<400> SEQUENCE: 58

Asp Ile Gln Leu Thr Gln Ser Pro Ser Phe Leu Ser Ala Ser Val Gly
 1               5                  10                  15

Asp Arg Val Thr Ile Thr Cys Arg Ala Ser Gln Gly Ile Ser Ser Tyr
                 20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro
                 85                  90                  95

<210> SEQ ID NO 59
<211> LENGTH: 95
<212> TYPE: PRT
<213> ORGANISM: Homo sapiens

<400> SEQUENCE: 59

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
                 20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro
                 85                  90                  95

<210> SEQ ID NO 60
<211> LENGTH: 95
<212> TYPE: PRT
<213> ORGANISM: Homo sapiens

<400> SEQUENCE: 60

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
                 20                  25                  30

Leu Ala Trp Tyr Gln Gln Lys Pro Gly Lys Ala Pro Lys Leu Leu Ile
```

```
                35                  40                  45
Tyr Ala Ala Ser Ser Leu Gln Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ala Asn Ser Phe Pro
                 85                  90                  95
```

<210> SEQ ID NO 61
<211> LENGTH: 95
<212> TYPE: PRT
<213> ORGANISM: Homo sapiens

<400> SEQUENCE: 61

```
Ala Ile Gln Leu Thr Gln Ser Pro Ser Ser Leu Ser Ala Ser Val Gly
  1               5                  10                  15
Asp Arg Val Thr Ile Thr Cys Arg Ala Ser Gln Gly Ile Ser Ser Ala
                 20                  25                  30
Leu Ala Trp Tyr Gln Gln Lys Pro Gly Lys Ala Pro Lys Leu Leu Ile
                 35                  40                  45
Tyr Asp Ala Ser Ser Leu Glu Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Phe Asn Ser Tyr Pro
                 85                  90                  95
```

<210> SEQ ID NO 62
<211> LENGTH: 95
<212> TYPE: PRT
<213> ORGANISM: Homo sapiens

<400> SEQUENCE: 62

```
Ala Ile Gln Leu Thr Gln Ser Pro Ser Ser Leu Ser Ala Ser Val Gly
  1               5                  10                  15
Asp Arg Val Thr Ile Thr Cys Arg Ala Ser Gln Gly Ile Ser Ser Ala
                 20                  25                  30
Leu Ala Trp Tyr Gln Gln Lys Pro Gly Lys Ala Pro Lys Leu Leu Ile
                 35                  40                  45
Tyr Asp Ala Ser Ser Leu Glu Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Phe Asn Asn Tyr Pro
                 85                  90                  95
```

<210> SEQ ID NO 63
<211> LENGTH: 95
<212> TYPE: PRT
<213> ORGANISM: Homo sapiens

<400> SEQUENCE: 63

```
Asp Ile Gln Met Thr Gln Ser Pro Ser Ser Leu Ser Ala Ser Val Gly
  1               5                  10                  15
Asp Arg Val Thr Ile Thr Cys Arg Ala Ser Gln Gly Ile Ser Asn Tyr
                 20                  25                  30
Leu Ala Trp Phe Gln Gln Lys Pro Gly Lys Ala Pro Lys Ser Leu Ile
                 35                  40                  45
```

```
Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro
                 85                  90                  95
```

<210> SEQ ID NO 64
<211> LENGTH: 95
<212> TYPE: PRT
<213> ORGANISM: Homo sapiens

<400> SEQUENCE: 64

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro
                 85                  90                  95
```

<210> SEQ ID NO 65
<211> LENGTH: 95
<212> TYPE: PRT
<213> ORGANISM: Homo sapiens

<400> SEQUENCE: 65

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
            50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro
                 85                  90                  95
```

<210> SEQ ID NO 66
<211> LENGTH: 95
<212> TYPE: PRT
<213> ORGANISM: Homo sapiens

<400> SEQUENCE: 66

```
Asn Ile Gln Met Thr Gln Ser Pro Ser Ala Met Ser Ala Ser Val Gly
 1               5                  10                  15

Asp Arg Val Thr Ile Thr Cys Arg Ala Arg Gln Gly Ile Ser Asn Tyr
            20                  25                  30

Leu Ala Trp Phe Gln Gln Lys Pro Gly Lys Val Pro Lys His Leu Ile
            35                  40                  45

Tyr Ala Ala Ser Ser Leu Gln Ser Gly Val Pro Ser Arg Phe Ser Gly
            50                  55                  60
```

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro
                85                  90                  95

<210> SEQ ID NO 67
<211> LENGTH: 95
<212> TYPE: PRT
<213> ORGANISM: Homo sapiens

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro
                85                  90                  95

<210> SEQ ID NO 68
<211> LENGTH: 95
<212> TYPE: PRT
<213> ORGANISM: Homo sapiens

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro
                85                  90                  95

<210> SEQ ID NO 69
<211> LENGTH: 95
<212> TYPE: PRT
<213> ORGANISM: Homo sapiens

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro

```
                  65                  70                  75                  80

Glu Asp Ile Ala Thr Tyr Tyr Cys Gln Gln Tyr Asp Asn Leu Pro
                  85                  90                  95

<210> SEQ ID NO 70
<211> LENGTH: 95
<212> TYPE: PRT
<213> ORGANISM: Homo sapiens

<400> SEQUENCE: 70

Asp Ile Gln Leu Thr Gln Ser Pro Ser Ser Leu Ser Ala Ser Val Gly
1               5                   10                  15

Asp Arg Val Thr Ile Thr Cys Arg Val Ser Gln Gly Ile Ser Ser Tyr
                20                  25                  30

Leu Asn Trp Tyr Arg Gln Lys Pro Gly Lys Val Pro Lys Leu Leu Ile
            35                  40                  45

Tyr Ser Ala Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Gly Gln Arg Thr Tyr Asn Ala Pro
                  85                  90                  95

<210> SEQ ID NO 71
<211> LENGTH: 95
<212> TYPE: PRT
<213> ORGANISM: Homo sapiens

<400> SEQUENCE: 71

Asp Ile Gln Leu Thr Gln Ser Pro Ser Ser Leu Ser Ala Ser Val Gly
1               5                   10                  15

Asp Arg Val Thr Ile Thr Cys Arg Val Ser Gln Gly Ile Ser Ser Tyr
                20                  25                  30

Leu Asn Trp Tyr Arg Gln Lys Pro Gly Lys Val Pro Lys Leu Leu Ile
            35                  40                  45

Tyr Ser Ala Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Gly Gln Arg Thr Tyr Asn Ala Pro
                  85                  90                  95

<210> SEQ ID NO 72
<211> LENGTH: 95
<212> TYPE: PRT
<213> ORGANISM: Homo sapiens

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Ser Tyr Ser Thr Pro
                85                  90                  95

<210> SEQ ID NO 73
<211> LENGTH: 95
<212> TYPE: PRT
<213> ORGANISM: Homo sapiens

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 74
<211> LENGTH: 95
<212> TYPE: PRT
<213> ORGANISM: Homo sapiens

<400> SEQUENCE: 74

Asp Ile Gln Met Ile Gln Ser Pro Ser Phe Leu Ser Ala Ser Val Gly
1               5                   10                  15

Asp Arg Val Ser Ile Ile Cys Trp Ala Ser Glu Gly Ile Ser Ser Asn
            20                  25                  30

Leu Ala Trp Tyr Leu Gln Lys Pro Gly Lys Ser Pro Lys Leu Phe Leu
        35                  40                  45

Tyr Asp Ala Lys Asp Leu His Pro Gly Val Pro Ser Arg Phe Ser Gly
    50                  55                  60

Arg Gly Ser Gly Thr Asp Phe Thr Leu Thr Ile Ile Ser Leu Lys Pro
65                  70                  75                  80

Glu Asp Phe Ala Ala Tyr Tyr Cys Lys Gln Asp Phe Ser Tyr Pro
                85                  90                  95

<210> SEQ ID NO 75
<211> LENGTH: 95
<212> TYPE: PRT
<213> ORGANISM: Homo sapiens

<400> SEQUENCE: 75

Ala Ile Arg Met Thr Gln Ser Pro Phe Ser Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Ala Lys Ala Pro Lys Leu Phe Ile
        35                  40                  45

Tyr Tyr Ala Ser Ser Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Ser Thr Pro
                85                  90                  95
```

<210> SEQ ID NO 76
<211> LENGTH: 100
<212> TYPE: PRT
<213> ORGANISM: Homo sapiens

<400> SEQUENCE: 76

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro
            100
```

<210> SEQ ID NO 77
<211> LENGTH: 100
<212> TYPE: PRT
<213> ORGANISM: Homo sapiens

<400> SEQUENCE: 77

```
Asp Ile Val Met Thr Gln Thr Pro Leu Ser Ser Pro Val Thr Leu Gly
1               5                   10                  15

Gln Pro Ala Ser Ile Ser Phe Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Thr Gln Ala
                85                  90                  95

Thr Gln Phe Pro
            100
```

<210> SEQ ID NO 78
<211> LENGTH: 100
<212> TYPE: PRT
<213> ORGANISM: Homo sapiens

<400> SEQUENCE: 78

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
```

```
65                  70                  75                  80
Ser Arg Val Glu Ala Glu Asp Val Gly Val Tyr Tyr Cys Met Gln Ala
                85                  90                  95

Leu Gln Thr Pro
            100

<210> SEQ ID NO 79
<211> LENGTH: 100
<212> TYPE: PRT
<213> ORGANISM: Homo sapiens

<400> SEQUENCE: 79

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro
            100

<210> SEQ ID NO 80
<211> LENGTH: 100
<212> TYPE: PRT
<213> ORGANISM: Homo sapiens

<400> SEQUENCE: 80

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro
            100

<210> SEQ ID NO 81
<211> LENGTH: 100
<212> TYPE: PRT
<213> ORGANISM: Homo sapiens

<400> SEQUENCE: 81

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30
```

-continued

```
Asp Gly Lys Thr Tyr Leu Tyr Trp Tyr Leu Gln Lys Pro Gly Gln Ser
            35                  40                  45

Pro Gln Leu Leu Ile Tyr Glu Val Ser Ser Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                85                  90                  95

Ile His Leu Pro
            100

<210> SEQ ID NO 82
<211> LENGTH: 100
<212> TYPE: PRT
<213> ORGANISM: Homo sapiens

<400> SEQUENCE: 82

Asp Val Val Met Thr Gln Ser Pro Leu Ser Leu Pro Val Thr Leu Gly
  1               5                  10                  15

Gln Pro Ala Ser Ile Ser Cys Arg Ser Ser Gln Ser Leu Val Tyr Ser
             20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Val Ser Asn Arg Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                85                  90                  95

Thr His Trp Pro
            100

<210> SEQ ID NO 83
<211> LENGTH: 100
<212> TYPE: PRT
<213> ORGANISM: Homo sapiens

<400> SEQUENCE: 83

Asp Val Val Met Thr Gln Ser Pro Leu Ser Leu Pro Val Thr Leu Gly
  1               5                  10                  15

Gln Pro Ala Ser Ile Ser Cys Arg Ser Ser Gln Ser Leu Val Tyr Ser
             20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Val Ser Asn Trp Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                85                  90                  95

Thr His Trp Pro
            100

<210> SEQ ID NO 84
<211> LENGTH: 101
<212> TYPE: PRT
<213> ORGANISM: Homo sapiens

<400> SEQUENCE: 84
```

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65              70                  75                  80

Ile Ser Arg Val Glu Ala Glu Asp Val Gly Val Tyr Tyr Cys Met Gln
                85                  90                  95

Arg Ile Glu Phe Pro
            100
```

<210> SEQ ID NO 85
<211> LENGTH: 101
<212> TYPE: PRT
<213> ORGANISM: Homo sapiens

<400> SEQUENCE: 85

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65              70                  75                  80

Ile Ser Arg Val Glu Ala Glu Asp Val Gly Val Tyr Tyr Cys Met Gln
                85                  90                  95

Arg Ile Glu Phe Pro
            100
```

<210> SEQ ID NO 86
<211> LENGTH: 96
<212> TYPE: PRT
<213> ORGANISM: Homo sapiens

<400> SEQUENCE: 86

```
Glu Ile Val Met Thr Gln Ser Pro Pro Thr Leu Ser Leu Ser Pro Gly
1               5                   10                  15

Glu Arg Val Thr Leu Ser Cys Arg Ala Ser Gln Ser Val Ser Ser Ser
            20                  25                  30

Tyr Leu Thr Trp Tyr Gln Gln Lys Pro Gly Gln Ala Pro Arg Leu Leu
        35                  40                  45

Ile Tyr Gly Ala Ser Thr Arg Ala Thr Ser Ile Pro Ala Arg Phe Ser
    50                  55                  60

Gly Ser Gly Ser Gly Thr Asp Phe Thr Leu Thr Ile Ser Ser Leu Gln
65              70                  75                  80

Pro Glu Asp Phe Ala Val Tyr Tyr Cys Gln Gln Asp His Asn Leu Pro
                85                  90                  95
```

<210> SEQ ID NO 87
<211> LENGTH: 96

```
<212> TYPE: PRT
<213> ORGANISM: Homo sapiens

<400> SEQUENCE: 87

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ser Trp Tyr Gln Gln Lys Pro Gly Gln Ala Pro Arg Leu Leu
            35                  40                  45

Ile Tyr Gly Ala Ser Thr Arg Ala Thr Gly Ile Pro Ala Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asn Leu Pro
                85                  90                  95

<210> SEQ ID NO 88
<211> LENGTH: 95
<212> TYPE: PRT
<213> ORGANISM: Homo sapiens

<400> SEQUENCE: 88

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90              95

<210> SEQ ID NO 89
<211> LENGTH: 95
<212> TYPE: PRT
<213> ORGANISM: Homo sapiens

<400> SEQUENCE: 89

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp His
                85                  90              95

<210> SEQ ID NO 90
<211> LENGTH: 95
<212> TYPE: PRT
<213> ORGANISM: Homo sapiens
```

-continued

```
<400> SEQUENCE: 90

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro
                85                  90                  95

<210> SEQ ID NO 91
<211> LENGTH: 95
<212> TYPE: PRT
<213> ORGANISM: Homo sapiens

<400> SEQUENCE: 91

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro
                85                  90                  95

<210> SEQ ID NO 92
<211> LENGTH: 96
<212> TYPE: PRT
<213> ORGANISM: Homo sapiens

<400> SEQUENCE: 92

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 93
<211> LENGTH: 96
<212> TYPE: PRT
<213> ORGANISM: Homo sapiens

<400> SEQUENCE: 93
```

```
Glu Ile Val Leu Thr Gln Ser Pro Ala Thr Leu Ser Leu Ser Pro Gly
1               5                   10                  15

Glu Arg Ala Thr Leu Ser Cys Gly Ala Ser Gln Ser Val Ser Ser Ser
            20                  25                  30

Tyr Leu Ala Trp Tyr Gln Gln Lys Pro Gly Leu Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95
```

<210> SEQ ID NO 94
<211> LENGTH: 101
<212> TYPE: PRT
<213> ORGANISM: Homo sapiens

<400> SEQUENCE: 94

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro
            100
```

<210> SEQ ID NO 95
<211> LENGTH: 95
<212> TYPE: PRT
<213> ORGANISM: Homo sapiens

<400> SEQUENCE: 95

```
Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro
                85                  90                  95
```

<210> SEQ ID NO 96
<211> LENGTH: 95
<212> TYPE: PRT
<213> ORGANISM: Homo sapiens

```
<400> SEQUENCE: 96

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro
                85                  90                  95

<210> SEQ ID NO 97
<211> LENGTH: 95
<212> TYPE: PRT
<213> ORGANISM: Homo sapiens

<400> SEQUENCE: 97

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro
                85                  90                  95

<210> SEQ ID NO 98
<211> LENGTH: 95
<212> TYPE: PRT
<213> ORGANISM: Homo sapiens

<400> SEQUENCE: 98

Asp Val Val Met Thr Gln Ser Pro Ala Phe Leu Ser Val Thr Pro Gly
1               5                   10                  15

Glu Lys Val Thr Ile Thr Cys Gln Ala Ser Glu Gly Ile Gly Asn Tyr
            20                  25                  30

Leu Tyr Trp Tyr Gln Gln Lys Pro Asp Gln Ala Pro Lys Leu Leu Ile
        35                  40                  45

Lys Tyr Ala Ser Gln Ser Ile Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Gly Asn Lys His Pro
                85                  90                  95

<210> SEQ ID NO 99
<211> LENGTH: 12
<212> TYPE: PRT
<213> ORGANISM: Homo sapiens

<400> SEQUENCE: 99
```

```
Trp Thr Phe Gly Gln Gly Thr Lys Val Glu Ile Lys
1               5                   10
```

<210> SEQ ID NO 100
<211> LENGTH: 12
<212> TYPE: PRT
<213> ORGANISM: Homo sapiens

<400> SEQUENCE: 100

```
Tyr Thr Phe Gly Gln Gly Thr Lys Leu Glu Ile Lys
1               5                   10
```

<210> SEQ ID NO 101
<211> LENGTH: 12
<212> TYPE: PRT
<213> ORGANISM: Homo sapiens

<400> SEQUENCE: 101

```
Phe Thr Phe Gly Pro Gly Thr Lys Val Asp Ile Lys
1               5                   10
```

<210> SEQ ID NO 102
<211> LENGTH: 12
<212> TYPE: PRT
<213> ORGANISM: Homo sapiens

<400> SEQUENCE: 102

```
Leu Thr Phe Gly Gly Gly Thr Lys Val Glu Ile Lys
1               5                   10
```

<210> SEQ ID NO 103
<211> LENGTH: 12
<212> TYPE: PRT
<213> ORGANISM: Homo sapiens

<400> SEQUENCE: 103

```
Ile Thr Phe Gly Gln Gly Thr Arg Leu Glu Ile Lys
1               5                   10
```

<210> SEQ ID NO 104
<211> LENGTH: 17
<212> TYPE: PRT
<213> ORGANISM: Homo sapiens

<400> SEQUENCE: 104

```
Ala Glu Tyr Phe Gln His Trp Gly Gln Gly Thr Leu Val Thr Val Ser
1               5                   10                  15

Ser
```

<210> SEQ ID NO 105
<211> LENGTH: 17
<212> TYPE: PRT
<213> ORGANISM: Homo sapiens

<400> SEQUENCE: 105

```
Tyr Trp Tyr Phe Asp Leu Trp Gly Arg Gly Thr Leu Val Thr Val Ser
1               5                   10                  15

Ser
```

<210> SEQ ID NO 106
<211> LENGTH: 15
<212> TYPE: PRT
<213> ORGANISM: Homo sapiens

<400> SEQUENCE: 106

```
Ala Phe Asp Val Trp Gly Gln Gly Thr Met Val Thr Val Ser Ser
1               5                  10                  15

<210> SEQ ID NO 107
<211> LENGTH: 15
<212> TYPE: PRT
<213> ORGANISM: Homo sapiens

<400> SEQUENCE: 107

Tyr Phe Asp Tyr Trp Gly Gln Gly Thr Leu Val Thr Val Ser Ser
1               5                  10                  15

<210> SEQ ID NO 108
<211> LENGTH: 16
<212> TYPE: PRT
<213> ORGANISM: Homo sapiens

<400> SEQUENCE: 108

Asn Trp Phe Asp Ser Trp Gly Gln Gly Thr Leu Val Thr Val Ser Ser
1               5                  10                  15

<210> SEQ ID NO 109
<211> LENGTH: 20
<212> TYPE: PRT
<213> ORGANISM: Homo sapiens

<400> SEQUENCE: 109

Tyr Tyr Tyr Tyr Tyr Gly Met Asp Val Trp Gly Gln Gly Thr Thr Val
1               5                  10                  15

Thr Val Ser Ser
            20

<210> SEQ ID NO 110
<211> LENGTH: 30
<212> TYPE: PRT
<213> ORGANISM: Murinae gen. sp.

<400> SEQUENCE: 110

Gln Val Gln Leu Gln Gln Ser Gly Pro Glu Leu Val Lys Pro Gly Ala
1               5                  10                  15

Ser Leu Lys Leu Ser Cys Thr Ala Ser Gly Phe Asn Ile Lys
            20                  25                  30

<210> SEQ ID NO 111
<211> LENGTH: 30
<212> TYPE: PRT
<213> ORGANISM: Homo sapiens

<400> SEQUENCE: 111

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr
            20                  25                  30

<210> SEQ ID NO 112
<211> LENGTH: 30
<212> TYPE: PRT
<213> ORGANISM: Homo sapiens

<400> SEQUENCE: 112

Gln Ile Thr Leu Lys Glu Ser Gly Pro Thr Leu Val Lys Pro Thr Gln
1               5                  10                  15

Thr Leu Thr Leu Thr Cys Thr Phe Ser Gly Phe Ser Leu Ser
```

20                  25                  30

<210> SEQ ID NO 113
<211> LENGTH: 30
<212> TYPE: PRT
<213> ORGANISM: Homo sapiens

<400> SEQUENCE: 113

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 114
<211> LENGTH: 30
<212> TYPE: PRT
<213> ORGANISM: Homo sapiens

<400> SEQUENCE: 114

Gln Val Gln Leu Gln Glu Ser Gly Pro Gly Leu Val Lys Pro Pro Gly
1               5                   10                  15

Thr Leu Ser Leu Thr Cys Ala Val Ser Gly Gly Ser Ile Ser
            20                  25                  30

<210> SEQ ID NO 115
<211> LENGTH: 30
<212> TYPE: PRT
<213> ORGANISM: Homo sapiens

<400> SEQUENCE: 115

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr
            20                  25                  30

<210> SEQ ID NO 116
<211> LENGTH: 30
<212> TYPE: PRT
<213> ORGANISM: Homo sapiens

<400> SEQUENCE: 116

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser
            20                  25                  30

<210> SEQ ID NO 117
<211> LENGTH: 30
<212> TYPE: PRT
<213> ORGANISM: Homo sapiens

<400> SEQUENCE: 117

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr
            20                  25                  30

<210> SEQ ID NO 118
<211> LENGTH: 111
<212> TYPE: PRT
<213> ORGANISM: Homo sapiens

<400> SEQUENCE: 118

```
Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Trp Thr Phe Gly Gly Gly Thr Lys Leu Glu Ile Lys
            100                 105                 110
```

<210> SEQ ID NO 119
<211> LENGTH: 117
<212> TYPE: PRT
<213> ORGANISM: Homo sapiens

<400> SEQUENCE: 119

```
Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Thr Trp Val Lys Gln Lys Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Val Asp Thr Ser Ser Ser Thr Ala Phe
65                  70                  75                  80

Met Gln Leu Ser Ser Leu Thr Ser Glu Asp Thr Ala Val Tyr Phe Cys
                85                  90                  95

Ala Asn Tyr Gly Asn Tyr Trp Phe Ala Tyr Trp Gly Gln Gly Thr Gln
            100                 105                 110

Val Thr Val Ser Ala
        115
```

<210> SEQ ID NO 120
<211> LENGTH: 111
<212> TYPE: PRT
<213> ORGANISM: Homo sapiens

<400> SEQUENCE: 120

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Asp Phe Asp
            20                  25                  30

Gly Asp Ser Tyr Leu Ala Trp Tyr Gln Gln Lys Pro Gly Gln Pro Pro
        35                  40                  45

Lys Leu Leu Ile Tyr Ala Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Trp Thr Phe Gly Gly Gly Thr Lys Leu Glu Ile Lys
```

```
                        100                 105                 110

<210> SEQ ID NO 121
<211> LENGTH: 117
<212> TYPE: PRT
<213> ORGANISM: Homo sapiens

<400> SEQUENCE: 121

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Arg Leu Glu Trp Met
        35                  40                  45

Gly Trp Ile Tyr Pro Gly Ser Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Gly Asn Tyr Trp Phe Ala Tyr Trp Gly Gln Gly Thr Leu
            100                 105                 110

Val Thr Val Ser Ser
        115

<210> SEQ ID NO 122
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 122

Asp Ile Val Leu Thr Gln Ser Pro Asp Ser Leu Ala Val Ser Leu Gly
1               5                   10                  15

Glu Arg Ala Thr Leu Ser Cys Gly Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Gln Gln Ser Asn
                85                  90                  95

Glu Asp Pro Trp Thr Phe Gly Gly Gly Thr Lys Xaa Glu Ile Lys
            100                 105                 110

<210> SEQ ID NO 123
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid
```

-continued

<400> SEQUENCE: 123

Asp Ile Val Leu Thr Gln Ser Pro Asp Ser Leu Ala Val Ser Leu Gly
1               5                   10                  15

Glu Arg Ala Thr Leu Ser Cys Arg Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Gln Gln Ser Asn
                85                  90                  95

Glu Asp Pro Trp Thr Phe Gly Gly Gly Thr Lys Xaa Glu Ile Lys
            100                 105                 110

<210> SEQ ID NO 124
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 124

Asp Ile Val Leu Thr Gln Ser Pro Asp Ser Leu Ala Val Ser Leu Gly
1               5                   10                  15

Glu Arg Ala Thr Leu Ser Cys Arg Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Phe Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Trp Thr Phe Gly Gly Gly Thr Lys Xaa Glu Ile Lys
            100                 105                 110

<210> SEQ ID NO 125
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 125

Asp Ile Val Leu Thr Gln Ser Pro Asp Ser Leu Ala Val Ser Leu Gly
1               5                   10                  15

Glu Arg Ala Thr Leu Ser Cys Arg Ala Ser Gln Ser Val Asp Phe Asp
            20                  25                  30

Gly Asp Ser Tyr Met Asn Trp Tyr Gln Gln Lys Pro Gly Gln Pro Pro

```
                    35                  40                  45
Lys Val Leu Ile Tyr Ala Ala Ser Asn Leu Glu Ser Gly Ile Pro Ala
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ser Asn
                     85                  90                  95

Glu Asp Pro Trp Thr Phe Gly Gly Gly Thr Lys Xaa Glu Ile Lys
                100                 105                 110

<210> SEQ ID NO 126
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 126

Asp Ile Val Leu Thr Gln Ser Pro Asp Ser Leu Ala Val Ser Leu Gly
  1               5                  10                  15

Glu Arg Ala Thr Leu Ser Cys Gly Ala Ser Gln Ser Val Asp Phe Asp
                 20                  25                  30

Gly Asp Ser Tyr Met Asn Trp Tyr Gln Gln Lys Pro Gly Gln Pro Pro
             35                  40                  45

Lys Val Leu Ile Tyr Ala Ala Ser Asn Leu Glu Ser Gly Ile Pro Ala
 50                  55                  60

Arg Phe Ser Gly Ser Gly Ser Gly Thr Asp Phe Thr Phe Thr Ile Ser
 65                  70                  75                  80

Ser Leu Gln Pro Glu Asp Phe Ala Thr Tyr Tyr Cys Gln Gln Ser Asn
                     85                  90                  95

Glu Asp Pro Trp Thr Phe Gly Gly Gly Thr Lys Xaa Glu Ile Lys
                100                 105                 110

<210> SEQ ID NO 127
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 127

Asp Ile Val Leu Thr Gln Ser Pro Asp Ser Leu Ala Val Ser Leu Gly
  1               5                  10                  15

Glu Arg Ala Thr Leu Ser Cys Gly Ala Ser Gln Ser Val Asp Phe Asp
                 20                  25                  30

Gly Asp Ser Tyr Met Asn Trp Tyr Gln Gln Lys Pro Gly Gln Pro Pro
             35                  40                  45

Lys Val Leu Ile Tyr Ala Ala Ser Asn Leu Glu Ser Gly Ile Pro Ala
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ser Asn
                     85                  90                  95
```

-continued

```
Glu Asp Pro Trp Thr Phe Gly Gly Gly Thr Lys Xaa Glu Ile Lys
            100                 105                 110

<210> SEQ ID NO 128
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 128

Asp Ile Val Leu Thr Gln Ser Pro Asp Ser Leu Ala Val Ser Leu Gly
1               5                   10                  15

Glu Arg Ala Thr Leu Ser Cys Gly Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Gln Pro Asp Asp Phe Ala Thr Tyr Tyr Cys Gln Gln Ser Asn
                85                  90                  95

Glu Asp Pro Trp Thr Phe Gly Gly Gly Thr Lys Xaa Glu Ile Lys
            100                 105                 110

<210> SEQ ID NO 129
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 129

Asp Ile Val Leu Thr Gln Ser Pro Asp Ser Leu Ala Val Ser Leu Gly
1               5                   10                  15

Glu Arg Ala Thr Leu Ser Cys Arg Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Gln Pro Asp Asp Phe Ala Thr Tyr Tyr Cys Gln Gln Ser Asn
                85                  90                  95

Glu Asp Pro Trp Thr Phe Gly Gly Gly Thr Lys Xaa Glu Ile Lys
            100                 105                 110

<210> SEQ ID NO 130
<211> LENGTH: 111
<212> TYPE: PRT
<213> ORGANISM: Artificial
<220> FEATURE:
```

<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 130

```
Asp Ile Val Leu Thr Gln Ser Pro Asp Ser Leu Ala Val Ser Leu Gly
1               5                   10                  15

Glu Arg Ala Thr Leu Ser Cys Arg Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Cys Leu Gln Ser Glu Asp Phe Ala Thr Tyr Tyr Cys Gln Gln Ser Asn
                85                  90                  95

Glu Asp Pro Trp Thr Phe Gly Gly Gly Thr Lys Xaa Glu Ile Lys
            100                 105                 110
```

<210> SEQ ID NO 131
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 131

```
Asp Ile Val Leu Thr Gln Ser Pro Asp Ser Leu Ala Val Ser Leu Gly
1               5                   10                  15

Glu Arg Ala Thr Leu Ser Cys Gly Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Cys Leu Gln Ser Glu Asp Phe Ala Thr Tyr Tyr Cys Gln Gln Ser Asn
                85                  90                  95

Glu Asp Pro Trp Thr Phe Gly Gly Gly Thr Lys Xaa Glu Ile Lys
            100                 105                 110
```

<210> SEQ ID NO 132
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 132

```
Asp Ile Val Leu Thr Gln Ser Pro Asp Ser Leu Ala Val Ser Leu Gly
1               5                   10                  15
```

```
Glu Arg Ala Thr Leu Ser Cys Arg Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Asn
                85                  90                  95

Glu Asp Pro Trp Thr Phe Gly Gly Gly Thr Lys Xaa Glu Ile Lys
            100                 105                 110

<210> SEQ ID NO 133
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 133

Asp Ile Val Leu Thr Gln Ser Pro Asp Ser Leu Ala Val Ser Leu Gly
1               5                   10                  15

Glu Arg Ala Thr Leu Ser Cys Gly Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Asn
                85                  90                  95

Glu Asp Pro Trp Thr Phe Gly Gly Gly Thr Lys Xaa Glu Ile Lys
            100                 105                 110

<210> SEQ ID NO 134
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 134

Asp Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60
```

```
Arg Phe Ser Gly Ser Gly Ser Gly Thr Asp Phe Thr Phe Thr Ile Ser
 65                  70                  75                  80

Ser Leu Gln Pro Glu Asp Phe Ala Thr Tyr Tyr Cys Gln Gln Ser Asn
                 85                  90                  95

Glu Asp Pro Trp Thr Phe Gly Gly Gly Thr Lys Xaa Glu Ile Lys
            100                 105                 110
```

<210> SEQ ID NO 135
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 135

```
Asp Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Asp Phe Asp
                 20                  25                  30

Gly Asp Ser Tyr Met Asn Trp Tyr Gln Gln Lys Pro Gly Gln Pro Pro
             35                  40                  45

Lys Val Leu Ile Tyr Ala Ala Ser Asn Leu Glu Ser Gly Ile Pro Ala
 50                  55                  60

Arg Phe Ser Gly Ser Gly Ser Gly Thr Asp Phe Thr Phe Thr Ile Ser
 65                  70                  75                  80

Ser Leu Gln Pro Glu Asp Phe Ala Thr Tyr Tyr Cys Gln Gln Ser Asn
                 85                  90                  95

Glu Asp Pro Trp Thr Phe Gly Gly Gly Thr Lys Xaa Glu Ile Lys
            100                 105                 110
```

<210> SEQ ID NO 136
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 136

```
Asp Ile Val Leu Thr Gln Ser Pro Ala Thr Leu Ser Val Ser Pro Gly
  1               5                  10                  15

Glu Arg Ala Thr Leu Ser Cys Gly Ala Ser Gln Ser Val Asp Phe Asp
                 20                  25                  30

Gly Asp Ser Tyr Met Asn Trp Tyr Gln Gln Lys Pro Gly Gln Pro Pro
             35                  40                  45

Lys Val Leu Ile Tyr Ala Ala Ser Asn Leu Glu Ser Gly Ile Pro Ala
 50                  55                  60

Arg Phe Ser Gly Ser Gly Ser Gly Thr Asp Phe Thr Phe Thr Ile Ser
 65                  70                  75                  80

Ser Leu Gln Pro Glu Asp Phe Ala Thr Tyr Tyr Cys Gln Gln Ser Asn
                 85                  90                  95

Glu Asp Pro Trp Thr Phe Gly Gly Gly Thr Lys Xaa Glu Ile Lys
            100                 105                 110
```

```
<210> SEQ ID NO 137
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 137

Asp Ile Val Leu Thr Gln Ser Pro Gly Thr Leu Ser Leu Ser Pro Gly
1               5                   10                  15

Glu Arg Ala Thr Leu Ser Cys Gly Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Trp Thr Phe Gly Gly Gly Thr Lys Xaa Glu Ile Lys
            100                 105                 110

<210> SEQ ID NO 138
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 138

Asp Ile Val Leu Thr Gln Ser Pro Ala Thr Leu Ser Leu Ser Pro Gly
1               5                   10                  15

Glu Arg Ala Thr Leu Ser Cys Gly Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Trp Thr Phe Gly Gly Gly Thr Lys Xaa Glu Ile Lys
            100                 105                 110

<210> SEQ ID NO 139
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid
```

```
<400> SEQUENCE: 139

Asp Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Cys Leu Gln Ser Glu Asp Phe Ala Thr Tyr Tyr Cys Gln Gln Ser Asn
                85                  90                  95

Glu Asp Pro Trp Thr Phe Gly Gly Gly Thr Lys Xaa Glu Ile Lys
            100                 105                 110

<210> SEQ ID NO 140
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 140

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Cys Leu Gln Ser Glu Asp Phe Ala Thr Tyr Tyr Cys Gln Gln Ser Asn
                85                  90                  95

Glu Asp Pro Trp Thr Phe Gly Gly Gly Thr Lys Xaa Glu Ile Lys
            100                 105                 110

<210> SEQ ID NO 141
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 141

Asp Ile Val Leu Thr Gln Ser Pro Gly Thr Leu Ser Leu Ser Pro Gly
1               5                   10                  15

Glu Arg Val Thr Leu Ser Cys Arg Ala Ser Gln Ser Val Asp Phe Asp
            20                  25                  30

Gly Asp Ser Tyr Met Asn Trp Tyr Gln Gln Lys Pro Gly Gln Pro Pro
```

```
                35                  40                  45
Lys Val Leu Ile Tyr Ala Ala Ser Asn Leu Glu Ser Gly Ile Pro Ala
 50                  55                  60

Arg Phe Ser Gly Ser Gly Ser Gly Thr Asp Phe Thr Leu Thr Ile Ser
 65                  70                  75                  80

Ser Leu Gln Pro Asp Asp Phe Ala Thr Tyr Tyr Cys Gln Gln Ser Asn
                 85                  90                  95

Glu Asp Pro Trp Thr Phe Gly Gly Gly Thr Lys Xaa Glu Ile Lys
            100                 105                 110

<210> SEQ ID NO 142
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 142

Asp Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Asp Phe Asp
                20                  25                  30

Gly Asp Ser Tyr Met Asn Trp Tyr Gln Gln Lys Pro Gly Gln Pro Pro
            35                  40                  45

Lys Val Leu Ile Tyr Ala Ala Ser Asn Leu Glu Ser Gly Ile Pro Ala
 50                  55                  60

Arg Phe Ser Gly Ser Gly Ser Gly Thr Asp Phe Thr Leu Thr Ile Asn
 65                  70                  75                  80

Ser Leu Glu Ala Glu Asp Ala Ala Thr Tyr Tyr Cys Gln Gln Ser Asn
                 85                  90                  95

Glu Asp Pro Trp Thr Phe Gly Gly Gly Thr Lys Xaa Glu Ile Lys
            100                 105                 110

<210> SEQ ID NO 143
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 143

Asp Ile Val Leu Thr Gln Ser Pro Gly Thr Leu Ser Leu Ser Pro Gly
 1               5                  10                  15

Glu Arg Val Thr Leu Ser Cys Arg Ala Ser Gln Ser Val Asp Phe Asp
                20                  25                  30

Gly Asp Ser Tyr Met Asn Trp Tyr Gln Gln Lys Pro Gly Gln Pro Pro
            35                  40                  45

Lys Val Leu Ile Tyr Ala Ala Ser Asn Leu Glu Ser Gly Ile Pro Ala
 50                  55                  60

Arg Phe Ser Gly Ser Gly Ser Gly Thr Asp Phe Thr Leu Thr Ile Asn
 65                  70                  75                  80

Ser Leu Glu Ala Glu Asp Ala Ala Thr Tyr Tyr Cys Gln Gln Ser Asn
                 85                  90                  95
```

```
Glu Asp Pro Trp Thr Phe Gly Gly Gly Thr Lys Xaa Glu Ile Lys
            100                 105                 110
```

<210> SEQ ID NO 144
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 144

```
Asp Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Gln Gln Ser Asn
                85                  90                  95

Glu Asp Pro Trp Thr Phe Gly Gly Gly Thr Lys Xaa Glu Ile Lys
            100                 105                 110
```

<210> SEQ ID NO 145
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 145

```
Asp Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Gln Gln Ser Asn
                85                  90                  95

Glu Asp Pro Trp Thr Phe Gly Gly Gly Thr Lys Xaa Glu Ile Lys
            100                 105                 110
```

<210> SEQ ID NO 146
<211> LENGTH: 111
<212> TYPE: PRT
<213> ORGANISM: Artificial
<220> FEATURE:

```
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 146

Asp Ile Val Leu Thr Gln Ser Pro Ala Thr Leu Ser Val Ser Pro Gly
1               5                   10                  15

Glu Arg Ala Thr Leu Ser Cys Gly Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Gln Gln Ser Asn
                85                  90                  95

Glu Asp Pro Trp Thr Phe Gly Gly Gly Thr Lys Xaa Glu Ile Lys
            100                 105                 110

<210> SEQ ID NO 147
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 147

Asp Ile Val Leu Thr Gln Ser Pro Ala Thr Leu Ser Leu Ser Pro Gly
1               5                   10                  15

Glu Arg Val Thr Leu Ser Cys Arg Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Gln Gln Ser Asn
                85                  90                  95

Glu Asp Pro Trp Thr Phe Gly Gly Gly Thr Lys Xaa Glu Ile Lys
            100                 105                 110

<210> SEQ ID NO 148
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 148

Asp Ile Val Leu Thr Gln Ser Pro Asp Ser Leu Ala Val Ser Leu Gly
1               5                   10                  15
```

-continued

```
Glu Arg Ala Thr Leu Ser Cys Gly Ala Ser Gln Ser Val Asp Phe Asp
                 20                  25                  30

Gly Asp Ser Tyr Met Asn Trp Tyr Gln Gln Lys Pro Gly Gln Pro Pro
             35                  40                  45

Lys Val Leu Ile Tyr Ala Ala Ser Asn Leu Glu Ser Gly Ile Pro Ala
         50                  55                  60

Arg Phe Ser Gly Ser Gly Ser Gly Thr Asp Phe Thr Leu Lys Ile Ser
 65                  70                  75                  80

Arg Val Glu Ala Glu Asp Val Gly Val Tyr Tyr Cys Gln Gln Ser Asn
                 85                  90                  95

Glu Asp Pro Trp Thr Phe Gly Gly Gly Thr Lys Xaa Glu Ile Lys
                100                 105                 110
```

<210> SEQ ID NO 149
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 149

```
Asp Ile Val Leu Thr Gln Ser Pro Asp Ser Leu Ala Val Ser Leu Gly
 1               5                  10                  15

Glu Arg Ala Thr Leu Ser Cys Arg Ala Ser Gln Ser Val Asp Phe Asp
                 20                  25                  30

Gly Asp Ser Tyr Met Asn Trp Tyr Gln Gln Lys Pro Gly Gln Pro Pro
             35                  40                  45

Lys Val Leu Ile Tyr Ala Ala Ser Asn Leu Glu Ser Gly Ile Pro Ala
         50                  55                  60

Arg Phe Ser Gly Ser Gly Ser Gly Thr Asp Phe Thr Leu Lys Ile Ser
 65                  70                  75                  80

Arg Val Glu Ala Glu Asp Val Gly Val Tyr Tyr Cys Gln Gln Ser Asn
                 85                  90                  95

Glu Asp Pro Trp Thr Phe Gly Gly Gly Thr Lys Xaa Glu Ile Lys
                100                 105                 110
```

<210> SEQ ID NO 150
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 150

```
Asp Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Asp Phe Asp
                 20                  25                  30

Gly Asp Ser Tyr Met Asn Trp Tyr Gln Gln Lys Pro Gly Gln Pro Pro
             35                  40                  45

Lys Val Leu Ile Tyr Ala Ala Ser Asn Leu Glu Ser Gly Ile Pro Ala
         50                  55                  60
```

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Asn
                85                  90                  95

Glu Asp Pro Trp Thr Phe Gly Gly Gly Thr Lys Xaa Glu Ile Lys
            100                 105                 110

<210> SEQ ID NO 151
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 151

Asp Ile Val Leu Thr Gln Ser Pro Leu Ser Leu Pro Val Thr Leu Gly
1               5                   10                  15

Gln Pro Ala Ser Ile Ser Cys Arg Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Cys Leu Gln Ser Glu Asp Phe Ala Thr Tyr Tyr Cys Gln Gln Ser Asn
                85                  90                  95

Glu Asp Pro Trp Thr Phe Gly Gly Gly Thr Lys Xaa Glu Ile Lys
            100                 105                 110

<210> SEQ ID NO 152
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 152

Asp Ile Val Leu Thr Gln Thr Pro Leu Ser Leu Ser Val Thr Pro Gly
1               5                   10                  15

Gln Pro Ala Ser Ile Ser Cys Arg Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Asn
                85                  90                  95

Glu Asp Pro Trp Thr Phe Gly Gly Gly Thr Lys Xaa Glu Ile Lys
            100                 105                 110

```
<210> SEQ ID NO 153
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 153

Asp Ile Val Leu Thr Gln Ser Pro Leu Ser Leu Pro Val Thr Leu Gly
1               5                   10                  15

Gln Pro Ala Ser Ile Ser Cys Arg Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Phe Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Trp Thr Phe Gly Gly Gly Thr Lys Xaa Glu Ile Lys
            100                 105                 110

<210> SEQ ID NO 154
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 154

Asp Ile Val Leu Thr Gln Ser Pro Leu Ser Leu Pro Val Thr Leu Gly
1               5                   10                  15

Gln Pro Ala Ser Ile Ser Cys Arg Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Gln Pro Asp Asp Phe Ala Thr Tyr Tyr Cys Gln Gln Ser Asn
                85                  90                  95

Glu Asp Pro Trp Thr Phe Gly Gly Gly Thr Lys Xaa Glu Ile Lys
            100                 105                 110

<210> SEQ ID NO 155
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid
```

-continued

<400> SEQUENCE: 155

Asp Ile Val Leu Thr Gln Ser Pro Leu Ser Leu Pro Val Thr Pro Gly
1               5                   10                  15

Glu Pro Ala Ser Ile Ser Cys Arg Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Trp Thr Phe Gly Gly Gly Thr Lys Xaa Glu Ile Lys
            100                 105                 110

<210> SEQ ID NO 156
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 156

Asp Ile Val Leu Thr Gln Thr Pro Leu Ser Leu Ser Val Thr Pro Gly
1               5                   10                  15

Gln Pro Ala Ser Ile Ser Cys Arg Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Phe Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Trp Thr Phe Gly Gly Gly Thr Lys Xaa Glu Ile Lys
            100                 105                 110

<210> SEQ ID NO 157
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 157

Asp Ile Val Leu Thr Gln Ser Pro Leu Ser Leu Pro Val Thr Pro Gly
1               5                   10                  15

Glu Pro Ala Ser Ile Ser Cys Arg Ala Ser Gln Ser Val Asp Phe Asp
            20                  25                  30

Gly Asp Ser Tyr Met Asn Trp Tyr Gln Gln Lys Pro Gly Gln Pro Pro

```
                35                  40                  45
Lys Val Leu Ile Tyr Ala Ala Ser Asn Leu Glu Ser Gly Ile Pro Ala
         50                  55                  60
Arg Phe Ser Gly Ser Gly Ser Gly Thr Asp Phe Thr Leu Thr Ile Asn
 65                  70                  75                  80
Ser Leu Glu Ala Glu Asp Ala Ala Thr Tyr Tyr Cys Gln Gln Ser Asn
                 85                  90                  95
Glu Asp Pro Trp Thr Phe Gly Gly Gly Thr Lys Xaa Glu Ile Lys
                100                 105                 110

<210> SEQ ID NO 158
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 158

Asp Ile Val Leu Thr Gln Thr Pro Leu Ser Leu Ser Val Thr Pro Gly
 1               5                  10                  15
Gln Pro Ala Ser Ile Ser Cys Arg Ala Ser Gln Ser Val Asp Phe Asp
                20                  25                  30
Gly Asp Ser Tyr Met Asn Trp Tyr Gln Gln Lys Pro Gly Gln Pro Pro
            35                  40                  45
Lys Val Leu Ile Tyr Ala Ala Ser Asn Leu Glu Ser Gly Ile Pro Ala
         50                  55                  60
Arg Phe Ser Gly Ser Gly Ser Gly Thr Asp Phe Thr Leu Thr Ile Asn
 65                  70                  75                  80
Ser Leu Glu Ala Glu Asp Ala Ala Thr Tyr Tyr Cys Gln Gln Ser Asn
                 85                  90                  95
Glu Asp Pro Trp Thr Phe Gly Gly Gly Thr Lys Xaa Glu Ile Lys
                100                 105                 110

<210> SEQ ID NO 159
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 159

Asp Ile Val Leu Thr Gln Ser Pro Ser Phe Leu Ser Ala Ser Val Gly
 1               5                  10                  15
Asp Arg Val Thr Ile Thr Cys Arg Ala Ser Gln Ser Val Asp Phe Asp
                20                  25                  30
Gly Asp Ser Tyr Met Asn Trp Tyr Gln Gln Lys Pro Gly Gln Pro Pro
            35                  40                  45
Lys Val Leu Ile Tyr Ala Ala Ser Asn Leu Glu Ser Gly Ile Pro Ala
         50                  55                  60
Arg Phe Ser Gly Ser Gly Ser Gly Thr Asp Phe Thr Leu Thr Ile Ser
 65                  70                  75                  80
Ser Leu Gln Pro Glu Asp Phe Ala Thr Tyr Tyr Cys Gln Gln Ser Asn
                 85                  90                  95
```

```
Glu Asp Pro Trp Thr Phe Gly Gly Gly Thr Lys Xaa Glu Ile Lys
            100                 105                 110
```

<210> SEQ ID NO 160
<211> LENGTH: 111
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (108)..(108)
<223> OTHER INFORMATION: Xaa can be any naturally occurring amino acid

<400> SEQUENCE: 160

```
Asp Ile Val Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Trp Thr Phe Gly Gly Gly Thr Lys Xaa Glu Ile Lys
            100                 105                 110
```

<210> SEQ ID NO 161
<211> LENGTH: 117
<212> TYPE: PRT
<213> ORGANISM: Artificial
<220> FEATURE:
<223> OTHER INFORMATION: Synthetic

<400> SEQUENCE: 161

```
Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Thr Gly Gln Gly Leu Glu Trp Met
        35                  40                  45

Gly Trp Ile Tyr Pro Gly Ser Gly Asn Thr Lys Tyr Asn Glu Lys Phe
    50                  55                  60

Gln Gly Arg Val Thr Ser Thr Val Asp Thr Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Asn Tyr Gly Asn Tyr Trp Phe Ala Tyr Trp Gly Gln Gly Thr Leu
            100                 105                 110

Val Thr Val Ser Ser
        115
```

<210> SEQ ID NO 162
<211> LENGTH: 117
<212> TYPE: PRT
<213> ORGANISM: Artificial
<220> FEATURE:
<223> OTHER INFORMATION: Synthetic

```
<400> SEQUENCE: 162

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile Thr Trp Val Arg Gln Ala Pro Gly Gln Gly Leu Glu Trp Met
            35                  40                  45

Gly Trp Ile Tyr Pro Gly Ser Gly Asn Thr Lys Tyr Asn Glu Lys Phe
    50                  55                  60

Gln Gly Arg Val Thr Ser Thr Val Asp Thr Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Asn Tyr Gly Asn Tyr Trp Phe Ala Tyr Trp Gly Gln Gly Thr Leu
                100                 105                 110

Val Thr Val Ser Ser
            115

<210> SEQ ID NO 163
<211> LENGTH: 117
<212> TYPE: PRT
<213> ORGANISM: Artificial
<220> FEATURE:
<223> OTHER INFORMATION: Synthetic

<400> SEQUENCE: 163

Gln Ile Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
                20                  25                  30

Tyr Ile Thr Trp Val Arg Gln Ala Pro Gly Gln Gly Leu Glu Trp Met
            35                  40                  45

Gly Trp Ile Tyr Pro Gly Ser Gly Asn Thr Lys Tyr Asn Glu Lys Phe
    50                  55                  60

Gln Gly Arg Val Thr Ser Thr Val Asp Thr Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Asn Tyr Gly Asn Tyr Trp Phe Ala Tyr Trp Gly Gln Gly Thr Leu
                100                 105                 110

Val Thr Val Ser Ser
            115

<210> SEQ ID NO 164
<211> LENGTH: 117
<212> TYPE: PRT
<213> ORGANISM: Artificial
<220> FEATURE:
<223> OTHER INFORMATION: Synthetic

<400> SEQUENCE: 164

Gln Ile Gln Leu Val Gln Ser Gly His Glu Val Lys Gln Pro Gly Ala
1               5                   10                  15

Ser Val Lys Val Ser Cys Lys Ala Ser Gly Tyr Thr Phe Thr Asp Tyr
                20                  25                  30

Tyr Ile Thr Trp Val Arg Gln Ala Thr Gly Gln Gly Leu Glu Trp Met
            35                  40                  45
```

Gly Trp Ile Tyr Pro Gly Ser Gly Asn Thr Lys Tyr Asn Glu Lys Phe
            50                  55                  60

Gln Gly Arg Val Thr Ser Thr Val Asp Thr Ser Ile Ser Thr Ala Tyr
 65                  70                  75                  80

Met Glu Leu Ser Ser Leu Arg Ser Glu Asp Thr Ala Val Tyr Phe Cys
                85                  90                  95

Ala Asn Tyr Gly Asn Tyr Trp Phe Ala Tyr Trp Gly Gln Gly Thr Leu
               100                 105                 110

Val Thr Val Ser Ser
            115

<210> SEQ ID NO 165
<211> LENGTH: 117
<212> TYPE: PRT
<213> ORGANISM: Artificial
<220> FEATURE:
<223> OTHER INFORMATION: Synthetic

<400> SEQUENCE: 165

Gln Ile Gln Leu Val Gln Ser Gly Pro Glu Val Lys Lys Pro Gly Thr
 1               5                  10                  15

Ser Val Lys Val Ser Cys Lys Ala Ser Gly Tyr Thr Phe Thr Asp Tyr
                20                  25                  30

Tyr Ile Thr Trp Val Arg Gln Ala Thr Gly Gln Gly Leu Glu Trp Met
            35                  40                  45

Gly Trp Ile Tyr Pro Gly Ser Gly Asn Thr Lys Tyr Asn Glu Lys Phe
        50                  55                  60

Gln Gly Arg Val Thr Ile Thr Val Asp Thr Ser Ala Ser Thr Ala Tyr
 65                  70                  75                  80

Met Glu Leu Ser Ser Leu Arg Ser Glu Asp Thr Ala Val Tyr Phe Cys
                85                  90                  95

Ala Asn Tyr Gly Asn Tyr Trp Phe Ala Tyr Trp Gly Gln Gly Thr Leu
               100                 105                 110

Val Thr Val Ser Ser
            115

<210> SEQ ID NO 166
<211> LENGTH: 117
<212> TYPE: PRT
<213> ORGANISM: Artificial
<220> FEATURE:
<223> OTHER INFORMATION: Synthetic

<400> SEQUENCE: 166

Gln Ile Gln Leu Val Gln Ser Gly Pro Glu Val Lys Lys Pro Gly Thr
 1               5                  10                  15

Ser Val Lys Val Ser Cys Lys Ala Ser Gly Tyr Thr Phe Thr Asp Tyr
                20                  25                  30

Tyr Ile Thr Trp Val Arg Gln Ala Pro Gly Gln Gly Leu Glu Trp Met
            35                  40                  45

Gly Trp Ile Tyr Pro Gly Ser Gly Asn Thr Lys Tyr Asn Glu Lys Phe
        50                  55                  60

Gln Gly Arg Val Thr Ile Thr Val Asp Thr Ser Ala Ser Thr Ala Tyr
 65                  70                  75                  80

Met Glu Leu Ser Ser Leu Arg Ser Glu Asp Thr Ala Val Tyr Phe Cys
                85                  90                  95

Ala Asn Tyr Gly Asn Tyr Trp Phe Ala Tyr Trp Gly Gln Gly Thr Leu
               100                 105                 110

Val Thr Val Ser Ser
        115

<210> SEQ ID NO 167
<211> LENGTH: 117
<212> TYPE: PRT
<213> ORGANISM: Artificial
<220> FEATURE:
<223> OTHER INFORMATION: Synthetic

<400> SEQUENCE: 167

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile Thr Trp Val Arg Gln Ala Thr Gly Gln Gly Leu Glu Trp Met
            35                  40                  45

Gly Trp Ile Tyr Pro Gly Ser Gly Asn Thr Lys Tyr Asn Glu Lys Phe
        50                  55                  60

Gln Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Asn Tyr Gly Asn Tyr Trp Phe Ala Tyr Trp Gly Gln Gly Thr Leu
            100                 105                 110

Val Thr Val Ser Ser
        115

<210> SEQ ID NO 168
<211> LENGTH: 117
<212> TYPE: PRT
<213> ORGANISM: Artificial
<220> FEATURE:
<223> OTHER INFORMATION: Synthetic

<400> SEQUENCE: 168

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile Thr Trp Val Arg Gln Ala Pro Gly Gln Gly Leu Glu Trp Met
            35                  40                  45

Gly Trp Ile Tyr Pro Gly Ser Gly Asn Thr Lys Tyr Asn Glu Lys Phe
        50                  55                  60

Gln Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Asn Tyr Gly Asn Tyr Trp Phe Ala Tyr Trp Gly Gln Gly Thr Leu
            100                 105                 110

Val Thr Val Ser Ser
        115

<210> SEQ ID NO 169
<211> LENGTH: 117
<212> TYPE: PRT
<213> ORGANISM: Artificial
<220> FEATURE:
<223> OTHER INFORMATION: Synthetic

<400> SEQUENCE: 169

-continued

Gln Ile Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Pro Gly Gln Gly Leu Glu Trp Met
        35                  40                  45

Gly Trp Ile Tyr Pro Gly Ser Gly Asn Thr Lys Tyr Asn Glu Lys Phe
    50                  55                  60

Gln Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Asn Tyr Gly Asn Tyr Trp Phe Ala Tyr Trp Gly Gln Gly Thr Leu
                100                 105                 110

Val Thr Val Ser Ser
        115

<210> SEQ ID NO 170
<211> LENGTH: 117
<212> TYPE: PRT
<213> ORGANISM: Artificial
<220> FEATURE:
<223> OTHER INFORMATION: Synthetic

<400> SEQUENCE: 170

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Pro Gly Gln Gly Leu Glu Trp Met
        35                  40                  45

Gly Trp Ile Tyr Pro Gly Ser Gly Asn Thr Lys Tyr Asn Glu Lys Phe
    50                  55                  60

Gln Gly Arg Val Thr Met Thr Val Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Asn Tyr Gly Asn Tyr Trp Phe Ala Tyr Trp Gly Gln Gly Thr Leu
                100                 105                 110

Val Thr Val Ser Ser
        115

<210> SEQ ID NO 171
<211> LENGTH: 117
<212> TYPE: PRT
<213> ORGANISM: Artificial
<220> FEATURE:
<223> OTHER INFORMATION: Synthetic

<400> SEQUENCE: 171

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Pro Gly Gln Gly Leu Glu Trp Met
        35                  40                  45

Gly Trp Ile Tyr Pro Gly Ser Gly Asn Thr Lys Tyr Asn Glu Lys Phe
    50                  55                  60

```
Gln Gly Arg Val Thr Ser Thr Val Asp Thr Ser Ile Ser Ala Tyr
65                  70                  75                  80

Met Glu Leu Ser Ser Leu Arg Ser Glu Asp Thr Ala Met Tyr Phe Cys
                85                  90                  95

Ala Asn Tyr Gly Asn Tyr Trp Phe Ala Tyr Trp Gly Gln Gly Thr Leu
            100                 105                 110

Val Thr Val Ser Ser
        115

<210> SEQ ID NO 172
<211> LENGTH: 117
<212> TYPE: PRT
<213> ORGANISM: Artificial
<220> FEATURE:
<223> OTHER INFORMATION: Synthetic

<400> SEQUENCE: 172

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Pro Gly Gln Gly Leu Glu Trp Met
        35                  40                  45

Gly Trp Ile Tyr Pro Gly Ser Gly Asn Thr Lys Tyr Asn Glu Lys Phe
    50                  55                  60

Gln Gly Arg Val Thr Ser Thr Val Asp Thr Ser Ile Ser Ala Tyr
65                  70                  75                  80

Met Glu Leu Ser Ser Leu Arg Ser Glu Asp Thr Ala Val Tyr Phe Cys
                85                  90                  95

Ala Asn Tyr Gly Asn Tyr Trp Phe Ala Tyr Trp Gly Gln Gly Thr Leu
            100                 105                 110

Val Thr Val Ser Ser
        115

<210> SEQ ID NO 173
<211> LENGTH: 117
<212> TYPE: PRT
<213> ORGANISM: Artificial
<220> FEATURE:
<223> OTHER INFORMATION: Synthetic

<400> SEQUENCE: 173

Gln Ile Gln Leu Val Gln Ser Gly His Glu Val Lys Gln Pro Gly Ala
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Pro Gly Gln Gly Leu Glu Trp Met
        35                  40                  45

Gly Trp Ile Tyr Pro Gly Ser Gly Asn Thr Lys Tyr Asn Glu Lys Phe
    50                  55                  60

Gln Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Asn Tyr Gly Asn Tyr Trp Phe Ala Tyr Trp Gly Gln Gly Thr Leu
            100                 105                 110

Val Thr Val Ser Ser
        115
```

<210> SEQ ID NO 174
<211> LENGTH: 117
<212> TYPE: PRT
<213> ORGANISM: Artificial
<220> FEATURE:
<223> OTHER INFORMATION: Synthetic

<400> SEQUENCE: 174

Gln Ile Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Thr Gly Gln Gly Leu Glu Trp Met
        35                  40                  45

Gly Trp Ile Tyr Pro Gly Ser Gly Asn Thr Lys Tyr Asn Glu Lys Phe
    50                  55                  60

Gln Gly Arg Val Thr Met Thr Val Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Asn Tyr Gly Asn Tyr Trp Phe Ala Tyr Trp Gly Gln Gly Thr Leu
            100                 105                 110

Val Thr Val Ser Ser
        115

<210> SEQ ID NO 175
<211> LENGTH: 117
<212> TYPE: PRT
<213> ORGANISM: Artificial
<220> FEATURE:
<223> OTHER INFORMATION: Synthetic

<400> SEQUENCE: 175

Gln Ile Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Thr Gly Gln Gly Leu Glu Trp Met
        35                  40                  45

Gly Trp Ile Tyr Pro Gly Ser Gly Asn Thr Lys Tyr Asn Glu Lys Phe
    50                  55                  60

Gln Gly Arg Val Thr Ser Thr Val Asp Thr Ser Ile Ser Thr Ala Tyr
65                  70                  75                  80

Met Glu Leu Ser Ser Leu Arg Ser Glu Asp Thr Ala Met Tyr Phe Cys
                85                  90                  95

Ala Asn Tyr Gly Asn Tyr Trp Phe Ala Tyr Trp Gly Gln Gly Thr Leu
            100                 105                 110

Val Thr Val Ser Ser
        115

<210> SEQ ID NO 176
<211> LENGTH: 117
<212> TYPE: PRT
<213> ORGANISM: Artificial
<220> FEATURE:
<223> OTHER INFORMATION: Synthetic

<400> SEQUENCE: 176

Gln Ile Gln Leu Val Gln Ser Gly Pro Glu Val Lys Lys Pro Gly Thr

-continued

Ser Val Lys Val Ser Cys Lys Ala Ser Gly Tyr Thr Phe Thr Asp Tyr
                20                  25                  30

Tyr Ile Thr Trp Val Arg Gln Ala Thr Gly Gln Gly Leu Glu Trp Met
            35                  40                  45

Gly Trp Ile Tyr Pro Gly Ser Gly Asn Thr Lys Tyr Asn Glu Lys Phe
        50                  55                  60

Gln Gly Arg Val Thr Ser Thr Val Asp Thr Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Asn Tyr Gly Asn Tyr Trp Phe Ala Tyr Trp Gly Gln Gly Thr Leu
                100                 105                 110

Val Thr Val Ser Ser
        115

<210> SEQ ID NO 177
<211> LENGTH: 117
<212> TYPE: PRT
<213> ORGANISM: Artificial
<220> FEATURE:
<223> OTHER INFORMATION: Synthetic

<400> SEQUENCE: 177

Gln Ile Gln Leu Val Gln Ser Gly His Glu Val Lys Gln Pro Gly Ala
1               5                   10                  15

Ser Val Lys Val Ser Cys Lys Ala Ser Gly Tyr Thr Phe Thr Asp Tyr
                20                  25                  30

Tyr Ile Thr Trp Val Arg Gln Ala Thr Gly Gln Gly Leu Glu Trp Met
            35                  40                  45

Gly Trp Ile Tyr Pro Gly Ser Gly Asn Thr Lys Tyr Asn Glu Lys Phe
        50                  55                  60

Gln Gly Arg Val Thr Met Thr Val Asp Thr Ser Ser Thr Ala Tyr
65                  70                  75                  80

Met Glu Leu Ser Ser Leu Arg Ser Glu Asp Thr Ala Val Tyr Phe Cys
                85                  90                  95

Ala Asn Tyr Gly Asn Tyr Trp Phe Ala Tyr Trp Gly Gln Gly Thr Leu
                100                 105                 110

Val Thr Val Ser Ser
        115

<210> SEQ ID NO 178
<211> LENGTH: 117
<212> TYPE: PRT
<213> ORGANISM: Artificial
<220> FEATURE:
<223> OTHER INFORMATION: Synthetic

<400> SEQUENCE: 178

Gln Ile Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
                20                  25                  30

Tyr Ile Thr Trp Val Arg Gln Ala Pro Gly Gln Gly Leu Glu Trp Met
            35                  40                  45

Gly Trp Ile Tyr Pro Gly Ser Gly Asn Thr Lys Tyr Asn Glu Lys Phe
        50                  55                  60

Gln Gly Arg Val Thr Met Thr Val Asn Thr Ser Ile Ser Thr Ala Tyr

```
                65                  70                  75                  80
Met Glu Leu Ser Ser Leu Arg Ser Glu Asp Thr Ala Val Tyr Phe Cys
                    85                  90                  95

Ala Asn Tyr Gly Asn Tyr Trp Phe Ala Tyr Trp Gly Gln Gly Thr Leu
                100                 105                 110

Val Thr Val Ser Ser
        115

<210> SEQ ID NO 179
<211> LENGTH: 117
<212> TYPE: PRT
<213> ORGANISM: Artificial
<220> FEATURE:
<223> OTHER INFORMATION: Synthetic

<400> SEQUENCE: 179

Gln Ile Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
                20                  25                  30

Tyr Ile Thr Trp Val Arg Gln Ala Pro Gly Gln Gly Leu Glu Trp Met
                35                  40                  45

Gly Trp Ile Tyr Pro Gly Ser Gly Asn Thr Lys Tyr Asn Glu Lys Phe
        50                  55                  60

Gln Gly Arg Val Thr Met Thr Val Asn Thr Ser Ile Ser Thr Ala Tyr
65                  70                  75                  80

Met Glu Leu Ser Ser Leu Arg Ser Glu Asp Thr Ala Met Tyr Phe Cys
                    85                  90                  95

Ala Asn Tyr Gly Asn Tyr Trp Phe Ala Tyr Trp Gly Gln Gly Thr Leu
                100                 105                 110

Val Thr Val Ser Ser
        115

<210> SEQ ID NO 180
<211> LENGTH: 117
<212> TYPE: PRT
<213> ORGANISM: Artificial
<220> FEATURE:
<223> OTHER INFORMATION: Synthetic

<400> SEQUENCE: 180

Gln Ile Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
                20                  25                  30

Tyr Ile Thr Trp Val Arg Gln Ala Thr Gly Gln Gly Leu Glu Trp Met
                35                  40                  45

Gly Trp Ile Tyr Pro Gly Ser Gly Asn Thr Lys Tyr Asn Glu Lys Phe
        50                  55                  60

Gln Gly Arg Val Thr Met Thr Val Asp Thr Ser Thr Ser Thr Ala Tyr
65                  70                  75                  80

Met Glu Leu Ser Ser Leu Arg Ser Glu Asp Thr Ala Val Tyr Phe Cys
                    85                  90                  95

Ala Asn Tyr Gly Asn Tyr Trp Phe Ala Tyr Trp Gly Gln Gly Thr Leu
                100                 105                 110

Val Thr Val Ser Ser
        115
```

```
<210> SEQ ID NO 181
<211> LENGTH: 117
<212> TYPE: PRT
<213> ORGANISM: Artificial
<220> FEATURE:
<223> OTHER INFORMATION: Synthetic

<400> SEQUENCE: 181
```

Gln Ile Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
                20                  25                  30

Tyr Ile Thr Trp Val Arg Gln Ala Pro Gly Gln Gly Leu Glu Trp Met
            35                  40                  45

Gly Trp Ile Tyr Pro Gly Ser Gly Asn Thr Lys Tyr Asn Glu Lys Phe
50                  55                  60

Gln Gly Arg Val Thr Met Thr Val Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Asn Tyr Gly Asn Tyr Trp Phe Ala Tyr Trp Gly Gln Gly Thr Leu
            100                 105                 110

Val Thr Val Ser Ser
        115

```
<210> SEQ ID NO 182
<211> LENGTH: 117
<212> TYPE: PRT
<213> ORGANISM: Artificial
<220> FEATURE:
<223> OTHER INFORMATION: Synthetic

<400> SEQUENCE: 182
```

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile Thr Trp Val Arg Gln Ala Thr Gly Gln Gly Leu Glu Trp Met
            35                  40                  45

Gly Trp Ile Tyr Pro Gly Ser Gly Asn Thr Lys Tyr Asn Glu Lys Phe
50                  55                  60

Gln Gly Arg Val Thr Met Thr Val Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Asn Tyr Gly Asn Tyr Trp Phe Ala Tyr Trp Gly Gln Gly Thr Leu
            100                 105                 110

Val Thr Val Ser Ser
        115

```
<210> SEQ ID NO 183
<211> LENGTH: 117
<212> TYPE: PRT
<213> ORGANISM: Artificial
<220> FEATURE:
<223> OTHER INFORMATION: Synthetic

<400> SEQUENCE: 183
```

Gln Ile Gln Leu Val Gln Ser Gly Ser Glu Leu Lys Lys Pro Gly Ala
1               5                   10                  15

```
Ser Val Lys Val Ser Cys Lys Ala Ser Gly Tyr Thr Phe Thr Asp Tyr
            20                  25                  30

Tyr Ile Thr Trp Val Arg Gln Ala Thr Gly Gln Gly Leu Glu Trp Met
            35                  40                  45

Gly Trp Ile Tyr Pro Gly Ser Gly Asn Thr Lys Tyr Asn Glu Lys Phe
 50                      55                  60

Gln Gly Arg Val Thr Ile Thr Val Asp Thr Ser Ala Ser Thr Ala Tyr
 65                      70                  75                  80

Met Glu Leu Ser Ser Leu Arg Ser Glu Asp Thr Ala Val Tyr Phe Cys
                     85                  90                  95

Ala Asn Tyr Gly Asn Tyr Trp Phe Ala Tyr Trp Gly Gln Gly Thr Leu
                100                 105                 110

Val Thr Val Ser Ser
            115

<210> SEQ ID NO 184
<211> LENGTH: 117
<212> TYPE: PRT
<213> ORGANISM: Artificial
<220> FEATURE:
<223> OTHER INFORMATION: Synthetic

<400> SEQUENCE: 184

Gln Ile Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Asp Tyr
            20                  25                  30

Tyr Ile Thr Trp Val Arg Gln Ala Pro Gly Gln Gly Leu Glu Trp Met
            35                  40                  45

Gly Trp Ile Tyr Pro Gly Ser Gly Asn Thr Lys Tyr Asn Glu Lys Phe
 50                      55                  60

Gln Gly Arg Val Thr Ile Thr Val Asp Thr Ser Ala Ser Thr Ala Tyr
 65                      70                  75                  80

Met Glu Leu Ser Ser Leu Arg Ser Glu Asp Thr Ala Val Tyr Phe Cys
                     85                  90                  95

Ala Asn Tyr Gly Asn Tyr Trp Phe Ala Tyr Trp Gly Gln Gly Thr Leu
                100                 105                 110

Val Thr Val Ser Ser
            115

<210> SEQ ID NO 185
<211> LENGTH: 117
<212> TYPE: PRT
<213> ORGANISM: Artificial
<220> FEATURE:
<223> OTHER INFORMATION: Synthetic

<400> SEQUENCE: 185

Gln Ile Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Asp Tyr
            20                  25                  30

Tyr Ile Thr Trp Val Arg Gln Ala Pro Gly Gln Gly Leu Glu Trp Met
            35                  40                  45

Gly Trp Ile Tyr Pro Gly Ser Gly Asn Thr Lys Tyr Asn Glu Lys Phe
 50                      55                  60

Gln Gly Arg Val Thr Ile Thr Val Asp Thr Ser Ala Ser Thr Ala Tyr
 65                      70                  75                  80
```

```
Met Glu Leu Ser Arg Leu Arg Ser Asp Asp Thr Val Val Tyr Phe Cys
             85                  90                  95

Ala Asn Tyr Gly Asn Tyr Trp Phe Ala Tyr Trp Gly Gln Gly Thr Leu
            100                 105                 110

Val Thr Val Ser Ser
        115

<210> SEQ ID NO 186
<211> LENGTH: 117
<212> TYPE: PRT
<213> ORGANISM: Artificial
<220> FEATURE:
<223> OTHER INFORMATION: Synthetic

<400> SEQUENCE: 186

Gln Ile Gln Leu Val Gln Ser Gly His Glu Val Lys Gln Pro Gly Ala
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Pro Gly Gln Gly Leu Glu Trp Met
        35                  40                  45

Gly Trp Ile Tyr Pro Gly Ser Gly Asn Thr Lys Tyr Asn Glu Lys Phe
    50                  55                  60

Gln Gly Arg Val Thr Met Thr Val Asp Thr Ser Thr Ser Thr Ala Tyr
65                  70                  75                  80

Met Glu Leu Arg Ser Leu Arg Ser Asp Asp Thr Ala Val Tyr Phe Cys
             85                  90                  95

Ala Asn Tyr Gly Asn Tyr Trp Phe Ala Tyr Trp Gly Gln Gly Thr Leu
            100                 105                 110

Val Thr Val Ser Ser
        115

<210> SEQ ID NO 187
<211> LENGTH: 117
<212> TYPE: PRT
<213> ORGANISM: Artificial
<220> FEATURE:
<223> OTHER INFORMATION: Synthetic

<400> SEQUENCE: 187

Gln Ile Gln Leu Val Gln Ser Gly His Glu Val Lys Gln Pro Gly Ala
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Pro Gly Gln Gly Leu Glu Trp Met
        35                  40                  45

Gly Trp Ile Tyr Pro Gly Ser Gly Asn Thr Lys Tyr Asn Glu Lys Phe
    50                  55                  60

Gln Gly Arg Val Thr Ile Thr Val Asp Thr Ser Ala Ser Thr Ala Tyr
65                  70                  75                  80

Met Glu Leu Ser Arg Leu Arg Ser Asp Asp Thr Val Val Tyr Phe Cys
             85                  90                  95

Ala Asn Tyr Gly Asn Tyr Trp Phe Ala Tyr Trp Gly Gln Gly Thr Leu
            100                 105                 110

Val Thr Val Ser Ser
        115

<210> SEQ ID NO 188
<211> LENGTH: 117
```

```
<212> TYPE: PRT
<213> ORGANISM: Artificial
<220> FEATURE:
<223> OTHER INFORMATION: Synthetic

<400> SEQUENCE: 188

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Thr Gly Gln Gly Leu Glu Trp Met
        35                  40                  45

Gly Trp Ile Tyr Pro Gly Ser Gly Asn Thr Lys Tyr Asn Glu Lys Phe
    50                  55                  60

Gln Gly Arg Val Thr Met Thr Val Asn Thr Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Asn Tyr Gly Asn Tyr Trp Phe Ala Tyr Trp Gly Gln Gly Thr Leu
            100                 105                 110

Val Thr Val Ser Ser
            115

<210> SEQ ID NO 189
<211> LENGTH: 117
<212> TYPE: PRT
<213> ORGANISM: Artificial
<220> FEATURE:
<223> OTHER INFORMATION: Synthetic

<400> SEQUENCE: 189

Gln Ile Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Pro Gly Gln Gly Leu Glu Trp Met
        35                  40                  45

Gly Trp Ile Tyr Pro Gly Ser Gly Asn Thr Lys Tyr Asn Glu Lys Phe
    50                  55                  60

Gln Gly Arg Val Thr Ile Thr Val Asp Thr Ser Ala Ser Thr Ala Tyr
65                  70                  75                  80

Met Glu Leu Ser Arg Leu Arg Ser Asp Asp Thr Val Val Tyr Phe Cys
                85                  90                  95

Ala Asn Tyr Gly Asn Tyr Trp Phe Ala Tyr Trp Gly Gln Gly Thr Leu
            100                 105                 110

Val Thr Val Ser Ser
            115

<210> SEQ ID NO 190
<211> LENGTH: 117
<212> TYPE: PRT
<213> ORGANISM: Artificial
<220> FEATURE:
<223> OTHER INFORMATION: Synthetic

<400> SEQUENCE: 190

Gln Ile Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30
```

```
Tyr Ile Thr Trp Val Arg Gln Ala Pro Gly Gln Gly Leu Glu Trp Met
            35                  40                  45

Gly Trp Ile Tyr Pro Gly Ser Gly Asn Thr Lys Tyr Asn Glu Ser Leu
 50                      55                  60

Lys Ser Arg Val Thr Ile Ser Val Asp Thr Ser Ala Ser Thr Ala Tyr
 65                  70                  75                  80

Met Glu Leu Ser Ser Leu Arg Ser Glu Asp Thr Ala Val Tyr Phe Cys
                 85                  90                  95

Ala Asn Tyr Gly Asn Tyr Trp Phe Ala Tyr Trp Gly Gln Gly Thr Leu
                100                 105                 110

Val Thr Val Ser Ser
        115

<210> SEQ ID NO 191
<211> LENGTH: 117
<212> TYPE: PRT
<213> ORGANISM: Artificial
<220> FEATURE:
<223> OTHER INFORMATION: Synthetic

<400> SEQUENCE: 191

Gln Ile Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Asp Tyr
                20                  25                  30

Tyr Ile Thr Trp Val Arg Gln Ala Pro Gly Gln Gly Leu Glu Trp Met
            35                  40                  45

Gly Trp Ile Tyr Pro Gly Ser Gly Asn Thr Lys Tyr Asn Glu Ser Leu
 50                      55                  60

Lys Ser Leu Val Thr Ile Ser Val Asp Thr Ser Ala Ser Thr Ala Tyr
 65                  70                  75                  80

Met Glu Leu Ser Ser Leu Arg Ser Glu Asp Thr Ala Val Tyr Phe Cys
                 85                  90                  95

Ala Asn Tyr Gly Asn Tyr Trp Phe Ala Tyr Trp Gly Gln Gly Thr Leu
                100                 105                 110

Val Thr Val Ser Ser
        115

<210> SEQ ID NO 192
<211> LENGTH: 117
<212> TYPE: PRT
<213> ORGANISM: Artificial
<220> FEATURE:
<223> OTHER INFORMATION: Synthetic

<400> SEQUENCE: 192

Gln Ile Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                20                  25                  30

Tyr Ile Thr Trp Val Arg Gln Ala Thr Gly Gln Gly Leu Glu Trp Met
            35                  40                  45

Gly Trp Ile Tyr Pro Gly Ser Gly Asn Thr Lys Tyr Asn Glu Ser Leu
 50                      55                  60

Lys Ser Leu Val Thr Ile Ser Val Asp Thr Ser Ala Ser Thr Ala Tyr
 65                  70                  75                  80

Met Glu Leu Ser Ser Leu Arg Ser Glu Asp Thr Ala Val Tyr Phe Cys
                 85                  90                  95
```

-continued

Ala Asn Tyr Gly Asn Tyr Trp Phe Ala Tyr Trp Gly Gln Gly Thr Leu
            100                 105                 110

Val Thr Val Ser Ser
        115

<210> SEQ ID NO 193
<211> LENGTH: 117
<212> TYPE: PRT
<213> ORGANISM: Artificial
<220> FEATURE:
<223> OTHER INFORMATION: Synthetic

<400> SEQUENCE: 193

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Pro Gly Gln Gly Leu Glu Trp Met
        35                  40                  45

Gly Trp Ile Tyr Pro Gly Ser Gly Asn Thr Lys Tyr Asn Glu Ser Leu
    50                  55                  60

Lys Ser Arg Val Thr Ile Ser Val Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Asn Tyr Gly Asn Tyr Trp Phe Ala Tyr Trp Gly Gln Gly Thr Leu
            100                 105                 110

Val Thr Val Ser Ser
        115

<210> SEQ ID NO 194
<211> LENGTH: 117
<212> TYPE: PRT
<213> ORGANISM: Artificial
<220> FEATURE:
<223> OTHER INFORMATION: Synthetic

<400> SEQUENCE: 194

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Thr Gly Gln Gly Leu Glu Trp Met
        35                  40                  45

Gly Trp Ile Tyr Pro Gly Ser Gly Asn Thr Lys Tyr Asn Glu Ser Leu
    50                  55                  60

Lys Ser Arg Val Thr Ile Ser Val Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Asn Tyr Gly Asn Tyr Trp Phe Ala Tyr Trp Gly Gln Gly Thr Leu
            100                 105                 110

Val Thr Val Ser Ser
        115

<210> SEQ ID NO 195
<211> LENGTH: 117
<212> TYPE: PRT
<213> ORGANISM: Artificial

```
<220> FEATURE:
<223> OTHER INFORMATION: Synthetic

<400> SEQUENCE: 195

Gln Ile Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Pro Gly Gln Gly Leu Glu Trp Met
        35                  40                  45

Gly Trp Ile Tyr Pro Gly Ser Gly Asn Thr Lys Tyr Asn Glu Ser Leu
    50                  55                  60

Lys Ser Leu Val Thr Ile Ser Val Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Asn Tyr Gly Asn Tyr Trp Phe Ala Tyr Trp Gly Gln Gly Thr Leu
            100                 105                 110

Val Thr Val Ser Ser
        115

<210> SEQ ID NO 196
<211> LENGTH: 117
<212> TYPE: PRT
<213> ORGANISM: Artificial
<220> FEATURE:
<223> OTHER INFORMATION: Synthetic

<400> SEQUENCE: 196

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Thr Gly Gln Gly Leu Glu Trp Met
        35                  40                  45

Gly Trp Ile Tyr Pro Gly Ser Gly Asn Thr Lys Tyr Asn Glu Ser Leu
    50                  55                  60

Lys Ser Leu Val Thr Ile Ser Val Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Asn Tyr Gly Asn Tyr Trp Phe Ala Tyr Trp Gly Gln Gly Thr Leu
            100                 105                 110

Val Thr Val Ser Ser
        115

<210> SEQ ID NO 197
<211> LENGTH: 117
<212> TYPE: PRT
<213> ORGANISM: Artificial
<220> FEATURE:
<223> OTHER INFORMATION: Synthetic

<400> SEQUENCE: 197

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Pro Gly Gln Gly Leu Glu Trp Met
```

```
                35                  40                  45
Gly Trp Ile Tyr Pro Gly Ser Gly Asn Thr Lys Tyr Asn Glu Ser Leu
         50                  55                  60
Lys Ser Arg Val Thr Ile Ser Val Asp Thr Ser Ala Ser Thr Ala Tyr
 65                  70                  75                  80
Met Glu Leu Ser Ser Leu Arg Ser Glu Asp Thr Ala Val Tyr Phe Cys
             85                  90                  95
Ala Asn Tyr Gly Asn Tyr Trp Phe Ala Tyr Trp Gly Gln Gly Thr Leu
                100                 105                 110
Val Thr Val Ser Ser
            115

<210> SEQ ID NO 198
<211> LENGTH: 117
<212> TYPE: PRT
<213> ORGANISM: Artificial
<220> FEATURE:
<223> OTHER INFORMATION: Synthetic

<400> SEQUENCE: 198

Gln Ile Gln Leu Val Gln Ser Gly Ala Glu Val Lys Lys Pro Gly Ala
 1               5                  10                  15
Ser Val Lys Val Ser Cys Lys Ala Ser Gly Tyr Thr Phe Thr Asp Tyr
             20                  25                  30
Tyr Ile Thr Trp Val Arg Gln Ala Pro Gly Gln Gly Leu Glu Trp Met
                35                  40                  45
Gly Trp Ile Tyr Pro Gly Ser Gly Asn Thr Lys Tyr Asn Glu Ser Leu
         50                  55                  60
Lys Ser Leu Val Thr Ile Ser Val Asp Thr Ser Ala Ser Thr Ala Tyr
 65                  70                  75                  80
Met Glu Leu Ser Arg Leu Arg Ser Asp Asp Thr Val Val Tyr Phe Cys
             85                  90                  95
Ala Asn Tyr Gly Asn Tyr Trp Phe Ala Tyr Trp Gly Gln Gly Thr Leu
                100                 105                 110
Val Thr Val Ser Ser
            115

<210> SEQ ID NO 199
<211> LENGTH: 117
<212> TYPE: PRT
<213> ORGANISM: Artificial
<220> FEATURE:
<223> OTHER INFORMATION: Synthetic

<400> SEQUENCE: 199

Gln Ile Gln Leu Val Glu Ser Gly Gly Gly Leu Val Lys Pro Gly Ala
 1               5                  10                  15
Ser Val Lys Val Ser Cys Lys Ala Ser Gly Tyr Thr Phe Thr Asp Tyr
             20                  25                  30
Tyr Ile Thr Trp Val Arg Gln Ala Thr Gly Gln Gly Leu Glu Trp Met
                35                  40                  45
Gly Trp Ile Tyr Pro Gly Ser Gly Asn Thr Lys Tyr Asn Glu Lys Phe
         50                  55                  60
Gln Gly Arg Val Thr Ser Thr Val Asp Thr Ser Ile Ser Thr Ala Tyr
 65                  70                  75                  80
Met Glu Leu Ser Ser Leu Arg Ser Glu Asp Thr Ala Val Tyr Phe Cys
             85                  90                  95
Ala Asn Tyr Gly Asn Tyr Trp Phe Ala Tyr Trp Gly Gln Gly Thr Leu
```

-continued

```
                100                 105                 110
Val Thr Val Ser Ser
        115

<210> SEQ ID NO 200
<211> LENGTH: 117
<212> TYPE: PRT
<213> ORGANISM: Artificial
<220> FEATURE:
<223> OTHER INFORMATION: Synthetic

<400> SEQUENCE: 200

Gln Ile Gln Leu Val Gln Ser Gly His Glu Val Lys Gln Pro Gly Ala
1               5                   10                  15

Ser Val Lys Val Ser Cys Lys Ala Ser Gly Tyr Thr Phe Thr Asp Tyr
                20                  25                  30

Tyr Ile Thr Trp Val Arg Gln Ala Thr Gly Gln Gly Leu Glu Trp Met
            35                  40                  45

Gly Trp Ile Tyr Pro Gly Ser Gly Asn Thr Lys Tyr Asn Glu Lys Phe
        50                  55                  60

Gln Gly Arg Val Thr Ser Thr Val Asp Thr Ser Ile Ser Thr Ala Tyr
65                  70                  75                  80

Leu Gln Ile Cys Ser Leu Lys Ala Glu Asp Thr Ala Val Tyr Phe Cys
                85                  90                  95

Ala Asn Tyr Gly Asn Tyr Trp Phe Ala Tyr Trp Gly Gln Gly Thr Leu
                100                 105                 110

Val Thr Val Ser Ser
        115

<210> SEQ ID NO 201
<211> LENGTH: 117
<212> TYPE: PRT
<213> ORGANISM: Artificial
<220> FEATURE:
<223> OTHER INFORMATION: Synthetic

<400> SEQUENCE: 201

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile Thr Trp Val Arg Gln Ala Thr Gly Gln Gly Leu Glu Trp Met
            35                  40                  45

Gly Trp Ile Tyr Pro Gly Ser Gly Asn Thr Lys Tyr Asn Glu Lys Phe
        50                  55                  60

Gln Gly Arg Val Thr Ser Thr Val Asp Thr Ser Ile Ser Thr Ala Tyr
65                  70                  75                  80

Leu Gln Ile Cys Ser Leu Lys Ala Glu Asp Thr Ala Val Tyr Phe Cys
                85                  90                  95

Ala Asn Tyr Gly Asn Tyr Trp Phe Ala Tyr Trp Gly Gln Gly Thr Leu
                100                 105                 110

Val Thr Val Ser Ser
        115

<210> SEQ ID NO 202
<211> LENGTH: 117
<212> TYPE: PRT
<213> ORGANISM: Artificial
<220> FEATURE:
<223> OTHER INFORMATION: Synthetic
```

<400> SEQUENCE: 202

Gln Ile Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Thr Gly Gln Gly Leu Glu Trp Met
        35                  40                  45

Gly Trp Ile Tyr Pro Gly Ser Gly Asn Thr Lys Tyr Asn Glu Lys Phe
    50                  55                  60

Gln Gly Arg Val Thr Ser Thr Val Asp Thr Ser Ile Ser Thr Ala Tyr
65                  70                  75                  80

Leu Gln Ile Cys Ser Leu Lys Ala Glu Asp Thr Ala Val Tyr Phe Cys
                85                  90                  95

Ala Asn Tyr Gly Asn Tyr Trp Phe Ala Tyr Trp Gly Gln Gly Thr Leu
            100                 105                 110

Val Thr Val Ser Ser
        115

<210> SEQ ID NO 203
<211> LENGTH: 117
<212> TYPE: PRT
<213> ORGANISM: Artificial
<220> FEATURE:
<223> OTHER INFORMATION: Synthetic

<400> SEQUENCE: 203

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Thr Gly Gln Gly Leu Glu Trp Met
        35                  40                  45

Gly Trp Ile Tyr Pro Gly Ser Gly Asn Thr Lys Tyr Asn Glu Lys Phe
    50                  55                  60

Gln Gly Arg Val Thr Ile Thr Val Asp Thr Ser Ala Ser Thr Ala Tyr
65                  70                  75                  80

Leu Gln Ile Cys Ser Leu Lys Ala Glu Asp Thr Ala Val Tyr Phe Cys
                85                  90                  95

Ala Asn Tyr Gly Asn Tyr Trp Phe Ala Tyr Trp Gly Gln Gly Thr Leu
            100                 105                 110

Val Thr Val Ser Ser
        115

<210> SEQ ID NO 204
<211> LENGTH: 117
<212> TYPE: PRT
<213> ORGANISM: Artificial
<220> FEATURE:
<223> OTHER INFORMATION: Synthetic

<400> SEQUENCE: 204

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Pro Gly Gln Gly Leu Glu Trp Met
        35                  40                  45

```
Gly Trp Ile Tyr Pro Gly Ser Gly Asn Thr Lys Tyr Asn Glu Lys Phe
 50                  55                  60

Gln Gly Arg Val Thr Ile Thr Val Asp Thr Ser Ala Ser Thr Ala Tyr
 65                  70                  75                  80

Leu Gln Ile Cys Ser Leu Lys Ala Glu Asp Thr Ala Val Tyr Phe Cys
                 85                  90                  95

Ala Asn Tyr Gly Asn Tyr Trp Phe Ala Tyr Trp Gly Gln Gly Thr Leu
                100                 105                 110

Val Thr Val Ser Ser
        115

<210> SEQ ID NO 205
<211> LENGTH: 117
<212> TYPE: PRT
<213> ORGANISM: Artificial
<220> FEATURE:
<223> OTHER INFORMATION: Synthetic

<400> SEQUENCE: 205

Gln Ile Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Asp Tyr
                 20                  25                  30

Tyr Ile Thr Trp Val Arg Gln Ala Pro Gly Gln Gly Leu Glu Trp Met
             35                  40                  45

Gly Trp Ile Tyr Pro Gly Ser Gly Asn Thr Lys Tyr Asn Glu Lys Phe
 50                  55                  60

Gln Gly Arg Val Thr Ile Thr Val Asp Thr Ser Ala Ser Thr Ala Tyr
 65                  70                  75                  80

Leu Gln Ile Cys Ser Leu Lys Ala Glu Asp Thr Ala Val Tyr Phe Cys
                 85                  90                  95

Ala Asn Tyr Gly Asn Tyr Trp Phe Ala Tyr Trp Gly Gln Gly Thr Leu
                100                 105                 110

Val Thr Val Ser Ser
        115

<210> SEQ ID NO 206
<211> LENGTH: 117
<212> TYPE: PRT
<213> ORGANISM: Artificial
<220> FEATURE:
<223> OTHER INFORMATION: Synthetic

<400> SEQUENCE: 206

Gln Ile Gln Leu Val Gln Ser Gly Pro Glu Val Lys Lys Pro Gly Thr
 1               5                  10                  15

Ser Val Lys Val Ser Cys Lys Ala Ser Gly Tyr Thr Phe Thr Asp Tyr
                 20                  25                  30

Tyr Ile Thr Trp Val Arg Gln Ala Pro Gly Gln Gly Leu Glu Trp Met
             35                  40                  45

Gly Trp Ile Tyr Pro Gly Ser Gly Asn Thr Lys Tyr Asn Glu Lys Phe
 50                  55                  60

Gln Gly Arg Val Thr Ile Thr Val Asp Thr Ser Ala Ser Thr Ala Tyr
 65                  70                  75                  80

Leu Gln Ile Cys Ser Leu Lys Ala Glu Asp Thr Ala Val Tyr Phe Cys
                 85                  90                  95

Ala Asn Tyr Gly Asn Tyr Trp Phe Ala Tyr Trp Gly Gln Gly Thr Leu
                100                 105                 110
```

Val Thr Val Ser Ser
        115

<210> SEQ ID NO 207
<211> LENGTH: 117
<212> TYPE: PRT
<213> ORGANISM: Artificial
<220> FEATURE:
<223> OTHER INFORMATION: Synthetic

<400> SEQUENCE: 207

Gln Ile Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
                20                  25                  30

Tyr Ile Thr Trp Val Arg Gln Ala Pro Gly Gln Gly Leu Glu Trp Met
            35                  40                  45

Gly Trp Ile Tyr Pro Gly Ser Gly Asn Thr Lys Tyr Asn Glu Lys Phe
    50                  55                  60

Gln Gly Arg Val Thr Met Thr Val Asp Thr Ser Thr Ser Thr Ala Tyr
65                  70                  75                  80

Leu Gln Ile Cys Ser Leu Lys Ala Glu Asp Thr Ala Val Tyr Phe Cys
                85                  90                  95

Ala Asn Tyr Gly Asn Tyr Trp Phe Ala Tyr Trp Gly Gln Gly Thr Leu
            100                 105                 110

Val Thr Val Ser Ser
        115

<210> SEQ ID NO 208
<211> LENGTH: 117
<212> TYPE: PRT
<213> ORGANISM: Artificial
<220> FEATURE:
<223> OTHER INFORMATION: Synthetic

<400> SEQUENCE: 208

Gln Ile Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
                20                  25                  30

Tyr Ile Thr Trp Val Arg Gln Ala Thr Gly Gln Gly Leu Glu Trp Met
            35                  40                  45

Gly Trp Ile Tyr Pro Gly Ser Gly Asn Thr Lys Tyr Asn Glu Lys Phe
    50                  55                  60

Gln Gly Arg Val Thr Ile Thr Val Asp Thr Ser Ala Ser Thr Ala Tyr
65                  70                  75                  80

Leu Gln Trp Ser Ser Leu Lys Ala Ser Asp Thr Ala Met Tyr Phe Cys
                85                  90                  95

Ala Asn Tyr Gly Asn Tyr Trp Phe Ala Tyr Trp Gly Gln Gly Thr Leu
            100                 105                 110

Val Thr Val Ser Ser
        115

<210> SEQ ID NO 209
<211> LENGTH: 117
<212> TYPE: PRT
<213> ORGANISM: Artificial
<220> FEATURE:
<223> OTHER INFORMATION: Synthetic

<400> SEQUENCE: 209

Gln Ile Gln Leu Val Gln Ser Gly Pro Glu Val Lys Pro Gly Thr
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Thr Gly Gln Gly Leu Glu Trp Met
        35                  40                  45

Gly Trp Ile Tyr Pro Gly Ser Gly Asn Thr Lys Tyr Asn Glu Lys Phe
    50                  55                  60

Gln Gly Arg Val Thr Ile Thr Val Asp Thr Ser Ala Ser Thr Ala Tyr
65                  70                  75                  80

Leu Gln Ile Ser Ser Leu Lys Ala Glu Asp Met Ala Met Tyr Phe Cys
                85                  90                  95

Ala Asn Tyr Gly Asn Tyr Trp Phe Ala Tyr Trp Gly Gln Gly Thr Leu
            100                 105                 110

Val Thr Val Ser Ser
        115

<210> SEQ ID NO 210
<211> LENGTH: 117
<212> TYPE: PRT
<213> ORGANISM: Artificial
<220> FEATURE:
<223> OTHER INFORMATION: Synthetic

<400> SEQUENCE: 210

Gln Ile Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Pro Gly Gln Gly Leu Glu Trp Met
        35                  40                  45

Gly Trp Ile Tyr Pro Gly Ser Gly Asn Thr Lys Tyr Asn Glu Lys Phe
    50                  55                  60

Gln Gly Arg Val Thr Met Thr Val Asn Thr Ser Ile Ser Thr Ala Tyr
65                  70                  75                  80

Leu Gln Ile Cys Ser Leu Lys Ala Glu Asp Thr Ala Val Tyr Phe Cys
                85                  90                  95

Ala Asn Tyr Gly Asn Tyr Trp Phe Ala Tyr Trp Gly Gln Gly Thr Leu
            100                 105                 110

Val Thr Val Ser Ser
        115

<210> SEQ ID NO 211
<211> LENGTH: 117
<212> TYPE: PRT
<213> ORGANISM: Artificial
<220> FEATURE:
<223> OTHER INFORMATION: Synthetic

<400> SEQUENCE: 211

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Pro Gly Gln Gly Leu Glu Trp Met
        35                  40                  45

Gly Trp Ile Tyr Pro Gly Ser Gly Asn Thr Lys Tyr Asn Glu Ser Leu
    50                  55                  60

```
Lys Ser Arg Val Thr Ile Ser Val Asp Thr Ser Val Ser Thr Ala Tyr
 65                  70                  75                  80

Leu Gln Ile Cys Ser Leu Lys Ala Glu Asp Thr Ala Val Tyr Phe Cys
             85                  90                  95

Ala Asn Tyr Gly Asn Tyr Trp Phe Ala Tyr Trp Gly Gln Gly Thr Leu
            100                 105                 110

Val Thr Val Ser Ser
            115

<210> SEQ ID NO 212
<211> LENGTH: 117
<212> TYPE: PRT
<213> ORGANISM: Artificial
<220> FEATURE:
<223> OTHER INFORMATION: Synthetic

<400> SEQUENCE: 212

Gln Ile Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
             20                  25                  30

Tyr Ile Thr Trp Val Arg Gln Ala Pro Gly Gln Gly Leu Glu Trp Met
             35                  40                  45

Gly Trp Ile Tyr Pro Gly Ser Gly Asn Thr Lys Tyr Asn Glu Ser Leu
         50                  55                  60

Lys Ser Leu Val Thr Ile Ser Val Asp Thr Ser Val Ser Thr Ala Tyr
 65                  70                  75                  80

Leu Gln Ile Cys Ser Leu Lys Ala Glu Asp Thr Ala Val Tyr Phe Cys
             85                  90                  95

Ala Asn Tyr Gly Asn Tyr Trp Phe Ala Tyr Trp Gly Gln Gly Thr Leu
            100                 105                 110

Val Thr Val Ser Ser
            115

<210> SEQ ID NO 213
<211> LENGTH: 117
<212> TYPE: PRT
<213> ORGANISM: Artificial
<220> FEATURE:
<223> OTHER INFORMATION: Synthetic

<400> SEQUENCE: 213

Gln Ile Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
             20                  25                  30

Tyr Ile Thr Trp Val Arg Gln Ala Thr Gly Gln Gly Leu Glu Trp Met
             35                  40                  45

Gly Trp Ile Tyr Pro Gly Ser Gly Asn Thr Lys Tyr Asn Glu Ser Leu
         50                  55                  60

Lys Ser Arg Val Thr Met Ser Val Asp Thr Ser Val Ser Thr Ala Tyr
 65                  70                  75                  80

Leu Gln Ile Cys Ser Leu Lys Ala Glu Asp Thr Ala Val Tyr Phe Cys
             85                  90                  95

Ala Asn Tyr Gly Asn Tyr Trp Phe Ala Tyr Trp Gly Gln Gly Thr Leu
            100                 105                 110

Val Thr Val Ser Ser
            115
```

```
<210> SEQ ID NO 214
<211> LENGTH: 117
<212> TYPE: PRT
<213> ORGANISM: Artificial
<220> FEATURE:
<223> OTHER INFORMATION: Synthetic

<400> SEQUENCE: 214

Gln Ile Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Thr Gly Gln Gly Leu Glu Trp Met
        35                  40                  45

Gly Trp Ile Tyr Pro Gly Ser Gly Asn Thr Lys Tyr Asn Glu Ser Leu
    50                  55                  60

Lys Ser Arg Val Thr Ile Ser Val Asp Thr Ser Val Ser Thr Ala Tyr
65                  70                  75                  80

Leu Gln Ile Cys Ser Leu Lys Ala Glu Asp Thr Ala Val Tyr Phe Cys
                85                  90                  95

Ala Asn Tyr Gly Asn Tyr Trp Phe Ala Tyr Trp Gly Gln Gly Thr Leu
            100                 105                 110

Val Thr Val Ser Ser
        115

<210> SEQ ID NO 215
<211> LENGTH: 117
<212> TYPE: PRT
<213> ORGANISM: Artificial
<220> FEATURE:
<223> OTHER INFORMATION: Synthetic

<400> SEQUENCE: 215

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Pro Gly Gln Gly Leu Glu Trp Met
        35                  40                  45

Gly Trp Ile Tyr Pro Gly Ser Gly Asn Thr Lys Tyr Asn Glu Ser Leu
    50                  55                  60

Lys Ser Arg Val Thr Ile Ser Val Asp Thr Ser Lys Ser Ile Ala Tyr
65                  70                  75                  80

Leu Gln Met Asn Ser Leu Lys Thr Glu Asp Thr Ala Val Tyr Phe Cys
                85                  90                  95

Ala Asn Tyr Gly Asn Tyr Trp Phe Ala Tyr Trp Gly Gln Gly Thr Leu
            100                 105                 110

Val Thr Val Ser Ser
        115

<210> SEQ ID NO 216
<211> LENGTH: 117
<212> TYPE: PRT
<213> ORGANISM: Artificial
<220> FEATURE:
<223> OTHER INFORMATION: Synthetic

<400> SEQUENCE: 216

Gln Ile Gln Leu Val Gln Ser Gly His Glu Val Lys Gln Pro Gly Ala
```

```
                1               5                  10                 15
Ser Val Lys Val Ser Cys Lys Ala Ser Gly Tyr Thr Phe Thr Asp Tyr
                    20                  25                  30

Tyr Ile Thr Trp Val Arg Gln Ala Pro Gly Gln Gly Leu Glu Trp Met
                    35                  40                  45

Gly Trp Ile Tyr Pro Gly Ser Gly Asn Thr Lys Tyr Asn Glu Ser Leu
        50                  55                  60

Lys Ser Arg Val Thr Ile Ser Val Asp Thr Ser Lys Ser Ile Ala Tyr
 65                  70                  75                  80

Leu Gln Met Asn Ser Leu Lys Thr Glu Asp Thr Ala Val Tyr Phe Cys
                    85                  90                  95

Ala Asn Tyr Gly Asn Tyr Trp Phe Ala Tyr Trp Gly Gln Gly Thr Leu
                100                 105                 110

Val Thr Val Ser Ser
        115
```

<210> SEQ ID NO 217
<211> LENGTH: 117
<212> TYPE: PRT
<213> ORGANISM: Artificial
<220> FEATURE:
<223> OTHER INFORMATION: Synthetic

<400> SEQUENCE: 217

```
Gln Ile Gln Leu Val Glu Ser Gly Gly Gly Leu Val Lys Pro Gly Gly
 1               5                  10                  15

Ser Leu Arg Leu Ser Cys Ala Ala Ser Gly Tyr Thr Phe Thr Asp Tyr
                    20                  25                  30

Tyr Ile Thr Trp Val Arg Gln Ala Pro Gly Gln Gly Leu Glu Trp Met
                    35                  40                  45

Gly Trp Ile Tyr Pro Gly Ser Gly Asn Thr Lys Tyr Asn Glu Lys Phe
        50                  55                  60

Gln Gly Arg Val Thr Met Thr Val Asp Thr Ser Thr Ser Thr Ala Tyr
 65                  70                  75                  80

Leu Gln Ile Cys Ser Leu Lys Ala Glu Asp Thr Ala Val Tyr Phe Cys
                    85                  90                  95

Ala Asn Tyr Gly Asn Tyr Trp Phe Ala Tyr Trp Gly Gln Gly Thr Leu
                100                 105                 110

Val Thr Val Ser Ser
        115
```

<210> SEQ ID NO 218
<211> LENGTH: 111
<212> TYPE: PRT
<213> ORGANISM: Homo sapiens

<400> SEQUENCE: 218

```
Asp Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Asp Phe Asp
                    20                  25                  30

Gly Asp Ser Tyr Met Asn Trp Tyr Gln Gln Lys Pro Gly Gln Pro Pro
                    35                  40                  45

Lys Val Leu Ile Tyr Ala Ala Ser Asn Leu Glu Ser Gly Ile Pro Ala
        50                  55                  60

Arg Phe Ser Gly Ser Gly Ser Gly Thr Asp Phe Thr Leu Thr Ile Ser
 65                  70                  75                  80
```

```
Ser Leu Gln Pro Glu Asp Phe Ala Thr Tyr Tyr Cys Gln Gln Ser Asn
            85                  90                  95

Glu Asp Pro Trp Thr Phe Gly Gly Gly Thr Lys Val Glu Ile Lys
        100                 105                 110

<210> SEQ ID NO 219
<211> LENGTH: 111
<212> TYPE: PRT
<213> ORGANISM: Homo sapiens

<400> SEQUENCE: 219

Asp Ile Val Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
            85                  90                  95

Glu Asp Pro Trp Thr Phe Gly Gly Gly Thr Lys Val Glu Ile Lys
        100                 105                 110

<210> SEQ ID NO 220
<211> LENGTH: 111
<212> TYPE: PRT
<213> ORGANISM: Homo sapiens

<400> SEQUENCE: 220

Asp Ile Val Leu Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Gln Gln Ser Asn
            85                  90                  95

Glu Asp Pro Trp Thr Phe Gly Gly Gly Thr Lys Val Glu Ile Lys
        100                 105                 110

<210> SEQ ID NO 221
<211> LENGTH: 117
<212> TYPE: PRT
<213> ORGANISM: Homo sapiens

<400> SEQUENCE: 221

Gln Ile Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Thr Trp Val Arg Gln Ala Pro Gly Gln Gly Leu Glu Trp Met
        35                  40                  45
```

Gly Trp Ile Tyr Pro Gly Ser Gly Asn Thr Lys Tyr Asn Glu Lys Phe
    50                  55                  60

Gln Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Asn Tyr Gly Asn Tyr Trp Phe Ala Tyr Trp Gly Gln Gly Thr Leu
                100                 105                 110

Val Thr Val Ser Ser
            115

<210> SEQ ID NO 222
<211> LENGTH: 117
<212> TYPE: PRT
<213> ORGANISM: Homo sapiens

<400> SEQUENCE: 222

Gln Ile Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Thr Asp Tyr
                20                  25                  30

Tyr Ile Thr Trp Val Arg Gln Ala Pro Gly Gln Gly Leu Glu Trp Met
                35                  40                  45

Gly Trp Ile Tyr Pro Gly Ser Gly Asn Thr Lys Tyr Asn Glu Lys Phe
    50                  55                  60

Gln Gly Arg Val Thr Met Thr Val Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Asn Tyr Gly Asn Tyr Trp Phe Ala Tyr Trp Gly Gln Gly Thr Leu
                100                 105                 110

Val Thr Val Ser Ser
            115

<210> SEQ ID NO 223
<211> LENGTH: 117
<212> TYPE: PRT
<213> ORGANISM: Homo sapiens

<400> SEQUENCE: 223

Gln Ile Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile Thr Trp Val Arg Gln Ala Pro Gly Gln Gly Leu Glu Trp Met
                35                  40                  45

Gly Trp Ile Tyr Pro Gly Ser Gly Asn Thr Lys Tyr Asn Glu Lys Phe
    50                  55                  60

Gln Gly Arg Phe Val Phe Ser Val Asp Thr Ser Ala Ser Thr Ala Tyr
65                  70                  75                  80

Leu Gln Ile Ser Ser Leu Lys Ala Glu Asp Thr Ala Val Tyr Phe Cys
                85                  90                  95

Ala Asn Tyr Gly Asn Tyr Trp Phe Ala Tyr Trp Gly Gln Gly Thr Leu
                100                 105                 110

Val Thr Val Ser Ser
            115

<210> SEQ ID NO 224
<211> LENGTH: 111
<212> TYPE: PRT
<213> ORGANISM: Homo sapiens

<400> SEQUENCE: 224

Glu Ile Val Leu Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Tyr Leu Asn Trp Tyr Gln Gln Lys Pro Gly Gln Pro Pro
        35                  40                  45

Lys Val Leu Ile Tyr Ala Ala Ser Thr Leu Gln Ser Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Gln Gln Ser Asn
                85                  90                  95

Glu Asp Pro Trp Thr Phe Gly Gly Gly Thr Lys Val Glu Ile Lys
            100                 105                 110

<210> SEQ ID NO 225
<211> LENGTH: 111
<212> TYPE: PRT
<213> ORGANISM: Homo sapiens

<400> SEQUENCE: 225

Ala Ile Val Leu Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Tyr Leu Asn Trp Tyr Gln Gln Lys Pro Gly Gln Pro Pro
        35                  40                  45

Lys Val Leu Ile Tyr Ala Ala Ser Thr Leu Glu Thr Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Gln Gln Ser Asn
                85                  90                  95

Glu Asp Pro Trp Thr Phe Gly Gly Gly Thr Lys Val Glu Ile Lys
            100                 105                 110

<210> SEQ ID NO 226
<211> LENGTH: 117
<212> TYPE: PRT
<213> ORGANISM: Homo sapiens

<400> SEQUENCE: 226

Gln Leu Gln Leu Val Gln Ser Gly Pro Glu Val Lys Lys Pro Gly Ala
1               5                   10                  15

Ser Val Lys Val Ser Cys Lys Val Ser Gly Tyr Thr Phe Thr Asp Tyr
            20                  25                  30

Tyr Ile Thr Trp Val Arg Gln Ala Pro Gly Gln Ala Leu Glu Trp Met
        35                  40                  45

Gly Trp Ile Tyr Pro Gly Ser Gly Asn Thr Lys Tyr Asn Glu Lys Phe
    50                  55                  60

Gln Gly Arg Phe Val Phe Ser Val Asp Thr Ser Ala Ser Thr Ala Tyr
65                  70                  75                  80

Leu Gln Ile Ser Ser Leu Lys Ala Glu Asp Thr Ala Val Tyr Phe Cys
                    85                  90                  95

Ala Asn Tyr Gly Asn Tyr Trp Phe Ala Tyr Trp Gly Gln Gly Thr Leu
                100                 105                 110

Val Thr Val Ser Ser
            115

<210> SEQ ID NO 227
<211> LENGTH: 117
<212> TYPE: PRT
<213> ORGANISM: Homo sapiens

<400> SEQUENCE: 227

Gln Leu Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Asp Tyr
                20                  25                  30

Tyr Ile Thr Trp Val Arg Gln Ala Pro Gly Gln Ala Leu Glu Trp Met
            35                  40                  45

Gly Trp Ile Tyr Pro Gly Ser Gly Asn Thr Lys Tyr Ser Gln Lys Phe
    50                  55                  60

Gln Gly Arg Phe Val Phe Ser Val Asp Thr Ser Ala Ser Thr Ala Tyr
65                  70                  75                  80

Leu Gln Ile Ser Ser Leu Lys Ala Glu Asp Thr Ala Val Tyr Tyr Cys
                    85                  90                  95

Ala Asn Tyr Gly Asn Tyr Trp Phe Ala Tyr Trp Gly Gln Gly Thr Leu
                100                 105                 110

Val Thr Val Ser Ser
            115

<210> SEQ ID NO 228
<211> LENGTH: 117
<212> TYPE: PRT
<213> ORGANISM: Homo sapiens

<400> SEQUENCE: 228

Gln Leu Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Ser Tyr
                20                  25                  30

Tyr Ile Ser Trp Val Arg Gln Ala Pro Gly Gln Ala Leu Glu Trp Met
            35                  40                  45

Gly Trp Ile Tyr Ala Gly Ser Gly Asn Thr Lys Tyr Ser Gln Lys Phe
    50                  55                  60

Gln Gly Arg Phe Val Phe Ser Val Asp Thr Ser Ala Ser Thr Ala Tyr
65                  70                  75                  80

Leu Gln Ile Ser Ser Leu Lys Ala Glu Asp Thr Ala Val Tyr Tyr Cys
                    85                  90                  95

Ala Asn Tyr Gly Asn Tyr Trp Phe Ala Tyr Trp Gly Gln Gly Thr Leu
                100                 105                 110

Val Thr Val Ser Ser
            115

<210> SEQ ID NO 229
<211> LENGTH: 218
<212> TYPE: PRT
<213> ORGANISM: Homo sapiens

<400> SEQUENCE: 229

```
Glu Ile Val Leu Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Tyr Leu Asn Trp Tyr Gln Gln Lys Pro Gly Gln Pro Pro
        35                  40                  45

Lys Val Leu Ile Tyr Ala Ala Ser Thr Leu Gln Ser Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Gln Gln Ser Asn
                85                  90                  95

Glu Asp Pro Trp Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 230
<211> LENGTH: 447
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (239)..(239)
<223> OTHER INFORMATION: Xaa can be Serine, Aspartic Acid, Glutamic
      Acid, Asparagine, Glutamine or Threonine
<220> FEATURE:
<221> NAME/KEY: misc_feature
<222> LOCATION: (264)..(264)
<223> OTHER INFORMATION: Xaa can be Valine, Isoleucine, Threonine or
      Tyrosine
<220> FEATURE:
<221> NAME/KEY: misc_feature
<222> LOCATION: (330)..(330)
<223> OTHER INFORMATION: Xaa can be Alanine, Tyrosine, Leucine or
      Isoleucine
<220> FEATURE:
<221> NAME/KEY: misc_feature
<222> LOCATION: (332)..(332)
<223> OTHER INFORMATION: Xaa can be Isoleucine, Aspartic Acid, Glutamic
      Acid, Asparagine or Glutamine

<400> SEQUENCE: 230

```
Gln Leu Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Ser Tyr
            20                  25                  30
```

```
Tyr Ile Ser Trp Val Arg Gln Ala Pro Gly Gln Ala Leu Glu Trp Met
            35                  40                  45
Gly Trp Ile Tyr Ala Gly Ser Gly Asn Thr Lys Tyr Ser Gln Lys Phe
    50                  55                  60
Gln Gly Arg Phe Val Phe Ser Val Asp Thr Ser Ala Ser Thr Ala Tyr
65                  70                  75                  80
Leu Gln Ile Ser Ser Leu Lys Ala Glu Asp Thr Ala Val Tyr Tyr Cys
                85                  90                  95
Ala Asn Tyr Gly Asn Tyr Trp Phe Ala Tyr Trp Gly Gln Gly Thr Leu
            100                 105                 110
Val Thr Val Ser Ser Ala Ser Thr Lys Gly Pro Ser Val Phe Pro Leu
        115                 120                 125
Ala Pro Ser Ser Lys Ser Thr Ser Gly Gly Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Lys Ala Glu Pro Lys Ser Cys Asp Lys Thr His
    210                 215                 220
Thr Cys Pro Pro Cys Pro Ala Pro Glu Leu Leu Gly Gly Pro Xaa Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Xaa Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Xaa Pro Xaa Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Asp Glu Leu Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445

<210> SEQ ID NO 231
```

<211> LENGTH: 447
<212> TYPE: PRT
<213> ORGANISM: Artificial
<220> FEATURE:
<223> OTHER INFORMATION: Synthetic

<400> SEQUENCE: 231

```
Gln Leu Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Ser Tyr
            20                  25                  30

Tyr Ile Ser Trp Val Arg Gln Ala Pro Gly Gln Ala Leu Glu Trp Met
        35                  40                  45

Gly Trp Ile Tyr Ala Gly Ser Gly Asn Thr Lys Tyr Ser Gln Lys Phe
    50                  55                  60

Gln Gly Arg Phe Val Phe Ser Val Asp Thr Ser Ala Ser Thr Ala Tyr
65                  70                  75                  80

Leu Gln Ile Ser Ser Leu Lys Ala Glu Asp Thr Ala Val Tyr Tyr Cys
                85                  90                  95

Ala Asn Tyr Gly Asn Tyr Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser Cys Asp Lys Thr His
    210                 215                 220

Thr Cys Pro Pro Cys Pro Ala Pro Glu Leu Leu Gly Gly Pro Asp Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Leu Pro Glu Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380
```

```
Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 232
<211> LENGTH: 444
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (230)..(230)
<223> OTHER INFORMATION: Xaa can be Proline or Glutamic Acid
<220> FEATURE:
<221> NAME/KEY: misc_feature
<222> LOCATION: (231)..(231)
<223> OTHER INFORMATION: Xaa can be Valine or Leucine
<220> FEATURE:
<221> NAME/KEY: misc_feature
<222> LOCATION: (232)..(232)
<223> OTHER INFORMATION: Xaa can be Alanine or Leucine
<220> FEATURE:
<221> NAME/KEY: misc_feature
<222> LOCATION: (233)..(233)
<223> OTHER INFORMATION: Xaa can be a deletion or Glycine
<220> FEATURE:
<221> NAME/KEY: misc_feature
<222> LOCATION: (236)..(236)
<223> OTHER INFORMATION: Xaa can be Serine, Aspartic Acid, Glutamic
      Acid, Asparagine, Glutamine or Threonine
<220> FEATURE:
<221> NAME/KEY: misc_feature
<222> LOCATION: (261)..(261)
<223> OTHER INFORMATION: Xaa can be Valine, Isoleucine, Threonine or
      Tyrosine
<220> FEATURE:
<221> NAME/KEY: misc_feature
<222> LOCATION: (324)..(324)
<223> OTHER INFORMATION: Xaa can be a Glycine or Alanine
<220> FEATURE:
<221> NAME/KEY: misc_feature
<222> LOCATION: (327)..(327)
<223> OTHER INFORMATION: Xaa can be Alanine, Tyrosine, Leucine or
      Isoleucine
<220> FEATURE:
<221> NAME/KEY: misc_feature
<222> LOCATION: (329)..(329)
<223> OTHER INFORMATION: Xaa can be Isoleucine, Aspartic Acid, Glutamic
      Acid, Asparagine or Glutamine

<400> SEQUENCE: 232

Gln Leu Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Ser Tyr
                20                  25                  30

Tyr Ile Ser Trp Val Arg Gln Ala Pro Gly Gln Ala Leu Glu Trp Met
            35                  40                  45

Gly Trp Ile Tyr Ala Gly Ser Gly Asn Thr Lys Tyr Ser Gln Lys Phe
        50                  55                  60

Gln Gly Arg Phe Val Phe Ser Val Asp Thr Ser Ala Ser Thr Ala Tyr
65                  70                  75                  80

Leu Gln Ile Ser Ser Leu Lys Ala Glu Asp Thr Ala Val Tyr Tyr Cys
                85                  90                  95
```

Ala Asn Tyr Gly Asn Tyr Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Xaa Xaa Xaa Xaa Gly Pro Xaa Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Xaa Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Glx Leu Pro Xaa Pro Xaa Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 233
<211> LENGTH: 444
<212> TYPE: PRT
<213> ORGANISM: Artificial
<220> FEATURE:
<223> OTHER INFORMATION: Synthetic

<400> SEQUENCE: 233

Gln Leu Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Ser Tyr

```
            20                  25                  30
Tyr Ile Ser Trp Val Arg Gln Ala Pro Gly Gln Ala Leu Glu Trp Met
        35                  40                  45
Gly Trp Ile Tyr Ala Gly Ser Gly Asn Thr Lys Tyr Ser Gln Lys Phe
        50                  55                  60
Gln Gly Arg Phe Val Phe Ser Val Asp Thr Ser Ala Ser Thr Ala Tyr
65                  70                  75                  80
Leu Gln Ile Ser Ser Leu Lys Ala Glu Asp Thr Ala Val Tyr Tyr Cys
                85                  90                  95
Ala Asn Tyr Gly Asn Tyr Trp Phe Ala Tyr Trp Gly Gln Gly Thr Leu
                100                 105                 110
Val Thr Val Ser Ser Ala Ser Thr Lys Gly Pro Ser Val Phe Pro Leu
            115                 120                 125
Ala Pro Cys Ser Arg Ser Thr Ser Glu Ser Thr Ala Ala Leu Gly Cys
        130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Asn
                180                 185                 190
Phe Gly Thr Gln Thr Tyr Thr Cys Asn Val Asp His Lys Pro Ser Asn
            195                 200                 205
Thr Lys Val Asp Lys Thr Val Glu Arg Lys Cys Cys Val Glu Cys Pro
        210                 215                 220
Pro Cys Pro Ala Pro Glu Leu Leu Gly Gly Pro Asp Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser His Glu Asp Pro Glu Val Gln Phe
                260                 265                 270
Asn Trp Tyr Val Asp Gly Val Glu Val His Asn Ala Lys Thr Lys Pro
            275                 280                 285
Arg Glu Glu Gln Phe Asn Ser Thr Phe Arg Val Val Ser Val Leu Thr
        290                 295                 300
Val Val His Gln Asp Trp Leu Asn Gly Lys Glu Tyr Lys Cys Lys Val
305                 310                 315                 320
Ser Asn Lys Gly Leu Pro Leu Pro Glu Glu Lys Thr Ile Ser Lys Thr
                325                 330                 335
Lys Gly Gln Pro Arg Glu Pro Gln Val Tyr Thr Leu Pro Pro Ser Arg
                340                 345                 350
Glu Glu Met Thr Lys Asn Gln Val Ser Leu Thr Cys Leu Val Lys Gly
            355                 360                 365
Phe Tyr Pro Ser Asp Ile Ala Val Glu Trp Glu Ser Asn Gly Gln Pro
        370                 375                 380
Glu Asn Asn Tyr Lys Thr Thr Pro Pro Met Leu Asp Ser Asp Gly Ser
385                 390                 395                 400
Phe Phe Leu Tyr Ser Lys Leu Thr Val Asp Lys Ser Arg Trp Gln Gln
                405                 410                 415
Gly Asn Val Phe Ser Cys Ser Val Met His Glu Ala Leu His Asn His
                420                 425                 430
Tyr Thr Gln Lys Ser Leu Ser Leu Ser Pro Gly Lys
            435                 440
```

-continued

<210> SEQ ID NO 234
<211> LENGTH: 107
<212> TYPE: PRT
<213> ORGANISM: Homo sapiens

<400> SEQUENCE: 234

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys
            100                 105

<210> SEQ ID NO 235
<211> LENGTH: 119
<212> TYPE: PRT
<213> ORGANISM: Homo sapiens

<400> SEQUENCE: 235

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115

<210> SEQ ID NO 236
<211> LENGTH: 107
<212> TYPE: PRT
<213> ORGANISM: Homo sapiens

<400> SEQUENCE: 236

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Thr Asn
            20                  25                  30

Leu His Trp Tyr Gln Gln Lys Pro Asp Gln Ser Pro Lys Leu Leu Ile
        35                  40                  45

Lys Tyr Ala Ser Glu Ser Ile Ser Gly Val Pro Ser Arg Phe Ser Gly
    50                  55                  60

```
Ser Gly Ser Gly Thr Asp Phe Thr Leu Thr Ile Asn Ser Leu Glu Ala
 65                  70                  75                  80

Glu Asp Ala Ala Thr Tyr Tyr Cys His Gln Asn Asn Asn Trp Pro Thr
                 85                  90                  95

Thr Phe Gly Ala Gly Thr Lys Leu Glu Ile Lys
            100                 105

<210> SEQ ID NO 237
<211> LENGTH: 119
<212> TYPE: PRT
<213> ORGANISM: Homo sapiens

<400> SEQUENCE: 237

Gln Val Gln Leu Gln Glu Ser Gly Pro Gly Leu Val Lys Pro Ser Gln
  1               5                  10                  15

Thr Leu Ser Leu Thr Cys Thr Val Ser Gly Phe Ser Leu Thr Asn Tyr
                 20                  25                  30

Gly Trp Ser Trp Ile Arg Gln Pro Pro Gly Lys Gly Leu Glu Trp Ile
             35                  40                  45

Gly Tyr Ile Trp Ser Gly Gly Asn Thr Tyr Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 238
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 238

Asp Ile Leu Leu Thr Gln Ser Pro Gly Thr Leu Ser Leu Ser Pro Gly
  1               5                  10                  15

Glu Arg Val Thr Leu Ser Cys Arg Ala Ser Gln Ser Ile Gly Thr Asn
                 20                  25                  30

Ile His Trp Tyr Gln Gln Lys Pro Asp Gln Ser Pro Lys Leu Leu Ile
             35                  40                  45

Lys Tyr Ala Ser Glu Ser Ile Ser Gly Ile Pro Ser Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Asn Asn Asn Trp Pro Thr
                 85                  90                  95

Thr Phe Gly Gln Gly Thr Lys Xaa Glu Ile Lys
            100                 105

<210> SEQ ID NO 239
<211> LENGTH: 107
```

```
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 239
```

Asp Ile Leu Leu Thr Gln Ser Pro Ala Thr Leu Ser Leu Ser Pro Gly
1               5                   10                  15

Glu Arg Val Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Asn Asn Trp Pro Thr
                85                  90                  95

Thr Phe Gly Gln Gly Thr Lys Xaa Glu Ile Lys
            100                 105

```
<210> SEQ ID NO 240
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 240
```

Asp Ile Leu Leu Thr Gln Ser Pro Ala Thr Leu Ser Leu Ser Pro Gly
1               5                   10                  15

Glu Arg Val Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Asn Asn Asn Trp Pro Thr
                85                  90                  95

Thr Phe Gly Gln Gly Thr Lys Xaa Glu Ile Lys
            100                 105

```
<210> SEQ ID NO 241
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 241
```

Asp Ile Leu Leu Thr Gln Ser Pro Ala Thr Leu Ser Val Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Asn Asn Asn Trp Pro Thr
                85                  90                  95

Thr Phe Gly Gln Gly Thr Lys Xaa Glu Ile Lys
            100                 105

<210> SEQ ID NO 242
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 242

Asp Ile Leu Leu Thr Gln Ser Pro Ser Ser Leu Ser Ala Ser Val Gly
1               5                   10                  15

Asp Arg Val Thr Ile Thr Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Asn Asn Asn Trp Pro Thr
                85                  90                  95

Thr Phe Gly Gln Gly Thr Lys Xaa Glu Ile Lys
            100                 105

<210> SEQ ID NO 243
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 243

Asp Ile Leu Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

```
Lys Tyr Ala Ser Glu Ser Ile Ser Gly Ile Pro Ser Arg Phe Ser Gly
        50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Asn Asn Asn Trp Pro Thr
                85                  90                  95

Thr Phe Gly Gln Gly Thr Lys Xaa Glu Ile Lys
            100                 105

<210> SEQ ID NO 244
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 244

Asp Ile Leu Leu Thr Gln Ser Pro Ser Phe Leu Ser Ala Ser Val Gly
1               5                   10                  15

Asp Arg Val Thr Ile Thr Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Asn Asn Asn Trp Pro Thr
                85                  90                  95

Thr Phe Gly Gln Gly Thr Lys Xaa Glu Ile Lys
            100                 105

<210> SEQ ID NO 245
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 245

Asp Ile Leu Leu Thr Gln Ser Pro Gly Thr Leu Ser Leu Ser Pro Gly
1               5                   10                  15

Glu Arg Val Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Asn Asn Asn Trp Pro Thr
                85                  90                  95

Thr Phe Gly Gln Gly Thr Lys Xaa Glu Ile Lys
```

<210> SEQ ID NO 246
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 246

Asp Ile Leu Leu Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Asn Asn Asn Trp Pro Thr
                85                  90                  95

Thr Phe Gly Gln Gly Thr Lys Xaa Glu Ile Lys
            100                 105

<210> SEQ ID NO 247
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 247

Asp Ile Leu Leu Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Asn Asn Asn Trp Pro Thr
                85                  90                  95

Thr Phe Gly Gln Gly Thr Lys Xaa Glu Ile Lys
            100                 105

<210> SEQ ID NO 248
<211> LENGTH: 107
<212> TYPE: PRT
<213> ORGANISM: Artificial
<220> FEATURE:
<223> OTHER INFORMATION: Synthetic
<220> FEATURE:

<221> NAME/KEY: misc_feature
<222> LOCATION: (104)..(104)
<223> OTHER INFORMATION: Xaa can be any naturally occurring amino acid

<400> SEQUENCE: 248

Asp Ile Leu Leu Thr Gln Ser Pro Ala Thr Leu Ser Leu Ser Pro Gly
1               5                   10                  15

Glu Arg Val Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Asn Asn Asn Trp Pro Thr
                85                  90                  95

Thr Phe Gly Gln Gly Thr Lys Xaa Glu Ile Lys
            100                 105

<210> SEQ ID NO 249
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 249

Asp Ile Leu Leu Thr Gln Ser Pro Ala Phe Leu Ser Val Thr Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Asn Asn Asn Trp Pro Thr
                85                  90                  95

Thr Phe Gly Gln Gly Thr Lys Xaa Glu Ile Lys
            100                 105

<210> SEQ ID NO 250
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 250

Asp Ile Leu Leu Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Asn

```
                    20                  25                  30

Ile His Trp Tyr Gln Gln Lys Pro Asp Gln Ser Pro Lys Leu Leu Ile
            35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Leu Thr Ile Asn Ser Leu Glu Ala
65                  70                  75                  80

Glu Asp Val Ala Val Tyr Tyr Cys Gln Gln Asn Asn Asn Trp Pro Thr
                85                  90                  95

Thr Phe Gly Gln Gly Thr Lys Xaa Glu Ile Lys
            100                 105

<210> SEQ ID NO 251
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 251

Asp Ile Leu Leu Thr Gln Ser Pro Ala Thr Leu Ser Leu Ser Pro Gly
1               5                   10                  15

Glu Arg Val Thr Leu Ser Cys Arg Ala Ser Gln Ser Ile Gly Thr Asn
                20                  25                  30

Ile His Trp Tyr Gln Gln Lys Pro Asp Gln Ser Pro Lys Leu Leu Ile
            35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Leu Thr Ile Asn Ser Leu Glu Ala
65                  70                  75                  80

Glu Asp Val Ala Val Tyr Tyr Cys Gln Gln Asn Asn Asn Trp Pro Thr
                85                  90                  95

Thr Phe Gly Gln Gly Thr Lys Xaa Glu Ile Lys
            100                 105

<210> SEQ ID NO 252
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 252

Asp Ile Leu Leu Thr Gln Ser Pro Ser Ser Leu Ser Ala Ser Val Gly
1               5                   10                  15

Asp Arg Val Thr Ile Thr Cys Arg Ala Ser Gln Ser Ile Gly Thr Asn
                20                  25                  30

Ile His Trp Tyr Gln Gln Lys Pro Asp Gln Ser Pro Lys Leu Leu Ile
            35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Leu Thr Ile Asn Asn Ile Glu Ser
65                  70                  75                  80
```

Glu Asp Ala Ala Thr Tyr Tyr Cys Gln Gln Asn Asn Asn Trp Pro Thr
                85                  90                  95

Thr Phe Gly Gln Gly Thr Lys Xaa Glu Ile Lys
            100                 105

<210> SEQ ID NO 253
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 253

Asp Ile Leu Leu Thr Gln Ser Pro Ser Phe Leu Ser Ala Ser Val Gly
1               5                   10                  15

Asp Arg Val Thr Ile Thr Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Asn Asn Ile Glu Ser
65                  70                  75                  80

Glu Asp Ala Ala Thr Tyr Tyr Cys Gln Gln Asn Asn Asn Trp Pro Thr
                85                  90                  95

Thr Phe Gly Gln Gly Thr Lys Xaa Glu Ile Lys
            100                 105

<210> SEQ ID NO 254
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 254

Asp Ile Leu Leu Thr Gln Ser Pro Gly Thr Leu Ser Leu Ser Pro Gly
1               5                   10                  15

Glu Arg Val Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Asn Asn Ile Glu Ser
65                  70                  75                  80

Glu Asp Phe Ala Val Tyr Tyr Cys Gln Gln Asn Asn Asn Trp Pro Thr
                85                  90                  95

Thr Phe Gly Gln Gly Thr Lys Xaa Glu Ile Lys
            100                 105

<210> SEQ ID NO 255
<211> LENGTH: 107

```
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 255
```

Asp Ile Leu Leu Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Asn Asn Ile Glu Ser
65                  70                  75                  80

Glu Asp Phe Ala Val Tyr Tyr Cys Gln Gln Asn Asn Asn Trp Pro Thr
                85                  90                  95

Thr Phe Gly Gln Gly Thr Lys Xaa Glu Ile Lys
            100                 105

```
<210> SEQ ID NO 256
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 256
```

Asp Ile Leu Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Asn Asn Ile Glu Ser
65                  70                  75                  80

Glu Asp Ala Ala Thr Tyr Tyr Cys Gln Gln Asn Asn Asn Trp Pro Thr
                85                  90                  95

Thr Phe Gly Gln Gly Thr Lys Xaa Glu Ile Lys
            100                 105

```
<210> SEQ ID NO 257
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 257
```

```
Asp Ile Leu Leu Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Thr Ile Asn Asn Ile Glu Ser
65                  70                  75                  80

Glu Asp Ala Ala Thr Tyr Tyr Cys Gln Gln Asn Asn Asn Trp Pro Thr
                85                  90                  95

Thr Phe Gly Gln Gly Thr Lys Xaa Glu Ile Lys
            100                 105
```

<210> SEQ ID NO 258
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 258

```
Asp Ile Leu Leu Thr Gln Ser Pro Gly Thr Leu Ser Leu Ser Pro Gly
1               5                   10                  15

Glu Arg Val Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Thr Ile Asn Asn Ile Glu Ser
65                  70                  75                  80

Glu Asp Ala Ala Thr Tyr Tyr Cys Gln Gln Asn Asn Asn Trp Pro Thr
                85                  90                  95

Thr Phe Gly Gln Gly Thr Lys Xaa Glu Ile Lys
            100                 105
```

<210> SEQ ID NO 259
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 259

```
Asp Ile Leu Leu Thr Gln Ser Pro Ala Thr Leu Ser Leu Ser Pro Gly
1               5                   10                  15

Glu Arg Val Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45
```

```
Lys Tyr Ala Ser Glu Ser Ile Ser Gly Ile Pro Ser Arg Phe Ser Gly
        50                  55                  60

Ser Gly Ser Gly Thr Asp Phe Thr Leu Thr Ile Asn Asn Ile Glu Ser
 65                  70                  75                  80

Glu Asp Ala Ala Thr Tyr Tyr Cys Gln Gln Asn Asn Asn Trp Pro Thr
                 85                  90                  95

Thr Phe Gly Gln Gly Thr Lys Xaa Glu Ile Lys
            100                 105

<210> SEQ ID NO 260
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 260

Asp Ile Leu Leu Thr Gln Ser Pro Ala Thr Leu Ser Leu Ser Pro Gly
 1               5                  10                  15

Glu Arg Val Thr Leu Ser Cys Arg Ala Ser Gln Ser Ile Gly Thr Asn
                20                  25                  30

Ile His Trp Tyr Gln Gln Lys Pro Asp Gln Ser Pro Lys Leu Leu Ile
             35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Leu Thr Ile Asn Asn Ile Glu Ser
 65                  70                  75                  80

Glu Asp Phe Ala Val Tyr Tyr Cys Gln Gln Asn Asn Asn Trp Pro Thr
                 85                  90                  95

Thr Phe Gly Gln Gly Thr Lys Xaa Glu Ile Lys
            100                 105

<210> SEQ ID NO 261
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 261

Asp Ile Leu Leu Thr Gln Ser Pro Ala Thr Leu Ser Val Ser Pro Gly
 1               5                  10                  15

Glu Arg Ala Thr Leu Ser Cys Arg Ala Ser Gln Ser Ile Gly Thr Asn
                20                  25                  30

Ile His Trp Tyr Leu Gln Lys Pro Gly Lys Ser Pro Lys Leu Leu Ile
             35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys Gln Gln Asn Asn Asn Trp Pro Thr
                 85                  90                  95

Thr Phe Gly Gln Gly Thr Lys Xaa Glu Ile Lys
```

<210> SEQ ID NO 262
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 262

Asp Ile Leu Leu Thr Gln Ser Pro Ala Thr Leu Ser Leu Ser Pro Gly
1               5                   10                  15

Glu Arg Val Thr Leu Ser Cys Arg Ala Ser Gln Ser Ile Gly Thr Asn
            20                  25                  30

Ile His Trp Tyr Leu Gln Lys Pro Gly Lys Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Asn Asn Asn Trp Pro Thr
                85                  90                  95

Thr Phe Gly Gln Gly Thr Lys Xaa Glu Ile Lys
            100                 105

<210> SEQ ID NO 263
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 263

Asp Ile Leu Leu Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Leu Gln Lys Pro Gly Gln Ser Pro Gln Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Asn Asn Asn Trp Pro Thr
                85                  90                  95

Thr Phe Gly Gln Gly Thr Lys Xaa Glu Ile Lys
            100                 105

<210> SEQ ID NO 264
<211> LENGTH: 119
<212> TYPE: PRT
<213> ORGANISM: Artificial
<220> FEATURE:
<223> OTHER INFORMATION: Synthetic

<400> SEQUENCE: 264

Gln Val Gln Leu Gln Gln Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ala Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Gln Val Val Leu
65                  70                  75                  80

Gln Met Asn Ser Leu Lys Thr Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 265
<211> LENGTH: 119
<212> TYPE: PRT
<213> ORGANISM: Artificial
<220> FEATURE:
<223> OTHER INFORMATION: Synthetic

<400> SEQUENCE: 265

Gln Val Gln Leu Gln Gln Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ala Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Gln Val Val Leu
65                  70                  75                  80

Gln Met Asn Ser Leu Arg Ala Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 266
<211> LENGTH: 119
<212> TYPE: PRT
<213> ORGANISM: Artificial
<220> FEATURE:
<223> OTHER INFORMATION: Synthetic

<400> SEQUENCE: 266

Gln Val Gln Leu Gln Gln Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ala Val Ile Trp Ser Gly Gly Asn Thr Asp Tyr Asn Thr Ser Leu Lys

```
                50                  55                  60
Ser Arg Leu Thr Ile Ser Lys Asp Asn Ser Lys Ser Gln Val Val Leu
 65                  70                  75                  80

Thr Met Asn Ser Leu Lys Thr Glu Asp Thr Ala Val Tyr Tyr Cys Ala
                 85                  90                  95

Arg Ala Leu Thr Tyr Tyr Asp Tyr Glu Phe Ala Tyr Trp Gly Gln Gly
                100                 105                 110

Thr Leu Val Thr Val Ser Ser
            115

<210> SEQ ID NO 267
<211> LENGTH: 119
<212> TYPE: PRT
<213> ORGANISM: Artificial
<220> FEATURE:
<223> OTHER INFORMATION: Synthetic

<400> SEQUENCE: 267

Gln Val Gln Leu Gln Gln Ser Gly Pro Gly Leu Val Lys Pro Ser Gln
 1               5                  10                  15

Thr Leu Ser Leu Thr Cys Thr Val Ser Gly Phe Ser Leu Thr Asn Tyr
                20                  25                  30

Gly Val His Trp Val Arg Gln Ala Pro Gly Lys Gly Leu Glu Trp Val
             35                  40                  45

Ala Val Ile Trp Ser Gly Gly Asn Thr Asp Tyr Asn Thr Ser Leu Lys
         50                  55                  60

Ser Arg Leu Thr Ile Ser Lys Asp Asn Ser Lys Ser Gln Val Val Leu
 65                  70                  75                  80

Thr Met Asn Ser Leu Arg Ala Glu Asp Thr Ala Val Tyr Tyr Cys Ala
                 85                  90                  95

Arg Ala Leu Thr Tyr Tyr Asp Tyr Glu Phe Ala Tyr Trp Gly Gln Gly
                100                 105                 110

Thr Leu Val Thr Val Ser Ser
            115

<210> SEQ ID NO 268
<211> LENGTH: 119
<212> TYPE: PRT
<213> ORGANISM: Artificial
<220> FEATURE:
<223> OTHER INFORMATION: Synthetic

<400> SEQUENCE: 268

Gln Val Gln Leu Gln Gln Ser Gly Pro Gly Leu Val Lys Pro Ser Gln
 1               5                  10                  15

Thr Leu Ser Leu Thr Cys Thr Val Ser Gly Phe Ser Leu Thr Asn Tyr
                20                  25                  30

Gly Val His Trp Val Arg Gln Ala Pro Gly Lys Gly Leu Glu Trp Val
             35                  40                  45

Ala Val Ile Trp Ser Gly Gly Asn Thr Asp Tyr Asn Thr Ser Leu Lys
         50                  55                  60

Ser Arg Leu Thr Ile Ser Lys Asp Asn Ser Lys Ser Gln Val Val Leu
 65                  70                  75                  80

Gln Met Asn Ser Leu Arg Ala Gly Asp Thr Ala Val Tyr Tyr Cys Ala
                 85                  90                  95

Arg Ala Leu Thr Tyr Tyr Asp Tyr Glu Phe Ala Tyr Trp Gly Gln Gly
                100                 105                 110

Thr Leu Val Thr Val Ser Ser
```

```
<210> SEQ ID NO 269
<211> LENGTH: 119
<212> TYPE: PRT
<213> ORGANISM: Artificial
<220> FEATURE:
<223> OTHER INFORMATION: Synthetic

<400> SEQUENCE: 269

Gln Val Gln Leu Gln Gln Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ala Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Gln Val Val Leu
65                  70                  75                  80

Thr Met Asn Ser Leu Arg Ala Gly Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 270
<211> LENGTH: 119
<212> TYPE: PRT
<213> ORGANISM: Artificial
<220> FEATURE:
<223> OTHER INFORMATION: Synthetic

<400> SEQUENCE: 270

Gln Val Gln Leu Gln Gln Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ala Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Ile Val Tyr Leu
65                  70                  75                  80

Gln Met Asn Ser Leu Lys Thr Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 271
<211> LENGTH: 119
<212> TYPE: PRT
<213> ORGANISM: Artificial
<220> FEATURE:
<223> OTHER INFORMATION: Synthetic

<400> SEQUENCE: 271
```

Gln Val Gln Leu Gln Gln Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
            35                  40                  45

Ala Val Ile Trp Ser Gly Gly Asn Thr Asp Tyr Asn Thr Ser Leu Lys
        50                  55                  60

Ser Arg Leu Thr Ile Ser Lys Asp Asn Ser Lys Ser Ile Val Tyr Leu
65                  70                  75                  80

Gln Met Asn Ser Leu Arg Ala Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
                100                 105                 110

Thr Leu Val Thr Val Ser Ser
            115

<210> SEQ ID NO 272
<211> LENGTH: 119
<212> TYPE: PRT
<213> ORGANISM: Artificial
<220> FEATURE:
<223> OTHER INFORMATION: Synthetic

<400> SEQUENCE: 272

Gln Val Gln Leu Gln Gln Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
            35                  40                  45

Ala Val Ile Trp Ser Gly Gly Asn Thr Asp Tyr Asn Thr Ser Leu Lys
        50                  55                  60

Ser Arg Leu Thr Ile Ser Lys Asp Asn Ser Lys Ser Gln Val Val Leu
65                  70                  75                  80

Thr Met Arg Ser Leu Arg Ser Asp Asp Thr Ala Val Tyr Tyr Cys Ala
                85                  90                  95

Arg Ala Leu Thr Tyr Tyr Asp Tyr Glu Phe Ala Tyr Trp Gly Gln Gly
                100                 105                 110

Thr Leu Val Thr Val Ser Ser
            115

<210> SEQ ID NO 273
<211> LENGTH: 119
<212> TYPE: PRT
<213> ORGANISM: Artificial
<220> FEATURE:
<223> OTHER INFORMATION: Synthetic

<400> SEQUENCE: 273

Gln Val Gln Leu Gln Gln Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
            35                  40                  45

Ala Val Ile Trp Ser Gly Gly Asn Thr Asp Tyr Asn Thr Ser Leu Lys
        50                  55                  60

Ser Arg Leu Thr Ile Ser Lys Asp Asn Ser Lys Ser Ile Val Tyr Leu
65                  70                  75                  80

Gln Met Asn Ser Leu Arg Ala Gly Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 274
<211> LENGTH: 119
<212> TYPE: PRT
<213> ORGANISM: Artificial
<220> FEATURE:
<223> OTHER INFORMATION: Synthetic

<400> SEQUENCE: 274

Gln Val Gln Leu Gln Gln Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ala Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Thr Val Tyr Leu
65                  70                  75                  80

Gln Trp Ser Ser Leu Lys Ala Ser Asp Thr Ala Met Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 275
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 275

Asp Ile Leu Leu Thr Gln Ser Pro Ala Phe Leu Ser Val Thr Pro Gly
1               5                   10                  15

Glu Lys Val Thr Ile Thr Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 276
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 276

Asp Ile Leu Leu Thr Gln Ser Pro Ala Phe Leu Ser Val Thr Pro Gly
1               5                   10                  15

Glu Lys Val Thr Ile Thr Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 277
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 277

Asp Ile Leu Leu Thr Gln Ser Pro Ala Phe Leu Ser Val Thr Pro Gly
1               5                   10                  15

Glu Lys Val Thr Ile Thr Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 278
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 278

```
Asp Ile Leu Leu Thr Gln Ser Pro Ala Phe Leu Ser Val Thr Pro Gly
1               5                   10                  15

Glu Lys Val Thr Ile Thr Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Asn Asn Asn Trp Pro Thr
            85                  90                  95

Thr Phe Gly Ala Gly Thr Lys Xaa Glu Ile Lys
            100                 105
```

<210> SEQ ID NO 279
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 279

```
Asp Ile Leu Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Asn Asn Asn Trp Pro Thr
            85                  90                  95

Thr Phe Gly Ala Gly Thr Lys Xaa Glu Ile Lys
            100                 105
```

<210> SEQ ID NO 280
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 280

```
Asp Ile Leu Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Thr Asn
            20                  25                  30
```

```
Ile His Trp Tyr Gln Gln Lys Pro Asp Gln Ser Pro Lys Leu Leu Ile
            35                  40                  45

Lys Tyr Ala Ser Glu Ser Ile Ser Gly Ile Pro Ser Arg Phe Ser Gly
     50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Asn Asn Asn Trp Pro Thr
                 85                  90                  95

Thr Phe Gly Ala Gly Thr Lys Xaa Glu Ile Lys
            100                 105
```

<210> SEQ ID NO 281
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 281

```
Asp Ile Leu Leu Thr Gln Ser Pro Asp Phe Gln Ser Val Thr Pro Lys
 1               5                  10                  15

Glu Lys Val Thr Ile Thr Cys Arg Ala Ser Gln Ser Ile Gly Thr Asn
             20                  25                  30

Ile His Trp Tyr Gln Gln Lys Pro Asp Gln Ser Pro Lys Leu Leu Ile
            35                  40                  45

Lys Tyr Ala Ser Glu Ser Ile Ser Gly Ile Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Asn Asn Asn Trp Pro Thr
                 85                  90                  95

Thr Phe Gly Ala Gly Thr Lys Xaa Glu Ile Lys
            100                 105
```

<210> SEQ ID NO 282
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 282

```
Asp Ile Leu Leu Thr Gln Ser Pro Ala Phe Leu Ser Val Thr Pro Gly
 1               5                  10                  15

Glu Lys Val Thr Ile Thr Cys Arg Ala Ser Gln Ser Ile Gly Thr Asn
             20                  25                  30

Ile His Trp Tyr Gln Gln Lys Pro Asp Gln Ser Pro Lys Leu Leu Ile
            35                  40                  45

Lys Tyr Ala Ser Glu Ser Ile Ser Gly Ile Pro Ser Arg Phe Ser Gly
     50                  55                  60

Ser Gly Ser Gly Thr Asp Phe Thr Leu Thr Ile Asn Ser Leu Glu Ala
 65                  70                  75                  80
```

```
Glu Asp Ala Ala Thr Tyr Tyr Cys Gln Gln Asn Asn Asn Trp Pro Thr
                85                  90                  95

Thr Phe Gly Ala Gly Thr Lys Xaa Glu Ile Lys
            100                 105
```

<210> SEQ ID NO 283
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 283

```
Asp Ile Leu Leu Thr Gln Ser Pro Ser Phe Leu Ser Ala Ser Val Gly
1               5                   10                  15

Asp Arg Val Thr Ile Thr Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Asn Asn Asn Trp Pro Thr
                85                  90                  95

Thr Phe Gly Ala Gly Thr Lys Xaa Glu Ile Lys
            100                 105
```

<210> SEQ ID NO 284
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 284

```
Asp Ile Leu Leu Thr Gln Ser Pro Ser Ser Leu Ser Ala Ser Val Gly
1               5                   10                  15

Asp Arg Val Thr Ile Thr Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Asn Asn Asn Trp Pro Thr
                85                  90                  95

Thr Phe Gly Ala Gly Thr Lys Xaa Glu Ile Lys
            100                 105
```

<210> SEQ ID NO 285
<211> LENGTH: 107
<212> TYPE: PRT

```
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 285

Asp Ile Leu Leu Thr Gln Ser Pro Ser Phe Leu Ser Ala Ser Val Gly
1               5                   10                  15

Asp Arg Val Thr Ile Thr Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 286
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 286

Asp Ile Leu Leu Thr Gln Ser Pro Ser Ser Leu Ser Ala Ser Val Gly
1               5                   10                  15

Asp Arg Val Thr Ile Thr Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 287
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 287
```

Asp Ile Leu Leu Thr Gln Ser Pro Ser Phe Leu Ser Ala Ser Val Gly
1               5                   10                  15

Asp Arg Val Thr Ile Thr Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 288
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 288

Asp Ile Leu Leu Thr Gln Ser Pro Ser Leu Ser Ala Ser Val Gly
1               5                   10                  15

Asp Arg Val Thr Ile Thr Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 289
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 289

Asp Ile Leu Leu Thr Gln Ser Pro Ser Ser Leu Ser Ala Ser Val Gly
1               5                   10                  15

Asp Arg Val Thr Ile Thr Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly

```
                  50                  55                  60
Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Asn Asn Asn Trp Pro Thr
                 85                  90                  95

Thr Phe Gly Ala Gly Thr Lys Xaa Glu Ile Lys
                100                 105

<210> SEQ ID NO 290
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 290

Asp Ile Leu Leu Thr Gln Ser Pro Ser Ser Leu Ser Ala Ser Val Gly
 1               5                  10                  15

Asp Arg Val Thr Ile Thr Cys Arg Ala Ser Gln Ser Ile Gly Thr Asn
                 20                  25                  30

Ile His Trp Tyr Gln Gln Lys Pro Asp Gln Ser Pro Lys Leu Leu Ile
             35                  40                  45

Lys Tyr Ala Ser Glu Ser Ile Ser Gly Ile Pro Ser Arg Phe Ser Gly
 50                  55                  60

Ser Gly Ser Gly Thr Asp Phe Thr Leu Lys Ile Ser Arg Val Glu Ala
 65                  70                  75                  80

Glu Asp Val Gly Val Tyr Tyr Cys Gln Gln Asn Asn Asn Trp Pro Thr
                 85                  90                  95

Thr Phe Gly Ala Gly Thr Lys Xaa Glu Ile Lys
                100                 105

<210> SEQ ID NO 291
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 291

Asp Ile Leu Leu Thr Gln Ser Pro Ala Thr Leu Ser Leu Ser Pro Gly
 1               5                  10                  15

Glu Arg Val Thr Leu Ser Cys Arg Ala Ser Gln Ser Ile Gly Thr Asn
                 20                  25                  30

Ile His Trp Tyr Gln Gln Lys Pro Asp Gln Ser Pro Lys Leu Leu Ile
             35                  40                  45

Lys Tyr Ala Ser Glu Ser Ile Ser Gly Ile Pro Ser Arg Phe Ser Gly
 50                  55                  60

Ser Gly Ser Gly Thr Asp Phe Thr Leu Thr Ile Ser Cys Leu Gln Ser
 65                  70                  75                  80

Glu Asp Phe Ala Thr Tyr Tyr Cys Gln Gln Asn Asn Asn Trp Pro Thr
                 85                  90                  95

Thr Phe Gly Ala Gly Thr Lys Xaa Glu Ile Lys
                100                 105
```

<210> SEQ ID NO 292
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 292

```
Asp Ile Leu Leu Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Asn Asn Asn Trp Pro Thr
                85                  90                  95

Thr Phe Gly Ala Gly Thr Lys Xaa Glu Ile Lys
            100                 105
```

<210> SEQ ID NO 293
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 293

```
Asp Ile Leu Leu Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Asn Asn Asn Trp Pro Thr
                85                  90                  95

Thr Phe Gly Ala Gly Thr Lys Xaa Glu Ile Lys
            100                 105
```

<210> SEQ ID NO 294
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature

```
<222> LOCATION: (104)..(104)
<223> OTHER INFORMATION: Xaa can be any naturally occurring amino acid

<400> SEQUENCE: 294

Asp Ile Leu Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 295
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 295

Asp Ile Leu Leu Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 296
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 296

Asp Ile Leu Leu Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Asn
            20                  25                  30
```

Ile His Trp Tyr Gln Gln Lys Pro Asp Gln Ser Pro Lys Leu Leu Ile
            35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 297
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 297

Asp Ile Leu Leu Thr Gln Ser Pro Gly Thr Leu Ser Leu Ser Pro Gly
1               5                   10                  15

Glu Arg Val Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
            35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 298
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 298

Asp Ile Leu Leu Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
            35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Phe Thr Ile Ser Ser Leu Gln Pro
65                  70                  75                  80

-continued

Glu Asp Phe Ala Thr Tyr Tyr Cys Gln Gln Asn Asn Asn Trp Pro Thr
            85                  90                  95

Thr Phe Gly Ala Gly Thr Lys Xaa Glu Ile Lys
            100                 105

<210> SEQ ID NO 299
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 299

Asp Ile Leu Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln Asn Asn Asn Trp Pro Thr
            85                  90                  95

Thr Phe Gly Ala Gly Thr Lys Xaa Glu Ile Lys
            100                 105

<210> SEQ ID NO 300
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 300

Asp Ile Leu Leu Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Asn Asn Asn Trp Pro Thr
            85                  90                  95

Thr Phe Gly Ala Gly Thr Lys Xaa Glu Ile Lys
            100                 105

<210> SEQ ID NO 301
<211> LENGTH: 107
<212> TYPE: PRT

```
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 301

Asp Ile Leu Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 302
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 302

Asp Ile Leu Leu Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 303
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 303
```

Asp Ile Leu Leu Thr Gln Ser Pro Ala Thr Leu Ser Leu Ser Pro Gly
1               5                   10                  15

Glu Arg Val Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 304
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 304

Asp Ile Leu Leu Thr Gln Ser Pro Gly Thr Leu Ser Leu Ser Pro Gly
1               5                   10                  15

Glu Arg Val Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 305
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 305

Asp Ile Leu Leu Thr Gln Ser Pro Gly Thr Leu Ser Leu Ser Pro Gly
1               5                   10                  15

Glu Arg Val Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly

```
                50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Asn Asn Asn Trp Pro Thr
                 85                  90                  95

Thr Phe Gly Ala Gly Thr Lys Xaa Glu Ile Lys
                100                 105

<210> SEQ ID NO 306
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 306

Asp Ile Leu Leu Thr Gln Ser Pro Ala Thr Leu Ser Leu Ser Pro Gly
 1               5                  10                  15

Glu Arg Ala Thr Leu Ser Cys Arg Ala Ser Gln Ser Ile Gly Thr Asn
                20                  25                  30

Ile His Trp Tyr Gln Gln Lys Pro Asp Gln Ser Pro Lys Leu Leu Ile
             35                  40                  45

Lys Tyr Ala Ser Glu Ser Ile Ser Gly Ile Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Ile Ala Thr Tyr Tyr Cys Gln Gln Asn Asn Asn Trp Pro Thr
                 85                  90                  95

Thr Phe Gly Ala Gly Thr Lys Xaa Glu Ile Lys
                100                 105

<210> SEQ ID NO 307
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 307

Asp Ile Leu Leu Thr Gln Ser Pro Ala Thr Leu Ser Leu Ser Pro Gly
 1               5                  10                  15

Glu Arg Val Thr Leu Ser Cys Arg Ala Ser Gln Ser Ile Gly Thr Asn
                20                  25                  30

Ile His Trp Tyr Gln Gln Lys Pro Asp Gln Ser Pro Lys Leu Leu Ile
             35                  40                  45

Lys Tyr Ala Ser Glu Ser Ile Ser Gly Ile Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Asn Asn Asn Trp Pro Thr
                 85                  90                  95

Thr Phe Gly Ala Gly Thr Lys Xaa Glu Ile Lys
                100                 105
```

```
<210> SEQ ID NO 308
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 308

Asp Ile Leu Leu Thr Gln Ser Pro Ala Thr Leu Ser Leu Ser Pro Gly
1               5                   10                  15

Glu Arg Val Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Ile Ala Thr Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 309
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 309

Asp Ile Leu Leu Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 310
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
```

```
<222> LOCATION: (104)..(104)
<223> OTHER INFORMATION: Xaa can be any naturally occurring amino acid

<400> SEQUENCE: 310

Asp Ile Leu Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 311
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 311

Asp Ile Leu Leu Thr Gln Ser Pro Ala Thr Leu Ser Leu Ser Pro Gly
1               5                   10                  15

Glu Arg Val Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 312
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 312

Asp Ile Leu Leu Thr Gln Ser Pro Ala Thr Leu Ser Leu Ser Pro Gly
1               5                   10                  15

Glu Arg Val Thr Leu Ser Cys Arg Ala Ser Gln Ser Ile Gly Thr Asn
            20                  25                  30
```

```
Ile His Trp Tyr Gln Gln Lys Pro Asp Gln Ser Pro Lys Leu Leu Ile
            35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Leu Thr Ile Ser Ser Leu Gln Pro
 65                 70                  75                  80

Glu Asp Ile Ala Thr Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 313
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 313

Asp Ile Leu Leu Thr Gln Ser Pro Gly Thr Leu Ser Leu Ser Pro Gly
 1               5                  10                  15

Glu Arg Val Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
            35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Leu Thr Ile Ser Ser Leu Gln Ser
 65                 70                  75                  80

Glu Asp Phe Ala Val Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 314
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 314

Asp Ile Leu Leu Thr Gln Ser Pro Gly Thr Leu Ser Leu Ser Pro Gly
 1               5                  10                  15

Glu Arg Val Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
            35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Leu Thr Ile Ser Ser Leu Gln Ala
 65                 70                  75                  80
```

-continued

Glu Asp Val Ala Val Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 315
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 315

Asp Ile Leu Leu Thr Gln Ser Pro Ala Thr Leu Ser Leu Ser Pro Gly
1               5                   10                  15

Glu Arg Val Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 316
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 316

Asp Ile Leu Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 317
<211> LENGTH: 107
<212> TYPE: PRT

<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 317

```
Asp Ile Leu Leu Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Asn Asn Asn Trp Pro Thr
                85                  90                  95

Thr Phe Gly Ala Gly Thr Lys Xaa Glu Ile Lys
            100                 105
```

<210> SEQ ID NO 318
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 318

```
Asp Ile Leu Leu Thr Gln Ser Pro Ala Thr Leu Ser Leu Ser Pro Gly
1               5                   10                  15

Glu Arg Val Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Asn Asn Asn Trp Pro Thr
                85                  90                  95

Thr Phe Gly Ala Gly Thr Lys Xaa Glu Ile Lys
            100                 105
```

<210> SEQ ID NO 319
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 319

Asp Ile Leu Leu Thr Gln Ser Pro Ala Thr Leu Ser Leu Ser Pro Gly
1               5                   10                  15

Glu Arg Val Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 320
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 320

Asp Ile Leu Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 321
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 321

Asp Ile Leu Leu Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly

```
                50                  55                  60
Ser Gly Ser Gly Thr Asp Phe Thr Leu Thr Ile Ser Cys Leu Gln Ser
 65                  70                  75                  80

Glu Asp Phe Ala Thr Tyr Tyr Cys Gln Gln Asn Asn Asn Trp Pro Thr
                 85                  90                  95

Thr Phe Gly Ala Gly Thr Lys Xaa Glu Ile Lys
                100                 105

<210> SEQ ID NO 322
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 322

Asp Ile Leu Leu Thr Gln Ser Pro Ala Thr Leu Ser Val Ser Pro Gly
  1               5                  10                  15

Glu Arg Ala Thr Leu Ser Cys Arg Ala Ser Gln Ser Ile Gly Thr Asn
                 20                  25                  30

Ile His Trp Tyr Gln Gln Lys Pro Asp Gln Ser Pro Lys Leu Leu Ile
             35                  40                  45

Lys Tyr Ala Ser Glu Ser Ile Ser Gly Ile Pro Ser Arg Phe Ser Gly
 50                  55                  60

Ser Gly Ser Gly Thr Glu Phe Thr Leu Thr Ile Ser Ser Leu Glu Pro
 65                  70                  75                  80

Glu Asp Phe Ala Val Tyr Tyr Cys Gln Gln Asn Asn Asn Trp Pro Thr
                 85                  90                  95

Thr Phe Gly Ala Gly Thr Lys Xaa Glu Ile Lys
                100                 105

<210> SEQ ID NO 323
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 323

Asp Ile Leu Leu Thr Gln Ser Pro Ala Thr Leu Ser Val Ser Pro Gly
  1               5                  10                  15

Glu Arg Ala Thr Leu Ser Cys Arg Ala Ser Gln Ser Ile Gly Thr Asn
                 20                  25                  30

Ile His Trp Tyr Gln Gln Lys Pro Asp Gln Ser Pro Lys Leu Leu Ile
             35                  40                  45

Lys Tyr Ala Ser Glu Ser Ile Ser Gly Ile Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys Gln Gln Asn Asn Asn Trp Pro Thr
                 85                  90                  95

Thr Phe Gly Ala Gly Thr Lys Xaa Glu Ile Lys
                100                 105
```

<210> SEQ ID NO 324
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 324

Asp Ile Leu Leu Thr Gln Ser Pro Ala Thr Leu Ser Leu Ser Pro Gly
1               5                   10                  15

Glu Arg Val Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 325
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 325

Asp Ile Leu Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 326
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature

```
<222> LOCATION: (104)..(104)
<223> OTHER INFORMATION: Xaa can be any naturally occurring amino acid

<400> SEQUENCE: 326

Asp Ile Leu Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 327
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 327

Asp Ile Leu Leu Thr Gln Ser Pro Ala Thr Leu Ser Leu Ser Pro Gly
1               5                   10                  15

Glu Arg Val Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 328
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 328

Asp Ile Leu Leu Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Asn
            20                  25                  30
```

Ile His Trp Tyr Gln Gln Lys Pro Asp Gln Ser Pro Lys Leu Leu Ile
            35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 329
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 329

Asp Ile Leu Leu Thr Gln Ser Pro Asp Ser Leu Ala Val Ser Leu Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
            35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Asn Asn Asn Trp Pro Thr
                85                  90                  95

Thr Phe Gly Ala Gly Thr Lys Xaa Glu Ile Lys
            100                 105

<210> SEQ ID NO 330
<211> LENGTH: 107
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (104)..(104)
<223> OTHER INFORMATION: Xaa can be any naturally occurring amino acid

<400> SEQUENCE: 330

Asp Ile Leu Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
            35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Leu Lys Ile Ser Arg Val Glu Ala
65                  70                  75                  80

```
Glu Asp Val Gly Val Tyr Tyr Cys Gln Gln Asn Asn Asn Trp Pro Thr
                85                  90                  95

Thr Phe Gly Ala Gly Thr Lys Xaa Glu Ile Lys
            100                 105
```

<210> SEQ ID NO 331
<211> LENGTH: 119
<212> TYPE: PRT
<213> ORGANISM: Artificial
<220> FEATURE:
<223> OTHER INFORMATION: Synthetic

<400> SEQUENCE: 331

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ser Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115
```

<210> SEQ ID NO 332
<211> LENGTH: 119
<212> TYPE: PRT
<213> ORGANISM: Artificial
<220> FEATURE:
<223> OTHER INFORMATION: Synthetic

<400> SEQUENCE: 332

```
Gln Val Gln Leu Gln Gln Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ser Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115
```

<210> SEQ ID NO 333
<211> LENGTH: 119
<212> TYPE: PRT
<213> ORGANISM: Artificial
<220> FEATURE:

<223> OTHER INFORMATION: Synthetic

<400> SEQUENCE: 333

Gln Val Gln Leu Gln Gln Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ser Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 334
<211> LENGTH: 119
<212> TYPE: PRT
<213> ORGANISM: Artificial
<220> FEATURE:
<223> OTHER INFORMATION: Synthetic

<400> SEQUENCE: 334

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ser Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 335
<211> LENGTH: 119
<212> TYPE: PRT
<213> ORGANISM: Artificial
<220> FEATURE:
<223> OTHER INFORMATION: Synthetic

<400> SEQUENCE: 335

Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

```
Ser Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Ala Leu Thr Tyr Tyr Asp Tyr Glu Phe Ala Tyr Trp Gly Gln Gly
                100                 105                 110

Thr Leu Val Thr Val Ser Ser
        115
```

<210> SEQ ID NO 336
<211> LENGTH: 119
<212> TYPE: PRT
<213> ORGANISM: Artificial
<220> FEATURE:
<223> OTHER INFORMATION: Synthetic

<400> SEQUENCE: 336

```
Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Asn Tyr
                20                  25                  30

Gly Val His Trp Val Arg Gln Ala Pro Gly Lys Gly Leu Glu Trp Val
                35                  40                  45

Ser Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Ala Leu Thr Tyr Tyr Asp Tyr Glu Phe Ala Tyr Trp Gly Gln Gly
                100                 105                 110

Thr Leu Val Thr Val Ser Ser
        115
```

<210> SEQ ID NO 337
<211> LENGTH: 119
<212> TYPE: PRT
<213> ORGANISM: Artificial
<220> FEATURE:
<223> OTHER INFORMATION: Synthetic

<400> SEQUENCE: 337

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
                20                  25                  30

Gly Val His Trp Val Arg Gln Ala Pro Gly Lys Gly Leu Glu Trp Val
                35                  40                  45

Ser Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Ile Val Tyr Leu
65                  70                  75                  80

Gln Met Asn Ser Leu Arg Ala Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
                100                 105                 110
```

Thr Leu Val Thr Val Ser Ser
        115

<210> SEQ ID NO 338
<211> LENGTH: 119
<212> TYPE: PRT
<213> ORGANISM: Artificial
<220> FEATURE:
<223> OTHER INFORMATION: Synthetic

<400> SEQUENCE: 338

Gln Val Gln Leu Gln Gln Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ser Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Ile Val Tyr Leu
65                  70                  75                  80

Gln Met Asn Ser Leu Arg Ala Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 339
<211> LENGTH: 119
<212> TYPE: PRT
<213> ORGANISM: Artificial
<220> FEATURE:
<223> OTHER INFORMATION: Synthetic

<400> SEQUENCE: 339

Gln Val Gln Leu Gln Gln Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ser Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Ile Val Tyr Leu
65                  70                  75                  80

Gln Met Asn Ser Leu Arg Ala Gly Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 340
<211> LENGTH: 119
<212> TYPE: PRT
<213> ORGANISM: Artificial
<220> FEATURE:
<223> OTHER INFORMATION: Synthetic

<400> SEQUENCE: 340

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ser Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Ile Val Tyr Leu
65                  70                  75                  80

Gln Met Asn Ser Leu Arg Ala Gly Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 341
<211> LENGTH: 119
<212> TYPE: PRT
<213> ORGANISM: Artificial
<220> FEATURE:
<223> OTHER INFORMATION: Synthetic

<400> SEQUENCE: 341

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ser Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Ile Val Tyr Leu
65                  70                  75                  80

Gln Met Asn Ser Leu Arg Ala Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 342
<211> LENGTH: 119
<212> TYPE: PRT
<213> ORGANISM: Artificial
<220> FEATURE:
<223> OTHER INFORMATION: Synthetic

<400> SEQUENCE: 342

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ser Val Ile Trp Ser Gly Gly Asn Thr Asp Tyr Asn Thr Ser Leu Lys

```
                   50                  55                  60
Ser Arg Leu Thr Ile Ser Lys Asp Asn Ser Lys Ser Ile Val Tyr Leu
 65                  70                  75                  80

Gln Met Asn Ser Leu Arg Ala Glu Asp Thr Ala Val Tyr Tyr Cys Ala
                 85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 343
<211> LENGTH: 119
<212> TYPE: PRT
<213> ORGANISM: Artificial
<220> FEATURE:
<223> OTHER INFORMATION: Synthetic

<400> SEQUENCE: 343

Gln Val Gln Leu Gln Gln Ser Gly Pro Gly Leu Val Lys Pro Ser Gln
  1               5                  10                  15

Thr Leu Ser Leu Thr Cys Thr Val Ser Gly Phe Ser Leu Thr Asn Tyr
                 20                  25                  30

Gly Val His Trp Val Arg Gln Ala Pro Gly Lys Gly Leu Glu Trp Val
            35                  40                  45

Ser Val Ile Trp Ser Gly Gly Asn Thr Asp Tyr Asn Thr Ser Leu Lys
 50                  55                  60

Ser Arg Leu Thr Ile Ser Lys Asp Asn Ser Lys Ser Gln Val Val Leu
 65                  70                  75                  80

Gln Met Asn Ser Leu Arg Ala Glu Asp Thr Ala Val Tyr Tyr Cys Ala
                 85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 344
<211> LENGTH: 119
<212> TYPE: PRT
<213> ORGANISM: Artificial
<220> FEATURE:
<223> OTHER INFORMATION: Synthetic

<400> SEQUENCE: 344

Gln Val Gln Leu Gln Glu Ser Gly Pro Gly Leu Val Lys Pro Ser Glu
  1               5                  10                  15

Thr Leu Ser Leu Thr Cys Thr Val Ser Gly Phe Ser Leu Thr Asn Tyr
                 20                  25                  30

Gly Val His Trp Val Arg Gln Ala Pro Gly Lys Gly Leu Glu Trp Val
            35                  40                  45

Ser Val Ile Trp Ser Gly Gly Asn Thr Asp Tyr Asn Thr Ser Leu Lys
 50                  55                  60

Ser Arg Leu Thr Ile Ser Lys Asp Asn Ser Lys Ser Gln Val Val Leu
 65                  70                  75                  80

Gln Met Asn Ser Leu Arg Ala Glu Asp Thr Ala Val Tyr Tyr Cys Ala
                 85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
```

```
<210> SEQ ID NO 345
<211> LENGTH: 119
<212> TYPE: PRT
<213> ORGANISM: Artificial
<220> FEATURE:
<223> OTHER INFORMATION: Synthetic

<400> SEQUENCE: 345

Gln Val Gln Leu Gln Gln Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ser Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Gln Val Val Leu
65                  70                  75                  80

Gln Met Asn Ser Leu Arg Ala Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 346
<211> LENGTH: 119
<212> TYPE: PRT
<213> ORGANISM: Artificial
<220> FEATURE:
<223> OTHER INFORMATION: Synthetic

<400> SEQUENCE: 346

Gln Val Gln Leu Gln Gln Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ser Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Gln Val Val Leu
65                  70                  75                  80

Gln Met Asn Ser Leu Arg Ala Gly Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 347
<211> LENGTH: 119
<212> TYPE: PRT
<213> ORGANISM: Artificial
<220> FEATURE:
<223> OTHER INFORMATION: Synthetic

<400> SEQUENCE: 347
```

```
Gln Val Gln Leu Gln Gln Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
            35                  40                  45

Ser Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Gln Val Val Leu
65                  70                  75                  80

Gln Met Asn Ser Leu Arg Ala Gly Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
            115

<210> SEQ ID NO 348
<211> LENGTH: 119
<212> TYPE: PRT
<213> ORGANISM: Artificial
<220> FEATURE:
<223> OTHER INFORMATION: Synthetic

<400> SEQUENCE: 348

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
            35                  40                  45

Ser Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Gln Val Val Leu
65                  70                  75                  80

Gln Met Asn Ser Leu Lys Thr Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
            115

<210> SEQ ID NO 349
<211> LENGTH: 119
<212> TYPE: PRT
<213> ORGANISM: Artificial
<220> FEATURE:
<223> OTHER INFORMATION: Synthetic

<400> SEQUENCE: 349

Gln Val Gln Leu Gln Gln Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
            35                  40                  45

Ser Val Ile Trp Ser Gly Gly Asn Thr Asp Tyr Asn Thr Ser Leu Lys
    50                  55                  60
```

```
Ser Arg Leu Thr Ile Ser Lys Asp Asn Ser Lys Ser Gln Val Val Leu
 65                  70                  75                  80

Gln Met Asn Ser Leu Lys Thr Glu Asp Thr Ala Val Tyr Tyr Cys Ala
                 85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 350
<211> LENGTH: 119
<212> TYPE: PRT
<213> ORGANISM: Artificial
<220> FEATURE:
<223> OTHER INFORMATION: Synthetic

<400> SEQUENCE: 350

Gln Val Gln Leu Gln Gln Ser Gly Pro Gly Leu Val Lys Pro Ser Glu
 1               5                  10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ser Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Gln Val Val Leu
 65                  70                  75                  80

Gln Met Asn Ser Leu Lys Thr Glu Asp Thr Ala Val Tyr Tyr Cys Ala
                 85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 351
<211> LENGTH: 119
<212> TYPE: PRT
<213> ORGANISM: Artificial
<220> FEATURE:
<223> OTHER INFORMATION: Synthetic

<400> SEQUENCE: 351

Gln Val Gln Leu Gln Gln Ser Gly Pro Gly Leu Val Lys Pro Ser Gln
 1               5                  10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ser Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Ile Val Tyr Leu
 65                  70                  75                  80

Gln Met Asn Ser Leu Lys Thr Glu Asp Thr Ala Val Tyr Tyr Cys Ala
                 85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115
```

<210> SEQ ID NO 352
<211> LENGTH: 119
<212> TYPE: PRT
<213> ORGANISM: Artificial
<220> FEATURE:
<223> OTHER INFORMATION: Synthetic

<400> SEQUENCE: 352

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ser Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Gln Val Val Leu
65                  70                  75                  80

Gln Met Gly Ser Leu Arg Ala Glu Asp Met Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 353
<211> LENGTH: 119
<212> TYPE: PRT
<213> ORGANISM: Artificial
<220> FEATURE:
<223> OTHER INFORMATION: Synthetic

<400> SEQUENCE: 353

Gln Val Gln Leu Gln Gln Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ser Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Thr Val Tyr Leu
65                  70                  75                  80

Gln Trp Ser Ser Leu Lys Ala Ser Asp Thr Ala Met Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 354
<211> LENGTH: 119
<212> TYPE: PRT
<213> ORGANISM: Artificial
<220> FEATURE:
<223> OTHER INFORMATION: Synthetic

<400> SEQUENCE: 354

Gln Val Gln Leu Gln Gln Ser Gly Pro Gly Leu Val Lys Pro Ser Glu
1               5                   10                  15

```
Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
            35                  40                  45

Ser Val Ile Trp Ser Gly Gly Asn Thr Asp Tyr Asn Thr Ser Leu Lys
 50                  55                  60

Ser Arg Leu Thr Ile Ser Lys Asp Asn Ser Lys Ser Thr Val Tyr Leu
 65                  70                  75                  80

Gln Trp Ser Ser Leu Lys Ala Ser Asp Thr Ala Met Tyr Tyr Cys Ala
            85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
            115

<210> SEQ ID NO 355
<211> LENGTH: 119
<212> TYPE: PRT
<213> ORGANISM: Artificial
<220> FEATURE:
<223> OTHER INFORMATION: Synthetic

<400> SEQUENCE: 355

Gln Val Gln Leu Gln Gln Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
            35                  40                  45

Ser Val Ile Trp Ser Gly Gly Asn Thr Asp Tyr Asn Thr Ser Leu Lys
 50                  55                  60

Ser Arg Leu Thr Ile Ser Lys Asp Asn Ser Lys Ser Thr Val Tyr Leu
 65                  70                  75                  80

Gln Ile Ser Ser Leu Lys Ala Glu Asp Met Ala Met Tyr Tyr Cys Ala
            85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
            115

<210> SEQ ID NO 356
<211> LENGTH: 119
<212> TYPE: PRT
<213> ORGANISM: Artificial
<220> FEATURE:
<223> OTHER INFORMATION: Synthetic

<400> SEQUENCE: 356

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
            35                  40                  45

Ser Val Ile Trp Ser Gly Gly Asn Thr Asp Tyr Asn Thr Ser Leu Lys
 50                  55                  60

Ser Arg Leu Thr Ile Ser Lys Asp Asn Ser Lys Ser Thr Val Tyr Leu
 65                  70                  75                  80
```

Gln Ile Ser Ser Leu Lys Ala Glu Asp Met Ala Met Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 357
<211> LENGTH: 119
<212> TYPE: PRT
<213> ORGANISM: Artificial
<220> FEATURE:
<223> OTHER INFORMATION: Synthetic

<400> SEQUENCE: 357

Gln Val Gln Leu Gln Gln Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ser Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Thr Val Tyr Leu
65                  70                  75                  80

Gln Ile Cys Ser Leu Lys Ala Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 358
<211> LENGTH: 119
<212> TYPE: PRT
<213> ORGANISM: Artificial
<220> FEATURE:
<223> OTHER INFORMATION: Synthetic

<400> SEQUENCE: 358

Gln Val Gln Leu Gln Gln Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ser Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Thr Val Tyr Leu
65                  70                  75                  80

Gln Ile Cys Ser Leu Lys Ala Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 359

```
<211> LENGTH: 119
<212> TYPE: PRT
<213> ORGANISM: Artificial
<220> FEATURE:
<223> OTHER INFORMATION: Synthetic

<400> SEQUENCE: 359

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ser Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Gln Val Val Leu
65                  70                  75                  80

Thr Met Asn Asn Leu Arg Ala Glu Gly Thr Ala Ala Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 360
<211> LENGTH: 119
<212> TYPE: PRT
<213> ORGANISM: Artificial
<220> FEATURE:
<223> OTHER INFORMATION: Synthetic

<400> SEQUENCE: 360

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ser Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Gln Val Val Leu
65                  70                  75                  80

Thr Met Asn Asn Leu Arg Ala Glu Gly Thr Ala Ala Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 361
<211> LENGTH: 119
<212> TYPE: PRT
<213> ORGANISM: Artificial
<220> FEATURE:
<223> OTHER INFORMATION: Synthetic

<400> SEQUENCE: 361

Gln Val Gln Leu Gln Gln Ser Gly Pro Gly Leu Val Lys Pro Ser Gln
1               5                   10                  15

Thr Leu Ser Leu Thr Cys Thr Val Ser Gly Phe Ser Leu Thr Asn Tyr
```

-continued

```
                  20                  25                  30
Gly Val His Trp Val Arg Gln Ala Pro Gly Lys Gly Leu Glu Trp Val
            35                  40                  45
Ser Val Ile Trp Ser Gly Gly Asn Thr Asp Tyr Asn Thr Ser Leu Lys
        50                  55                  60
Ser Arg Leu Thr Ile Ser Lys Asp Asn Ser Lys Ser Gln Val Val Leu
65                  70                  75                  80
Thr Met Asn Asn Leu Arg Ala Glu Gly Thr Ala Ala Tyr Tyr Cys Ala
                85                  90                  95
Arg Ala Leu Thr Tyr Tyr Asp Tyr Glu Phe Ala Tyr Trp Gly Gln Gly
            100                 105                 110
Thr Leu Val Thr Val Ser Ser
            115

<210> SEQ ID NO 362
<211> LENGTH: 119
<212> TYPE: PRT
<213> ORGANISM: Artificial
<220> FEATURE:
<223> OTHER INFORMATION: Synthetic

<400> SEQUENCE: 362

Gln Val Gln Leu Gln Gln Ser Gly Pro Gly Leu Val Lys Pro Ser Glu
1               5                   10                  15
Thr Leu Ser Leu Thr Cys Thr Val Ser Gly Phe Ser Leu Thr Asn Tyr
            20                  25                  30
Gly Val His Trp Val Arg Gln Ala Pro Gly Lys Gly Leu Glu Trp Val
            35                  40                  45
Ser Val Ile Trp Ser Gly Gly Asn Thr Asp Tyr Asn Thr Ser Leu Lys
        50                  55                  60
Ser Arg Leu Thr Ile Ser Lys Asp Asn Ser Lys Ser Gln Val Val Leu
65                  70                  75                  80
Thr Met Asn Asn Leu Arg Ala Glu Gly Thr Ala Ala Tyr Tyr Cys Ala
                85                  90                  95
Arg Ala Leu Thr Tyr Tyr Asp Tyr Glu Phe Ala Tyr Trp Gly Gln Gly
            100                 105                 110
Thr Leu Val Thr Val Ser Ser
            115

<210> SEQ ID NO 363
<211> LENGTH: 119
<212> TYPE: PRT
<213> ORGANISM: Artificial
<220> FEATURE:
<223> OTHER INFORMATION: Synthetic

<400> SEQUENCE: 363

Gln Val Gln Leu Gln Gln Ser Gly Pro Gly Leu Val Lys Pro Ser Gln
1               5                   10                  15
Thr Leu Ser Leu Thr Cys Thr Val Ser Gly Phe Ser Leu Thr Asn Tyr
            20                  25                  30
Gly Val His Trp Val Arg Gln Ala Pro Gly Lys Gly Leu Glu Trp Val
            35                  40                  45
Ser Val Ile Trp Ser Gly Gly Asn Thr Asp Tyr Asn Thr Ser Leu Lys
        50                  55                  60
Ser Arg Leu Thr Ile Ser Lys Asp Asn Ser Lys Ser Gln Val Ser Leu
65                  70                  75                  80
Gln Leu Asn Ser Val Thr Pro Glu Asp Thr Ala Val Tyr Tyr Cys Ala
```

```
                  85                  90                  95

Arg Ala Leu Thr Tyr Tyr Asp Tyr Glu Phe Ala Tyr Trp Gly Gln Gly
                100                 105                 110

Thr Leu Val Thr Val Ser Ser
            115

<210> SEQ ID NO 364
<211> LENGTH: 119
<212> TYPE: PRT
<213> ORGANISM: Artificial
<220> FEATURE:
<223> OTHER INFORMATION: Synthetic

<400> SEQUENCE: 364

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ser Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Gln Val Ser Leu
65                  70                  75                  80

Gln Leu Asn Ser Val Thr Pro Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
                100                 105                 110

Thr Leu Val Thr Val Ser Ser
            115

<210> SEQ ID NO 365
<211> LENGTH: 119
<212> TYPE: PRT
<213> ORGANISM: Artificial
<220> FEATURE:
<223> OTHER INFORMATION: Synthetic

<400> SEQUENCE: 365

Gln Val Gln Leu Gln Gln Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ser Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Val Asp Thr Ala Val Tyr Tyr Cys Ala
                85                  90                  95

Arg Ala Leu Thr Tyr Tyr Asp Tyr Glu Phe Ala Tyr Trp Gly Gln Gly
                100                 105                 110

Thr Leu Val Thr Val Ser Ser
            115

<210> SEQ ID NO 366
<211> LENGTH: 119
<212> TYPE: PRT
```

```
<213> ORGANISM: Artificial
<220> FEATURE:
<223> OTHER INFORMATION: Synthetic

<400> SEQUENCE: 366

Gln Val Gln Leu Gln Gln Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ser Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Val Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 367
<211> LENGTH: 119
<212> TYPE: PRT
<213> ORGANISM: Artificial
<220> FEATURE:
<223> OTHER INFORMATION: Synthetic

<400> SEQUENCE: 367

Gln Val Gln Leu Gln Gln Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ser Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 368
<211> LENGTH: 119
<212> TYPE: PRT
<213> ORGANISM: Artificial
<220> FEATURE:
<223> OTHER INFORMATION: Synthetic

<400> SEQUENCE: 368

Gln Val Gln Leu Gln Gln Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30
```

Gly Val His Trp Val Arg Gln Ala Pro Gly Lys Gly Leu Glu Trp Val
            35                  40                  45

Ser Val Ile Trp Ser Gly Gly Asn Thr Asp Tyr Asn Thr Ser Leu Lys
 50                  55                  60

Ser Arg Leu Thr Ile Thr Lys Asp Asn Ser Thr Ser Thr Val Tyr Met
65                  70                  75                  80

Glu Leu Ser Ser Leu Arg Ser Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
            115

<210> SEQ ID NO 369
<211> LENGTH: 119
<212> TYPE: PRT
<213> ORGANISM: Artificial
<220> FEATURE:
<223> OTHER INFORMATION: Synthetic

<400> SEQUENCE: 369

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
            35                  40                  45

Ser Val Ile Trp Ser Gly Gly Asn Thr Asp Tyr Asn Thr Ser Leu Lys
 50                  55                  60

Ser Arg Leu Thr Ile Thr Lys Asp Asn Ser Thr Ser Thr Val Tyr Met
65                  70                  75                  80

Glu Leu Ser Ser Leu Arg Ser Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
            115

<210> SEQ ID NO 370
<211> LENGTH: 119
<212> TYPE: PRT
<213> ORGANISM: Artificial
<220> FEATURE:
<223> OTHER INFORMATION: Synthetic

<400> SEQUENCE: 370

Gln Val Gln Leu Gln Gln Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
            35                  40                  45

Ser Val Ile Trp Ser Gly Gly Asn Thr Asp Tyr Asn Thr Ser Leu Lys
 50                  55                  60

Ser Arg Leu Thr Ile Thr Lys Asp Asn Ser Thr Ser Thr Val Tyr Met
65                  70                  75                  80

Glu Leu Ser Ser Leu Arg Ser Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
                100                 105                 110

Thr Leu Val Thr Val Ser Ser
        115

<210> SEQ ID NO 371
<211> LENGTH: 119
<212> TYPE: PRT
<213> ORGANISM: Artificial
<220> FEATURE:
<223> OTHER INFORMATION: Synthetic

<400> SEQUENCE: 371

Gln Val Gln Leu Gln Gln Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ser Val Ile Trp Ser Gly Gly Asn Thr Asp Tyr Asn Thr Ser Leu Lys
    50                  55                  60

Ser Arg Leu Thr Ile Thr Lys Asp Asn Ser Thr Ser Thr Val Tyr Met
65                  70                  75                  80

Glu Leu Ser Ser Leu Arg Ser Glu Asp Thr Ala Met Tyr Tyr Cys Ala
                85                  90                  95

Arg Ala Leu Thr Tyr Tyr Asp Tyr Glu Phe Ala Tyr Trp Gly Gln Gly
                100                 105                 110

Thr Leu Val Thr Val Ser Ser
        115

<210> SEQ ID NO 372
<211> LENGTH: 119
<212> TYPE: PRT
<213> ORGANISM: Artificial
<220> FEATURE:
<223> OTHER INFORMATION: Synthetic

<400> SEQUENCE: 372

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ser Val Ile Trp Ser Gly Gly Asn Thr Asp Tyr Asn Thr Ser Leu Lys
    50                  55                  60

Ser Arg Leu Thr Ile Thr Lys Asp Asn Ser Thr Ser Thr Val Tyr Met
65                  70                  75                  80

Glu Leu Ser Ser Leu Arg Ser Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
                100                 105                 110

Thr Leu Val Thr Val Ser Ser
        115

<210> SEQ ID NO 373
<211> LENGTH: 119
<212> TYPE: PRT
<213> ORGANISM: Artificial
<220> FEATURE:

<223> OTHER INFORMATION: Synthetic

<400> SEQUENCE: 373

Gln Val Gln Leu Gln Gln Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ser Val Ile Trp Ser Gly Gly Asn Thr Asp Tyr Asn Thr Ser Leu Lys
50                  55                  60

Ser Arg Leu Thr Ile Thr Lys Asp Asn Ser Thr Ser Thr Val Tyr Met
65                  70                  75                  80

Glu Leu Ser Arg Leu Arg Ser Asp Asp Thr Val Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 374
<211> LENGTH: 119
<212> TYPE: PRT
<213> ORGANISM: Artificial
<220> FEATURE:
<223> OTHER INFORMATION: Synthetic

<400> SEQUENCE: 374

Gln Val Gln Leu Val Glu Ser Gly Gly Gly Leu Val Gln Pro Gly Arg
1               5                   10                  15

Ser Leu Arg Leu Ser Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ser Val Ile Trp Ser Gly Gly Asn Thr Asp Tyr Asn Thr Ser Leu Lys
50                  55                  60

Ser Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 375
<211> LENGTH: 119
<212> TYPE: PRT
<213> ORGANISM: Artificial
<220> FEATURE:
<223> OTHER INFORMATION: Synthetic

<400> SEQUENCE: 375

Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ser Val Ile Trp Ser Gly Gly Asn Thr Asp Tyr Asn Thr Ser Leu Lys
        50                  55                  60

Ser Arg Leu Thr Ile Ser Lys Asp Asn Ser Lys Ser Gln Val Val Leu
65                  70                  75                  80

Gln Met Asn Ser Leu Arg Ala Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
                100                 105                 110

Thr Leu Val Thr Val Ser Ser
        115

<210> SEQ ID NO 376
<211> LENGTH: 119
<212> TYPE: PRT
<213> ORGANISM: Artificial
<220> FEATURE:
<223> OTHER INFORMATION: Synthetic

<400> SEQUENCE: 376

Gln Val Gln Leu Val Glu Ser Gly Gly Gly Leu Val Gln Pro Gly Arg
1               5                   10                  15

Ser Leu Arg Leu Ser Cys Thr Val Ser Gly Phe Ser Leu Thr Asn Tyr
                20                  25                  30

Gly Val His Trp Val Arg Gln Ala Pro Gly Lys Gly Leu Glu Trp Val
            35                  40                  45

Ser Val Ile Trp Ser Gly Gly Asn Thr Asp Tyr Asn Thr Ser Leu Lys
        50                  55                  60

Ser Arg Leu Thr Ile Thr Lys Asp Asn Ser Thr Ser Thr Val Tyr Met
65                  70                  75                  80

Glu Leu Ser Ser Leu Arg Ser Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
                100                 105                 110

Thr Leu Val Thr Val Ser Ser
        115

<210> SEQ ID NO 377
<211> LENGTH: 119
<212> TYPE: PRT
<213> ORGANISM: Artificial
<220> FEATURE:
<223> OTHER INFORMATION: Synthetic

<400> SEQUENCE: 377

Gln Val Gln Leu Val Glu Ser Gly Gly Gly Leu Val Gln Pro Gly Arg
1               5                   10                  15

Ser Leu Arg Leu Ser Cys Thr Val Ser Gly Phe Ser Leu Thr Asn Tyr
                20                  25                  30

Gly Val His Trp Val Arg Gln Ala Pro Gly Lys Gly Leu Glu Trp Val
            35                  40                  45

Ser Val Ile Trp Ser Gly Gly Asn Thr Asp Tyr Asn Thr Ser Leu Lys
        50                  55                  60

Ser Arg Leu Thr Ile Ser Lys Asp Asn Ser Lys Ser Gln Val Ser Leu
65                  70                  75                  80

Lys Leu Ser Ser Val Thr Ala Val Asp Thr Ala Val Tyr Tyr Cys Ala
                85                  90                  95

Arg Ala Leu Thr Tyr Tyr Asp Tyr Glu Phe Ala Tyr Trp Gly Gln Gly
                100                 105                 110

Thr Leu Val Thr Val Ser Ser
        115

<210> SEQ ID NO 378
<211> LENGTH: 119
<212> TYPE: PRT
<213> ORGANISM: Artificial
<220> FEATURE:
<223> OTHER INFORMATION: Synthetic

<400> SEQUENCE: 378

Glu Val Gln Leu Val Glu Ser Gly Gly Leu Val Gln Pro Gly Arg
1               5                   10                  15

Ser Leu Arg Leu Ser Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ser Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Gln Val Val Leu
65                  70                  75                  80

Gln Met Asn Ser Leu Lys Thr Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 379
<211> LENGTH: 107
<212> TYPE: PRT
<213> ORGANISM: Homo sapiens

<400> SEQUENCE: 379

Asp Ile Leu Leu Thr Gln Ser Pro Ala Thr Leu Ser Leu Ser Pro Gly
1               5                   10                  15

Glu Arg Val Thr Leu Ser Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Asp Tyr Tyr Cys Gln Gln Asn Asn Asn Trp Pro Thr
                85                  90                  95

Thr Phe Gly Ala Gly Thr Lys Leu Glu Ile Lys
            100                 105

<210> SEQ ID NO 380
<211> LENGTH: 107
<212> TYPE: PRT
<213> ORGANISM: Homo sapiens

<400> SEQUENCE: 380

Asp Ile Leu Leu Thr Gln Ser Pro Ser Leu Ser Ala Ser Val Gly
1               5                   10                  15

Asp Arg Val Thr Ile Thr Cys Arg Ala Ser Gln Ser Ile Gly Thr Asn
            20                  25                  30

Ile His Trp Tyr Gln Gln Lys Pro Asp Gln Ser Pro Lys Leu Leu Ile
            35                  40                  45

Lys Tyr Ala Ser Glu Ser Ile Ser Gly Ile Pro Ser Arg Phe Ser Gly
 50                  55                  60

Ser Gly Ser Gly Thr Asp Phe Thr Leu Thr Ile Ser Ser Leu Gln Ala
 65                  70                  75                  80

Glu Asp Val Ala Val Tyr Tyr Cys Gln Gln Asn Asn Asn Trp Pro Thr
                 85                  90                  95

Thr Phe Gly Ala Gly Thr Lys Leu Glu Ile Lys
            100                 105

<210> SEQ ID NO 381
<211> LENGTH: 107
<212> TYPE: PRT
<213> ORGANISM: Homo sapiens

<400> SEQUENCE: 381

Asp Ile Leu Leu Thr Gln Ser Pro Ala Phe Leu Ser Val Thr Pro Gly
 1               5                  10                  15

Glu Lys Val Thr Ile Thr Cys Arg Ala Ser Gln Ser Ile Gly Thr Asn
            20                  25                  30

Ile His Trp Tyr Gln Gln Lys Pro Asp Gln Ser Pro Lys Leu Leu Ile
            35                  40                  45

Lys Tyr Ala Ser Glu Ser Ile Ser Gly Ile Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys Gln Gln Asn Asn Asn Trp Pro Thr
                 85                  90                  95

Thr Phe Gly Ala Gly Thr Lys Leu Glu Ile Lys
            100                 105

<210> SEQ ID NO 382
<211> LENGTH: 119
<212> TYPE: PRT
<213> ORGANISM: Homo sapiens

<400> SEQUENCE: 382

Gln Val Gln Leu Gln Gln Ser Gly Pro Gly Leu Val Lys Pro Ser Gln
 1               5                  10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Leu
            35                  40                  45

Gly Val Ile Trp Ser Gly Gly Asn Thr Asp Tyr Asn Thr Ser Leu Lys
 50                  55                  60

Ser Arg Leu Thr Ile Ser Lys Asp Asn Ser Lys Ser Gln Val Val Leu
 65                  70                  75                  80

Gln Met Asn Ser Leu Arg Ala Glu Asp Thr Ala Val Tyr Tyr Cys Ala
                 85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
            115

<210> SEQ ID NO 383
<211> LENGTH: 119

-continued

```
<212> TYPE: PRT
<213> ORGANISM: Homo sapiens

<400> SEQUENCE: 383

Gln Val Gln Leu Gln Gln Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Leu
        35                  40                  45

Gly Val Ile Trp Ser Gly Gly Asn Thr Asp Tyr Asn Thr Ser Leu Lys
    50                  55                  60

Ser Arg Leu Thr Ile Ser Lys Asp Asn Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 384
<211> LENGTH: 119
<212> TYPE: PRT
<213> ORGANISM: Homo sapiens

<400> SEQUENCE: 384

Gln Val Gln Leu Gln Gln Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Leu
        35                  40                  45

Gly Val Ile Trp Ser Gly Gly Asn Thr Asp Tyr Asn Thr Pro Leu Thr
    50                  55                  60

Ser Arg Leu Thr Ile Asn Lys Asp Asn Ser Lys Ser Gln Val Val Leu
65                  70                  75                  80

Gln Met Asn Ser Leu Arg Ala Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 385
<211> LENGTH: 119
<212> TYPE: PRT
<213> ORGANISM: Homo sapiens

<400> SEQUENCE: 385

Gln Val Gln Leu Gln Gln Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Ala Pro Gly Lys Gly Leu Glu Trp Val
        35                  40                  45

Gly Val Ile Trp Ser Gly Gly Asn Thr Asp Tyr Asn Thr Ser Val Lys
    50                  55                  60
```

```
Gly Arg Phe Thr Ile Ser Lys Asp Asn Ser Lys Ser Gln Val Tyr Leu
 65                  70                  75                  80

Gln Met Asn Ser Leu Arg Ala Glu Asp Thr Ala Val Tyr Tyr Cys Ala
                 85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
            115

<210> SEQ ID NO 386
<211> LENGTH: 119
<212> TYPE: PRT
<213> ORGANISM: Homo sapiens

<400> SEQUENCE: 386

Gln Val Gln Leu Gln Gln Ser Gly Pro Gly Leu Val Lys Pro Ser Gln
  1               5                  10                  15

Thr Leu Ser Leu Thr Cys Thr Val Ser Gly Phe Ser Leu Thr Asn Tyr
                 20                  25                  30

Gly Val His Trp Val Arg Gln Pro Pro Gly Lys Gly Leu Glu Trp Ile
             35                  40                  45

Gly Val Ile Trp Ser Gly Gly Asn Thr Asp Tyr Asn Thr Ser Leu Lys
 50                  55                  60

Ser Arg Val Thr Ile Ser Lys Asp Asn Ser Lys Ser Gln Val Ser Leu
 65                  70                  75                  80

Lys Leu Ser Ser Val Thr Ala Ala Asp Thr Ala Val Tyr Tyr Cys Ala
                 85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
            115

<210> SEQ ID NO 387
<211> LENGTH: 119
<212> TYPE: PRT
<213> ORGANISM: Homo sapiens

<400> SEQUENCE: 387

Gln Val Gln Leu Val Glu Ser Gly Gly Gly Leu Val Gln Pro Gly Arg
  1               5                  10                  15

Ser Leu Arg Leu Ser Cys Ala Val Ser Gly Phe Ser Leu Thr Asn Tyr
                 20                  25                  30

Gly Val His Trp Val Arg Gln Ala Pro Gly Lys Gly Leu Glu Trp Val
             35                  40                  45

Ser Val Ile Trp Ser Gly Gly Asn Thr Asp Tyr Asn Thr Ser Val Lys
 50                  55                  60

Gly Arg Phe Thr Ile Ser Lys Asp Asn Ser Lys Ser Thr Val Tyr Leu
 65                  70                  75                  80

Gln Met Asn Ser Leu Arg Ala Glu Asp Thr Ala Val Tyr Tyr Cys Ala
                 85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
            115

<210> SEQ ID NO 388
<211> LENGTH: 106
```

-continued

```
<212> TYPE: PRT
<213> ORGANISM: Homo sapiens

<400> SEQUENCE: 388

Asp Ile Gln Met Thr Gln Ser Pro Ser Phe Leu Ser Ala Ser Val Gly
1               5                   10                  15

Asp Arg Val Thr Ile Asn Cys Lys Ala Ser Gln Asn Ile Asn Asn Tyr
            20                  25                  30

Leu Asn Trp Tyr Gln Gln Lys Leu Gly Glu Ala Pro Lys Arg Leu Ile
        35                  40                  45

Tyr Asn Thr Asn Asn Leu Gln Thr Gly Ile Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Leu Gln His Asn Ser Phe Pro Thr
                85                  90                  95

Phe Gly Ala Gly Thr Lys Leu Glu Leu Lys
            100                 105

<210> SEQ ID NO 389
<211> LENGTH: 120
<212> TYPE: PRT
<213> ORGANISM: Homo sapiens

<400> SEQUENCE: 389

Gln Val Asn Leu Leu Gln Ser Gly Ala Ala Leu Val Lys Pro Gly Ala
1               5                   10                  15

Ser Val Lys Leu Ser Cys Lys Gly Ser Gly Phe Thr Phe Thr Asp Tyr
            20                  25                  30

Lys Ile His Trp Val Lys Gln Ser His Gly Lys Ser Leu Glu Trp Ile
        35                  40                  45

Gly Tyr Phe Asn Pro Asn Ser Gly Tyr Ser Thr Tyr Asn Glu Lys Phe
50                  55                  60

Lys Ser Lys Ala Thr Leu Thr Ala Asp Lys Ser Thr Asp Thr Ala Tyr
65                  70                  75                  80

Met Glu Leu Thr Ser Leu Thr Ser Glu Asp Ser Ala Thr Tyr Tyr Cys
                85                  90                  95

Thr Arg Leu Ser Pro Gly Gly Tyr Tyr Val Met Asp Ala Trp Gly Gln
            100                 105                 110

Gly Ala Ser Val Thr Val Ser Ser
        115                 120

<210> SEQ ID NO 390
<211> LENGTH: 106
<212> TYPE: PRT
<213> ORGANISM: Homo sapiens

<400> SEQUENCE: 390

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asn Asn Tyr
            20                  25                  30

Leu Gly Trp Tyr Gln Gln Lys Pro Gly Lys Ala Pro Lys Arg Leu Ile
        35                  40                  45

Tyr Asn Thr Asn Asn Leu Gln Thr Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80
```

Glu Asp Phe Ala Thr Tyr Tyr Cys Leu Gln His Asn Ser Phe Pro Thr
            85                  90                  95

Phe Gly Ala Gly Thr Lys Leu Glu Ile Lys
            100                 105

<210> SEQ ID NO 391
<211> LENGTH: 120
<212> TYPE: PRT
<213> ORGANISM: Homo sapiens

<400> SEQUENCE: 391

Glu Val Gln Leu Val Gln Ser Gly Ala Glu Val Lys Lys Pro Gly Ala
1               5                   10                  15

Thr Val Lys Ile Ser Cys Lys Val Ser Gly Phe Thr Phe Thr Asp Tyr
            20                  25                  30

Lys Met His Trp Val Gln Gln Ala Pro Gly Lys Gly Leu Glu Trp Met
        35                  40                  45

Gly Leu Val Asn Pro Asn Ser Gly Tyr Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
            85                  90                  95

Ala Thr Leu Ser Pro Gly Gly Tyr Tyr Val Met Asp Ala Trp Gly Gln
            100                 105                 110

Gly Thr Leu Val Thr Val Ser Ser
        115                 120

<210> SEQ ID NO 392
<211> LENGTH: 106
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (103)..(103)
<223> OTHER INFORMATION: Xaa can be any naturally occurring amino acid

<400> SEQUENCE: 392

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Asn Ile Asn Asn Tyr
            20                  25                  30

Leu Asn Trp Tyr Gln Gln Lys Pro Gly Lys Ala Pro Lys Arg Leu Ile
        35                  40                  45

Tyr Asn Thr Asn Asn Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Leu Gln His Asn Ser Phe Pro Thr
            85                  90                  95

Phe Gly Ala Gly Thr Lys Xaa Glu Ile Lys
            100                 105

<210> SEQ ID NO 393
<211> LENGTH: 106
<212> TYPE: PRT
<213> ORGANISM: Artificial
<220> FEATURE:

<223> OTHER INFORMATION: Synthetic
<220> FEATURE:
<221> NAME/KEY: misc_feature
<222> LOCATION: (103)..(103)
<223> OTHER INFORMATION: Xaa can be any naturally occurring amino acid

<400> SEQUENCE: 393

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Asn Ile Asn Asn Tyr
            20                  25                  30

Leu Asn Trp Tyr Gln Gln Lys Pro Gly Lys Ala Pro Lys Arg Leu Ile
        35                  40                  45

Tyr Asn Thr Asn Asn Leu Gln Thr Gly Ile Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Leu Gln His Asn Ser Phe Pro Thr
                85                  90                  95

Phe Gly Ala Gly Thr Lys Xaa Glu Ile Lys
            100                 105

<210> SEQ ID NO 394
<211> LENGTH: 106
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (103)..(103)
<223> OTHER INFORMATION: Xaa can be any naturally occurring amino acid

<400> SEQUENCE: 394

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Asn Ile Asn Asn Tyr
            20                  25                  30

Leu Asn Trp Tyr Gln Gln Lys Pro Gly Lys Ala Pro Lys Arg Leu Ile
        35                  40                  45

Tyr Asn Thr Asn Asn Leu Gln Thr Gly Ile Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Leu Gln His Asn Ser Phe Pro Thr
                85                  90                  95

Phe Gly Ala Gly Thr Lys Xaa Glu Ile Lys
            100                 105

<210> SEQ ID NO 395
<211> LENGTH: 106
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (103)..(103)
<223> OTHER INFORMATION: Xaa can be any naturally occurring amino acid

<400> SEQUENCE: 395

Asp Ile Gln Met Thr Gln Ser Pro Ser Ser Leu Ser Ala Ser Val Gly
1               5                   10                  15

```
Asp Arg Val Thr Ile Thr Cys Trp Ala Ser Gln Asn Ile Asn Asn Tyr
            20                  25                  30

Leu Asn Trp Tyr Gln Gln Lys Pro Gly Lys Ala Pro Lys Arg Leu Ile
        35                  40                  45

Tyr Asn Thr Asn Asn Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Leu Gln His Asn Ser Phe Pro Thr
                85                  90                  95

Phe Gly Ala Gly Thr Lys Xaa Glu Ile Lys
                100                 105

<210> SEQ ID NO 396
<211> LENGTH: 106
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (103)..(103)
<223> OTHER INFORMATION: Xaa can be any naturally occurring amino acid

<400> SEQUENCE: 396

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Asn Ile Asn Asn Tyr
            20                  25                  30

Leu Asn Trp Tyr Gln Gln Lys Pro Gly Lys Ala Pro Lys Arg Leu Ile
        35                  40                  45

Tyr Asn Thr Asn Asn Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Leu Gln His Asn Ser Phe Pro Thr
                85                  90                  95

Phe Gly Ala Gly Thr Lys Xaa Glu Ile Lys
                100                 105

<210> SEQ ID NO 397
<211> LENGTH: 106
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (103)..(103)
<223> OTHER INFORMATION: Xaa can be any naturally occurring amino acid

<400> SEQUENCE: 397

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Asn Ile Asn Asn Tyr
            20                  25                  30

Leu Asn Trp Tyr Gln Gln Lys Pro Gly Lys Ala Pro Lys Arg Leu Ile
        35                  40                  45

Tyr Asn Thr Asn Asn Leu Gln Thr Gly Ile Pro Ser Arg Phe Ser Gly
    50                  55                  60
```

```
Ser Gly Ser Gly Thr Asp Tyr Thr Leu Thr Ile Ser Ser Leu Gln Pro
 65                  70                  75                  80

Glu Asp Phe Ala Thr Tyr Phe Cys Leu Gln His Asn Ser Phe Pro Thr
                 85                  90                  95

Phe Gly Ala Gly Thr Lys Xaa Glu Ile Lys
            100                 105
```

<210> SEQ ID NO 398
<211> LENGTH: 106
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (103)..(103)
<223> OTHER INFORMATION: Xaa can be any naturally occurring amino acid

<400> SEQUENCE: 398

```
Asp Ile Gln Met Thr Gln Ser Pro Ser Thr Leu Ser Ala Ser Val Gly
 1               5                  10                  15

Asp Arg Val Thr Ile Thr Cys Gln Ala Ser Gln Asn Ile Asn Asn Tyr
                 20                  25                  30

Leu Asn Trp Tyr Gln Gln Lys Pro Gly Lys Ala Pro Lys Arg Leu Ile
             35                  40                  45

Tyr Asn Thr Asn Asn Leu Gln Thr Gly Ile Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Phe Cys Leu Gln His Asn Ser Phe Pro Thr
                 85                  90                  95

Phe Gly Ala Gly Thr Lys Xaa Glu Ile Lys
            100                 105
```

<210> SEQ ID NO 399
<211> LENGTH: 106
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (103)..(103)
<223> OTHER INFORMATION: Xaa can be any naturally occurring amino acid

<400> SEQUENCE: 399

```
Asp Ile Gln Met Ile Gln Ser Pro Ser Phe Leu Ser Ala Ser Val Gly
 1               5                  10                  15

Asp Arg Val Thr Ile Thr Cys Gln Ala Ser Gln Asn Ile Asn Asn Tyr
                 20                  25                  30

Leu Asn Trp Tyr Gln Gln Lys Pro Gly Lys Ala Pro Lys Arg Leu Ile
             35                  40                  45

Tyr Asn Thr Asn Asn Leu Gln Thr Gly Ile Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Phe Cys Leu Gln His Asn Ser Phe Pro Thr
                 85                  90                  95

Phe Gly Ala Gly Thr Lys Xaa Glu Ile Lys
            100                 105
```

```
<210> SEQ ID NO 400
<211> LENGTH: 106
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (103)..(103)
<223> OTHER INFORMATION: Xaa can be any naturally occurring amino acid

<400> SEQUENCE: 400

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asn Ile Asn Asn Tyr
            20                  25                  30

Leu Asn Trp Tyr Gln Gln Lys Pro Gly Lys Ala Pro Lys Arg Leu Ile
        35                  40                  45

Tyr Asn Thr Asn Asn Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Leu Gln His Asn Ser Phe Pro Thr
                85                  90                  95

Phe Gly Ala Gly Thr Lys Xaa Glu Ile Lys
            100                 105

<210> SEQ ID NO 401
<211> LENGTH: 106
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (103)..(103)
<223> OTHER INFORMATION: Xaa can be any naturally occurring amino acid

<400> SEQUENCE: 401

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asn Asn Tyr
            20                  25                  30

Leu Asn Trp Tyr Gln Gln Lys Pro Gly Lys Ala Pro Lys Arg Leu Ile
        35                  40                  45

Tyr Asn Thr Asn Asn Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Leu Gln His Asn Ser Phe Pro Thr
                85                  90                  95

Phe Gly Ala Gly Thr Lys Xaa Glu Ile Lys
            100                 105

<210> SEQ ID NO 402
<211> LENGTH: 106
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (103)..(103)
<223> OTHER INFORMATION: Xaa can be any naturally occurring amino acid
```

<400> SEQUENCE: 402

Asp Ile Gln Met Ile Gln Ser Pro Ser Phe Leu Ser Ala Ser Val Gly
1               5                   10                  15

Asp Arg Val Thr Ile Thr Cys Trp Ala Ser Gln Asn Ile Asn Asn Tyr
            20                  25                  30

Leu Asn Trp Tyr Gln Gln Lys Pro Gly Lys Ala Pro Lys Arg Leu Ile
        35                  40                  45

Tyr Asn Thr Asn Asn Leu Gln Thr Gly Ile Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Leu Gln His Asn Ser Phe Pro Thr
                85                  90                  95

Phe Gly Ala Gly Thr Lys Xaa Glu Ile Lys
            100                 105

<210> SEQ ID NO 403
<211> LENGTH: 106
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (103)..(103)
<223> OTHER INFORMATION: Xaa can be any naturally occurring amino acid

<400> SEQUENCE: 403

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Asn Ile Asn Asn Tyr
            20                  25                  30

Leu Asn Trp Tyr Gln Gln Lys Pro Gly Lys Ala Pro Lys Arg Leu Ile
        35                  40                  45

Tyr Asn Thr Asn Asn Leu Gln Thr Gly Ile Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Leu Gln His Asn Ser Phe Pro Thr
                85                  90                  95

Phe Gly Ala Gly Thr Lys Xaa Glu Ile Lys
            100                 105

<210> SEQ ID NO 404
<211> LENGTH: 106
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (103)..(103)
<223> OTHER INFORMATION: Xaa can be any naturally occurring amino acid

<400> SEQUENCE: 404

Asp Ile Gln Met Ile Gln Ser Pro Ser Phe Leu Ser Ala Ser Val Gly
1               5                   10                  15

Asp Arg Val Thr Ile Thr Cys Arg Ala Ser Gln Asn Ile Asn Asn Tyr
            20                  25                  30

Leu Asn Trp Tyr Gln Gln Lys Pro Gly Lys Ala Pro Lys Arg Leu Ile

-continued

```
                35                  40                  45
Tyr Asn Thr Asn Asn Leu Gln Thr Gly Ile Pro Ser Arg Phe Ser Gly
 50                  55                  60
Ser Gly Ser Gly Thr Asp Tyr Thr Leu Thr Ile Ser Ser Leu Gln Pro
 65                  70                  75                  80
Glu Asp Phe Ala Thr Tyr Phe Cys Leu Gln His Asn Ser Phe Pro Thr
                 85                  90                  95
Phe Gly Ala Gly Thr Lys Xaa Glu Ile Lys
            100                 105

<210> SEQ ID NO 405
<211> LENGTH: 106
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (103)..(103)
<223> OTHER INFORMATION: Xaa can be any naturally occurring amino acid

<400> SEQUENCE: 405

Asp Ile Gln Met Ile Gln Ser Pro Ser Phe Leu Ser Ala Ser Val Gly
 1               5                  10                  15
Asp Arg Val Thr Ile Thr Cys Gln Ala Ser Gln Asn Ile Asn Asn Tyr
                20                  25                  30
Leu Asn Trp Tyr Gln Gln Lys Pro Gly Lys Ala Pro Lys Arg Leu Ile
             35                  40                  45
Tyr Asn Thr Asn Asn Leu Gln Thr Gly Ile Pro Ser Arg Phe Ser Gly
 50                  55                  60
Ser Gly Ser Gly Thr Asp Tyr Thr Leu Thr Ile Ser Ser Leu Gln Pro
 65                  70                  75                  80
Glu Asp Phe Ala Thr Tyr Phe Cys Leu Gln His Asn Ser Phe Pro Thr
                 85                  90                  95
Phe Gly Ala Gly Thr Lys Xaa Glu Ile Lys
            100                 105

<210> SEQ ID NO 406
<211> LENGTH: 106
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (103)..(103)
<223> OTHER INFORMATION: Xaa can be any naturally occurring amino acid

<400> SEQUENCE: 406

Asp Ile Gln Met Ile Gln Ser Pro Ser Phe Leu Ser Ala Ser Val Gly
 1               5                  10                  15
Asp Arg Val Thr Ile Thr Cys Trp Ala Ser Gln Asn Ile Asn Asn Tyr
                20                  25                  30
Leu Asn Trp Tyr Gln Gln Lys Pro Gly Lys Ala Pro Lys Arg Leu Ile
             35                  40                  45
Tyr Asn Thr Asn Asn Leu Gln Thr Gly Ile Pro Ser Arg Phe Ser Gly
 50                  55                  60
Ser Gly Ser Gly Thr Asp Tyr Thr Leu Thr Ile Ser Ser Leu Gln Pro
 65                  70                  75                  80
Glu Asp Phe Ala Thr Tyr Phe Cys Leu Gln His Asn Ser Phe Pro Thr
                 85                  90                  95
```

-continued

Phe Gly Ala Gly Thr Lys Xaa Glu Ile Lys
            100                 105

<210> SEQ ID NO 407
<211> LENGTH: 106
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (103)..(103)
<223> OTHER INFORMATION: Xaa can be any naturally occurring amino acid

<400> SEQUENCE: 407

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Asn Ile Asn Asn Tyr
            20                  25                  30

Leu Asn Trp Tyr Gln Gln Lys Pro Gly Lys Ala Pro Lys Arg Leu Ile
        35                  40                  45

Tyr Asn Thr Asn Asn Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Leu Gln His Asn Ser Phe Pro Thr
                85                  90                  95

Phe Gly Ala Gly Thr Lys Xaa Glu Ile Lys
            100                 105

<210> SEQ ID NO 408
<211> LENGTH: 106
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (103)..(103)
<223> OTHER INFORMATION: Xaa can be any naturally occurring amino acid

<400> SEQUENCE: 408

Asp Ile Gln Met Ile Gln Ser Pro Ser Phe Leu Ser Ala Ser Val Gly
1               5                   10                  15

Asp Arg Val Thr Ile Thr Cys Gln Ala Ser Gln Asn Ile Asn Asn Tyr
            20                  25                  30

Leu Asn Trp Tyr Gln Gln Lys Pro Gly Lys Ala Pro Lys Arg Leu Ile
        35                  40                  45

Tyr Asn Thr Asn Asn Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Leu Gln His Asn Ser Phe Pro Thr
                85                  90                  95

Phe Gly Ala Gly Thr Lys Xaa Glu Ile Lys
            100                 105

<210> SEQ ID NO 409
<211> LENGTH: 106
<212> TYPE: PRT
<213> ORGANISM: Artificial
<220> FEATURE:

<223> OTHER INFORMATION: Synthetic
<220> FEATURE:
<221> NAME/KEY: misc_feature
<222> LOCATION: (103)..(103)
<223> OTHER INFORMATION: Xaa can be any naturally occurring amino acid

<400> SEQUENCE: 409

Asp Ile Gln Met Thr Gln Ser Pro Ser Thr Leu Ser Ala Ser Val Gly
1               5                   10                  15

Asp Arg Val Thr Ile Thr Cys Trp Ala Ser Gln Asn Ile Asn Asn Tyr
            20                  25                  30

Leu Asn Trp Tyr Gln Gln Lys Pro Gly Lys Ala Pro Lys Arg Leu Ile
        35                  40                  45

Tyr Asn Thr Asn Asn Leu Gln Thr Gly Ile Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Leu Gln His Asn Ser Phe Pro Thr
                85                  90                  95

Phe Gly Ala Gly Thr Lys Xaa Glu Ile Lys
            100                 105

<210> SEQ ID NO 410
<211> LENGTH: 106
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (103)..(103)
<223> OTHER INFORMATION: Xaa can be any naturally occurring amino acid

<400> SEQUENCE: 410

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asn Ile Asn Asn Tyr
            20                  25                  30

Leu Asn Trp Tyr Gln Gln Lys Pro Gly Lys Ala Pro Lys Arg Leu Ile
        35                  40                  45

Tyr Asn Thr Asn Asn Leu Gln Thr Gly Ile Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Leu Gln His Asn Ser Phe Pro Thr
                85                  90                  95

Phe Gly Ala Gly Thr Lys Xaa Glu Ile Lys
            100                 105

<210> SEQ ID NO 411
<211> LENGTH: 106
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (103)..(103)
<223> OTHER INFORMATION: Xaa can be any naturally occurring amino acid

<400> SEQUENCE: 411

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asn Asn Tyr
            20                  25                  30

Leu Asn Trp Tyr Gln Gln Lys Pro Gly Lys Ala Pro Lys Arg Leu Ile
         35                  40                  45

Tyr Asn Thr Asn Asn Leu Gln Thr Gly Ile Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Phe Cys Leu Gln His Asn Ser Phe Pro Thr
             85                  90                  95

Phe Gly Ala Gly Thr Lys Xaa Glu Ile Lys
            100                 105

<210> SEQ ID NO 412
<211> LENGTH: 120
<212> TYPE: PRT
<213> ORGANISM: Artificial
<220> FEATURE:
<223> OTHER INFORMATION: Synthetic

<400> SEQUENCE: 412

Gln Val Gln Leu Gln Gln Ser Gly Pro Gly Leu Val Lys Pro Gly Ala
1               5                   10                  15

Ser Val Lys Val Ser Cys Lys Gly Ser Gly Phe Thr Phe Thr Asp Tyr
            20                  25                  30

Lys Ile His Trp Val Arg Gln Ala Pro Gly Lys Ser Leu Glu Trp Met
         35                  40                  45

Gly Tyr Phe Asn Pro Asn Ser Gly Tyr Ser Thr Tyr Asn Glu Lys Phe
 50                  55                  60

Gln Gly Arg Val Thr Ile Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
             85                  90                  95

Thr Arg Leu Ser Pro Gly Gly Tyr Tyr Val Met Asp Ala Trp Gly Gln
            100                 105                 110

Gly Thr Leu Val Thr Val Ser Ser
        115                 120

<210> SEQ ID NO 413
<211> LENGTH: 120
<212> TYPE: PRT
<213> ORGANISM: Artificial
<220> FEATURE:
<223> OTHER INFORMATION: Synthetic

<400> SEQUENCE: 413

Gln Val Gln Leu Gln Gln Ser Gly Pro Gly Leu Val Lys Pro Gly Ala
1               5                   10                  15

Ser Val Lys Val Ser Cys Lys Gly Ser Gly Phe Thr Phe Thr Asp Tyr
            20                  25                  30

Lys Ile His Trp Val Arg Gln Ala Pro Gly Lys Ser Leu Glu Trp Met
         35                  40                  45

Gly Tyr Phe Asn Pro Asn Ser Gly Tyr Ser Thr Tyr Asn Glu Lys Phe
 50                  55                  60

Gln Gly Arg Val Thr Ile Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
             85                  90                  95

Thr Arg Leu Ser Pro Gly Gly Tyr Tyr Val Met Asp Ala Trp Gly Gln
            100                 105                 110

Gly Thr Leu Val Thr Val Ser Ser
        115                 120

<210> SEQ ID NO 414
<211> LENGTH: 120
<212> TYPE: PRT
<213> ORGANISM: Artificial
<220> FEATURE:
<223> OTHER INFORMATION: Synthetic

<400> SEQUENCE: 414

Gln Val Gln Leu Gln Gln Ser Gly Pro Gly Leu Val Lys Pro Gly Ala
1               5                   10                  15

Ser Val Lys Val Ser Cys Lys Gly Ser Gly Phe Thr Phe Thr Asp Tyr
            20                  25                  30

Lys Ile His Trp Val Arg Gln Ala Pro Gly Lys Ser Leu Glu Trp Met
        35                  40                  45

Gly Tyr Phe Asn Pro Asn Ser Gly Tyr Ser Thr Tyr Asn Glu Lys Phe
    50                  55                  60

Gln Gly Arg Val Thr Ile Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
            100                 105                 110

Gly Thr Leu Val Thr Val Ser Ser
        115                 120

<210> SEQ ID NO 415
<211> LENGTH: 120
<212> TYPE: PRT
<213> ORGANISM: Artificial
<220> FEATURE:
<223> OTHER INFORMATION: Synthetic

<400> SEQUENCE: 415

Gln Val Gln Leu Gln Gln Ser Gly Pro Gly Leu Val Lys Pro Gly Ala
1               5                   10                  15

Ser Val Lys Val Ser Cys Lys Gly Ser Gly Phe Thr Phe Thr Asp Tyr
            20                  25                  30

Lys Ile His Trp Val Arg Gln Ala Pro Gly Lys Ser Leu Glu Trp Met
        35                  40                  45

Gly Tyr Phe Asn Pro Asn Ser Gly Tyr Ser Thr Tyr Asn Glu Lys Phe
    50                  55                  60

Gln Gly Arg Val Thr Ile Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
            100                 105                 110

Gly Thr Leu Val Thr Val Ser Ser
        115                 120

<210> SEQ ID NO 416
<211> LENGTH: 120
<212> TYPE: PRT
<213> ORGANISM: Artificial

```
<220> FEATURE:
<223> OTHER INFORMATION: Synthetic

<400> SEQUENCE: 416

Gln Val Gln Leu Gln Gln Ser Gly Pro Gly Leu Val Lys Pro Gly Ala
1               5                   10                  15

Ser Val Lys Val Ser Cys Lys Gly Ser Gly Phe Thr Phe Thr Asp Tyr
                20                  25                  30

Lys Ile His Trp Val Arg Gln Ala Pro Gly Lys Ser Leu Glu Trp Met
            35                  40                  45

Gly Tyr Phe Asn Pro Asn Ser Gly Tyr Ser Thr Tyr Asn Glu Lys Phe
        50                  55                  60

Gln Gly Arg Val Thr Ile Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
                100                 105                 110

Gly Thr Leu Val Thr Val Ser Ser
        115                 120

<210> SEQ ID NO 417
<211> LENGTH: 120
<212> TYPE: PRT
<213> ORGANISM: Artificial
<220> FEATURE:
<223> OTHER INFORMATION: Synthetic

<400> SEQUENCE: 417

Gln Val Gln Leu Gln Gln Ser Gly Pro Gly Leu Val Lys Pro Gly Ala
1               5                   10                  15

Ser Val Lys Val Ser Cys Lys Gly Ser Gly Phe Thr Phe Thr Asp Tyr
                20                  25                  30

Lys Ile His Trp Val Arg Gln Ala Pro Gly Lys Ser Leu Glu Trp Met
            35                  40                  45

Gly Tyr Phe Asn Pro Asn Ser Gly Tyr Ser Thr Tyr Asn Glu Lys Phe
        50                  55                  60

Gln Gly Arg Val Thr Ile Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
                100                 105                 110

Gly Thr Leu Val Thr Val Ser Ser
        115                 120

<210> SEQ ID NO 418
<211> LENGTH: 120
<212> TYPE: PRT
<213> ORGANISM: Artificial
<220> FEATURE:
<223> OTHER INFORMATION: Synthetic

<400> SEQUENCE: 418

Gln Val Gln Leu Gln Gln Ser Gly Pro Gly Leu Val Lys Pro Gly Ala
1               5                   10                  15

Ser Val Lys Val Ser Cys Lys Gly Ser Gly Phe Thr Phe Thr Asp Tyr
                20                  25                  30

Lys Ile His Trp Val Arg Gln Ala Pro Gly Lys Ser Leu Glu Trp Met
```

```
                35                  40                  45
Gly Tyr Phe Asn Pro Asn Ser Gly Tyr Ser Thr Tyr Asn Glu Lys Phe
 50                  55                  60

Gln Gly Arg Val Thr Ile Thr Ala Asp Lys Ser Thr Asp Thr Ala Tyr
 65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
                100                 105                 110

Gly Thr Leu Val Thr Val Ser Ser
                115                 120

<210> SEQ ID NO 419
<211> LENGTH: 120
<212> TYPE: PRT
<213> ORGANISM: Artificial
<220> FEATURE:
<223> OTHER INFORMATION: Synthetic

<400> SEQUENCE: 419

Gln Val Gln Leu Gln Gln Ser Gly Pro Gly Leu Val Lys Pro Gly Ala
 1               5                  10                  15

Ser Val Lys Val Ser Cys Lys Gly Ser Gly Phe Thr Phe Thr Asp Tyr
                20                  25                  30

Lys Ile His Trp Val Gln Gln Ala Pro Gly Lys Ser Leu Glu Trp Met
                35                  40                  45

Gly Tyr Phe Asn Pro Asn Ser Gly Tyr Ser Thr Tyr Asn Glu Lys Phe
 50                  55                  60

Gln Gly Arg Val Thr Ile Thr Ala Asp Lys Ser Thr Asp Thr Ala Tyr
 65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
                100                 105                 110

Gly Thr Leu Val Thr Val Ser Ser
                115                 120

<210> SEQ ID NO 420
<211> LENGTH: 120
<212> TYPE: PRT
<213> ORGANISM: Artificial
<220> FEATURE:
<223> OTHER INFORMATION: Synthetic

<400> SEQUENCE: 420

Gln Val Gln Leu Gln Gln Ser Gly Pro Gly Leu Val Lys Pro Gly Ala
 1               5                  10                  15

Ser Val Lys Val Ser Cys Lys Gly Ser Gly Phe Thr Phe Thr Asp Tyr
                20                  25                  30

Lys Ile His Trp Val Gln Gln Ala Pro Gly Lys Ser Leu Glu Trp Met
                35                  40                  45

Gly Tyr Phe Asn Pro Asn Ser Gly Tyr Ser Thr Tyr Asn Glu Lys Phe
 50                  55                  60

Gln Gly Arg Val Thr Ile Thr Ala Asp Lys Ser Thr Asp Thr Ala Tyr
 65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
```

-continued

```
                100                 105                 110
Gly Thr Leu Val Thr Val Ser Ser
        115                 120

<210> SEQ ID NO 421
<211> LENGTH: 120
<212> TYPE: PRT
<213> ORGANISM: Artificial
<220> FEATURE:
<223> OTHER INFORMATION: Synthetic

<400> SEQUENCE: 421

Gln Val Gln Leu Gln Gln Ser Gly Pro Gly Leu Val Lys Pro Gly Ala
1               5                   10                  15

Ser Val Lys Val Ser Cys Lys Gly Ser Gly Phe Thr Phe Thr Asp Tyr
            20                  25                  30

Lys Ile His Trp Val Gln Gln Ala Pro Gly Lys Ser Leu Glu Trp Met
        35                  40                  45

Gly Tyr Phe Asn Pro Asn Ser Gly Tyr Ser Thr Tyr Asn Glu Lys Phe
    50                  55                  60

Gln Gly Arg Val Thr Ile Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
            100                 105                 110

Gly Thr Leu Val Thr Val Ser Ser
        115                 120

<210> SEQ ID NO 422
<211> LENGTH: 120
<212> TYPE: PRT
<213> ORGANISM: Artificial
<220> FEATURE:
<223> OTHER INFORMATION: Synthetic

<400> SEQUENCE: 422

Gln Val Gln Leu Val Glu Ser Gly Gly Gly Leu Val Lys Pro Gly Ala
1               5                   10                  15

Ser Val Lys Val Ser Cys Lys Gly Ser Gly Phe Thr Phe Thr Asp Tyr
            20                  25                  30

Lys Ile His Trp Val Arg Gln Ala Pro Gly Lys Ser Leu Glu Trp Met
        35                  40                  45

Gly Tyr Phe Asn Pro Asn Ser Gly Tyr Ser Thr Tyr Asn Glu Lys Phe
    50                  55                  60

Gln Gly Arg Val Thr Ile Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
            100                 105                 110

Gly Thr Leu Val Thr Val Ser Ser
        115                 120

<210> SEQ ID NO 423
<211> LENGTH: 120
<212> TYPE: PRT
<213> ORGANISM: Artificial
<220> FEATURE:
<223> OTHER INFORMATION: Synthetic
```

<400> SEQUENCE: 423

Gln Val Gln Leu Val Glu Ser Gly Gly Gly Leu Val Lys Pro Gly Ala
1               5                   10                  15

Ser Val Lys Val Ser Cys Lys Gly Ser Gly Phe Thr Phe Thr Asp Tyr
            20                  25                  30

Lys Ile His Trp Val Arg Gln Ala Pro Gly Lys Ser Leu Glu Trp Met
        35                  40                  45

Gly Tyr Phe Asn Pro Asn Ser Gly Tyr Ser Thr Tyr Asn Glu Lys Phe
    50                  55                  60

Gln Gly Arg Val Thr Ile Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
            100                 105                 110

Gly Thr Leu Val Thr Val Ser Ser
            115                 120

<210> SEQ ID NO 424
<211> LENGTH: 120
<212> TYPE: PRT
<213> ORGANISM: Artificial
<220> FEATURE:
<223> OTHER INFORMATION: Synthetic

<400> SEQUENCE: 424

Gln Val Gln Leu Val Glu Ser Gly Gly Gly Leu Val Lys Pro Gly Ala
1               5                   10                  15

Ser Val Lys Val Ser Cys Lys Gly Ser Gly Phe Thr Phe Thr Asp Tyr
            20                  25                  30

Lys Ile His Trp Val Arg Gln Ala Pro Gly Lys Ser Leu Glu Trp Met
        35                  40                  45

Gly Tyr Phe Asn Pro Asn Ser Gly Tyr Ser Thr Tyr Asn Glu Lys Phe
    50                  55                  60

Gln Gly Arg Val Thr Ile Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
            100                 105                 110

Gly Thr Leu Val Thr Val Ser Ser
            115                 120

<210> SEQ ID NO 425
<211> LENGTH: 120
<212> TYPE: PRT
<213> ORGANISM: Artificial
<220> FEATURE:
<223> OTHER INFORMATION: Synthetic

<400> SEQUENCE: 425

Gln Val Gln Leu Val Glu Ser Gly Gly Gly Leu Val Lys Pro Gly Ala
1               5                   10                  15

Ser Val Lys Val Ser Cys Lys Gly Ser Gly Phe Thr Phe Thr Asp Tyr
            20                  25                  30

Lys Ile His Trp Val Arg Gln Ala Pro Gly Lys Ser Leu Glu Trp Met
        35                  40                  45

Gly Tyr Phe Asn Pro Asn Ser Gly Tyr Ser Thr Tyr Asn Glu Lys Phe
            50                  55                  60

Gln Gly Arg Val Thr Ile Thr Ala Asp Lys Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Thr Arg Leu Ser Pro Gly Gly Tyr Tyr Val Met Asp Ala Trp Gly Gln
            100                 105                 110

Gly Thr Leu Val Thr Val Ser Ser
            115                 120

<210> SEQ ID NO 426
<211> LENGTH: 120
<212> TYPE: PRT
<213> ORGANISM: Artificial
<220> FEATURE:
<223> OTHER INFORMATION: Synthetic

<400> SEQUENCE: 426

Gln Val Gln Leu Val Glu Ser Gly Gly Gly Leu Val Lys Pro Gly Ala
 1               5                  10                  15

Ser Val Lys Val Ser Cys Lys Gly Ser Gly Phe Thr Phe Thr Asp Tyr
            20                  25                  30

Lys Ile His Trp Val Arg Gln Ala Pro Gly Lys Ser Leu Glu Trp Met
        35                  40                  45

Gly Tyr Phe Asn Pro Asn Ser Gly Tyr Ser Thr Tyr Asn Glu Lys Phe
    50                  55                  60

Gln Gly Arg Val Thr Ile Thr Ala Asp Lys Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Thr Arg Leu Ser Pro Gly Gly Tyr Tyr Val Met Asp Ala Trp Gly Gln
            100                 105                 110

Gly Thr Leu Val Thr Val Ser Ser
            115                 120

<210> SEQ ID NO 427
<211> LENGTH: 120
<212> TYPE: PRT
<213> ORGANISM: Artificial
<220> FEATURE:
<223> OTHER INFORMATION: Synthetic

<400> SEQUENCE: 427

Gln Val Gln Leu Val Glu Ser Gly Gly Gly Leu Val Lys Pro Gly Ala
 1               5                  10                  15

Ser Val Lys Val Ser Cys Lys Gly Ser Gly Phe Thr Phe Thr Asp Tyr
            20                  25                  30

Lys Ile His Trp Val Gln Gln Ala Pro Gly Lys Ser Leu Glu Trp Met
        35                  40                  45

Gly Tyr Phe Asn Pro Asn Ser Gly Tyr Ser Thr Tyr Asn Glu Lys Phe
    50                  55                  60

Gln Gly Arg Val Thr Ile Thr Ala Asp Lys Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Thr Arg Leu Ser Pro Gly Gly Tyr Tyr Val Met Asp Ala Trp Gly Gln
            100                 105                 110

```
Gly Thr Leu Val Thr Val Ser Ser
        115                 120

<210> SEQ ID NO 428
<211> LENGTH: 120
<212> TYPE: PRT
<213> ORGANISM: Artificial
<220> FEATURE:
<223> OTHER INFORMATION: Synthetic

<400> SEQUENCE: 428

Gln Val Gln Leu Val Glu Ser Gly Gly Gly Leu Val Lys Pro Gly Ala
1               5                   10                  15

Ser Val Lys Val Ser Cys Lys Gly Ser Gly Phe Thr Phe Thr Asp Tyr
            20                  25                  30

Lys Ile His Trp Val Gln Gln Ala Pro Gly Lys Ser Leu Glu Trp Met
        35                  40                  45

Gly Tyr Phe Asn Pro Asn Ser Gly Tyr Ser Thr Tyr Asn Glu Lys Phe
    50                  55                  60

Gln Gly Arg Val Thr Ile Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
            100                 105                 110

Gly Thr Leu Val Thr Val Ser Ser
        115                 120

<210> SEQ ID NO 429
<211> LENGTH: 120
<212> TYPE: PRT
<213> ORGANISM: Artificial
<220> FEATURE:
<223> OTHER INFORMATION: Synthetic

<400> SEQUENCE: 429

Gln Val Gln Leu Val Glu Ser Gly Gly Gly Leu Val Lys Pro Gly Ala
1               5                   10                  15

Ser Val Lys Val Ser Cys Lys Gly Ser Gly Phe Thr Phe Thr Asp Tyr
            20                  25                  30

Lys Ile His Trp Val Gln Gln Ala Pro Gly Lys Ser Leu Glu Trp Met
        35                  40                  45

Gly Tyr Phe Asn Pro Asn Ser Gly Tyr Ser Thr Tyr Asn Glu Lys Phe
    50                  55                  60

Gln Gly Arg Val Thr Ile Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
            100                 105                 110

Gly Thr Leu Val Thr Val Ser Ser
        115                 120

<210> SEQ ID NO 430
<211> LENGTH: 120
<212> TYPE: PRT
<213> ORGANISM: Artificial
<220> FEATURE:
<223> OTHER INFORMATION: Synthetic

<400> SEQUENCE: 430
```

Gln Val Gln Leu Val Glu Ser Gly Gly Gly Leu Val Lys Pro Gly Ala
1               5                   10                  15

Ser Val Lys Val Ser Cys Lys Gly Ser Gly Phe Thr Phe Thr Asp Tyr
                20                  25                  30

Lys Ile His Trp Val Gln Gln Ala Pro Gly Lys Ser Leu Glu Trp Met
            35                  40                  45

Gly Tyr Phe Asn Pro Asn Ser Gly Tyr Ser Thr Tyr Asn Glu Lys Phe
        50                  55                  60

Gln Gly Arg Val Thr Ile Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
                100                 105                 110

Gly Thr Leu Val Thr Val Ser Ser
        115                 120

<210> SEQ ID NO 431
<211> LENGTH: 120
<212> TYPE: PRT
<213> ORGANISM: Artificial
<220> FEATURE:
<223> OTHER INFORMATION: Synthetic

<400> SEQUENCE: 431

Gln Val Gln Leu Val Glu Ser Gly Gly Gly Leu Val Lys Pro Gly Ala
1               5                   10                  15

Ser Val Lys Val Ser Cys Lys Gly Ser Gly Phe Thr Phe Thr Asp Tyr
                20                  25                  30

Lys Ile His Trp Val Gln Gln Ala Pro Gly Lys Ser Leu Glu Trp Met
            35                  40                  45

Gly Tyr Phe Asn Pro Asn Ser Gly Tyr Ser Thr Tyr Asn Glu Lys Phe
        50                  55                  60

Gln Gly Arg Val Thr Ile Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
                100                 105                 110

Gly Thr Leu Val Thr Val Ser Ser
        115                 120

<210> SEQ ID NO 432
<211> LENGTH: 120
<212> TYPE: PRT
<213> ORGANISM: Artificial
<220> FEATURE:
<223> OTHER INFORMATION: Synthetic

<400> SEQUENCE: 432

Gln Val Gln Leu Val Gln Ser Gly Ala Glu Val Lys Lys Pro Gly Ala
1               5                   10                  15

Ser Val Lys Val Ser Cys Lys Gly Ser Gly Phe Thr Phe Thr Asp Tyr
                20                  25                  30

Lys Ile His Trp Val Arg Gln Ala Pro Gly Lys Ser Leu Glu Trp Met
            35                  40                  45

Gly Tyr Phe Asn Pro Asn Ser Gly Tyr Ser Thr Tyr Asn Glu Lys Phe
        50                  55                  60

Gln Gly Arg Val Thr Ile Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
            100                 105                 110

Gly Thr Leu Val Thr Val Ser Ser
        115                 120

<210> SEQ ID NO 433
<211> LENGTH: 120
<212> TYPE: PRT
<213> ORGANISM: Artificial
<220> FEATURE:
<223> OTHER INFORMATION: Synthetic

<400> SEQUENCE: 433

Gln Val Gln Leu Val Gln Ser Gly Ala Glu Val Lys Lys Pro Gly Ala
1               5                   10                  15

Ser Val Lys Val Ser Cys Lys Gly Ser Gly Phe Thr Phe Thr Asp Tyr
            20                  25                  30

Lys Ile His Trp Val Gln Gln Ala Pro Gly Lys Ser Leu Glu Trp Met
        35                  40                  45

Gly Tyr Phe Asn Pro Asn Ser Gly Tyr Ser Thr Tyr Asn Glu Lys Phe
    50                  55                  60

Gln Gly Arg Val Thr Ile Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
            100                 105                 110

Gly Thr Leu Val Thr Val Ser Ser
        115                 120

<210> SEQ ID NO 434
<211> LENGTH: 120
<212> TYPE: PRT
<213> ORGANISM: Artificial
<220> FEATURE:
<223> OTHER INFORMATION: Synthetic

<400> SEQUENCE: 434

Gln Val Gln Leu Val Gln Ser Gly Ser Glu Leu Lys Lys Pro Gly Ala
1               5                   10                  15

Ser Val Lys Val Ser Cys Lys Gly Ser Gly Phe Thr Phe Thr Asp Tyr
            20                  25                  30

Lys Ile His Trp Val Arg Gln Ala Pro Gly Lys Ser Leu Glu Trp Met
        35                  40                  45

Gly Tyr Phe Asn Pro Asn Ser Gly Tyr Ser Thr Tyr Asn Glu Lys Phe
    50                  55                  60

Gln Gly Arg Val Thr Ile Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
            100                 105                 110

Gly Thr Leu Val Thr Val Ser Ser
        115                 120

<210> SEQ ID NO 435
<211> LENGTH: 120
<212> TYPE: PRT
<213> ORGANISM: Artificial
<220> FEATURE:
<223> OTHER INFORMATION: Synthetic

<400> SEQUENCE: 435

Gln Val Gln Leu Val Gln Ser Gly Ser Glu Leu Lys Lys Pro Gly Ala
1               5                   10                  15

Ser Val Lys Val Ser Cys Lys Gly Ser Gly Phe Thr Phe Thr Asp Tyr
            20                  25                  30

Lys Ile His Trp Val Arg Gln Ala Pro Gly Gln Ser Leu Glu Trp Met
        35                  40                  45

Gly Tyr Phe Asn Pro Asn Ser Gly Tyr Ser Thr Tyr Asn Glu Lys Phe
    50                  55                  60

Gln Gly Arg Val Thr Ile Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
            100                 105                 110

Gly Thr Leu Val Thr Val Ser Ser
        115                 120

<210> SEQ ID NO 436
<211> LENGTH: 120
<212> TYPE: PRT
<213> ORGANISM: Artificial
<220> FEATURE:
<223> OTHER INFORMATION: Synthetic

<400> SEQUENCE: 436

Gln Val Gln Leu Val Gln Ser Gly Ser Glu Leu Lys Lys Pro Gly Ala
1               5                   10                  15

Ser Val Lys Val Ser Cys Lys Gly Ser Gly Phe Thr Phe Thr Asp Tyr
            20                  25                  30

Lys Ile His Trp Val Gln Gln Ala Pro Gly Lys Ser Leu Glu Trp Met
        35                  40                  45

Gly Tyr Phe Asn Pro Asn Ser Gly Tyr Ser Thr Tyr Asn Glu Lys Phe
    50                  55                  60

Gln Gly Arg Val Thr Ile Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
            100                 105                 110

Gly Thr Leu Val Thr Val Ser Ser
        115                 120

<210> SEQ ID NO 437
<211> LENGTH: 120
<212> TYPE: PRT
<213> ORGANISM: Artificial
<220> FEATURE:
<223> OTHER INFORMATION: Synthetic

<400> SEQUENCE: 437

Gln Val Gln Leu Val Gln Ser Gly Ala Glu Val Lys Lys Pro Gly Ala

```
                1               5                  10                 15
Ser Val Lys Val Ser Cys Lys Gly Ser Gly Phe Thr Phe Thr Asp Tyr
                    20                  25                 30

Lys Ile His Trp Val Arg Gln Ala Pro Gly Lys Ser Leu Glu Trp Met
            35                  40                  45

Gly Tyr Phe Asn Pro Asn Ser Gly Tyr Ser Thr Tyr Asn Glu Ser Leu
        50                  55                  60

Lys Ser Arg Val Thr Ile Ser Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
                100                 105                 110

Gly Thr Leu Val Thr Val Ser Ser
            115                 120

<210> SEQ ID NO 438
<211> LENGTH: 120
<212> TYPE: PRT
<213> ORGANISM: Artificial
<220> FEATURE:
<223> OTHER INFORMATION: Synthetic

<400> SEQUENCE: 438

Gln Val Gln Leu Val Gln Ser Gly Ala Glu Val Lys Lys Pro Gly Ala
1               5                   10                  15

Ser Val Lys Val Ser Cys Lys Gly Ser Gly Phe Thr Phe Thr Asp Tyr
                    20                  25                  30

Lys Ile His Trp Val Arg Gln Ala Pro Gly Gln Ser Leu Glu Trp Met
            35                  40                  45

Gly Tyr Phe Asn Pro Asn Ser Gly Tyr Ser Thr Tyr Asn Glu Ser Leu
        50                  55                  60

Lys Ser Arg Val Thr Ile Ser Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
                100                 105                 110

Gly Thr Leu Val Thr Val Ser Ser
            115                 120

<210> SEQ ID NO 439
<211> LENGTH: 120
<212> TYPE: PRT
<213> ORGANISM: Artificial
<220> FEATURE:
<223> OTHER INFORMATION: Synthetic

<400> SEQUENCE: 439

Gln Val Gln Leu Val Gln Ser Gly Ser Glu Leu Lys Lys Pro Gly Ala
1               5                   10                  15

Ser Val Lys Val Ser Cys Lys Gly Ser Gly Phe Thr Phe Thr Asp Tyr
                    20                  25                  30

Lys Ile His Trp Val Arg Gln Ala Pro Gly Lys Ser Leu Glu Trp Met
            35                  40                  45

Gly Tyr Phe Asn Pro Asn Ser Gly Tyr Ser Thr Tyr Asn Glu Ser Leu
        50                  55                  60

Lys Ser Arg Val Thr Ile Ser Ala Asp Lys Ser Thr Asp Thr Ala Tyr
```

```
                65                  70                  75                  80
Met Glu Leu Ser Ser Leu Arg Ser Glu Asp Thr Ala Val Tyr Tyr Cys
                    85                  90                  95

Thr Arg Leu Ser Pro Gly Gly Tyr Tyr Val Met Asp Ala Trp Gly Gln
                100                 105                 110

Gly Thr Leu Val Thr Val Ser Ser
            115                 120

<210> SEQ ID NO 440
<211> LENGTH: 120
<212> TYPE: PRT
<213> ORGANISM: Artificial
<220> FEATURE:
<223> OTHER INFORMATION: Synthetic

<400> SEQUENCE: 440

Gln Val Gln Leu Val Gln Ser Gly Ala Glu Val Lys Lys Pro Gly Ala
1               5                   10                  15

Ser Val Lys Val Ser Cys Lys Gly Ser Gly Phe Thr Phe Thr Asp Tyr
                20                  25                  30

Lys Ile His Trp Val Gln Gln Ala Pro Gly Lys Ser Leu Glu Trp Met
            35                  40                  45

Gly Tyr Phe Asn Pro Asn Ser Gly Tyr Ser Thr Tyr Asn Glu Ser Leu
        50                  55                  60

Lys Ser Arg Val Thr Ile Ser Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
                100                 105                 110

Gly Thr Leu Val Thr Val Ser Ser
            115                 120

<210> SEQ ID NO 441
<211> LENGTH: 120
<212> TYPE: PRT
<213> ORGANISM: Artificial
<220> FEATURE:
<223> OTHER INFORMATION: Synthetic

<400> SEQUENCE: 441

Gln Val Gln Leu Val Gln Ser Gly Ser Glu Leu Lys Lys Pro Gly Ala
1               5                   10                  15

Ser Val Lys Val Ser Cys Lys Gly Ser Gly Phe Thr Phe Thr Asp Tyr
                20                  25                  30

Lys Ile His Trp Val Gln Gln Ala Pro Gly Lys Ser Leu Glu Trp Met
            35                  40                  45

Gly Tyr Phe Asn Pro Asn Ser Gly Tyr Ser Thr Tyr Asn Glu Ser Leu
        50                  55                  60

Lys Ser Arg Val Thr Ile Ser Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
                100                 105                 110

Gly Thr Leu Val Thr Val Ser Ser
            115                 120
```

```
<210> SEQ ID NO 442
<211> LENGTH: 120
<212> TYPE: PRT
<213> ORGANISM: Artificial
<220> FEATURE:
<223> OTHER INFORMATION: Synthetic

<400> SEQUENCE: 442

Glu Val Gln Leu Val Glu Ser Gly Gly Gly Leu Val Lys Pro Gly Ala
1               5                   10                  15

Ser Val Lys Val Ser Cys Lys Gly Ser Gly Phe Thr Phe Thr Asp Tyr
            20                  25                  30

Lys Ile His Trp Val Arg Gln Ala Pro Gly Lys Ser Leu Glu Trp Met
        35                  40                  45

Gly Tyr Phe Asn Pro Asn Ser Gly Tyr Ser Thr Tyr Asn Glu Lys Phe
    50                  55                  60

Gln Gly Arg Val Thr Ile Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
            100                 105                 110

Gly Thr Leu Val Thr Val Ser Ser
        115                 120

<210> SEQ ID NO 443
<211> LENGTH: 120
<212> TYPE: PRT
<213> ORGANISM: Artificial
<220> FEATURE:
<223> OTHER INFORMATION: Synthetic

<400> SEQUENCE: 443

Gln Val Gln Leu Val Glu Ser Gly Gly Gly Leu Val Lys Pro Gly Ala
1               5                   10                  15

Ser Val Lys Val Ser Cys Lys Gly Ser Gly Phe Thr Phe Thr Asp Tyr
            20                  25                  30

Lys Ile His Trp Val Arg Gln Ala Pro Gly Lys Ser Leu Glu Trp Met
        35                  40                  45

Gly Tyr Phe Asn Pro Asn Ser Gly Tyr Ser Thr Tyr Asn Glu Lys Phe
    50                  55                  60

Gln Gly Arg Val Thr Ile Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
            100                 105                 110

Gly Thr Leu Val Thr Val Ser Ser
        115                 120

<210> SEQ ID NO 444
<211> LENGTH: 120
<212> TYPE: PRT
<213> ORGANISM: Artificial
<220> FEATURE:
<223> OTHER INFORMATION: Synthetic

<400> SEQUENCE: 444

Glu Val Gln Leu Val Glu Ser Gly Gly Gly Leu Val Lys Pro Gly Ala
1               5                   10                  15
```

```
Ser Val Lys Val Ser Cys Lys Gly Ser Gly Phe Thr Phe Thr Asp Tyr
            20                  25                  30

Lys Ile His Trp Val Gln Gln Ala Pro Gly Lys Ser Leu Glu Trp Met
        35                  40                  45

Gly Tyr Phe Asn Pro Asn Ser Gly Tyr Ser Thr Tyr Asn Glu Lys Phe
    50                  55                  60

Gln Gly Arg Val Thr Ile Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
            100                 105                 110

Gly Thr Leu Val Thr Val Ser Ser
        115                 120

<210> SEQ ID NO 445
<211> LENGTH: 120
<212> TYPE: PRT
<213> ORGANISM: Artificial
<220> FEATURE:
<223> OTHER INFORMATION: Synthetic

<400> SEQUENCE: 445

Gln Val Gln Leu Gln Gln Ser Gly Pro Gly Leu Val Lys Pro Gly Ala
1               5                   10                  15

Ser Val Lys Val Ser Cys Lys Gly Ser Gly Phe Thr Phe Thr Asp Tyr
            20                  25                  30

Lys Ile His Trp Val Arg Gln Ala Pro Gly Lys Ser Leu Glu Trp Met
        35                  40                  45

Gly Tyr Phe Asn Pro Asn Ser Gly Tyr Ser Thr Tyr Asn Glu Lys Phe
    50                  55                  60

Gln Gly Arg Val Thr Ile Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
            100                 105                 110

Gly Thr Leu Val Thr Val Ser Ser
        115                 120

<210> SEQ ID NO 446
<211> LENGTH: 120
<212> TYPE: PRT
<213> ORGANISM: Artificial
<220> FEATURE:
<223> OTHER INFORMATION: Synthetic

<400> SEQUENCE: 446

Gln Val Gln Leu Gln Gln Ser Gly Pro Gly Leu Val Lys Pro Gly Ala
1               5                   10                  15

Ser Val Lys Val Ser Cys Lys Gly Ser Gly Phe Thr Phe Thr Asp Tyr
            20                  25                  30

Lys Ile His Trp Val Arg Gln Ala Pro Gly Gln Ser Leu Glu Trp Met
        35                  40                  45

Gly Tyr Phe Asn Pro Asn Ser Gly Tyr Ser Thr Tyr Asn Glu Lys Phe
    50                  55                  60

Gln Gly Arg Val Thr Ile Thr Ala Asp Lys Ser Thr Asp Thr Ala Tyr
65                  70                  75                  80
```

```
Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
            100                 105                 110

Gly Thr Leu Val Thr Val Ser Ser
        115                 120

<210> SEQ ID NO 447
<211> LENGTH: 120
<212> TYPE: PRT
<213> ORGANISM: Artificial
<220> FEATURE:
<223> OTHER INFORMATION: Synthetic

<400> SEQUENCE: 447

Gln Val Gln Leu Gln Gln Ser Gly Pro Gly Leu Val Lys Pro Gly Ala
1               5                   10                  15

Ser Val Lys Val Ser Cys Lys Gly Ser Gly Phe Thr Phe Thr Asp Tyr
            20                  25                  30

Lys Ile His Trp Val Gln Gln Ala Pro Gly Lys Ser Leu Glu Trp Met
        35                  40                  45

Gly Tyr Phe Asn Pro Asn Ser Gly Tyr Ser Thr Tyr Asn Glu Lys Phe
    50                  55                  60

Gln Gly Arg Val Thr Ile Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
            100                 105                 110

Gly Thr Leu Val Thr Val Ser Ser
        115                 120

<210> SEQ ID NO 448
<211> LENGTH: 120
<212> TYPE: PRT
<213> ORGANISM: Artificial
<220> FEATURE:
<223> OTHER INFORMATION: Synthetic

<400> SEQUENCE: 448

Gln Val Thr Leu Arg Glu Ser Gly Pro Ala Leu Val Lys Pro Gly Ala
1               5                   10                  15

Ser Val Lys Val Ser Cys Lys Gly Ser Gly Phe Thr Phe Thr Asp Tyr
            20                  25                  30

Lys Ile His Trp Val Arg Gln Ala Pro Gly Lys Ser Leu Glu Trp Met
        35                  40                  45

Gly Tyr Phe Asn Pro Asn Ser Gly Tyr Ser Thr Tyr Asn Glu Lys Phe
    50                  55                  60

Gln Gly Arg Val Thr Ile Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
            100                 105                 110

Gly Thr Leu Val Thr Val Ser Ser
        115                 120

<210> SEQ ID NO 449
<211> LENGTH: 120
```

-continued

```
<212> TYPE: PRT
<213> ORGANISM: Artificial
<220> FEATURE:
<223> OTHER INFORMATION: Synthetic

<400> SEQUENCE: 449

Glu Val Gln Leu Val Glu Ser Gly Gly Gly Leu Val Lys Pro Gly Ala
1               5                   10                  15

Ser Val Lys Val Ser Cys Lys Gly Ser Gly Phe Thr Phe Thr Asp Tyr
            20                  25                  30

Lys Ile His Trp Val Arg Gln Ala Pro Gly Lys Ser Leu Glu Trp Met
        35                  40                  45

Gly Tyr Phe Asn Pro Asn Ser Gly Tyr Ser Thr Tyr Asn Glu Ser Leu
    50                  55                  60

Lys Ser Arg Val Thr Ile Ser Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
            100                 105                 110

Gly Thr Leu Val Thr Val Ser Ser
        115                 120

<210> SEQ ID NO 450
<211> LENGTH: 120
<212> TYPE: PRT
<213> ORGANISM: Artificial
<220> FEATURE:
<223> OTHER INFORMATION: Synthetic

<400> SEQUENCE: 450

Gln Val Gln Leu Val Glu Ser Gly Gly Gly Leu Val Lys Pro Gly Ala
1               5                   10                  15

Ser Val Lys Val Ser Cys Lys Gly Ser Gly Phe Thr Phe Thr Asp Tyr
            20                  25                  30

Lys Ile His Trp Val Arg Gln Ala Pro Gly Lys Ser Leu Glu Trp Met
        35                  40                  45

Gly Tyr Phe Asn Pro Asn Ser Gly Tyr Ser Thr Tyr Asn Glu Ser Leu
    50                  55                  60

Lys Ser Arg Val Thr Ile Ser Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
            100                 105                 110

Gly Thr Leu Val Thr Val Ser Ser
        115                 120

<210> SEQ ID NO 451
<211> LENGTH: 120
<212> TYPE: PRT
<213> ORGANISM: Artificial
<220> FEATURE:
<223> OTHER INFORMATION: Synthetic

<400> SEQUENCE: 451

Glu Val Gln Leu Val Glu Ser Gly Gly Gly Leu Val Lys Pro Gly Ala
1               5                   10                  15

Ser Val Lys Val Ser Cys Lys Gly Ser Gly Phe Thr Phe Thr Asp Tyr
            20                  25                  30
```

```
Lys Ile His Trp Val Gln Gln Ala Pro Gly Lys Ser Leu Glu Trp Met
            35                  40                  45

Gly Tyr Phe Asn Pro Asn Ser Gly Tyr Ser Thr Tyr Asn Glu Ser Leu
    50                  55                  60

Lys Ser Arg Val Thr Ile Ser Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
                100                 105                 110

Gly Thr Leu Val Thr Val Ser Ser
            115                 120
```

<210> SEQ ID NO 452
<211> LENGTH: 120
<212> TYPE: PRT
<213> ORGANISM: Artificial
<220> FEATURE:
<223> OTHER INFORMATION: Synthetic

<400> SEQUENCE: 452

```
Gln Val Gln Leu Val Glu Ser Gly Gly Gly Leu Val Lys Pro Gly Ala
1               5                   10                  15

Ser Val Lys Val Ser Cys Lys Gly Ser Gly Phe Thr Phe Thr Asp Tyr
                20                  25                  30

Lys Ile His Trp Val Gln Gln Ala Pro Gly Lys Ser Leu Glu Trp Met
            35                  40                  45

Gly Tyr Phe Asn Pro Asn Ser Gly Tyr Ser Thr Tyr Asn Glu Ser Leu
    50                  55                  60

Lys Ser Arg Val Thr Ile Ser Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
                100                 105                 110

Gly Thr Leu Val Thr Val Ser Ser
            115                 120
```

<210> SEQ ID NO 453
<211> LENGTH: 120
<212> TYPE: PRT
<213> ORGANISM: Artificial
<220> FEATURE:
<223> OTHER INFORMATION: Synthetic

<400> SEQUENCE: 453

```
Gln Val Gln Leu Gln Gln Ser Gly Pro Gly Leu Val Lys Pro Gly Ala
1               5                   10                  15

Ser Val Lys Val Ser Cys Lys Gly Ser Gly Phe Thr Phe Thr Asp Tyr
                20                  25                  30

Lys Ile His Trp Val Arg Gln Ala Pro Gly Lys Ser Leu Glu Trp Met
            35                  40                  45

Gly Tyr Phe Asn Pro Asn Ser Gly Tyr Ser Thr Tyr Asn Glu Ser Leu
    50                  55                  60

Lys Ser Arg Val Thr Ile Ser Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95
```

Thr Arg Leu Ser Pro Gly Gly Tyr Tyr Val Met Asp Ala Trp Gly Gln
            100                 105                 110

Gly Thr Leu Val Thr Val Ser Ser
        115                 120

<210> SEQ ID NO 454
<211> LENGTH: 120
<212> TYPE: PRT
<213> ORGANISM: Artificial
<220> FEATURE:
<223> OTHER INFORMATION: Synthetic

<400> SEQUENCE: 454

Gln Val Gln Leu Gln Gln Ser Gly Pro Gly Leu Val Lys Pro Gly Ala
1               5                   10                  15

Ser Val Lys Val Ser Cys Lys Gly Ser Gly Phe Thr Phe Thr Asp Tyr
            20                  25                  30

Lys Ile His Trp Val Gln Gln Ala Pro Gly Lys Ser Leu Glu Trp Met
        35                  40                  45

Gly Tyr Phe Asn Pro Asn Ser Gly Tyr Ser Thr Tyr Asn Glu Ser Leu
    50                  55                  60

Lys Ser Arg Val Thr Ile Ser Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
            100                 105                 110

Gly Thr Leu Val Thr Val Ser Ser
        115                 120

<210> SEQ ID NO 455
<211> LENGTH: 120
<212> TYPE: PRT
<213> ORGANISM: Artificial
<220> FEATURE:
<223> OTHER INFORMATION: Synthetic

<400> SEQUENCE: 455

Gln Val Thr Leu Arg Glu Ser Gly Pro Ala Leu Val Lys Pro Gly Ala
1               5                   10                  15

Ser Val Lys Val Ser Cys Lys Gly Ser Gly Phe Thr Phe Thr Asp Tyr
            20                  25                  30

Lys Ile His Trp Val Arg Gln Ala Pro Gly Lys Ser Leu Glu Trp Met
        35                  40                  45

Gly Tyr Phe Asn Pro Asn Ser Gly Tyr Ser Thr Tyr Asn Glu Ser Leu
    50                  55                  60

Lys Ser Arg Val Thr Ile Ser Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Tyr Val Met Asp Ala Trp Gly Gln
            100                 105                 110

Gly Thr Leu Val Thr Val Ser Ser
        115                 120

<210> SEQ ID NO 456
<211> LENGTH: 106
<212> TYPE: PRT
<213> ORGANISM: Homo sapiens

<400> SEQUENCE: 456

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asn Asn Tyr
            20                  25                  30

Leu Asn Trp Tyr Gln Gln Lys Pro Gly Lys Ala Pro Lys Arg Leu Ile
        35                  40                  45

Tyr Asn Thr Asn Asn Leu Gln Thr Gly Ile Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Leu Gln His Asn Ser Phe Pro Thr
                85                  90                  95

Phe Gly Ala Gly Thr Lys Leu Glu Ile Lys
            100                 105

<210> SEQ ID NO 457
<211> LENGTH: 120
<212> TYPE: PRT
<213> ORGANISM: Homo sapiens

<400> SEQUENCE: 457

Gln Val Gln Leu Gln Gln Ser Gly Pro Gly Leu Val Lys Pro Gly Ala
1               5                   10                  15

Ser Val Lys Val Ser Cys Lys Gly Ser Gly Phe Thr Phe Thr Asp Tyr
            20                  25                  30

Lys Ile His Trp Val Arg Gln Ala Pro Gly Lys Ser Leu Glu Trp Met
        35                  40                  45

Gly Tyr Phe Asn Pro Asn Ser Gly Tyr Ser Thr Tyr Asn Glu Lys Phe
50                  55                  60

Gln Gly Arg Val Thr Ile Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Leu Ser Pro Gly Gly Tyr Val Met Asp Ala Trp Gly Gln
            100                 105                 110

Gly Thr Leu Val Thr Val Ser Ser
        115                 120

<210> SEQ ID NO 458
<211> LENGTH: 120
<212> TYPE: PRT
<213> ORGANISM: Homo sapiens

<400> SEQUENCE: 458

Gln Val Gln Leu Val Gln Ser Gly Ala Glu Val Lys Lys Pro Gly Ala
1               5                   10                  15

Ser Val Lys Val Ser Cys Lys Gly Ser Gly Phe Thr Phe Thr Asp Tyr
            20                  25                  30

Lys Ile His Trp Val Arg Gln Ala Pro Gly Lys Ser Leu Glu Trp Met
        35                  40                  45

Gly Tyr Phe Asn Pro Asn Ser Gly Tyr Ser Thr Tyr Asn Glu Lys Phe
50                  55                  60

Gln Gly Arg Val Thr Ile Thr Ala Asp Lys Ser Thr Asp Thr Ala Tyr
65                  70                  75                  80

```
Met Glu Leu Ser Ser Leu Arg Ser Glu Asp Thr Ala Val Tyr Tyr Cys
                85              90                  95
Thr Arg Leu Ser Pro Gly Gly Tyr Tyr Val Met Asp Ala Trp Gly Gln
            100             105                 110
Gly Thr Leu Val Thr Val Ser Ser
        115             120
```